(12) United States Patent
Holson et al.

(10) Patent No.: US 12,428,373 B2
(45) Date of Patent: Sep. 30, 2025

(54) DOPAMINE D2 RECEPTOR LIGANDS

(71) Applicants: The Broad Institute, Inc., Cambridge, MA (US); Massachusetts Institute of Technology, Cambridge, MA (US)

(72) Inventors: Edward Holson, Cambridge, MA (US); Florence Fevrier Wagner, Cambridge, MA (US); Michel Weiwer, Cambridge, MA (US); Edward Scolnick, Cambridge, MA (US); Michelle Palmer, Cambridge, MA (US); Luka Dordevic, Cambridge, MA (US); Michael C. Lewis, Cambridge, MA (US); Jennifer Q. Pan, Cambridge, MA (US); Yan-Ling Zhang, Cambridge, MA (US); Qihong Xu, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 72 days.

(21) Appl. No.: 17/962,346

(22) Filed: Oct. 7, 2022

(65) Prior Publication Data
US 2023/0143552 A1    May 11, 2023

Related U.S. Application Data

(63) Continuation of application No. 16/826,028, filed on Mar. 20, 2020, now Pat. No. 11,498,896, which is a continuation of application No. 15/537,741, filed as application No. PCT/US2015/066928 on Dec. 18, 2015, now Pat. No. 10,633,336.

(60) Provisional application No. 62/094,670, filed on Dec. 19, 2014.

(51) Int. Cl.
| | | |
|---|---|---|
| A61K 31/445 | (2006.01) |
| A61P 25/16 | (2006.01) |
| A61P 25/18 | (2006.01) |
| C07D 207/12 | (2006.01) |
| C07D 211/18 | (2006.01) |
| C07D 211/22 | (2006.01) |
| C07D 211/38 | (2006.01) |
| C07D 211/42 | (2006.01) |
| C07D 211/48 | (2006.01) |
| C07D 211/58 | (2006.01) |
| C07D 211/62 | (2006.01) |
| C07D 211/70 | (2006.01) |
| C07D 401/04 | (2006.01) |
| C07D 401/06 | (2006.01) |
| C07D 401/12 | (2006.01) |
| C07D 405/06 | (2006.01) |
| C07D 413/12 | (2006.01) |
| C07D 417/12 | (2006.01) |
| C07D 451/06 | (2006.01) |
| C07D 471/10 | (2006.01) |
| C07D 491/048 | (2006.01) |
| C07D 491/052 | (2006.01) |
| C07D 491/056 | (2006.01) |
| C07D 491/107 | (2006.01) |
| C07K 14/705 | (2006.01) |

(52) U.S. Cl.
CPC ............ *C07D 207/12* (2013.01); *A61P 25/16* (2018.01); *A61P 25/18* (2018.01); *C07D 211/18* (2013.01); *C07D 211/22* (2013.01); *C07D 211/38* (2013.01); *C07D 211/42* (2013.01); *C07D 211/48* (2013.01); *C07D 211/58* (2013.01); *C07D 211/62* (2013.01); *C07D 211/70* (2013.01); *C07D 401/04* (2013.01); *C07D 401/06* (2013.01); *C07D 401/12* (2013.01); *C07D 405/06* (2013.01); *C07D 413/12* (2013.01); *C07D 417/12* (2013.01); *C07D 451/06* (2013.01); *C07D 471/10* (2013.01); *C07D 491/048* (2013.01); *C07D 491/052* (2013.01); *C07D 491/056* (2013.01); *C07D 491/107* (2013.01); *C07K 14/70571* (2013.01)

(58) Field of Classification Search
CPC ...... C07D 211/48; A61K 31/445; A61P 25/18
USPC .......................................... 546/242; 514/315
See application file for complete search history.

(56) References Cited

U.S. PATENT DOCUMENTS

| | | |
|---|---|---|
| 3,041,344 A | 6/1962 | Janssen |
| 3,097,209 A | 7/1963 | Janssen |
| 3,161,644 A | 12/1964 | Janssen |
| 3,166,561 A | 1/1965 | Jan |
| 3,238,216 A | 3/1966 | Janssen |

(Continued)

FOREIGN PATENT DOCUMENTS

| | | |
|---|---|---|
| CA | 2608807 A1 | 4/2001 |
| DE | 22 41 027 A1 | 3/1973 |

(Continued)

OTHER PUBLICATIONS

Extended European Search Report for European Application No. 15871169.7 dated Jun. 21, 2018.

(Continued)

*Primary Examiner* — Charanjit Aulakh
(74) *Attorney, Agent, or Firm* — Wolf, Greenfield & Sacks, P.C.

(57) ABSTRACT

The present invention relates to novel dopamine D2 receptor ligands. The invention further relates to functionally-biased dopamine D2 receptor ligands and the use of these compounds for treating or preventing central nervous system and systemic disorders associated with dysregulation of dopaminergic activity.

37 Claims, 11 Drawing Sheets

(56) References Cited

U.S. PATENT DOCUMENTS

| | | | |
|---|---|---|---|
| 3,344,145 A | 9/1967 | Grogan et al. | |
| 3,679,666 A | 7/1972 | Malatestinic et al. | |
| 3,691,176 A * | 9/1972 | Hallas | C07D 211/58 |
| | | | 568/656 |
| 3,743,645 A * | 7/1973 | Helsley | C07D 211/22 |
| | | | 514/960 |
| 3,919,242 A | 11/1975 | Cavalla et al. | |
| 3,998,834 A | 12/1976 | Janssen et al. | |
| 4,104,396 A | 8/1978 | Huebner | |
| 4,179,569 A | 12/1979 | Janssen et al. | |
| 4,244,961 A | 1/1981 | Kluge et al. | |
| 4,255,432 A | 3/1981 | Kluge et al. | |
| 4,366,162 A | 12/1982 | Björk et al. | |
| 4,427,680 A | 1/1984 | Friebe et al. | |
| 4,948,797 A | 8/1990 | Manghisi et al. | |
| 5,182,292 A | 1/1993 | Stack | |
| 5,594,024 A | 1/1997 | Svensson et al. | |
| 5,741,789 A | 4/1998 | Hibschman et al. | |
| 5,808,064 A | 9/1998 | Chen et al. | |
| 5,889,026 A | 3/1999 | Alanine et al. | |
| 5,891,889 A | 4/1999 | Anthony et al. | |
| 6,124,323 A * | 9/2000 | Bigge | C07D 417/12 |
| | | | 546/237 |
| 6,133,291 A | 10/2000 | Wolin et al. | |
| 6,172,085 B1 | 1/2001 | Ohkawa et al. | |
| 6,284,774 B1 * | 9/2001 | Wright | C07D 413/12 |
| | | | 546/198 |
| 6,297,259 B1 | 10/2001 | Maynard et al. | |
| 6,303,593 B1 | 10/2001 | Bao et al. | |
| 6,359,138 B1 | 3/2002 | Alanine et al. | |
| 6,528,529 B1 | 3/2003 | Brann et al. | |
| 6,593,322 B1 | 7/2003 | Bhagwat et al. | |
| 8,618,133 B2 | 12/2013 | Li et al. | |
| 8,716,280 B2 | 5/2014 | Gaucher et al. | |
| 10,633,336 B2 | 4/2020 | Holson et al. | |
| 10,752,588 B2 | 8/2020 | Holson et al. | |
| 11,498,896 B2 | 11/2022 | Holson et al. | |
| 2004/0000250 A1 | 1/2004 | Stratum | |
| 2005/0054850 A1 | 3/2005 | Wu et al. | |
| 2006/0205719 A1 | 9/2006 | Hubschwerlen et al. | |
| 2007/0213359 A1 | 9/2007 | Burnstein et al. | |
| 2008/0004286 A1 | 1/2008 | Wang et al. | |
| 2008/0027039 A1 | 1/2008 | Arakawa et al. | |
| 2008/0194630 A1 | 8/2008 | Barchuk et al. | |
| 2008/0247964 A1 | 10/2008 | Xu et al. | |
| 2009/0029958 A1 | 1/2009 | Alcaraz et al. | |
| 2009/0325905 A1 | 12/2009 | Peterson et al. | |
| 2009/0325934 A1 | 12/2009 | Navratil et al. | |
| 2009/0325959 A1 | 12/2009 | Vittitow et al. | |
| 2009/0325960 A1 | 12/2009 | Fulcher et al. | |
| 2010/0168080 A1 | 7/2010 | Khamrai et al. | |
| 2010/0331294 A1 | 12/2010 | Black et al. | |
| 2011/0160176 A1 | 6/2011 | Drescher et al. | |
| 2013/0137679 A1 | 5/2013 | Jin et al. | |
| 2018/0155283 A1 | 6/2018 | Holson et al. | |
| 2019/0345105 A9 | 11/2019 | Holson et al. | |
| 2021/0147355 A1 | 5/2021 | Holson et al. | |

FOREIGN PATENT DOCUMENTS

| | | |
|---|---|---|
| DE | 26 10 228 A1 | 9/1976 |
| DE | 28 47 624 A1 | 5/1979 |
| DE | 196 13 329 A1 | 10/1997 |
| DE | 103 16 081 A1 | 10/2004 |
| DE | 10 2004 000 026 A1 | 2/2006 |
| EP | 0 100 046 A1 | 2/1984 |
| EP | 0 297 661 A1 | 1/1989 |
| EP | 0 325 755 A1 | 8/1989 |
| EP | 0 393 738 A1 | 10/1990 |
| EP | 0 396 282 A2 | 11/1990 |
| EP | 0 474 561 A1 | 3/1992 |
| EP | 0 824 098 A1 | 2/1998 |
| EP | 1 254 661 A1 | 11/2002 |
| EP | 1 829 869 A1 | 9/2007 |
| FR | 2 738 245 A1 | 3/1997 |
| JP | 47038970 B | 12/1972 |
| WO | WO 92/01687 A1 | 2/1992 |
| WO | WO 92/06958 A1 | 4/1992 |
| WO | WO 94/02462 A1 | 2/1994 |
| WO | WO 95/06037 A1 | 3/1995 |
| WO | WO 97/18201 A1 | 5/1997 |
| WO | WO 97/23202 A1 | 7/1997 |
| WO | WO 97/23216 A1 | 7/1997 |
| WO | WO 98/08842 A1 | 3/1998 |
| WO | WO 98/35959 A1 | 8/1998 |
| WO | WO 99/01423 A1 | 1/1999 |
| WO | WO 99/04794 A1 | 2/1999 |
| WO | WO 99/21539 A1 | 5/1999 |
| WO | WO 00/00197 A1 | 1/2000 |
| WO | WO 00/12074 A2 | 3/2000 |
| WO | WO 00/29406 A2 | 5/2000 |
| WO | WO 00/55137 A1 | 9/2000 |
| WO | WO 00/66551 A1 | 11/2000 |
| WO | WO 01/05763 A2 | 1/2001 |
| WO | WO 01/25200 A1 | 4/2001 |
| WO | WO 01/29000 A2 | 4/2001 |
| WO | WO 01/40184 A2 | 6/2001 |
| WO | WO 01/60796 A1 | 8/2001 |
| WO | WO 01/81309 A2 | 11/2001 |
| WO | WO 01/83472 A1 | 11/2001 |
| WO | WO 01/87839 A1 | 11/2001 |
| WO | WO 01/98266 A2 | 12/2001 |
| WO | WO 02/055496 A1 | 7/2002 |
| WO | WO 03/020029 A1 | 3/2003 |
| WO | WO 03/049736 A1 | 6/2003 |
| WO | WO 03/068760 A2 | 8/2003 |
| WO | WO 03/068772 A1 | 8/2003 |
| WO | WO 03/087086 A2 | 10/2003 |
| WO | WO 2004/005295 A1 | 1/2004 |
| WO | WO 2004/011438 A1 | 2/2004 |
| WO | WO 2004/078114 A2 | 9/2004 |
| WO | WO 2004/101518 A1 | 11/2004 |
| WO | WO 2005/012296 A1 | 2/2005 |
| WO | WO 2005/012297 A1 | 2/2005 |
| WO | WO 2005/023794 A2 | 3/2005 |
| WO | WO 2005/030722 A1 | 4/2005 |
| WO | WO 2005/033073 A2 | 4/2005 |
| WO | WO 2005/036961 A2 | 4/2005 |
| WO | WO 2005/061499 A1 | 7/2005 |
| WO | WO 2006/001752 A1 | 1/2006 |
| WO | WO 2006/003147 A1 | 1/2006 |
| WO | WO 2006/101245 A1 | 9/2006 |
| WO | WO 2006/137465 A1 | 12/2006 |
| WO | WO 2007/009462 A1 | 1/2007 |
| WO | WO 2007/011833 A2 | 1/2007 |
| WO | WO 2007/038669 A2 | 4/2007 |
| WO | WO 2007/042325 A1 | 4/2007 |
| WO | WO 2008/027932 A2 | 3/2008 |
| WO | WO 2008/033299 A2 | 3/2008 |
| WO | WO 2008/103126 A1 | 8/2008 |
| WO | WO 2008/144268 A1 | 11/2008 |
| WO | WO 2008/150848 A1 | 12/2008 |
| WO | WO 2009/032885 A2 | 3/2009 |
| WO | WO 2009/076212 A1 | 6/2009 |
| WO | WO 2009/094428 A2 | 7/2009 |
| WO | WO 2009/136350 A1 | 11/2009 |
| WO | WO 2009/137843 A2 | 11/2009 |
| WO | WO 2009/158587 A1 | 12/2009 |
| WO | WO 2010/027567 A2 | 3/2010 |
| WO | WO 2010/028862 A1 | 3/2010 |
| WO | WO 2010/058333 A1 | 5/2010 |
| WO | WO 2010/065782 A1 | 6/2010 |
| WO | WO 2011/125006 A2 | 10/2011 |
| WO | WO 2011/160084 A1 | 12/2011 |
| WO | WO 2012/012366 A1 | 1/2012 |
| WO | WO 2013/039802 A1 | 3/2013 |
| WO | WO 2013/149704 A1 | 10/2013 |
| WO | WO 2013/170072 A2 | 11/2013 |

(56) References Cited

FOREIGN PATENT DOCUMENTS

| WO | WO 2016/100823 A1 | 6/2016 |
|----|-------------------|--------|
| WO | WO 2016/100940 A1 | 6/2016 |

OTHER PUBLICATIONS

European Office Action for European Application No. 15871169.7 dated Apr. 30, 2020.
International Search Report and Written Opinion mailed Mar. 4, 2016 for Application No. PCT/US2015/066689.
International Preliminary Report on Patentability mailed Jun. 29, 2017 for Application No. PCT/US2015/066689.
Extended European Search Report for European Application No. 15871250.5 dated Jul. 6, 2018.
European Office Communication mailed Jul. 24, 2018 for Application No. EP 15871250.5.
Invitation to Pay Additional Fees mailed Feb. 4, 2016 for Application No. PCT/US2015/066928.
International Search Report and Written Opinion mailed Apr. 29, 2016 for Application No. PCT/US2015/066928.
[No Author Listed] Capulus Accession No. 2004:453186. Copyright 2019 ACS on STN.
[No Author Listed] Capulus Accession No. 2006:1356865.
[No Author Listed], RN-1528719-86-9: 4-Piperidinol, 1-[(2,3-dihydro-1,4-benzodioxin-2-yl)methyl]-4-methyl—In: Chemical catalog, Jan. 23, 2014, Aurora Fine Chemicals, XP055487301. 1 page.
[No Author Listed], RN-1514639-84-9: 4-Piperidinol, 1-[(2-(2-fluorophenoxy)ethyl]-4-methyl—In: Chemical catalog, Jan. 8, 2014, Aurora Fine Chemicals, XP055487303. 1 page.
[No Author Listed], RN-1506817-27-1:—4-Piperidinol, 4-methyl-1-(2-phenoxyethyl)—In: Chemical catalog, Dec. 30, 2013, Aurora Fine Chemicals, XP055487304. 1 page.
[No Author Listed], Chemical Abstracts STN Database Record for RN 136647-02-4, STN Entry Date Oct. 11, 1991.
[No Author Listed], Chemical Abstracts STN Database Record for RN 370086-17-2, STN Entry Date Nov. 15, 2001.
[No Author Listed], Chemical Abstracts STN Database Record for RN 1027427-24-2, STN Entry Date Jun. 11, 2008.
[No Author Listed], Chemical Abstracts STN Database Record for RN 1222869-57-9, STN Entry Date May 13, 2010.
[No Author Listed], Chemical Abstracts STN Database Record for RN 1348075-95-5, STN Entry Date Dec. 4, 2011.
[No Author Listed], Chemical Abstracts STN Database Record for RN 1381735-89-2, STN Entry Date Jul. 5, 2012.
[No Author Listed], Chemical Abstracts STN Database Record for RN 1381650-39-0, STN Entry Date Jul. 5, 2012.
[No Author Listed], Chemical Abstracts STN Database Record for RN 37603-24-0, STN Entry Date Nov. 16, 1984.
[No Author Listed], Chemical Abstracts STN Database Record for RN 1229823-16-8, STN Entry Date Jul. 9, 2010.
[No Author Listed], Pubchem, Substance record for SID 148597868, Create Date: Oct. 22, 2012. Retrieved on Jan. 29, 2016 from the Internet <https://pubchem.ncbi.nlm.nih.gov/substance/148597868/version/1#section=Top>.
[No Author Listed], Schizophrenia Working Group of the Psychiatric Genomics Consortium. Biological insights from 108 schizophrenia-associated genetic loci. Nature. Jul. 24, 2014;511(7510):421-7. doi: 10.1038/nature13595. Epub Jul. 22, 2014.
Allen et al., Discovery of β-arrestin-biased dopamine D2 ligands for probing signal transduction pathways essential for antipsychotic efficacy. Proc Natl Acad Sci U S A. Nov. 8, 2011;108(45):18488-93. doi: 10.1073/pnas.1104807108. Epub Oct. 24, 2011.
Bagley et al., New 1-(heterocyclylalkyl)-4-(propionanilido)-4-piperidinyl methyl ester and methylene methyl ether analgesics. J Med Chem. Feb. 1991;34(2):827-41.
Beaulieu et al., An Akt/beta-arrestin 2/PP2A signaling complex mediates dopaminergic neurotransmission and behavior. Cell. Jul. 29, 2005;122(2):261-73.

Burgess et al., The SAR of UK-78,282: A novel blocker of human T cell Kv1.3 potassium channels. Bioorganic & Medicinal Chemistry Letters (1997), 7(8), 1047-1052.
Catafau et al., Characterization of the SPECT 5-HT2A receptor ligand 123I-R91150 in healthy volunteers: part 2—ketanserin displacement. J Nucl Med. Jun. 2006;47(6):929-37.
Chen et al., Structure-functional selectivity relationship studies of β-arrestin-biased dopamine $D_2$ receptor agonists. J Med Chem. Aug. 23, 2012;55(16):7141-53. doi: 10.1021/jm300603y. Epub Aug. 13, 2012.
Choi et al., Novel (bisarylmethoxy)butylpiperidine analogues as neurotransmitter transporter inhibitors with activity at dopamine receptor sites. Bioorg Med Chem. Dec. 2002;10(12):4091-102.
Conceição et al., Effects of microgram doses of haloperidol on open-field behavior in mice. Pharmacol Biochem Behav. Apr. 1996;53(4):833-8.
Davis et al., 3-substituted-1,2-benzisoxazoles: novel antipsychotic agents. Drug Des Discov. Feb. 1992;8(3):225-40.
Dutta et al., Structure-activity relationship studies of novel 4-[2-[bis(4-fluorophenyl)methoxy]ethyl]-1-(3-phenylpropyl)piperidine analogs: synthesis and biological evaluation at the dopamine and serotonin transporter sites. J Med Chem. Feb. 2, 1996;39(3):749-56.
Gastambide et al., The mGlu$_5$ positive allosteric modulator LSN2463359 differentially modulates motor, instrumental and cognitive effects of NMDA receptor antagonists in the rat. Neuropharmacology. Jan. 2013;64:240-7. doi: 10.1016/j.neuropharm.2012.07.039. Epub Aug. 1, 2012.
Gilligan et al., Novel piperidine sigma receptor ligands as potential antipsychotic drugs. J Med Chem. Nov. 13, 1992;35(23):4344-61.
Grogan et al., Spiranes. VII. Neuroleptics Derived From Azaspiranes. J Med Chem. Jan. 1, 1965;8:62-73.
Hamprecht et al., 5-HT2C antagonists based on fused heterotricyclic templates: design, synthesis and biological evaluation. Bioorg Med Chem Lett. Jan. 15, 2007;17(2):424-7. Epub Oct. 17, 2006.
Henegar et al., Process Development and Scale-up of a β-Secretase Inhibitor via a Stereospecific Jocic Reaction. Org. Process Res. Dev., 2013, 17 (7), pp. 985-990.
Hoffman et al., Catalepsy as a rodent model for detecting antipsychotic drugs with extrapyramidal side effect liability. Psychopharmacology (Berl). Jul. 1995;120(2):128-33.
Kane et al., Clozapine for the treatment-resistant schizophrenic. A double-blind comparison with chlorpromazine. Arch Gen Psychiatry. Sep. 1988;45(9):789-96.
Lee et al., Stereoselective synthesis of spiropiperidines as BACE-1 aspartyl protease inhibitors via late stage N-arylation of a 1,8-diazaspiro[4.5]dec-3-en-2-one pharmacophore. J Org Chem. Mar. 15, 2013;78(6):2661-9. doi: 10.1021/jo400016m. Epub Mar. 4, 2013.
Leucht et al., Comparative efficacy and tolerability of 15 antipsychotic drugs in schizophrenia: a multiple-treatments meta-analysis. Lancet. Sep. 14, 2013;382(9896):951-62. doi: 10.1016/S0140-6736(13)60733-3. Epub Jun. 27, 2013. Review. Erratum in: Lancet. Sep. 14, 2013;382(9896):940.
Liang et al., Synthesis of UK-78282. The State Key Lab. of Applied Organic Chemistry and Institute of Organic Chemistry, Lanzhou University, Lanzhou, Gansu Province, 318000, Peop. Rep. China. Zhongguo Yiyao Gongye Zazhi (2005), 36(4), 193-195. Abstract.
Lowes et al., Optimization of propafenone analogues as antimalarial leads. J Med Chem. Nov. 10, 2011;54(21):7477-85. doi: 10.1021/jm2005546. Epub Oct. 10, 2011.
Maillard et al., Composes cycloalcane-spiro heterocycliques [Heterocyclic cycloalkane-spiro compounds]. European Journal of Medicinal Chemistry—Chimica Therapeutica, Edifor, FR, vol. 6(4); Jan. 1, 1971. pp. 257-261. XP008152319, ISSN: 0009-4374.
Masri et al., Antagonism of dopamine D2 receptor/beta-arrestin 2 interaction is a common property of clinically effective antipsychotics. Proc Natl Acad Sci U S A. Sep. 9, 2008;105(36):13656-61. doi: 10.1073/pnas.0803522105. Epub Sep. 3, 2008.
McCalmont et al., Design, synthesis, and biological evaluation of novel T-Type calcium channel antagonists. Bioorg Med Chem Lett. Jul. 16, 2004;14(14):3691-5.

(56) References Cited

OTHER PUBLICATIONS

Natesan et al., Amisulpride the 'atypical' atypical antipsychotic—comparison to haloperidol, risperidone and clozapine. Schizophr Res. Oct. 2008;105(1-3):224-35. doi:10.1016/j.schres.2008.07.005. Epub Aug. 16, 2008.

Nguyen et al., Structure-activity relationship exploration of Kv1.3 blockers based on diphenoxylate. Bioorg Med Chem Lett. Dec. 1, 2012;22(23):7106-9. doi:10.1016/j.bmcl.2012.09.080. Epub Sep. 29, 2012.

Schaefer et al., Drug interactions on spontaneous locomotor activity in rats. Neuroleptics and amphetamine-induced hyperactivity. Neuropharmacology. Aug. 1984;23(8):909-14.

Sharma et al., Eccentric Connectivity Index: A Novel Highly Discriminating Topological Descriptor for Structure-Property and Structure-Activity Studies. J. Chem. Inf. Comput. Sci., 1997, 37 (2), pp. 273-282.

Shonberg et al., A structure-activity analysis of biased agonism at the dopamine D2 receptor. J Med Chem. Nov. 27, 2013;56(22):9199-221. doi: 10.1021/jm401318w. Epub Nov. 8, 2013.

Su et al., A dopamine D2 receptor-DISC1 protein complex may contribute to antipsychotic-like effects. Neuron. Dec. 17, 2014;84(6):1302-16. doi: 10.1016/j.neuron.2014.11.007. Epub Nov. 26, 2014.

Watanuki et al., Synthesis and pharmacological evaluation of 1-alkyl-N-[(1R)-1-(4-fluorophenyl)-2-methylpropyl]piperidine-4-carboxamide derivatives as novel antihypertensive agents. Chem Pharm Bull (Tokyo). 2011;59(11):1376-85.

Wise et al., Examination of a series of 8-[3-[bis(4-fluorophenyl)amino]propyl]-1-aryl-1,3,8-triazaspiro[4.5]decan-4-ones as potential antipsychotic agents. J Med Chem. Dec. 1985;28(12):1811-7.

Yang et al., Anesthetic activity of some 4-substituted fentanyl derivatives in mice. Nanjing General Hospital, Nanjing Command, Nanjing, 210002, Peop. Rep. China. 1998, 13(2), 80-82. Abstract.

Yang et al., Synthesis and analgesic activity of analogs of 4-methoxymethyl fentanyl. Yao Xue Xue Bao. 1991;26(7):493-8. Chinese. Abstract.

Zhou et al., 4-Hydroxy-1-[2-(4-hydroxyphenoxy)ethyl]-4-(4-methylbenzyl)piperidine: a novel, potent, and selective NR1/2B NMDA receptor antagonist. J Med Chem. Jul. 29, 1999;42(15):2993-3000.

* cited by examiner

Example 157

Example 90

Example 158

Example 125

DOPAMINE D2 RECEPTOR LIGANDS

RELATED APPLICATIONS

The present-application is a continuation of U.S. patent application Ser. No. 16/826,028, filed Mar. 20, 2020, which is a continuation of U.S. patent application Ser. No. 15/537,741, filed Jun. 19, 2017, which is a national stage filing under 35 U.S.C. § 371 of international PCT application, PCT/US2015/066928, filed Dec. 18, 2015, which claims priority under 35 U.S.C. § 119 (e) to U.S. provisional patent application, U.S. Ser. No. 62/094,670, filed Dec. 19, 2014, each of which is incorporated herein by reference.

FIELD OF THE INVENTION

The present invention relates to novel ligands of dopamine D2 receptors, in particular, functionally selective ligands of dopamine D2 receptors. The invention also relates to the use of these compounds in treating or preventing central nervous system disorders as well as systemic disorders associated with dopamine D2 receptors.

BACKGROUND OF THE INVENTION

G-protein-coupled receptors (GPCRs), also known as 7-transmembrane receptors, are the single largest class of drug targets, with more than 800 members in the human genome (Lefkowitz, Trends in Pharmacological Sciences (2004), 413). Dopamine receptors represent prototypic examples of GPCRs that mediate neurotransmission (Missale et al., Physiological Reviews (1998), 189). Dopamine is a monoamine neurotransmitter that exerts its action on neuronal circuitry via dopamine receptors. As dopaminergic innervations are most prominent in the brain, dopaminergic dysfunction can critically affect vital central nervous system (CNS) functions, ranging from voluntary movement, feeding, reward, affection, sleep, attention, working memory and learning (Carlsson, Science (2001), 1021, Beaulieu et al., Pharmacological Reviews (2011), 182). Apart from CNS functions, dopamine is also involved in important physiological roles such as the regulation of olfaction, cardiovascular functions, sympathetic regulation, hormonal regulation, retinal processes, immune system and renal function. Dysregulation of dopaminergic neurotransmission has been associated with multiple neurological and psychiatric conditions such as Parkinson's disease, Huntington's disease, attention deficit hyperactivity disorder (ADHD), mood disorders and schizophrenia (Carlsson, Science (2001), 1021), as well as various somatic disorders such as hypertension and kidney dysfunction (Missale et al., Physiological Reviews (1998), 189, Beaulieu et al., Pharmacological Reviews (2011), 182).

With the complex array of critical cellular functions mediated by dopamine receptors, and the multilevel interactions that are known to occur between dopamine and other extracellular messengers in the signaling pathways, there remains a need to better manage dopamine-related pathologic conditions by precise targeting of post-receptor intracellular signaling modalities, either directly or through ligand-biased signaling pharmacology.

As drug targets, GPCRs known to mediate dopamine functions can be broadly classified into D1 and D2 class receptors. D1 class receptors (D1R and D5R) are mostly coupled to Gαs and positively regulate the production of second messenger cAMP and the activity of protein kinase A (PKA) (Missale et al., Physiological Reviews (1998), 189). D2 class receptors (D2R, D3R and D4R) couple to Gαi/o, downregulating cAMP production and PKA activity (Missale et al., Physiological Reviews (1998), 189). Additionally, D2 class dopamine receptors also modulate intracellular $Ca^{2+}$ levels, resulting in changes in activity of $Ca^{2+}$ regulated signaling proteins such as protein phosphatase calcineurin (Nishi et al., J. Neurosci., 1997, 17, 8147).

D2 class dopamine (D2R) receptors are presently the best-established targets for antipsychotic drugs. Recent studies suggest that β-arrestin 2 deficiency in mice results in reduction of dopamine-dependent behaviours (Beaulieu et al., Cell (2005), 261). The connection between β-arrestin 2 and dopamine-associated behaviours suggests that β-arrestin 2 could be a positive mediator of dopaminergic synaptic transmission and a potential pharmacological target for dopamine-related psychiatric disorders (Beaulieu et al., Cell (2005), 261).

Currently, all clinically marketed antipsychotics modulate dopamine by targeting D2R either as antagonists/inverse agonists (first- and second-generation antipsychotics, for example, chlorpromazine, clozapine) or partial agonists (third-generation antipsychotics, with aripiprazole as the sole example of this ligand class in the clinic). Antagonism of dopamine D2 receptor/β-arrestin 2 interaction has been found to be a common property of clinically-effective antipsychotics (Masri et al., Proceedings of the National Academy of Sciences of the United States of America (2008), 13656).

Structure-functional selectivity relationship studies of β-arrestin-biased dopamine D2 receptor agonists, based on the aripiprazole scaffold, have been conducted (Chen et al., Journal of Medicinal Chemistry (2012), 7141, Roth et al., US 2013/0137679, Shonberg et al., Journal of Medicinal Chemistry (2013), 9199). Known antipsychotics, even those that share a common mechanistic pathway such as haloperidol, clozapine, and risperidone, show highly diverse effects on D2R/G protein signaling and are not selective across GPCR receptors. There remains a lack of clinical drug candidates that offer highly functionalized targeting of dopamine D2 receptors that improve the clinical efficacy of antipsychotics, while at the same time limiting the undesirable side effects associated with D2-dopaminergic activity.

Selectively antagonizing the β-arrestin pathway at the D2 receptor could be sufficient to produce an antipsychotic effect, while at the same time, reduce potential side effects that could arise from antagonizing the cAMP pathway. Modulation of the β-arrestin-2 dependent pathway could lead to modulation of AKT and GSK3P target genes (Beaulieu et al., Frontiers in molecular neuroscience (2011), 38). Development of compounds with cAMP biased agonist or antagonist or β-arrestin biased agonist or antagonist activity could offer a functionally selective means to modulate or treat dopamine-associated disorders, including Parkinson's disease, Huntington's disease, mood disorders, schizophrenia, attention deficit hyperactivity disorder (ADHD), restless legs syndrome (RLS), pituitary disorders such as pituitary adenoma or pituitary tumor (prolactinoma) or endocrine disorders, e.g., galactorrhea. Further, development of ligands that exhibit functional selectivity as agonists, antagonists, and partial agonists, as well as selectivity against other GPCRs, allows modulation of activity at the dopamine D2 receptors to be more finely-tuned to increase selectivity and hence clinical efficacy and safety in treatment. By increasing selectivity at dopamine D2 receptors while minimising undesirable side-effects, drugs in this category would also offer greater success potential with patient acceptance and compliance.

SUMMARY OF THE INVENTION

The present invention relates to novel compounds that modulate dopamine D2 receptors. In particular, compounds of the present invention show functional selectivity at the dopamine D2 receptors and exhibit selectivity downstream of the D2 receptors, on the β-arrestin pathway and/or on the cAMP pathway. Compounds of the present invention exhibit different activity profiles either as agonist, antagonist, inverse agonist, or partial agonist. As these compounds are functionally selective downstream of the D2 receptors, they offer more selectivity and functionality in treatment of diseases or disorders in which dopamine plays a role, such as central nervous system disorders associated with D2 receptors, while minimizing potential associated side effects. Use of β-arrestin biased D2 receptor antagonists which selectively antagonize the β-arrestin pathway may offer a means to treat psychotic disorders while also minimizing potential undesirable side-effects associated with D2 receptor activity. Similarly, biased D2 receptor agonists which selectively activate either the β-arrestin pathway or the cAMP pathway may also be advantageous in treatment of disorders associated with dopamine receptors, such as Parkinson's disease, ADHD and restless leg syndrome or an endocrine disorder, e.g., galactorrhea, with fewer side-effects.

The present invention provides a compound having Formula I:

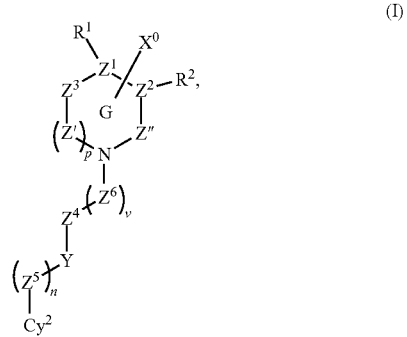

or a stereoisomer, racemate, tautomer, polymorph, hydrate, or solvate thereof, or a pharmaceutically acceptable salt thereof, wherein each of the variables is defined and illustrated in detail herein.

The present invention also provides a pharmaceutical composition comprising a compound of the invention or a pharmaceutically acceptable salt, stereoisomer, racemate, tautomer, polymorph, hydrate, or solvate thereof, and one or more pharmaceutically acceptable excipients or carriers.

The present invention also provides a method of modulating D2 receptor activity by administering a selective β-arrestin antagonist or a pharmaceutically acceptable salt, stereoisomer, racemate, tautomer, polymorph, hydrate, or solvate thereof.

The present invention also provides a method of modulating D2 receptor activity by administering a compound which is a β-arrestin antagonist and a cAMP agonist, or a pharmaceutically acceptable salt, stereoisomer, racemate, tautomer, polymorph, hydrate, or solvate thereof.

The present invention also provides a method of modulating D2 receptor activity by administering a compound of the invention or a pharmaceutically acceptable salt, stereoisomer, racemate, tautomer, polymorph, hydrate, or solvate thereof.

The present invention also provides use of a compound of the invention or a pharmaceutically acceptable salt, stereoisomer, racemate, tautomer, polymorph, hydrate, or solvate thereof, as a β-arrestin biased D2 receptor agonist or antagonist. The present invention also provides use of a compound of the invention or a pharmaceutically acceptable salt, stereoisomer, racemate, tautomer, polymorph, hydrate, or solvate thereof, as a cAMP biased agonist or antagonist. The present invention also provides use of a compound of the invention or a pharmaceutically acceptable salt, stereoisomer, racemate, tautomer, polymorph, hydrate, or solvate thereof, as a β-arrestin biased antagonist and cAMP biased agonist.

The present invention also provides a method of treating or preventing a disease or disorder in which modulation of D2 receptors (e.g., β-arrestin or Gi/cAMP) plays a role by administering to a subject in need thereof, a therapeutically effective amount of a selective β-arrestin antagonist, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a compound which is a β-arrestin antagonist and a cAMP agonist, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a compound of the invention, or a pharmaceutically acceptable salt, stereoisomer, racemate, tautomer, polymorph, hydrate, or solvate thereof, in combination with a pharmaceutically acceptable excipient or carrier, such that the disease or disorder is treated or prevented.

The present invention also provides a method of treating or preventing a disease or disorder in which modulation of D2 receptors (e.g., β-arrestin or Gi/cAMP) plays a role by administering to a subject in need thereof, a therapeutically effective amount of a pharmaceutical composition of the invention, such that the disease or disorder is treated or prevented.

The present invention also provides use of a selective β-arrestin antagonist, or a pharmaceutically acceptable salt, stereoisomer, racemate, tautomer, polymorph, hydrate, or solvate thereof, for treating or preventing a disease or disorder in which modulation of D2 receptors (e.g., β-arrestin or Gi/cAMP) plays a role in a subject in need thereof.

The present invention also provides use of a compound which is a β-arrestin antagonist and a cAMP agonist, or a pharmaceutically acceptable salt, stereoisomer, racemate, tautomer, polymorph, hydrate, or solvate thereof, for treating or preventing a disease or disorder in which modulation of D2 receptors (e.g., β-arrestin or Gi/cAMP) plays a role in a subject in need thereof.

The present invention also provides use of a compound of the invention, or a pharmaceutically acceptable salt, stereoisomer, racemate, tautomer, polymorph, hydrate, or solvate thereof, or use of a pharmaceutical composition of the invention, for treating or preventing a disease or disorder in which modulation of D2 receptors (e.g., β-arrestin or Gi/cAMP) plays a role in a subject in need thereof.

The present invention also provides use of a selective β-arrestin antagonist, or a pharmaceutically acceptable salt, stereoisomer, racemate, tautomer, polymorph, hydrate, or solvate thereof, in the manufacture of a medicament for the treatment or prevention of a disease or disorder in which modulation of D2 receptors (e.g., β-arrestin or Gi/cAMP) plays a role in a subject in need thereof.

The present invention also provides use of a compound which is a β-arrestin antagonist and a cAMP agonist, or a pharmaceutically acceptable salt, stereoisomer, racemate, tautomer, polymorph, hydrate, or solvate thereof, in the manufacture of a medicament for the treatment or prevention of a disease or disorder in which modulation of D2 receptors (e.g., β-arrestin or Gi/cAMP) plays a role in a subject in need thereof.

The present invention also provides use of a compound of the invention, or a pharmaceutically acceptable salt, stereoisomer, racemate, tautomer, polymorph, hydrate, or solvate thereof, or use of a pharmaceutical composition of the invention, in the manufacture of a medicament for the treatment or prevention of a disease or disorder in which modulation of D2 receptors (e.g., β-arrestin or Gi/cAMP) plays a role in a subject in need thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the present invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

The following detailed description, given by way of example, but not intended to limit the invention solely to the specific embodiments described, may be understood in conjunction with the accompanying drawings, in which:

FIG. 7A shows that activation of D2R reduces GSK3-α/β (Ser 21/9) phosphorylation in HEK293T cells expressing both D2R and DISC1, and this effect can be blocked by 10 µM and 30 µM of Example 90, which is similar to the effect of D2R antagonist, haloperidol. FIGS. 7B and 7C show the densitometric analysis of the intensity of phosphorylated GSK3β (Ser9)/t GSK3β (FIG. 7B), and phosphorylated GSK3α (Ser21)/t GSK3α (FIG. 7C), respectively, *p<0.05, as compared to control group, ##p<0.01, ###p<0.001 as compared to quinpirole group, n=3, One-way ANOVA.

DETAILED DESCRIPTION OF THE INVENTION

Compounds of the Invention

Figure 1:
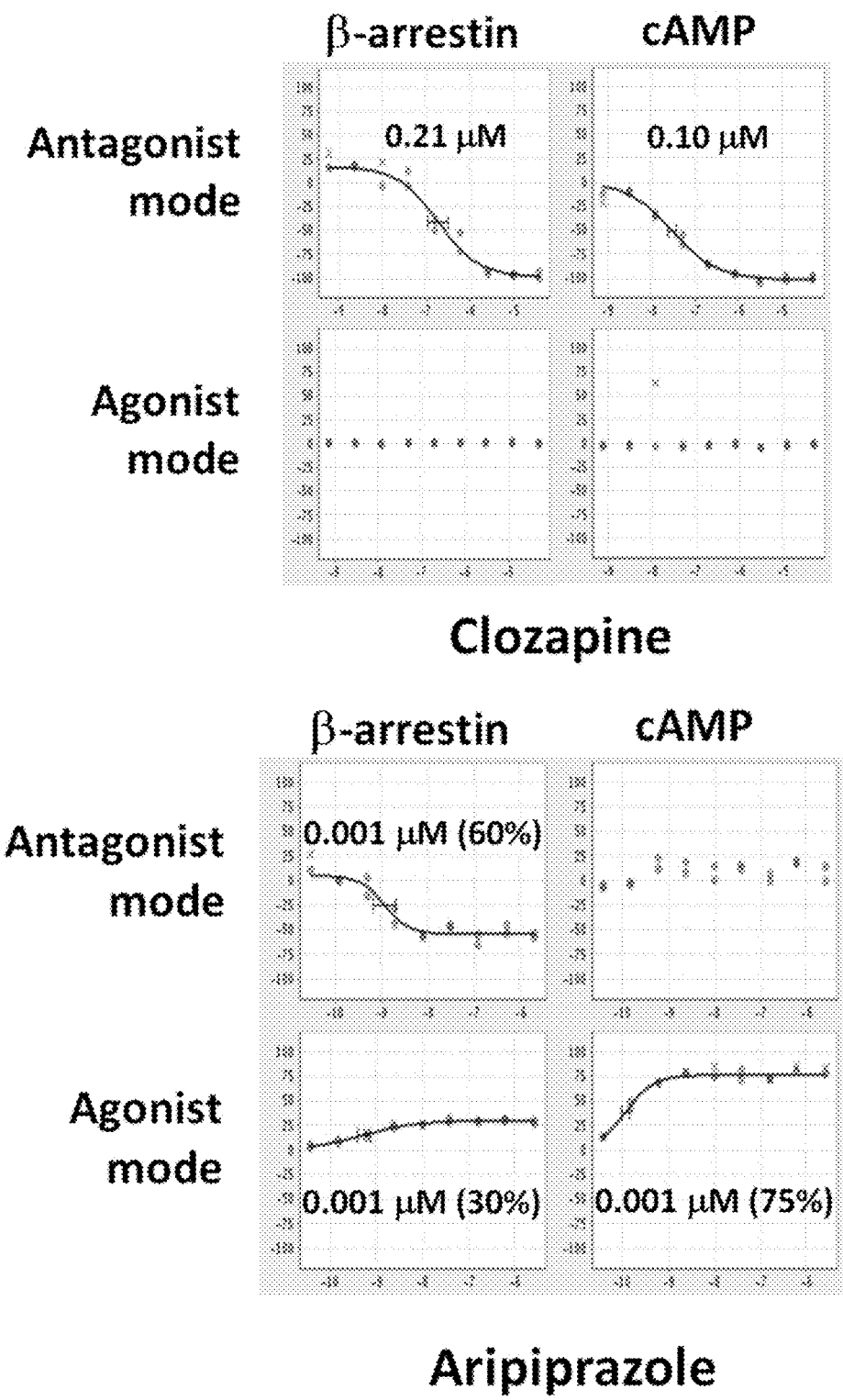
FIG. 1 shows representative curves for compounds 90, 157, 158, 125, and control compounds clozapine and aripiprazole across the β-arrestin and cAMP cell based assays in agonist and antagonist modes (see also Table 1).
Figure 1:
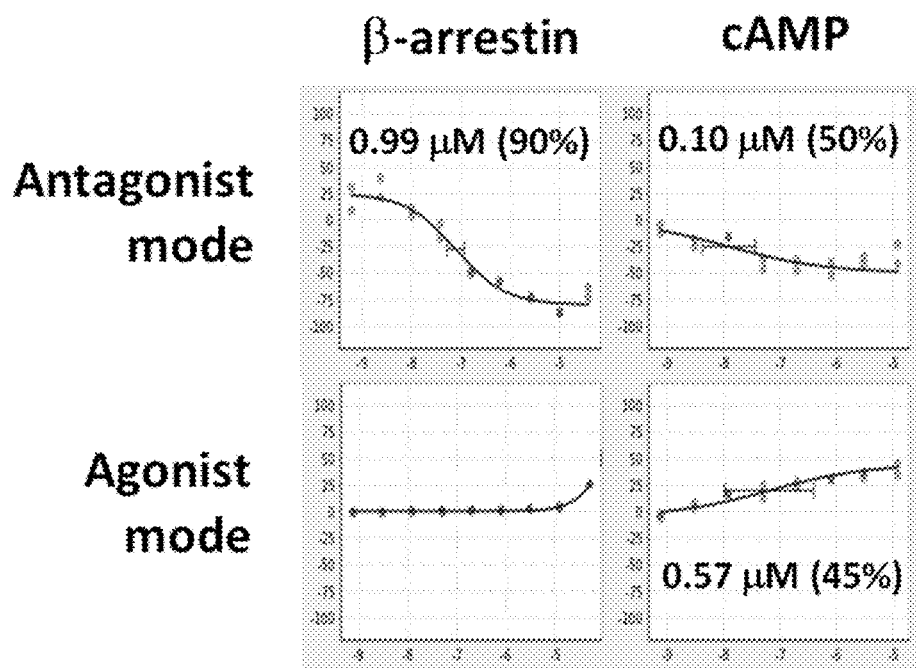
Figure 1:
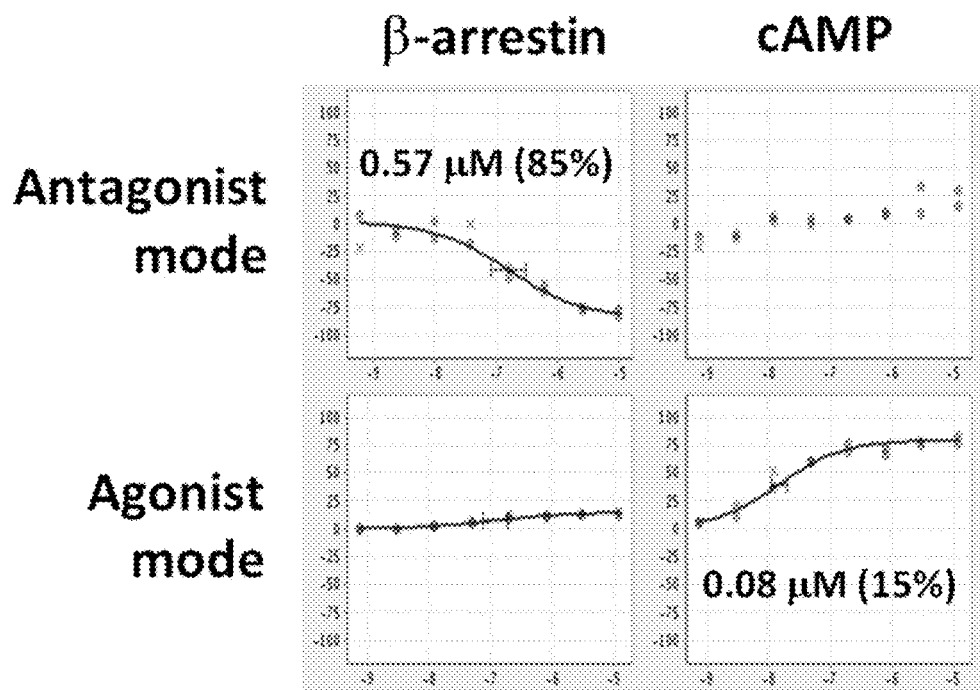
Figure 1:
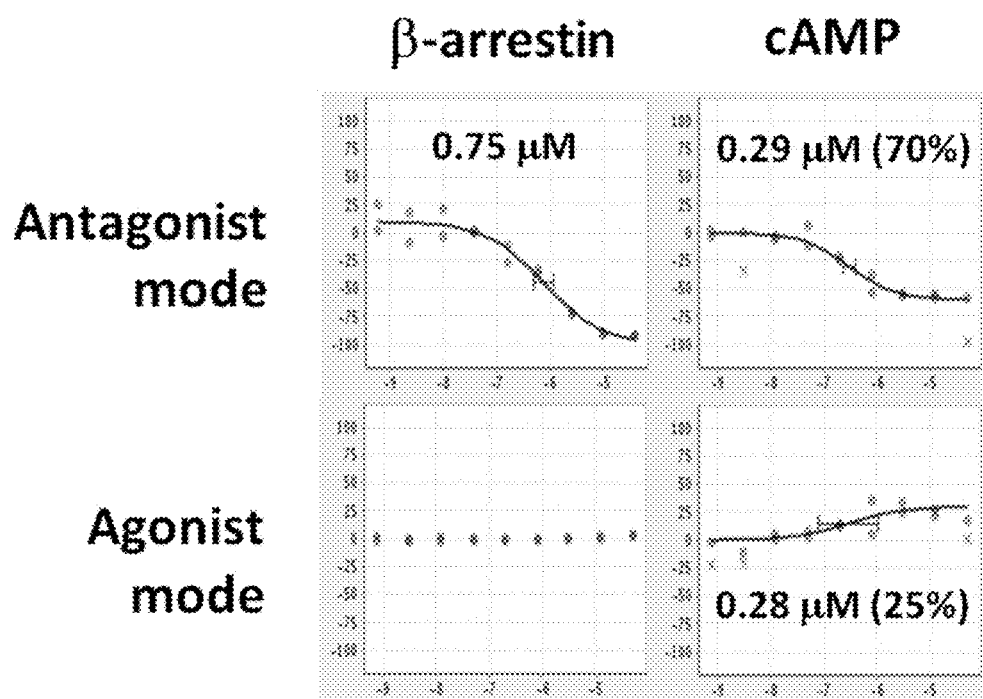
Figure 1:
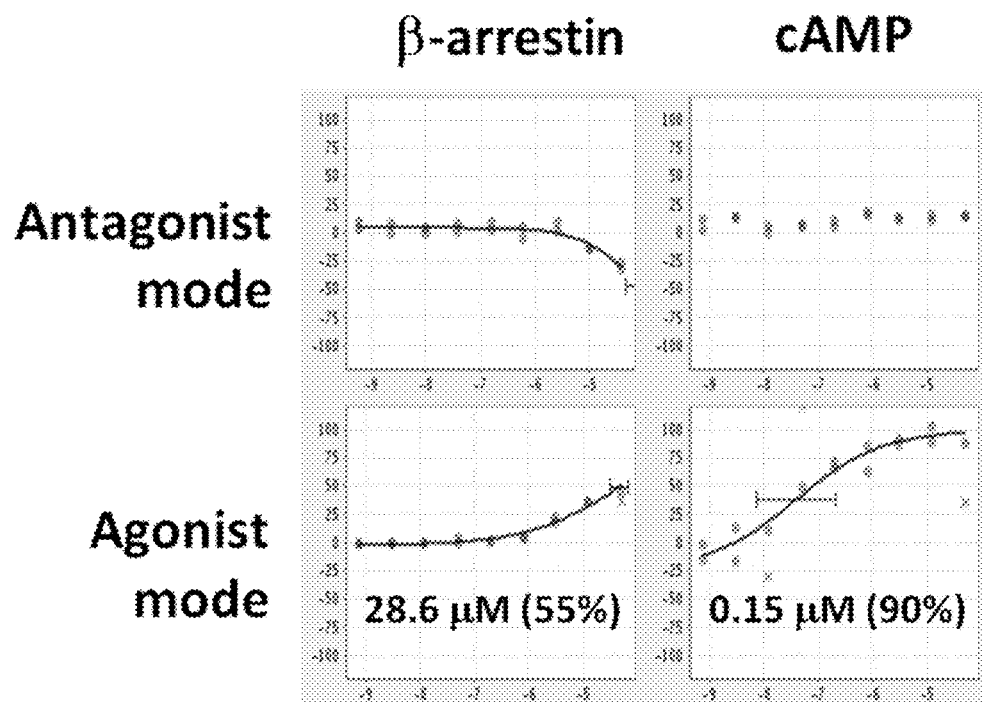
Figure 1:
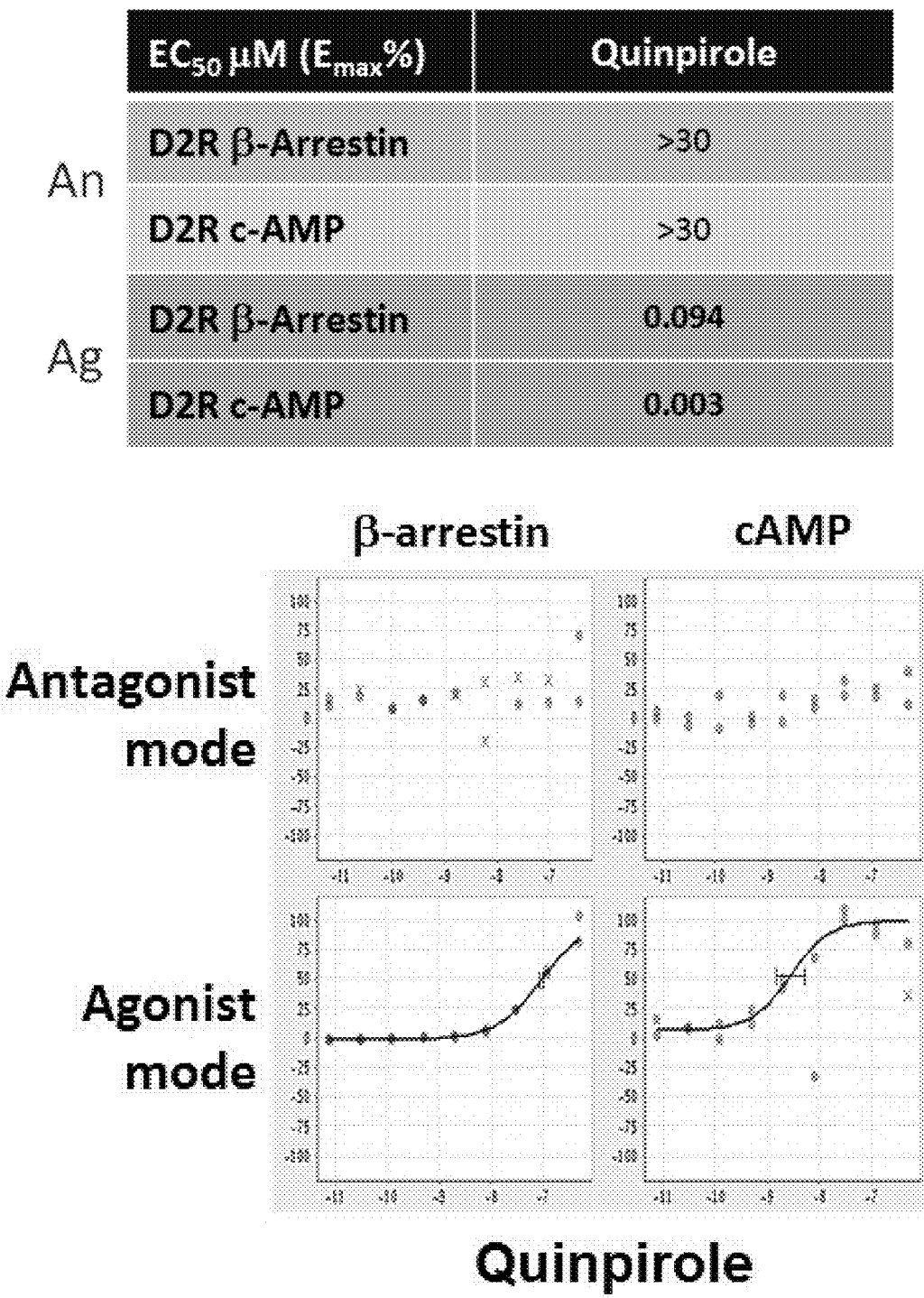

The present invention relates to novel ligands of dopamine D2 receptors. In particular, the invention relates to a compound having Formula I:

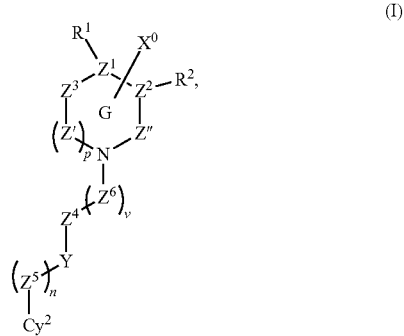

or a stereoisomer, racemate, tautomer, polymorph, hydrate, or solvate thereof, or a pharmaceutically acceptable salt thereof, wherein:

$X^0$ is $C_1$-$C_6$ alkyl, X—$Cy^1$, $C(O)NR^4R^{4'}$, $NR^4C(O)R^{4'}$, or $CR^3R^{3'}$—$NR^4R^{4'}$, and is bonded to $Z^1$ or $Z^2$;

X is $C(O)$, $CR^3R^{3'}$, $NR^4$, O, S, $S(O)$, or $S(O)_2$, and is bonded to $Z^1$ or $Z^2$, or $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure, provided that $R^1$ is not optionally substituted phenyl, 2-furyl or 3-furyl, or X—$Z^1$—$R^1$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure when n is 0 and v is 1 or 3, or X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

each $R^4$ is independently H, $C_1$-$C_6$ alkyl, or $C_1$-$C_6$ haloalkyl;

$R^{4'}$ is H, $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$Z^1$ is $CR^7$, or $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure, provided that $R^1$ is not optionally substituted phenyl, 2-furyl or 3-furyl, or X—$Z^1$—$R^1$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure when n is 0 and v is 1 or 3;

$R^7$ is H, halogen, $C_1$-$C_6$ alkyl, or $C_1$-$C_6$ haloalkyl, or when $X^0$ or X is bonded to $Z^1$, absent;

$R^1$ is H, halogen, OH, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, provided that when $X^0$ or X forms a bond with $Z^1$, $R^1$ is not H and provided that when X is bonded to $Z^1$ and is $NR^4$, O, S, S(O), or $S(O)_2$, $R^1$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl; or X—$Z^1$—$R^1$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure when n is 0 and v is 1 or 3, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Z^2$ is $CR^8$, or $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure, provided that $R^1$ is not optionally substituted phenyl, 2-furyl or 3-furyl, or X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure;

$R^8$ is H, halogen, $C_1$-$C_6$ alkyl, or $C_1$-$C_6$ haloalkyl, or when $X^0$ or X is bonded to $Z^2$, absent;

$R^2$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, provided that when $X^0$ or X forms a bond with $Z^2$, $R^2$ is not H and provided that when X is bonded to $Z^2$ and is $NR^4$, O, S, S(O), or $S(O)_2$, $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl; or X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy; or two $R^{18}$ together with the carbon atom to which they are bonded form a C(O);

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, or N—($C_6$-$C_{10}$ aryl) when X is $CR^3R^{3'}$ and when X—$Z^1$—$R^1$ form a 3- to 7-membered heterocyclyl ring, wherein the aryl, benzyl, and heteroaryl are independently optionally substituted with one or more $R^{16}$, provided that when p is 1, X is NH and is bonded to $Z^1$, and $R^1$ is $C(O)NH_2$, then $Cy^1$ is not unsubstituted phenyl, when p is 1, X is $CH_2$ and is bonded to $Z^1$, and $R^1$ is OH or halogen, then $Cy^1$ is not optionally substituted phenyl, benzoimidazolyl, benzoimidazolonyl, or dihydroquinoxaline-2,3-dione; and when p is 1, X is C(O) and is bonded to $Z^1$, Y is O, and $R^1$ is OH or methoxy, then $Cy^1$ is not optionally substituted phenyl;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, NH$_2$, N($C_1$-$C_6$ alkyl)$_2$, CN, $C_6$-$C_{10}$ aryl, or NO$_2$;

$Z^3$ is C(R$^9$)$_2$;

each $R^9$ is independently H, halogen, $C_1$-$C_6$ alkyl, or $C_1$-$C_6$ haloalkyl;

p is 0 or 1;

Z' is C(R$^{12}$)$_2$; or

Z' and $Z^3$ together with the atom(s) to which they are bonded form a 4- to 7-membered cycloalkyl or heterocyclyl ring which, together with ring G, forms a fused ring structure; or Z' and $Z^3$ together with the atom(s) to which they are bonded form a 4- to 7-membered aryl or heteroaryl ring which, together with ring G, forms a fused ring structure;

Z" is C(R$^{13}$)$_2$; or

Z" and $Z^2$ together with the atom(s) to which they are bonded form a 4- to 7-membered cycloalkyl or heterocyclyl ring which, together with ring G, forms a fused ring structure; or Z" and $Z^2$ together with the atom(s) to which they are bonded form a 4- to 7-membered aryl or heteroaryl ring which, together with ring G, forms a fused ring structure;

each $R^{12}$ is independently H, $C_1$-$C_3$ alkyl, $C_1$-$C_3$ haloalkyl, or halogen, or two $R^{12}$ together with the carbon atom to which they are bonded form a 3- to 6-membered cycloalkyl or heterocyclyl ring which, together with ring G, forms a spirocyclic ring structure;

each $R^{13}$ is independently H, $C_1$-$C_3$ alkyl, $C_1$-$C_3$ haloalkyl, or halogen, or two $R^{13}$ together with the carbon atom to which they are bonded form a 3- to 6-membered cycloalkyl or heterocyclyl ring which, together with ring G, forms a spirocyclic ring structure; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is C(R$^{14}$)$_2$;

v is 1, 2, or 3;

each $R^{14}$ is independently H or $C_1$-$C_3$ alkyl;

$Z^4$ is when n is 0 or 1, C(R$^{10}$)$_2$, or when n is 0, Y—$Z^4$—R$^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, NH$_2$, N($C_1$-$C_6$ alkyl)$_2$, CN, $C_6$-$C_{10}$ aryl, or NO$_2$; or two $R^{17}$ together with the carbon atoms to which they are bonded form a $C_6$-$C_{10}$ aryl or heteroaryl optionally substituted with one or more $R^{19}$, or when n is 0, Y—$Z^4$—R$^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is when n is 0 or 1, C(O), CR$^5$R$^{5'}$, NR$^6$, O, S, S(O), or S(O)$_2$, or when n is 0 or 1, Y—$Z^4$—$Z^6$ form a 4- to 7-membered heterocyclyl ring optionally substituted with one or more $R^{19}$, or when n is 0, Y—$Z^4$—R$^{17}$ form a 4- to 7-membered heterocyclyl ring optionally substituted with one or more $R^{19}$, or when n is 0 and Cy$^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl;

$Z^5$ is C(R$^{11}$)$_2$;

each $R^{11}$ is independently H, $C_1$-$C_6$ alkyl, $C_1$-$C_6$ haloalkyl, or halogen;

n is 0 or 1;

Cy$^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when n is 0 and Y is pyridinonyl, wherein the cycloalkyl, heterocyclyl, aryl, and heteroaryl are independently optionally substituted with one or more $R^{17}$; and provided that a compound of Formula (I) is not 1-(methylsulfonyl)-5-(3-(4-oxo-1-phenyl-1,3,8-triazaspiro[4.5]decan-8-yl)propyl)-1H-indole-3-carbonitrile; or 5-(3-(4-oxo-1-phenyl-1,3,8-triazaspiro[4.5]decan-8-yl)propyl)-1H-indole-3-carbonitrile.

In certain embodiments, the present invention relates to a compound of Formula (I), wherein:

$X^0$ is $C_1$-$C_6$ alkyl or X—Cy$^1$, and is bonded to $Z^1$ or $Z^2$;

X is C(O), CR$^3$R$^{3'}$, NR$^4$, O, S, S(O), or S(O)$_2$, and is bonded to $Z^1$ or $Z^2$, or $Z^2$—$Z^1$—X form a 4- to 7-membered heterocyclyl ring optionally substituted with one or more $R^{18}$, wherein the heterocyclyl ring, ring G, and Cy$^1$ form a three-ring fused ring structure, provided that $R^1$ is not optionally substituted phenyl, 2-furyl or 3-furyl, or X—$Z^1$—$R^1$ form a 3- to 7-membered cycloalkyl or heterocyclyl ring optionally substituted with one or more $R^{18}$, wherein the cycloalkyl or heterocyclyl ring is bonded to Cy$^1$, or the cycloalkyl or heterocyclyl ring and Cy$^1$ form a fused ring structure when n is 0 and v is 1 or 3, or X—$Z^2$—$R^2$ form a 3- to 7-membered cycloalkyl or heterocyclyl ring optionally substituted with one or more $R^{18}$, wherein the cycloalkyl or heterocyclyl ring is bonded to Cy$^1$, or the cycloalkyl or heterocyclyl ring and Cy$^1$ form a fused ring structure;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$Z^1$ is CR$^7$, or $Z^2$—$Z^1$—X form a 4- to 7-membered heterocyclyl ring optionally substituted with one or more $R^{18}$, wherein the heterocyclyl ring, ring G, and Cy$^1$ form a three-ring fused ring structure, provided that $R^1$ is not optionally substituted phenyl, 2-furyl or 3-furyl, or X—$Z^1$—$R^1$ form a 3- to 7-membered cycloalkyl or heterocyclyl ring optionally substituted with one or more $R^{18}$, wherein the cycloalkyl or heterocyclyl ring is bonded to Cy$^1$, or the cycloalkyl or heterocyclyl ring and Cy$^1$ form a fused ring structure when n is 0 and v is 1 or 3;

$R^7$ is H, halogen, $C_1$-$C_6$ alkyl, or $C_1$-$C_6$ haloalkyl, or when $X^0$ or X is bonded to $Z^1$, absent;

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms selected from N, O, and S, $C_3$-$C_6$ cycloalkyl, or heterocyclyl comprising one 4- to 6-membered ring and one to four heteroatoms selected from N, O, and S, provided that when $X^0$ or X forms a bond with $Z^1$, $R^1$ is not H and provided that when X is bonded to $Z^1$ and is $NR^4$, O, S, S(O), or $S(O)_2$, $R^1$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl; or X—$Z^1$—$R^1$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure when n is 0 and v is 1 or 3, wherein the aryl, benzyl, heteroaryl, cycloalkyl, and heterocyclyl are optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Z^2$ is $CR^8$, or $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure, provided that $R^1$ is not optionally substituted phenyl, 2-furyl or 3-furyl, or X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure;

$R^8$ is H, halogen, $C_1$-$C_6$ alkyl, or $C_1$-$C_6$ haloalkyl, or when $X^0$ or X is bonded to $Z^2$, absent;

$R^2$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms selected from N, O, and S, $C_3$-$C_6$ cycloalkyl, or heterocyclyl comprising one 4- to 6-membered ring and one to four heteroatoms selected from N, O, and S, provided that when $X^0$ or X forms a bond with $Z^2$, $R^2$ is not H and provided that when X is bonded to $Z^2$ and is $NR^4$, O, S, S(O), or $S(O)_2$, $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl; or X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$, or the cycloalkyl or heterocyclyl ring and $Cy^1$ form a fused ring structure, wherein the aryl, benzyl, heteroaryl, cycloalkyl, and heterocyclyl are optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy; or two $R^{18}$ together with the carbon atom to which they are bonded form a C(O);

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms selected from N, O, and S wherein each ring is aromatic or partially unsaturated, or N—($C_6$-$C_{10}$ aryl) when X is $CR^3R^{3'}$ and when X—$Z^1$—$R^1$ form a 3- to 7-membered heterocyclyl ring, wherein the aryl, benzyl, and heteroaryl are optionally substituted with one or more $R^{16}$, provided that when p is 1, X is NH and is bonded to $Z^1$, and $R^1$ is $C(O)NH_2$, then $Cy^1$ is not unsubstituted phenyl, when p is 1, X is $CH_2$ and is bonded to $Z^1$, and $R^1$ is OH or halogen, then $Cy^1$ is not optionally substituted phenyl, benzoimidazolyl, benzoimidazolonyl, or dihydroquinoxaline-2,3-dione; and when p is 1, X is C(O) and is bonded to $Z^1$, Y is O, and $R^1$ is OH or methoxy, then $Cy^1$ is not optionally substituted phenyl;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

$Z^3$ is $C(R^9)_2$;

each $R^9$ is independently H, halogen, $C_1$-$C_6$ alkyl, or $C_1$-$C_6$ haloalkyl;

p is 0 or 1;

Z' is $C(R^{12})_2$; or

Z' and $Z^3$ together with the atom(s) to which they are bonded form a 4- to 7-membered cycloalkyl or heterocyclyl ring which, together with ring G, forms a fused ring structure; or Z' and $Z^3$ together with the atom(s) to which they are bonded form a 4- to 7-membered aryl or heteroaryl ring which, together with ring G, forms a fused ring structure;

Z" is $C(R^{13})_2$; or

Z" and $Z^2$ together with the atom(s) to which they are bonded form a 4- to 7-membered cycloalkyl or heterocyclyl ring which, together with ring G, forms a fused ring structure; or Z" and $Z^2$ together with the atom(s) to which they are bonded form a 4- to 7-membered aryl or heteroaryl ring which, together with ring G, forms a fused ring structure;

each $R^{12}$ is independently H, $C_1$-$C_3$ alkyl, $C_1$-$C_3$ haloalkyl, or halogen, or two $R^{12}$ together with the carbon atom to which they are bonded form a 3- to 6-membered cycloalkyl or heterocyclyl ring which, together with ring G, forms a spirocyclic ring structure;

each $R^{13}$ is independently H, $C_1$-$C_3$ alkyl, $C_1$-$C_3$ haloalkyl, or halogen, or two $R^{13}$ together with the carbon atom to which they are bonded form a 3- to 6-membered cycloalkyl or heterocyclyl ring which, together with ring G, forms a spirocyclic ring structure; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is when n is 0 or 1, $C(R^{10})_2$, or when n is 0, Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, NH$_2$, N($C_1$-$C_6$ alkyl)$_2$, CN, $C_6$-$C_{10}$ aryl, or NO$_2$; or two $R^{17}$ together with the carbon atoms to which they are bonded form a $C_6$-$C_{10}$ aryl or heteroaryl optionally substituted with one or more $R^{19}$, or when n is 0, Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is
when n is 0 or 1, C(O), CR$^5$R$^{5'}$, NR$^6$, O, S, S(O), or S(O)$_2$, or when n is 0 or 1, Y—$Z^4$—$Z^6$ form a 4- to 7-membered heterocyclyl ring optionally substituted with one or more $R^{19}$, or when n is 0, Y—$Z^4$—$R^{17}$ form a 4 to 7-membered heterocyclyl ring optionally substituted with one or more $R^{19}$, or when n is 0 and Cy$^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl;

$Z^5$ is C(R$^{11}$)$_2$;

each $R^{11}$ is independently H, $C_1$-$C_6$ alkyl, $C_1$-$C_6$ haloalkyl, or halogen;

n is 0 or 1;

Cy$^2$ is $C_3$-$C_8$ cycloalkyl, heterocyclyl comprising one 4- to 7-membered ring and one to four heteroatoms selected from N, O, and S, $C_6$-$C_{10}$ aryl, or heteroaryl comprising one or two 5- or 6-membered rings and one to four heteroatoms selected from N, O, and S, or absent when n is 0 and Y is pyridinonyl, wherein the cycloalkyl, heterocyclyl, aryl, and heteroaryl are optionally substituted with one or more $R^{17}$; and provided that a compound of Formula (I) is not 1-(methylsulfonyl)-5-(3-(4-oxo-1-phenyl-1,3,8-triazaspiro[4.5]decan-8-yl)propyl)-1H-indole-3-carbonitrile; or
5-(3-(4-oxo-1-phenyl-1,3,8-triazaspiro[4.5]decan-8-yl)propyl)-1H-indole-3-carbonitrile.

In one embodiment, the present invention relates to a compound of Formula (I) having Formula (II):

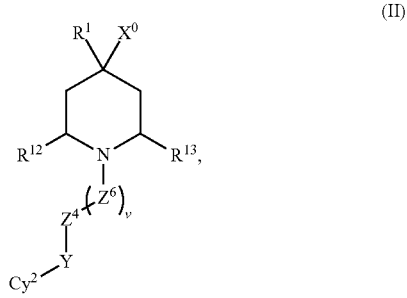

(II)

or a stereoisomer, racemate, tautomer, polymorph, hydrate, or solvate thereof, or a pharmaceutically acceptable salt thereof, wherein:

$X^0$ is $C_1$-$C_6$ alkyl, X—Cy$^1$, C(O)NR$^4$R$^{4'}$, NR$^4$C(O)R$^{4'}$, or CR$^3$R$^{3'}$—NR$^4$R$^{4'}$;

X is C(O), CR$^3$R$^{3'}$, NR$^4$, O, S, S(O), or S(O)$_2$;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, NR$^{20}$R$^{21}$, C(O)NR$^{20}$R$^{21}$, S(O)$_q$—$C_1$-$C_6$ alkyl, S(O)$_2$NR$^{20}$R$^{21}$, NR$^{20}$S(O)$_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, provided that when $X^0$ or X forms a bond with $Z^1$, $R^1$ is not H and provided that when X is NR$^4$, O, S, S(O), or S(O)$_2$, $R^1$ is not OH, $C_1$-$C_6$ alkoxy, NR$^{20}$R$^{21}$, $C_1$-$C_6$ haloalkoxy, S(O)$_q$—$C_1$-$C_6$ alkyl, S(O)$_2$NR$^{20}$R$^{21}$, or NR$^{20}$S(O)$_2$—$C_1$-$C_6$ alkyl, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

Cy$^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$, provided that when X is NH and $R^1$ is C(O)NH$_2$, then Cy$^1$ is not unsubstituted phenyl, when X is CH$_2$ and $R^1$ is OH or halogen, then Cy$^1$ is not optionally substituted phenyl, benzoimidazolyl, benzoimidazolonyl, or dihydroquinoxaline-2,3-dione; and when X is C(O), Y is O, and $R^1$ is OH or methoxy, then Cy$^1$ is not optionally substituted phenyl;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, NH$_2$, N($C_1$-$C_6$ alkyl)$_2$, CN, $C_6$-$C_{10}$ aryl, or NO$_2$;

$R^{12}$ and $R^{13}$ are each independently H, $C_1$-$C_3$ alkyl, $C_1$-$C_3$ haloalkyl, or halogen, or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is C(R$^{14}$)$_2$;

v is 1, 2, or 3;

each $R^{14}$ is independently H or $C_1$-$C_3$ alkyl;

$Z^4$ is C(R$^{10}$)$_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, NH$_2$, N($C_1$-$C_6$ alkyl)$_2$, CN, $C_6$-$C_{10}$ aryl, or NO$_2$; or two $R^{17}$ together with the carbon atoms to which they are bonded form a $C_6$-$C_{10}$ aryl or heteroaryl optionally substituted with one or more $R^{19}$, or Y—Z⁴—R¹⁷ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when $Cy^2$ is absent, pyridinonyl optionally substituted with one more $R^{17}$, or $R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In certain embodiments, in Formula II, $X^0$ is $C_1$-$C_6$ alkyl or X—$Cy^1$.

In certain embodiments, in Formula II, when X=—C(O)Et, then $R^1$ is not —$CH_2OMe$ or Ph.

In certain embodiments, in Formula II, when $Cy^1$ taken together with the piperidine ring forms a fused ring, then $R^1$ is not Ph, 2-furyl, or 3-furyl.

In certain embodiments, a compound of Formula (II) is of the formula:

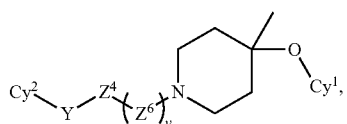

or a stereoisomer, racemate, tautomer, polymorph, hydrate, or solvate thereof, or a pharmaceutically acceptable salt thereof.

In certain embodiments, a compound of Formula (II) is of the formula:

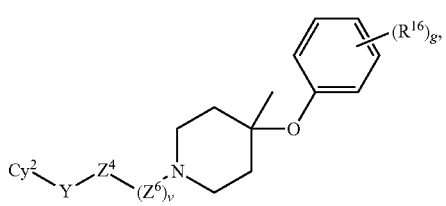

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (II) is of the formula:

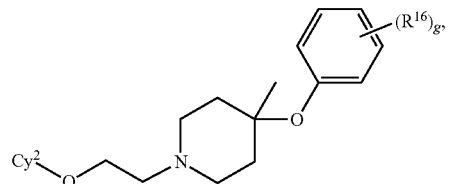

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (II) is of the formula:

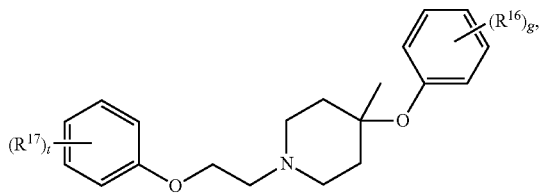

or a stereoisomer, racemate, tautomer, polymorph, hydrate, or solvate thereof, or a pharmaceutically acceptable salt thereof, wherein g is 0, 1, 2, 3, 4, or 5; and t is 0, 1, 2, 3, 4, or 5.

In certain embodiments, a compound of Formula (II) is of the formula:

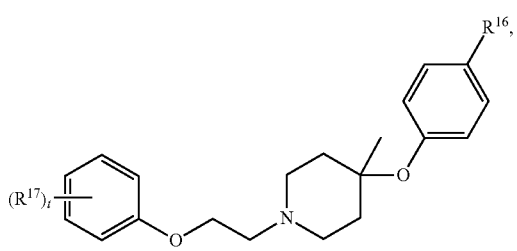

or a stereoisomer, racemate, tautomer, polymorph, hydrate, or solvate thereof, or a pharmaceutically acceptable salt thereof, wherein t is 0, 1, 2, 3, 4, or 5.

In certain embodiments, a compound of Formula (II) is of the formula:

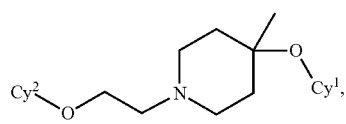

or a stereoisomer, racemate, tautomer, polymorph, hydrate, or solvate thereof, or a pharmaceutically acceptable salt thereof.

In certain embodiments, a compound of Formula (II) is of the formula:

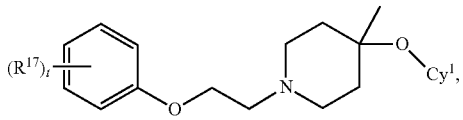

or a stereoisomer, racemate, tautomer, polymorph, hydrate, or solvate thereof, or a pharmaceutically acceptable salt thereof.

In certain embodiments, a compound of Formula (II) is of the formula:

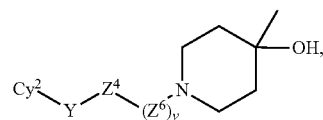

or a stereoisomer, racemate, tautomer, polymorph, hydrate, or solvate thereof, or a pharmaceutically acceptable salt thereof.

In certain embodiments, a compound of Formula (II) is of the formula:

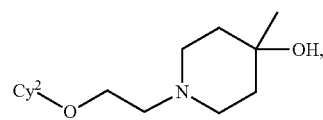

or a stereoisomer, racemate, tautomer, polymorph, hydrate, or solvate thereof, or a pharmaceutically acceptable salt thereof.

In certain embodiments, a compound of Formula (II) is of the formula:

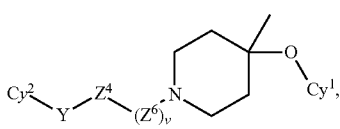

or a stereoisomer, racemate, tautomer, polymorph, hydrate, or solvate thereof, or a pharmaceutically acceptable salt thereof.

In certain embodiments, a compound of Formula (II) is of the formula:

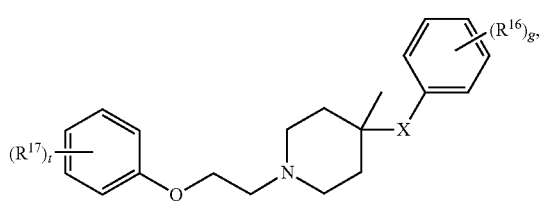

or a stereoisomer, racemate, tautomer, polymorph, hydrate, or solvate thereof, or a pharmaceutically acceptable salt thereof, wherein g is 0, 1, 2, 3, 4, or 5; and t is 0, 1, 2, 3, 4, or 5.

In another embodiment, the present invention relates to a compound of Formula (I) having Formula (III):

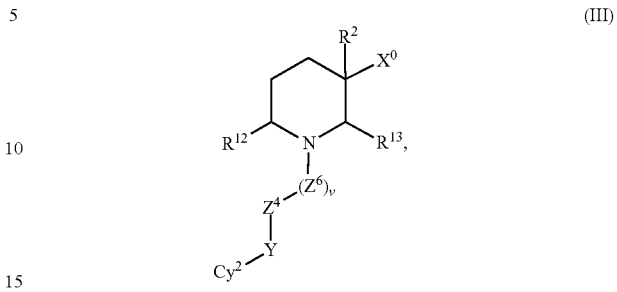

or a stereoisomer, racemate, tautomer, polymorph, hydrate, or solvate thereof, or a pharmaceutically acceptable salt thereof, wherein:

$X^0$ is $C_1$-$C_6$ alkyl or X—$Cy^1$;

X is C(O), $CR^3R^{3'}$, $NR^4$, O, S, S(O), or $S(O)_2$;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^2$ is halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, provided that when X is $NR^4$, O, S, S(O), or $S(O)_2$, $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl; wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or $Y-Z^4-R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, $C(O)-C_1$-$C_3$ alkyl, $S(O)_q-C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or $Y-Z^4-R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form $C(O)$;

Y is $C(O)$, $CR^5R^{5'}$, $NR^6$, O, S, $S(O)$, or $S(O)_2$, or $Y-Z^4-Z^6$ form a 4- to 7-membered heterocyclyl ring optionally substituted with one or more $R^{19}$, or $Y-Z^4-R^{17}$ form a 4- to 7-membered heterocyclyl ring optionally substituted with one or more $R^{19}$, or when $Cy^2$ is absent, pyridinonyl optionally substituted with one more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In certain embodiments, a compound of Formula (III) is of the formula:

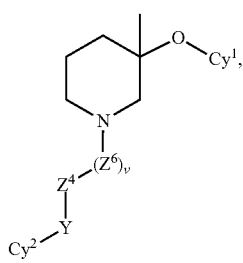

or a stereoisomer, racemate, tautomer, polymorph, hydrate, or solvate thereof, or a pharmaceutically acceptable salt thereof.

In certain embodiments, a compound of Formula (III) is of the formula:

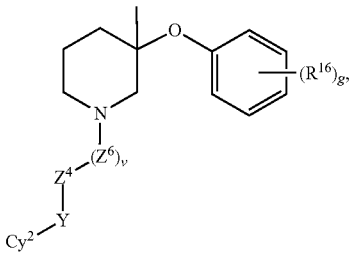

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (III) is of the formula:

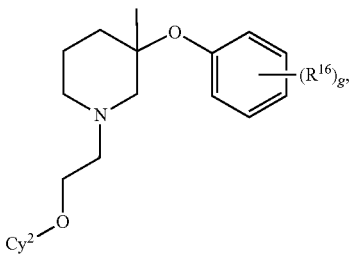

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (III) is of the formula:

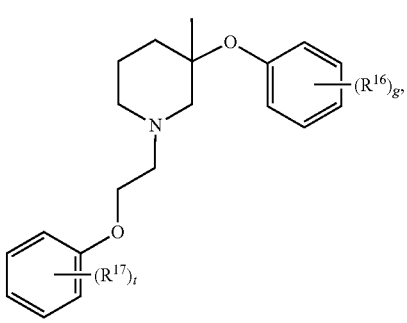

or a stereoisomer, racemate, tautomer, polymorph, hydrate, or solvate thereof, or a pharmaceutically acceptable salt thereof, wherein g is 0, 1, 2, 3, 4, or 5; and t is 0, 1, 2, 3, 4, or 5.

In another embodiment, the present invention relates to a compound of Formula (I) having Formula (IV):

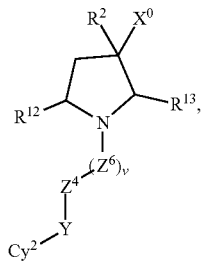

(IV)

or a stereoisomer, racemate, tautomer, polymorph, hydrate, or solvate thereof, or a pharmaceutically acceptable salt thereof, wherein:

$X^0$ is $C_1$-$C_6$ alkyl or X—$Cy^1$;

X is C(O), $CR^3R^{3'}$, $NR^4$, O, S, S(O), or $S(O)_2$;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^2$ is halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, provided that when X is $NR^4$, O, S, S(O), or $S(O)_2$, $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when $Cy^2$ is absent, pyridinonyl optionally substituted with one more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In certain embodiments, a compound of Formula (IV) is of the formula:

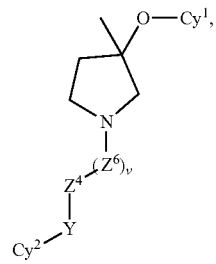

or a stereoisomer, racemate, tautomer, polymorph, hydrate, or solvate thereof, or a pharmaceutically acceptable salt thereof.

In certain embodiments, a compound of Formula (IV) is of the formula:

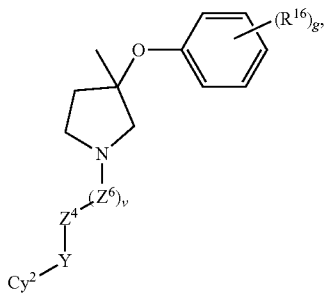

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (IV) is of the formula:

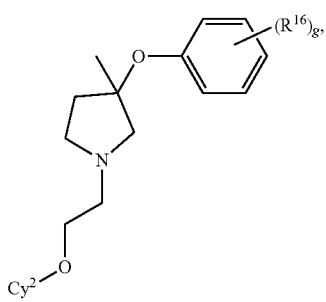

or a stereoisomer, racemate, tautomer, polymorph, hydrate, or solvate thereof, or a pharmaceutically acceptable salt thereof, wherein g is 0, 1, 2, 3, 4, or 5.

In certain embodiments, a compound of Formula (IV) is of the formula:

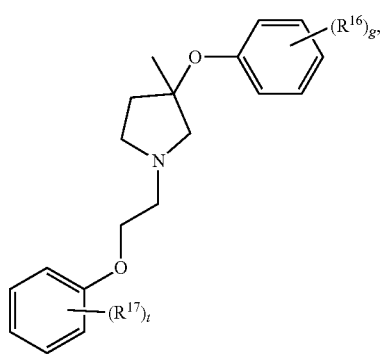

or a stereoisomer, racemate, tautomer, polymorph, hydrate, or solvate thereof, or a pharmaceutically acceptable salt thereof, wherein g is 0, 1, 2, 3, 4, or 5; and t is 0, 1, 2, 3, 4, or 5.

In certain embodiments, a compound of Formula (IV) is of the formula:

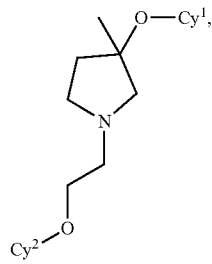

or a stereoisomer, racemate, tautomer, polymorph, hydrate, or solvate thereof, or a pharmaceutically acceptable salt thereof.

In certain embodiments, a compound of Formula (IV) is of the formula:

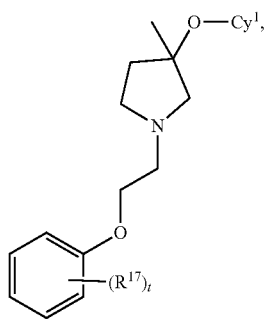

or a stereoisomer, racemate, tautomer, polymorph, hydrate, or solvate thereof, or a pharmaceutically acceptable salt thereof, wherein t is 0, 1, 2, 3, 4, or 5.

In another embodiment, the present invention relates to a compound of Formula (I) having Formula (V):

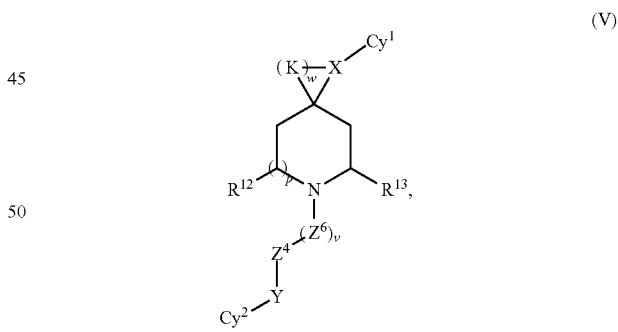

(V)

or a stereoisomer, racemate, tautomer, polymorph, hydrate, or solvate thereof, or a pharmaceutically acceptable salt thereof, wherein:

X is $CR^3$ or N;

$R^3$ is H, $C_1$-$C_6$ alkyl, OH, $C_1$-$C_6$ alkoxy, $C_1$-$C_6$ haloalkyl, or $C_1$-$C_6$ haloalkoxy;

each K is independently $NR^{22}$, C(O), O, or $CR^{22}R^{23}$;

each $R^{22}$ and $R^{23}$ is independently H, OH, $C_1$-$C_6$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, and $C_1$-$C_6$ haloalkoxy;

Cy¹ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, $NH_2$, N($C_1$-$C_6$ alkyl)$_2$, CN, $C_6$-$C_{10}$ aryl, or $NO_2$;

q is 0, 1, or 2;

w is 1, 2, 3, or 4;

p is 0 or 1;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is C($R^{14}$)$_2$;

v is 1, 2, or 3;

each $R^{14}$ is independently H or $C_1$-$C_3$ alkyl;

$Z^4$ is C($R^{10}$)$_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, $NH_2$, N($C_1$-$C_6$ alkyl)$_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), CR$^5$R$^{5'}$, NR$^6$, O, S, S(O), or S(O)$_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when Cy² is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl;

Cy² is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$; and provided that a compound of Formula (V) is not 1-(methylsulfonyl)-5-(3-(4-oxo-1-phenyl-1,3,8-triazaspiro[4.5]decan-8-yl)propyl)-1H-indole-3-carbonitrile; or 5-(3-(4-oxo-1-phenyl-1,3,8-triazaspiro[4.5]decan-8-yl)propyl)-1H-indole-3-carbonitrile.

In certain embodiments, in Formula (V), Cy² is not benzopyridyl.

In another embodiment, a compound of Formula (V) is of the formula:

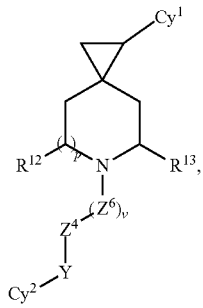

or a stereoisomer, racemate, tautomer, polymorph, hydrate, or solvate thereof, or a pharmaceutically acceptable salt thereof.

In another embodiment, a compound of Formula (V) is of the formula:

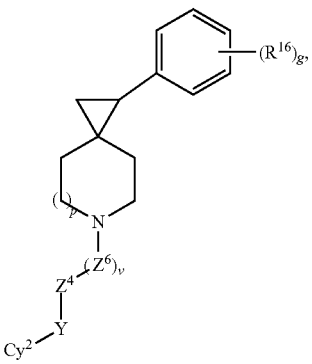

or a stereoisomer, racemate, tautomer, polymorph, hydrate, or solvate thereof, or a pharmaceutically acceptable salt thereof, wherein g is 0, 1, 2, 3, 4, or 5.

In another embodiment, a compound of Formula (V) is of the formula:

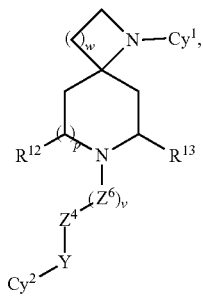

or a stereoisomer, racemate, tautomer, polymorph, hydrate, or solvate thereof, or a pharmaceutically acceptable salt thereof, wherein w is 1 or 2.

In another embodiment, a compound of Formula (V) is of the formula:

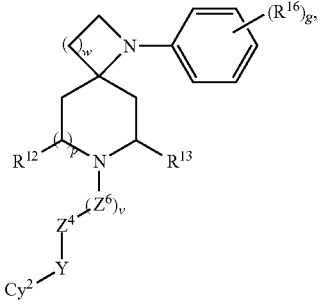

or a stereoisomer, racemate, tautomer, polymorph, hydrate, or solvate thereof, or a pharmaceutically acceptable salt thereof, wherein w is 1 or 2; and g is 0, 1, 2, 3, 4, or 5.

In another embodiment, the present invention relates to a compound of Formula (I) having Formula (VI):

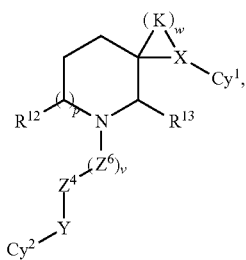

(VI)

or a stereoisomer, racemate, tautomer, polymorph, hydrate, or solvate thereof, or a pharmaceutically acceptable salt thereof, wherein:

X is $CR^3$ or N;

$R^3$ is H, $C_1$-$C_6$ alkyl, OH, $C_1$-$C_6$ alkoxy, $C_1$-$C_6$ haloalkyl, or $C_1$-$C_6$ haloalkoxy;

each K is independently $NR^{22}$, C(O), O, or $CR^{22}R^{23}$;

each $R_{22}$ and $R_{23}$ is independently H, OH, $C_1$-$C_6$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, and $C_1$-$C_6$ haloalkoxy;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

q is 0, 1, or 2;

w is 1, 2, 3, or 4;

p is 0 or 1;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is
C(O), $CR^5R^{5'}$, $NR^6$, O, S, S(O), or $S(O)_2$, or
Y—$Z^4$—$Z^6$ form a 4- to 7-membered heterocyclyl ring optionally substituted with one or more $R^{19}$, or
Y—$Z^4$—$R^{17}$ form a 4- to 7-membered heterocyclyl ring optionally substituted with one or more $R^{19}$, or
when $Cy^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In another embodiment, the present invention relates to a compound of Formula (I) having Formula (VII):

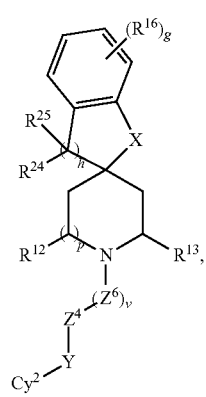

(VII)

or a stereoisomer, racemate, tautomer, polymorph, hydrate, or solvate thereof, or a pharmaceutically acceptable salt thereof, wherein:

X is $CR^{3R^{3'}}$, $NR^4$, or O;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, NH$_2$, N($C_1$-$C_6$ alkyl)$_2$, CN, $C_6$-$C_{10}$ aryl, or NO$_2$;

q is 0, 1, or 2;

h is 1, 2, or 3;

g is 0, 1, 2, 3, or 4;

p is 0 or 1;

each $R^{24}$ and $R^{25}$ are independently H, $C_1$-$C_3$ alkyl, OH, $C_1$-$C_6$ alkoxy, $C_1$-$C_6$ haloalkyl, or $C_1$-$C_6$ haloalkoxy, or $R^{24}$ and $R^{25}$ together with the carbon atom to which they are bonded form C(O);

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is C($R^{14}$)$_2$;

v is 1, 2, or 3;

each $R^{14}$ is independently H or $C_1$-$C_3$ alkyl;

$Z^4$ is C($R^{10}$)$_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, NH$_2$, N($C_1$-$C_6$ alkyl)$_2$, CN, $C_6$-$C_{10}$ aryl, or NO$_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), CR$^5$R$^{5'}$, NR$^6$, O, S, S(O), or S(O)$_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when Cy$^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and

Cy$^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In certain embodiments, a compound of Formula (VII) is of the formula:

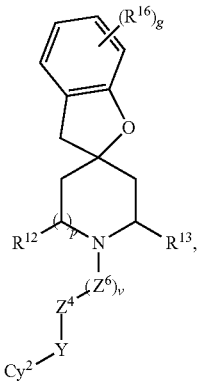

or a stereoisomer, racemate, tautomer, polymorph, hydrate, or solvate thereof, or a pharmaceutically acceptable salt thereof.

In another embodiment, the present invention relates to a compound of Formula (I) having Formula (VIII):

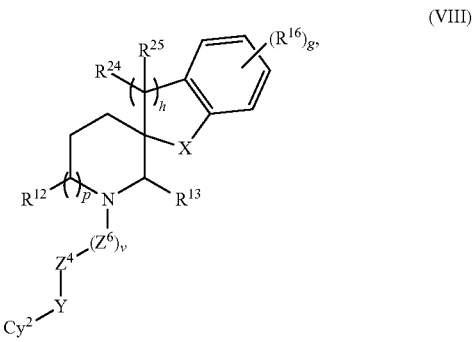

(VIII)

or a stereoisomer, racemate, tautomer, polymorph, hydrate, or solvate thereof, or a pharmaceutically acceptable salt thereof, wherein:

X is CR$^3$R$^{3'}$, NR$^4$, or O;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, NH$_2$, N($C_1$-$C_6$ alkyl)$_2$, CN, $C_6$-$C_{10}$ aryl, or NO$_2$;

q is 0, 1, or 2;

h is 1, 2, or 3;

g is 0, 1, 2, 3, or 4;

p is 0 or 1;

each $R^{24}$ and $R^{25}$ are independently H, $C_1$-$C_3$ alkyl, OH, $C_1$-$C_6$ alkoxy, $C_1$-$C_6$ haloalkyl, or $C_1$-$C_6$ haloalkoxy, or $R^{24}$ and $R^{25}$ together with the carbon atom to which they are bonded form C(O);

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when $Cy^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In another embodiment, the present invention relates to a compound of Formula (I) having Formula (IX):

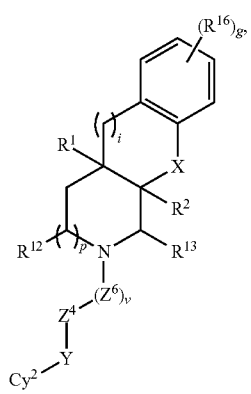

(IX)

or a stereoisomer, racemate, tautomer, polymorph, hydrate, or solvate thereof, or a pharmaceutically acceptable salt thereof, wherein:

X is $CR^3R^{3'}$, $NR^4$, or O;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^1$ is H, halogen, OH, $C_1$-$C_6$ alkyl, $C_1$-$C_6$ haloalkyl, $C_1$-$C_6$ alkoxy, or $C_1$-$C_6$ haloalkoxy;

$R^2$ is H, halogen, OH, $C_1$-$C_6$ alkyl, $C_1$-$C_6$ haloalkyl, $C_1$-$C_6$ alkoxy, or $C_1$-$C_6$ haloalkoxy, provided that when X is $NR^4$ or O, $R^2$ is not OH, $C_1$-$C_6$ alkoxy, or $C_1$-$C_6$ haloalkoxy;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

q is 0, 1, or 2;

i is 0, 1, or 2;

g is 0, 1, 2, 3, or 4;

p is 0 or 1;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when $Cy^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In another embodiment, the present invention relates to a compound of Formula (I) having Formula (X):

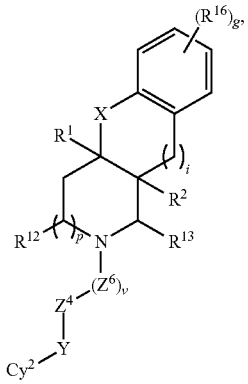

or a stereoisomer, racemate, tautomer, polymorph, hydrate, or solvate thereof, or a pharmaceutically acceptable salt thereof, wherein:

X is $CR^3R^{3'}$, $NR^4$, or O;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^1$ is H, halogen, OH, $C_1$-$C_6$ alkyl, $C_1$-$C_6$ haloalkyl, $C_1$-$C_6$ alkoxy, or $C_1$-$C_6$ haloalkoxy, provided that when X is $NR^4$ or O, $R^1$ is not OH, $C_1$-$C_6$ alkoxy, or $C_1$-$C_6$ haloalkoxy;

$R^2$ is H, halogen, OH, $C_1$-$C_6$ alkyl, $C_1$-$C_6$ haloalkyl, $C_1$-$C_6$ alkoxy, or $C_1$-$C_6$ haloalkoxy;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)— ($C_1$-$C_3$ alkyl), $S(O)_q$—($C_1$-$C_3$) alkyl, $NH_2$, $N(C_1$-$C_6$ alkyl$)_2$, CN, $C_6$-$C_{10}$ aryl, or $NO_2$;

q is 0, 1, or 2;

i is 0, 1, or 2;

g is 0, 1, 2, 3, or 4;

p is 0 or 1;

$R^{12}$ and $R^{13}$ are each independently H, $C_1$-$C_3$ alkyl, $C_1$-$C_3$ haloalkyl, or halogen; or $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)— $C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$, or when $Cy^2$ is absent, pyridinonyl optionally substituted with one or more $R^{17}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl; and $Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, or absent when Y is pyridinonyl, wherein the cycloalkyl, heterocyclyl, aryl, and heteroaryl are independently optionally substituted with one or more $R^{17}$.

In one embodiment, the present invention relates to a compound of the formula:

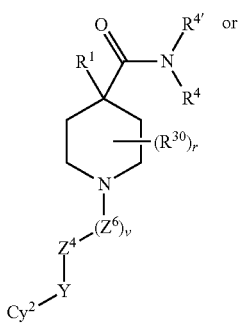

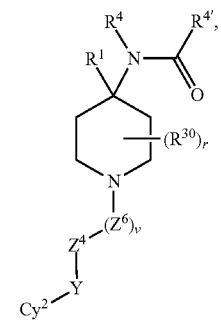

or a stereoisomer, racemate, tautomer, polymorph, hydrate, or solvate thereof, or a pharmaceutically acceptable salt thereof, wherein:

$R^4$ is H, $C_1$-$C_6$ alkyl, or $C_1$-$C_6$ haloalkyl;

$R^{4'}$ is H, $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each q is independently 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Z^6$ is $C(R^{14})_2$;

v is 1, 2, or 3;

each $R^{14}$ is independently H or $C_1$-$C_3$ alkyl;

$Z^4$ is $C(R^{10})_2$, or $Y$—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or $Y$—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or $Y$—$Z^4$—$Z^6$ form a 4- to 7-membered heterocyclyl ring optionally substituted with one or more $R^{19}$, or $Y$—$Z^4$—$R^{17}$ form a 4- to 7-membered heterocyclyl ring optionally substituted with one or more $R^{19}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

each $R^{30}$ is independently halogen, $C_{1-6}$ alkyl, or $C_{1-6}$ haloalkyl; and r is 0, 1, 2, 3, or 4.

In certain embodiments, a compound of Formula (XI) is of the formula:

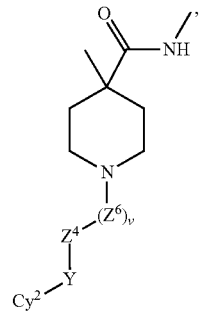

or a stereoisomer, racemate, tautomer, polymorph, hydrate, or solvate thereof, or a pharmaceutically acceptable salt thereof.

In certain embodiments, a compound of Formula (XI) is of the formula:

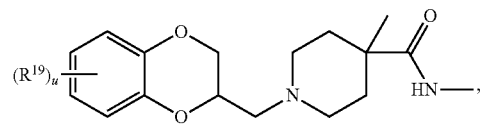

or a stereoisomer, racemate, tautomer, polymorph, hydrate, or solvate thereof, or a pharmaceutically acceptable salt thereof, wherein u is 0, 1, 2, 3, or 4.

In certain embodiments, a compound of Formula (XI) is of the formula:

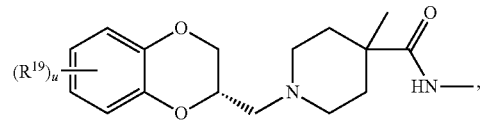

or a stereoisomer, racemate, tautomer, polymorph, hydrate, or solvate thereof, or a pharmaceutically acceptable salt thereof, wherein u is 0, 1, 2, 3, or 4.

In certain embodiments, a compound of Formula (XII) is of the formula:

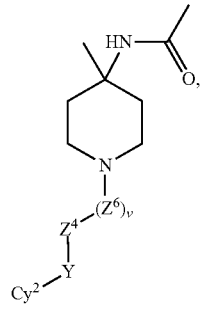

or a stereoisomer, racemate, tautomer, polymorph, hydrate, or solvate thereof, or a pharmaceutically acceptable salt thereof.

In certain embodiments, a compound of Formula (XII) is of the formula:

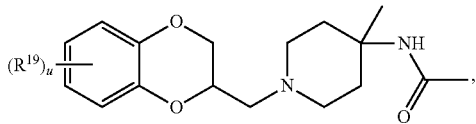

or a stereoisomer, racemate, tautomer, polymorph, hydrate, or solvate thereof, or a pharmaceutically acceptable salt thereof, wherein u is 0, 1, 2, 3, or 4.

In certain embodiments, a compound of Formula (XII) is of the formula:

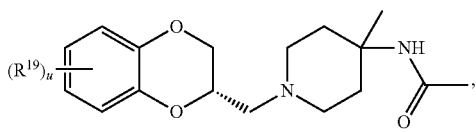

or a stereoisomer, racemate, tautomer, polymorph, hydrate, or solvate thereof, or a pharmaceutically acceptable salt thereof, wherein u is 0, 1, 2, 3, or 4.

In one embodiment, the present invention relates to a compound of the formula:

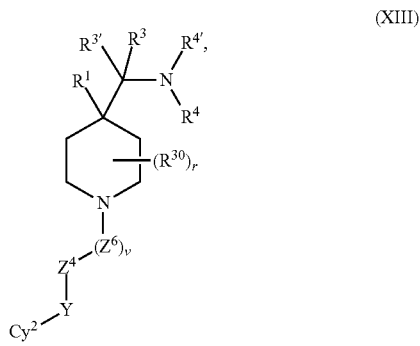

(XIII)

or a stereoisomer, racemate, tautomer, polymorph, hydrate, or solvate thereof, or a pharmaceutically acceptable salt thereof, wherein:

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^4$ is H, $C_1$-$C_6$ alkyl, or $C_1$-$C_6$ haloalkyl;

$R^{4'}$ is H, $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each q is independently 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Z^6$ is $C(R^{14})_2$;

v is 1, 2, or 3;

each $R^{14}$ is independently H or $C_1$-$C_3$ alkyl;

$Z^4$ is $C(R^{10})_2$, or Y—$Z^4$—$R^{17}$ form a 4- to 7-membered cycloalkyl or heterocyclyl ring optionally substituted with one or more $R^{19}$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or Y—$Z^4$—$R^{17}$ form a 4- to 7-membered heterocyclyl ring optionally substituted with one or more $R^{19}$;

each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is

C(O), $CR^5R^{5'}$, $NR^6$, O, S, S(O), or $S(O)_2$, or

Y—$Z^4$—$Z^6$ form a 4- to 7-membered heterocyclyl ring optionally substituted with one or more $R^{19}$, or Y—$Z^4$—$R^{17}$ form a 4- to 7-membered heterocyclyl ring optionally substituted with one or more $R^{19}$;

$R^5$ and $R^{5'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

$R^6$ is H, $C_1$-$C_6$ alkyl, or $C_1$-$C_6$ haloalkyl;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

each $R^{30}$ is independently halogen, $C_{1-6}$ alkyl, or $C_{1-6}$ haloalkyl; and r is 0, 1, 2, 3, or 4.

In certain embodiments, a compound of Formula (XIII) is of the formula:

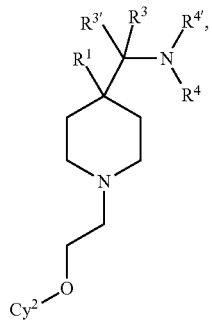

or a stereoisomer, racemate, tautomer, polymorph, hydrate, or solvate thereof, or a pharmaceutically acceptable salt thereof.

In certain embodiments, a compound of Formula (XIII) is of the formula:

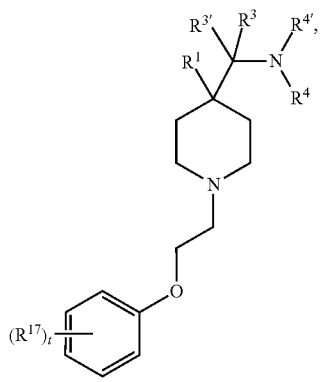

or a stereoisomer, racemate, tautomer, polymorph, hydrate, or solvate thereof, or a pharmaceutically acceptable salt thereof.

In certain embodiments, a compound of Formula (XIII) is of the formula:

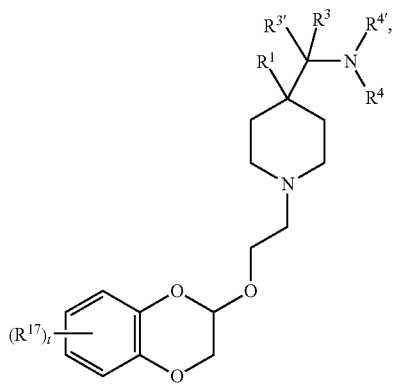

or a stereoisomer, racemate, tautomer, polymorph, hydrate, or solvate thereof, or a pharmaceutically acceptable salt thereof, wherein t is 0, 1, 2, 3, or 4.

In one embodiment, $X^0$ is $C_1$-$C_6$ alkyl or X—$Cy^1$. In another embodiment, $X^0$ is $C_1$-$C_3$ alkyl or X—$Cy^1$. In yet another embodiment, $X^0$ is $C_1$-$C_3$ alkyl. In another embodiment, $X^0$ is X—$Cy^1$. In one embodiment, $X^0$ is bonded to $Z^1$. In another embodiment, $X^0$ is bonded to $Z^2$. In certain embodiments, $X^0$ is $C_1$-$C_6$ alkyl, and $R^1$ is OH. In certain embodiments, $X^0$ is Me, and $R^1$ is OH.

In one embodiment, X is $CR^3R^{3'}$, $NR^4$, or O. In another embodiment, X is $CR^3R^{3'}$. In another embodiment, X is $NR^4$. In yet another embodiment, X is O. In another embodiment, X is $CR^3$. In another embodiment, X is C(O). In a further embodiment, X is O, N(CH$_3$), CH(OH), C(O), or CH$_2$ In one embodiment, Y is C(O), $CR^5R^{5'}$, $NR^6$, or O. In another embodiment, Y is $CR^5R^{5'}$. In another embodiment, Y is $NR^6$. In yet another embodiment, Y is O. In another embodiment, Y is $CR^5$. In another yet embodiment, Y is C(O). In a further embodiment, Y is O, C(O), NH, C(CH$_3$)OH, or CH$_2$. In yet another embodiment, Y—$Z^4$—$R^{17}$ form a 4- to 7-membered heterocyclyl ring optionally substituted with one or more $R^{19}$ when n is 0. In another embodiment, Y—$Z^4$—$Z^6$ form a 4- to 7-membered heterocyclyl ring optionally substituted with one or more $R^{19}$;

In one embodiment, $Z^1$ is C. In another embodiment, $Z^1$ is $CR_7$. In another embodiment, $Z^1$ is CH.

In one embodiment, $Z^2$ is C. In another embodiment, $Z^2$ is $CR_8$. In another embodiment, $Z^2$ is CH.

In one embodiment, Z' is $C(R^{12})_2$. In another embodiment, Z' and $Z^3$ together with the atom(s) to which they are bonded form a 4- to 7-membered cycloalkyl or heterocyclyl ring which, together with ring G, forms a fused ring structure. In yet another embodiment, Z' and $Z^3$ together with the atom(s) to which they are bonded form a 4- to 7-membered aryl or heteroaryl ring which, together with ring G, forms a fused ring structure.

In one embodiment, Z" is $C(R^{13})_2$. In another embodiment, Z" and $Z^2$ together with the atom(s) to which they are bonded form a 4- to 7-membered cycloalkyl or heterocyclyl ring which, together with ring G, forms a fused ring structure. In yet another embodiment, Z" and $Z^2$ together with the atom(s) to which they are bonded form a 4- to 7-membered aryl or heteroaryl ring which, together with ring G, forms a fused ring structure.

In one embodiment, $R^1$ is H, $C_1$-$C_6$ alkyl, halogen, OH, $C_1$-$C_6$ alkoxy, $C_1$-$C_6$ haloalkyl, $C_1$-$C_6$ haloalkoxy, $NR^{20}R^{21}$ or benzyl. In another embodiment, $R^1$ is H, $C_1$-$C_6$ alkyl, halogen, or OH. In yet another embodiment, $R^1$ is H, methyl, isopropyl, F, OH or benzyl. In another embodiment, $R^1$ is H, methyl, F, or OH. In certain embodiments, $R^1$ is H. In certain embodiments, $R^1$ is $C_1$-$C_6$ alkyl. In certain embodiments, $R^1$ is Me. In certain embodiments, $R^1$ is isopropyl. In certain embodiments, $R^1$ is $C_1$-$C_6$ hydroxyalkyl. In certain embodiments, $R^1$ is —CH$_2$OH. In certain embodiments, $R^1$ is $C_2$-$C_6$ alkenyl (e.g., vinyl). In certain embodiments, $R^1$ is $C_2$-$C_6$ alkynyl (e.g., —C≡CH). In certain embodiments, $R^1$ is halogen (e.g., F). In certain embodiments, $R^1$ is $C_1$-$C_6$ alkoxy (e.g., OMe). In another embodiment, when X is bonded to $Z^1$ and is $NR^4$, O, S, S(O), or S(O)$_2$, $R^1$ is not OH, $C_1$-$C_6$ alkoxy, $NR^{20}R^{21}$, $C_1$-$C_6$ haloalkoxy, S(O)$_q$—$C_1$-$C_6$ alkyl, S(O)$_2NR^{20}R^{21}$, or $NR^{20}S(O)_2$—$C_1$-$C_6$ alkyl.

In one embodiment, when $X^0$ or X forms a bond with $Z^1$, $R^1$ is not H. In another embodiment, when $X^0$ or X forms a bond with $Z^1$, $R^1$ is $C_1$-$C_6$ alkyl, halogen, OH, $C_1$-$C_6$ alkoxy, $C_1$-$C_6$ haloalkyl, $C_1$-$C_6$ haloalkoxy, $NR^{20}R^{21}$ or benzyl. In another embodiment, when $X^0$ or X forms a bond with $Z^1$, $R^1$ is OH or $C_1$-$C_6$ alkoxy. In certain embodiments, $R^1$ is as described herein, provided that $R^1$ is not OH. In certain embodiments, when $X^0$ is —CH$_2$—$Cy^1$ or —C(O)—$Cy^1$, $R^1$ is not OH. In certain embodiments, when $X^0$ is —CH$_2$-phenyl or —C(O)-phenyl, wherein the phenyl is optionally substituted with one or more $R^{16}$, then $R^1$ is not OH. In certain embodiments, $R^1$ is as described herein, provided that $R^1$ is not $C_1$-$C_6$ alkoxy (e.g., —OMe). In certain embodiments, when $X^0$ is C(O)-phenyl, wherein the phenyl is optionally substituted with one or more $R^{16}$, then $R^1$ is not $C_1$-$C_6$ alkoxy (e.g., —OMe). In certain embodiments, $R^1$ is as described herein, provided that $R^1$ is not $C(O)NR^{20}R^{21}$ (e.g., $C(O)NH_2$).

In one embodiment, $R^2$ is H, $C_1$-$C_6$ alkyl, halogen, OH, $C_1$-$C_6$ alkoxy, $C_1$-$C_6$ haloalkyl, $C_1$-$C_6$ haloalkoxy, $NR^{20}R^{21}$ or benzyl. In another embodiment, $R^2$ is H, $C_1$-$C_6$ alkyl, halogen, or OH. In yet another embodiment, $R^2$ is H, methyl, F, or OH. In another embodiment, when $X^0$ or X forms a bond with $Z^2$, $R^2$ is not H. In another embodiment, when $X^0$ or X forms a bond with $Z^2$, $R^2$ is $C_1$-$C_6$ alkyl, halogen, OH, $C_1$-$C_6$ alkoxy, $C_1$-$C_6$ haloalkyl, $C_1$-$C_6$ haloalkoxy, $NR^{20}R^{21}$ or benzyl. In yet another embodiment, when $X^0$ or X forms a bond with $Z^2$, $R^2$ is OH or $C_1$-$C_6$ alkoxy. In one embodiment, $R^2$ is H. In one embodiment, $R^2$ is $C_1$-$C_6$ alkyl. In one embodiment, $R^2$ is Me. In one embodiment, $R^2$ is halogen. In one embodiment, $R^2$ is F. In one embodiment, $R^2$ is OH.

In another embodiment, when X is bonded to $Z^2$ and is $NR^4$, O, S, S(O), or $S(O)_2$, $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl.

In one embodiment, $R^3$ is H or $(C_1$-$C_6)$ alkyl. In another embodiment, $R^3$ is H or $(C_1$-$C_3)$ alkyl. In yet another embodiment, $R^3$ is H, methyl, ethyl, propyl, or iso-propyl.

In one embodiment, $R^{3'}$ is H or $(C_1$-$C_6)$ alkyl. In another embodiment, $R^{3'}$ is H or $(C_1$-$C_3)$ alkyl. In yet another embodiment, $R^{3'}$ is H, methyl, ethyl, propyl, or iso-propyl.

In one embodiment, at least one instance of $R^4$ is H or $(C_1$-$C_6)$ alkyl. In another embodiment, at least one instance of $R^4$ is H or $(C_1$-$C_3)$ alkyl. In another embodiment, at least one instance of $R^4$ is H, methyl, ethyl, propyl, or iso-propyl. In certain embodiments, at least one instance of $R^4$ is H. In certain embodiments, each $R^4$ is H. In certain embodiments, at least one instance of $R^4$ is $(C_1$-$C_6)$ alkyl (e.g., Me). In certain embodiments, all instances of $R^4$ are the same.

In certain embodiments, $R^{4'}$ is H. In certain embodiments, $R^{4'}$ is $C_1$-$C_6$ alkyl (e.g., Me). In certain embodiments, $R^{4'}$ is $C_1$-$C_6$ haloalkyl (e.g., —$CF_3$). In certain embodiments, $R^{4'}$ is $C_3$-$C_8$ cycloalkyl optionally substituted with one or more $R^{17}$. In certain embodiments, $R^{4'}$ is cyclopropyl. In certain embodiments, $R^{4'}$ is heterocyclyl comprising one 4- to 7-membered ring and one to four heteroatoms independently selected from N, O, and S, wherein the heterocyclyl is optionally substituted with one or more $R^{17}$. In certain embodiments, $R^{4'}$ is $C_6$-$C_{10}$ aryl (e.g., phenyl) optionally substituted with one or more $R^{17}$. In certain embodiments, $R^{4'}$ is Ph. In certain embodiments, $R^{4'}$ is heteroaryl comprising one 5- or 6-membered ring and one to four heteroatoms independently selected from N, O, and S, wherein the heteroaryl is optionally substituted with one or more $R^{17}$. In certain embodiments, $R^{4'}$ is heteroaryl comprising two 5- or 6-membered rings and one to four heteroatoms independently selected from N, O, and S, wherein the heteroaryl is optionally substituted with one or more $R^{17}$.

In certain embodiments, $R^4$ and $R^{4'}$ on the same nitrogen atom together with the nitrogen atom form a monocyclic, 4- to 7-membered heterocyclyl ring (e.g., a pyrrolidinyl ring) optionally substituted with one or more $R^{18}$. In certain embodiments, $R^4$ and $R^{4'}$ on the same nitrogen atom together with the nitrogen atom form a pyrrolidinyl ring.

Each of $R^4$ and $R^{4'}$ is not benzyl or benzhydryl.

In one embodiment, $R^5$ is H, halogen, $(C_1$-$C_6)$ alkyl, or OH. In another embodiment, $R^5$ is H, $(C_1$-$C_3)$ alkyl, or OH. In yet another embodiment, $R^5$ is H, methyl, ethyl, propyl, iso-propyl, or OH.

In one embodiment, $R^{5'}$ is H, $(C_1$-$C_6)$ alkyl, or OH. In another embodiment, $R^{5'}$ is H, $(C_1$-$C_3)$ alkyl, or OH. In yet another embodiment, $R^{5'}$ is H, methyl, ethyl, propyl, iso-propyl, or OH.

In one embodiment, $R^6$ is H or $(C_1$-$C_6)$ alkyl. In another embodiment, $R^6$ is H or $(C_1$-$C_3)$. In yet another embodiment, $R^6$ is H, methyl, ethyl, propyl or iso-propyl.

In one embodiment, $R^7$ is H, halogen, $C_1$-$C_6$ alkyl, or $C_1$-$C_6$ haloalkyl. In another embodiment, $R^7$ is H, or $C_1$-$C_3$ alkyl. In yet another embodiment, $R^7$ is H, methyl, ethyl, propyl, or isopropyl. In another embodiment, $R^7$ is absent. In another embodiment, $R^7$ is absent when $X^0$ or X forms a bond with $Z^1$.

In one embodiment, $R^8$ is H, halogen, $C_1$-$C_6$ alkyl, or $C_1$-$C_6$ haloalkyl. In another embodiment, $R^8$ is H, or $C_1$-$C_3$ alkyl. In yet another embodiment, $R^8$ is H, methyl, ethyl, propyl, or isopropyl. In another embodiment, $R^8$ is absent. In another embodiment, $R^8$ is absent when $X^0$ or X forms a bond with $Z^2$.

In one embodiment, $R^9$ is H, halogen, $C_1$-$C_6$ alkyl, or $C_1$-$C_6$ haloalkyl. In another embodiment, $R^9$ is H or $C_1$-$C_6$ alkyl. In yet another embodiment, $R^9$ is H or $C_1$-$C_3$ alkyl. In further embodiment, $R^9$ is H, methyl, ethyl, propyl, or isopropyl. In a preferred embodiment, $R^9$ is H.

In one embodiment, $R^{10}$ is H or $C_1$-$C_6$ alkyl. In another embodiment, $R^{10}$ is H or $C_1$-$C_3$ alkyl. In yet another embodiment, $R^{10}$ is H, methyl, ethyl, propyl, or isopropyl. In a preferred embodiment, $R^{10}$ is H.

In one embodiment, $R^{11}$ is H or $C_1$-$C_6$ alkyl. In another embodiment, $R^{11}$ is H or $C_1$-$C_3$ alkyl. In yet another embodiment, $R^{11}$ is H, methyl, ethyl, propyl, or isopropyl. In a preferred embodiment, $R^{11}$ is H.

In one embodiment, $R^{12}$ is H or $C_1$-$C_3$ alkyl. In another embodiment, $R^{12}$ is H, methyl, ethyl, propyl, or isopropyl. In a preferred embodiment, $R^{12}$ is H or methyl. In another embodiment, two $R^{12}$ together with the carbon atom to which they are bonded form a 3- to 6-membered cycloalkyl or heterocyclyl ring which, together with ring G, forms a spirocyclic ring structure.

In one embodiment, $R^{13}$ is H or $C_1$-$C_3$ alkyl. In another embodiment, $R^{13}$ is H, methyl, ethyl, propyl, or isopropyl. In a preferred embodiment, $R^{13}$ is H or methyl. In another embodiment, two $R^{13}$ together with the carbon atom to which they are bonded form a 3- to 6-membered cycloalkyl or heterocyclyl spirocyclic ring which, together with ring G, forms a spirocyclic ring structure.

In another embodiment, $R^{12}$ and $R^{13}$, together with the carbon atoms to which they are bonded and the nitrogen atom in ring G, form a 5- to 7-membered heterocyclyl ring, wherein the heterocyclyl ring and ring G form a bridged ring structure.

In one embodiment, $R^{14}$ is H or $C_1$-$C_3$ alkyl. In another embodiment, $R^{14}$ is H, methyl, ethyl, propyl, or isopropyl. In a preferred embodiment, $R^{14}$ is H or methyl.

In one embodiment, each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$(C_1$-$C_3$ alkyl), $S(O)_q$—$(C_1$-$C_3$ alkyl), $NH_2$, $N(C_1$-$C_6$ alkyl$)_2$, CN, $C_6$-$C_{10}$ aryl, or $NO_2$. In another embodiment, each $R^{16}$ is independently halogen, $C_1$-$C_2$ alkyl, OH, $C_1$-$C_2$ alkoxy, $C_1$-$C_2$ haloalkyl, $C_1$-$C_2$ haloalkoxy, $C(O)(C_1$-$C_3)$ alkyl, $S(O)_q(C_1$-$C_2)$ alkyl, $NH_2$, $N(C_1$-$C_2$ alkyl$)_2$, CN, $(C_6$-$C_{10})$ aryl, or $NO_2$. In yet another embodiment, each $R^{16}$ is independently F, Cl, methyl, ethyl, $OCH_3$, $OCF_3$, $CF_3$, $NH_2$, $N(CH_3)_2$, $NO_2$, $S(O)_2CH_3$, $C(O)CH_3$, or CN.

In one embodiment, each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, $C(O)$—$C_1$-$C_3$ alkyl, $S(O)_q$—$C_1$-$C_3$ alkyl, $NH_2$, $N(C_1$-$C_6$ alkyl$)_2$, CN, $C_6$-$C_{10}$ aryl, or $NO_2$. In another embodiment, each $R^{17}$ is independently halogen, halogen, $C_1$-$C_2$ alkyl, OH, $C_1$-$C_2$ alkoxy, $C_1$-$C_2$ haloalkyl, $C_1$-$C_2$ haloalkoxy, $C(O)$—$C_1$-$C_3$ alkyl, $S(O)_q$—$C_1$-$C_3$ alkyl, $NH_2$, $N(C_1$-$C_2$ alkyl$)_2$, CN, $C_6$-$C_{10}$ aryl, or $NO_2$. In yet another embodiment, each $R^{17}$ is independently F, Cl, methyl, ethyl, $OCH_3$, $OCF_3$, $CF_3$, $NH_2$, $N(CH_3)_2$, $NO_2$, $S(O)_2CH_3$, $C(O)CH_3$, CN or phenyl. In another embodiment, $Y$—$Z^4$—$R^{17}$ form a 4- to 7-membered heterocyclyl ring optionally substituted with one or more $R^{19}$. In another embodiment, two $R^{17}$ together with the carbon atoms to which they are bonded form a $C_6$-$C_{10}$ aryl or heteroaryl optionally substituted with one or more $R^{19}$.

In one embodiment, each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy. In another embodiment, each $R^{18}$ is independently $C_1$-$C_3$ alkyl, $C_1$-$C_3$ alkoxy, $C_1$-$C_3$ haloalkyl, or $C_1$-$C_3$ haloalkoxy. In yet another embodiment, each $R^{18}$ is independently methyl, $OCH_3$, $OCH_2CH_3$, $OCF_3$, $CF_3$, $CHF_2$, or $CH_2CF_3$. In another embodiment, two $R^{18}$ together with the carbon atom to which they are bonded form a $C(O)$.

In one embodiment, each $R^{19}$ is independently $C_1$-$C_6$ alkyl, $C_1$-$C_6$ alkoxy, $C_1$-$C_6$ haloalkyl, or $C_1$-$C_6$ haloalkoxy. In another embodiment, each $R^{19}$ is independently $C_1$-$C_3$ alkyl, $C_1$-$C_3$ alkoxy, $C_1$-$C_3$ haloalkyl, or $C_1$-$C_3$ haloalkoxy. In yet another embodiment, each $R^{19}$ is independently methyl, $OCH_3$, $OCH_2CH_3$, $OCF_3$, $CF_3$, $CHF_2$, or $CH_2CF_3$.

In one embodiment, $R^{20}$ is H, $C_1$-$C_6$ alkyl, or unsubstituted $C_6$-$C_{10}$ aryl. In another embodiment, $R^{20}$ is H, $C_1$-$C_3$ alkyl, or unsubstituted $C_6$ aryl. In yet another embodiment, $R^{20}$ is H, methyl, ethyl, propyl, isopropyl, or phenyl.

In one embodiment, $R^{21}$ is H, $C_1$-$C_6$ alkyl, or unsubstituted $C_6$-$C_{10}$ aryl. In another embodiment, $R^{21}$ is H, $C_1$-$C_4$ alkyl, or unsubstituted $C_6$ aryl. In yet another embodiment, $R^{21}$ is H, methyl, ethyl, propyl, isopropyl, butyl, iso-butyl, tert-butyl, or phenyl.

In one embodiment, $R^{22}$ is H, OH, $C_1$-$C_6$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, or $C_1$-$C_6$ haloalkoxy. In another embodiment, $R^{22}$ is H, $C_1$-$C_3$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, or $C_1$-$C_6$ haloalkoxy. In yet another embodiment, $R^{22}$ is H, methyl, ethyl, propyl, isopropyl or phenyl optionally substituted with halogen.

In one embodiment, $R^{23}$ is H, OH, $C_1$-$C_6$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, or $C_1$-$C_6$ haloalkoxy. In another embodiment, $R^{23}$ is H, $C_1$-$C_3$ alkyl, or $C_6$-$C_{10}$ aryl, wherein the aryl is optionally substituted with one or more substituents independently selected from halogen, $C_1$-$C_6$ alkyl, $C_1$-$C_6$ alkoxy, $C_1$-$C_6$ haloalkyl, or $C_1$-$C_6$ haloalkoxy. In yet another embodiment, $R^{23}$ is H, OH, methyl, ethyl, propyl, isopropyl or phenyl optionally substituted with halogen.

In one embodiment, each $R^{24}$ is independently H, $C_1$-$C_3$ alkyl, OH, $C_1$-$C_6$ alkoxy, $C_1$-$C_6$ haloalkyl, or $C_1$-$C_6$ haloalkoxy. In another embodiment, each $R^{24}$ is independently H, $C_1$-$C_3$ alkyl, OH, $C_1$-$C_3$ alkoxy, $C_1$-$C_3$ haloalkyl, or $C_1$-$C_3$ haloalkoxy. In yet embodiment, each $R^{24}$ is independently H, $C_1$-$C_3$ alkyl, OH, or $C_1$-$C_3$ alkoxy.

In one embodiment, each $R^{25}$ is independently H, $C_1$-$C_3$ alkyl, OH, $C_1$-$C_6$ alkoxy, $C_1$-$C_6$ haloalkyl, or $C_1$-$C_6$ haloalkoxy. In another embodiment, each $R^{25}$ is independently H, $C_1$-$C_3$ alkyl, OH, $C_1$-$C_3$ alkoxy, $C_1$-$C_3$ haloalkyl, or $C_1$-$C_3$ haloalkoxy. In yet embodiment, each $R^{25}$ is independently H, $C_1$-$C_3$ alkyl, OH, or $C_1$-$C_3$ alkoxy.

In another embodiment, $R^{24}$ and $R^{25}$ together with the carbon atom to which they are bonded form $C(O)$.

In one embodiment, K is $NR^{22}$. In another embodiment, K is O. In yet another embodiment, K is $CR^{22}R^{23}$. In certain embodiments, K is as described herein, provided that no instance of K is $C(O)$.

In one embodiment, $Cy^1$ is $C_6$-$C_{10}$ aryl optionally substituted with one or more $R^{16}$. In another embodiment, $Cy^1$ is benzyl optionally substituted with one or more $R^{16}$. In yet another embodiment, $Cy^1$ is heteroaryl comprising one or two 5- or 6-membered rings and one to four heteroatoms independently selected from N, O, or S optionally substituted one or more $R^{16}$. In another embodiment, $Cy^1$ is N—($C_6$-$C_{10}$ aryl) when X is $CR^3R^{3'}$ and when X—$Z^1$—$R^1$ form a 3- to 7-membered heterocyclyl ring optionally substituted one or more $R^{16}$. In another embodiment, $Cy^1$ is phenyl, pyridinyl, pyrazinyl, or benzothiazole, wherein the phenyl, pyridinyl, pyrazinyl, and benzothiazole are independently optionally substituted with one or more $R^{16}$.

In one embodiment, when p is 1, X is NH and is bonded to $Z^1$, and $R^1$ is $C(O)NH_2$, $Cy^1$ is not unsubstituted phenyl. In another embodiment, when p is 1, X is $CH_2$ and is bonded to $Z^1$, and $R^1$ is OH or halogen, then $Cy^1$ is not phenyl, benzoimidazolyl, benzoimidazolonyl, or dihydroquinoxaline-2,3-dione. In another embodiment, when p is 1, X is $C(O)$ and is bonded to $Z^1$, Y is O, and $R^1$ is OH or methoxy, then $Cy^1$ is not optionally substituted phenyl.

In one embodiment, $Cy^2$ is $C_3$-$C_8$ cycloalkyl optionally substituted one or more $R^{17}$. In another embodiment, $Cy^2$ is heterocyclyl comprising one 4- to 7-membered ring and one to four heteroatoms independently selected from N, O, or S optionally substituted one or more $R^{17}$. In yet another embodiment, $Cy^2$ is $C_6$-$C_{10}$ aryl optionally substituted one or more $R^{17}$. In another embodiment, $Cy^2$ is heteroaryl comprising one or two 5- or 6-membered rings and one to four heteroatoms independently selected from N, O, or S optionally substituted one or more $R^{17}$. In another embodiment, $Cy^2$ is absent when n is 0 and Y is pyridinonyl.

In one embodiment, X—$Z^2$—$Z^1$ form a 4- to 7-membered heterocyclyl ring optionally substituted with one or more $R^{18}$, wherein the heterocyclyl ring, ring G, and $Cy^1$ form a three-ring fused ring structure.

In one embodiment, X—$Z^1$—$R^1$ form a 3- to 7-membered cycloalkyl or heterocyclyl ring optionally substituted with one or more $R^{18}$, wherein the cycloalkyl or heterocyclyl ring is bonded to $Cy^1$. In another embodiment, X—$Z^1$—$R^1$ form a 3- to 7-membered cycloalkyl or heterocyclyl ring optionally substituted with one or more $R^{18}$, wherein the cycloalkyl or heterocyclyl ring and $Cy^1$ form a fused ring structure when n is 0 and v is 0 or 1.

In one embodiment, X—$Z^2$—$R^2$ form a 3- to 7-membered cycloalkyl or heterocyclyl ring optionally substituted with one or more $R^{18}$, wherein the cycloalkyl or heterocyclyl ring is bonded to $Cy^1$. In another embodiment, X—$Z^2$—$R^2$ form a 3- to 7-membered cycloalkyl or heterocyclyl ring optionally substituted with one or more $R^{18}$, wherein the cycloalkyl or heterocyclyl ring and $Cy^1$ form a fused ring structure.

In one embodiment, $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure. In another embodiment, when $Z^2$—$Z^1$—X form a 4- to 7-membered heterocyclyl ring optionally substituted with one or more $R^{18}$, wherein the heterocyclyl ring, ring G, and $Cy^1$ form a three-ring fused ring structure, $R^1$ is not optionally substituted phenyl, 2-furyl or 3-furyl.

In one embodiment, q is 0. In another embodiment, q is 1. In yet another embodiment, q is 2.

In one embodiment, v is 1. In another embodiment, v is 2. In yet another embodiment, v is 3.

In one embodiment, n is 0. In another embodiment, n is 1.

In one embodiment, p is 0. In another embodiment, p is 1.

In one embodiment, w is 1, 2, 3, or 4. In another embodiment, w is 1. In yet another embodiment, w is 2. In another embodiment, w is 3.

In one embodiment, h is 1, 2, or 3. In another embodiment, h is 1 or 2. In a preferred embodiment, h is 1.

In one embodiment, g is 0. In one embodiment, g is 1. In another embodiment, g is 2. In yet another embodiment, g is 3. In another embodiment, g is 4. In a preferred embodiment, g is 1 or 2.

In one embodiment, i is 0. In another embodiment, i is 1. In yet another embodiment, i is 2.

In certain embodiments, t is 0, In certain embodiments, t is 1. In certain embodiments, t is 2, 3, 4. In certain embodiments, t is 5.

In certain embodiments, u is 0. In certain embodiments, u is 1. In certain embodiments, u is 2 or 3. In certain embodiments, u is 4.

In one embodiment, $Cy^1$ is not

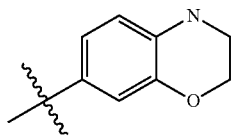 [SMILES: *c1ccc2c(c1)OCCN2]

when p is 1 and X is bound to $Z^1$.

In another embodiment $Cy^2$ is not

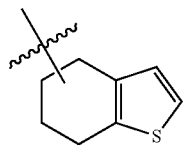

when p is 1 and X is bound to $Z^1$.

In another embodiment, $Cy^1$ and $Cy^2$ are

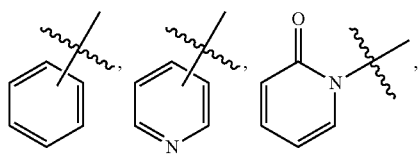

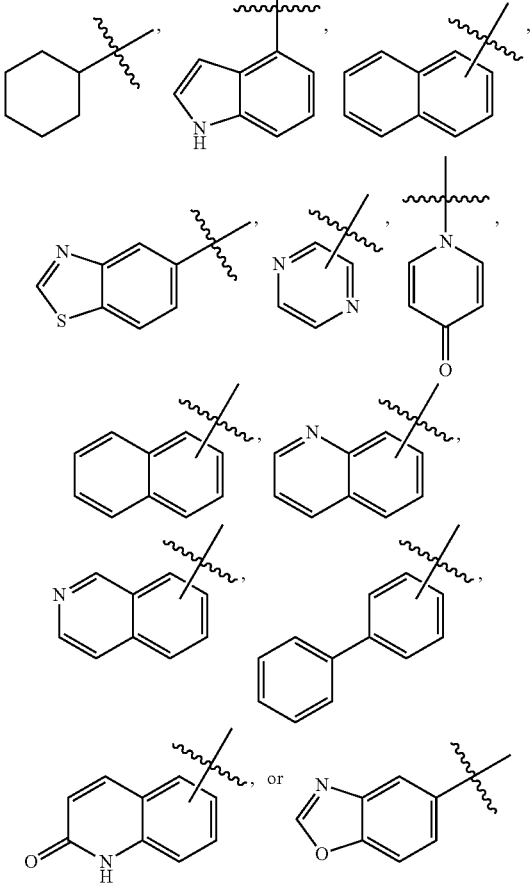

optionally substituted with one or more preferred substituents.

In one embodiment, $X^0$ is X—$Cy^1$ and X is bonded to $Z^1$. In another embodiment, $X^0$ is X—$Cy^1$, X is bonded to $Z^1$ and $R^1$ is methyl. In yet another embodiment, $X^0$ is X—$Cy^1$, X is bonded to $Z^1$, $R^1$ is methyl and $R^9$ is H. In another embodiment, $X^0$ is X—$Cy^1$, X is bonded to $Z^1$, $R^1$ is methyl, $R^9$ is H, and $R^{12}$ is H. In another embodiment, $X^0$ is X—$Cy^1$, X is bonded to $Z^1$, $R^1$ is methyl, $R^9$ is H, $R^{12}$ is H, and $R^{13}$ is H.

In one embodiment, $X^0$ is X—$Cy^1$ and X is bonded to $Z^2$. In another embodiment, $X^0$ is X—$Cy^1$, X is bonded to $Z^2$ and $R^2$ is methyl. In yet another embodiment, $X^0$ is X—$Cy^1$, X is bonded to $Z^2$, $R^2$ is methyl and $R^9$ is H. In another embodiment, $X^0$ is X—$Cy^1$, X is bonded to $Z^2$, $R^2$ is methyl, $R^9$ is H, and $R^{12}$ is H. In another embodiment, $X^0$ is X—$Cy^1$, X is bonded to $Z^2$, $R^2$ is methyl, $R^9$ is H, $R^{12}$ is H, and $R^{13}$ is H.

In one embodiment, $X^0$ is X—$Cy^1$, X is bonded to $Z^1$, $R^1$ is methyl and X is $NR^4$. In another embodiment, $X^0$ is X—$Cy^1$, X is bonded to $Z^1$, $R^1$ is methyl and X is $CR^3R^{3'}$. In yet another embodiment, $X^0$ is X—$Cy^1$, X is bonded to $Z^1$, $R^1$ is methyl and X is C(O). In another embodiment, $X^0$ is X—$Cy^1$, X is bonded to $Z^1$, $R^1$ is methyl and X is O.

In one embodiment, $X^0$ is X—$Cy^1$, X is bonded to $Z^2$, $R^2$ is methyl and X is $NR^4$. In another embodiment, $X^0$ is X—$Cy^1$, X is bonded to $Z^2$, $R^2$ is methyl and X is $CR^3R^{3'}$. In yet another embodiment, $X^0$ is X—$Cy^1$, X is bonded to $Z^2$, $R^2$ is methyl and X is C(O). In another embodiment, $X^0$ is X—$Cy^1$, X is bonded to $Z^1$, $R^2$ is methyl and X is O.

In certain embodiments, $X^O$ is $C(O)NR^4R^{4'}$. In certain embodiments, $X^O$ is $C(O)NHR^{4'}$ (e.g., $C(O)NH(C_1-C_6$ alkyl)). In certain embodiments, $X^O$ is $C(O)NHMe$. In certain embodiments, $X^O$ is $C(O)N(C_1-C_6$ alkyl)$_2$. In certain embodiments, $X^O$ is $C(O)N(Me)_2$. In certain embodiments, $X^O$ is $C(O)NHR^{4'}$, wherein $R^{4'}$ is $C_3-C_8$ cycloalkyl (e.g., cyclopropyl) optionally substituted with one or more $R^{17}$. In certain embodiments, $X^O$ is $C(O)NH(cyclopropyl)$. In certain embodiments, $X^O$ is $C(O)NHR^{4'}$, wherein $R^{4'}$ is phenyl optionally substituted with one or more $R^{17}$. In certain embodiments, $X^O$ is $C(O)NHPh$. In certain embodiments, $X^O$ is $C(O)NR^4R^{4'}$, wherein $R^4$ and $R^{4'}$ together with the nitrogen atom to which $R^4$ and $R^{4'}$ are bound form a monocyclic, 4- to 7-membered heterocyclyl ring (e.g., a pyrrolidinyl ring) optionally substituted with one or more $R^{18}$. In certain embodiments, $X^O$ is

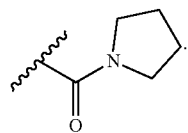 [SMILES: *C(=O)N1CCCC1]

In certain embodiments, $X^O$ is $NR^4C(O)R^{4'}$. In certain embodiments, $X^O$ is $NHC(O)R^{4'}$. In certain embodiments, $X^O$ is $NHC(O)(C_1-C_6$ alkyl). In certain embodiments, $X^O$ is $NHC(O)Me$. In certain embodiments, $X^O$ is $NHC(O)(C_1-C_6$ haloalkyl). In certain embodiments, $X^O$ is $NHC(O)CF_3$. In certain embodiments, $X^O$ is $N(C_1-C_6$ alkyl)$C(O)R^{4'}$. In certain embodiments, $X^O$ is $NMeC(O)R^{4'}$ (e.g., $NMeC(O)Me$). In certain embodiments, $X^O$ is $NHC(O)R^{4'}$, wherein $R^{4'}$ is $C_3-C_8$ cycloalkyl optionally substituted with one or more $R^{17}$. In certain embodiments, $X^O$ is $NHC(O)(cyclopropyl)$.

In certain embodiments, $X^O$ is $CR^3R^{3'}$—$NR^4R^{4'}$. In certain embodiments, $X^O$ is $CH_2$—$NR^4R^{4'}$. In certain embodiments, $X^O$ is $CH_2$—$NHR^{4'}$. In certain embodiments, $X^O$ is $CH_2$—$NH(C_1-C_6$ alkyl) (e.g., $CH_2$—$NHMe$).

In certain embodiments, at least one instance of $R^{30}$ is halogen. In certain embodiments, at least one instance of $R^{30}$ is F. In certain embodiments, at least one instance of $R^{30}$ is Cl, Br, or I. In certain embodiments, at least one instance of $R^{30}$ is $C_{1-6}$ alkyl. In certain embodiments, at least one instance of $R^{30}$ is Me. In certain embodiments, at least one instance of $R^{30}$ is Et, Pr, or Bu. In certain embodiments, at least one instance of $R^{30}$ is $C_{1-6}$ haloalkyl. In certain embodiments, at least one instance of $R^{30}$ is —$CF_3$. In certain embodiments, r is 0. In certain embodiments, r is 1, 2, or 3. In certain embodiments, r is 4.

In one embodiment, the compound of Formula (I) or (V) is not 1-(methylsulfonyl)-5-(3-(4-oxo-1-phenyl-1,3,8-triazaspiro[4.5]decan-8-yl)propyl)-1H-indole-3-carbonitrile. In another embodiment, the compound of Formula (I) or (V) is not 5-(3-(4-oxo-1-phenyl-1,3,8-triazaspiro[4.5]decan-8-yl)propyl)-1H-indole-3-carbonitrile.

In one embodiment, when X is NH and $R^1$ is $C(O)NH_2$, $Cy^1$ is not unsubstituted phenyl. In another embodiment, when X is $CH_2$ and $R^1$ is OH or halogen, then $Cy^1$ is not optionally substituted phenyl, benzoimidazolyl, benzoimidazolonyl, or dihydroquinoxaline-2,3-dione.

Non-limiting illustrative compounds of the invention include:

3-(4-chlorophenoxy)-3-methyl-1-(2-phenoxyethyl)pyrrolidine;
3-(4-chlorophenoxy)-1-(2-(2-methoxyphenoxy)ethyl)-3-methylpyrrolidine;
3-(4-chlorophenoxy)-1-(2-(3-methoxyphenoxy)ethyl)-3-methylpyrrolidine;
3-(4-chlorophenoxy)-1-(2-(4-methoxyphenoxy)ethyl)-3-methylpyrrolidine;
3-(4-chlorophenoxy)-1-(2-(2-fluorophenoxy)ethyl)-3-methylpyrrolidine;
3-(4-chlorophenoxy)-1-(2-(3-fluorophenoxy)ethyl)-3-methylpyrrolidine;
3-(4-chlorophenoxy)-1-(2-(4-fluorophenoxy)ethyl)-3-methylpyrrolidine;
3-(4-chlorophenoxy)-1-(2-(2,4-difluorophenoxy)ethyl)-3-methylpyrrolidine;
3-(4-chlorophenoxy)-1-(2-(2,5-difluorophenoxy)ethyl)-3-methylpyrrolidine;
3-(4-chlorophenoxy)-1-(2-(2-chlorophenoxy)ethyl)-3-methylpyrrolidine;
3-(4-chlorophenoxy)-1-(2-(3-chlorophenoxy)ethyl)-3-methylpyrrolidine;
3-(4-chlorophenoxy)-1-(2-(4-chlorophenoxy)ethyl)-3-methylpyrrolidine;
3-(4-chlorophenoxy)-1-(2-(3,4-dichlorophenoxy)ethyl)-3-methylpyrrolidine;
3-(4-chlorophenoxy)-3-methyl-1-(2-(o-tolyloxy)ethyl)pyrrolidine;
3-(4-chlorophenoxy)-3-methyl-1-(2-(m-tolyloxy)ethyl)pyrrolidine;
3-(4-chlorophenoxy)-3-methyl-1-(2-(p-tolyloxy)ethyl)pyrrolidine;
3-(4-chlorophenoxy)-3-methyl-1-(2-(2-(trifluoromethyl)phenoxy)ethyl)pyrrolidine;
3-(4-chlorophenoxy)-3-methyl-1-(2-(3-(trifluoromethyl)phenoxy)ethyl)pyrrolidine;
3-(4-chlorophenoxy)-3-methyl-1-(2-(4-(trifluoromethyl)phenoxy)ethyl)pyrrolidine;
1-(2-(3-(4-chlorophenoxy)-3-methylpyrrolidin-1-yl)ethyl)pyridin-2(1H)-one;
3-(2-(3-(4-chlorophenoxy)-3-methylpyrrolidin-1-yl)ethoxy)pyridine;
5-(2-(3-(4-chlorophenoxy)-3-methylpyrrolidin-1-yl)ethoxy)-2-(trifluoromethyl)pyridine;
1-(2-(3-(4-chlorophenoxy)-3-methylpyrrolidin-1-yl)ethyl)pyridin-4(1H)-one;
3-(4-chlorophenoxy)-1-(2-(cyclohexyloxy)ethyl)-3-methylpyrrolidine;
3-(4-chlorophenoxy)-3-methyl-1-(2-(naphthalen-1-yloxy)ethyl)pyrrolidine;
3-(4-chlorophenoxy)-3-methyl-1-(2-(naphthalen-2-yloxy)ethyl)pyrrolidine;
6-(2-(3-(4-chlorophenoxy)-3-methylpyrrolidin-1-yl)ethoxy)quinolone;
6-(2-(3-(4-chlorophenoxy)-3-methylpyrrolidin-1-yl)ethoxy)isoquinoline;
7-(2-(3-(4-chlorophenoxy)-3-methylpyrrolidin-1-yl)ethoxy)isoquinoline;
7-(2-(3-(4-chlorophenoxy)-3-methylpyrrolidin-1-yl)ethoxy)quinolone;
7-(2-(3-(4-chlorophenoxy)-3-methylpyrrolidin-1-yl)ethoxy)quinolin-2(1H)-one;
6-(2-(3-(4-chlorophenoxy)-3-methylpyrrolidin-1-yl)ethoxy)benzo[d]thiazole;
6-(2-(3-(4-chlorophenoxy)-3-methylpyrrolidin-1-yl)ethoxy)benzo[d]oxazole;
1-(2-([1,1'-biphenyl]-3-yloxy)ethyl)-3-(4-chlorophenoxy)-3-methylpyrrolidine;
6-(4-(3-(4-chlorophenoxy)-3-methylpyrrolidin-1-yl)butoxy)benzo[d]thiazole;

3-(4-chlorophenoxy)-3-methyl-1-(3-phenoxypropyl)pyrrolidine;
3-(4-chlorophenoxy)-3-methyl-1-(4-phenoxybutyl)pyrrolidine;
3-(4-chlorophenoxy)-1-(4-(2-fluorophenoxy)butyl)-3-methylpyrrolidine;
3-(4-chlorophenoxy)-1-(4-(2-chlorophenoxy)butyl)-3-methylpyrrolidine;
3-(4-chlorophenoxy)-3-methyl-1-(3-phenylpropyl)pyrrolidine;
5-chloro-1'-(2-phenoxyethyl)-3H-spiro[benzofuran-2,3'-pyrrolidine];
(3aS,9aR)-7-chloro-2-(2-phenoxyethyl)-1,2,3,3a,9,9a-hexahydrochromeno[2,3-c]pyrrole;
4-((1-(2-phenoxyethyl)-3-phenylpyrrolidin-3-yl)oxy)aniline;
3-(4-nitrophenoxy)-1-(2-phenoxyethyl)-3-phenylpyrrolidine;
3-methyl-3-phenoxy-1-(2-phenoxyethyl)pyrrolidine;
3-methyl-3-(2-nitrophenoxy)-1-(2-phenoxyethyl)pyrrolidine;
3-methyl-3-(3-nitrophenoxy)-1-(2-phenoxyethyl)pyrrolidine;
3-methyl-3-(4-nitrophenoxy)-1-(2-phenoxyethyl)pyrrolidine;
4-((3-methyl-1-(2-phenoxyethyl)pyrrolidin-3-yl)oxy)aniline;
3-((3-methyl-1-(2-phenoxyethyl)pyrrolidin-3-yl)oxy)aniline;
2-((3-methyl-1-(2-phenoxyethyl)pyrrolidin-3-yl)oxy)aniline;
3-methyl-1-(2-phenoxyethyl)-3-(o-tolyloxy)pyrrolidine;
3-(2-methoxyphenoxy)-3-methyl-1-(2-phenoxyethyl)pyrrolidine;
3-(2-fluorophenoxy)-3-methyl-1-(2-phenoxyethyl)pyrrolidine;
3-(3-fluorophenoxy)-3-methyl-1-(2-phenoxyethyl)pyrrolidine;
3-(4-fluorophenoxy)-3-methyl-1-(2-phenoxyethyl)pyrrolidine;
3-(2-chlorophenoxy)-3-methyl-1-(2-phenoxyethyl)pyrrolidine;
3-(3-chlorophenoxy)-3-methyl-1-(2-phenoxyethyl)pyrrolidine;
3-(2,3-dichlorophenoxy)-3-methyl-1-(2-phenoxyethyl)pyrrolidine;
3-(3,4-dichlorophenoxy)-3-methyl-1-(2-phenoxyethyl)pyrrolidine;
3-(2,4-dichlorophenoxy)-3-methyl-1-(2-phenoxyethyl)pyrrolidine;
3-methyl-1-(2-phenoxyethyl)-3-(2-(trifluoromethyl)phenoxy)pyrrolidine;
3-methyl-1-(2-phenoxyethyl)-3-(3-(trifluoromethyl)phenoxy)pyrrolidine;
3-methyl-1-(2-phenoxyethyl)-3-(4-(trifluoromethyl)phenoxy)pyrrolidine;
2-((3-methyl-1-(2-phenoxyethyl)pyrrolidin-3-yl)oxy)pyridine;
3-((3-methyl-1-(2-phenoxyethyl)pyrrolidin-3-yl)oxy)pyridine;
4-((3-methyl-1-(2-phenoxyethyl)pyrrolidin-3-yl)oxy)pyridine;
2-((3-methyl-1-(2-phenoxyethyl)pyrrolidin-3-yl)oxy)pyrazine;
4-(4-chlorophenoxy)-4-methyl-1-(2-phenoxyethyl)piperidine;
4-(4-chlorophenoxy)-4-methyl-1-(4-phenoxybutyl)piperidine;
4-methyl-4-phenoxy-1-(4-phenoxybutyl)piperidine;
4-(4-chlorophenoxy)-1-(2-(2-fluorophenoxy)ethyl)-4-methylpiperidine;
4-(4-chlorophenoxy)-1-(2-(2-chlorophenoxy)ethyl)-4-methylpiperidine;
4-(4-chlorophenoxy)-4-methyl-1-(2-(2-(trifluoromethoxy)phenoxy)ethyl)piperidine;
4-(4-chlorophenoxy)-4-methyl-1-(2-(2-(trifluoromethyl)phenoxy)ethyl)piperidine;
4-(4-chlorophenoxy)-4-methyl-1-(2-(4-(trifluoromethyl)phenoxy)ethyl)piperidine;
5-(2-(4-(4-chlorophenoxy)-4-methylpiperidin-1-yl)ethoxy)-2-(trifluoromethyl)pyridine;
2-(2-(4-(4-chlorophenoxy)-4-methylpiperidin-1-yl)ethoxy)-5-(trifluoromethyl)pyridine;
4-(4-chlorophenoxy)-4-methyl-1-(2-(4-(methylsulfonyl)phenoxy)ethyl)piperidine;
1-(4-(2-(4-(4-chlorophenoxy)-4-methylpiperidin-1-yl)ethoxy)phenyl)ethan-1-one;
1-(4-(2-(4-(4-chlorophenoxy)-4-methylpiperidin-1-yl)ethoxy)phenyl)ethan-1-ol;
2-(4-(2-(4-(4-chlorophenoxy)-4-methylpiperidin-1-yl)ethoxy)phenyl)propan-2-ol;
4-(4-chlorophenoxy)-1-(2-(4-fluorophenoxy)ethyl)-4-methylpiperidine;
4-(4-chlorophenoxy)-1-(2-(4-chlorophenoxy)ethyl)-4-methylpiperidine;
4-(4-chlorophenoxy)-4-methyl-1-(2-(p-tolyloxy)ethyl)piperidine;
2-((4-methyl-1-(2-(4-(trifluoromethyl)phenoxy)ethyl)piperidin-4-yl)oxy)pyridine;
4-(4-chlorophenoxy)-1-(2-(5-fluoro-2-(trifluoromethyl)phenoxy)ethyl)-4-methylpiperidine;
4-(4-chlorophenoxy)-1-(2-(4-fluoro-2-(trifluoromethyl)phenoxy)ethyl)-4-methylpiperidine;
4-(4-chlorophenoxy)-1-(2-(3-fluoro-2-(trifluoromethyl)phenoxy)ethyl)-4-methylpiperidine;
4-(4-chlorophenoxy)-1-(2-(4-fluoro-2-(methylsulfonyl)phenoxy)ethyl)-4-methylpiperidine;
4-(4-chlorophenoxy)-1-(2-(5-fluoro-2-methoxyphenoxy)ethyl)-4-methylpiperidine;
4-(4-chlorophenoxy)-1-(2-(4-fluoro-2-methoxyphenoxy)ethyl)-4-methylpiperidine;
1-(2-(5-chloro-2-(trifluoromethyl)phenoxy)ethyl)-4-(4-chlorophenoxy)-4-methylpiperidine;
5-(2-(4-(4-chlorophenoxy)-4-methylpiperidin-1-yl)ethoxy)thiazole;
6-(2-(4-(4-chlorophenoxy)-4-methylpiperidin-1-yl)ethoxy)benzo[d]oxazole;
7-(2-(4-(4-chlorophenoxy)-4-methylpiperidin-1-yl)ethoxy)-3,4-dihydroquinolin-2(1H)-one;
4-(benzyloxy)-4-methyl-1-(2-(2-(trifluoromethyl)phenoxy)ethyl)piperidine;
2-(2-(4-(4-chlorophenoxy)-4-methylpiperidin-1-yl)ethoxy)-3-(trifluoromethyl)pyridine;
3-(2-(4-(4-chlorophenoxy)-4-methylpiperidin-1-yl)ethoxy)-4-(trifluoromethyl)pyridine;
4-(2-(4-(4-chlorophenoxy)-4-methylpiperidin-1-yl)ethoxy)-3-(trifluoromethyl)pyridine;
3-(2-(4-(4-chlorophenoxy)-4-methylpiperidin-1-yl)ethoxy)-2-(trifluoromethyl)pyridine;
2-(4-(4-chlorophenoxy)-4-methylpiperidin-1-yl)-N-(2-(trifluoromethyl)phenyl)acetamide;
N-(2-(4-(4-chlorophenoxy)-4-methylpiperidin-1-yl)ethyl)-2-(trifluoromethyl)aniline;

N-(2-(4-(4-chlorophenoxy)-4-methylpiperidin-1-yl)ethyl)-N-methyl-2-(trifluoromethyl)aniline;
N-(2-(4-(4-chlorophenoxy)-4-methylpiperidin-1-yl)ethyl)-N-(2-(trifluoromethyl)phenyl) acetamide;
1-(2-(4-(4-chlorophenoxy)-4-methylpiperidin-1-yl)ethyl)-8-(trifluoromethyl)quinolin-2(1H)-one;
2-(2-(4-(4-chlorophenoxy)-4-methylpiperidin-1-yl)ethoxy)-8-(trifluoromethyl)quinolone;
4-(4-chlorophenoxy)-1-(2-(cyclohexyloxy)ethyl)-4-methylpiperidine;
4-(4-chlorophenoxy)-1-((2,3-dihydrobenzo[b][1,4]dioxin-2-yl)methyl)-4-methylpiperidine;
1-(2-(2-fluorophenoxy)ethyl)-4-methyl-4-phenoxypiperidine;
1-(2-(2-chlorophenoxy)ethyl)-4-methyl-4-phenoxypiperidine;
4-methyl-4-phenoxy-1-(2-(o-tolyloxy)ethyl)piperidine;
1-(2-(2-ethylphenoxy)ethyl)-4-methyl-4-phenoxypiperidine;
1-(2-(2-isopropylphenoxy)ethyl)-4-methyl-4-phenoxypiperidine;
1-(2-(4-methyl-4-phenoxypiperidin-1-yl)ethyl)-3-(trifluoromethyl)pyridin-2(1H)-one;
4-methyl-4-phenoxy-1-(2-(2-(trifluoromethyl)phenoxy)ethyl)piperidine;
4-methyl-4-phenoxy-1-(2-(3-(trifluoromethyl)phenoxy)ethyl)piperidine;
4-methyl-4-phenoxy-1-(2-(4-(trifluoromethyl)phenoxy)ethyl)piperidine;
1-(2-(5-fluoro-2-(trifluoromethyl)phenoxy)ethyl)-4-methyl-4-phenoxypiperidine;
1-(2-(4-fluoro-2-(trifluoromethyl)phenoxy)ethyl)-4-methyl-4-phenoxypiperidine;
4-methyl-4-phenoxy-1-(2-(2-(trifluoromethoxy)phenoxy)ethyl)piperidine;
1-(2-(2-methoxyphenoxy)ethyl)-4-methyl-4-phenoxypiperidine;
4-methyl-1-(2-(2-(methylsulfonyl)phenoxy)ethyl)-4-phenoxypiperidine;
2-(2-(4-methyl-4-phenoxypiperidin-1-yl)ethoxy)benzonitrile;
N,N-dimethyl-2-(2-(4-methyl-4-phenoxypiperidin-1-yl)ethoxy)aniline;
2-(2-(4-methyl-4-phenoxypiperidin-1-yl)ethoxy)pyridine;
4-(2-(4-methyl-4-phenoxypiperidin-1-yl)ethoxy)pyridine;
1-(2-(4-methyl-4-phenoxypiperidin-1-yl)ethyl)pyridin-2(1H)-one;
4-methyl-1-(2-(naphthalen-1-yloxy)ethyl)-4-phenoxypiperidine;
4-(2-(4-methyl-4-phenoxypiperidin-1-yl)ethoxy)-1H-indole;
2-((4-methyl-1-(2-(2-(trifluoromethyl)phenoxy)ethyl)piperidin-4-yl)oxy)pyridine;
4-(2-chlorophenoxy)-4-methyl-1-(2-(2-(trifluoromethyl)phenoxy)ethyl)piperidine;
(1R,3r,5S)-3-methyl-3-phenoxy-8-(2-(2-(trifluoromethyl)phenoxy)ethyl)-8-azabicyclo[3.2.1]octane;
(1R,3s,5S)-3-methyl-3-phenoxy-8-(2-(2-(trifluoromethyl)phenoxy)ethyl)-8-azabicyclo[3.2.1]octane;
1-(4-chlorophenyl)-6-(2-(2-(trifluoromethyl)phenoxy)ethyl)-6-azaspiro[2.5]octane;
2,4,6-trimethyl-4-phenoxy-1-(2-(2-(trifluoromethyl)phenoxy)ethyl)piperidine;
4-methyl-1-(2-methyl-1-(2-(trifluoromethyl)phenoxy)propan-2-yl)-4-phenoxypiperidine;
4-methyl-4-phenoxy-1-(1-(2-(trifluoromethyl)phenoxy)propan-2-yl)piperidine;
4-methyl-4-phenoxy-1-(3-(2-(trifluoromethyl)phenyl)propyl)piperidine;
4-(4-(4-chlorophenoxy)-4-methylpiperidin-1-yl)-2-(2-(trifluoromethyl)phenyl)butan-2-ol;
3-(4-methyl-4-phenoxypiperidin-1-yl)-1-(2-(trifluoromethyl)phenyl)propan-1-one;
1-phenyl-6-(2-(2-(trifluoromethyl)phenoxy)ethyl)-6-azaspiro[2.5]octane;
1-phenyl-7-(2-(2-(trifluoromethyl)phenoxy)ethyl)-1,7-diazaspiro[3.5]nonane;
1-(4-chlorophenyl)-7-(2-(2-(trifluoromethyl)phenoxy)ethyl)-1,7-diazaspiro[3.5]nonane;
1-(4-chlorophenyl)-7-(2-(2-fluorophenoxy)ethyl)-1,7-diazaspiro[3.5]nonane;
1-(4-chlorophenyl)-8-((2,3-dihydrobenzo[b][1,4]dioxin-2-yl)methyl)-1,8-diazaspiro[4.5]decane;
1-(4-chlorophenyl)-8-(2-(2-(trifluoromethyl)phenoxy)ethyl)-1,8-diazaspiro[4.5]decane;
N,4-dimethyl-N-phenyl-1-(2-(2-(trifluoromethyl)phenoxy)ethyl)piperidin-4-amine;
1'-(2-(2-(trifluoromethyl)phenoxy)ethyl)-3H-spiro[benzofuran-2,4'-piperidine];
4-(hydroxy(phenyl)methyl)-1-(2-(2-(trifluoromethyl)phenoxy)ethyl)piperidin-4-ol;
2,2-dimethyl-4-phenyl-8-(2-(2-(trifluoromethyl)phenoxy)ethyl)-1,3-dioxa-8-azaspiro[4.5]decane;
(4-methyl-1-(2-(2-(trifluoromethyl)phenoxy)ethyl)piperidin-4-yl)(phenyl)methanone;
(4-methyl-1-(2-(2-(trifluoromethyl)phenoxy)ethyl)piperidin-4-yl)(phenyl)methanol;
3-(4-chlorophenoxy)-3-methyl-1-(2-phenoxyethyl)piperidine;
3-(4-chlorophenoxy)-3-methyl-1-(2-methyl-1-phenoxypropan-2-yl)piperidine;
3-(4-chlorophenoxy)-1-(2-(2-fluorophenoxy)ethyl)-3-methylpiperidine;
3-(4-chlorophenoxy)-1-(2-(2-chlorophenoxy)ethyl)-3-methylpiperidine;
5-(2-(3-(4-chlorophenoxy)-3-methylpiperidin-1-yl)ethoxy)benzo[d]thiazole;
3-methyl-1-(2-phenoxyethyl)-3-(3-(trifluoromethyl)phenoxy)piperidine;
1-(2-(2-fluorophenoxy)ethyl)-3-methyl-3-(3-(trifluoromethyl)phenoxy)piperidine;
1-(2-(2-chlorophenoxy)ethyl)-3-methyl-3-(3-(trifluoromethyl)phenoxy)piperidine;
4-methoxy-4-methyl-1-(2-(2-(trifluoromethyl)phenoxy)ethyl)piperidine;
4-methyl-1-(2-(2-(trifluoromethyl)phenoxy)ethyl)piperidin-4-ol;
3-methyl-1-(2-(2-(trifluoromethyl)phenoxy)ethyl)piperidin-3-ol;
(1R,3r,5S)-3-methyl-8-(2-(2-(trifluoromethyl)phenoxy)ethyl)-8-azabicyclo[3.2.1]octan-3-ol;
(1R,3s,5S)-3-methyl-8-(2-(2-(trifluoromethyl)phenoxy)ethyl)-8-azabicyclo[3.2.1]octan-3-ol;
3-methyl-1-(2-(2-(trifluoromethyl)phenoxy)ethyl)pyrrolidin-3-ol;
4-methyl-1-(3-(2-(trifluoromethyl)phenoxy)propyl)piperidin-4-ol;
4-methyl-1-(2-(4-(trifluoromethyl)phenoxy)ethyl)piperidin-4-ol;
4-isopropyl-1-(2-(2-(trifluoromethyl)phenoxy)ethyl)piperidin-4-ol;
4-methyl-1'-(2-(trifluoromethyl)phenyl)-[1,3'-bipiperidin]-4-ol;

1-((2,3-dihydrobenzo[b][1,4]dioxin-2-yl)methyl)-4-methylpiperidin-4-ol;
4-methyl-1-(2-phenoxyethyl)piperidin-4-ol;
1-(2-(2-fluorophenoxy)ethyl)-4-methylpiperidin-4-ol;
1-(2-phenoxyethyl)-3-phenylpyrrolidin-3-ol;
1-(2-(2,5-difluorophenoxy)ethyl)-3-methyl-3-(3-(trifluoromethyl)phenoxy)piperidine, or
  a stereoisomer, racemate, tautomer, polymorph, hydrate, or solvate thereof, or a pharmaceutically acceptable salt thereof.

Additional exemplary compounds of the invention include, but are not limited to: 3-(4-chlorophenoxy)-1-(2-(3-fluorophenoxy)ethyl)-3-methylpyrrolidine;
1'-(2-phenoxyethyl)-3H-spiro[benzofuran-2,3'-pyrrolidine];
3-(2-(4-(4-chlorophenoxy)-4-methylpiperidin-1-yl)ethoxy)pyridine;
4-(2-(4-(4-chlorophenoxy)-4-methylpiperidin-1-yl)ethoxy)pyridine;
5-(2-(4-(4-chlorophenoxy)-4-methylpiperidin-1-yl)ethoxy)-2-(trifluoromethyl)phenol;
4-(2-(4-(4-chlorophenoxy)-4-methylpiperidin-1-yl)ethoxy)benzonitrile;
1-(2-((1H-pyrazol-4-yl)oxy)ethyl)-4-(4-chlorophenoxy)-4-methylpiperidine;
1-(2-(2-(4-(4-chlorophenoxy)-4-methylpiperidin-1-yl)ethoxy)-5-fluorophenyl)ethan-1-one;
4-(4-chlorophenoxy)-1-(2-(2-methoxyphenoxy)ethyl)-4-methylpiperidine;
4-(4-chlorophenoxy)-1-(2-(4,5-difluoro-2-methoxyphenoxy)ethyl)-4-methylpiperidine;
4-(4-chlorophenoxy)-1-(2-(5-fluoro-2-isopropoxyphenoxy)ethyl)-4-methylpiperidine;
4-(4-chlorophenoxy)-1-(2-(4-fluoro-2-isopropoxyphenoxy)ethyl)-4-methylpiperidine;
4-(4-chlorophenoxy)-4-isopropyl-1-(2-(2-(trifluoromethyl)phenoxy)ethyl)piperidine;
4-(4-chlorophenoxy)-4-ethynyl-1-(2-(2-(trifluoromethyl)phenoxy)ethyl)piperidine;
4-ethynyl-4-phenoxy-1-(2-(2-(trifluoromethyl)phenoxy)ethyl)piperidine;
1-(2-(4-(4-chlorophenoxy)-4-methylpiperidin-1-yl)ethyl)-3-(trifluoromethyl)pyridin-2(1H)-one;
(1R,3s,5S)-3-methyl-8-(2-(2-(trifluoromethyl)phenoxy)ethyl)-8-azabicyclo[3.2.1]octan-3-ol;
(1R,3r,5S)-3-methyl-8-(2-(2-(trifluoromethyl)phenoxy)ethyl)-8-azabicyclo[3.2.1]octan-3-ol;
N,4-dimethyl-1-(2-(2-(trifluoromethyl)phenoxy)ethyl)piperidine-4-carboxamide;
N,4-dimethyl-1-(2-phenoxyethyl)piperidine-4-carboxamide;
1-(2-(2-fluorophenoxy)ethyl)-N,4-dimethylpiperidine-4-carboxamide;
1-(2-(2-methoxyphenoxy)ethyl)-N,4-dimethylpiperidine-4-carboxamide;
1-((2,3-dihydrobenzo[b][1,4]dioxin-2-yl)methyl)-N,4-dimethylpiperidine-4-carboxamide;
N-cyclopropyl-1-((2,3-dihydrobenzo[b][1,4]dioxin-2-yl)methyl)-4-methylpiperidine-4-carboxamide;
1-((2,3-dihydrobenzo[b][1,4]dioxin-2-yl)methyl)-4-methyl-N-phenylpiperidine-4-carboxamide;
(S)-1-((2,3-dihydrobenzo[b][1,4]dioxin-2-yl)methyl)-N,N,4-trimethylpiperidine-4-carboxamide;
(S)-(1-((2,3-dihydrobenzo[b][1,4]dioxin-2-yl)methyl)-4-methylpiperidin-4-yl)(pyrrolidin-1-yl)methanone;
(S)-1-(1-((2,3-dihydrobenzo[b][1,4]dioxin-2-yl)methyl)-4-methylpiperidin-4-yl)-N-methylmethanamine;
(S)—N-(1-((2,3-dihydrobenzo[b][1,4]dioxin-2-yl)methyl)-4-methylpiperidin-4-yl)acetamide;
(S)—N-(1-((2,3-dihydrobenzo[b][1,4]dioxin-2-yl)methyl)-4-methylpiperidin-4-yl)cyclopropanecarboxamide;
(S)—N-(1-((7-fluoro-2,3-dihydrobenzo[b][1,4]dioxin-2-yl)methyl)-4-methylpiperidin-4-yl)acetamide;
(S)—N-(1-((7-bromo-2,3-dihydrobenzo[b][1,4]dioxin-2-yl)methyl)-4-methylpiperidin-4-yl)acetamide;
(S)—N-(1-((2,3-dihydrobenzo[b][1,4]dioxin-2-yl)methyl)-4-methylpiperidin-4-yl)-2,2,2-trifluoroacetamide;
(S)—N-(1-((2,3-dihydrobenzo[b][1,4]dioxin-2-yl)methyl)-4-methylpiperidin-4-yl)-N-methylacetamide;
(4-(4-chlorobenzyl)-1-(2-(2-(trifluoromethyl)phenoxy)ethyl)piperidin-4-yl)methanol;
4-(4-chlorobenzyl)-4-methyl-1-(2-(2-(trifluoromethyl)phenoxy)ethyl)piperidine;
1-(4-chlorophenyl)-6-(2-(2-(trifluoromethyl)phenoxy)ethyl)-6-azaspiro[2.5]octane;
N-cyclohexyl-N,4-dimethyl-1-(2-(2-(trifluoromethyl)phenoxy)ethyl)piperidin-4-amine;
4-methyl-N-phenyl-1-(2-(2-(trifluoromethyl)phenoxy)ethyl)piperidine-4-carboxamide;
1-(2-(2-fluorophenoxy)ethyl)-4-methyl-N-phenylpiperidine-4-carboxamide;
and stereoisomers, racemates, tautomers, polymorphs, hydrates, solvates, and pharmaceutically acceptable salts thereof.

In certain embodiments, a compound of the invention is:
4-(4-Chlorophenoxy)-4-methyl-1-(2-(2-(trifluoromethyl)phenoxy)ethyl) piperidine (compound 90);
4-(4-Chlorophenoxy)-4-methyl-1-(2-(4-(trifluoromethyl)phenoxy) ethyl) piperidine (compound 125);
4-(4-chlorophenoxy)-1-(2-(4-fluoro-2-(trifluoromethyl)phenoxy)ethyl)-4-methylpiperidine (compound 157);
1-((2,3-dihydrobenzo[b][1,4]dioxin-2-yl)methyl)-N,4-dimethylpiperidine-4-carboxamide (compound 202);
(S)—N-(1-((2,3-dihydrobenzo[b][1,4]dioxin-2-yl)methyl)-4-methylpiperidin-4-yl)acetamide (compound 208);
(S)—N-(1-((7-fluoro-2,3-dihydrobenzo[b][1,4]dioxin-2-yl)methyl)-4-methylpiperidin-4-yl)acetamide (compound 210);
or a stereoisomer, racemate, tautomer, polymorph, hydrate, or solvate thereof, or a pharmaceutically acceptable salt thereof.

The present invention relates to novel compounds that modulate dopamine D2 receptors. For example, compounds of the present invention have an $EC_{50}<0.1$ μM in the assay for β-arrestin antagonist activity. For example, compounds of the present invention have an $EC_{50}$ of 0.1-1.0 μM in the assay for β-arrestin antagonist activity. For example, compounds of the present invention have an $EC_{50}$ of 1.0-10.0 μM in the assay for β-arrestin antagonist activity. For example, compounds of the present invention have an $EC_{50}$ of 10.0-30.0 μM in the assay for β-arrestin antagonist activity. Accordingly, compounds of the present invention are useful in treating or preventing a disease or disorder in which modulation of D2 receptors plays a role.

For example, compounds of the present invention are selective antagonists of D2 receptors. For example, compounds of the present invention are selective β-arrestin antagonists, but not cAMP antagonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger β-arrestin antagonist activity than cAMP antagonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for β-arrestin antagonist activity than cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$<0.1 μM in the assay for β-arrestin antagonist activity and an $EC_{50}$≥0.1 μM in the assay for cAMP antagonist activity. For example, compounds of the present invention have an $EC_{50}$<0.1 μM in the assay for β-arrestin antagonist activity and an $EC_{50}$ of 0.1-1.0 μM in the assay for cAMP antagonist activity. For example, compounds of the present invention have an $EC_{50}$<0.1 μM in the assay for β-arrestin antagonist activity and an $EC_{50}$ of 1.0-10.0 μM in the assay for cAMP antagonist activity. For example, compounds of the present invention have an $EC_{50}$<0.1 μM in the assay for β-arrestin antagonist activity and an $EC_{50}$ of 10.0-30.0 μM in the assay for cAMP antagonist activity. For example, compounds of the present invention have an $EC_{50}$<0.1 μM in the assay for β-arrestin antagonist activity and an $EC_{50}$≥30.0 μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 μM in the assay for β-arrestin antagonist activity and an $EC_{50}$>1.0 μM in the assay for cAMP antagonist activity. For example, compounds of the present invention have an $EC_{50}$ of 0.1-1.0 μM in the assay for β-arrestin antagonist activity and an $EC_{50}$ of 1.0-10.0 μM in the assay for cAMP antagonist activity. For example, compounds of the present invention have an $EC_{50}$ of 0.1-1.0 μM in the assay for β-arrestin antagonist activity and an $EC_{50}$ of 10.0-30.0 μM in the assay for cAMP antagonist activity. For example, compounds of the present invention have an $EC_{50}$ of 0.1-1.0 μM in the assay for β-arrestin antagonist activity and an $EC_{50}$≥30.0 μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for β-arrestin antagonist activity and an $EC_{50}$>10.0 μM in the assay for cAMP antagonist activity. For example, compounds of the present invention have an $EC_{50}$ of of 1.0-10.0 μM in the assay for β-arrestin antagonist activity and an $EC_{50}$ of 10.0-30.0 μM in the assay for cAMP antagonist activity. For example, compounds of the present invention have an $EC_{50}$ of of 1.0-10.0 μM in the assay for β-arrestin antagonist activity and an $EC_{50}$≥30.0 μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 μM in the assay for β-arrestin antagonist activity and an $EC_{50}$>30.0 μM in the assay for cAMP antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective β-arrestin antagonists and cAMP agonists. For example, compounds of the present invention have an $EC_{50}$<0.1 μM in the assay for β-arrestin antagonist activity and an $EC_{50}$<0.1 μM in the assay for cAMP agonist activity. For example, compounds of the present invention have an $EC_{50}$<0.1 μM in the assay for β-arrestin antagonist activity and an $EC_{50}$ of 0.1-1.0 μM in the assay for cAMP agonist activity. For example, compounds of the present invention have an $EC_{50}$<0.1 μM in the assay for β-arrestin antagonist activity and an $EC_{50}$ of 1.0-10.0 μM in the assay for cAMP agonist activity. For example, compounds of the present invention have an $EC_{50}$<0.1 μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 μM in the assay for β-arrestin antagonist activity and an $EC_{50}$<0.1 μM in the assay for cAMP agonist activity. For example, compounds of the present invention have an $EC_{50}$ of 0.1-1.0 μM in the assay for β-arrestin antagonist activity and an $EC_{50}$ of 0.1-1.0 μM in the assay for cAMP agonist activity. For example, compounds of the present invention have an $EC_{50}$ of 0.1-1.0 μM in the assay for β-arrestin antagonist activity and an $EC_{50}$ of 1.0-10.0 μM in the assay for cAMP agonist activity. For example, compounds of the present invention have an $EC_{50}$ of 0.1-1.0 μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for β-arrestin antagonist activity and an $EC_{50}$<0.1 μM in the assay for cAMP agonist activity. For example, compounds of the present invention have an $EC_{50}$ of 1.0-10.0 μM in the assay for β-arrestin antagonist activity and an $EC_{50}$ of 0.1-1.0 μM in the assay for cAMP agonist activity. For example, compounds of the present invention have an $EC_{50}$ of 1.0-10.0 μM in the assay for β-arrestin antagonist activity and an $EC_{50}$ of 1.0-10.0 μM in the assay for cAMP agonist activity. For example, compounds of the present invention have an $EC_{50}$ of 1.0-10.0 μM in the assay for β-arrestin antagonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 µM in the assay for β-arrestin antagonist activity and an $EC_{50}$<0.1 µM in the assay for cAMP agonist activity. For example, compounds of the present invention have an $EC_{50}$ of 10.0-30.0 µM in the assay for β-arrestin antagonist activity and an $EC_{50}$ of 0.1-1.0 µM in the assay for cAMP agonist activity. For example, compounds of the present invention have an $EC_{50}$ of 10.0-30.0 µM in the assay for β-arrestin antagonist activity and an $EC_{50}$ of 1.0-10.0 µM in the assay for cAMP agonist activity. For example, compounds of the present invention have an $EC_{50}$ of 10.0-30.0 µM in the assay for β-arrestin antagonist activity and an $EC_{50}$ of 10.0-30.0 µM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective β-arrestin antagonists and agonists of cAMP and β-arrestin. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are β-arrestin antagonists and cAMP antagonists. For example, compounds of the present invention have an $EC_{50}$<0.1 µM in the assay for β-arrestin antagonist activity and an $EC_{50}$<0.1 µM in the assay for cAMP antagonist activity. For example, compounds of the present invention have an $EC_{50}$<0.1 µM in the assay for β-arrestin antagonist activity and an $EC_{50}$ of 0.1-1.0 µM in the assay for cAMP antagonist activity. For example, compounds of the present invention have an $EC_{50}$ of 0.1-1.0 µM in the assay for β-arrestin antagonist activity and an $EC_{50}$ of 0.1-1.0 µM in the assay for cAMP antagonist activity. For example, compounds of the present invention have an $EC_{50}$ of 0.1-1.0 µM in the assay for β-arrestin antagonist activity and an $EC_{50}$ of 1.0-10.0 µM in the assay for cAMP antagonist activity. For example, compounds of the present invention have an $EC_{50}$ of 1.0-10.0 µM in the assay for β-arrestin antagonist activity and an $EC_{50}$ of 1.0-10.0 µM in the assay for cAMP antagonist activity. For example, compounds of the present invention have an $EC_{50}$ of of 1.0-10.0 µM in the assay for β-arrestin antagonist activity and an $EC_{50}$ of 10.0-30.0 µM in the assay for cAMP antagonist activity. For example, compounds of the present invention have an $EC_{50}$ of 10.0-30.0 µM in the assay for β-arrestin antagonist activity and an $EC_{50}$ of 10.0-30.0 µM in the assay for cAMP antagonist activity. Accordingly, compounds of the present invention are useful in treating or preventing a disease or disorder in which modulation of D2 receptors plays a role.

The present invention relates to novel compounds that modulate dopamine D2 receptors. For example, compounds of the present invention have an $EC_{50}$<0.1 µM in the assay for β-arrestin agonist activity. For example, compounds of the present invention have an $EC_{50}$ of 0.1-1.0 µM in the assay for β-arrestin agonist activity. For example, compounds of the present invention have an $EC_{50}$ of 1.0-10.0 µM in the assay for β-arrestin agonist activity. For example, compounds of the present invention have an $EC_{50}$ of 10.0-30.0 µM in the assay for β-arrestin agonist activity. Accordingly, compounds of the present invention are useful in treating or preventing a disease or disorder in which modulation of D2 receptors plays a role.

For example, compounds of the present invention are selective agonists of D2 receptors. For example, compounds of the present invention are selective β-arrestin agonists, but not cAMP agonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger β-arrestin agonist activity than cAMP agonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for β-arrestin agonist activity than cAMP agonist activity. Accordingly, compounds of the present invention are useful in treating or preventing a disease or disorder in which modulation of D2 receptors plays a role.

For example, compounds of the present invention have an $EC_{50}$<0.1 µM in the assay for β-arrestin agonist activity and an $EC_{50}$≥0.1 µM in the assay for cAMP agonist activity. For example, compounds of the present invention have an $EC_{50}$<0.1 µM in the assay for β-arrestin agonist activity and an $EC_{50}$ of 0.1-1.0 µM in the assay for cAMP agonist activity. For example, compounds of the present invention have an $EC_{50}$<0.1 µM in the assay for β-arrestin agonist activity and an $EC_{50}$ of 1.0-10.0 µM in the assay for cAMP agonist activity. For example, compounds of the present invention have an $EC_{50}$<0.1 µM in the assay for β-arrestin agonist activity and an $EC_{50}$ of 10.0-30.0 µM in the assay for cAMP agonist activity. For example, compounds of the present invention have an $EC_{50}$<0.1 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of 0.1-1.0 µM in the assay for β-arrestin agonist activity and an $EC_{50}$>1.0 µM in the assay for cAMP agonist activity. For example, compounds of the present invention have an $EC_{50}$ of 0.1-1.0 µM in the assay for β-arrestin agonist activity and an $EC_{50}$ of 1.0-10.0 µM in the assay for cAMP agonist activity. For example, compounds of the present invention have an $EC_{50}$ of 0.1-1.0 µM in the assay for β-arrestin agonist activity and an $EC_{50}$ of 10.0-30.0 µM in the assay for cAMP agonist activity. For example, compounds of the present invention have an $EC_{50}$ of 0.1-1.0 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of 1.0-10.0 µM in the assay for β-arrestin agonist activity and an $EC_{50}$>10.0 µM in the assay for cAMP agonist activity. For example, compounds of the present invention have an $EC_{50}$ of of 1.0-10.0 µM in the assay for β-arrestin agonist activity and an $EC_{50}$ of 10.0-30.0 µM in the assay for cAMP agonist activity. For example, compounds of the present invention have an $EC_{50}$ of of 1.0-10.0 µM in the assay for β-arrestin agonist activity and an $EC_{50}$≥30.0 µM in the assay for cAMP agonist activity. Accordingly, compounds of the present invention are useful in treating or preventing a disease or disorder in which modulation of D2 receptors plays a role.

For example, compounds of the present invention have an $EC_{50}$ of of 10.0-30.0 μM in the assay for β-arrestin agonist activity and an $EC_{50}$>30.0 μM in the assay for cAMP agonist activity. Accordingly, compounds of the present invention are useful in treating or preventing a disease or disorder in which modulation of D2 receptors plays a role.

For example, compounds of the present invention are selective β-arrestin agonists and cAMP antagonists. For example, compounds of the present invention have an $EC_{50}$<0.1 μM in the assay for β-arrestin agonist activity and an $EC_{50}$<0.1 μM in the assay for cAMP antagonist activity. For example, compounds of the present invention have an $EC_{50}$<0.1 μM in the assay for β-arrestin agonist activity and an $EC_{50}$ of 0.1-1.0 μM in the assay for cAMP antagonist activity. For example, compounds of the present invention have an $EC_{50}$<0.1 μM in the assay for β-arrestin agonist activity and an $EC_{50}$ of 1.0-10.0 μM in the assay for cAMP antagonist activity. For example, compounds of the present invention have an $EC_{50}$<0.1 μM in the assay for β-arrestin agonist activity and an $EC_{50}$ of 10.0-30.0 μM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 0.1-1.0 μM in the assay for β-arrestin agonist activity and an $EC_{50}$<0.1 μM in the assay for cAMP antagonist activity. For example, compounds of the present invention have an $EC_{50}$ of 0.1-1.0 μM in the assay for β-arrestin agonist activity and an $EC_{50}$ of 0.1-1.0 μM in the assay for cAMP antagonist activity. For example, compounds of the present invention have an $EC_{50}$ of 0.1-1.0 μM in the assay for β-arrestin agonist activity and an $EC_{50}$ of 1.0-10.0 μM in the assay for cAMP antagonist activity. For example, compounds of the present invention have an $EC_{50}$ of 0.1-1.0 μM in the assay for β-arrestin agonist activity and an $EC_{50}$ of 10.0-30.0 μM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 1.0-10.0 μM in the assay for β-arrestin agonist activity and an $EC_{50}$<0.1 μM in the assay for cAMP antagonist activity. For example, compounds of the present invention have an $EC_{50}$ of 1.0-10.0 μM in the assay for β-arrestin agonist activity and an $EC_{50}$ of 0.1-1.0 μM in the assay for cAMP antagonist activity. For example, compounds of the present invention have an $EC_{50}$ of 1.0-10.0 μM in the assay for β-arrestin agonist activity and an $EC_{50}$ of 1.0-10.0 μM in the assay for cAMP antagonist activity. For example, compounds of the present invention have an $EC_{50}$ of 1.0-10.0 μM in the assay for β-arrestin agonist activity and an $EC_{50}$ of 10.0-30.0 μM in the assay for cAMP antagonist activity. Accordingly, compounds of the present invention are useful in treating or preventing a disease or disorder in which modulation of D2 receptors plays a role.

For example, compounds of the present invention have an $EC_{50}$ of 10.0-30.0 μM in the assay for β-arrestin agonist activity and an $EC_{50}$<0.1 μM in the assay for cAMP antagonist activity. For example, compounds of the present invention have an $EC_{50}$ of 10.0-30.0 μM in the assay for β-arrestin agonist activity and an $EC_{50}$ of 0.1-1.0 μM in the assay for cAMP antagonist activity. For example, compounds of the present invention have an $EC_{50}$ of 10.0-30.0 μM in the assay for β-arrestin agonist activity and an $EC_{50}$ of 1.0-10.0 μM in the assay for cAMP antagonist activity. For example, compounds of the present invention have an $EC_{50}$ of 10.0-30.0 μM in the assay for β-arrestin agonist activity and an $EC_{50}$ of 10.0-30.0 μM in the assay for cAMP antagonist activity. Accordingly, compounds of the present invention are useful in treating or preventing a disease or disorder in which modulation of D2 receptors plays a role.

For example, compounds of the present invention are selective β-arrestin agonists and antagonists of cAMP and β-arrestin. Accordingly, compounds of the present invention are useful in treating or preventing a disease or disorder in which modulation of D2 receptors plays a role.

For example, compounds of the present invention are β-arrestin agonists and cAMP agonists. For example, compounds of the present invention have an $EC_{50}$<0.1 μM in the assay for β-arrestin agonist activity and an $EC_{50}$<0.1 μM in the assay for cAMP agonist activity. For example, compounds of the present invention have an $EC_{50}$<0.1 μM in the assay for β-arrestin agonist activity and an $EC_{50}$ of 0.1-1.0 μM in the assay for cAMP agonist activity. For example, compounds of the present invention have an $EC_{50}$ of 0.1-1.0 μM in the assay for β-arrestin agonist activity and an $EC_{50}$ of 0.1-1.0 μM in the assay for cAMP agonist activity. For example, compounds of the present invention have an $EC_{50}$ of 0.1-1.0 μM in the assay for β-arrestin agonist activity and an $EC_{50}$ of 1.0-10.0 μM in the assay for cAMP agonist activity. For example, compounds of the present invention have an $EC_{50}$ of 1.0-10.0 μM in the assay for β-arrestin agonist activity and an $EC_{50}$ of 1.0-10.0 μM in the assay for cAMP agonist activity. For example, compounds of the present invention have an $EC_{50}$ of of 1.0-10.0 μM in the assay for β-arrestin agonist activity and an $EC_{50}$ of 10.0-30.0 μM in the assay for cAMP agonist activity. For example, compounds of the present invention have an $EC_{50}$ of 10.0-30.0 μM in the assay for β-arrestin agonist activity and an $EC_{50}$ of 10.0-30.0 μM in the assay for cAMP agonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

The present invention relates to novel compounds that modulate dopamine D2 receptors. For example, compounds of the present invention have an $EC_{50}$<0.1 μM in the assay for cAMP antagonist activity. For example, compounds of the present invention have an $EC_{50}$ of 0.1-1.0 μM in the assay for cAMP antagonist activity. For example, compounds of the present invention have an $EC_{50}$ of 1.0-10.0 μM in the assay for cAMP antagonist activity. For example, compounds of the present invention have an $EC_{50}$ of 10.0-30.0 μM in the assay for cAMP antagonist activity. Accordingly, compounds of the present invention are useful in treating or preventing a disease or disorder in which modulation of D2 receptors plays a role.

For example, compounds of the present invention are selective antagonists of D2 receptors. For example, compounds of the present invention are selective cAMP antagonists, but not β-arrestin antagonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger cAMP antagonist activity than β-arrestin antagonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for cAMP antagonist activity than β-arrestin antagonist activity. Accordingly, compounds of the present invention are useful in treating or preventing a disease or disorder in which modulation of D2 receptors plays a role.

For example, compounds of the present invention have an $EC_{50}$<0.1 μM in the assay for cAMP antagonist activity and an $EC_{50}$≥0.1 μM in the assay for β-arrestin antagonist activity. For example, compounds of the present invention have an $EC_{50}$<0.1 μM in the assay for cAMP antagonist activity and an $EC_{50}$ of 0.1-1.0 μM in the assay for β-arrestin antagonist activity. For example, compounds of the present invention have an $EC_{50}$<0.1 μM in the assay for cAMP antagonist activity and an $EC_{50}$ of 1.0-10.0 μM in the assay for β-arrestin antagonist activity. For example, compounds of the present invention have an $EC_{50}$<0.1 μM in the assay for cAMP antagonist activity and an $EC_{50}$ of 10.0-30.0 μM in the assay for β-arrestin antagonist activity. For example, compounds of the present invention have an $EC_{50}$<0.1 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of 0.1-1.0 μM in the assay for cAMP antagonist activity and an $EC_{50}$>1.0 μM in the assay for β-arrestin antagonist activity. For example, compounds of the present invention have an $EC_{50}$ of 0.1-1.0 μM in the assay for cAMP antagonist activity and an $EC_{50}$ of 1.0-10.0 μM in the assay for β-arrestin antagonist activity. For example, compounds of the present invention have an $EC_{50}$ of 0.1-1.0 μM in the assay for cAMP antagonist activity and an $EC_{50}$ of 10.0-30.0 μM in the assay for β-arrestin antagonist activity. For example, compounds of the present invention have an $EC_{50}$ of 0.1-1.0 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of 1.0-10.0 μM in the assay for cAMP antagonist activity and an $EC_{50}$>10.0 μM in the assay for β-arrestin antagonist activity. For example, compounds of the present invention have an $EC_{50}$ of of 1.0-10.0 μM in the assay for cAMP antagonist activity and an $EC_{50}$ of 10.0-30.0 μM in the assay for β-arrestin antagonist activity. For example, compounds of the present invention have an $EC_{50}$ of of 1.0-10.0 μM in the assay for cAMP antagonist activity and an $EC_{50}$≥30.0 μM in the assay for β-arrestin antagonist activity. Accordingly, compounds of the present invention are useful in treating or preventing a disease or disorder in which modulation of D2 receptors plays a role.

For example, compounds of the present invention have an $EC_{50}$ of of 10.0-30.0 μM in the assay for cAMP antagonist activity and an $EC_{50}$>30.0 μM in the assay for β-arrestin antagonist activity. Accordingly, compounds of the present invention are useful in treating or preventing a disease or disorder in which modulation of D2 receptors plays a role.

For example, compounds of the present invention are selective cAMP antagonists and β-arrestin agonists. For example, compounds of the present invention have an $EC_{50}$<0.1 μM in the assay for cAMP antagonist activity and an $EC_{50}$<0.1 μM in the assay for β-arrestin agonist activity. For example, compounds of the present invention have an $EC_{50}$<0.1 μM in the assay for cAMP antagonist activity and an $EC_{50}$ of 0.1-1.0 μM in the assay for β-arrestin agonist activity. For example, compounds of the present invention have an $EC_{50}$<0.1 μM in the assay for cAMP antagonist activity and an $EC_{50}$ of 1.0-10.0 μM in the assay for β-arrestin agonist activity. For example, compounds of the present invention have an $EC_{50}$<0.1 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 0.1-1.0 μM in the assay for cAMP antagonist activity and an $EC_{50}$<0.1 μM in the assay for β-arrestin agonist activity. For example, compounds of the present invention have an $EC_{50}$ of 0.1-1.0 μM in the assay for cAMP antagonist activity and an $EC_{50}$ of 0.1-1.0 μM in the assay for β-arrestin agonist activity. For example, compounds of the present invention have an $EC_{50}$ of 0.1-1.0 μM in the assay for cAMP antagonist activity and an $EC_{50}$ of 1.0-10.0 μM in the assay for β-arrestin agonist activity. For example, compounds of the present invention have an $EC_{50}$ of 0.1-1.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 1.0-10.0 μM in the assay for cAMP antagonist activity and an $EC_{50}$<0.1 μM in the assay for β-arrestin agonist activity. For example, compounds of the present invention have an $EC_{50}$ of 1.0-10.0 μM in the assay for cAMP antagonist activity and an $EC_{50}$ of 0.1-1.0 μM in the assay for β-arrestin agonist activity. For example, compounds of the present invention have an $EC_{50}$ of 1.0-10.0 μM in the assay for cAMP antagonist activity and an $EC_{50}$ of 1.0-10.0 μM in the assay for β-arrestin agonist activity. For example, compounds of the present invention have an $EC_{50}$ of 1.0-10.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 10.0-30.0 μM in the assay for cAMP antagonist activity and an $EC_{50}$<0.1 μM in the assay for β-arrestin agonist activity. For example, compounds of the present invention have an $EC_{50}$ of 10.0-30.0 μM in the assay for cAMP antagonist activity and an $EC_{50}$ of 0.1-1.0 μM in the assay for β-arrestin agonist activity. For example, compounds of the present invention have an $EC_{50}$ of 10.0-30.0 μM in the assay for cAMP antagonist activity and an $EC_{50}$ of 1.0-10.0 μM in the assay for β-arrestin agonist activity. For example, compounds of the present invention have an $EC_{50}$ of 10.0-30.0 μM in the assay for cAMP antagonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

For example, compounds of the present invention are selective cAMP antagonists and agonists of cAMP and β-arrestin. Accordingly, compounds of the present invention are useful in treating or preventing a disease or disorder in which modulation of D2 receptors plays a role.

For example, compounds of the present invention are cAMP antagonists and β-arrestin antagonists. For example, compounds of the present invention have an $EC_{50}$<0.1 μM in the assay for cAMP antagonist activity and an $EC_{50}$<0.1 μM in the assay for β-arrestin antagonist activity. For example, compounds of the present invention have an $EC_{50}$<0.1 µM in the assay for cAMP antagonist activity and an $EC_{50}$ of 0.1-1.0 µM in the assay for β-arrestin antagonist activity. For example, compounds of the present invention have an $EC_{50}$ of 0.1-1.0 µM in the assay for cAMP antagonist activity and an $EC_{50}$ of 0.1-1.0 µM in the assay for β-arrestin antagonist activity. For example, compounds of the present invention have an $EC_{50}$ of 0.1-1.0 µM in the assay for cAMP antagonist activity and an $EC_{50}$ of 1.0-10.0 µM in the assay for β-arrestin antagonist activity. For example, compounds of the present invention have an $EC_{50}$ of 1.0-10.0 µM in the assay for cAMP antagonist activity and an $EC_{50}$ of 1.0-10.0 µM in the assay for β-arrestin antagonist activity. For example, compounds of the present invention have an $EC_{50}$ of of 1.0-10.0 µM in the assay for cAMP antagonist activity and an $EC_{50}$ of 10.0-30.0 µM in the assay for β-arrestin antagonist activity. For example, compounds of the present invention have an $EC_{50}$ of 10.0-30.0 µM in the assay for cAMP antagonist activity and an $EC_{50}$ of 10.0-30.0 µM in the assay for β-arrestin antagonist activity. Accordingly, compounds of the present invention are useful in treating or preventing a disease or disorder in which modulation of D2 receptors plays a role.

The present invention relates to novel compounds that modulate dopamine D2 receptors. For example, compounds of the present invention have an $EC_{50}$<0.1 µM in the assay for cAMP agonist activity. For example, compounds of the present invention have an $EC_{50}$ of 0.1-1.0 µM in the assay for cAMP agonist activity. For example, compounds of the present invention have an $EC_{50}$ of 1.0-10.0 µM in the assay for cAMP agonist activity. For example, compounds of the present invention have an $EC_{50}$ of 10.0-30.0 µM in the assay for cAMP agonist activity. Accordingly, compounds of the present invention are useful in treating or preventing a disease or disorder in which modulation of D2 receptors plays a role.

For example, compounds of the present invention are selective agonists of D2 receptors. For example, compounds of the present invention are selective cAMP agonists, but not β-arrestin agonists. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold stronger cAMP agonist activity than β-arrestin agonist activity. For example, compounds of the present invention display at least 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, or 100-fold decrease in $EC_{50}$ for cAMP agonist activity than β-arrestin agonist activity.

For example, compounds of the present invention have an $EC_{50}$<0.1 µM in the assay for cAMP agonist activity and an $EC_{50}$≥0.1 µM in the assay for β-arrestin agonist activity. For example, compounds of the present invention have an $EC_{50}$<0.1 µM in the assay for cAMP agonist activity and an $EC_{50}$ of 0.1-1.0 µM in the assay for β-arrestin agonist activity. For example, compounds of the present invention have an $EC_{50}$<0.1 µM in the assay for cAMP agonist activity and an $EC_{50}$ of 1.0-10.0 µM in the assay for β-arrestin agonist activity. For example, compounds of the present invention have an $EC_{50}$<0.1 µM in the assay for cAMP agonist activity and an $EC_{50}$ of 10.0-30.0 µM in the assay for β-arrestin agonist activity. For example, compounds of the present invention have an $EC_{50}$<0.1 µM in the assay for cAMP agonist activity and an $EC_{50}$≥30.0 µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 0.1-1.0 µM in the assay for cAMP agonist activity and an $EC_{50}$>1.0 µM in the assay for β-arrestin agonist activity. For example, compounds of the present invention have an $EC_{50}$ of 0.1-1.0 µM in the assay for cAMP agonist activity and an $EC_{50}$ of 1.0-10.0 µM in the assay for β-arrestin agonist activity. For example, compounds of the present invention have an $EC_{50}$ of 0.1-1.0 µM in the assay for cAMP agonist activity and an $EC_{50}$ of 10.0-30.0 µM in the assay for β-arrestin agonist activity. For example, compounds of the present invention have an $EC_{50}$ of 0.1-1.0 µM in the assay for cAMP agonist activity and an $EC_{50}$≥30.0 µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of 1.0-10.0 µM in the assay for cAMP agonist activity and an $EC_{50}$>10.0 µM in the assay for β-arrestin agonist activity. For example, compounds of the present invention have an $EC_{50}$ of of 1.0-10.0 µM in the assay for cAMP agonist activity and an $EC_{50}$ of 10.0-30.0 µM in the assay for β-arrestin agonist activity. For example, compounds of the present invention have an $EC_{50}$ of of 1.0-10.0 µM in the assay for cAMP agonist activity and an $EC_{50}$≥30.0 µM in the assay for β-arrestin agonist activity. Accordingly, compounds of the present invention are useful in treating or preventing a disease or disorder in which modulation of D2 receptors plays a role.

For example, compounds of the present invention have an $EC_{50}$ of of 10.0-30.0 µM in the assay for cAMP agonist activity and an $EC_{50}$≥30.0 µM in the assay for β-arrestin agonist activity. Accordingly, compounds of the present invention are useful in treating or preventing a disease or disorder in which modulation of D2 receptors plays a role.

For example, compounds of the present invention are selective cAMP agonists and β-arrestin antagonists. For example, compounds of the present invention have an $EC_{50}$<0.1 µM in the assay for cAMP agonist activity and an $EC_{50}$<0.1 µM in the assay for β-arrestin antagonist activity. For example, compounds of the present invention have an $EC_{50}$<0.1 µM in the assay for cAMP agonist activity and an $EC_{50}$ of 0.1-1.0 µM in the assay for β-arrestin antagonist activity. For example, compounds of the present invention have an $EC_{50}$<0.1 µM in the assay for cAMP agonist activity and an $EC_{50}$ of 1.0-10.0 µM in the assay for β-arrestin antagonist activity. For example, compounds of the present invention have an $EC_{50}$<0.1 µM in the assay for cAMP agonist activity and an $EC_{50}$ of 10.0-30.0 µM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 0.1-1.0 µM in the assay for cAMP agonist activity and an $EC_{50}$<0.1 µM in the assay for β-arrestin antagonist activity. For example, compounds of the present invention have an $EC_{50}$ of 0.1-1.0 µM in the assay for cAMP agonist activity and an $EC_{50}$ of 0.1-1.0 µM in the assay for β-arrestin antagonist activity. For example, compounds of the present invention have an $EC_{50}$ of 0.1-1.0 µM in the assay for cAMP agonist activity and an $EC_{50}$ of 1.0-10.0 µM in the assay for β-arrestin antagonist activity. For example, compounds of the present invention have an $EC_{50}$ of 0.1-1.0 µM in the assay for cAMP agonist activity and an $EC_{50}$ of 10.0-30.0

μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 1.0-10.0 μM in the assay for cAMP agonist activity and an $EC_{50}$<0.1 μM in the assay for β-arrestin antagonist activity. For example, compounds of the present invention have an $EC_{50}$ of 1.0-10.0 μM in the assay for cAMP agonist activity and an $EC_{50}$ of 0.1-1.0 μM in the assay for β-arrestin antagonist activity. For example, compounds of the present invention have an $EC_{50}$ of 1.0-10.0 μM in the assay for cAMP agonist activity and an $EC_{50}$ of 1.0-10.0 μM in the assay for β-arrestin antagonist activity. For example, compounds of the present invention have an $EC_{50}$ of 1.0-10.0 μM in the assay for cAMP agonist activity and an $EC_{50}$ of 10.0-30.0 μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention have an $EC_{50}$ of 10.0-30.0 μM in the assay for cAMP agonist activity and an $EC_{50}$<0.1 μM in the assay for β-arrestin antagonist activity. For example, compounds of the present invention have an $EC_{50}$ of 10.0-30.0 μM in the assay for cAMP agonist activity and an $EC_{50}$ of 0.1-1.0 μM in the assay for β-arrestin antagonist activity. For example, compounds of the present invention have an $EC_{50}$ of 10.0-30.0 μM in the assay for cAMP agonist activity and an $EC_{50}$ of 1.0-10.0 μM in the assay for β-arrestin antagonist activity. For example, compounds of the present invention have an $EC_{50}$ of 10.0-30.0 μM in the assay for cAMP agonist activity and an $EC_{50}$ of 10.0-30.0 μM in the assay for β-arrestin antagonist activity. Accordingly, compounds of the present invention are useful in treating or preventing a disease or disorder in which modulation of D2 receptors plays a role, while at the same time, can reduce the undesirable side effects associated with D2 receptor activity (e.g., side effects arising from antagonizing the cAMP pathway).

For example, compounds of the present invention are selective cAMP agonists and antagonists of cAMP and β-arrestin. Accordingly, compounds of the present invention are useful in treating or preventing a disease or disorder in which modulation of D2 receptors plays a role.

For example, compounds of the present invention are cAMP agonists and β-arrestin agonists. For example, compounds of the present invention have an $EC_{50}$<0.1 μM in the assay for cAMP agonist activity and an $EC_{50}$<0.1 μM in the assay for β-arrestin agonist activity. For example, compounds of the present invention have an $EC_{50}$<0.1 μM in the assay for cAMP agonist activity and an $EC_{50}$ of 0.1-1.0 μM in the assay for β-arrestin agonist activity. For example, compounds of the present invention have an $EC_{50}$ of 0.1-1.0 μM in the assay for cAMP agonist activity and an $EC_{50}$ of 0.1-1.0 μM in the assay for β-arrestin agonist activity. For example, compounds of the present invention have an $EC_{50}$ of 0.1-1.0 μM in the assay for cAMP agonist activity and an $EC_{50}$ of 1.0-10.0 μM in the assay for β-arrestin agonist activity. For example, compounds of the present invention have an $EC_{50}$ of 1.0-10.0 μM in the assay for cAMP agonist activity and an $EC_{50}$ of 1.0-10.0 μM in the assay for β-arrestin agonist activity. For example, compounds of the present invention have an $EC_{50}$ of 1.0-10.0 μM in the assay for cAMP agonist activity and an $EC_{50}$ of 10.0-30.0 μM in the assay for β-arrestin agonist activity. For example, compounds of the present invention have an $EC_{50}$ of 10.0-30.0 μM in the assay for cAMP agonist activity and an $EC_{50}$ of 10.0-30.0 μM in the assay for β-arrestin agonist activity. Accordingly, compounds of the present invention are useful in treating or preventing a disease or disorder in which modulation of D2 receptors plays a role.

Abbreviations

Binap 2,2'-bis(diphenylphosphino)-1,1'-binaphthyl
Boc: tert-butyloxycarbonyl
t-BuOK: potassium tert-butoxide
DAST: diethylaminosulfur trifluoride
Dba: Dibenzylideneacetone
DCM: Dichloromethane
DIPEA: N,N-diisopropylethylamine
DMF: N,N-dimethylformamide
DMP: Dess Martin periodinane
DMSO: Dimethylsulfoxide
DMU: N-Nitroso-N-methylurea
EDCI: 1-Ethyl-3-(3-dimethylaminopropyl)carbodiimide
$Et_2O$: diethyl ether
EtOAc: ethyl acetate
EtOH: Ethanol
$Et_3N$: Triethylamine
Fmoc: 9-fluorenylmethoxycarbonyl
HATU: 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide
HOBt: Hydroxybenzotriazole
LAH: lithium aluminium hydride
MeOH: Methanol
[O]: oxidation using suitable oxidants such as Dess Martin periodinane, pyridinium chlorochromate, pyridinium dichromate, or oxidation reagents used in Swern oxidation, Parikh-Doering oxidation, Corey-Kim oxidation or Pfitzner-Moffatt oxidation
MS: mass spectrometry
MsCl: Methanesulfonyl chloride
$Pd(OAc)_2$: Palladium(II) acetate
TPP: Triphenyl phosphine
THF: Tetrahydrofuran
TFA: trifluoroacetic acid The terms "compounds of the invention", "compound of the invention", "compounds of the present invention" and "compounds of the present invention", and the like, unless the context indicates otherwise, refer collectively to the novel compounds of any formulae or specific compounds described herein, and their salts, solvates, stereoisomers, tautomers, racemates, polymorphs and hydrates.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl. For example "1-6" is intended to encompass, 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6.

As used herein, the term "halogen" refers to fluorine, chlorine, bromine or iodine.

As used herein, the term "alkyl" refers to a radical of a straight-chain or branched saturated hydrocarbon group having from 1 to 20 carbon atoms ("$C_1$-$C_{20}$ alkyl"). In some embodiments, an alkyl group has 1 to 10 carbon atoms ("$C_1$-$C_{10}$ alkyl"). In some embodiments, an alkyl group has 1 to 9 carbon atoms ("$C_1$-$C_9$ alkyl"). In some embodiments, an alkyl group has 1 to 8 carbon atoms ("$C_1$-$C_8$ alkyl"). In some embodiments, an alkyl group has 1 to 7 carbon atoms ("$C_1$-$C_7$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$ alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, e.g., unsubstituted (an "unsubstituted alkyl") or substituted (a "substituted alkyl") with one or more substituents.

The term "substituted alkyl" refers to alkyl moieties having substituents replacing one or more hydrogen atoms on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_1$-$C_8$ haloalkyl"). In some embodiments, the haloalkyl moiety has 1 to 6 carbon atoms ("$C_1$-$C_6$ haloalkyl"). In some embodiments, the haloalkyl moiety has 1 to 4 carbon atoms ("$C_1$-$C_4$ haloalkyl"). In some embodiments, the haloalkyl moiety has 1 to 3 carbon atoms ("$C_1$-$C_3$ haloalkyl"). In some embodiments, the haloalkyl moiety has 1 to 2 carbon atoms ("$C_1$-$C_2$ haloalkyl"). Examples of haloalkyl groups include —$CH_2F$, —$CHF_2$, —$CF_3$, —$CH_2CF_3$, —$CF_2CF_3$, —$CF_2CF_2CF_3$, —$CCl_3$, —$CFCl_2$, —$CF_2Cl$, and the like.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=$CHCH_3$ or

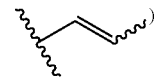

) may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$-6 alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, the term "cyclic ring" or "cyclic group" refers to a saturated or unsaturated carbocyclic ring, i.e., a ring composed exclusively of carbon atoms, or to a saturated or unsaturated heterocyclic ring, i.e., a carbocyclic ring wherein one or more ring atoms are replaced with an heteroatom independently selected from oxygen, nitrogen, and sulfur. Cyclic rings may involve 3-10 atoms that form the ring. In some embodiments, the cyclic rings involve 3-5 ring atoms, in other embodiments, the cyclic rings involve 4-6 ring atoms, in yet other embodiments, cyclic rings involve 5-7 ring atoms. The cyclic rings can be monocyclic rings or fused systems that may include bicyclic rings, for example, 5-5, 5-6, 6-5, 6-6 as well as spirocyclic systems such as 4-4, 4-5, 4-6, 5-6 and 6-6. The cyclic ring may be further substituted with substituents such as C1-C6 alkyl (linear, branched, cyclic or heterocyclic): In some embodiments, cyclic groups may include pseudo-cyclic groups comprising straight- or branched substituted or subsubstituted alkyl groups, for example $C_3$-$C_{10}$ alkyl groups.

As used herein, the term "cycloalkyl" refers to a saturated or unsaturated cyclic monovalent hydrocarbon, containing one or two rings and comprising 3-10 ring atoms, preferably 4-8 ring atoms, and more preferably 5-6 ring carbon atoms. Examples of a cycloalkyl useful in the context of the present invention are cyclopropyl, cyclobutyl, cyclopentyl, cyclohexyl, cycloheptyl and cyclooctyl, preferably cyclopentyl and cyclohexyl, more preferably cyclohexyl. Cycloalkyl also includes hydrocarbon spirocyclique groups.

As used herein, the term "heterocyclyl" refers to a saturated or unsaturated cycloalkyl wherein one or more ring atoms are replaced with an heteroatom independently selected from oxygen, nitrogen, and sulfur. The term heterocyclyl also encompasses partially hydrogenated and oxo derivatives of heteroaryl compounds. Examples of a heterocyclyl useful in the context of the present invention are pyrrolidinyl, tetrahydrofuranyl, tetrahydrothiophenyl, piperidinyl, tetrahydropyranyl, tetrahydrothiopyranyl, imidazolidinyl, pyrazolidinyl, oxazolidinyl, isoxazolidinyl, thiazolidinyl, isothiazolidinyl, dioxolanyl, and dithiolanyl.

As used herein, the term "bicyclic group" refers to a group containing two cyclic groups, with 5-12 or 6-12 ring atoms, optionally containing 1-3 heteroatoms independently selected from nitrogen, oxygen or sulfur, said two cyclic groups being fused or bridged or forming a spirocycle. Preferably, the two cyclic groups are fused and one of the two cyclic groups is a phenyl while the other is a cycloalkyl or heterocycloalkyl, wherein the phenyl, cycloalkyl and heterocycloalkyl are independently optionally substituted. Examples of a bicyclic group useful in the context of the present invention are oxo-tetrahydroquinolinyl, benzodioxolyl, difluorobenzodioxolyl and dihydroindenyl. Each cycle in the bicyclic group can be independently aromatic, unsaturated, partially saturated, or saturated.

As used herein, the term "spirocycle" refers to a bicyclic compound wherein the two cyclic groups connect only through one atom.

Further examples of bicyclic groups include bridged ring systems such as bicycloalkanes and azabicycloalkanes although such bridged ring systems are generally less preferred. By "bridged ring systems" is meant ring systems in which two rings share more than two atoms, see for example Advanced Organic Chemistry, by Jerry March, 4th. Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

As used herein, the term "aryl" refers to a polyunsaturated aromatic carbocyclic group comprising one ring (i.e., phenyl) or several fused rings (for example naphthyl) or several rings linked via a covalent bond (for example biphenyl), which typically contain 5 to 12 and preferentially 6 to 10 carbon atoms, and wherein at least one ring is aromatic. Examples of an aryl useful in the context of the present invention are phenyl, naphtyl and biphenyl, preferably phenyl.

As used herein, the term "heteroaryl" refers to an aryl containing 1-4 ring heteroatoms independently selected from nitrogen, oxygen, and sulfur. The nitrogen heteroatom may be substituted or unsubstituted with substituents, for example with an alkyl group and/or the nitrogen heteroatom may be derivatised to form a salt or amine oxide. Examples of a heteroaryl useful in the context of the present invention are furyl, thienyl, pyrrolyl, pyranyl, thiopyranyl, imidazolyl, pyrazolyl, oxazolyl, isoxazolyl, thiazolyl, isothiazolyl, pyridyl, quinolinyl, isoquinolinyl, indolyl, benzofuranyl, benzoxazolyl, benzisoxazolyl, benzothiazolyl, benzisothiazolyl, benzoimidazolyl and benzopyrazole, preferably pyridyl, quinolinyl, benzofuranyl, benzoxazolyl and benzothiazolyl.

The terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, and indolizine. In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran. Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "x- to y-membered ring" (wherein x is an integer independently selected from 3, 4, 5, 6, 7, and 8, preferably from 3, 4, and 5, and more preferably from 3 and 4; and y is an integer independently selected from 4, 5, 6, 7, 8, 9, 10, 11, and 12, preferably from 5, 6, 7, 8, and 9, and 10) includes cyclic ring, cyclic group, carbocycle, heterocycle, aryl, and heteroaryl, each having x- to y-number of ring atoms, as defined herein.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is independently selected independently from the definition of $R_1$. Also, combinations of substituents and/or variables are permissible, but only if such combinations result in stable compounds.

Except as described herein, any of the above defined alkyl, cycloalkyl, aryl, heteroaryl, carbocycle, heterocycle, and alkoxy, may be unsubstituted or independently substituted with up to six, preferably one, two or three substituents, independently selected from the group consisting of: halo (such as F, Cl or Br); hydroxy; lower alkyl (such as $C_1$-$C_6$ alkyl, $C_1$-$C_3$ alkyl), wherein the lower alkyl may be substituted with any of the substituents defined herein; lower alkanoyl; lower alkoxy (such as methoxy); aryl (such as phenyl or naphthyl); substituted aryl (such as fluoro phenyl or methoxy phenyl); aryl lower alkyl such as benzyl; amino; mono or di-lower alkyl amino (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or iso-propoxy carbonyl); lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono(—P(=O)(OH)$_2$); hydroxy-lower alkoxy phosphoryl or di-lower alkoxyphosphoryl; urea and substituted urea; and alkyl carbamic acid ester or carbamates (such as ethyl-N-phenylcarbamate).

The compounds of the present invention are capable of further forming salts. All of these forms are also contemplated within the scope of the claimed invention.

As used herein, a salt of the compound of the invention refers to derivatives of the compounds of the present invention wherein the parent compound is modified by making acid or base salts thereof. Examples of salts include, but are not limited to, mineral or organic acid salts of basic residues such as amines, alkali or organic salts of acidic residues such as carboxylic acids, and the like. The salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids independently selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of salts of the compounds of the invention include salts with the following acid: hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The free base of the compounds of the present invention can be protonated at the N atom(s) of an amine and/or N containing heterocycle moiety to form a salt. The term "free base" refers to the amine compounds in non-salt form. The free form of the specific salt compounds described may be isolated using techniques known in the art. For example, the free form may be regenerated by treating the salt with a suitable dilute aqueous base solution such as dilute aqueous sodium hydroxide, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The salts can be synthesized from the compounds of the invention which contain basic moieties by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents.

The salts of the instant invention can be prepared from compounds of the invention by reacting with an inorganic, organic acid or polymeric acid. For example, conventional non-toxic salts include those derived from acids such as hydrochloric acid, toluenesulfonic acid, sulfuric acid, benzenesulfonic acid, fumaric acid or succinic acid, especially toluenesulfonic acid, pamoic acid (see for example, WO2005/016261; U.S. Pat. No. 6,987,111; US 20050032836; US 20060040922).

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

As used herein, the term "combination", as applied to two or more compounds and/or agents (also referred to herein as the components), is intended to define material in which the two or more compounds/agents are associated. The terms "combined" and "combining" in this context are to be interpreted accordingly.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g., before or after) or simultaneously, either in the same pharmaceutical formulation (i.e., together), or in different pharmaceutical formulations (i.e., separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

The term "drug" or "active substance" as used herein includes the free base, or pharmaceutically acceptable salts, solvates, stereoisomers, racemates, tautomers, polymorphs and hydrates thereof, or mixtures thereof.

As used herein, the term "selective" when used to describe β-arrestin antagonist, β-arrestin agonist, cAMP antagonist, or cAMP agonist means "biased" β-arrestin antagonist, β-arrestin agonist, cAMP antagonist, or cAMP agonist, unless the specific circumstances dictate otherwise (i.e., "selective" and "biased" are used interchangeably). The term "selective" or "biased" means that a compound preferentially binds to or otherwise interacts with one of β-arrestin and cAMP over the other. For example, the compound binds to or otherwise interacts with one of β-arrestin and cAMP with an $EC_{50}$ that is lower that the $EC_{50}$ for the other, such as described herein.

Synthesis of the Compounds of the Invention

The present invention provides methods for the synthesis of the compounds of each of the formulae described herein. The present invention also provides detailed methods for the synthesis of various disclosed compounds of the present invention according to the following schemes and examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; and Greene, T. W., Wuts, P. G. M., *Protective Groups in Organic Synthesis,* $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds each of the formulae described herein may be prepared according to the following procedure, together with synthetic methods known in the art of synthetic organic chemistry, or variations thereon as appreciated by those skilled in the art from commercially available starting materials or starting materials which can be prepared using literature procedures. These procedures show the preparation of representative compounds of the invention.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

Preferred methods include but are not limited to those methods described below. Compounds of the present invention can be synthesized by following the steps outlined in General Scheme 1 which comprise different sequences of assembling intermediates Ia, Ib, Ic, Id, Ie, If, Ig, Ih, Ii, Ik, and Il. Starting materials are either commercially available or made by known procedures in the reported literature or as illustrated.

General Scheme 1

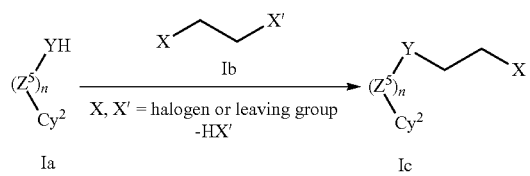

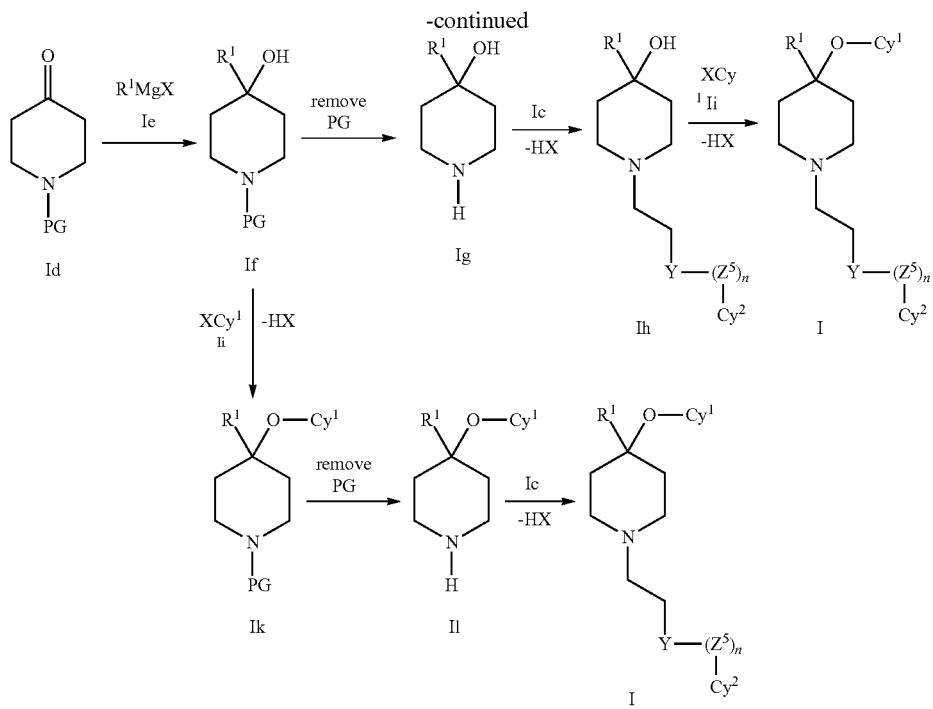

The general way of preparing target molecules I by using intermediates Ia, Ib, Ic, Id, Ie, Ig, Ih, Ii, Ik, and Il is outlined in General Scheme 1. Nucleophilic addition of Ia to Ib using a base, i.e., potassium carbonate ($K_2CO_3$) or sodium hydroxide (NaOH), in solvent, i.e., acetone or water, at elevated temperatures provides intermediate Ic. Alkylation of ketone Id with Grignard reagent Ie in a solvent, i.e., tetrahydrofuran or diethylether, provides intermediate If. Removal of the amine protecting group, i.e., di-tert-butyl dicarbonate, of If yields intermediate Ig. Alkylation of Ig with intermediate Ic using a base, i.e., potassium carbonate ($K_2CO_3$), in solvent, i.e., acetonitrile, at elevated temperatures provides intermediate Ih. Alkylation of Ih with intermediate Ii using a base, i.e., sodium hydride, in solvent, i.e., tetrahydrofuran, at elevated temperatures provides the compound of Formula (I). Alternatively, treatment of intermediate If with intermediate Ii and a base, i.e., sodium hydride, in solvent, i.e., tetrahydrofuran, at elevated temperatures provides intermediate Ik. Subsequent removal of the amine protecting group, i.e., di-tert-butyl dicarbonate, of Ik yields intermediate Il. Alkylation of Il with intermediate Ic using a base, i.e., potassium carbonate ($K_2CO_3$), in solvent, i.e., acetonitrile, at elevated temperatures provides the compound of Formula (I).

Assays for Activities of the Compounds of the Invention

The present invention provides methods for assessing the in vitro and in vivo biological activities (e.g., antagonistic or agonistic activities) of the compounds of the invention. Biological activities (e.g., antagonistic or agonistic activities) of the compounds of the present invention can be tested in a variety of ways using commercially available materials, reagents known in the literature or readily prepared, by employing routine methods and procedures either known to those skilled in the art, or which will be apparent to the skilled artisan in light of the teachings herein. Theses methods and procedures can be obtained from the relevant scientific literature or from standard textbooks in the field. The following descriptions of assays are designed to illustrate, but not to limit, general procedures for evaluating the activities of compounds of the present invention.

A general description of the assays is presented below.
Preparation of Cells for Biological Assays Cells are prepared for assays by growing cultures for the requisite period of time (e.g., up to 2 weeks). Frozen cells are thawed, and then transferred into growth media. If necessary, the cells can be gently centrifuged and then resuspended in growth media. When the cells reached the necessary confluence (e.g., ~95%), the cells are passaged and used for various biological assays, such as those described herein below.

β-Arrestin Agonist Assay

The assays can be performed using proper detection reagents either prepared using routine methods known in the art or commercially available (e.g., PathHunter® β-Arrestin Detecting Kit (DiscoveR$_X$)). Cells are grown to the necessary confluence and then detached. The cells are then centrifuged, washed, resuspended, and seeded into a container (e.g., 384-well plate). The cells are incubated (e.g., at 37° C., 5% $CO_2$) for the appropriate period of time (e.g., 24 hours), before various compounds (e.g., a compound of the invention or a control compound) are added to the cells. After incubation of the cells with the compounds, detection reagents (e.g., a buffer containing Emerald II: Galactor-Star as provided DiscoveR$_X$) are added to the cells. The read-out (e.g., luminescence, or fluorescence) is detected using standard equipment.

β-Arrestin Antagonist Assay

The assays can be conducted in the same manner as the β-arrestin agonist assay, except that before addition of the detection reagents, a D2 receptor agonist (e.g., Quinpirole) is added to the cells. The detection reagents are then added, and the read-out is detected.

Gi/cAMP Agonist Assay

The assays can be performed using proper detection reagents either prepared using routine methods known in the art or commercially available (e.g., PE Lance Ultra cAMP kit (TRF0263)). Cells are grown to the necessary confluence and then detached. The cells are then centrifuged, washed, resuspended, and seeded into a container (e.g., a 384-well plate). The cells are incubated (e.g., at 37° C., 5% $CO_2$) for the appropriate period of time (e.g., 24 hours), before various compounds (e.g., a compound of the invention or a control compound) are added to the cells. Afterwards, cAMP inducing agents (e.g., Forskolin) are added to and incubated with the cells before detection reagents (e.g., a cAMP antibody, such as ULight-anti-cAMP solution) are added to the cells. Read-out (e.g., luminescence, or fluorescence) is detected using standard equipment.

Gi/cAMP Antagonist Assay

The assays can be conducted in the same manner as the Gi/cAMP agonist assay, except that before addition of the detection reagents, a D2 receptor agonist (e.g., Quinpirole) is added to the cells. The detection reagents are then added, and the read-out is detected.

Pharmacokinetic Studies on Mice Brains

Test animals are administered (e.g., intraperitoneally, intravenously, orally) with a dose of test compounds (e.g., compounds of the invention). Blood samples are collected and plasma is harvested from the blood. Brain tissues are also isolated and homogenized. Concentrations of the test compounds administered in the plasma and brain samples are determined using routine analytic methods, such as LC-MS/MS.

Positron Emission Tomography Studies on Rodents

Non-radiolabeled test compounds (e.g., vehicle, compounds of the invention, control compounds) are administered to the test animal, followed by administration of a radiotracer (e.g., carbon 11-labeled raclopride ([$^{11}$C]RAC), which can be synthesized from the O-desmethyl RAC precursor and [11C] methyl iodide and subsequently purified by high-performance liquid chromatography as previously described (Farde L, et al. (1985) PNAS, USA 82(11):3863-3867)). Positron emission tomography (PET) and skeletal computed tomography (CT) data are collected using standard equipment, such as a GammaMedica Triumph trimodal PET/SPECT/CT scanner (Quebec, Canada) or a Concorde Microsystems R4 microPET scanner (Knoxville, TN, USA). Routine data processing is employed, including substraction of random coincidences collected in a delayed time window, and reconstruction of scatter-corrected sinograms using a known algorithm (e.g., 3-dimensional iterative maximum likelihood expectation maximization (3D-MLEM) algorithm). Regions of Interest (ROIs) are drawn on reconstructed images estimating peak [$^{11}$C]RAC uptake in striata (averaged between left and right hemispheres) and cerebellum as reference region for non-displaceable (ND) tracer uptake. ROI dimensions, placement and striatal D2/D3 binding potential ($BP_{ND}$) are evaluated by graphical analysis (e.g., using Logan distribution volume ratio (DVR) linearization as previously described ($BP_{ND}$. DVR-1; Alexoff D, et al. (2002) J Nuc Med 44(5): 815-822; Logan J, et al. (1996) J Cerebral Blood Flow and Metabolism 16(5):843-840)).

Amphetamine Induced Hyperactivity Studies

Amphetamine-induced hyperactivity (AIH) can be examined using routine behavior methods, such as in open-field chambers. Activity is detected by various methods, such as infrared beam. Daily sessions are binned for statistical analysis. AIH can be run over various time frames, according to the need of the study, such as follows:

Day 1: test animals are acclimated to the injection procedure by injecting prior to being placed in the chambers. Test animals are then placed into the open-field a certain time period (e.g., 20 min) and then removed for a saline injection. Test animals are placed back into the open-field for an additional period of time (e.g., 30 min), at which point the test animals are returned to their home cage.

Day 2: repeat Day 1, with the exception that the timing may be different (e.g., the second day may last for one hour (20 minutes→injection→40 minutes)).

Day 3: test animals are challenged by amphetamine. Test animals are pre-treated with D2 antagonist compounds (e.g., compounds of the invention) prior to being placed in the open field. After a certain period of time, test animals are removed and challenged with amphetamine, following protocols known to one skilled in the art, for example Jones C. A, et. al. Br J Pharmacol. 2011, 164(4):1162-1194; Pan J Q, et. al. Neuropsychopharmacology. 2011, 36(7):1397-1411.

Rotarod Performance

In the test, test animals are placed on a horizontally oriented, rotating cylinder (rod) suspended above a cage floor. The test animals naturally try to stay on the rotating cylinder, or rotarod, and avoid falling to the ground. Test animals are administered with various compounds (e.g., compounds of the invention or control compounds). The length of time that a given animal stays on this rotating rod is a measure of the animal's balance, coordination, physical condition, and motor-planning. The speed of the rotarod is mechanically driven, and can be held constant.

Pharmaceutical Compositions

The present invention also provides a pharmaceutical composition comprising a compound of any formulae or independently selected from any compounds described herein, and at least one pharmaceutically acceptable excipient or carrier. In one embodiment, the present invention relates to pharmaceutical composition comprising a compound of any one of Formulae (I)-(X), or a pharmaceutically acceptable salt, stereoisomer, racemate, tautomer, polymorph, hydrate, or solvate thereof, and one or more pharmaceutically acceptable excipients or carriers.

The term "pharmaceutical composition" is defined herein as comprising an effective amount of at least one active substance (e.g., compounds of the present invention), and at least one pharmaceutically acceptable carrier or excipient, in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, parenteral, topical, intranasal, ophthalmic, otic, rectal, transdermal, and transmucosal, and the like. Dosage forms for the topical or transdermal administration of a compound of the invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The term "pharmaceutically acceptable" as used herein pertains to compounds, materials, compositions, and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "pharmaceutically acceptable carrier or excipient" refers to a carrier medium which does not interfere with the effectiveness of the biological activity of the active compound(s) and which is not excessively toxic to the host at the concentration at which it is administered. The term includes solvents, dispersion media, coatings, isotonic agents, adsorption delaying agents, and the like. The use of such media and agents for pharmaceutically active substances is well known in the art (see for example", E. W. Martin, $18^{th}$ Ed., 1990, Mack Publishing Co.: Easton, PA, which is incorporated herein by reference in its entirety). In certain embodiments, the pharmaceutically acceptable carrier or excipient is a veterinary acceptable carrier or excipient.

The term "therapeutically effective amount" or "effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics independently selected for administration. Therapeutically effective amounts for a given situation can be determined by routine experimentation that is within the skill and judgment of the clinician.

For any compound, the therapeutically effective amount can be estimated initially either in cell culture assays, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The compounds may be in fine particulate form, freeze-dried as a powder formulation (see for example, CA 2837693; WO2009/017250; US 20100196486), in a low hygroscopic form (see for example, U.S. Pat. Nos. 7,910, 589, 8,017,615, 8,399,469, 8,580,796, 8,642,760; US 20040058935), or liquid or gel formulations (see for example, US 20130209552; US 20130171237; WO2012/058091).

Any suitable pharmaceutically acceptable excipient can be added to the compositions of the invention. Excipients may be added for numerous reasons, for example to facilitate manufacture, enhance stability, control release, enhance product characteristics, enhance bioavailability, enhance patient acceptability and combinations thereof. Examples of pharmaceutically acceptable excipients include diluents, vehicles, binders, disintegrants, glidants, compression aids, colouring agents, organoleptic ingredients such as flavoring agents or sweeteners, suspending agents, dispersing agents, film formers, printing inks, lubricants, preservatives, fillers, buffers, stabilisers, or other materials well known to those skilled in the art. These excipients may be used in a conventional manner, and alone or in any combination.

Exemplary binders, which may be used to help to hold the dosage form together, include polyvinyl pyrrolidone, hydroxypropyl cellulose, hydroxypropyl methylcellulose, methylcellulose, hydroxyethyl cellulose, sugars, and combinations thereof. Disintegrants (such as croscarmellose sodium) expand when wet causing a tablet to break apart. Lubricants typically aid in the processing of powder materials. Exemplary lubricants include calcium stearate, glycerol behenate, magnesium stearate, mineral oil, polyethylene glycol, sodium stearylfumarate, stearic acid, talc, vegetable oil, zinc stearate, and combinations thereof An example of a glidant is silicon dioxide.

The formulations described herein may contain a filler, such as a water insoluble or water soluble filler, or combinations thereof. Typical water insoluble fillers include silicon dioxide, titanium dioxide, talc, alumina, starch, kaolin, polacrilin potassium, powdered cellulose, microcrystalline cellulose, and combinations thereof. Typical water-soluble fillers include water soluble sugars and sugar alcohols, preferably lactose, glucose, fructose, sucrose, mannose, dextrose, galactose, the corresponding sugar alcohols and other sugar alcohols, such as mannitol, sorbitol, xylitol, and combinations thereof.

The present invention further provides pharmaceutical compositions, as defined above, and methods of making a pharmaceutical composition comprising admixing such as blending, filling, granulation and compressing, at least one active compound, as defined above, together with one or more pharmaceutically acceptable carriers or excipients, as described herein. The compositions of the invention can be prepared for example by Direct compression and wet granulation. These and other methods are described and/or exemplified in more detail herein.

The pharmaceutical compositions can be in any form suitable for administration via various routes, including but not limited to, oral, parenteral, topical, intranasal, ophthalmic, otic, rectal, transdermal, and transmucosal. Where the compositions are intended for parenteral administration, they can be formulated for intravenous, intramuscular, intraperitoneal, or subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile solutions which may contain a sterile diluent such as water, saline solution, fixed oils, polyethylene glycols, glycerine, propylene glycol or other synthetic solvents; antioxidants such as ascorbic acid or sodium bisulfite; buffers such as acetates, citrates or phosphates; bacteriostats such as benzyl alcohol or methyl parabens; co-solvents; organic solvent mixtures; chelating agents such as ethylenediaminetetraacetic acid; agents for the adjustment of tonicity such as sodium chloride or dextrose; cyclodextrin complexation agents; emulsifying agents (for forming and stabilizing emulsion formulations); liposome components for forming liposomes; gellable polymers for forming polymeric gels; lyophilisation protectants; and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230). Pharmaceutical formulations for parenteral administration may also be provided in finely divided sterile powder form for making up extemporaneously with sterile water for injection.

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules, vials and disposable syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g., vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g., less than 5%, e.g., less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g., in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for intravenous administration, for example by injection or infusion. In another preferred embodiment, the pharmaceutical composition is in a form suitable for subcutaneous (s.c.) administration.

The compounds may be in the form of a solid or solution, or modified so as to be suitable for oral administration (see for example, U.S. Pat. Nos. 7,655,798, 8,093,387, 8,529, 949; US 20020193438, WO2006/097344). Suitable formulated may also include wet granulation pharmaceutical compositions (see for example, US 20070154544; WO2007/081366), inclusion complexes, for example with cyclodextrin (see for example, U.S. Pat. Nos. 7,115,587, 7,550,445; WO2004/017897), formulated with microspheres (see for example, US 20090043898; WO2009/00169) or formulated as a patch for transdermal delivery (see for example, US 20130171237; US 20130209552; WO2012/058091). Compounds of the present invention may also be formulated to have extended-release profiles, see for example, U.S. Pat. Nos. 8,338,427, 8,338,428; WO2005/016262, WO2013/133448).

Pharmaceutical compositions containing a compound of the invention can be formulated in accordance with known techniques, e.g., by means of conventional mixing, dissolving, granulating, dragee-making, levigating, emulsifying, encapsulating, entrapping, or lyophilizing processes, see for example, Remington's Pharmaceutical Sciences, Mack Publishing Company, Easton, Pa., USA. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Tablet compositions can contain a unit dosage of active compound together with an inert diluent or carrier such as a sugar or sugar alcohol, e.g., lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g., swellable crosslinked polymers such as crosslinked carboxymethylcellulose), lubricating agents (e.g., stearates), preservatives (e.g., parabens), antioxidants (e.g., BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (tablets, capsules etc.) can be coated or un-coated, but typically have a coating, for example a protective film coating (e.g., a wax or varnish) or a release controlling coating. The coating (e.g., a Eudragit™ type polymer) can be designed to release the active component at a desired location within the gastro-intestinal tract. Thus, the coating can be independently selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Further examples of topical compositions include dressings such as bandages and adhesive plasters impregnated with active ingredients and optionally one or more excipients or diluents. Carriers which may be used include e.g., polyhydric alcohols such as polyethylene glycols, propylene glycol or glycerol. Suitable excipients are those known in the art to be appropriate.

Examples of formulations for rectal or intra-vaginal administration include pessaries and suppositories which may be, for example, formed from a shaped mouldable or waxy material containing the active compound. Thus, unit-dose suppositories or pessaries may be prepared by admixture of the active ingredient with one or more conventional solid carriers, for example coca butter, and shaping the resulting mixture. Further examples of mouldable waxy materials include polymers such as high molecular weight polyalkylene glycols, e.g., high molecular weight polyethylene glycols. Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose. The compounds are delivered in the form of an aerosol spray from pressured container or dispenser, which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical formulations can be included in a container, pack, or dispenser together with instructions for administration. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The invention also provides a pharmaceutical composition comprising one or more compounds of the present invention and a pharmaceutically acceptable carrier or excipient, in combination with another pharmaceutically active substance independently selected from a lithium compound independently selected from lithium carbonate, lithium citrate, lithium orotate, lithium bromide or lithium chloride; valproate; a serotonin reuptake inhibitor independently selected from fluoxetine, venlafaxine, citalopram, paroxetine, sertraline, indalpine, zimelidine, dapoxetine, fluvoxamine, tianeptine, duloxetine or escitalopram; chlorpromazine, droperidol, fluphenazine, haloperidol, loxapine, molindone, perphenazine, pimozide, prochlorperazine, thiothixene, thioridazine, trifluoperazine, levomepromazine, aripiprazole, asenapine, clozapine, iloperidone, lurasidone, olanzapine, paliperidone, quetiapine, risperidone, ziprasidone, amisulpride, blonanserin, clotiapine, mosapramine, perospirone, sertindole, sulpiride; caffeine, a caffeine derivative, nicotine, a nicotine derivative, phencyclidine, quinpirole, salvinorin a, apomorphine, bromocriptine, cabergoline, ciladopa, dihydrexidine, dinapsoline, doxanthrine, epicriptine, lisuride, pergolide, piribedil, pramipexole, propylnorapomorphine, quinagolide, ropinirole, rotigotine, roxindole, sumanirole; other compounds with interact with dopamine D2 receptor independently selected from amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−)3-PPP], saritozan, olanzapine, dopamine, quinpirole, bromocriptine; anti-depressants independently selected from agomelatine, amitriptyline, amoxapine, clomipramine, desipramine, dosulepine hydrochloride, doxepine, imipramine, maprotiline, a mixture of nortriptyline and fluphénazine, opipramol, quinupramine, trimipramine, a mixture of mélitracène and flupentixol, pranipexole.

The invention also provides a kit comprising (i) one or more compounds of the present invention, (ii) an additional compound independently selected from a lithium compound independently selected from lithium carbonate, lithium citrate, lithium orotate, lithium bromide or lithium chloride; valproate; a serotonin reuptake inhibitor independently selected from fluoxetine, venlafaxine, citalopram, paroxetine, sertraline, indalpine, zimelidine, dapoxetine, fluvoxamine, tianeptine, duloxetine or escitalopram; Chlorpromazine, Droperidol, Fluphenazine, Haloperidol, Loxapine, Molindone, Perphenazine, Pimozide, Prochlorperazine, Thiothixene, Thioridazine, Trifluoperazine, Levomepromazine, Aripiprazole, Asenapine, Clozapine, Iloperidone, Lurasidone, Olanzapine, Paliperidone, Quetiapine, Risperidone, Ziprasidone, Amisulpride, Blonanserin, Clotiapine, Mosapramine, Perospirone, Sertindole, Sulpiride; caffeine, a caffeine derivative, nicotine, a nicotine derivative, Phencyclidine, Quinpirole, Salvinorin A, Apomorphine, Bromocriptine, Cabergoline, Ciladopa, Dihydrexidine, Dinapsoline, Doxanthrine, Epicriptine, Lisuride, Pergolide, Piribedil, Pramipexole, Propylnorapomorphine, Quinagolide, Ropinirole, Rotigotine, Roxindole, Sumanirole; other compounds with interact with dopamine D2 receptor independently selected from Amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−)3-PPP], saritozan, olanzapine, dopamine, quinpirole, bromocriptine; other anti-depressants independently selected from Agomelatine, amitriptyline, amoxapine, clomipramine, desipramine, dosulepine hydrochloride, doxepine, imipramine, maprotiline, a mixture of nortriptyline and fluphénazine, opipramol, quinupramine, trimipramine, a mixture of melitracene and flupentixol, pranipexole, and (iii) instructions for administration of (i) and (ii). The association of the two or more compounds/agents in a combination may be physical or non-physical. Examples of physically associated combined compounds/agents include: compositions (e.g., unitary formulations) comprising the two or more compounds/agents in a mixture (for example within the same unit dose); compositions comprising material in which the two or more compounds/agents are chemically/physicochemically linked (for example by crosslinking, molecular agglomeration or binding to a common vehicle moiety); compositions comprising material in which the two or more compounds/agents are chemically/physicochemically co-packaged (for example, disposed on or within lipid vesicles, particles (e.g., micro- or nanoparticles) or emulsion droplets); pharmaceutical kits, pharmaceutical packs or patient packs in which the two or more compounds/agents are co-packaged or co-presented (e.g., as part of an array of unit doses);

Examples of non-physically associated combined compounds/agents include: material (e.g., a non-unitary formulation) comprising at least one of the two or more compounds/agents together with instructions for the extemporaneous association of the at least one compound to form a physical association of the two or more compounds/agents; material (e.g., a non-unitary formulation) comprising at least one of the two or more compounds/agents together with instructions for combination therapy with the two or more compounds/agents; material comprising at least one of the two or more compounds/agents together with instructions for administration to a patient population in which the other(s) of the two or more compounds/agents have been (or are being) administered; material comprising at least one of the two or more compounds/agents in an amount or in a form which is specifically adapted for use in combination with the other(s) of the two or more compounds/agents.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

As used herein, the term "pharmaceutical kit" or "kit" defines an array of one or more unit doses of a pharmaceutical composition together with dosing means (e.g., measuring device) and/or delivery means (e.g., inhaler or syringe), optionally all contained within common outer packaging. In pharmaceutical kits comprising a combination of two or more compounds/agents, the individual compounds/agents may be unitary or non-unitary formulations. The unit dose(s) may be contained within a blister pack. The pharmaceutical kit may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The term "stable" as used herein, refers to dosage form which is physically, or polymorphically stable. The dosage form according to present invention may remain physically stable, that is there are no substantial changes with respect to physical attributes like colour etc. The dosage form according to present invention may remain polymorphically stable that is the polymorph (crystalline or amorphous) in the dosage form does not rearranges into another form upon storage.

Method of Use

The term "patient" refers to a warm-blood animal, preferably a human being, i.e., a subject of both genders and at any stage development (i.e., neonate, infant, juvenile, adolescent, adult). The invention is particularly directed to adolescents and adults. Some embodiments, in particular concerning regulation of galactorrhea, are specifically directed to female.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "modulation", as applied to the activity of the dopamine activity at D2 receptors, is intended to define a change in the level of biological activity of the dopaminergic activity. Thus, modulation encompasses physiological changes which effect an increase or decrease in the dopaminergic activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of dopaminergic activity. Thus, modulation may imply elevated/suppressed expression or over- or under-expression of dopaminergic activity, including gene amplification (i.e., multiple gene copies) and/or increased or decreased expression by a transcriptional effect, as well as hyper- (or hypo-) activity and (de)activation of dopaminergic activity (including (de)activation) by mutation(s). The terms "modulated", "modulating" and "modulate" are to be interpreted accordingly.

The present invention provides a method of modulating D2 receptor activity by administering one or more compounds of the present invention to a subject. The active compound will be administered to a subject in need thereof (for example a human or animal patient) in an amount sufficient to achieve the desired therapeutic effect. In one embodiment, the present invention relates to a method of modulating D2 receptor activity, comprising administering a compound of any one of Formulae (I)-(X), or a pharmaceutically acceptable salt, stereoisomer, racemate, tautomer, polymorph, hydrate, or solvate thereof.

The present invention also provides use of one or more compounds of the present invention as a β-arrestin biased D2 receptor agonist or antagonist. The present invention also provides use of one or more compounds of the present invention as a biased cAMP agonist or antagonist. In one embodiment, the present invention relates to the use of a compound of any one of Formulae (I)-(X), or a pharmaceutically acceptable salt, stereoisomer, racemate, tautomer, polymorph, hydrate, or solvate thereof, for modulating the β-arrestin pathway downstream of the D2 receptor (β-arrestin biased) as an agonist or antagonist. In another embodiment, the present invention relates to the use of a compound of any one of Formulae (I)-(X), or a pharmaceutically acceptable salt, stereoisomer, racemate, tautomer, polymorph, hydrate, or solvate thereof, for modulating the Gi/cAMP pathway downstream of the D2 receptor (Gi/cAMP biased) as an agonist or antagonist.

The present invention provides a method of treating or preventing a disease or disorder, comprising administering a compound of the invention, wherein modulation of the D2 receptors (e.g., β-arrestin or Gi/cAMP) plays a role in the disease or disorder (iniation, development, etc.). In one embodiment, the disease or disorder is a nervous system disease or disorder in which modulation of D2 receptors (e.g., β-arrestin or Gi/cAMP) plays a role. In one embodiment, the present invention relates to a method of treating or preventing a disease or disorder in which modulation of D2 receptors plays a role, comprising administering to a subject in need thereof, a therapeutically effective amount of a compound of any one of Formulae (I)-(X), or a pharmaceutically acceptable salt, stereoisomer, racemate, tautomer, polymorph, hydrate, or solvate thereof, in combination with a pharmaceutically acceptable excipient or carrier. The nervous system disorder is independently selected from an anxiety disorder (e.g., phobias, generalized anxiety disorder, social anxiety disorder, panic disorder, agoraphobia, obsessive-compulsive disorder, and post-traumatic stress disorder), a dissociative disorder (e.g., dissociative amnesia, dissociative fugue, dissociative identity (multiple personality) disorder, and depersonalization disorder), a mood disorder (e.g., depression, dysthymia, bipolar disorder, mania, hypomania, and Cyclothymic Disorder), an eating disorder (e.g., anorexia nervosa, bulimia nervosa, exercise bulimia, and binge eating disorder), a sleep disorder (insomnia, hypersomnia, narcolepsy, nightmare disorder, sleep terror disorder, and sleepwalking), a developmental disorder (e.g., autism spectrum disorders, oppositional defiant disorder and conduct disorder, and attention deficit hyperactivity disorder), a somatoform disorder (e.g., body dysmorphic disorder, conversion disorder, hypochondriasis disorder, pain disorder, and somatization disorder), a personality disorder (e.g., antisocial personality disorder, borderline personality disorder, narcissistic personality disorder), a psychiatric syndrome (e.g., Capgras syndrome, De Clerambault syndrome, Othello syndrome, Ganser syndrome, Cotard delusion, and Ekbom syndrome, and additional disorders such as the Couvade syndrome and Geschwind syndrome), a psychotic disorder (e.g., brief psychotic disorder, delusional disorder, Schizoaffective disorder, Schizophrenia, Schizophreniform, shared psychotic disorder), substance abuse, Parkinson's disease, Huntington's disease, Alzheimer's disease, dementia, Niemann-Pick disorder, a pituitary disorder (e.g., pituitary adenoma, and a pituitary tumor such as prolactinoma)), Tourette's syndrome, Tourette-like disorders, and restless leg syndrome.

In another aspect, the present invention relates to the use of a compound of any one of Formulae (I)-(X), or a pharmaceutically acceptable salt, stereoisomer, racemate, tautomer, polymorph, hydrate, or solvate thereof, for the treatment or prevention of a disease or disorder in which modulation of D2 receptors plays a role.

Another aspect of the present invention relates to the use of a compound of any one of Formulae (I)-(X), or a pharmaceutically acceptable salt, stereoisomer, racemate, tautomer, polymorph, hydrate, or solvate thereof, in the manufacture of a medicament for the treatment or prevention of a disease or disorder in which modulation of D2 receptors plays a role.

In one embodiment, the present invention provides a method of treating or preventing a disease or disorder in which modulation of D2 receptors (e.g., β-arrestin or Gi/cAMP) plays a role, independently selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome.

In another embodiment, the disease or disorder is a non-nervous system disease or disorder in which modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

The present invention also provides a method of treating or preventing a disease or disorder in which modulation of D2 receptors (e.g., β-arrestin or Gi/cAMP) plays a role (e.g., the diseases and disorders described above), comprising administering a compound of the invention and an additional therapeutic agent. In one embodiment, the additional therapeutic agent is lithium carbonate, lithium citrate, lithium orotate, lithium bromide or lithium chloride. In another embodiment, the additional therapeutic agent is valproate. In another embodiment, the additional therapeutic agent is caffeine (e.g., as to Parkinsons), a caffeine derivative (e.g., as to Parkinsons), nicotine (e.g., as to Parkinsons), a nicotine derivative (e.g., as to Parkinsons), Phencyclidine (a.k.a. PCP), Quinpirole, Salvinorin A (chief active constituent of the herb salvia divinorum), Apomorphine (Apokyn) (e.g., as to Parkinson's disease, restless leg syndrome), Bromocriptine (Parlodel) (e.g., as to Parkinson's disease, restless leg syndrome), Cabergoline (Dostinex) (e.g., as to Parkinson's disease, restless leg syndrome), Ciladopa (e.g., as to Parkinson's disease, restless leg syndrome), Dihydrexidine (e.g., as to Parkinson's disease, restless leg syndrome), Dinapsoline (e.g., as to Parkinson's disease, restless leg syndrome), Doxanthrine (e.g., as to Parkinson's disease, restless leg syndrome), Epicriptine (e.g., as to Parkinson's disease, restless leg syndrome), Lisuride (e.g., as to Parkinson's disease, restless leg syndrome), Pergolide (e.g., as to Parkinson's disease, restless leg syndrome), Piribedil (e.g., as to Parkinson's disease, restless leg syndrome), Pramipexole (e.g., as to Parkinson's disease, restless leg syndrome) (Mirapex and Sifrol), Propylnorapomorphine (e.g., as to Parkinson's disease, restless leg syndrome), Quinagolide (Norprolac) (e.g., as to Parkinson's disease, restless leg syndrome), Ropinirole (e.g., as to Parkinson's disease, restless leg syndrome) (Requip), Rotigotine (e.g., as to Parkinson's disease, restless leg syndrome) (Neupro), Roxindole (e.g., as to Parkinson's disease, restless leg syndrome), or Sumanirole (e.g., as to Parkinson's disease, restless leg syndrome).

The present invention also provides a method of treating or preventing a disease or disorder in which modulation of D2 receptors (e.g., β-arrestin or Gi/cAMP) plays a role (e.g., the diseases and disorders described above), comprising administering a compound of the invention and a serotonin reuptake inhibitor such as fluoxetine, venlafaxine, citalopram, paroxetine, sertraline, indalpine, zimelidine, dapoxetine, fluvoxamine, tianeptine, duloxetine or escitalopram (see for example, US20060154938).

The present invention also provides a method of treating or preventing a disease or disorder in which modulation of D2 receptors (e.g., β-arrestin or Gi/cAMP) plays a role (e.g., the diseases and disorders described above), comprising administering a compound of the invention alone or in combination with antipsychotics. Examples of typical (first generation) antipsychotics include Chlorpromazine, Droperidol, Fluphenazine, Haloperidol, Loxapine, Molindone, Perphenazine, Pimozide, Prochlorperazine, Thiothixene, Thioridazine, Trifluoperazine, Levomepromazine. Examples of atypical (second generation) antipsychotics include Aripiprazole, Asenapine, Clozapine, Iloperidone, Lurasidone, Olanzapine, Paliperidone, Quetiapine, Risperidone, Ziprasidone, Amisulpride, Blonanserin, Clotiapine, Mosapramine, Perospirone, Sertindole, Sulpiride. Other compounds which can be used in combination with the compounds of the invention are for example compounds that interact with dopamine D2 receptor independently selected from amisulpride, nemomapride, nemoxipride, eticlopride, reclopride, talipexole, roxindole, bifeprunox, aplindore, mesoridazine, haloperidol, thixathene, flupenthixol, butyrophenone, perclamol [(−)3-PPP], saritozan, olanzapine, dopamine, quinpirole, bromocriptine; other anti-depressants independently selected from Agomelatine, amitriptyline, amoxapine, clomipramine, desipramine, dosulepine hydrochloride, doxepine, imipramine, maprotiline, a mixture of nortriptyline and fluphénazine, opipramol, quinupramine, trimipramine, a mixture of melitracene and flupentixol, pranipexole.

The compounds are generally administered to a subject in need of such administration, for example, a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity. The quantity of compound administered and the type of composition used will be commensurate with the nature of the disease or physiological condition being treated and will be at the discretion of the physician.

The compounds may be administered over a prolonged term to maintain beneficial therapeutic effects or may be administered for a short period only. Alternatively they may be administered in a pulsatile or continuous manner.

The compounds as defined herein can be administered as the sole therapeutic agent or they can be administered in combination therapy with one of more other compounds for treatment of a particular disease state, for example, a nervous system disorder. The compounds of the invention may also be administered in conjunction with other treatments such as radiotherapy, photodynamic therapy, gene therapy, surgery and controlled diets.

Where the compound is administered in combination with other therapeutic agents, the compounds can be administered simultaneously or sequentially. When administered sequentially, they can be administered at closely spaced intervals (e.g., within minutes) or at longer intervals (e.g., hours apart, or longer), the precise dosage regimen being commensurate with the properties of the therapeutic agent(s).

For use in combination therapy with another therapeutic agent, the compound and other therapeutic agents can be, for example, formulated together in a dosage form. In an alternative, the individual therapeutic agents may be formulated separately and presented together in the form of a kit, optionally with instructions for their use.

Actual dosage levels of the active ingredients in the pharmaceutical compositions of the invention may be varied so as to obtain an amount of the active ingredient which is effective to achieve the desired therapeutic response for a particular patient, composition, and mode of administration, without being toxic to the patient.

The independently selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A person skilled in the art would know through his or her common general knowledge the use of suitable dosing regimes and combination therapies. The regimen of administration can affect what constitutes an effective amount. The compound of the invention can be administered to the subject either prior to or after the onset of a dopaminergic disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

While it is possible for a compound of the present invention to be administered alone, it is preferable to administer the compound as a pharmaceutical composition.

The present invention also relates to use of a compound of the invention or a pharmaceutically acceptable salt, stereoisomer, racemate, tautomer, polymorph, hydrate, or solvate thereof, or use of a pharmaceutical composition of the invention, for treating treating or preventing a disease or disorder in which modulation of D2 receptors (e.g., β-arrestin or Gi/cAMP) plays a role (e.g., diseases and disorders described herein). In one embodiment, the disease or disorder is a nervous system disease or disorder independently selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome. In another embodiment, the disease or disorder is a non-nervous system disease or disorder in which modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

The present invention also relates to use of a compound of the invention, or a pharmaceutically acceptable salt, stereoisomer, racemate, tautomer, polymorph, hydrate, or solvate thereof, or use of a pharmaceutical composition of the invention, in the manufacture of a medicament for the treatment or prevention of a disease or disorder in which modulation of D2 receptors (e.g., β-arrestin or Gi/cAMP) plays a role (e.g., diseases and disorders described herein). In one embodiment, the disease or disorder is a nervous system disease or disorder independently selected from obsessive-compulsive disorder, post-traumatic stress disorder, depression, bipolar disorder, mania, hypomania, autism spectrum disorders, attention deficit hyperactivity disorder, delusional disorder, Schizoaffective disorder, Schizophrenia, Schizophreniform, substance abuse, Parkinson's disease, Huntington's disease, Alzheimer's disease, dementia, Niemann-Pick disorder, a pituitary disorder, Tourette's syndrome, Tourette-like disorders, and restless leg syndrome. In another embodiment, the disease or disorder is a non-nervous system disease or disorder associated in which modulation of D2 receptors (e.g., β-arrestin or Gi/cAMP) plays a role, such as cardiovascular diseases or disorders (e.g., hypertension), renal diseases or disorders (e.g., a disease or disorder associated with diuresis and natriuresis), and endocrine diseases or disorders (e.g., galactorrhea), and immunological diseases or disorders.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Synthesis of Intermediate-1

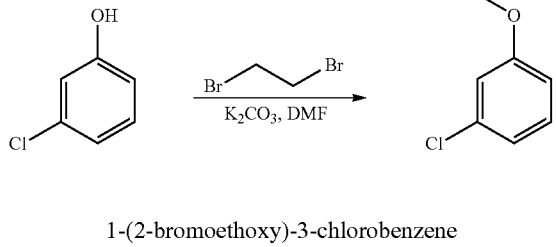

1-(2-bromoethoxy)-3-chlorobenzene

To a stirred solution of 3-chlorophenol (5 g, 39.06 mmol) in DMF (30 mL) under argon atmosphere were added 1,2-dibromo ethane (6.7 mL, 77.71 mmol, 2 equiv) and potassium carbonate (5.4 g, 39.13 mmol, 1 equiv) at room temperature. The reaction mixture was heated at 100° C. and stirred for 16 h. After completion, the reaction mixture was diluted with water and extracted with EtOAc. The combined organic extract was washed with brine, dried over sodium sulphate, filtered and concentrated under reduced pressure. Purification using silica gel column chromatography (2% EtOAc/Hexanes as eluent) afforded 3.1 g of 1-(2-bromoethoxy)-3-chlorobenzene (Yield=34%).

Synthesis of Intermediate-2

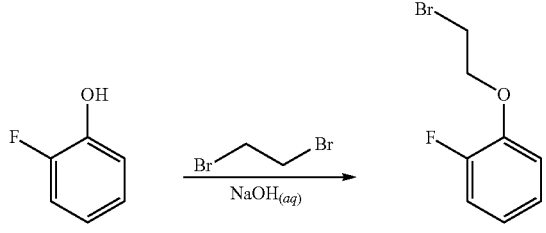

1-(2-Bromoethoxy)-2-fluorobenzene

To a stirred solution of 2-fluorophenol (0.5 g, 4.46 mmol) in aqueous sodium hydroxide solution (0.78 g, 4.46 mmol, 1 equiv, in 5 mL of water) was added 1,2-dibromo ethane (1.25 g, 6.69 mmol, 1.5 equiv) at room temperature. The reaction mixture was heated at 130° C. and stirred for 16 h. After completion, the reaction mixture was extracted with EtOAc. The combined organic extract was washed with brine, dried over sodium sulphate, filtered and concentrated under reduced pressure. Purification using silica gel column chromatography (2% EtOAc/Hexanes as eluent) afforded 0.340 g of 1-(2-bromoethoxy)-2-fluorobenzene (Yield=34.8%).

Synthesis of Intermediate-3

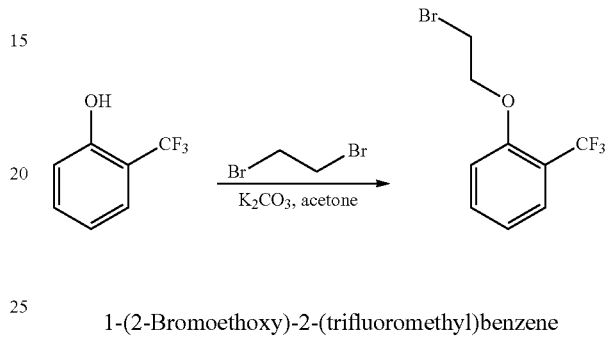

1-(2-Bromoethoxy)-2-(trifluoromethyl)benzene

To a stirred solution of 2-(trifluoromethyl) phenol (1 g, 6.17 mmol) in acetone (20 mL) under argon atmosphere were added potassium carbonate (0.851 g, 6.15 mmol, 1 equiv) and 1,2-dibromo ethane (1.07 mL, 12.34 mmol, 2 equiv) at room temperature. The reaction mixture was heated at 60° C. and stirred for 16 h. After completion, the reaction mixture was diluted with water and extracted with EtOAc. The combined organic extract was dried over sodium sulfate, filtered and concentrated under reduced pressure. Purification using silica gel column chromatography (2% EtOAc/Hexanes as eluent) afforded 0.40 g of 1-(2-bromoethoxy)-2-(trifluoromethyl) benzene (Yield=24%).

Synthesis of Intermediate-4

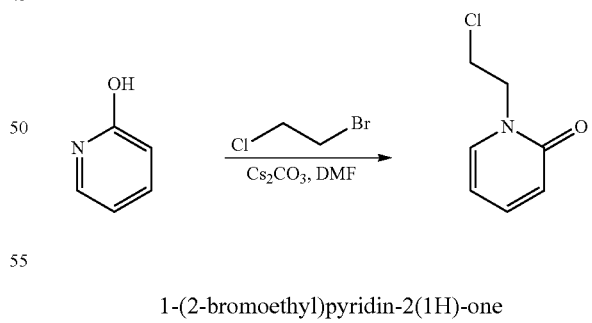

1-(2-bromoethyl)pyridin-2(1H)-one

To a stirred solution of pyridin-2-ol (5 g, 52.57 mmol) in DMF (50 mL) under argon atmosphere were added cesium carbonate (17.03 g, 52.56 mmol, 1.0 equiv) and 1-chloro-2-bromo ethane (15.06 g, 104.94 mmol, 2 equiv) at room temperature and stirred for 16 h. After completion, the reaction mixture was diluted with water and extracted with CH$_2$Cl$_2$. The combined organic extract was dried over sodium sulfate, filtered and concentrated under reduced pressure. Purification using silica gel column chromatography (1% MeOH/CH₂Cl₂ as eluent) afforded 1.0 g of 1-(2-bromoethyl)pyridin-2(1H)-one (Yield=12%). ESI+MS: m/z 158.1 ([M+H]⁺).

Synthesis of Intermediate-5

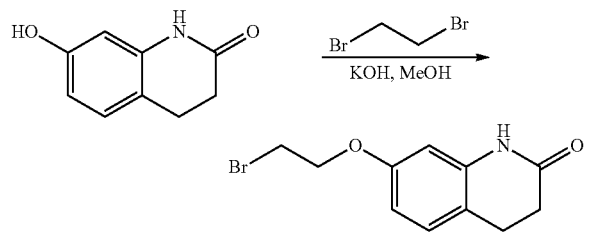

7-(2-Bromoethoxy)-3,4-dihydroquinolin-2(1H)-one

To a stirred solution of 7-hydroxy-3,4-dihydroquinolin-2 (1H)-one (1 g, 6.21 mmol) in MeOH (20 mL) under argon atmosphere were added 1,2-dibromo ethane (1.74 g, 9.31 mmol, 1.5 equiv) and potassium hydroxide (0.453 g, 8.07 mmol, 1.3 equiv) at room temperature. The reaction mixture was heated at 65° C. and stirred for 4 h. After completion, the volatiles were removed under reduced pressure. The residue was diluted with water and extracted with EtOAc. The combined organic extract was dried over sodium sulfate, filtered and concentrated under reduced pressure. Purification using silica gel column chromatography (1% MeOH/CH₂Cl₂ as eluent) afforded 7-(2-bromoethoxy)-3, 4-dihydroquinolin-2(1H)-one 0.27 g (Yield=16.2%). ESI+MS: m/z 267.9 ([M+H]⁺).

Intermediate-6

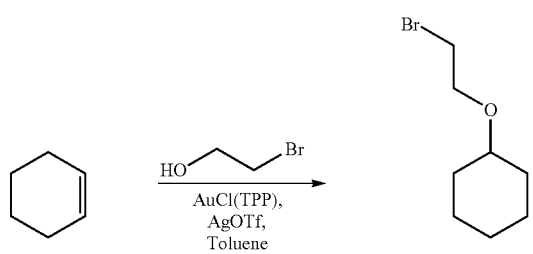

(2-Bromoethoxy) cyclohexane

To a stirred solution of trifluoromethane sulfonic acid silver salt (0.14 g, 0.54 mmol, 0.03 equiv) in toluene (10 mL) under argon atmosphere were added triphenyl phosphine (0.14 g, 0.54 mmol, 0.03 equiv), AuCl(TPP) (0.27 g, 0.54 mmol, 0.03 equiv) and purged with argon for 5 min in a sealed tube. To this cyclohexene (1.5 g, 18.25 mmol) and 2-bromo ethanol (4.52 g, 36.45 mmol, 2 equiv) were added at room temperature. The reaction mixture was heated at 85° C. and stirred for 24 h. After completion, the reaction mixture was diluted with diethyl ether and filtered. The filtrate was concentrated under reduced pressure. Purification using silica gel column chromatography (2% EtOAc/Hexanes) afforded 0.26 g of (2-bromoethoxy) cyclohexane (Yield=10%).

One skilled in the art will recognize that other compounds described below were prepared in a similar manner to the procedures described above.

(2-Bromoethoxy)benzene

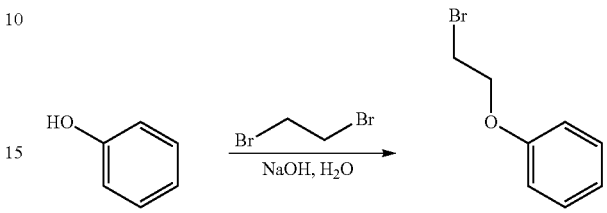

Title compound was prepared from phenol (20 g, 213 mmol) using the general methodology of Int-2 and afforded 26 g of (2-bromoethoxy)benzene (Yield=61%).

1-(2-Bromoethoxy)-2-chlorobenzene

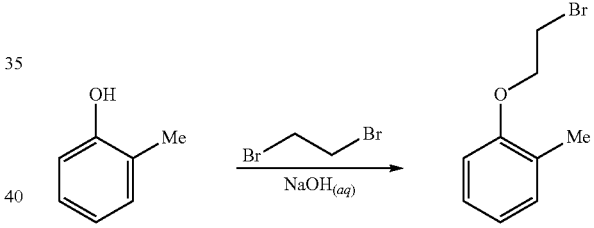

Title compound was prepared from o-cresol (5 g, 46.2 mmol) using general methodology of Intermediate-2 to afford 5.2 g of 1-(2-bromoethoxy)-2-methylbenzene (Yield=52%).

1-(2-Bromoethoxy)-3-methylbenzene

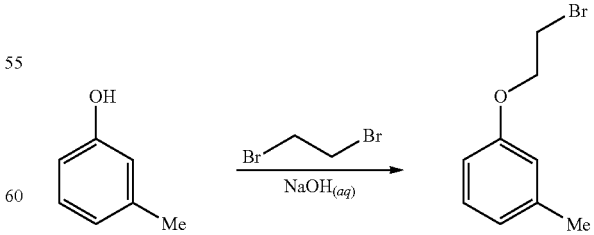

Title compound was prepared from m-cresol (5 g, 46.2 mmol) using the general methodology of Intermediate-2 to afford 5.4 g of 1-(2-bromoethoxy)-3-methylbenzene (Yield=54%).

101

1-(2-Bromoethoxy)-4-methylbenzene

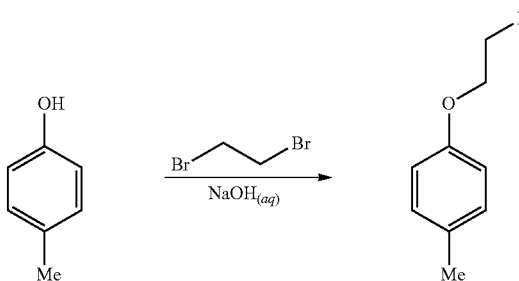

Title compound was prepared from p-cresol (5 g, 46.2 mmol) using the general methodology of Intermediate-2 to afford 4 g of 1-(2-bromoethoxy)-4-methylbenzene (Yield=40%).

1-(2-bromoethoxy)-2-chlorobenzene

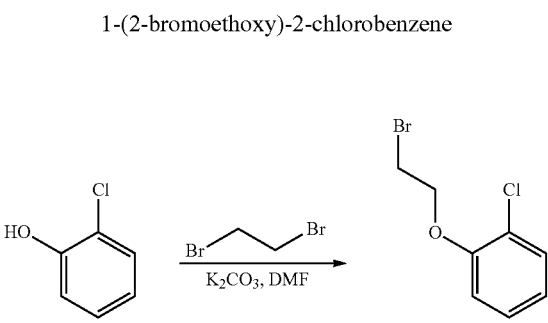

Title compound was prepared from 2-chlorophenol (1 g, 7.78 mmol) using general methodology of Intermediate-1 to obtain 0.348 g of 1-(2-bromoethoxy)-2-chlorobenzene (Yield=19%).

1-(2-Bromoethoxy)-4-chlorobenzene

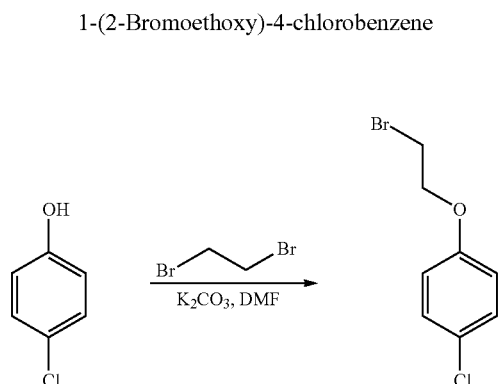

Title compound was prepared from 4-chlorophenol (5 g, 39.06 mmol) using the general methodology of Intermediate-1 and afforded 3 g of 1-(2-Bromoethoxy)-4-chlorobenzene (Yield=33%).

4-(2-Bromoethoxy)-1,2-dichlorobenzene

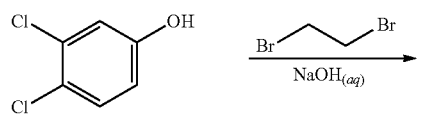

102

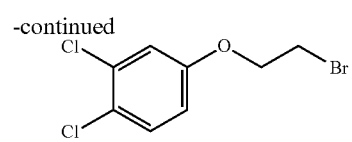

Title compound was prepared from 3,4-dichlorophenol (2 g, 12.27 mmol) using the general methodology of Intermediate-2. Purification using silica gel column chromatography (10% EtOAc/Hexanes) afforded 2 g of 4-(2-bromoethoxy)-1, 2-dichlorobenzene (Yield=60%).

1-(2-Bromoethoxy)-3-fluorobenzene

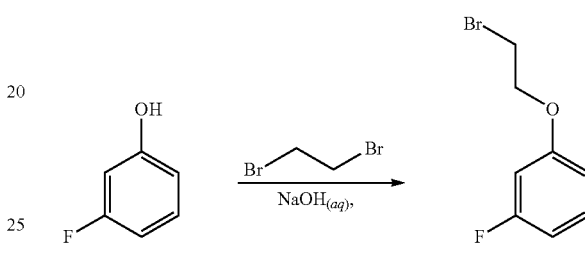

Title compound was prepared from 3-fluorophenol (4 g, 35.71 mmol) using the general methodology of Intermediate-2 and afforded 3 g of 1-(2-bromoethoxy)-3-fluorobenzene (Yield=38%).

1-(2-bromoethoxy)-4-fluorobenzene

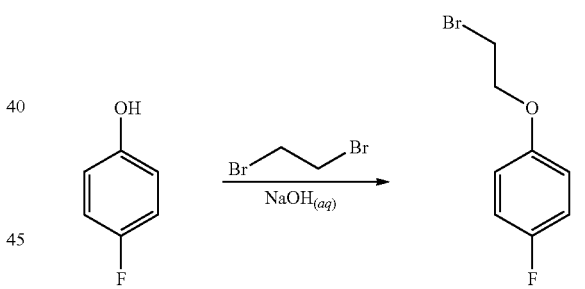

Title compound was prepared from 4-fluorophenol (4 g, 35.71-mmol) using the general methodology of Intermediate-2 and afforded 2.8 g of 1-(2-bromoethoxy)-4-fluorobenzene (Yield=35%).

2-(2-Bromoethoxy)-1,4-difluorobenzene

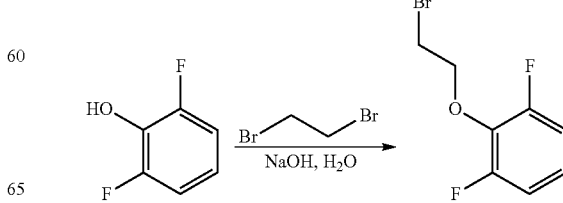

Title compound was prepared from 2,6-difluorophenol (1 g, 7.69 mmol) using the general methodology of Intermediate-2 and afforded 1.1 g of 2-(2-bromoethoxy)-1,4-difluorobenzene (Yield=60%).

1-(2-Bromoethoxy)-2,4-difluorobenzene

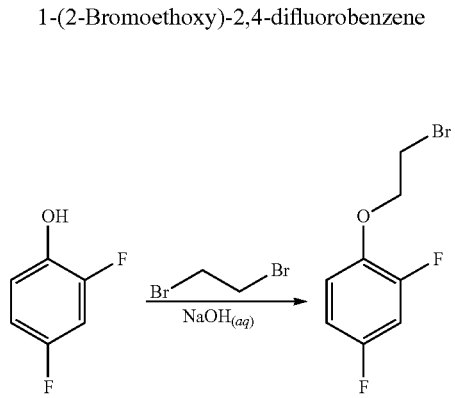

Title compound was prepared from 2, 4-difluorophenol (5 g, 38.4 mmol) using the general methodology of Intermediate-2 to afford 2.5 g of 2-(2-bromoethoxy)-1,4-difluorobenzene (Yield=27%).

2-(2-bromoethoxy)-1,4-difluorobenzene

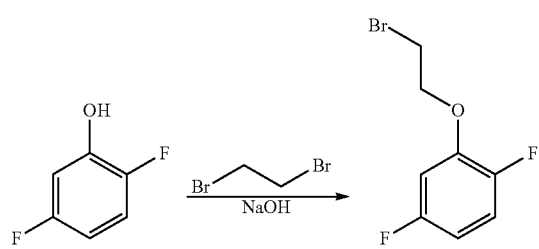

Title compound was prepared from 2,5-difluorophenol (5 g, 38.4 mmol) using the general methodology of Int-2 and afforded 3.5 g of 2-(2-bromoethoxy)-1, 4-difluorobenzene (Yield=39%).

1-(2-bromoethoxy)-3-(trifluoromethyl)benzene

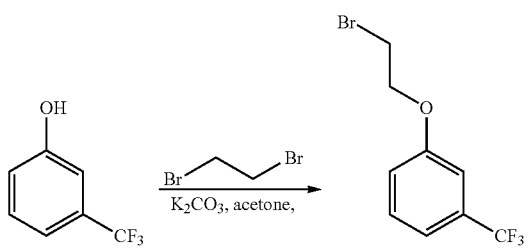

Title compound was prepared from 3-(trifluoromethyl) phenol (2 g, 12.34 mmol) using general methodology of Intermediate-3 and afforded 0.74 g of 1-(2-bromoethoxy)-3-(trifluoromethyl) benzene (Yield=22%).

1-(2-bromoethoxy)-4-(trifluoromethyl)benzene

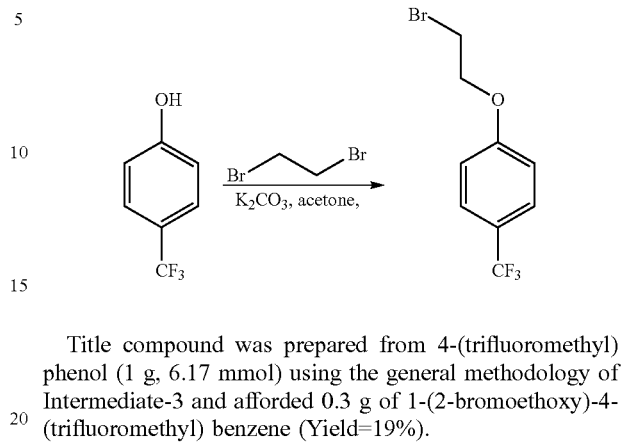

Title compound was prepared from 4-(trifluoromethyl) phenol (1 g, 6.17 mmol) using the general methodology of Intermediate-3 and afforded 0.3 g of 1-(2-bromoethoxy)-4-(trifluoromethyl) benzene (Yield=19%).

5-(2-bromoethoxy)-2-(trifluoromethyl)pyridine

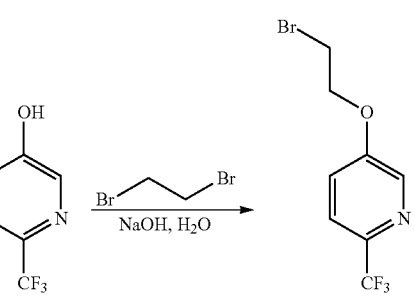

Title compound was prepared from 6-(trifluoromethyl) pyridin-3-ol (0.5 g, 3.1 mmol) using the general methodology of Intermediate-2 and afforded 0.085 g 5-(2-bromoethoxy)-2-(trifluoromethyl)pyridine (Yield=10%).

3-(2-Bromoethoxy) pyridine

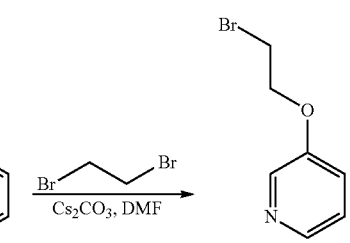

Title compound was prepared from pyridin-3-ol (5 g, 52.57 mmol) using the general methodology of Intermediate-4 and afforded 0.6 g of 3-(2-bromoethoxy) pyridine (Yield=6%).

1-(2-bromoethyl)pyridin-4(1H)-one

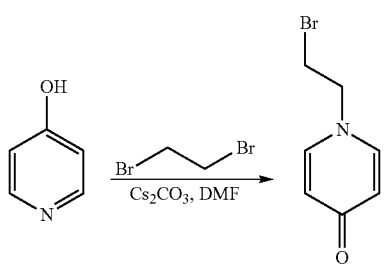

Title compound was prepared from pyridin-4-ol (5 g, 52.5 mmol) using the general methodology of Intermediate-4 and afforded 0.85 g of 1-(2-bromoethyl)pyridin-4(1H)-one (Yield=8%).

1-(2-Bromoethoxy)-2-methoxybenzene

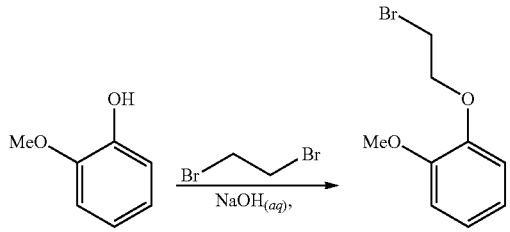

Title compound was prepared from 2-methoxyphenol (5 g, 40.3 mmol) using the general methodology of Intermediate-2. Purification by silica gel column chromatography (5% EtOAc/Hexanes) afforded 2.85 g of 1-(2-bromoethoxy)-2-methoxybenzene (Yield=30%).

1-(2-bromoethoxy)-3-methoxybenzene

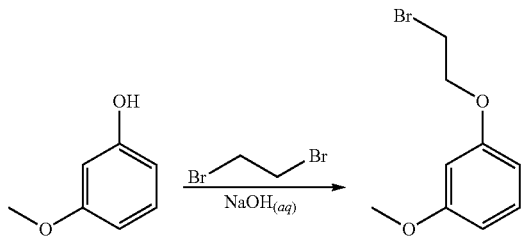

Title compound was prepared from 3-methoxyphenol (5 g, 40.27 mmol) using the general methodology of Intermediate-2 and afforded 3.6 g of 1-(2-bromoethoxy)-3-methoxybenzene (Yield=39%).

1-(2-bromoethoxy)-4-methoxybenzene

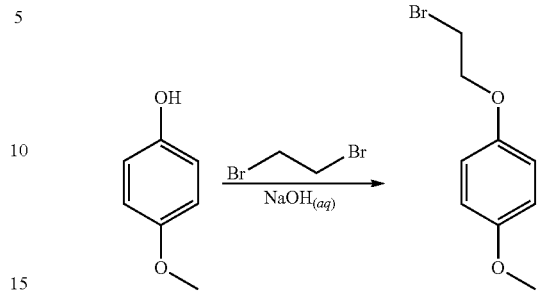

Title compound was prepared from 3-methoxyphenol (5 g, 40.27 mmol) using the general methodology of Int-2 and afforded 3.5 g of 1-(2-bromoethoxy)-4-methoxybenzene (Yield=38%).

1-(2-bromoethoxy)-4-fluoro-2-methoxybenzene

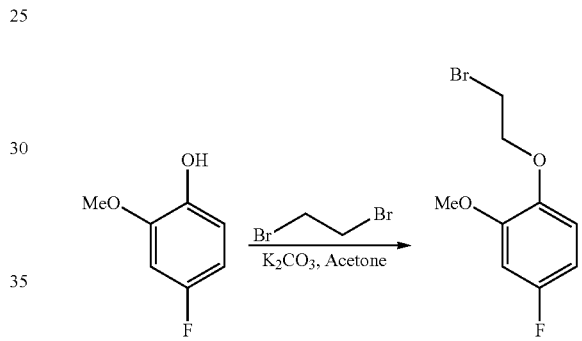

Title compound was prepared from 4-fluoro-2-methoxyphenol (1 g, 7.04 mmol) using the general methodology of Intermediate-3. Purification by silica gel column chromatography (10% EtOAc/Hexanes) afforded 0.20 g of 1-(2-bromoethoxy)-4-fluoro-2-methoxybenzene (Yield=12%).

2-(2-bromoethoxy)-4-fluoro-1-methoxybenzene

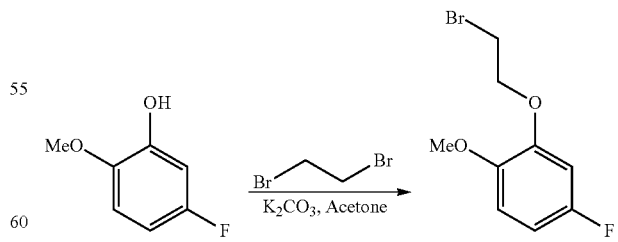

Title compound was prepared from 4-fluoro-2-methoxyphenol (1 g, 7.04 mmol) using the general methodology of Intermediate-3. Purification by silica gel column chromatography (10% EtOAc/Hexanes) afforded 0.50 g of 2-(2-bromoethoxy)-4-fluoro-1-methoxybenzene (Yield=29%).

1-(2-Bromoethoxy)-2-ethylbenzene

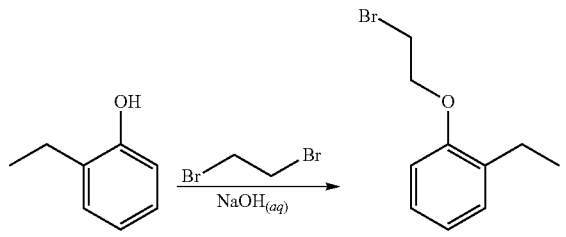

Title compound was prepared from 2-ethylphenol (5 g, 40.9 mmol, 1 equiv) using the general methodology of Intermediate-2. Purification using silica gel column chromatography (2% MeOH/DCM) afforded 3.0 g of 1-(2-bromoethoxy)-2-ethylbenzene (Yield=32%).

1-(2-bromoethoxy)-2-isopropylbenzene

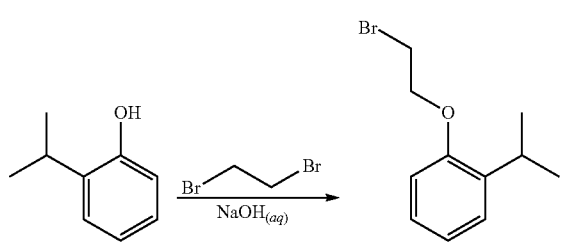

Title compound was prepared from 2-isopropylphenol (5 g, 36.7 mmol, 1 equiv) using the general methodology of Intermediate-2. Purification using silica gel column chromatography (5% EtOAc in Hexanes) afforded 5.5 g of 1-(2-bromoethoxy)-2-isopropylbenzene (Yield=62%).

2-(2-Bromoethoxy)benzonitrile

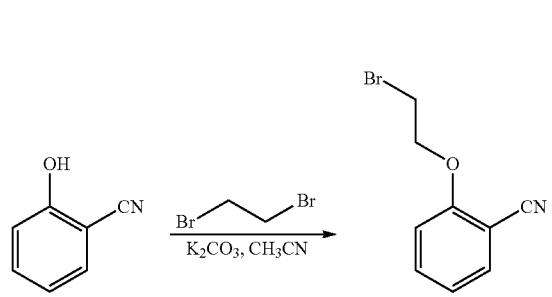

Title compound was prepared from 2-hydroxybenzonitrile (1 g, 8.40 mmol) and 1,2-dibromoethane (3.15 g, 16.8 mmol, 2 equiv) using the general methodology of Intermediate-1. Purification using silica gel chromatography (2% MeOH/CH$_2$Cl$_2$) afforded 0.22 g of 2-(2-bromoethoxy)benzonitrile (Yield=11%).

1-(2-bromoethoxy)-2-(trifluoromethoxy)benzene

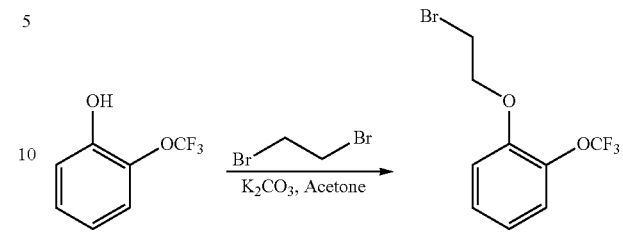

Title compound was prepared from 2-(trifluoromethoxy)phenol (1 g, 5.6 mmol) using the general methodology of Intermediate-3. Purification using silica gel chromatography (2% EtOAc/Hexane) afforded 1.0 g of 1-(2-bromoethoxy)-2-(trifluoromethoxy)benzene (Yield=63%).

1-(2-Bromoethoxy)-4-fluoro-2-(trifluoromethyl)benzene

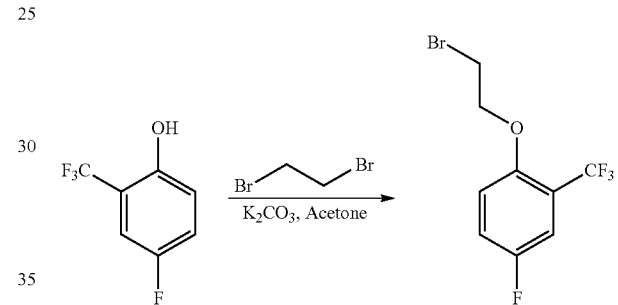

Title compound was prepared from 4-fluoro-2-(trifluoromethyl)phenol (2 g, 11.1 mmol) using the general methodology of Intermediate-3. Purification using silica gel column chromatography (15% EtOAc in Hexanes) afforded 1.6 g of 1-(2-bromoethoxy)-4-fluoro-2-(trifluoromethyl)benzene (Yield=50%).

2-(2-Bromoethoxy)-4-fluoro-1-(trifluoromethyl)benzene

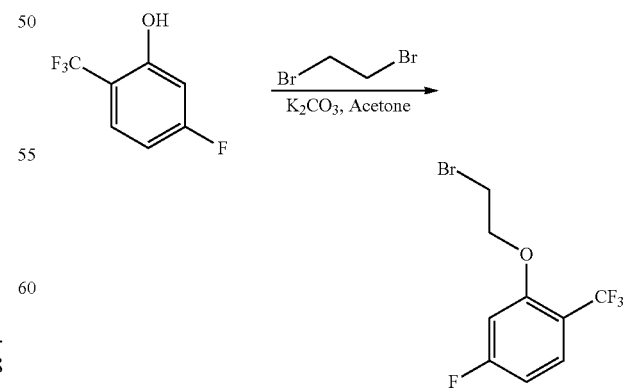

Title compound was prepared from 5-fluoro-2-(trifluoromethyl)phenol (1 g, 5.5 mmol) using the general methodology of Intermediate-3. Purification by silica gel column chromatography (5% EtOAc/Hexanes) afforded 0.7 g of 2-(2-bromoethoxy)-4-fluoro-1-(trifluoromethyl)benzene (Yield=44%).

3-(2-Bromoethoxy)-4-(trifluoromethyl)pyridine

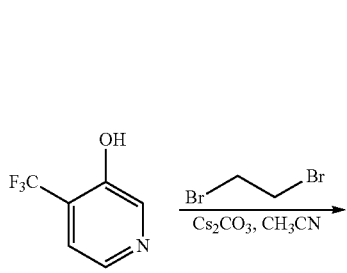

Title compound was prepared from 3-(2-bromoethoxy)-4-(trifluoromethyl)pyridine (0.2 g, 1.22 mmol) using the general methodology of Intermediate-4. Purification using silica gel column chromatography (10% EtOAc/Hexanes) afforded 0.11 g of 3-(2-bromoethoxy)-4-(trifluoromethyl) pyridine (Yield=33%).

3-(2-bromoethoxy)-2-(trifluoromethyl)pyridine

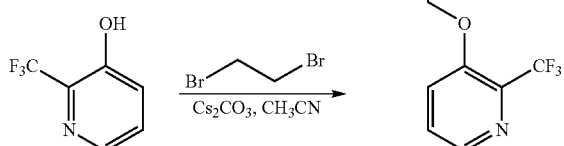

Title compound was prepared from 2-(trifluoromethyl) pyridin-3-ol (0.5 g, 3.1 mmol) using the general methodology of Intermediate-4. Purification using silica gel column chromatography (10% EtOAc/Hexanes) afforded 0.20 g of 3-(2-bromoethoxy)-2-(trifluoromethyl)pyridine (Yield=24%).

1-(2-bromoethyl)-3-(trifluoromethyl)pyridin-2(1H)-one

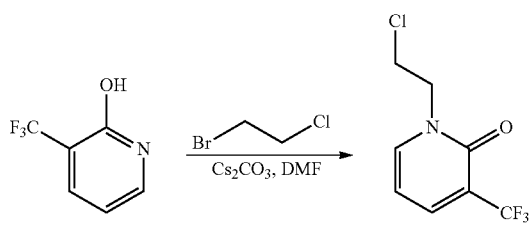

Title compound was prepared from 3-(trifluoromethyl) pyridin-2-ol (0.2 g, 1.22 mmol) and 1-bromo-2-chloroethane (0.52 g, 3.68 mmol, 3 equiv) using the general methodology of Intermediate-4. Purification using silica gel column chromatography (20% EtOAc/Hexanes) afforded 0.1 g of 1-(2-bromoethyl)-3-(trifluoromethyl)pyridin-2(1H)-one (Yield=36%).

1-(2-Bromoethoxy)naphthalene

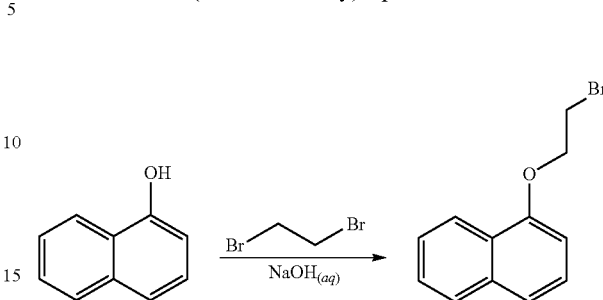

Title compound was prepared from naphthalen-1-ol (3 g, 20.81 mmol) using the general methodology of Intermediate-2. Purification using silica gel column chromatography (7% EtOAc/Hexanes) afforded 2.5 g of 1-(2-bromoethoxy) naphthalene (Yield=48%).

2-(2-Bromoethoxy)naphthalene

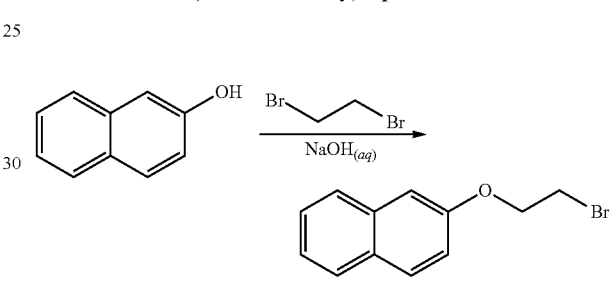

Title compound was prepared from naphthalen-2-ol (3 g, 20.81 mmol) using the general methodology of Intermediate-2. Purification using silica gel column chromatography (10% EtOAc/Hexanes) afforded 2.5 g of 2-(2-bromoethoxy) naphthalene (Yield=48%).

7-(2-bromoethoxy) quinolone

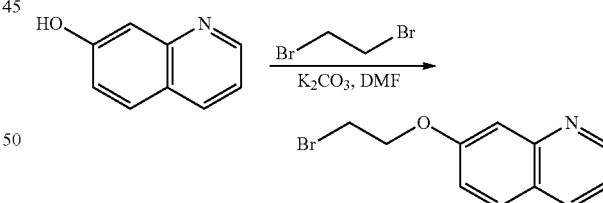

Title compound was prepared from quinolin-7-ol (1 g, 6.89 mmol) using the general methodology of Int-1 and afforded 0.21 g of 7-(2-bromoethoxy) quinolone (Yield=21%).

6-(2-Bromoethoxy)isoquinoline

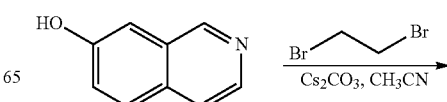

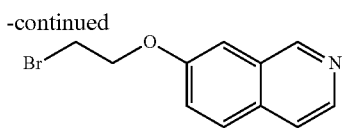

Title compound was prepared from isoquinolin-6-ol (0.5 g, 3.44 mmol) using the general methodology of Intermediate-4. Purification using silica gel column chromatography (2% MeOH/DCM) afforded 0.15 g of 6-(2-bromoethoxy) isoquinoline (Yield=17%).

6-(2-Bromoethoxy)isoquinoline

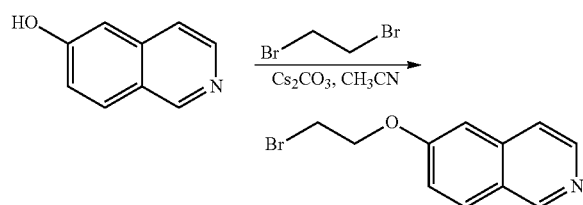

Title compound was prepared from isoquinolin-6-ol (0.5 g, 3.44 mmol) using the general methodology of Intermediate-4. Purification using silica gel column chromatography (2% MeOH/DCM) afforded 0.15 g of 6-(2-bromoethoxy) isoquinoline (Yield=17%).

6-(2-Bromoethoxy)quinolone

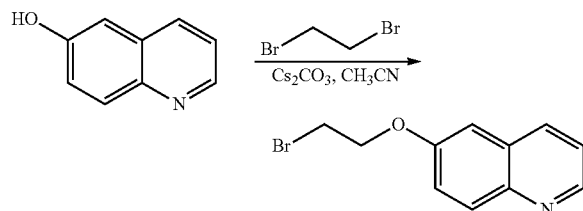

Title compound was prepared from quinolin-6-ol (1 g, 6.89 mmol) using the general methodology of Intermediate-4. Purification using silica gel column chromatography (2% MeOH/DCM) afforded 0.25 g of 6-(2-bromoethoxy)quinolone (Yield=14%).

5-(2-Bromoethoxy)benzo[d]thiazole

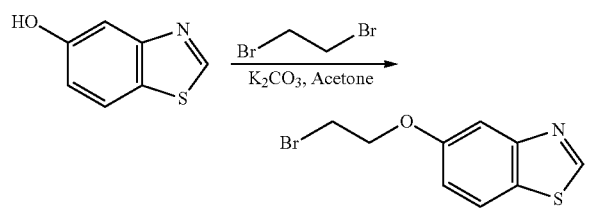

Title compound was prepared from benzo[d]thiazol-5-ol (0.10 g, 0.66 mmol) using the general methodology of Intermediate-3. Purification using silica gel column chromatography (15% EtOAc/hexanes) afforded 0.04 g of 5-(2-bromoethoxy)benzo[d]thiazole (Yield=23%).

6-(2-Bromoethoxy) benzo[d] thiazole

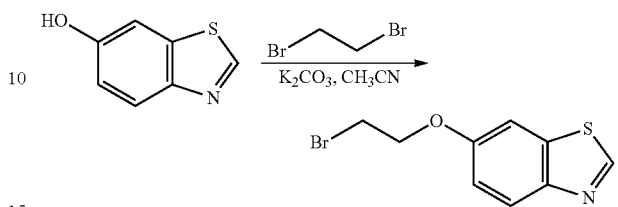

Title compound was prepared from benzo[d] thiazol-6-ol (1 g, 6.62 mmol) using the general methodology of Int-1 and afforded 0.39 g of 6-(2-bromoethoxy) benzo[d] thiazole (Yield=23%).

6-(2-bromoethoxy)benzo[d]oxazole

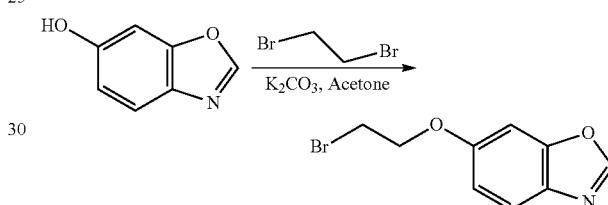

Title compound was prepared from benzo[d]oxazol-6-ol (0.20 g, 1.48 mmol, 1 equiv) using the general methodology of Intermediate-3. Purification by column chromatography (20% EtOAc/Hexane) afforded 0.08 g of 6-(2-bromoethoxy) benzo[d]oxazole (Yield=22%).

2-(2-chloroethoxy)-8-(trifluoromethyl)quinoline

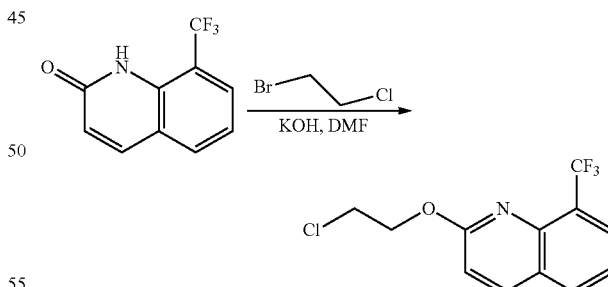

To a stirred solution of 8-(trifluoromethyl)quinolin-2 (1H)-one (100 mg, 0.47 mmol) in DMF (1 mL) was added KOH (53 mg, 0.94 mmol) at 0° C. and the mixture was stirred for 1 h. Then 1-bromo-2-chloroethane (135 mg, 0.94 mmol) was added at 0° C. and the reaction mixture was stirred at RT for 16 h. After completion, the reaction was quenched with aq.NH$_4$Cl and extracted with EtOAc. The organic layer was separated, dried over Na$_2$SO$_4$ and concentrated under reduced pressure. The crude compound was purified by column chromatography eluting with 5% EtOAc in hexanes to obtain 90 mg of 2-(2-chloroethoxy)-8-(trifluoromethyl)quinoline (Yield=70%).

3-(2-Bromoethoxy)-1,1'-biphenyl

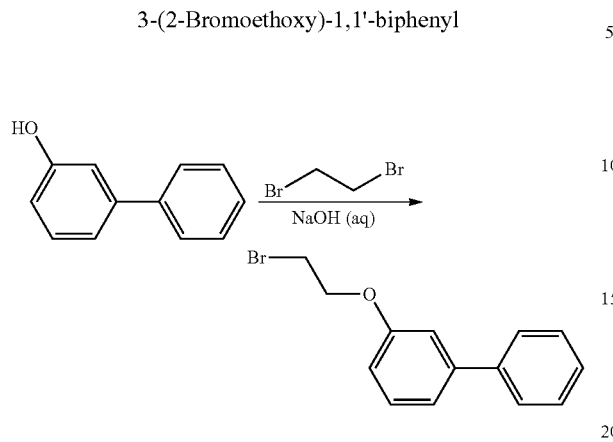

Title compound was prepared from [1,1'-biphenyl]-3-ol (0.5 g, 2.94 mmol) using the general methodology of Intermediate-2. Purification using silica gel column chromatography (15% EtOAc/Hexanes) afforded 0.1 g of 3-(2-bromoethoxy)-1,1'-biphenyl (Yield=12%).

(3-bromopropoxy)benzene

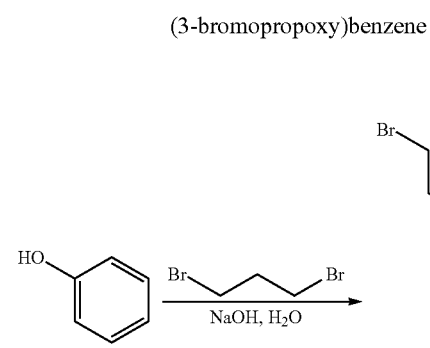

Title compound was prepared from phenol (5 g, 53.1 mmol) using the general methodology of Intermediate-2 and afforded 9 g of (3-bromopropoxy)benzene (Yield=79%).

1-(3-Bromopropoxy)-2-(trifluoromethyl)benzene

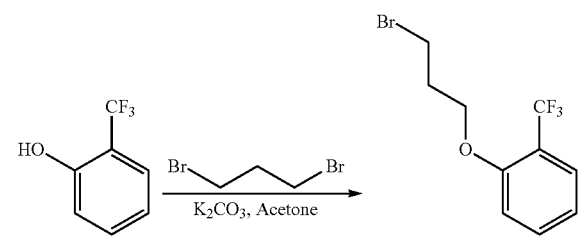

Title compound was prepared from 2-(trifluoromethyl)phenol (1 g, 6.17 mmol) using the general methodology of Intermediate-3. Purification using silica gel column chromatography (2% MeOH/DCM) afforded 1.2 g of 4-methyl-1-(2-(2-(trifluoromethyl)phenoxy)ethyl)piperidine (Yield=69%).

(4-bromobutoxy)benzene

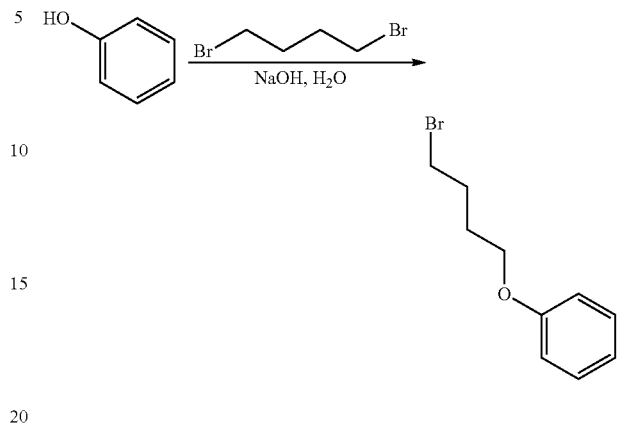

Title compound was prepared from phenol (5 g, 53.1 mmol) using the general methodology of Intermediate-2 and afforded 10 g of (3-bromopropoxy)benzene (Yield=82%).

1-(4-Bromobutoxy)-2-fluorobenzene

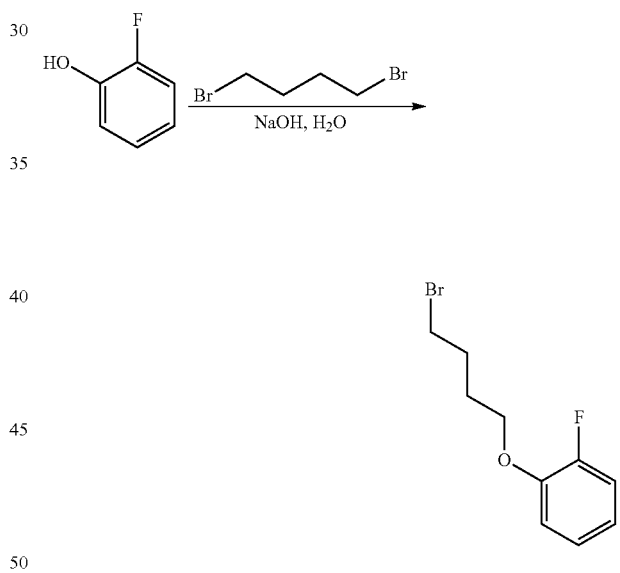

Title compound was prepared from 2-fluorophenol (1 g, 8.9 mmol) using the general methodology of Intermediate-2 and afforded 0.64 g of 1-(4-bromobutoxy)-2-fluorobenzene (Yield=29%).

1-(4-Bromobutoxy)-2-chlorobenzene

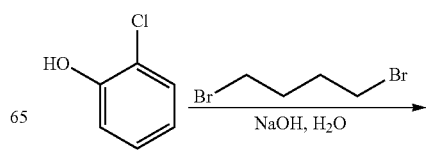

115

-continued

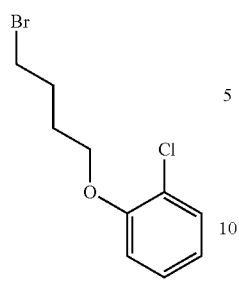

Title compound was prepared from 2-chlorophenol (1 g, 7.8 mmol) using the general methodology of Intermediate-2 and afforded 0.62 g of 1-(4-bromobutoxy)-2-chlorobenzene (Yield=30%).

6-(4-Bromobutoxy)benzo[d]thiazole

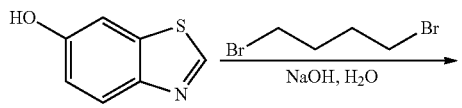

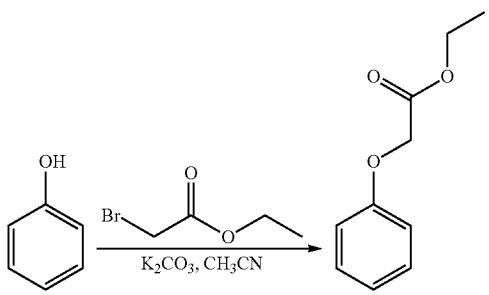

Title compound was prepared from benzo[d]thiazol-6-ol (0.5 g, 3.31 mmol) using the general methodology of Intermediate-2. Purification using silica gel column chromatography (10% EtOAc/Hexanes) afforded 0.3 g of 6-(4-bromobutoxy)benzo[d]thiazole (Yield=32%).

Ethyl 2-phenoxyacetate

Title compound was prepared from phenol (5 g, 53.1 mmol) and ethyl 2-bromoacetate using the general methodology of Example-1. Purification using silica gel column chromatography (40% EtOAc/Hexanes as eluent) to afford 7.5 g of 1-(3-(4-chlorophenoxy)-3-methyl pyrrolidin-1-yl)-2-phenoxyethan-1-one (Yield=78%).

116

2-Phenoxyacetic acid

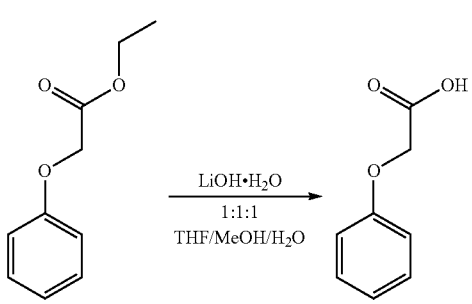

To a solution of ethyl 2-phenoxyacetate (2 g, 11.1 mmol) in 1:1:1 mixture of THF/MeOH/H$_2$O (40 mL) was added lithium hydroxide monohydrate at 0° C. The reaction was stirred at room temperature for 12 h. After completion, the volatiles were removed under reduced pressure, diluted with water, neutralized with 1N HCl and the volatiles were removed under pressure. The residue was dissolved in EtOH (15 mL) and the solids were filtered. The filtrate was concentrated under reduced pressure to afford 1.6 g of 2-phenoxyacetic acid (Yield=95%). ESI+MS: m/z 151 ([M−H]−).

2-Bromo-N-(2-(trifluoromethyl)phenyl)acetamide

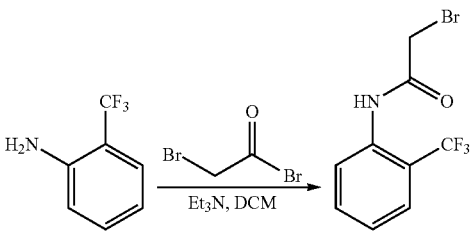

To a solution of 2-(trifluoromethyl)aniline (0.5 g, 3.10 mmol) in CH$_2$Cl$_2$ (5 mL) were added triethylamine (0.649 mL, 4.65 mmol, 1.5 equiv) and 2-bromoacetyl bromide (0.75 g, 3.72 mmol, 1.2 equiv) at 0° C. The reaction mixture was stirred at room temperature for 16 h. After completion, the reaction was diluted water and extracted with CH$_2$Cl$_2$. The organic extract was dried over sodium sulfate, filtered and concentrated under reduced pressure. Purification using silica gel column chromatography (15% EtOAc/Hexanes as eluent) to afford 0.2 g of 2-bromo-N-(2-(trifluoromethyl)phenyl)acetamide (Yield=23%).

2-(2-(methylsulfonyl)phenoxy)ethyl methanesulfonate

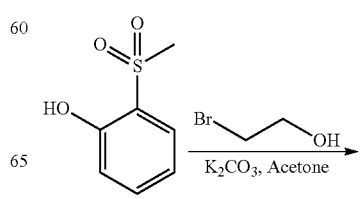

1-(4-(2-bromoethoxy)phenyl)ethanone

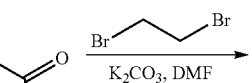
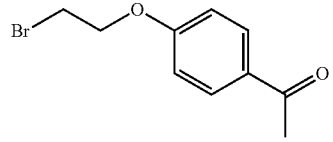

Title compound was prepared from 1-(4-hydroxyphenyl) ethanone (2.0 g, 14.7 mmol) using the general methodology of Int-1 and afforded 2.0 g of 1-(4-(2-bromoethoxy)phenyl) ethanone (Yield=56%).

1-(2-bromoethoxy)-4-(methylsulfonyl)benzene

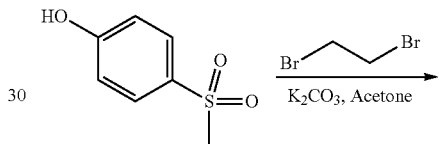
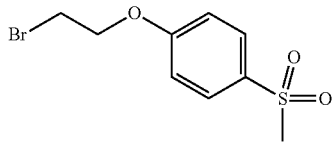

Title compound was prepared from 4-(methylsulfonyl) phenol (0.2 g, 1.16 mmol) using the general methodology of Int-3 and afforded 0.1 g of 1-(2-bromoethoxy)-4-(methylsulfonyl)benzene (Yield=31%).

4-(2-bromoethoxy)benzonitrile

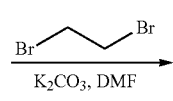
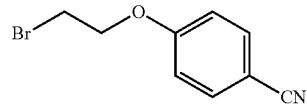

Title compound was prepared from 4-hydroxybenzonitrile (2.0 g, 16.79 mmol) using the general methodology of Int-1 and afforded 0.4 g of 4-(2-bromoethoxy)benzonitrile (Yield=11%).

---

-continued

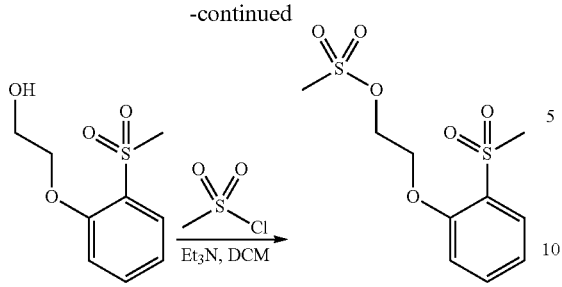

2-(2-(methylsulfonyl)phenyl)ethan-1-ol

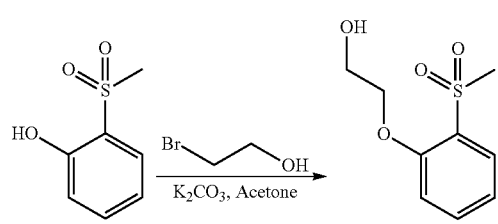

To a solution of 2-(methyl sulfonyl) phenol (1.0 g, 5.8 mmol) in acetone (20 mL) was added $K_2CO_3$ (1.61 g, 11.61 mmol) and 2-bromoethanol (2.18 g, 17.4 mmol) at 0° C. The reaction mixture was heated at 60° C. and stirred for 6 h. After completion of the reaction (monitored by TLC), the reaction mass was diluted with water and extracted with EtOAc. The organic layer was dried over $Na_2SO_4$ and concentrated under reduced pressure to obtain crude material.

The crude compound was purified by column chromatography eluting with 3% MeOH in DCM to afford 0.9 g of 2-(2-(methylsulfonyl)phenyl)ethan-1-ol as thick syrup (Yield=72%). 2-(2-(methylsulfonyl)phenoxy)ethyl methanesulfonate:

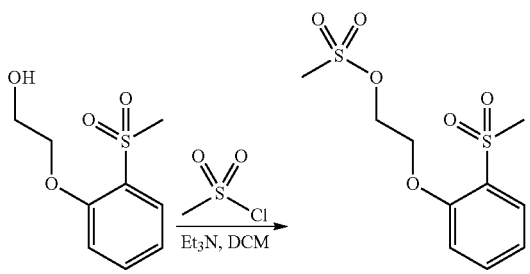

To a stirred solution of 2-(2-(methylsulfonyl)phenyl) ethan-1-ol (0.1 g, 0.46 mmol) in DCM (10 mL) cooled to 0° C. was added triethylamine (0.16 mL, 1.16 mmol) followed by MsCl (0.04 mL, 0.51 mmol). The reaction mixture was stirred at RT for 16 h. After completion of the reaction (monitored by TLC), diluted with water and extracted with DCM. The organic layer was separated, dried over anhydrous $Na_2SO_4$ and concentrated under reduced pressure to afford the crude. The crude compound was purified by column chromatography eluent with 2% MeOH in DCM to afford 0.13 g of 2-(2-(methylsulfonyl)phenoxy)ethyl methanesulfonate as thick syrup (Yield=95%).

1-(2-(2-bromoethoxy)-5-fluorophenyl)ethan-1-one

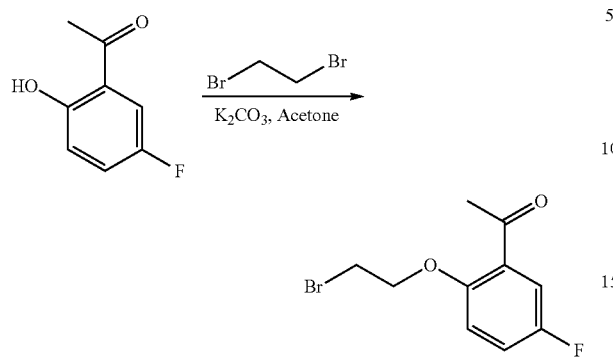

Title compound was prepared from 1-(5-fluoro-2-hydroxyphenyl)ethanone (0.5 g, 3.24 mmol) using the general methodology of Int-3 and afforded 0.19 g of 1-(2-(2-bromoethoxy)-5-fluorophenyl)ethan-1-one (Yield=23%).

1-(2-bromoethoxy)-2-methoxybenzene

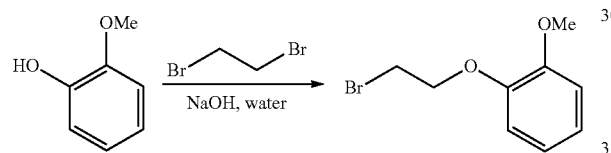

Title compound was prepared from 2-methoxyphenol (2.0 g, 16.11 mmol) using the general methodology of Int-2 and afforded 1.0 g of 1-(2-bromoethoxy)-2-methoxybenzene (Yield=27%).

1-(2-bromoethoxy)-4,5-difluoro-2-methoxybenzene

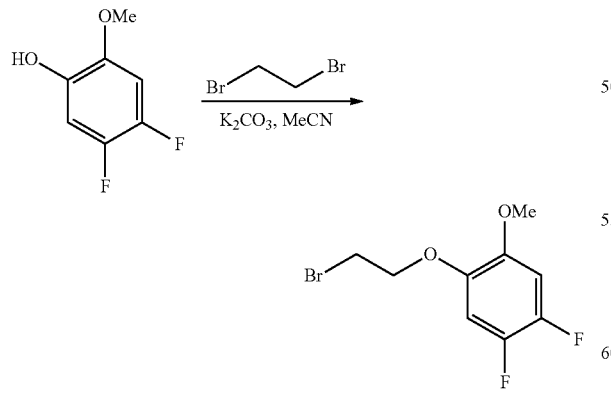

Title compound was prepared from 4,5-difluoro-2-methoxyphenol (0.5 g, 3.12 mmol) using the general methodology of Example-1 and afforded 0.3 g of 1-(2-bromoethoxy)-4,5-difluoro-2-methoxybenzene (Yield=36%).

1-(2-bromoethoxy)-4-fluoro-2-isopropoxybenzene

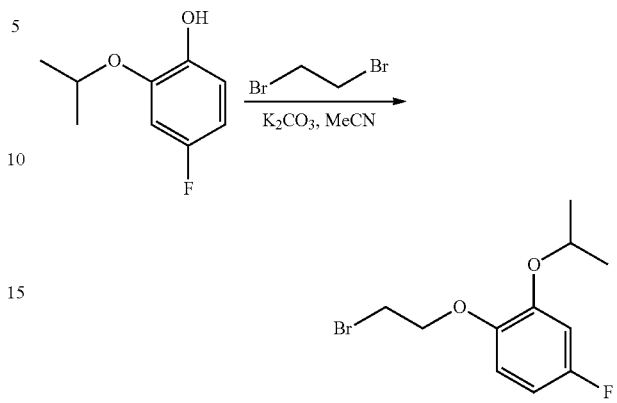

Title compound was prepared from 4-fluoro-2-isopropoxyphenol (0.25 g, 1.47 mmol) using the general methodology of Example-1 and afforded 0.1 g of 1-(2-bromoethoxy)-4-fluoro-2-isopropoxybenzene (Yield=25%).

2-((3-(trifluoromethyl)pyridin-2-yl)oxy)ethyl methanesulfonate

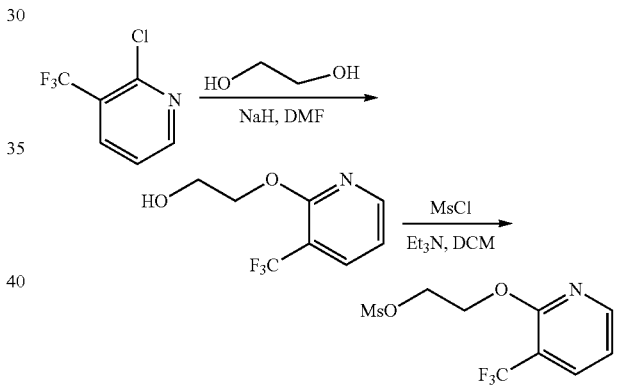

((3-(trifluoromethyl)pyridin-2-yl)oxy)ethan-1-ol

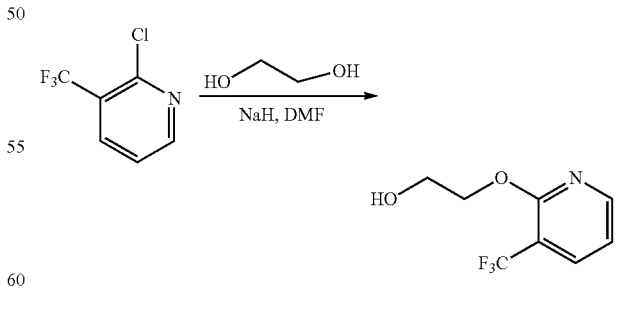

To a stirred solution of 2-chloro-3-(trifluoromethyl)pyridine (300 mg, 1.65 mmol) in DMF (2 mL) was added NaH (60% suspension, 132 mg, 3.3 mmol) followed by ethylene glycol (411 mg, 6.6 mmol) at room temperature. The reaction mixture was heated at 100° C. for 16 h. The reaction mass was diluted with water and extracted with ethyl acetate. The organic layer was dried over Na₂SO₄, filtered and concentrated Purification by column chromatography (eluting with 40% EtOAc in hexane) afforded 200 mg of 2-((3-(trifluoromethyl)pyridin-2-yl)oxy)ethan-1-ol (Yield=58%).

2-((3-(trifluoromethyl)pyridin-2-yl)oxy)ethyl methanesulfonate

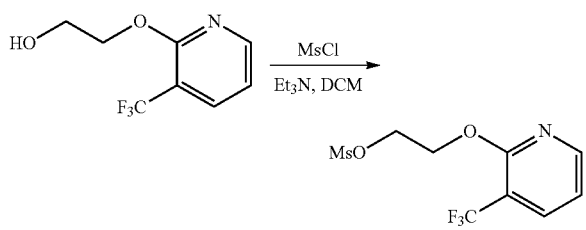

To a stirred solution of 2-((3-(trifluoromethyl)pyridin-2-yl)oxy)ethanol (200 mg, 0.97 mmol) in DCM (10 mL) was added triethylamine (0.53 mL, 0.2 mmol) followed by methanesulfonyl chloride (0.12 mL, 1.16 mmol) at 0° C. The reaction mixture was stirred at room temperature for 4 h. After completion, the reaction was diluted with water and extracted with DCM. The organic layer was dried over Na₂SO₄, filtered and concentrated to afford 200 mg of 2-((3-(trifluoromethyl)pyridin-2-yl)oxy)ethyl methanesulfonate (Yield=73%).

(S)-(2,3-dihydrobenzo[b][1,4]dioxin-2-yl)methanol

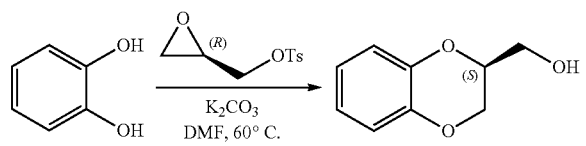

To a suspension of pyrocathecol (0.58 g, 5.26 mmol) and K₂CO₃ (0.73 g, 5.26 mmol) in anhydrous DMF (22 mL), was added (2R)-(−)-glycidyl tosylate (1.00 g, 4.38 mmol). The mixture was left stirring at 60° C. for 16 hours, then poured into ice-water and extracted with Et₂O until the organic phase was colorless. The organic layers were washed with brine, dried over Na₂SO₄ filtered and concentrated. Purification by flash chromatography (hexanes/EtOAc 80:20) afforded the pure product as white solid (0.41 g, 56% yield). [α]$_D^{25}$=−33.1° (EtOH; c=0.26). ¹H-NMR (300 MHz, CDCl₃): δ 6.97-6.76 (m, 4H), 4.33-4.22 (m, 2H), 4.17-4.05 (m, 1H), 3.87 (qd, J=11.9, 4.4 Hz, 2H). ESI-MS calcd for C₉H₁₀O₃ m/z 166.06, found 167.43 [M+H]⁺.

(R)-(2,3-dihydrobenzo[b][1,4]dioxin-2-yl)methanol

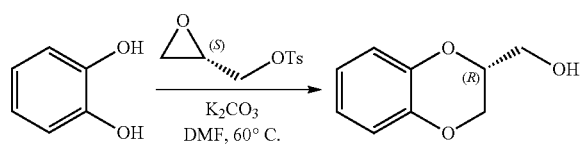

To a suspension of pyrocathecol (0.58 g, 5.26 mmol) and K₂CO₃ (0.73 g, 5.26 mmol) in anhydrous DMF (22 mL) was added (2S)-(−)-glycidyl tosylate (1.00 g, 4.38 mmol). The mixture was left stirring at 60° C. for 16 hours, then poured into ice-water and extracted with Et₂O until the organic phase was colorless. The organic layers were washed with brine, dried over Na₂SO₄ and evaporated to give crude product. Purification by flash chromatography (n-hexane/EtOAc 80:20) afforded the pure product as white solid (0.43 g, 60% yield). [α]$_D^{25}$=+32.5° (EtOH; c=0.20). ¹H-NMR (400 MHz, CDCl₃): δ 6.95-6.79 (m, 4H), 4.33-4.22 (m, 2H), 4.17-4.05 (m, 1H), 3.87 (qd, J=11.9, 4.4 Hz, 2H). ESI-MS calcd for C₉H₁₀O₃ m/z 166.06, found 167.43 [M+H]⁺.

(R)-2-(bromomethyl)-2,3-dihydrobenzo[b][1,4]dioxine

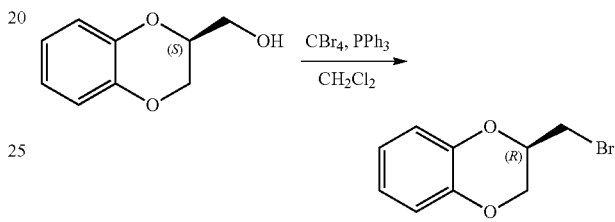

A solution of (S)-(2,3-dihydrobenzo[b][1,4]dioxin-2-yl)methanol (0.40 g, 2.41 mmol) and CBr₄ (0.87 g, 2.62 mmol) in CH₂Cl₂ (1.0 mL) was cooled to 0° C. PPh₃ (0.69 g, 2.65 mmol) was added in portions over 30 min with vigorous stirring. Upon the addition of the phosphine, the colorless solution turned a pale brown color and was stirred for an additional 2 h at room temperature. The mixture was concentrated and n-hexane was added, the white precipitate filtered and purified by flash chromatography (n-hexane 100%) to obtain pure product as colorless oil (0.32 g, 58% yield). [α]$_D^{25}$=−20.8° (EtOH; c=0.94). ¹H-NMR (400 MHz, CDCl₃): δ 6.92-6.83 (m, 4H), 4.44-4.38 (m, 1H), 4.35 (dd, J=11.5, 2.3 Hz, 1H), 4.19 (dd, J=11.4, 5.9 Hz, 1H), 3.59-3.47 (m, 2H).

(S)-2-(bromomethyl)-2,3-dihydrobenzo[b][1,4]dioxine

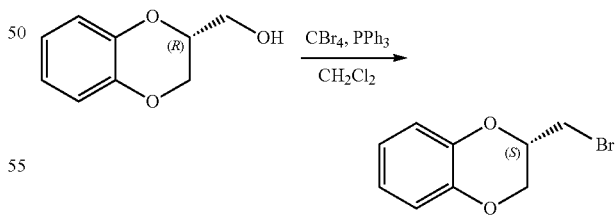

A solution of (R)-(2,3-dihydrobenzo[b][1,4]dioxin-2-yl)methanol (400 mg, 2.41 mmol) and CBr₄ (870 mg, 2.62 mmol) in CH₂Cl₂ (1.0 mL) was cooled to 0° C. PPh₃ (694 mg, 2.65 mmol) was added in portions over 30 min with vigorous stirring. Upon the addition of the phosphine, the colorless solution turned a pale brown color and was stirred for an additional 2 h at room temperature. The mixture was concentrated and hexane was added, the white precipitate filtered and purified by flash chromatography (n-hexane 100%) to obtain pure product as colorless oil (0.31 g, 56% yield). $[\alpha]_D^{25}$=+19.4° (EtOH; c=0.86). $^1$H-NMR (400 MHz, CDCl$_3$): δ 6.92-6.83 (m, 4H), 4.44-4.38 (m, 1H), 4.35 (dd, J=11.5, 2.3 Hz, 1H), 4.19 (dd, J=11.4, 5.9 Hz, 1H), 3.59-3.47 (m, 2H).

(R)-(2,3-dihydrobenzo[b][1,4]dioxin-2-yl)methyl 4-methylbenzenesulfonate

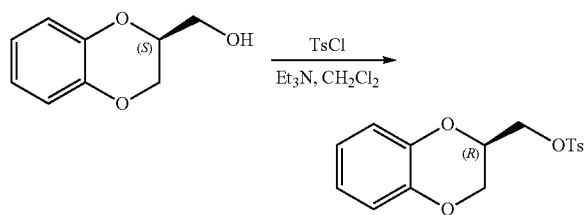

To a solution of (S)-(2,3-dihydrobenzo[b][1,4]dioxin-2-yl)methanol (1.65 g, 9.93 mmol) and Et$_3$N (2.78 mL, 19.86 mmol) in CH$_2$Cl$_2$ (10 mL) was slowly added a solution of tosyl chloride (2.08 g, 10.92 mmol) in CH$_2$Cl$_2$ (20 mL) at 0° C., under a N$_2$ atmosphere. The reaction mixture was stirred at room temperature overnight, then poured into water (50 mL) and the aqueous layer was extracted with CH$_2$Cl$_2$. The organic layers were combined and washed with 3M aq. sol. HCl, 2M aq. sol. Na$_2$CO$_3$, and H$_2$O. The organic phase was dried over MgSO$_4$ and concentrated. Purification by flash chromatography (n-hexane/EtOAc 80:20) afforded the pure product as white solid (2.42 g, 76% yield). $[\alpha]_D^{25}$=−13.6° (CHCl$_3$; c=0.60). $^1$H-NMR (300 MHz, Chloroform-d): δ 7.80 (d, J=8.3 Hz, 2H), 7.36 (d, J=8.3 Hz, 2H), 6.88-6.75 (m, 4H), 4.47-4.35 (m, 1H), 4.30-4.20 (m, 3H), 4.04 (dd, J=11.6, 6.3 Hz, 1H), 2.46 (s, 3H). ESI–MS calcd for C$_{16}$H$_{16}$O$_5$S m/z 320.07, found 320.20 [M]$^+$.

(R)-2-(bromomethyl)-7-fluoro-2,3-dihydrobenzo[b][1,4]dioxine

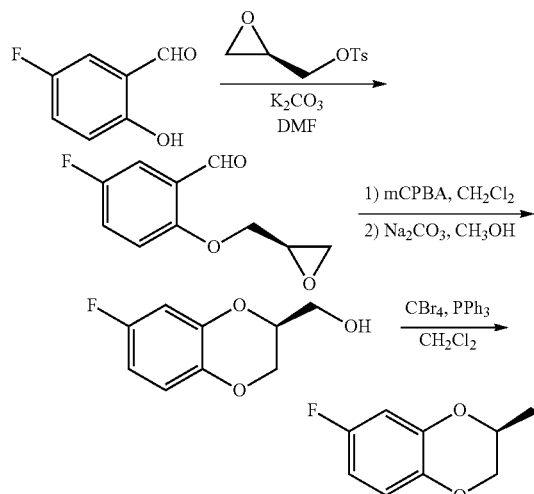

To a solution of 5-fluoro-2-hydroxybenzaldehyde (0.31 g, 2.19 mmol) in an. DMF (0.9 mL) at room temperature was added (2R)-(−)-glycidyl tosylate (0.50 g, 2.19 mmol) and K$_2$CO$_3$ (0.36 g, 2.63 mmol) and the mixture was heated at 60° C. for 2 hours. The reaction was diluted with Et$_2$O and the organic phase washed with H$_2$O, 5% aq. LiCl and brine. The organic phase was dried over Na$_2$SO$_4$, filtered and removed under reduced pressure. Filtration over silica gave the epoxide intermediate, which was carried over in the next reaction.

The crude epoxide intermediate (0.33 g) was dissolved in an. CH$_2$Cl$_2$ (5.6 mL), 3-chlorobenzoperoxoic acid (0.32 g, 1.85 mmol) was added and the solution was left to stir for 90 minutes. The suspension was filtered and filtered over silica gel. The crude was dissolved in CH$_3$OH (3.5 mL) and Na$_2$CO$_3$ (100 mg) was added and the mixture was left stirring overnight. The mixture was diluted with water and neutralized with a 0.1 M aq. HCl. The aqueous phase was extracted with CH$_2$Cl$_2$, the organic phases collected, dried over MgSO$_4$, filtered and concentrated. Filtration over silica gel gave a crude containing ~50% of the intermediate alcohol and was carried over in the next reaction.

A solution of crude intermediate alcohol (190 mg) and CBr$_4$ (373 mg, 1.14 mmol) in CH$_2$Cl$_2$ (0.45 mL) was cooled to 0° C. PPh$_3$ (298 mg, 0.13 mmol) was added under vigorous stirring. Upon the addition of the phosphine, the colorless solution turned a pale brown color and was stirred overnight at room temperature. The mixture was concentrated and n-hexane was added, the white precipitate filtered and purified by flash chromatography (n-hexane 100%) to afford 51 mg of (R)-2-(bromomethyl)-7-fluoro-2,3-dihydrobenzo[b][1,4]dioxine as colorless oil (Yield=20%). $[\alpha]_D^{25}$=−5.0° (CHCl$_3$; c=0.65). $^1$H-NMR (300 MHz, Chloroform-d): δ 6.82 (dd, J=8.9, 5.4 Hz, 1H), 6.66-6.53 (m, 2H), 4.47-4.36 (m, 1H), 4.32 (dd, J=11.6, 2.3 Hz, 1H), 4.16 (dd, J=11.5, 5.9 Hz, 1H), 3.60-3.45 (m, 2H).

(R)-7-bromo-2-(bromomethyl)-2,3-dihydrobenzo[b][1,4]dioxine

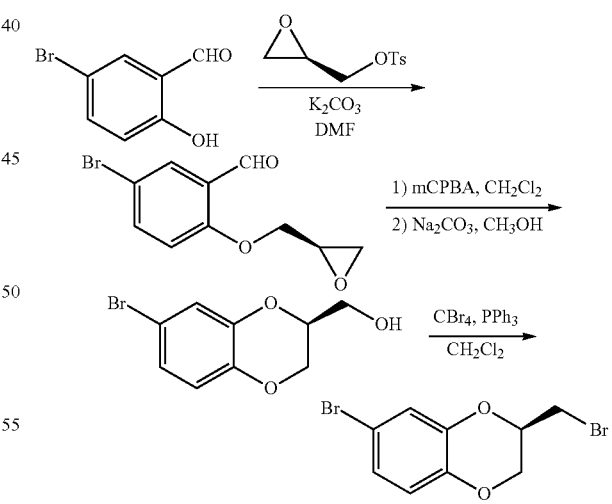

Title compound was prepared using the same strategy described above for the synthesis of (R)-2-(bromomethyl)-7-fluoro-2,3-dihydrobenzo[b][1,4]dioxine starting from 5-bromo-2-hydroxybenzaldehyde in place of 5-fluoro-2-hydroxybenzaldehyde and afforded 60 mg of (R)-7-bromo-2-(bromomethyl)-2,3-dihydrobenzo[b][1,4]dioxine (Yield=56%). $[\alpha]_D^{25}$=−11.1° (CHCl$_3$; c=0.90). $^1$H-NMR (400 MHz, Chloroform-d): δ 7.06 (d, J=2.3 Hz, 1H), 6.96

(dd, J=8.6, 2.3 Hz, 1H), 6.77 (d, J=8.6 Hz, 1H), 4.44-4.36 (m, 1H), 4.33 (dd, J=11.5, 2.3 Hz, 1H), 4.17 (dd, J=11.6, 5.9 Hz, 1H), 3.58-3.46 (m, 2H).

Synthesis of Key Intermediate-I 3-(4-Chlorophenoxy)-3-methylpyrrolidine (Int-I)

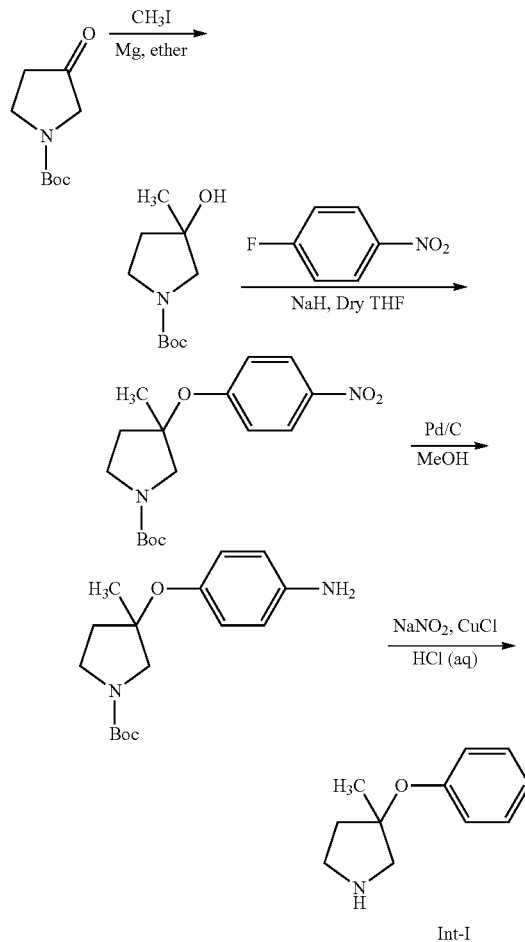

tert-butyl 3-hydroxy-3-methylpyrrolidine-1-carboxylate

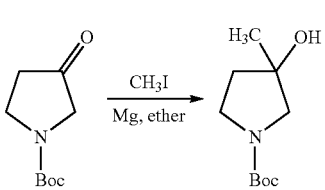

To a stirred suspension of magnesium (2.59 g, 106 mmol, 1.97 equiv) in 50 mL of dry ether were added iodine (catalytic) and methyl iodide (6.7 mL, 108 mmol, 2 equiv) slowly drop wise at 0° C. under argon atmosphere. This was added to a solution of tert-butyl 3-oxopyrrolidine-1-carboxylate (10 g, 54 mmol, 1 equiv) in 50 mL of ether at 0° C. The reaction mixture was warmed to room temperature and stirred for 1.5 h. After completion, the reaction was quenched with saturated ammonium chloride solution at 0° C. and extracted with EtOAc. The combined organic extract was dried over sodium sulfate, filtered and concentrated under reduced pressure. Purification using silica gel column chromatography (20% EtOAc/hexanes) afforded 7.0 g of tert-butyl 3-hydroxy-3-methylpyrrolidine-1-carboxylate (Yield=64%).

tert-butyl 3-methyl-3-(4-nitrophenoxy)pyrrolidine-1-carboxylate

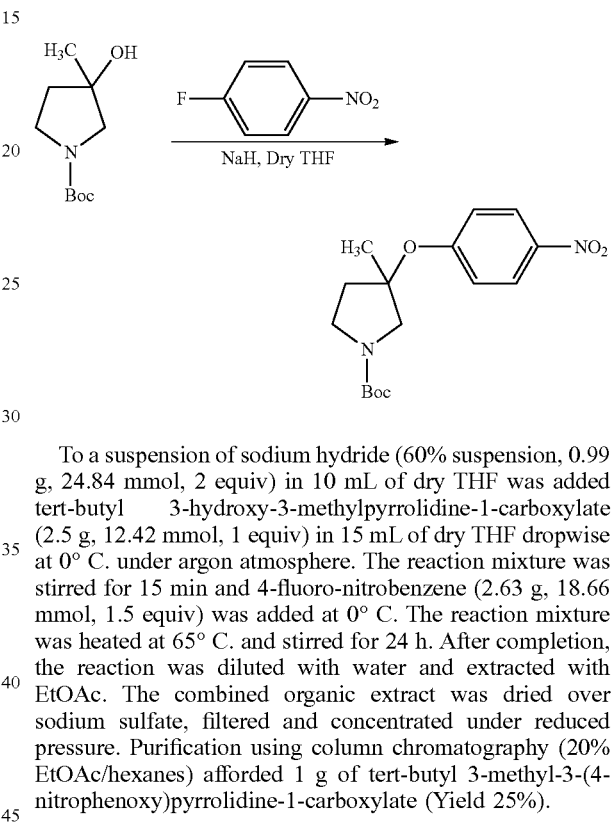

To a suspension of sodium hydride (60% suspension, 0.99 g, 24.84 mmol, 2 equiv) in 10 mL of dry THF was added tert-butyl 3-hydroxy-3-methylpyrrolidine-1-carboxylate (2.5 g, 12.42 mmol, 1 equiv) in 15 mL of dry THF dropwise at 0° C. under argon atmosphere. The reaction mixture was stirred for 15 min and 4-fluoro-nitrobenzene (2.63 g, 18.66 mmol, 1.5 equiv) was added at 0° C. The reaction mixture was heated at 65° C. and stirred for 24 h. After completion, the reaction was diluted with water and extracted with EtOAc. The combined organic extract was dried over sodium sulfate, filtered and concentrated under reduced pressure. Purification using column chromatography (20% EtOAc/hexanes) afforded 1 g of tert-butyl 3-methyl-3-(4-nitrophenoxy)pyrrolidine-1-carboxylate (Yield 25%).

tert-butyl 3-(4-aminophenoxy)-3-methylpyrrolidine-1-carboxylate

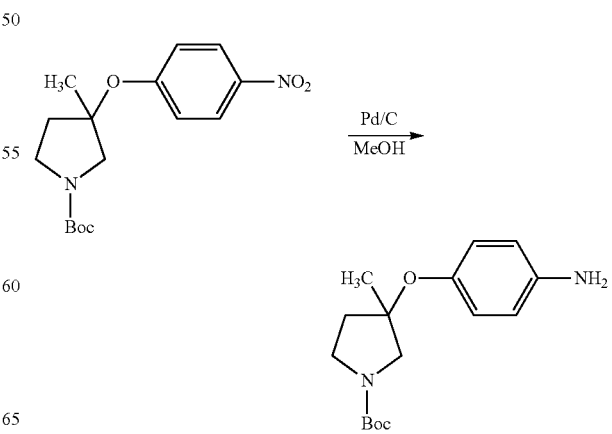

To a solution of tert-butyl 3-methyl-3-(4-nitrophenoxy) pyrrolidine-1-carboxylate (0.95 g, 2.95 mmol, 1 equiv) in 10 mL of MeOH was added 10% Pd/C (0.25 g) under argon atmosphere. The reaction mixture was stirred at room temperature under hydrogen balloon pressure for 4 h. After completion, the reaction mixture was filtered through celite bed, washed with MeOH and the filtrate was concentrated under reduced pressure to afford 0.8 g of tert-butyl 3-(4-aminophenoxy)-3-methylpyrrolidine-1-carboxylate (Yield 93%).

3-(4-Chlorophenoxy)-3-methylpyrrolidine (Int-1)

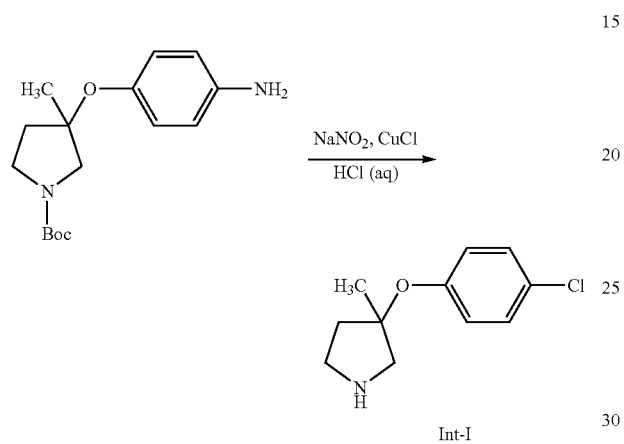

Int-I

To a solution of tert-butyl 3-(4-aminophenoxy)-3-methylpyrrolidine-1-carboxylate (0.2 g, 0.68 mmol, 1 equiv) in 3 mL of 50% aqueous HCl was added aqueous sodium nitrate (0.061 g, 0.889 mmol, 1.3 equiv) drop wise at 0° C. and stirred for 1 h. This was added to a solution of cuprous chloride (0.1 g, 1.09 mmol, 1.6 equiv) in 1 mL of aqueous HCl at 0° C. and stirred at room temperature for 16 h. After completion, the pH was adjusted to 10 with aqueous sodium carbonate and extracted with EtOAc. The combined organic extract was dried over sodium sulfate, filtered and concentrated under reduced pressure. The crude was washed with n-hexane and dried under reduced pressure to afford 0.12 g of 3-(4-chlorophenoxy)-3-methylpyrrolidine along with des chloro compound (Yield 83%). ESI+MS: m/z 212 [M+H]$^+$.

Synthesis of Key Intermediate-II

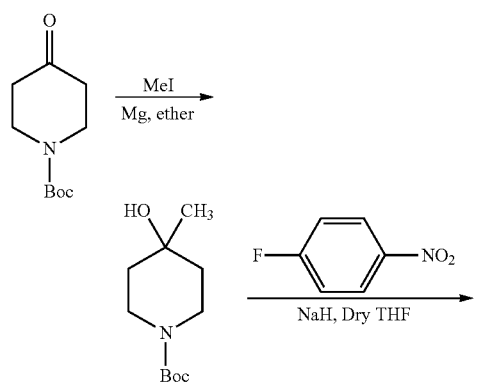

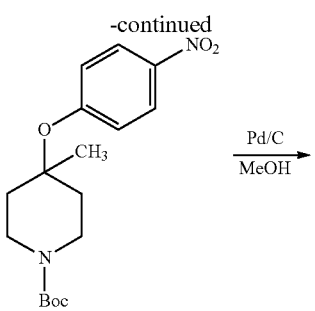

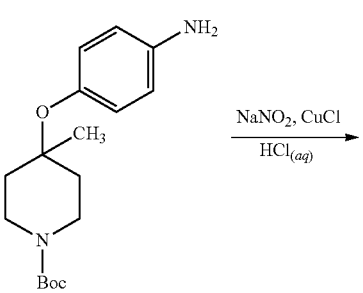

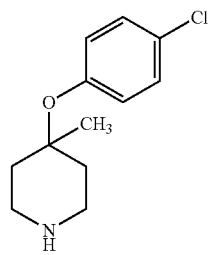

Int-II tert-butyl 4-hydroxy-4-methylpiperidine-1-carboxylate

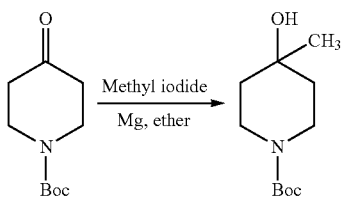

Title compound was prepared from tert-butyl 4-oxopiperidine-1-carboxylate (5 g, 25.09 mmol) using the general methodology of step 1 in key Intermediate-I. Purification using silica gel column chromatography (20% EtOAc/Hexane) afforded 2.4 g of tert-butyl 4-hydroxy-4-methylpiperidine-1-carboxylate (Yield=44%).

tert-butyl 4-methyl-4-(4-nitrophenoxy)piperidine-1-carboxylate

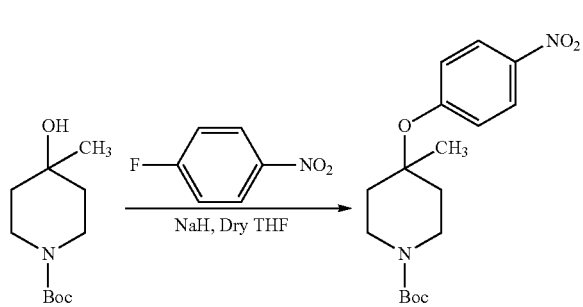

To a suspension of sodium hydride (60% suspension, 0.36 g, 9.29 mmol, 2 equiv) in 3 mL of dry THF was added tert-butyl 4-hydroxy-4-methylpiperidine-1-carboxylate (1 g, 4.64 mmol, 1 equiv) in dry THF (7 mL) drop wise at 0° C. The reaction mixture was stirred for 15 min, 4-fluoro nitro benzene (0.98 g, 6.97 mmol, 1.5 equiv) was added at 0° C. and the reaction was heated at 70° C. for 12 h. After completion, the reaction was quenched with ice cold water and extracted with EtOAc. The organic extract was dried over sodium sulfate, filtered and concentrated under reduced pressure. Purification using silica gel column chromatography (10% EtOAc/hexane as eluent) to afford 1.0 g of tert-butyl 4-methyl-4-(4-nitrophenoxy)piperidine-1-carboxylate (Yield=64%).

tert-butyl 4-(4-aminophenoxy)-4-methylpiperidine-1-carboxylate

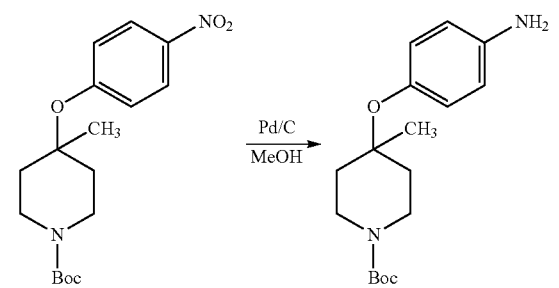 [SMILES: "MeOH" ; CC(C)(C)OC(=O)N1CCC(C)(Oc2ccc([N+](=O)[O-])cc2)CC1 ; CC(C)(C)OC(=O)N1CCC(C)(Oc2ccc(N)cc2)CC1]

Title compound was prepared from tert-butyl 4-methyl-4-(4-nitrophenoxy)piperidine-1-carboxylate (1 g, 2.97 mmol) using the general methodology of step 3 in key Intermediate-I. Purification using silica gel column chromatography (40% EtOAc/Hexane) afforded 0.65 g tert-butyl 4-(4-aminophenoxy)-4-methylpiperidine-1-carboxylate (Yield=71%). ESI+MS: m/z 307 ([M+H]$^+$).

4-(4-Chlorophenoxy)-4-methylpiperidine (Int-II)

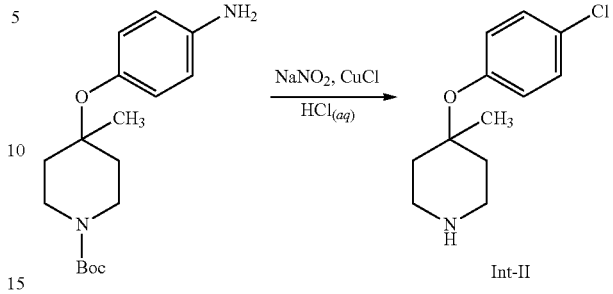

Title compound was prepared from tert-butyl 4-(4-aminophenoxy)-4-methylpiperidine-1-carboxylate (0.25 g, 0.816 mmol) using the general methodology of step 4 in key Intermediate-I. Purification using silica gel column chromatography (40% EtOAc/Hexane) afforded 0.105 g 4-(4-chlorophenoxy)-4-methylpiperidine (Yield=57%). ESI+MS: m/z 226 ([M+H]$^+$).

Key Intermediate-IV

3-Methyl-1-(2-phenoxyethyl)pyrrolidin-3-ol (Int-IV)

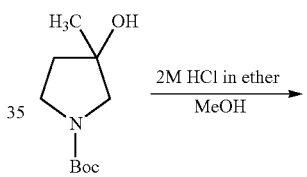

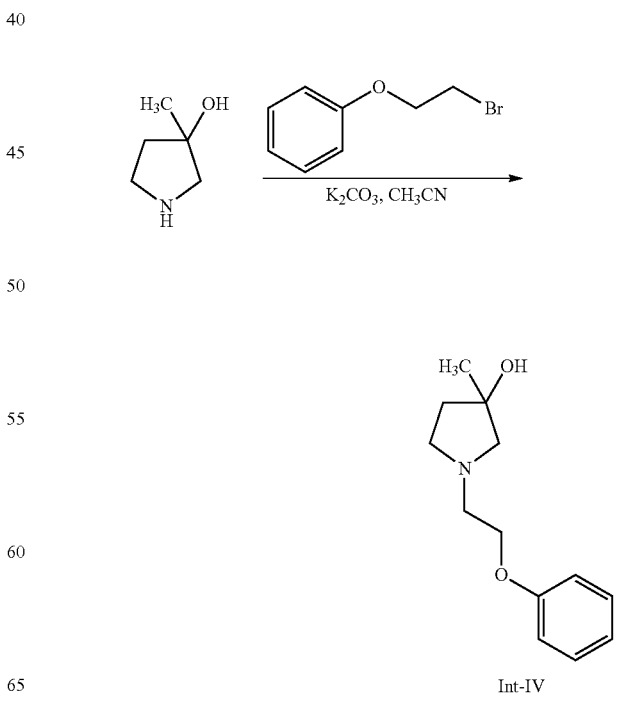

3-Methylpyrrolidin-3-ol hydrochloride

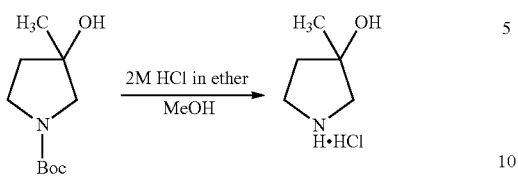

tert-butyl 3-hydroxy-3-methylpyrrolidine-1-carboxylate (6 g, 29.8 mmol) was dissolved in methanol (80 mL) and the mixture was cooled to 0° C. A solution of HCl in ether (2N, 66 mL) was then added and the reaction mixture was stirred at RT for 4 h. After completion of the reaction (monitored by TLC), solvent was completely removed and washed with ether to afford compound as brown solid. The crude was further washed with diethyl ether to afford 2.8 g of 3-methylpyrrolidin-3-ol hydrochloride (Yield=68%).

3-Methyl-1-(2-phenoxyethyl)pyrrolidin-3-ol (Int-IV)

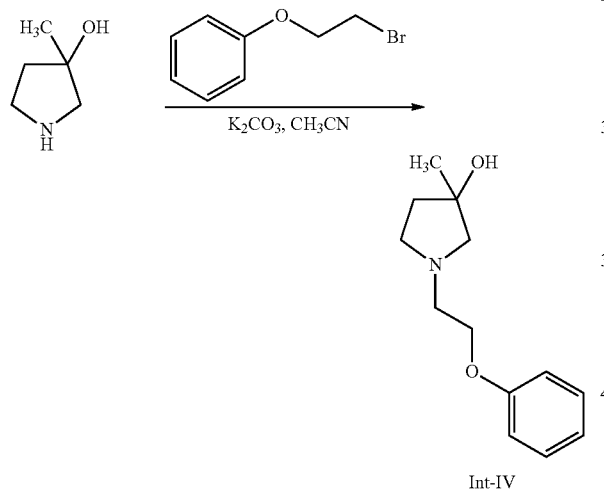

Title compound was prepared from 3-methylpyrrolidin-3-ol hydrochloride (0.9 g, 6.54 mmol) and (2-bromoethoxy)benzene (1.3 g, 6.54 mmol, 1 equiv) using the general methodology of Example-1. Purification using silica gel column chromatography (5% MeOH/$CH_2Cl_2$) afforded 1.37 g of 3-methyl-1-(2-phenoxyethyl)pyrrolidin-3-ol (Yield=95%).

Synthesis of Key Intermediate-V 1-(2-(2-Fluorophenoxy) ethyl)-3-methyl-3-(3-(trifluoromethyl) phenoxy) piperidine (Int-V)

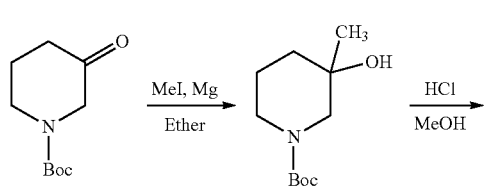

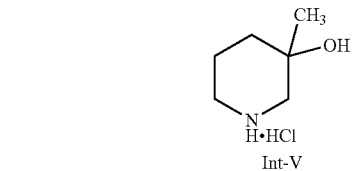

tert-butyl 3-hydroxy-3-methylpiperidine-1-carboxylate

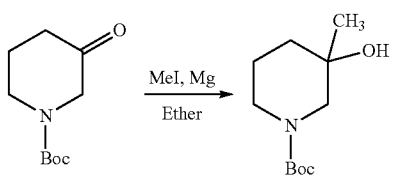

Title compound was prepared from N-Boc-3-piperidone (5 g, 25.09 mmol) using the general methodology of step 1 in Key Intermediate-I. Purification using silica gel column chromatography (30% EtOAc/Hexanes as eluent) to afford 1.1 g tert-butyl 3-hydroxy-3-methylpiperidine-1-carboxylate (Yield=20%).

3-Methylpiperidin-3-ol hydrochloride (Int-V)

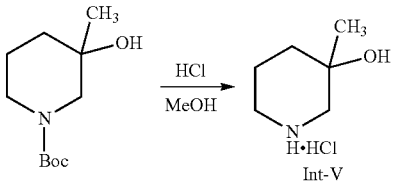

To a solution of tert-butyl 3-hydroxy-3-methylpiperidine-1-carboxylate (0.3 g, 1.39 mmol) in MeOH (5 mL) was added 4.0 M HCl in Dioxane (1.73 mL) at 0° C. The reaction mixture was stirred at room temperature for 4 h. After completion, volatiles were removed under reduced pressure to afford 0.15 g of 3-methylpiperidin-3-ol hydrochloride (Yield=71%).

Synthesis of Key Intermediate-VI:

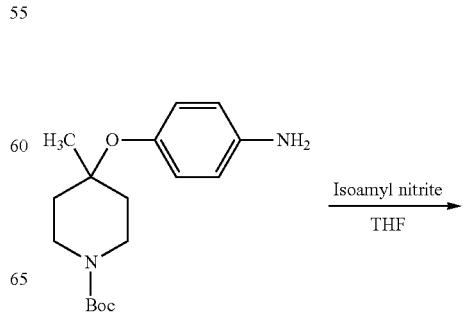

134

4-Methyl-4-phenoxypiperidine hydrochloride (Int-VI)

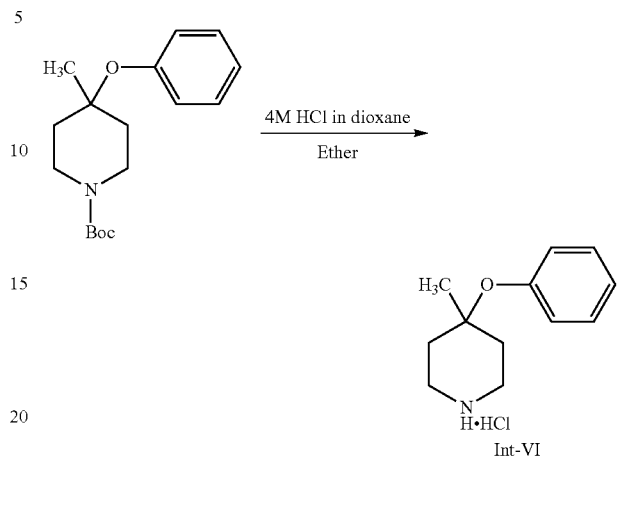

To a solution of tert-butyl 4-methyl-4-phenoxypiperidine-1-carboxylate (0.25 g, 0.85 mmol) in diethyl ether (1 mL) was added 4 M HCl in 1,4-Dioxane (1 mL) at room temperature. The reaction mixture was stirred at room temperature for 16 h. After completion, the reaction mass was concentrated under reduced pressure to afford 0.19 g of 4-methyl-4-phenoxypiperidine hydrochloride (Quantitative).

Synthesis of Key Intermediate-VII

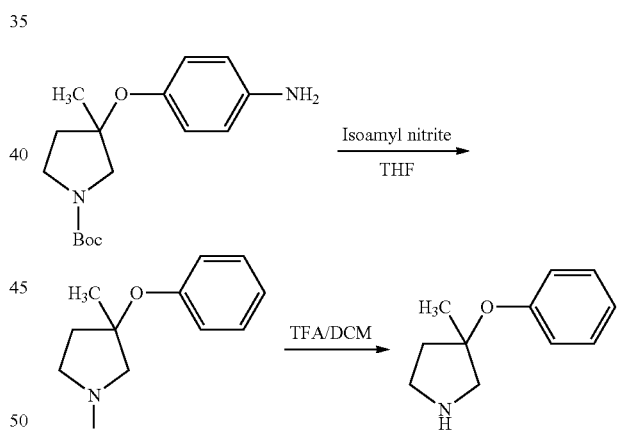

tert-butyl 3-methyl-3-phenoxypyrrolidine-1-carboxylate

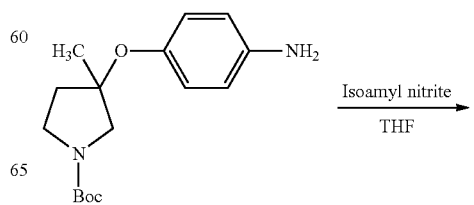

133

-continued

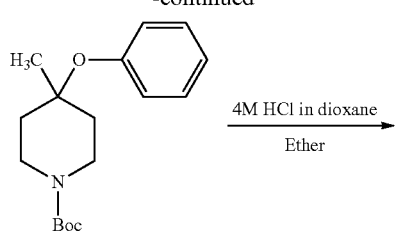

tert-butyl 4-methyl-4-phenoxypiperidine-1-carboxylate

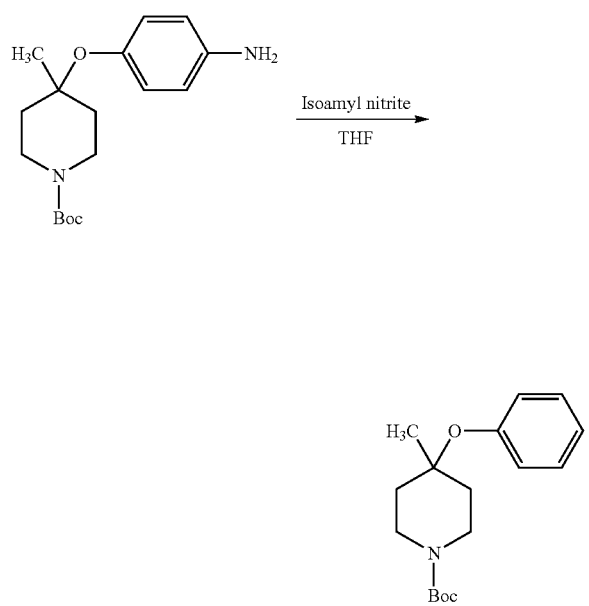

tert-butyl 4-(4-aminophenoxy)-4-methylpiperidine-1-carboxylate (0.5 g, 1.63 mmol) was dissolved in THF (10 mL) and cooled to 0° C. Isoamyl nitrite (2.2 mL, 16.3 mmol) was then added and the reaction mixture was stirred at 60° C. for 5 h. After completion of the reaction (monitored by TLC), the mixture was diluted with water and extracted with diethyl ether and concentrated under reduced pressure to afford the crude. The crude compound was purified by column chromatography eluting with 5% EA in hexane to afford the product as thick syrup 0.30 g of tert-butyl 4-methyl-4-phenoxypiperidine-1-carboxylate (Yield=63%).

135
-continued

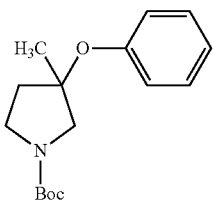

To a stirred solution of tert-butyl 3-(4-aminophenoxy)-3-methylpyrrolidine-1-carboxylate (0.2 g, 0.684 mmol) in THF (3 mL) was added isoamyl nitrite (0.27 mL, 2.05 mmol, 3 equiv) at room temperature. The reaction mixture was heated at 75° C. for 3 h. After completion, the volatiles were removed under reduced pressure. The crude was diluted with EtOAc, washed with water, separated, dried over sodium sulfate and concentrated. Purification using silica gel column chromatography (15% EtOAc/Hexane) afforded 0.11 g of tert-butyl 3-methyl-3-phenoxypyrrolidine-1-carboxylate (Yield=58%). ESI+MS: m/z 278 ([M+H]⁺).

3-Methyl-3-phenoxypyrrolidine

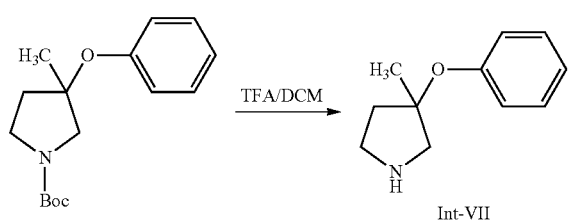 [SMILES: CC(C)(C)OC(=O)N1CCC(C)(Oc2ccccc2)C1 ; CC1(Oc2ccccc2)CCNC1]

To a stirred solution of tert-butyl 3-methyl-3-phenoxypyrrolidine-1-carboxylate (0.1 g, 0.36 mmol) in CH₂Cl₂ (3 mL) under argon atmosphere was added trifluoro acetic acid (1 mL) at 0° C. The reaction mixture was warmed to room temperature and stirred for 3 h. After completion of the reaction, volatiles were removed under reduced pressure, the pH was adjusted to ~7 with saturated NaHCO₃ solution and extracted with CH₂Cl₂. The combined organic extract was dried over sodium sulfate, filtered and concentrated under reduced pressure to afford 0.05 g of 3-methyl-3-phenoxypyrrolidine (Yield=78%). ESI+MS: m/z 178 ([M+H]⁺).

Synthesis of Key Intermediate-IX 3-(4-Chlorophenoxy)-3-methylpiperidine (Int-IX)

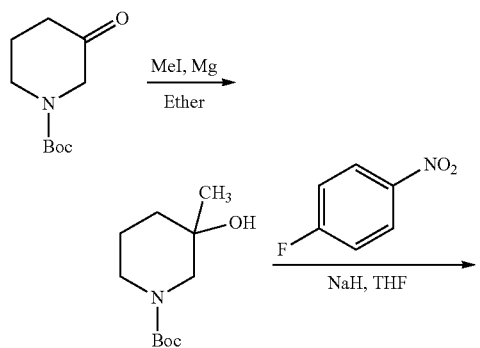

136
-continued

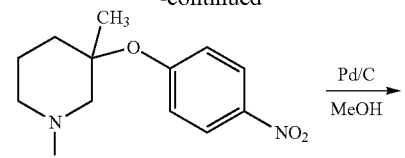


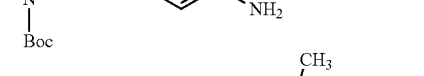

tert-butyl 3-hydroxypiperidine-1-carboxylate

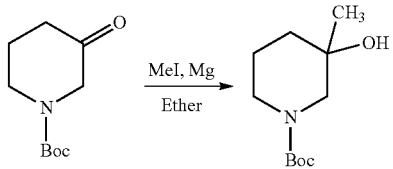

Title compound was prepared from tert-butyl 3-oxopiperidine-1-carboxylate (5 g, 25.09 mmol) using the general methodology of step 1 in Key Intermediate-I. Purification using silica gel column chromatography (15% EtOAc/hexanes) afforded 1.5 g of tert-butyl 3-hydroxypiperidine-1-carboxylate (Yield=27%).

tert-butyl 3-methyl-3-(4-nitrophenoxy)piperidine-1-carboxylate

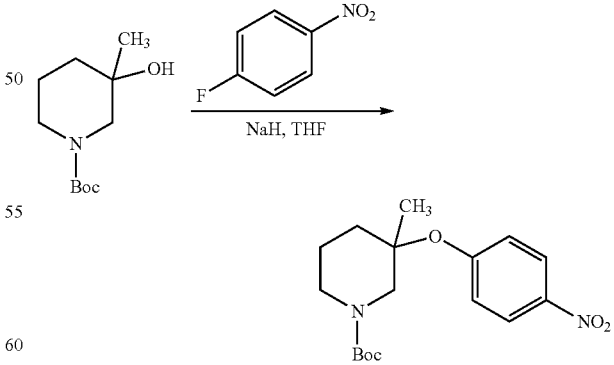

Title compound was prepared from tert-butyl 3-hydroxypiperidine-1-carboxylate (1 g, 4.64 mmol) and 1-fluoro-4-nitrobenzene (0.98 g, 6.97 mmol, 1.5 equiv) using the general methodology of step 2 in Key Intermediate-I. Purification using silica gel column chromatography (15% EtOAc/hexanes) afforded 1 g of tert-butyl 3-methyl-3-(4-nitrophenoxy)piperidine-1-carboxylate (Yield=64%).

tert-butyl 3-(4-aminophenoxy)-3-methylpiperidine-1-carboxylate

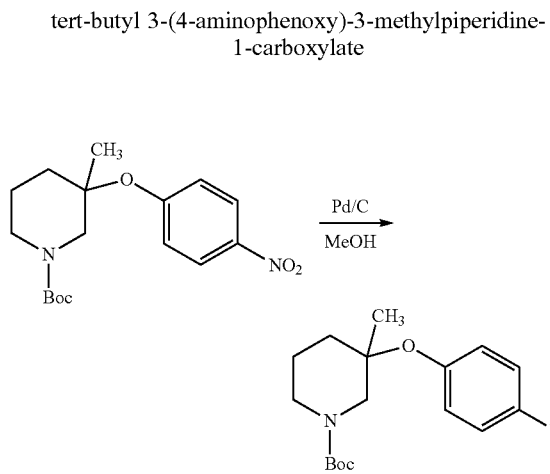

Title compound was prepared from tert-butyl 3-methyl-3-(4-nitrophenoxy)piperidine-1-carboxylate (1 g, 2.97 mmol) using the general methodology of step 3 in Key Intermediate-I and afforded 0.78 g of tert-butyl 3-(4-aminophenoxy)-3-methylpiperidine-1-carboxylate (Yield=86%). ESI+MS: m/z 307 ([M+H]$^+$).

3-(4-Chlorophenoxy)-3-methylpiperidine (Int-IX)

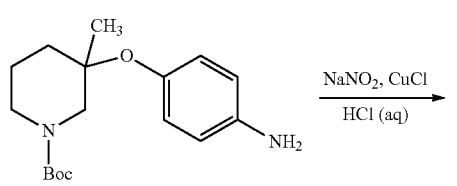

Title compound was prepared from tert-butyl 3-(4-aminophenoxy)piperidine-1-carboxylate (0.2 g, 0.65 mmol) using general methodology of step 4 in Key Intermediate-I and afforded 0.13 g of 3-(4-chlorophenoxy)-3-methylpiperidine (Yield=88%). ESI+MS: m/z 226 ([M+H]$^+$).

Key Intermediate-X

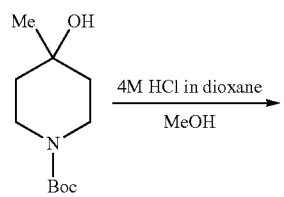

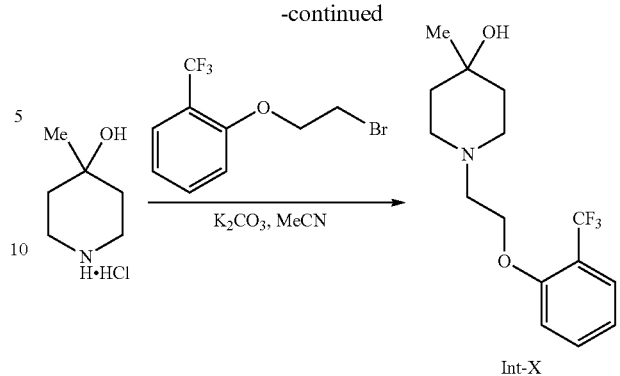

4-Methylpiperidin-4-ol hydrochloride

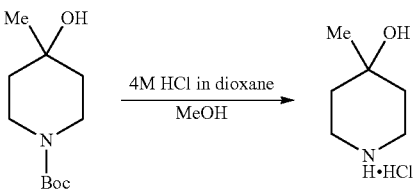

To solution of tert-butyl 4-hydroxy-4-methylpiperidine-1-carboxylate (5 g, 23.2 mmol) in MeOH (5 mL) was added 4.0 M HCl in 1,4-Dioxane (17 mL) at 0° C. The reaction mixture was stirred at room temperature for 4 h. After completion, the volatiles were concentrated under reduced pressure to afford 3 g of 4-methylpiperidin-4-ol hydrochloride (Quantitative).

4-Methyl-1-(2-(2-(trifluoromethyl)phenoxy)ethyl)piperidin-4-ol (Int-X)

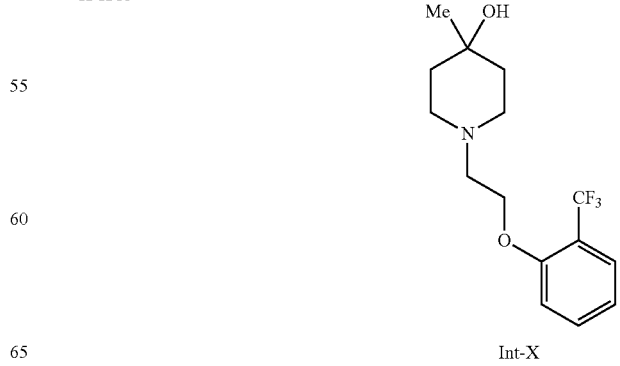

Title compound was prepared from 4-methylpiperidin-4-ol hydrochloride (3 g, 19.8 mmol) and 1-(2-bromoethoxy)-2-(trifluoromethyl) benzene using general methodology of step 2 in key intermediate-IV to afford 5 g of 4-methyl-1-(2-(2-(trifluoromethyl)phenoxy)ethyl)piperidin-4-ol (Yield=83%).

Example-1: 3-(4-chlorophenoxy)-3-methyl-1-(2-phenoxyethyl)pyrrolidine

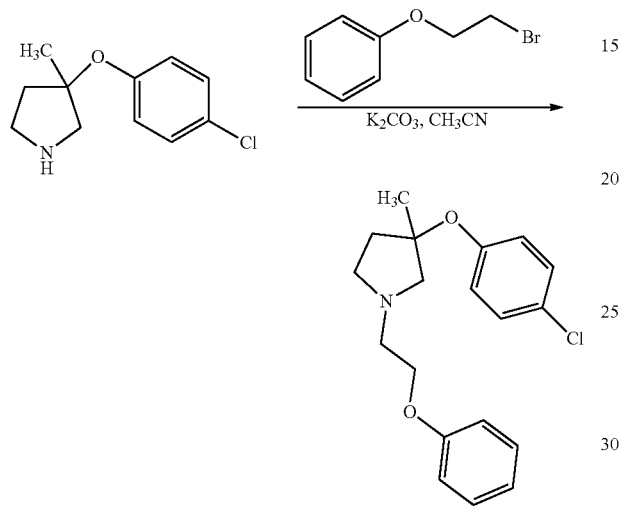

To a stirred solution of 3-(4-chlorophenoxy)-3-methylpyrrolidine (0.1 g, 0.47 mmol) in 5 mL of CH$_3$CN were added potassium carbonate (0.19 g, 1.41 mmol, 3 equiv) and (2-bromoethoxy)benzene (0.095 g, 0.47 mmol, 1 equiv) at room temperature. The reaction mixture was heated at 80° C. and stirred for 16 h. After completion, the reaction mixture was diluted with water and extracted with CH$_2$Cl$_2$. The combined organic extract was dried over sodium sulfate, filtered and concentrated under reduced pressure. Purification using preparative HPLC afforded 0.035 g of 3-(4-chlorophenoxy)-3-methyl-1-(2-phenoxyethyl) pyrrolidine (Yield=22%). $^1$H NMR (400 MHz, DMSO-d$_6$): δ 7.30-7.25 (m, 4H), 6.97-6.90 (m, 5H), 4.05 (t, J=6.0 Hz, 2H), 3.00 (d, J=10.0 Hz, 1H), 2.84-2.75 (m, 3H), 2.69-2.61 (m, 2H), 2.21-2.14 (m, 1H), 1.95-1.89 (m, 1H), 1.45 (s, 3H); ESI+MS: m/z: 332 ([M+H]$^+$).

Example-2: 3-(4-Chlorophenoxy)-1-(2-(2-methoxyphenoxy)ethyl)-3-methyl pyrrolidine

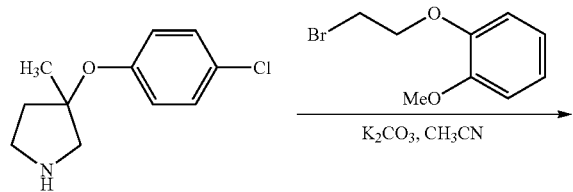

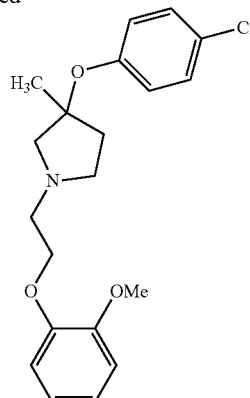

Title compound was prepared from 3-(4-chlorophenoxy)-3-methylpyrrolidine (0.11 g, 0.52 mmol) using the general methodology of Example-1. The crude material was purified by preparative HPLC purification to afford 0.09 g of 3-(4-chlorophenoxy)-1-(2-(2-methoxyphenoxy)ethyl)-3-methylpyrrolidine (Yield=47%). $^1$H NMR (500 MHz, DMSO-d$_6$): δ 7.26-7.23 (m, 2H), 6.97-6.94 (m, 4H), 6.90-6.85 (m, 2H), 4.02 (t, J=6.0 Hz, 2H), 3.73 (s, 3H), 3.01 (d, J=10.0 Hz, 1H), 2.83-2.75 (m, 3H), 2.69-2.62 (m, 2H), 2.18-2.14 (m, 1H), 1.93-1.89 (m, 1H), 1.44 (s, 3H); ESI+MS: m/z: 362 ([M+H]$^+$).

Example-3: 3-(4-chlorophenoxy)-3-methyl-1-(4-phenoxybutyl)pyrrolidine

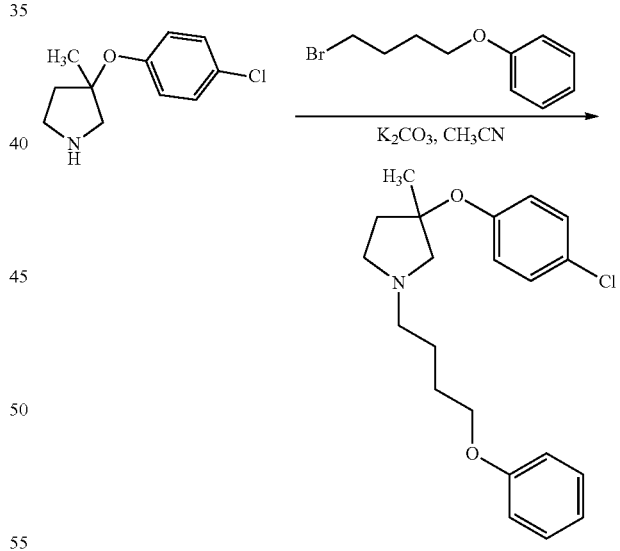

Title compound was prepared from 3-(4-chlorophenoxy)-3-methylpyrrolidine (0.11 g, 0.52 mmol) using the general methodology of Example-1. The crude material was purified by preparative HPLC to afford 0.03 g of 3-(4-chlorophenoxy)-3-methyl-1-(4-phenoxybutyl)pyrrolidine (Yield=15%). $^1$H NMR (400 MHz, DMSO-d$_6$): δ 7.29-7.24 (m, 4H), 6.96 (d, J=8.8 Hz, 2H), 6.92-6.90 (m, 3H), 3.97 (t, J=6.4 Hz, 2H), 2.87 (br s, 1H), 2.67-2.62 (m, 2H), 2.47-2.30 (m, 2H), 2.20-2.17 (m, 2H), 1.93-1.89 (m, 1H), 1.77-1.70 (m, 2H), 1.62-1.57 (m, 2H), 1.42 (s, 3H); ESI+MS: m/z: 360 ([M+H]$^+$).

Example-4: 3-(4-chlorophenoxy)-3-methyl-1-(3-phenoxypropyl)pyrrolidine

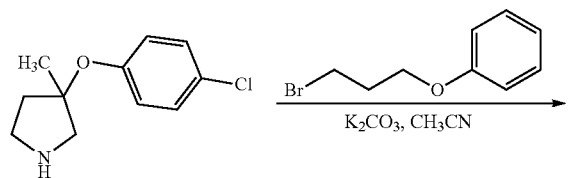

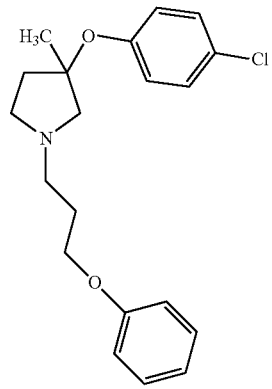

Title compound was prepared from 3-(4-chlorophenoxy)-3-methylpyrrolidine (0.10 g, 0.47 mmol) using the general methodology of Example-1. Purification using silica gel column chromatography (50% EtOAc/Hexane as eluent) to afford 0.068 g of 3-(4-chlorophenoxy)-3-methyl-1-(3-phenoxypropyl)pyrrolidine (Yield=39%). $^1$H NMR (500 MHz, DMSO-$d_6$): δ 7.28-7.25 (m, 4H), 6.97-6.90 (m, 5H), 3.99 (t, J=6.5 Hz, 2H), 2.89 (d, J=10.0 Hz, 1H), 2.70-2.50 (m, 6H), 2.21-2.16 (m, 1H), 1.94-1.83 (m, 2H), 1.45 (s, 3H); ESI+MS: m/z: 346 ([M+H]$^+$).

Example-5: 3-(4-chlorophenoxy)-1-(2-(2-chlorophenoxy)ethyl)-3-methylpyrrolidine

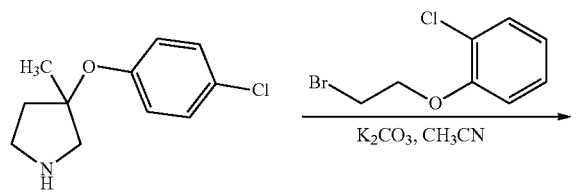

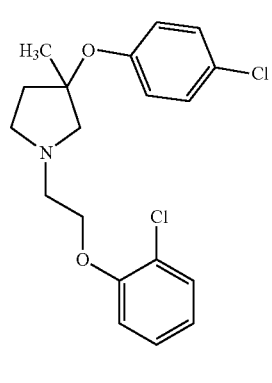

Title compound was prepared from 3-(4-chlorophenoxy)-3-methylpyrrolidine (0.10 g, 0.47 mmol) using the general methodology of Example-1. The crude was purified by preparative HPLC to afford 0.09 g of 3-(4-chlorophenoxy)-1-(2-(2-chlorophenoxy)ethyl)-3-methylpyrrolidine (Yield=51%). $^1$H NMR (400 MHz, DMSO-$d_6$): δ 7.41 (dd, J=7.6, 1.2 Hz, 1H), 7.31-7.24 (m, 3H), 7.15 (d, J=7.2 Hz, 1H), 6.97-6.92 (m, 3H), 4.15 (d, J=5.6 Hz, 2H), 3.07-3.04 (m, 1H), 2.84-2.80 (m, 3H), 2.75-2.71 (m, 2H), 2.21-2.15 (m, 1H), 1.95-1.89 (m, 1H), 1.45 (s, 3H); ESI+MS: m/z: 366 ([M+H]$^+$).

Example-6: 3-(4-chlorophenoxy)-3-methyl-1-(2-(o-tolyloxy)ethyl)pyrrolidine

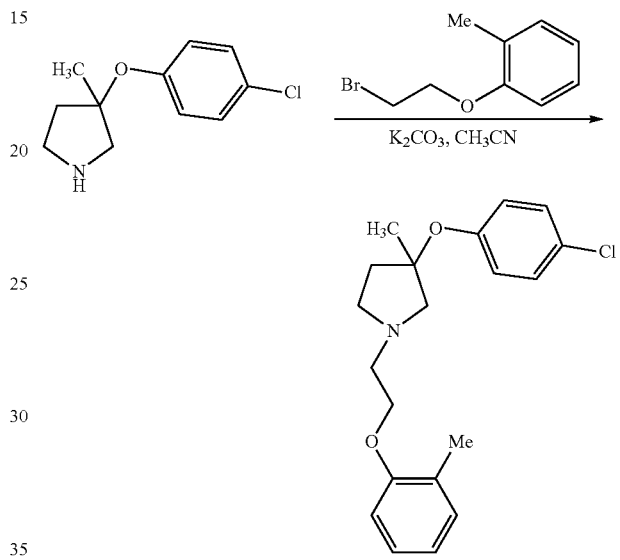

To a stirred solution of 3-(4-chlorophenoxy)-3-methylpyrrolidine (0.1 g, 0.47 mmol) in 5 mL of CH$_3$CN were added potassium carbonate (0.196 g, 1.41 mmol, 3 equiv) and (2-bromoethoxy)benzene (0.102 g, 0.47 mmol, 1 equiv) at room temperature. The reaction mixture was heated at 65° C. and stirred for 12 h. After completion, the reaction mixture was diluted with water and extracted with EtOAc. The combined organic extract was dried over sodium sulfate, filtered and concentrated under reduced pressure. Purification using silica gel column chromatography (4% MeOH/CH$_2$Cl$_2$ as eluent) to afford 0.036 g of 3-(4-chlorophenoxy)-3-methyl-1-(2-(o-tolyloxy)ethyl)pyrrolidine (Yield=22%). $^1$H NMR (400 MHz, CDCl$_3$): δ 7.26 (d, J=8.8 Hz, 2H), 7.13 (t, J=6.8 Hz, 2H), 6.97-6.91 (m, 3H), 6.82 (t, J=7.6 Hz, 1H), 4.07 (br s, 2H), 3.02 (br s, 1H), 2.83 (s, 2H), 2.72-2.61 (m, 2H), 2.19-2.17 (m, 2H), 2.14 (s, 3H), 1.94-1.93 (m, 1H), 1.46 (s, 3H); ESI+MS: m/z: 346 ([M+H]$^+$).

Example-7: 1-(2-(3-(4-chlorophenoxy)-3-methylpyrrolidin-1-yl)ethyl)pyridin-2(1H)-one

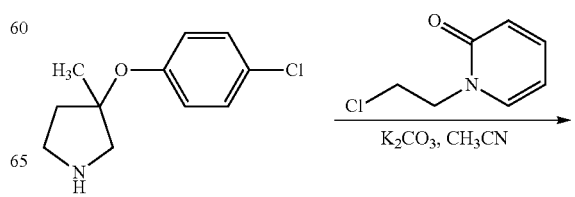

-continued

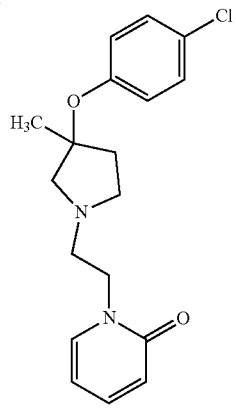

Title compound was prepared from 3-(4-chlorophenoxy)-3-methylpyrrolidine (0.1 g, 0.47 mmol) and 1-(2-chloroethyl)pyridin-2(1H)-one (0.082 g, 0.52 mmol, 1.1 equiv) using the general methodology of Example-1. The crude was purified by preparative HPLC to afford 0.12 g of 1-(2-(3-(4-chlorophenoxy)-3-methylpyrrolidin-1-yl)ethyl)pyridin-2(1H)-one (Yield=76%). $^1$H NMR (500 MHz, DMSO-d$_6$): δ 7.62 (dd, J=7.0, 2.0 Hz, 1H), 7.38 (dt, J=7.0, 2.0 Hz, 1H), 7.25 (d, J=8.5 Hz, 2H) 6.92 (d, J=9.5 Hz, 2H), 6.35 (d, J=9.0 Hz, 1H), 6.17 (t, J=5.5 Hz, 1H), 3.95 (t, J=12.5 Hz, 2H), 2.89 (d, J=9.5 Hz, 1H), 2.76-2.71 (m, 1H), 2.68-2.66 (m, 3H), 2.61-2.57 (m, 1H), 2.17-2.12 (m, 1H), 1.89-1.84 (m, 1H), 1.41 (s, 3H); ESI+MS: m/z: 333 ([M+H]$^+$).

Example-8: 3-(4-chlorophenoxy)-3-methyl-1-(2-(2-(trifluoromethyl)phenoxy) ethyl) pyrrolidine

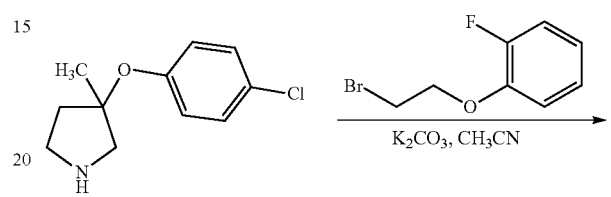

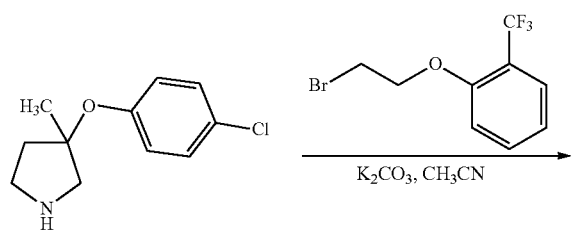

Title compound was prepared from 3-(4-chlorophenoxy)-3-methylpyrrolidine (0.10 g, 0.47 mmol) and 1-(2-bromoethoxy)-2-(trifluoromethyl)benzene (0.12 g, 0.47 mmol, 1 equiv) using the general methodology of Example-1. The crude was purified by preparative HPLC to afford 0.05 g of 3-(4-chlorophenoxy)-3-methyl-1-(2-(2-(trifluoromethyl)phenoxy) ethyl)pyrrolidine (Yield=25%). $^1$H NMR (400 MHz, DMSO-d$_6$): δ 7.60 (d, J=7.6 Hz, 2H), 7.28-7.23 (m, 3H), 7.08 (t, J=7.6 Hz, 1H), 6.97-6.93 (m, 2H), 4.20 (t, J=5.6 Hz, 2H), 3.00 (d, J=10.0 Hz, 1H), 2.87-2.77 (m, 3H), 2.72-2.64 (m, 2H), 2.20-2.14 (m, 1H), 1.94-1.87 (m, 1H), 1.44 (s, 3H), ESI+MS: m/z: 400 ([M+H]$^+$).

Example-9: 3-(4-chlorophenoxy)-1-(2-(2-fluorophenoxy)ethyl)-3-methylpyrrolidine

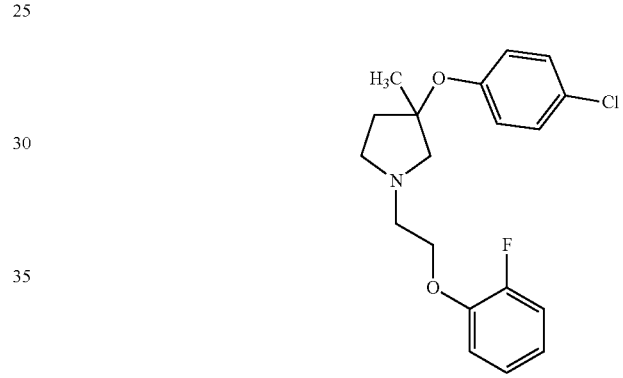

Title compound was prepared from 3-(4-chlorophenoxy)-3-methylpyrrolidine (0.1 g, 0.47 mmol) using the general methodology of Example-1. The crude was purified by preparative HPLC to afford 0.09 g of 3-(4-chlorophenoxy)-1-(2-(2-fluorophenoxy)ethyl)-3-methylpyrrolidine (Yield=54%). $^1$H NMR (400 MHz, DMSO-d$_6$): δ 7.33-7.24 (m, 3H), 6.96 (d, J=8.8 Hz, 2H), 6.84-6.72 (m, 3H), 4.08 (t, J=6.0 Hz, 2H), 3.01 (d, J=10.0 Hz, 1H), 2.80-2.79 (m, 3H), 2.69-2.64 (m, 2H), 2.21-2.15 (m, 1H), 1.95-1.89 (m, 1H), 1.45 (s, 3H), ESI+MS: m/z: 350 ([M+H]$^+$).

Example-10: 3-(4-chlorophenoxy)-1-(2-(3-chlorophenoxy)ethyl)-3-methylpyrrolidine

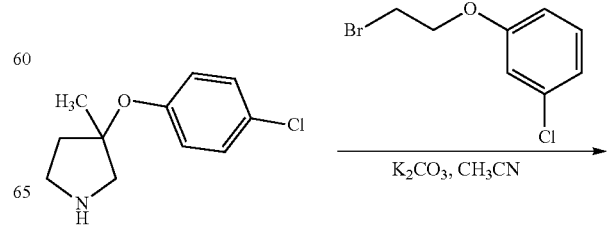

-continued

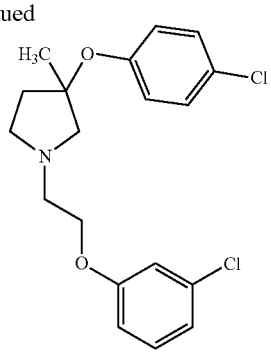

Title compound was prepared from 3-(4-chlorophenoxy)-3-methylpyrrolidine (0.1 g, 0.47 mmol) and 1-(2-bromoethoxy)-3-chlorobenzene (0.11 g, 0.47 mmol, 1 equiv) using the general methodology of Example-1. The crude was purified by preparative HPLC purification to afford 0.08 g of 3-(4-chlorophenoxy)-1-(2-(3-chlorophenoxy)ethyl)-3-methylpyrrolidine (Yield=45%). $^1$H NMR (400 MHz, DMSO-d$_6$): δ 7.30-7.21 (m, 3H), 7.03-6.90 (m, 5H), 4.09 (br s, 2H), 2.99 (br s, 1H), 2.79 (br s, 3H), 2.67-2.66 (m, 2H), 2.20-2.17 (m, 1H), 1.94-1.90 (m, 1H), 1.45 (s, 3H); ESI+MS: m/z: 367 ([M+H]$^+$).

Example-11: 3-(4-chlorophenoxy)-3-methyl-1-(2-(m-tolyloxy)ethyl)pyrrolidine

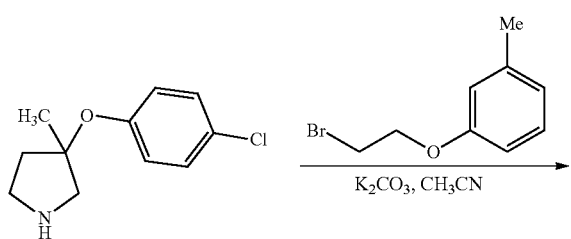

Title compound was prepared from 3-(4-chlorophenoxy)-3-methylpyrrolidine (0.11 g, 0.52 mmol) using the general methodology of Example-1. The crude was purified by preparative HPLC purification to afford 0.1 g of 3-(4-chlorophenoxy)-3-methyl-1-(2-(m-tolyloxy)ethyl)pyrrolidine (Yield=55%). $^1$HNMR (400 MHz, DMSO-d$_6$): δ 7.26 (d, J=8.8 Hz, 2H), 7.14 (t, J=8.8 Hz, 1H), 6.96 (d, J=8.8 Hz, 2H), 6.75-6.70 (m, 3H), 4.03 (t, J=5.6 Hz, 2H), 3.00 (d, J=10.0 Hz, 1H), 2.82-2.76 (m, 3H), 2.69-2.63 (m, 2H), 2.26 (s, 3H), 2.21-2.14 (m, 1H), 1.95-1.90 (m, 1H), 1.45 (s, 3H); ESI+MS: m/z: 346 ([M+H]$^+$).

Example-12: 3-(2-(3-(4-chlorophenoxy)-3-methylpyrrolidin-1-yl)ethoxy)pyridine

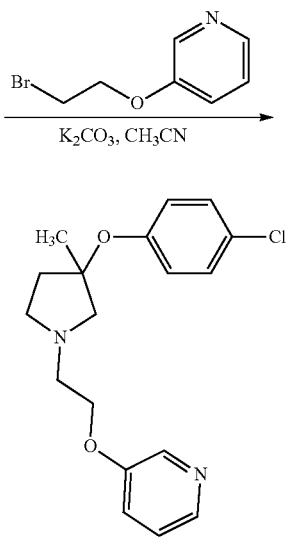

Title compound was prepared from 3-(4-chlorophenoxy)-3-methylpyrrolidine (0.1 g, 0.47 mmol) using the general methodology of Example-1. The crude was purified by preparative HPLC purification to afford 0.035 g of 3-(2-(3-(4-chlorophenoxy)-3-methylpyrrolidin-1-yl)ethoxy)pyridine (Yield=21%). $^1$H NMR (500 MHz, DMSO-d$_6$): δ 8.28 (d, J=2.5 Hz, 1H), 8.15 (d, J=4.5 Hz, 1H), 7.39-7.29 (m, 2H), 7.25 (d, J=8.5 Hz, 2H), 6.95 (d, J=8.5 Hz, 2H), 4.13 (t, J=6.0 Hz, 2H), 2.99 (d, J=10.5 Hz, 1H), 2.85-2.76 (m, 3H), 2.68-2.62 (m, 2H), 2.20-2.14 (m, 1H), 1.94-1.88 (m, 1H), 1.44 (s, 3H); ESI+MS: m/z: 333 ([M+H]$^+$). The enantiomers of 12 were separated using chiral HPLC (method G) and afforded the pure enantiomers 12a and 12b.

Example-13: 3-(4-chlorophenoxy)-3-methyl-1-(2-(3-(trifluoromethyl) phenoxy) ethyl) pyrrolidine

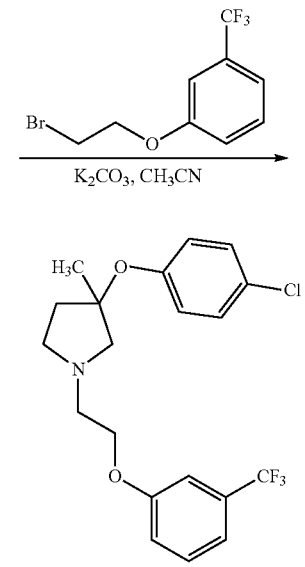

Title compound was prepared from 3-(4-chlorophenoxy)-3-methylpyrrolidine (0.1 g, 0.47 mmol) using the general methodology of Example-1. The crude was purified by preparative HPLC to afford 0.09 g of 3-(4-chlorophenoxy)-3-methyl-1-(2-(3-(trifluoro methyl)phenoxy)ethyl)pyrrolidine (Yield=47%). $^1$H NMR (400 MHz, DMSO-$d_6$): δ 7.52 (t, J=8.0 Hz, 1H), 7.29-7.24 (m, 5H), 6.96 (d, J=8.8 Hz, 2H), 4.17-4.14 (m, 2H), 3.02-3.00 (m, 1H), 2.81 (br s, 3H), 2.70-2.64 (m, 2H), 2.22-2.15 (m, 1H), 1.95-1.89 (m, 1H), 1.45 (s, 3H); ESI+MS: m/z: 400 ([M+H]$^+$).

Example-14: 3-(4-chlorophenoxy)-1-(2-(4-fluorophenoxy)ethyl)-3-methylpyrrolidine

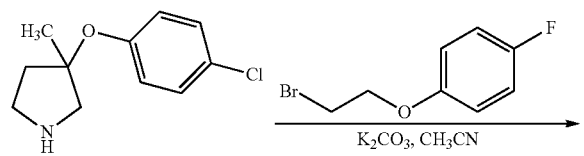

Title compound was prepared from 3-(4-chlorophenoxy)-3-methylpyrrolidine (0.1 g, 0.47 mmol) using the general methodology of Example-1. The crude material was purified by preparative HPLC to afford 0.067 g of 3-(4-chlorophenoxy)-1-(2-(4-fluorophenoxy)ethyl)-3-methylpyrrolidine (Yield=40%). $^1$H NMR (400 MHz, DMSO-$d_6$): δ 7.23 (dd, J=6.8, 2.4 Hz, 2H), 7.07 (t, J=8.8 Hz, 2H), 6.94-6.90 (m, 4H), 4.01 (t, J=5.6 Hz, 2H), 2.97 (d, J=10.0 Hz, 1H), 2.78-2.76 (m, 3H), 2.66-2.61 (m, 2H), 2.18-2.12 (m, 1H), 1.92-1.86 (m, 1H), 1.42 (s, 3H); ESI+MS: m/z: 350 ([M+H]$^+$).

Example-15: 3-(4-chlorophenoxy)-1-(2-(4-chlorophenoxy)ethyl)-3-methylpyrrolidine

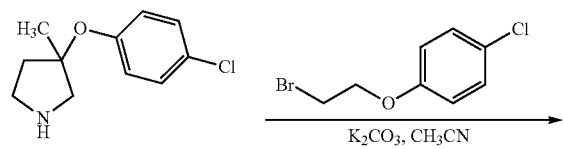

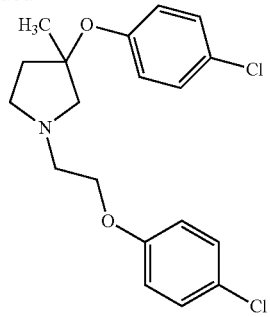

Title compound was prepared from 3-(4-chlorophenoxy)-3-methylpyrrolidine (0.1 g, 0.47 mmol) using the general methodology of Example-1. The crude was purified by preparative HPLC to afford 0.086 g of 3-(4-chlorophenoxy)-1-(2-(4-chlorophenoxy)ethyl)-3-methylpyrrolidine (Yield=49%). $^1$H NMR (400 MHz, DMSO-$d_6$): δ 7.32 (d, J=8.8 Hz, 2H), 7.27 (d, J=8.8 Hz, 2H), 6.98-6.95 (m, 4H), 4.06 (s, 2H), 2.99 (br s, 1H), 2.79 (br s, 3H), 2.67 (br s, 2H), 2.22-2.15 (m, 1H), 1.94-1.90 (m, 1H), 1.45 (s, 3H); ESI+MS: m/z: 367 ([M+H]$^+$).

Example-16: 3-(4-Chlorophenoxy)-3-methyl-1-(2-(p-tolyloxy)ethyl)pyrrolidine

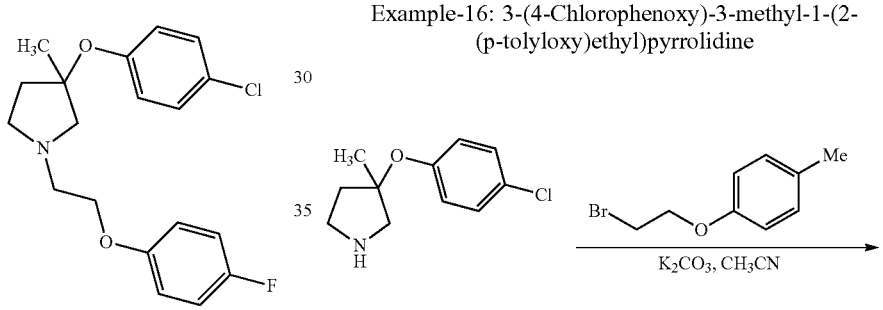

Title compound was prepared from 3-(4-chlorophenoxy)-3-methylpyrrolidine (0.09 g, 0.42 mmol) using the general methodology of Example-1. The crude material was purified by preparative HPLC to afford 0.07 g of 3-(4-chlorophenoxy)-3-methyl-1-(2-(p-tolyloxy)ethyl)pyrrolidine (Yield=46%). $^1$H NMR (500 MHz, DMSO-$d_6$): δ 7.25 (d, J=8.5 Hz, 2H), 7.06 (d, J=8.5 Hz, 2H), 6.95 (d, J=8.5 Hz, 2H), 6.81 (d, J=8.5 Hz, 2H), 4.00 (t, J=6.0 Hz, 2H), 2.98 (d, J=10.0 Hz, 1H), 2.81-2.73 (m, 3H), 2.67-2.62 (m, 2H), 2.21 (s, 3H), 2.16-2.15 (m, 1H), 1.92-1.89 (m, 1H), 1.44 (s, 3H); ESI+MS: m/z: 346 ([M+H]$^+$).

Example-17: 3-(4-chlorophenoxy)-3-methyl-1-(2-(4-(trifluoromethyl)phenoxy) ethyl) pyrrolidine

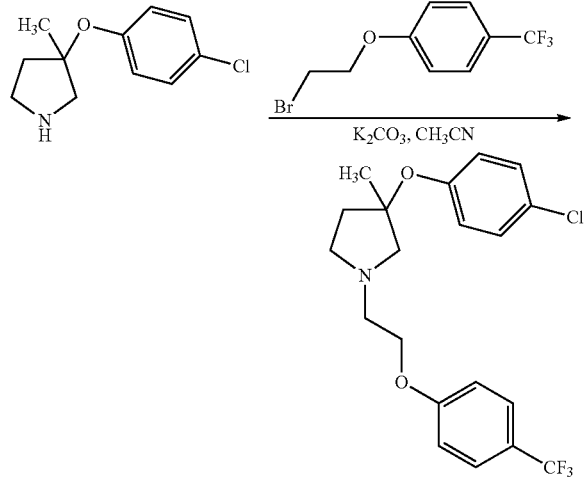

Title compound was prepared from 3-(4-chlorophenoxy)-3-methylpyrrolidine (0.1 g, 0.47 mmol) using the general methodology of Example-1. Purification using silica gel column chromatography (40% EtOAc/Hexanes as eluent) to afford 0.12 g of 3-(4-chlorophenoxy)-3-methyl-1-(2-(4-(trifluoromethyl)phenoxy) ethyl) pyrrolidine (Yield=60%). $^1$H NMR (400 MHz, DMSO-d$_6$): δ 7.64 (d, J=8.4 Hz, 2H), 7.26 (d, J=8.8 Hz, 2H), 7.13 (d, J=8.4 Hz, 2H), 6.96 (d, J=8.4 Hz, 2H), 4.16 (s, 2H), 3.01 (br s, 1H), 2.82 (br s, 3H), 2.67 (br s, 2H), 2.22-2.17 (m, 1H), 1.94-1.91 (m, 1H), 1.45 (s, 3H), ESI+MS: m/z: 400 ([M+H]$^+$).

Example-18: 6-(2-(3-(4-chlorophenoxy)-3-methylpyrrolidin-1-yl)ethoxy) benzo[d] thiazole

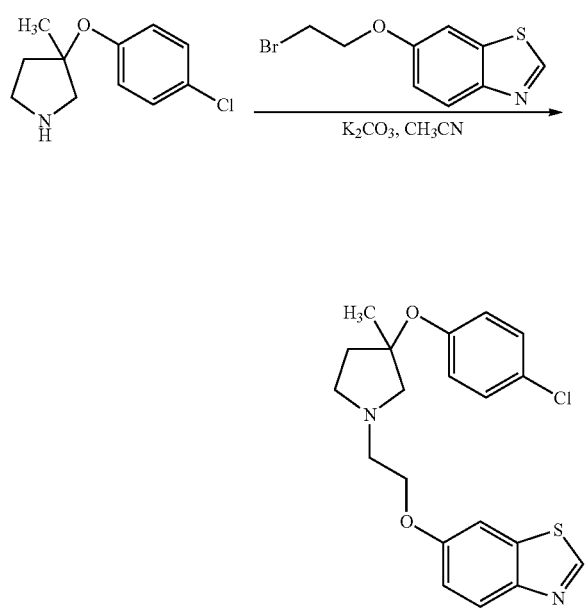

Title compound was prepared from 3-(4-chlorophenoxy)-3-methylpyrrolidine (0.1 g, 0.47 mmol) using the general methodology of Example-1. The crude material was purified by preparative HPLC to afford 0.07 g of 6-(2-(3-(4-chlorophenoxy)-3-methylpyrrolidin-1-yl)ethoxy) benzo[d]thiazole (Yield=38%). $^1$H NMR (500 MHz, DMSO-d$_6$): δ 9.17 (s, 1H), 7.94 (d, J=9.0 Hz, 1H), 7.73-7.72 (m, 1H), 7.24 (d, J=8.5 Hz, 2H), 7.13 (dd, J=9.0, 2.5 Hz, 1H), 6.95 (d, J=8.5 Hz, 2H), 4.14 (t, J=6.0 Hz, 2H), 3.01 (d, J=10.0 Hz, 1H), 2.87-2.79 (m, 3H), 2.70-2.62 (m, 2H), 2.19-2.16 (m, 1H), 1.93-1.91 (m, 1H), 1.44 (s, 3H), ESI+MS: m/z: 389 ([M+H]$^+$). The enantiomers of 18 were separated using chiral HPLC (method I) and afforded the pure enantiomers 18a and 18b.

Example-19: 3-(4-chlorophenoxy)-1-(2-(3-methoxyphenoxy)ethyl)-3-methyl pyrrolidine

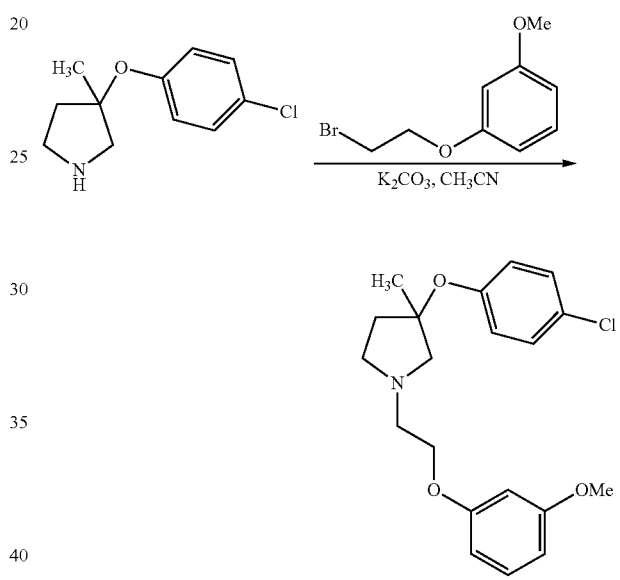

Title compound was prepared from 3-(4-chlorophenoxy)-3-methylpyrrolidine (0.1 g, 0.47 mmol) using the general methodology of Example-1. Purification using silica gel column chromatography to afford 0.11 g of 3-(4-chlorophenoxy)-1-(2-(3-methoxyphenoxy) ethyl)-3-methyl pyrrolidine (Yield=64%). $^1$H NMR (500 MHz, DMSO-d$_6$): δ 7.25 (d, J=8.5 Hz, 2H), 7.15 (t, J=7.5 Hz, 1H), 6.95 (d, J=8.5 Hz, 2H), 6.51-6.47 (m, 3H), 4.03 (t, J=5.0 Hz, 2H), 3.71 (s, 3H), 2.99 (d, J=10.5 Hz, 1H), 2.82-2.74 (m, 3H), 2.67-2.62 (m, 2H), 2.18-2.16 (m, 1H), 1.92-1.89 (m, 1H), 1.44 (s, 3H); ESI+MS: m/z: 362 ([M+H]$^+$).

Example-20: 3-(4-chlorophenoxy)-1-(2-(4-methoxyphenoxy)ethyl)-3-methyl pyrrolidine

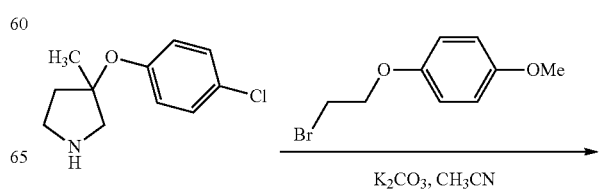

-continued

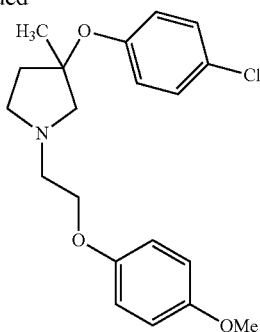

Title compound was prepared from 3-(4-chlorophenoxy)-3-methylpyrrolidine (0.1 g, 0.47 mmol) using the general methodology of Example-1. Purification using silica gel column chromatography to afford 0.09 g of 3-(4-chlorophenoxy)-1-(2-(4-methoxyphenoxy)ethyl)-3-methylpyrrolidine (Yield=52%). $^1$H NMR (500 MHz, DMSO-$d_6$): δ 7.25 (d, J=8.5 Hz, 2H), 6.95 (d, J=8.5 Hz, 2H), 6.86-6.82 (m, 4H), 3.98 (t, J=5.5 Hz, 2H), 3.68 (s, 3H), 2.98 (d, J=10.5 Hz, 1H), 2.77-2.71 (m, 3H), 2.67-2.62 (m, 2H), 2.19-2.14 (m, 1H), 1.93-1.88 (m, 1H), 1.44 (s, 3H); ESI+MS: m/z: 362 ([M+H]$^+$).

Example-21: 3-(4-chlorophenoxy)-1-(2-(cyclohexyloxy)ethyl)-3-methylpyrrolidine

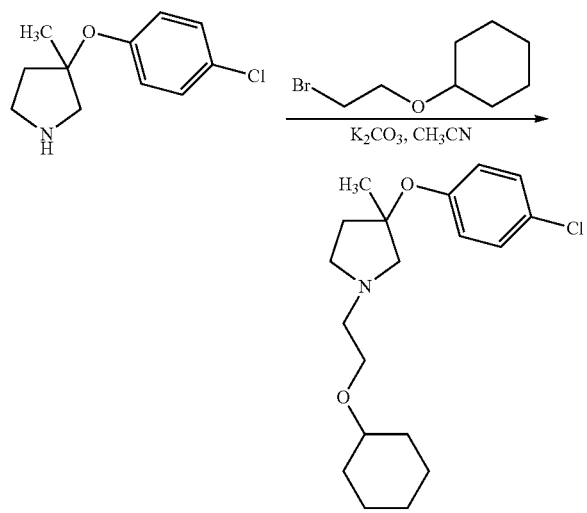

Title compound was prepared from 3-(4-chlorophenoxy)-3-methylpyrrolidine (0.15 g, 0.70 mmol) and Intermediate-5 (0.147 g, 0.709 mmol, 1 equiv) using the general methodology of Example-1. Purification using preparative HPLC to afford 0.048 g of 3-(4-chlorophenoxy)-1-(2-(cyclohexyloxy)ethyl)-3-methylpyrrolidine (Yield=20%). $^1$HNMR (500 MHz, DMSO-$d_6$) δ: 7.27 (d, J=9.0 Hz, 2H), 6.95 (d, J=9.0 Hz, 2H), 3.46 (t, J=6.0 Hz, 2H), 3.22-3.19 (m, 1H), 2.94 (d, J=10.0 Hz, 1H), 2.73-2.69 (m, 1H), 2.63-2.58 (m, 3H), 2.53-2.52 (m, 1H), 2.17-2.12 (m, 1H), 1.90-1.85 (m, 1H), 1.81-1.76 (m, 2H), 1.64-1.60 (m, 2H), 1.49-1.46 (m, 1H), 1.44 (s, 3H), 1.25-1.19 (m, 5H); ESI+MS: m/z: 338 ([M+H]$^+$).

Example-22: 3-(4-chlorophenoxy)-1-(2-(2,4-difluorophenoxy)ethyl)-3-methyl pyrrolidine

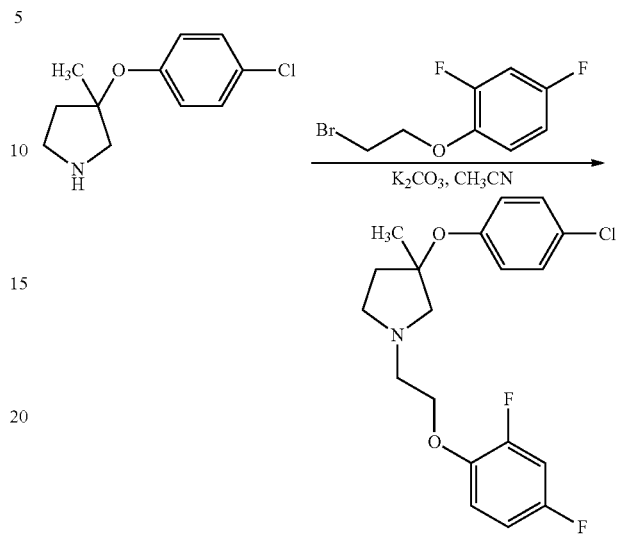

Title compound was prepared from 3-(4-chlorophenoxy)-3-methylpyrrolidine (0.1 g, 0.47 mmol) using the general methodology of Example-1. Purification using preparative HPLC to afford 0.09 g of 3-(4-chlorophenoxy)-1-(2-(2,4-difluorophenoxy)ethyl)-3-methylpyrrolidine (Yield=49%). $^1$H NMR (400 MHz, DMSO-$d_6$): δ 7.29-7.17 (m, 4H), 7.02-6.94 (m, 3H), 4.12 (t, J=5.6 Hz, 2H), 3.00 (d, J=10.0 Hz, 1H), 2.85-2.76 (m, 3H), 2.69-2.62 (m, 2H), 2.21-2.14 (m, 1H), 1.94-1.88 (m, 1H), 1.44 (s, 3H); ESI+MS: m/z: 368 ([M+H]$^+$).

Example-23: 3-(4-chlorophenoxy)-1-(2-(2,5-difluorophenoxy)ethyl)-3-methyl pyrrolidine

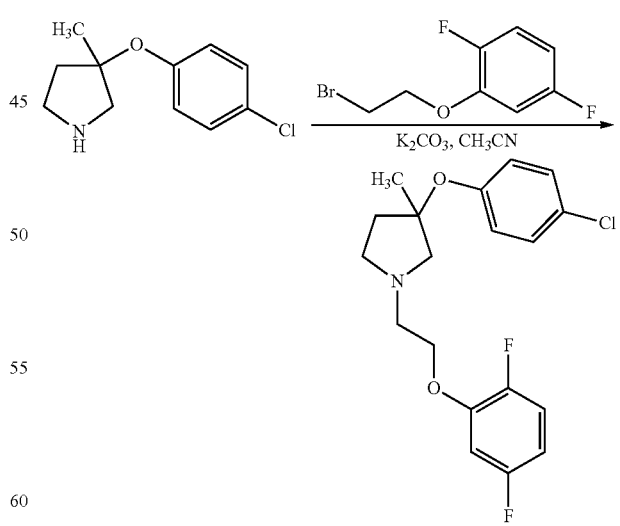

Title compound was prepared from 3-(4-chlorophenoxy)-3-methylpyrrolidine (0.1 g, 0.47 mmol) using the general methodology of Example-1. Purification using preparative HPLC to afford 0.115 g of 3-(4-chlorophenoxy)-1-(2-(2,5-difluorophenoxy)ethyl)-3-methylpyrrolidine (Yield=66%).

$^1$H NMR (400 MHz, DMSO-d$_6$): δ 7.27-7.21 (m, 3H), 7.16-7.11 (m, 1H), 6.96 (d, J=9.2 Hz, 2H), 6.77-6.72 (m, 1H), 4.15 (t, J=5.6 Hz, 2H), 3.05-2.98 (m, 1H), 2.85-2.78 (m, 3H), 2.69-2.64 (m, 2H), 2.21-2.14 (m, 1H), 1.95-1.88 (m, 1H), 1.44 (s, 3H); ESI+MS: m/z: 368 ([M+H]$^+$).

Example-24: 7-(2-(3-(4-chlorophenoxy)-3-methylpyrrolidin-1-yl)ethoxy)quinolone

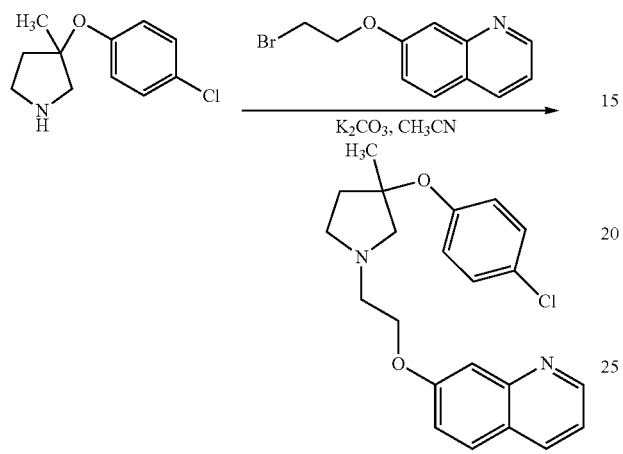

Title compound was prepared from 3-(4-chlorophenoxy)-3-methylpyrrolidine (0.09 g, 0.42 mmol) using the general methodology of Example-1. Purification using preparative HPLC to afford 0.04 g of 7-(2-(3-(4-chlorophenoxy)-3-methylpyrrolidin-1-yl)ethoxy) quinolone (Yield=24%). $^1$H NMR (500 MHz, DMSO-d$_6$): δ 8.81-8.80 (m, 1H), 8.27 (d, J=8.0 Hz, 1H), 7.88 (d, J=8.5 Hz, 1H), 7.41-7.35 (m, 2H), 7.28-7.24 (m, 3H), 6.97 (d, J=9.0 Hz, 2H), 4.25 (t, J=5.5 Hz, 2H), 3.04 (d, J=10.0 Hz, 1H), 2.93-2.81 (m, 3H), 2.73-2.66 (m, 2H), 2.22-2.17 (m, 1H), 1.96-1.91 (m, 1H), 1.46 (s, 3H); ESI+MS: m/z: 383 ([M+H]$^+$).

Example-25: 7-(2-(3-(4-chlorophenoxy)-3-methylpyrrolidin-1-yl)ethoxy)quinolin-2(1H)-one

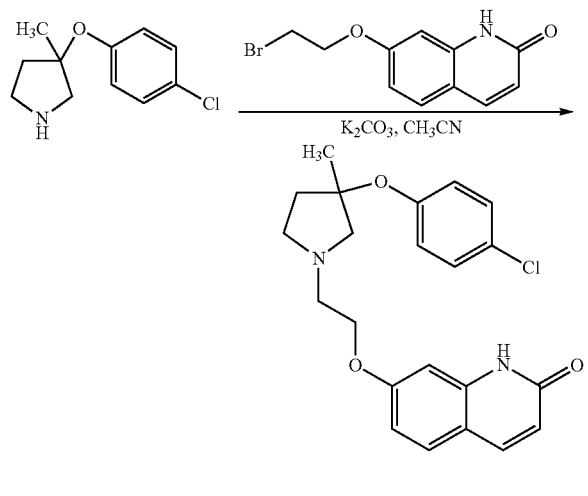

Title compound was prepared from 3-(4-chlorophenoxy)-3-methylpyrrolidine (0.1 g, 0.47 mmol) and 7-(2-bromoethoxy)quinolin-2(1H)-one (0.12 g, 0.47 mmol, 1.0 equiv) using the general methodology of Example-1. The crude was purified by preparative HPLC to afford 0.035 g of 7-(2-(3-(4-chlorophenoxy)-3-methylpyrrolidin-1-yl)ethoxy)quinolin-2(1H)-one (Yield=18%). $^1$H NMR (500 MHz, DMSO-d$_6$): δ 11.57 (s, 1H), 7.79 (d, J=9.5 Hz, 1H), 7.55 (d, J=8.0 Hz, 1H), 7.25 (d, J=8.5 Hz, 2H), 6.95 (d, J=8.5 Hz, 2H), 6.79 (d, J=8.0 Hz, 2H), 6.28 (d, J=9.0 Hz, 1H), 4.09 (t, J=5.5 Hz, 2H), 3.00 (d, J=10.0 Hz, 1H), 2.86-2.77 (m, 3H), 2.68-2.63 (m, 2H), 2.18-2.16 (m, 1H), 1.93-1.90 (m, 1H), 1.44 (s, 3H); ESI+MS: m/z: 399 ([M+H]$^+$).

Example-26: 3-(4-chlorophenoxy)-3-methyl-1-(3-phenylpropyl)pyrrolidine

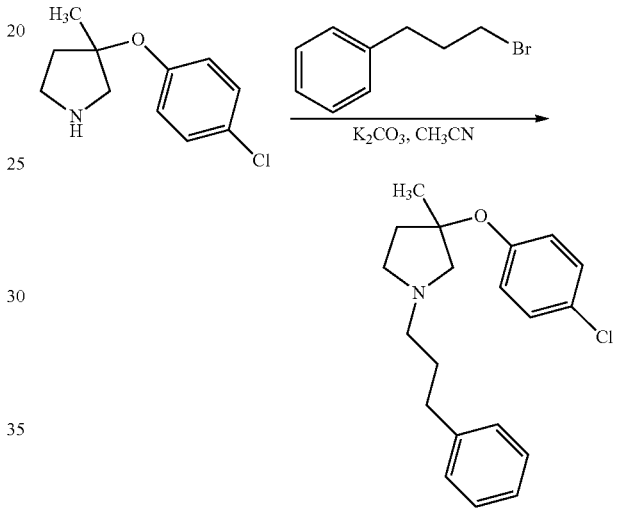

Title compound was prepared from 3-(4-chlorophenoxy)-3-methylpyrrolidine (0.09 g, 0.42 mmol) and (3-bromopropyl)benzene (0.085 g, 0.425 mmol, 3 equiv) using the general methodology of Example-1. Purification using preparative HPLC to afford 0.05 g of 3-(4-chlorophenoxy)-3-methyl-1-(3-phenylpropyl)pyrrolidine (Yield=36%). $^1$H NMR (500 MHz, DMSO-d$_6$): δ 7.29-7.22 (m, 4H), 7.19-7.12 (m, 3H), 6.96 (d, J=8.5 Hz, 2H), 2.89-2.86 (m, 1H), 2.73-2.55 (m, 5H), 2.42-2.38 (m, 2H), 2.25-2.10 (m, 1H), 1.95-1.85 (m, 1H), 1.75-1.65 (m, 2H), 1.44 (s, 3H); ESI+MS: m/z: 330 ([M+H]$^+$).

Example-27: 3-(4-chlorophenoxy)-1-(4-(2-fluorophenoxy)butyl)-3-methylpyrrolidine

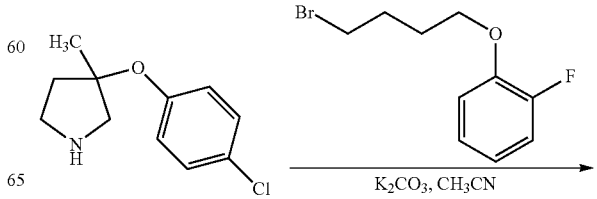

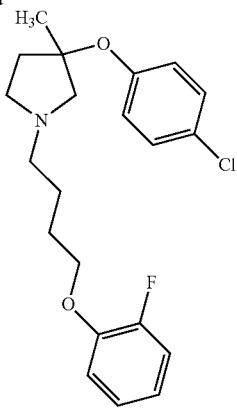

Title compound was prepared from 3-(4-chlorophenoxy)-3-methylpyrrolidine (0.1 g, 0.47 mmol) using the general methodology of Example-1. The crude was purified by preparative HPLC to afford 0.031 g of 3-(4-chlorophenoxy)-1-(4-(2-fluorophenoxy)butyl)-3-methylpyrrolidine (Yield=17%). $^1$H NMR (400 MHz, CD$_3$OD): δ 7.26-7.19 (m, 2H), 7.07-7.02 (m, 3H), 6.93-6.86 (m, 3H), 4.06 (t, J=12.0 Hz, 2H), 3.10 (d, J=10.4 Hz, 1H), 2.89-2.83 (m, 1H), 2.67-2.59 (m, 2H), 2.56-2.51 (m, 2H), 2.36-2.29 (m, 1H), 2.00-1.93 (m, 1H), 1.85-1.79 (m, 2H), 1.76-1.68 (m, 2H), 1.49 (s, 3H); ESI+MS: m/z: 378 ([M+H]$^+$).

Example-28: 3-(4-chlorophenoxy)-1-(4-(2-chlorophenoxy)butyl)-3-methylpyrrolidine

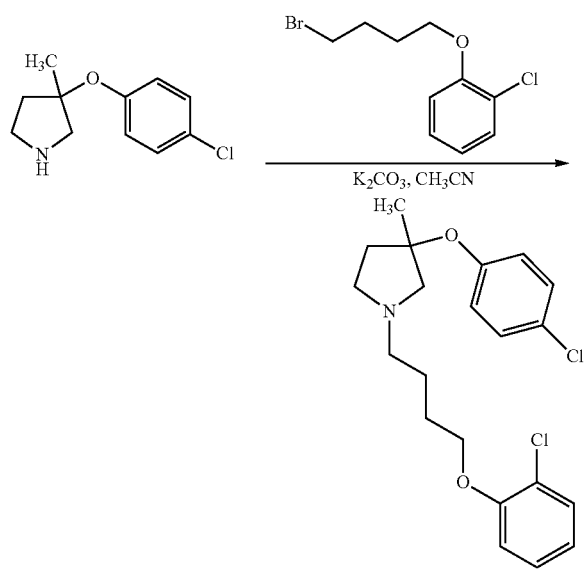

Title compound was prepared from 3-(4-chlorophenoxy)-3-methylpyrrolidine (0.1 g, 0.47 mmol) using the general methodology of Example-1. The crude was purified using preparative HPLC to afford 0.03 g of 3-(4-chlorophenoxy)-1-(4-(2-chlorophenoxy)butyl)-3-methylpyrrolidine (Yield=16%). $^1$H NMR (400 MHz, CD$_3$OD): δ 7.35-7.32 (m, 1H), 7.25-7.20 (m, 3H), 7.05-7.03 (m, 1H), 6.94-6.87 (m, 3H), 4.08 (t, J=12.0 Hz, 2H), 3.12 (d, J=10.4 Hz, 1H), 2.91-2.85 (m, 1H), 2.70-2.57 (m, 4H), 2.38-2.31 (m, 1H), 2.01-1.94 (m, 1H), 1.90-1.74 (m, 4H), 1.50 (s, 3H); ESI+MS: m/z: 395 ([M+H]$^+$).

Example-29: 6-(4-(3-(4-chlorophenoxy)-3-methylpyrrolidin-1-yl)butoxy) benzo[d] thiazole

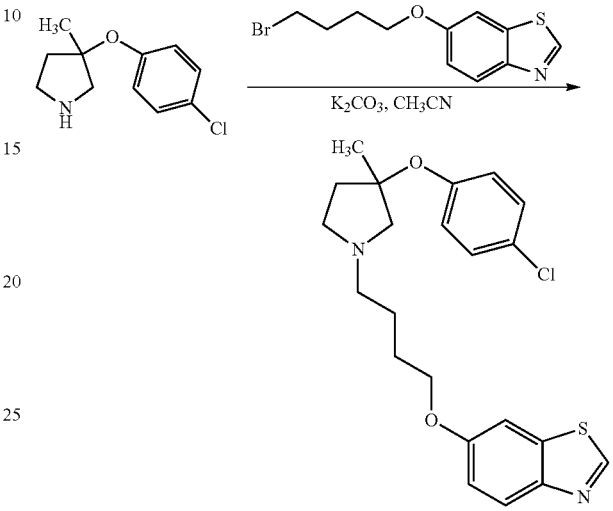

Title compound was prepared from 3-(4-chlorophenoxy)-3-methylpyrrolidine (0.1 g, 0.47 mmol) using the general methodology of Example-1. The crude was purified using preparative HPLC to afford 0.03 g of 6-(4-(3-(4-chlorophenoxy)-3-methylpyrrolidin-1-yl)butoxy)benzo[d]thiazole (Yield=16%). $^1$H NMR (400 MHz, DMSO-d$_6$): δ 9.16 (s, 1H), 7.94 (d, J=8.8 Hz, 1H), 7.71 (d, J=2.4 Hz, 1H), 7.27 (d, J=8.8 Hz, 2H), 7.12 (dd, J=8.8, 2.4 Hz, 1H), 6.95 (d, J=8.8 Hz, 2H), 4.07 (t, J=6.4 Hz, 2H), 2.86 (d, J=10.0 Hz, 1H), 2.66-2.54 (m, 2H), 2.45-2.42 (m, 3H), 2.20-2.14 (m, 1H), 1.93-1.86 (m, 1H), 1.81-1.75 (m, 2H), 1.62-1.55 (m, 2H), 1.43 (s, 3H), ESI+MS: m/z: 417 ([M+H]$^+$).

Example-30: 5-(2-(3-(4-Chlorophenoxy)-3-methylpyrrolidin-1-yl)ethoxy)-2-(trifluoromethyl)pyridine

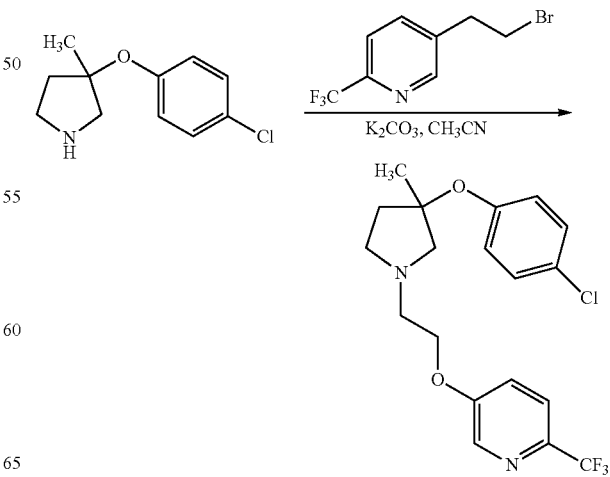

Title compound was prepared from 3-(4-chlorophenoxy)-3-methylpyrrolidine (0.05 g, 0.23 mmol) using the general methodology of Example-1. The crude was purified using preparative HPLC to afford 0.03 g of 5-(2-(3-(4-chlorophenoxy)-3-methylpyrrolidin-1-yl)ethoxy)-2-(trifluoromethyl) pyridine (Yield=32%). $^1$H NMR (400 MHz, CD$_3$OD): δ 8.38 (d, J=2.8 Hz, 1H), 7.75 (d, J=8.8 Hz, 1H), 7.56 (dd, J=8.8, 2.4 Hz, 1H), 7.23-7.19 (m, 2H), 6.95-6.91 (m, 2H), 4.28 (t, J=5.6 Hz, 2H), 3.22 (d, J=10.4 Hz, 1H), 3.05-2.92 (m, 3H), 2.80-2.74 (m, 2H), 2.39-2.33 (m, 1H), 2.03-1.97 (m, 1H), 1.52 (s, 3H); ESI+MS: m/z: 401 ([M+H]$^+$).

Example-31: 3-(4-Chlorophenoxy)-3-methyl-1-(2-(naphthalen-2-yloxy)ethyl) pyrrolidine

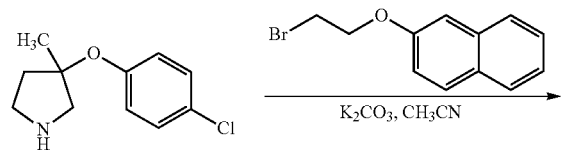

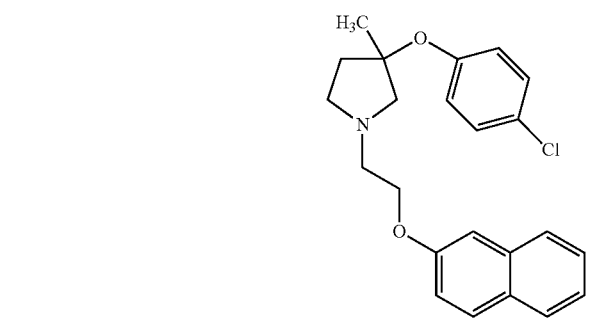

Title compound was prepared from 3-(4-chlorophenoxy)-3-methylpyrrolidine (0.1 g, 0.47 mmol) using the general methodology of Example-1. The crude was purified by preparative HPLC to afford 0.07 g of 3-(4-chlorophenoxy)-3-methyl-1-(2-(naphthalen-2-yloxy)ethyl)pyrrolidine (Yield=39%). $^1$H NMR (400 MHz, DMSO-d$_6$): δ 7.80 (t, J=9.6 Hz, 3H), 7.45 (t, J=7.2 Hz, 1H), 7.35-7.31 (m, 2H), 7.26 (d, J=9.2 Hz, 2H), 7.14 (dd, J=9.2, 2.8 Hz, 1H), 6.97 (d, J=8.8 Hz, 2H), 4.19 (t, J=5.6 Hz, 2H), 3.04 (d, J=10.4 Hz, 1H), 2.94-2.80 (m, 3H), 2.73-2.65 (m, 2H), 2.23-2.16 (m, 1H), 1.97-1.90 (m, 1H), 1.46 (s, 3H); ESI+MS: m/z: 382 ([M+H]$^+$).

Example-32: 6-(2-(3-(4-chlorophenoxy)-3-methylpyrrolidin-1-yl)ethoxy)quinolone

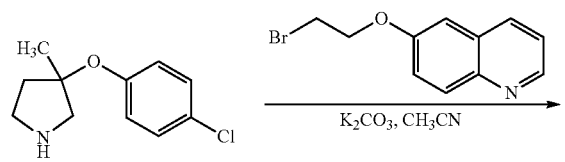

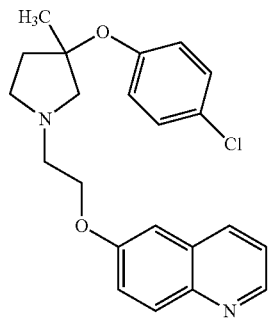

Title compound was prepared from 3-(4-chlorophenoxy)-3-methylpyrrolidine (0.1 g, 0.47 mmol) using the general methodology of Example-1. The crude was purified using preparative HPLC to afford 0.04 g of 6-(2-(3-(4-chlorophenoxy)-3-methylpyrrolidin-1-yl)ethoxy)quinolone (Yield=22%). $^1$HNMR (500 MHz, DMSO-d$_6$): δ 8.73-8.72 (m, 1H), 8.23 (d, J=8.5 Hz, 1H), 7.91 (d, J=8.5 Hz, 1H), 7.48-7.45 (m, 1H), 7.42-7.39 (m, 2H), 7.25 (d, J=9.0 Hz, 2H), 6.97 (d, J=8.5 Hz, 2H), 4.21 (t, J=11.0 Hz, 2H), 3.04 (d, J=10.5 Hz, 1H), 2.93-2.81 (m, 3H), 2.73-2.63 (m, 2H), 2.21-2.18 (m, 1H), 1.95-1.92 (m, 1H), 1.46 (s, 3H), ESI+MS: m/z: 383 ([M+H]$^+$).

Example-33: 6-(2-(3-(4-chlorophenoxy)-3-methylpyrrolidin-1-yl)ethoxy)isoquinoline

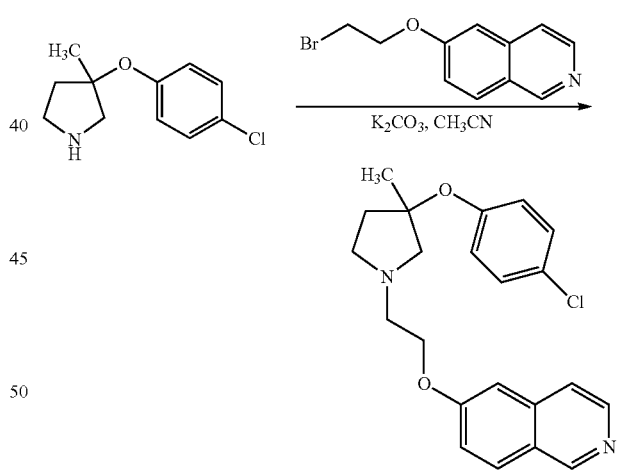

Title compound was prepared from 3-(4-chlorophenoxy)-3-methylpyrrolidine (0.1 g, 0.47 mmol) using the general methodology of Example-1. The crude was purified using preparative HPLC to afford 0.02 g of 6-(2-(3-(4-chlorophenoxy)-3-methylpyrrolidin-1-yl)ethoxy)isoquinoline (Yield=11%). $^1$H NMR (500 MHz, DMSO-d$_6$): δ 9.14 (s, 1H), 8.39 (d, J=6.0 Hz, 1H), 8.02 (d, J=9.0 Hz, 1H), 7.68 (d, J=6.0 Hz, 1H), 7.36 (s, 1H), 7.31-7.29 (m, 1H), 7.25 (d, J=7.2 Hz, 2H), 6.96 (d, J=8.5 Hz, 2H), 4.24 (t, J=12.0 Hz, 2H), 3.04 (d, J=10.0 Hz, 1H), 2.94-2.81 (m, 3H), 2.73-2.66 (m, 2H), 2.22-2.17 (m, 1H), 1.96-1.91 (m, 1H), 1.46 (s, 3H); ESI+MS: m/z: 383 ([M+H]$^+$).

Example-34: 7-(2-(3-(4-chlorophenoxy)-3-methylpyrrolidin-1-yl)ethoxy)isoquinoline

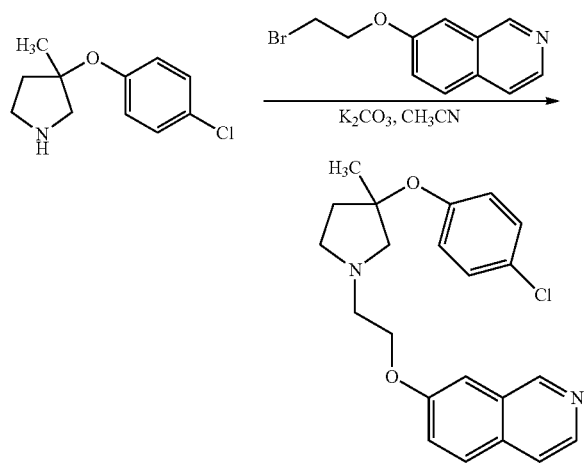

Title compound was prepared from 3-(4-chlorophenoxy)-3-methylpyrrolidine (0.05 g, 0.23 mmol) using the general methodology of Example-1. The crude was purified using preparative HPLC to afford 0.02 g of 7-(2-(3-(4-chlorophenoxy)-3-methylpyrrolidin-1-yl)ethoxy)isoquinoline (Yield=22%). $^1$H NMR (400 MHz, DMSO-d$_6$): δ 9.18 (s, 1H), 8.36 (d, J=5.2 Hz, 1H), 7.89 (d, J=8.8 Hz, 1H), 7.74 (d, J=5.6 Hz, 1H), 7.54-7.53 (m, 1H), 7.43 (dd, J=9.6, 2.4 Hz, 1H), 7.27-7.23 (m, 2H), 6.98-6.95 (m, 2H), 4.23 (t, J=5.6 Hz, 2H), 3.04 (d, J=10.0 Hz, 1H), 2.95-2.81 (m, 3H), 2.73-2.66 (m, 2H), 2.23-2.16 (m, 1H), 1.97-1.90 (m, 1H), 1.46 (s, 3H); ESI+MS: m/z: 383 ([M+H]$^+$).

Example-35: 3-(4-chlorophenoxy)-1-(2-(3,4-dichlorophenoxy)ethyl)-3-methyl pyrrolidine

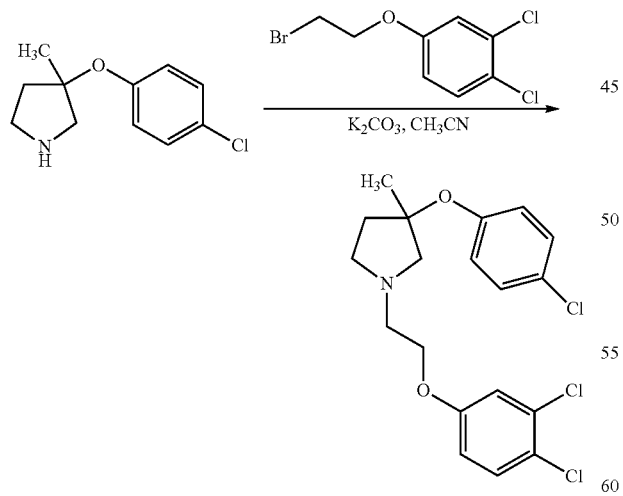

Title compound was prepared from 3-(4-chlorophenoxy)-3-methylpyrrolidine (0.1 g, 0.47 mmol) using the general methodology of Example-1. The crude was purified using preparative HPLC to afford 0.05 g of 3-(4-chlorophenoxy)-1-(2-(3,4-dichlorophenoxy)ethyl)-3-methylpyrrolidine (Yield=26%). $^1$H NMR (400 MHz, DMSO-d$_6$): δ 7.50 (d, J=9.2 Hz, 1H), 7.28-7.24 (m, 3H), 6.98-6.93 (m, 3H), 4.09 (t, J=5.6 Hz, 2H), 2.99 (d, J=10.0 Hz, 1H), 2.85-2.72 (m, 3H), 2.68-2.60 (m, 2H), 2.21-2.14 (m, 1H), 1.95-1.88 (m, 1H), 1.44 (s, 3H); ESI+MS: m/z: 401 ([M+H]$^+$).

Example-36: 3-(4-chlorophenoxy)-3-methyl-1-(2-(naphthalen-1-yloxy)ethyl) pyrrolidine

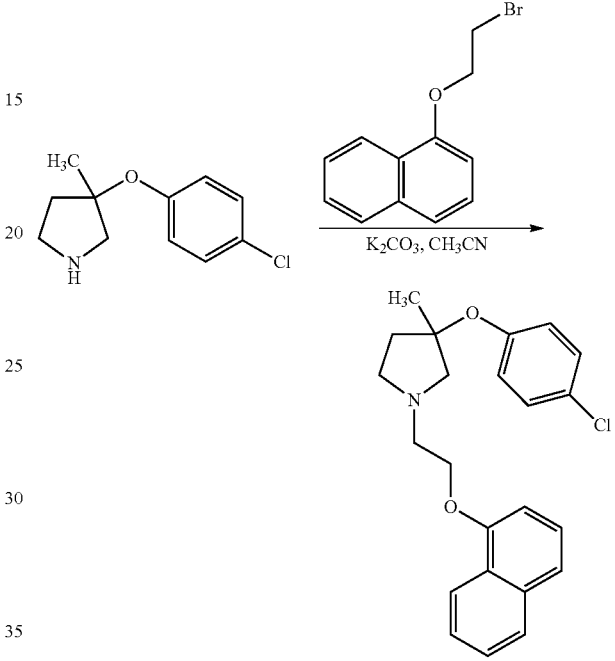

Title compound was prepared from 3-(4-chlorophenoxy)-3-methylpyrrolidine (0.1 g, 0.47 mmol) using the general methodology of Example-1. The crude was purified using preparative HPLC to afford 0.07 g of 3-(4-chlorophenoxy)-3-methyl-1-(2-(naphthalen-1-yloxy)ethyl)pyrrolidine (Yield=39%). $^1$H NMR (400 MHz, CD$_3$OD): δ 8.25 (d, J=8.0 Hz, 1H), 7.81 (d, J=7.2 Hz, 1H), 7.51-7.43 (m, 3H), 7.39 (t, J=7.6 Hz, 1H), 7.16 (d, J=8.00 Hz, 2H), 6.92 (d, J=8.8 Hz, 3H), 4.35 (t, J=5.2 Hz, 2H), 3.36-3.31 (m, 1H), 3.18-3.05 (m, 3H), 2.88-2.84 (m, 2H), 2.42-2.35 (m, 1H), 2.07-2.00 (m, 1H), 1.54 (s, 3H); ESI+MS: m/z: 382 ([M+H]$^+$).

Example-37: 1-(2-([1,1'-biphenyl]-3-yloxy)ethyl)-3-(4-chlorophenoxy)-3-methylpyrrolidine

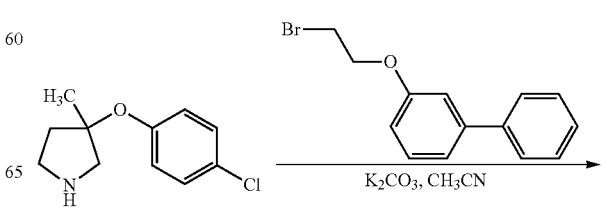

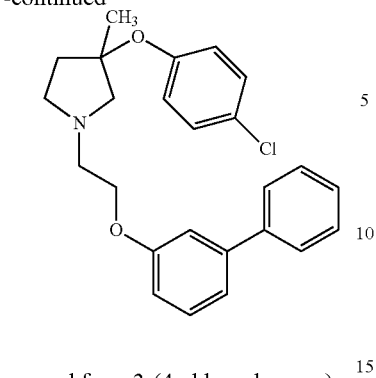

Title compound was prepared from 3-(4-chlorophenoxy)-3-methylpyrrolidine (0.1 g, 0.47 mmol) using the general methodology of Example-1. The crude was purified using preparative HPLC to afford 0.029 g of 1-(2-([1,1'-biphenyl]-3-yloxy)ethyl)-3-(4-chlorophenoxy)-3-methylpyrrolidine (Yield=15%). $^1$H NMR (400 MHz, CD$_3$OD): δ 7.60-7.58 (m, 2H), 7.42 (t, J=7.6 Hz, 2H), 7.33 (d, J=8.0 Hz, 2H), 7.19-7.15 (m, 4H), 6.92 (d, J=6.8 Hz, 3H), 4.19 (t, J=5.6 Hz, 2H), 3.24 (d, J=10.8 Hz, 1H), 3.01-2.88 (m, 3H), 2.79-2.72 (m, 2H), 2.38-2.31 (m, 1H), 2.02-1.95 (m, 1H), 1.51 (s, 3H); ESI+MS: m/z: 408 ([M+H]$^+$).

Example-38: 4-(4-chlorophenoxy)-4-methyl-1-(2-phenoxyethyl)piperidine

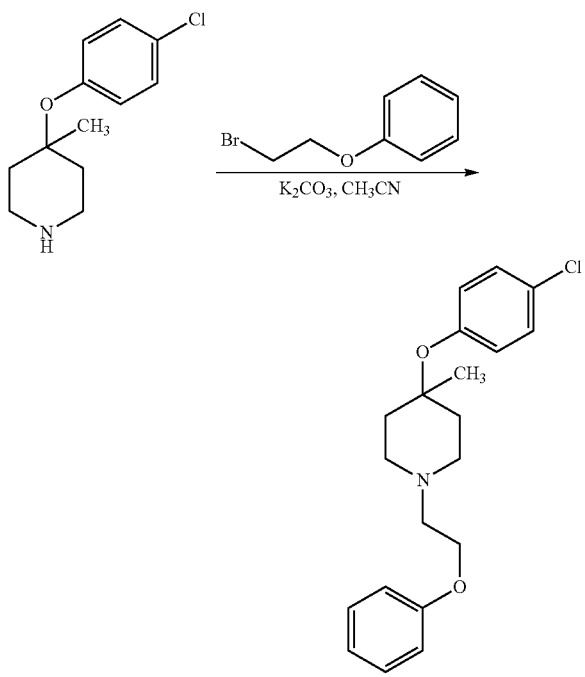

Title compound was prepared from 4-(4-chlorophenoxy)-4-methylpiperidine (0.1 g, 0.443 mmol) using the general methodology of Example-1. The crude was purified by preparative HPLC to afford 0.066 g of 4-(4-chlorophenoxy)-4-methyl-1-(2-phenoxyethyl)piperidine (Yield=43%). $^1$H NMR (500 MHz, DMSO-d$_6$): δ 7.31-7.24 (m, 4H), 7.00 (d, J=8.5 Hz, 2H), 6.90 (d, J=8.0 Hz, 3H), 4.05 (t, J=6.0 Hz, 2H), 2.71-2.69 (m, 2H), 2.52-2.48 (m, 4H), 1.86-1.83 (m, 2H), 1.64-1.59 (m, 2H), 1.22 (s, 3H); ESI+MS: m/z: 346 ([M+H]$^+$).

Example-39: 3-methyl-3-phenoxy-1-(2-phenoxyethyl)pyrrolidine

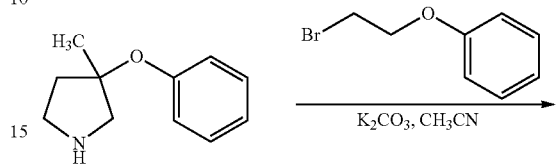

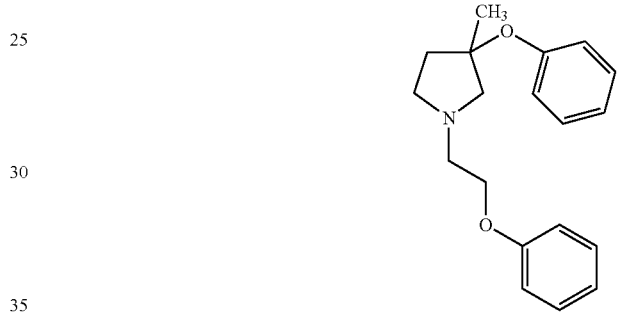

Title compound was prepared from 3-methyl-3-phenoxypyrrolidine (0.05 g, 0.282 mmol) and (2-bromoethoxy)benzene (0.057 g, 0.282 mmol, 1 equiv) using the general methodology of Example-1. The crude was purified by preparative HPLC purification to afford 0.06 g of 3-(4-chlorophenoxy)-1-(2-(2-methoxyphenoxy)ethyl)-3-methylpyrrolidine (Yield=70%). $^1$H NMR (500 MHz, DMSO-d$_6$): δ 7.28-7.21 (m, 4H), 6.92-6.89 (m, 6H), 4.05 (t, J=5.5 Hz, 2H), 3.00 (d, J=10.0 Hz, 1H), 2.83-2.78 (m, 3H), 2.71-2.65 (m, 2H), 2.22-2.17 (m, 1H), 1.94-1.88 (m, 1H), 1.45 (s, 3H), ESI+MS: m/z: 298 ([M+H]$^+$).

Example-40: 3-Methyl-3-(3-nitrophenoxy)-1-(2-phenoxyethyl)pyrrolidine

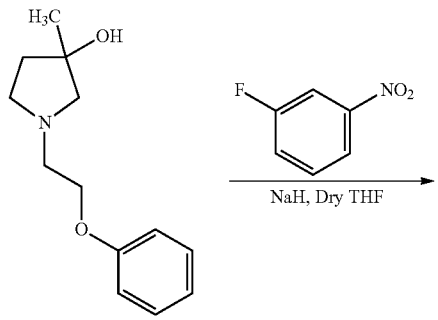

-continued

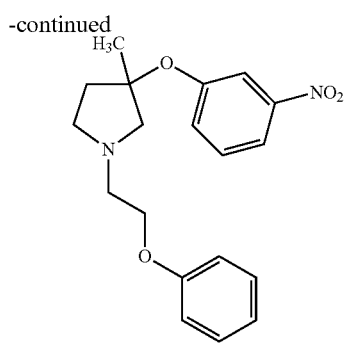

Title compound was prepared from 3-methyl-1-(2-phenoxyethyl)pyrrolidin-3-ol (0.15 g, 0.67 mmol) and 1-fluoro-3-nitro benzene (0.096 g, 0.67 mmol, 1 equiv) using the general methodology of step 2 of key Intermediate-I. Purification using silica gel column chromatography (2% MeOH/CH$_2$Cl$_2$) to afford 0.11 g of 3-methyl-3-(3-nitrophenoxy)-1-(2-phenoxyethyl)pyrrolidine (Yield=47%). $^1$H NMR (500 MHz, DMSO-d$_6$): δ 7.81-7.78 (m, 2H), 7.71-7.68 (m, 1H), 7.53 (t, J=8.5 Hz, 2H), 7.44-7.42 (m, 1H), 7.27 (t, J=7.5 Hz, 2H), 6.92 (d, J=7.5 Hz, 1H), 4.41-4.12 (m, 1H), 4.07 (t, J=5.5 Hz, 1H), 3.11 (d, J=10.5 Hz, 1H), 2.92-2.78 (m, 2H), 2.74-2.64 (m, 1H), 2.27-2.22 (m, 1H), 2.01-1.96 (m, 1H), 1.53 (s, 3H), 1.28-1.23 (m, 2H); ESI+MS: m/z: 343 ([M+H]$^+$).

Example-41: 3-((3-methyl-1-(2-phenoxyethyl)pyrrolidin-3-yl)oxy)aniline

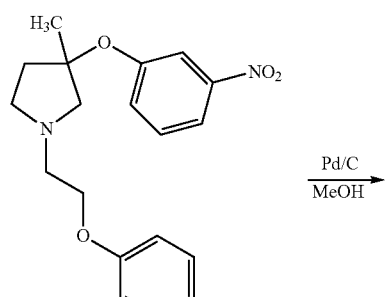

Title compound was prepared from 3-methyl-3-(3-nitrophenoxy)-1-(2-phenoxyethyl) pyrrolidine (0.20 g, 0.58 mmol) using the general methodology of step 3 of Key Intermediate-I. Purification using silica gel column chromatography (2% MeOH/CH$_2$Cl$_2$) to afford 0.11 g of 3-((3-methyl-1-(2-phenoxyethyl)pyrrolidin-3-yl)oxy)aniline (Yield=60%). $^1$H NMR (400 MHz, DMSO-d$_6$): δ 7.29-7.25 (m, 2H), 6.94-6.91 (m, 3H), 6.86-6.82 (m, 1H), 6.16-6.14 (m, 2H), 6.07-6.04 (m, 1H), 4.95 (br s, 2H), 4.06-4.03 (m, 2H), 2.94 (d, J=10.0 Hz, 1H), 2.83-2.74 (m, 2H), 2.73-2.65 (m, 3H), 2.20-2.13 (m, 1H), 1.89-1.83 (m, 1H), 1.43 (s, 3H); ESI+MS: m/z: 313 ([M+H]$^+$).

Example-42: 3-(3-chlorophenoxy)-3-methyl-1-(2-phenoxyethyl)pyrrolidine

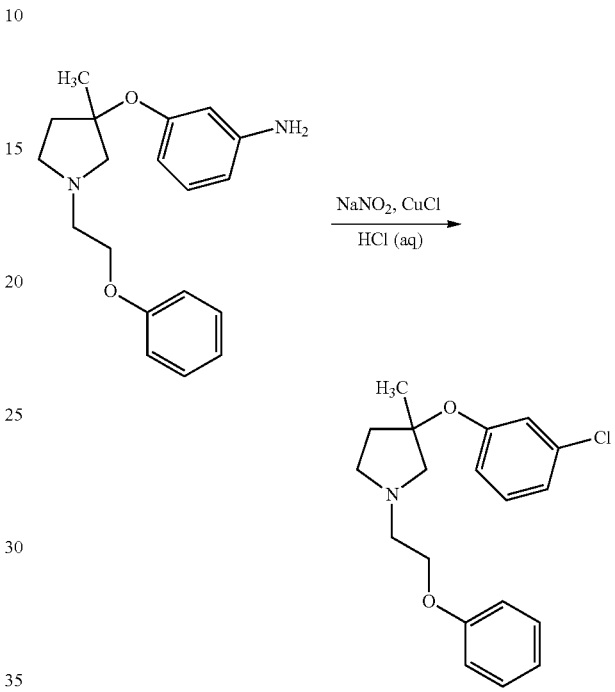

Title compound was prepared from 3-((3-methyl-1-(2-phenoxyethyl)pyrrolidin-3-yl)oxy) aniline (0.11 g, 0.35 mmol) using the general methodology of step 4 of Key Intermediate-I. Purification using silica gel column chromatography (2% MeOH/CH$_2$Cl$_2$) to afford 0.032 g of 3-(3-chlorophenoxy)-3-methyl-1-(2-phenoxyethyl)pyrrolidine (Yield=26%). $^1$H NMR (400 MHz, CD$_3$OD): δ 7.28-7.18 (m, 3H), 6.97-6.88 (m, 6H), 4.13 (t, J=5.6 Hz, 2H), 3.31-3.25 (m, 1H), 3.00-2.89 (m, 3H), 2.80-2.77 (m, 2H), 2.40-2.34 (m, 1H), 2.06-1.99 (m, 1H), 1.54 (s, 3H), ESI+MS: m/z: 332 ([M+H]$^+$).

Example-43: 3-Methyl-3-(4-nitrophenoxy)-1-(2-phenoxyethyl)pyrrolidine

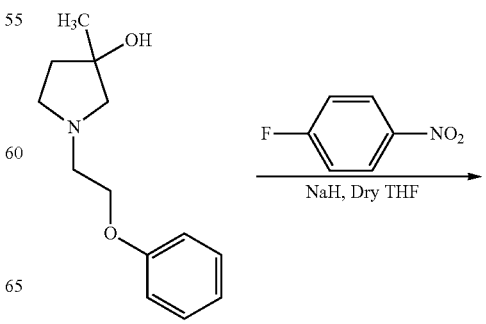

-continued

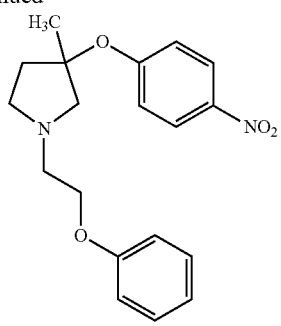

To a stirred solution of 3-methyl-1-(2-phenoxyethyl)pyrrolidin-3-ol (0.3 g, 1.35 mmol, 1 equiv) in 8 mL of THF was added sodium hydride (60% suspension, 0.08 g, 2.03 mmol, 1.5 equiv) at 0° C. under argon atmosphere followed by 1-fluoro-4-nitrobenzene (0.19 g, 1.35 mmol, 1 equiv). The reaction was heated at 80° C. for 24 h, after completion, the reaction was quenched with ice cold water and extracted with ether. The organic extract was dried over sodium sulfate, filtered and concentrated under reduced pressure. The combined organic extract was dried over sodium sulfate, filtered and concentrated under reduced pressure. Purification using column chromatography (2% MeOH/CH$_2$Cl$_2$) to afford 0.28 g of 3-methyl-3-(4-nitrophenoxy)-1-(2-phenoxyethyl)pyrrolidine (Yield=60%). $^1$H NMR (500 MHz, DMSO-d$_6$): δ 8.14 (d, J=9.0 Hz, 2H), 7.29-7.25 (m, 2H), 7.15 (d, J=9.0 Hz, 2H), 6.94-6.90 (m, 3H), 4.08-4.05 (m, 2H), 3.09 (d, J=10.0 Hz, 1H), 2.83-2.78 (m, 4H), 2.67-2.63 (m, 1H), 2.27-2.21 (m, 1H), 2.09-2.03 (m, 1H), 1.57 (s, 3H), ESI+MS: m/z: 343 ([M+H]$^+$).

Example-44: 4-((3-methyl-1-(2-phenoxyethyl)pyrrolidin-3-yl)oxy)aniline

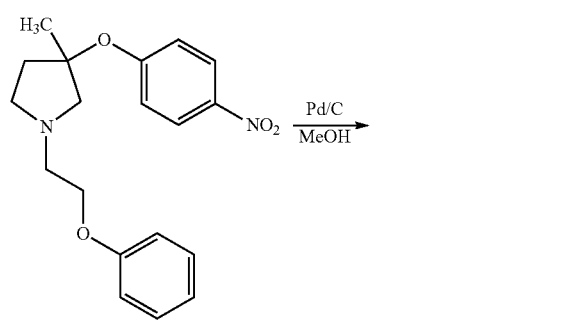

Title compound was prepared from 3-methyl-3-(4-nitrophenoxy)-1-(2-phenoxyethyl) pyrrolidine (0.24 g, 0.7 mmol) using the general methodology of step 3 of Key Intermediate-I. The crude was purified using silica gel column chromatography (2% MeOH/CH$_2$Cl$_2$) to afford 0.18 g of 4-((3-methyl-1-(2-phenoxyethyl)pyrrolidin-3-yl)oxy) aniline (Yield=80%). $^1$HNMR (500 MHz, DMSO-d$_6$): δ 7.30-7.27 (m, 2H), 6.95-6.92 (m, 3H), 6.66 (d, J=9.0 Hz, 2H), 6.45 (d, J=9.0 Hz, 2H), 5.01 (br s, 2H), 4.08 (br s, 2H), 2.86-2.64 (m, 6H), 2.15-2.12 (m, 1H), 1.77 (br s, 1H), 1.32 (s, 3H); ESI+MS: m/z: 313 ([M+H]$^+$).

Example-45: 3-methyl-3-(2-nitrophenoxy)-1-(2-phenoxyethyl)pyrrolidine

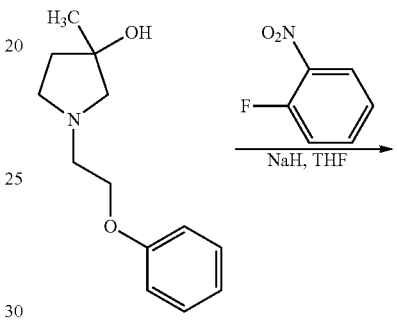

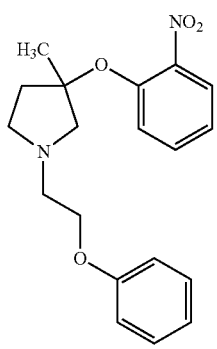

Title compound was prepared from 3-methyl-1-(2-phenoxyethyl)pyrrolidin-3-ol (0.30 g, 1.35 mmol) and 2-fluoro nitro benzene (0.19 g, 1.35 mmol, 1 equiv) using the general methodology of step 2 of Key intermediate-I. Purification using silica gel column chromatography (2% MeOH/CH$_2$Cl$_2$) to afford 0.27 g of 3-methyl-3-(2-nitrophenoxy)-1-(2-phenoxyethyl) pyrrolidine (Yield=56%). $^1$H NMR (500 MHz, DMSO-d$_6$): δ 7.79-7.78 (m, 1H), 7.56-7.52 (m, 1H), 7.41 (d, J=8.0 Hz, 1H), 7.29-7.26 (m, 2H), 7.13-7.10 (m, 1H), 6.94-6.90 (m, 3H), 4.05 (t, J=5.5 Hz, 2H), 3.02-3.00 (m, 1H), 2.81-2.75 (m, 4H), 2.70-2.63 (m, 1H), 2.24-2.19 (m, 1H), 2.03-1.97 (m, 1H), 1.52 (s, 3H); ESI+MS: m/z: 343 ([M+H]$^+$).

Example-46: 2-((3-methyl-1-(2-phenoxyethyl)pyrrolidin-3-yl)oxy)aniline

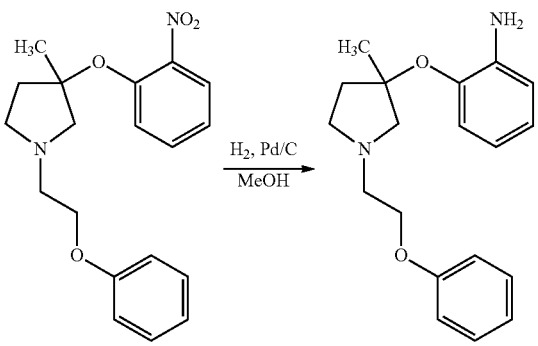 [SMILES: "MeOH" ; CC1(Oc2ccccc2[N+](=O)[O-])CCN(CCOc2ccccc2)C1 ; CC1(Oc2ccccc2N)CCN(CCOc2ccccc2)C1]

Title compound was prepared from 3-methyl-3-(2-nitrophenoxy)-1-(2-phenoxyethyl) pyrrolidine (0.25 g, 0.73 mmol) using the general methodology of step 3 of Key Intermediate-I. Purification using silica gel column chromatography (2% MeOH/CH$_2$Cl$_2$) to afford 0.11 g of 2-((3-methyl-1-(2-phenoxyethyl)pyrrolidin-3-yl)oxy)aniline (Yield=48%). $^1$H NMR (500 MHz, DMSO-d$_6$): δ 7.29 (t, J=8.0 Hz, 2H), 6.95-6.92 (m, 3H), 6.66 (d, J=9.0 Hz, 2H), 6.45 (d, J=9.0 Hz, 2H), 4.95 (br s, 2H), 4.08 (br s, 2H), 2.86 (br s, 6H), 2.15-2.12 (m, 1H), 1.77 (br s, 1H), 1.32 (s, 3H); ESI+MS: m/z: 313 ([M+H]$^+$).

Example-47: 3-(2-chlorophenoxy)-3-methyl-1-(2-phenoxyethyl)pyrrolidine

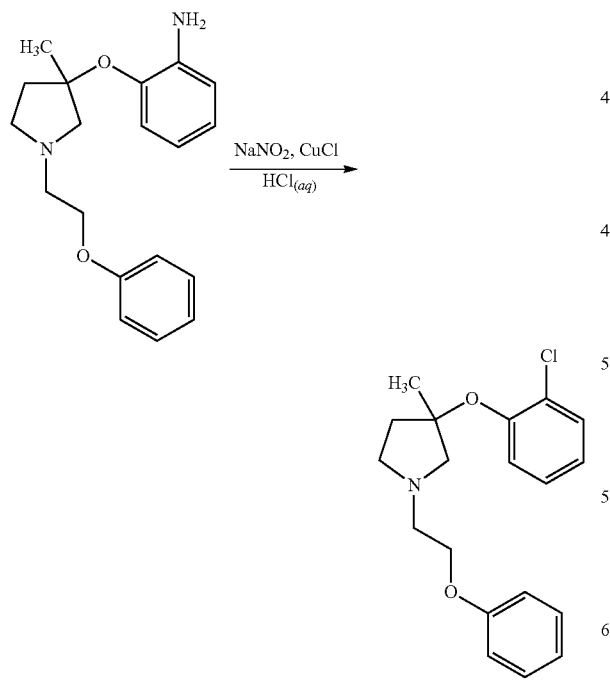

Title compound was prepared from 2-((3-methyl-1-(2-phenoxyethyl)pyrrolidin-3-yl)oxy)aniline (0.09 g, 0.288 mmol) using the general methodology of step 4 of Key Intermediate-I to afford 0.02 g of 3-(2-chlorophenoxy)-3-methyl-1-(2-phenoxyethyl)pyrrolidine (Yield=21%).
$^1$HNMR (400 MHz, CDCl$_3$): δ 7.35 (dd, J=8.0 Hz, 1.6 Hz, 1H), 7.30-7.27 (m, 2H), 7.14-7.10 (m, 1H), 7.07-7.04 (m, 1H), 6.96-6.88 (m, 4H), 4.10 (t, J=6.0 Hz, 2H), 3.16 (d, J=10.0 Hz, 1H), 2.95-2.80 (m, 5H), 2.47-2.40 (m, 1H), 2.01-1.94 (m, 1H), 1.55 (s, 3H); ESI+MS: m/z: 332 ([M+H]$^+$).

Example-48: 3-(2,4-dichlorophenoxy)-3-methyl-1-(2-phenoxyethyl)pyrrolidine

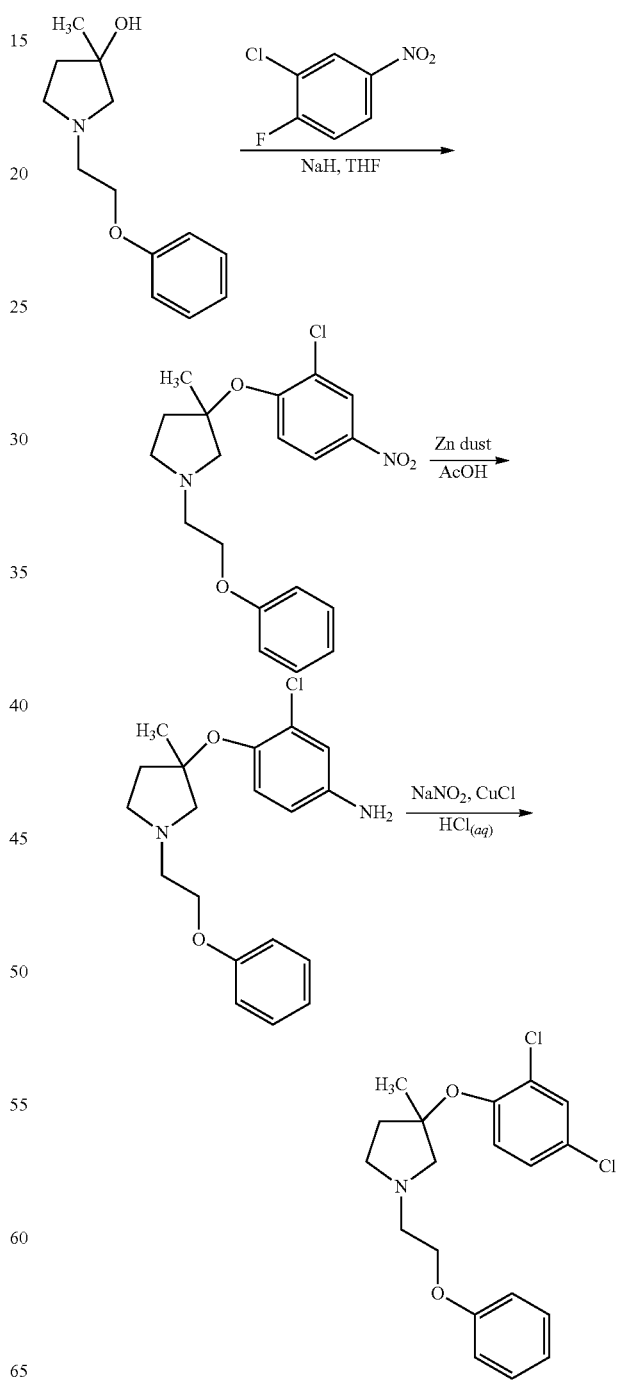

3-(2-chloro-4-nitrophenoxy)-3-methyl-1-(2-phenoxyethyl)pyrrolidine

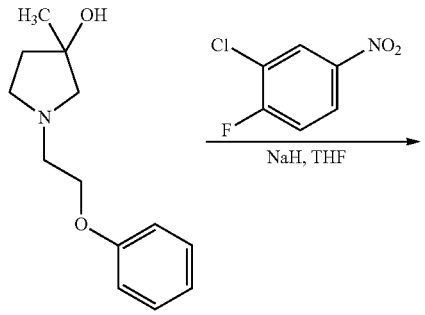

Title compound was prepared from 3-methyl-1-(2-phenoxyethyl)pyrrolidin-3-ol (0.80 g, 3.62 mmol) and 2-chloro-1-fluoro-4-nitrobenzene (0.69 g, 3.98 mmol, 1.1 equiv) using the general methodology of step 2 of key intermediate-I. The crude was purified using silica gel column chromatography (2% MeOH/CH$_2$Cl$_2$) to afford 0.6 g of 3-(2-chloro-4-nitrophenoxy)-3-methyl-1-(2-phenoxyethyl)pyrrolidine (Yield=44%). ESI+MS: m/z 377 ([M+H]$^+$).

3-chloro-4-((3-methyl-1-(2-phenoxyethyl)pyrrolidin-3-yl)oxy)aniline

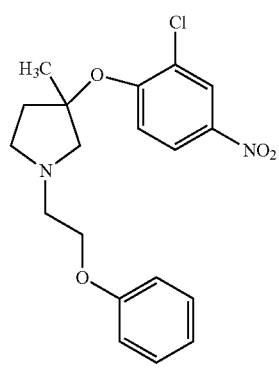

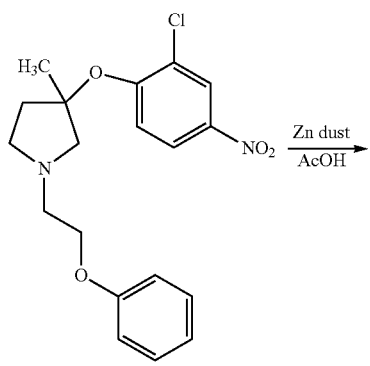

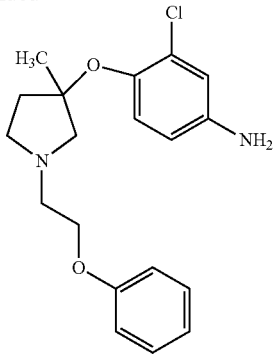

To a stirred solution of 3-(2-chloro-4-nitrophenoxy)-3-methyl-1-(2-phenoxyethyl)pyrrolidine (0.5 g, 1.32 mmol) in acetic acid (3 mL) under argon atmosphere was added Zn-dust (0.26 g, 3.98 mmol, 3 equiv) at 0° C. The reaction was stirred at room temperature for 16 h. After completion, the volatiles were removed under reduced pressure, the pH was adjusted to ~8 with 10% NaHCO$_3$ solution and extracted with EtOAc. The combined organic extract was dried over sodium sulfate, filtered and concentrated under reduced pressure to afford 0.3 g of 3-(2-chloro-4-nitrophenoxy)-3-methyl-1-(2-phenoxyethyl)pyrrolidine (Yield=65%). Ion trap: m/z 347 ([M+H]$^+$).

3-(2,4-dichlorophenoxy)-3-methyl-1-(2-phenoxyethyl)pyrrolidine

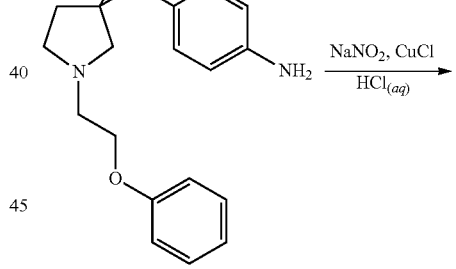

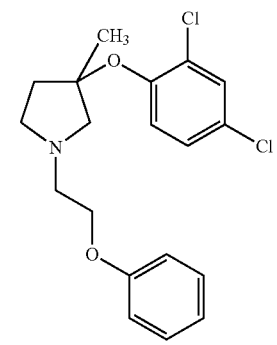

To a solution of 3-chloro-4-((3-methyl-1-(2-phenoxyethyl)pyrrolidin-3-yl)oxy)aniline in a 2 mL of a 1:1 mixture of aqueous HCl was added aqueous sodium nitrite (0.064 g, 0.93 mmol, 1.3 equiv) drop wise at 0° C. and stirred for 1 h. This was added to a solution of cuprous chloride (0.11 g, 1.15 mmol, 1.6 equiv) in 1 mL of aqueous HCl at 0° C. and stirred at room temperature for 1 h. After completion, the pH was adjusted to 14 with aqueous sodium hydroxide and extracted with EtOAc. The combined organic extract was dried over sodium sulfate, filtered and concentrated under reduced pressure. The crude was washed with n-hexane and dried under reduced pressure to afford 0.015 g of 3-(2,4-dichlorophenoxy)-3-methyl-1-(2-phenoxyethyl)pyrrolidine (Yield 17%). $^1$H NMR (400 MHz, DMSO-$d_6$): δ 7.55 (br s, 1H), 7.29-7.25 (m, 4H), 6.94-6.92 (m, 3H), 4.05 (t, J=6.0 Hz, 2H), 3.05 (d, J=10.0 Hz, 1H), 2.81-2.75 (m, 4H), 2.67-2.66 (m, 1H), 2.25-2.19 (m, 1H), 1.98-1.93 (m, 1H), 1.48 (s, 3H); ESI+MS: m/z: 367 ([M+H]$^+$).

Example-49: 3-(2,4-Dichlorophenoxy)-3-methyl-1-(2-phenoxyethyl)pyrrolidine

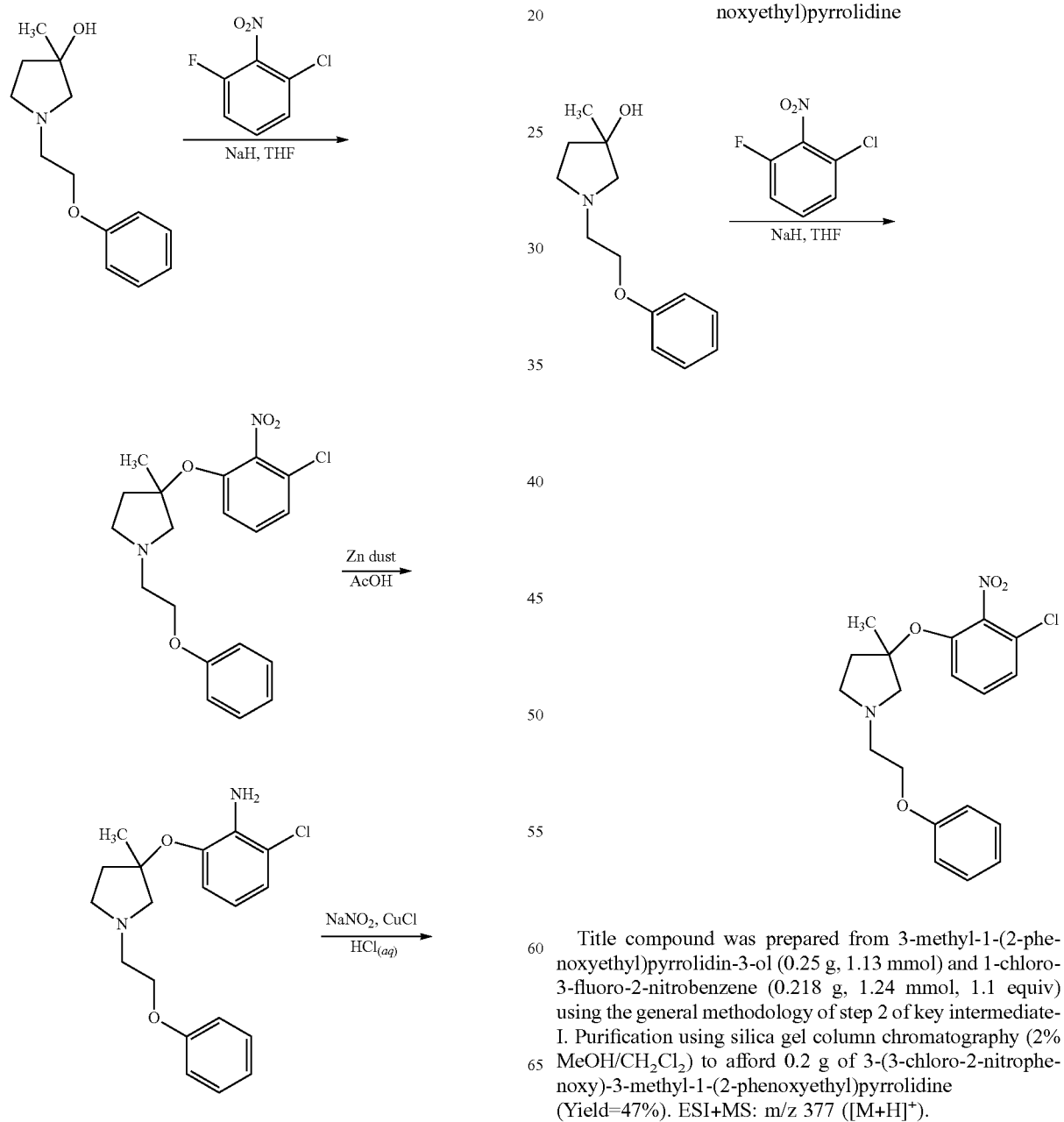

3-(3-Chloro-2-nitrophenoxy)-3-methyl-1-(2-phenoxyethyl)pyrrolidine

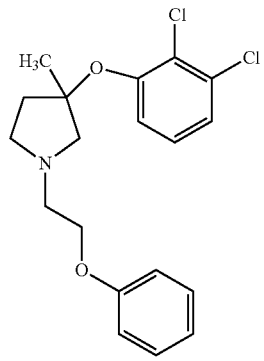

Title compound was prepared from 3-methyl-1-(2-phenoxyethyl)pyrrolidin-3-ol (0.25 g, 1.13 mmol) and 1-chloro-3-fluoro-2-nitrobenzene (0.218 g, 1.24 mmol, 1.1 equiv) using the general methodology of step 2 of key intermediate-I. Purification using silica gel column chromatography (2% MeOH/CH$_2$Cl$_2$) to afford 0.2 g of 3-(3-chloro-2-nitrophenoxy)-3-methyl-1-(2-phenoxyethyl)pyrrolidine (Yield=47%). ESI+MS: m/z 377 ([M+H]$^+$).

173

2-Chloro-6-((3-methyl-1-(2-phenoxyethyl)pyrroli-
din-3-yl)oxy)aniline

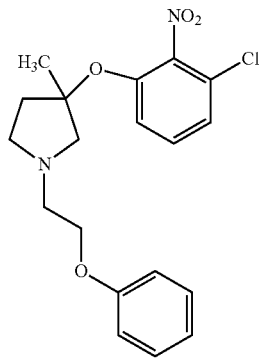

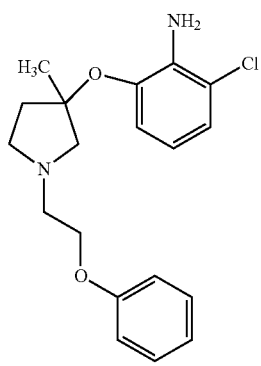

To a stirred solution of 3-(3-chloro-2-nitrophenoxy)-3-methyl-1-(2-phenoxyethyl)pyrrolidine (0.2 g, 0.531 mmol) in acetic acid (2 mL) under argon atmosphere was added Zn-dust (0.104 g, 1.59 mmol, 3 equiv) at 0° C. The reaction mixture was heated at 80° C. and stirred for 4 h. After completion, the volatiles were removed under reduced pressure, the pH was adjusted to ~8 with 10% NaHCO$_3$ solution and extracted with EtOAc. The combined organic extract was dried over sodium sulfate, filtered and concentrated under reduced pressure to afford 0.13 g of 2-chloro-6-((3-methyl-1-(2-phenoxyethyl)pyrrolidin-3-yl)oxy)aniline (Yield=70%).

3-(2,3-dichlorophenoxy)-3-methyl-1-(2-phenoxy-
ethyl)pyrrolidine

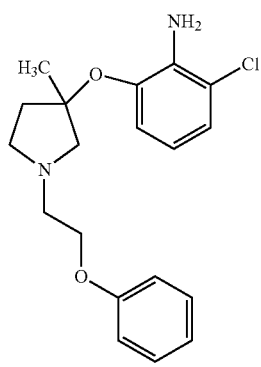

174

-continued

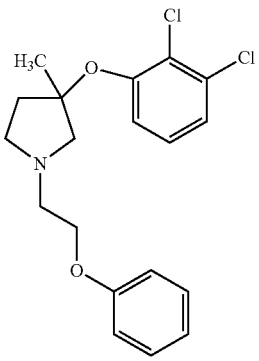

Title compound was prepared from 2-chloro-6-((3-methyl-1-(2-phenoxyethyl)pyrrolidin-3-yl)oxy)aniline (0.13 g, 0.375 mmol, 1 equiv) using general methodology of step 4 of key intermediate-I. The crude was purified by preparative HPLC purification to afford 0.015 g of 3-(2,3-dichlorophenoxy)-3-methyl-1-(2-phenoxyethyl)pyrrolidine (Yield=10%). $^1$H NMR (400 MHz, DMSO-d$_6$): δ 7.29-7.22 (m, 5H), 6.94-6.90 (m, 3H), 4.06 (br s, 2H), 3.07-3.05 (m, 1H), 2.82-2.80 (m, 4H), 2.69-2.63 (m, 1H), 2.25 (br s, 1H), 2.01-2.00 (m, 1H), 1.51 (s, 3H); ESI+MS: m/z: 367 ([M+H]$^+$).

Example-50: 3-(2,3-dichlorophenoxy)-3-methyl-1-
(2-phenoxyethyl)pyrrolidine

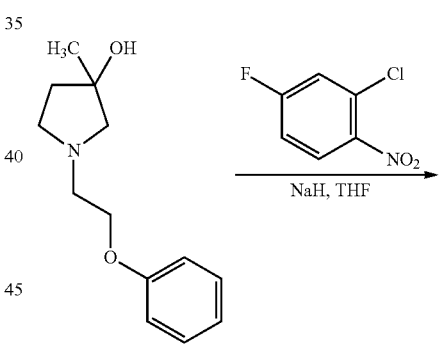

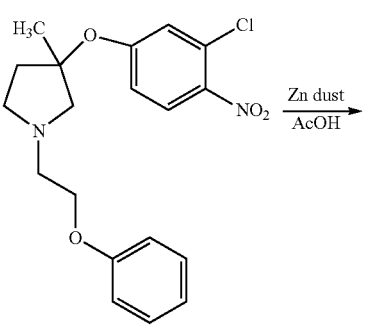

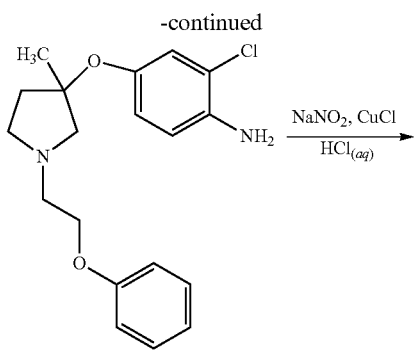

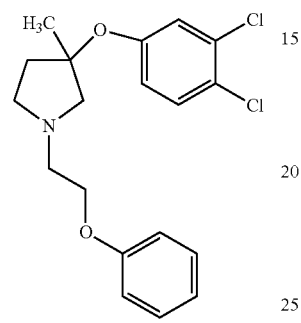

3-(3-Chloro-4-nitrophenoxy)-3-methyl-1-(2-phenoxyethyl)pyrrolidine

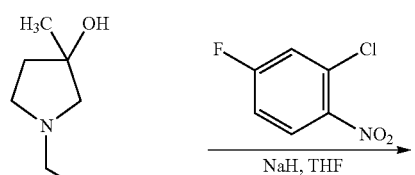

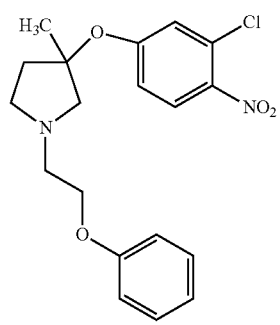

Title compound was prepared from 3-methyl-1-(2-phenoxyethyl)pyrrolidin-3-ol (0.25 g, 1.13 mmol) and 2-chloro-4-fluoro-1-nitrobenzene (0.218 g, 1.24 mmol, 1.1 equiv) using the general methodology of step 2 of key intermediate-I. The crude was purified using silica gel column chromatography (40% EtOAc/Hexane) to afford 0.2 g of 3-(3-chloro-4-nitrophenoxy)-3-methyl-1-(2-phenoxyethyl)pyrrolidine (Yield=47%). ESI+MS: m/z 377 ([M+H]+).

2-chloro-4-((3-methyl-1-(2-phenoxyethyl)pyrrolidin-3-yl)oxy)aniline

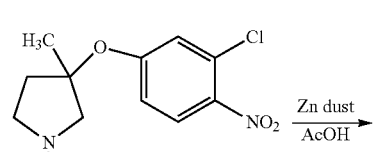

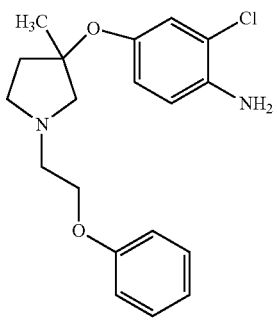

Title compound was prepared from 3-(3-chloro-4-nitrophenoxy)-3-methyl-1-(2-phenoxyethyl)pyrrolidine (0.20 g, 0.53 mmol) using the general methodology of step 2 of Example-49 to afford 0.149 g of 2-chloro-4-((3-methyl-1-(2-phenoxyethyl)pyrrolidin-3-yl)oxy)aniline (Yield=81%).

3-(2,3-dichlorophenoxy)-3-methyl-1-(2-phenoxyethyl)pyrrolidine

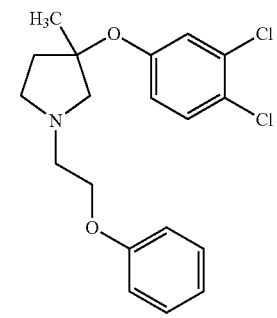

Title compound was prepared from 2-chloro-4-((3-methyl-1-(2-phenoxyethyl)pyrrolidin-3-yl)oxy)aniline (0.15 g, 0.43 mmol, 1 equiv) using general methodology of step 4 of key intermediate-I. The crude was purified by preparative HPLC purification to afford 0.015 g of 3-(2,3-dichlorophenoxy)-3-methyl-1-(2-phenoxyethyl)pyrrolidine (Yield=9%). $^1$H NMR (500 MHz, DMSO-d$_6$): δ 7.45 (d, J=9.0 Hz, 1H), 7.29-7.21 (m, 3H), 6.99-6.95 (m, 1H), 6.93-6.88 (m, 3H), 4.05 (t, J=5.5 Hz, 2H), 3.04 (d, J=10.0 Hz, 1H), 2.85-2.77 (m, 3H), 2.70-2.61 (m, 2H), 2.21-2.16 (m, 1H), 1.97-1.91 (m, 1H), 1.47 (s, 3H); ESI+MS: m/z: 367 ([M+H]$^+$).

Example-51: 3-(4-fluorophenoxy)-3-methyl-1-(2-phenoxyethyl)pyrrolidine

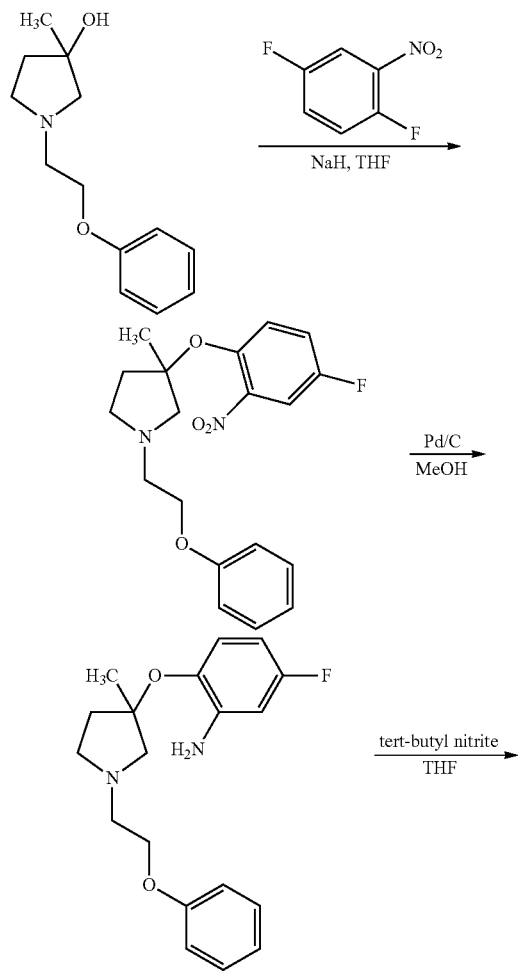

3-(4-fluoro-2-nitrophenoxy)-3-methyl-1-(2-phenoxyethyl)pyrrolidine

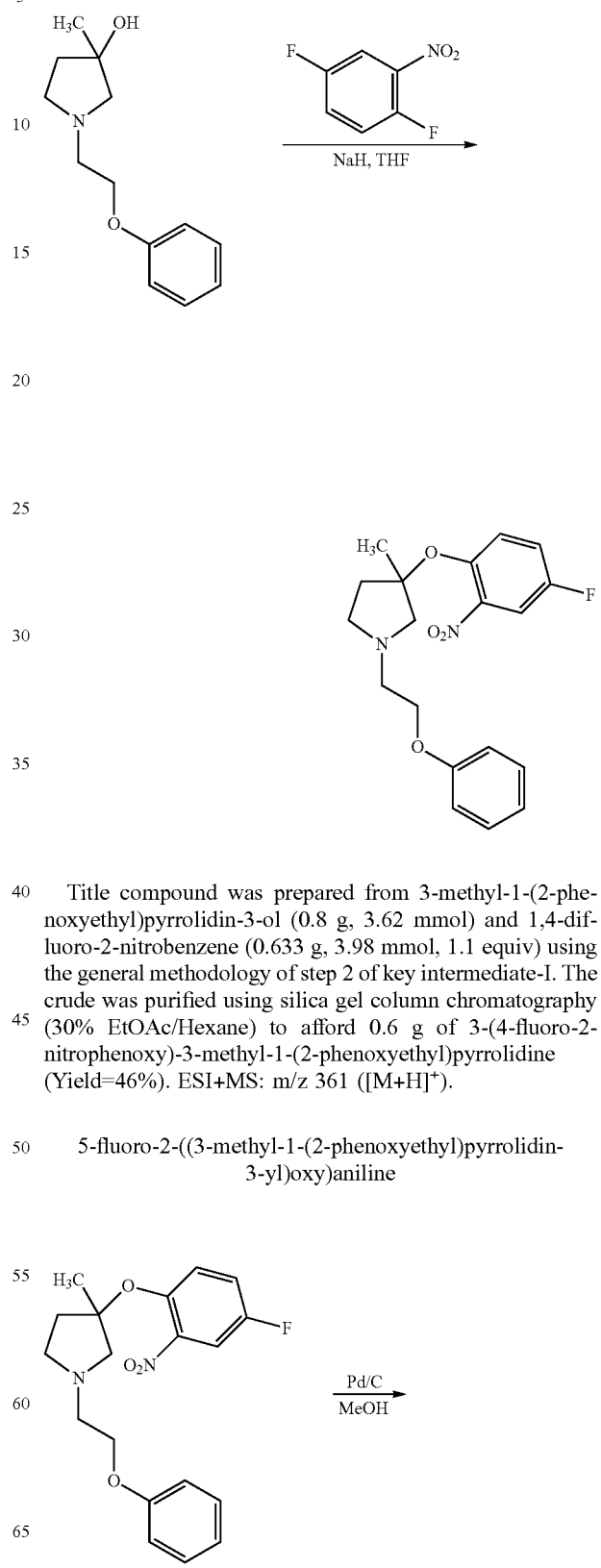

Title compound was prepared from 3-methyl-1-(2-phenoxyethyl)pyrrolidin-3-ol (0.8 g, 3.62 mmol) and 1,4-difluoro-2-nitrobenzene (0.633 g, 3.98 mmol, 1.1 equiv) using the general methodology of step 2 of key intermediate-I. The crude was purified using silica gel column chromatography (30% EtOAc/Hexane) to afford 0.6 g of 3-(4-fluoro-2-nitrophenoxy)-3-methyl-1-(2-phenoxyethyl)pyrrolidine (Yield=46%). ESI+MS: m/z 361 ([M+H]$^+$).

5-fluoro-2-((3-methyl-1-(2-phenoxyethyl)pyrrolidin-3-yl)oxy)aniline

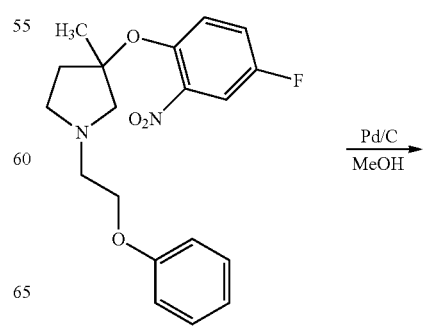

-continued

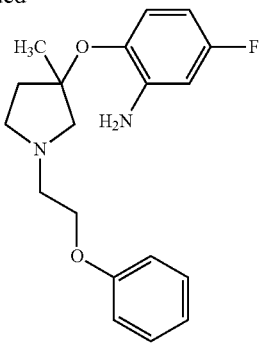

Title compound was prepared from 3-(4-fluoro-2-nitrophenoxy)-3-methyl-1-(2-phenoxyethyl)pyrrolidine (0.6 g, 1.66 mmol) using the general methodology of step 3 of key intermediate-I. The crude was purified using silica gel column chromatography (30% EtOAc/Hexane) to afford 0.39 g of 5-fluoro-2-((3-methyl-1-(2-phenoxyethyl)pyrrolidin-3-yl)oxy)aniline (Yield=71%). ESI+MS: m/z 331 ([M+H]$^+$).

3-(4-fluorophenoxy)-3-methyl-1-(2-phenoxyethyl)pyrrolidine

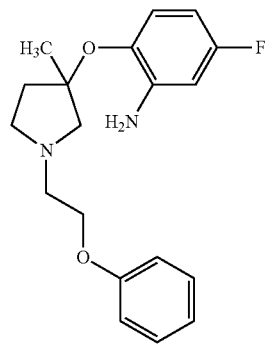

To a stirred solution of 5-fluoro-2-((3-methyl-1-(2-phenoxyethyl)pyrrolidin-3-yl)oxy)aniline (0.25 g, 0.757 mmol, 1 equiv) in 5 mL of THF was added tert-butyl nitrite (0.78 g, 7.57 mmol, 1 equiv). The reaction was stirred at room temperature for 16 h; after completion, the reaction was quenched with ice cold water and extracted with ethyl acetate. The organic extract was dried over sodium sulfate, filtered and concentrated under reduced pressure. Purification by preparative HPLC to afford 0.025 g of 3-(4-fluorophenoxy)-3-methyl-1-(2-phenoxyethyl)pyrrolidine (Yield=10%). $^1$H NMR (400 MHz, CD$_3$OD): δ 7.29-7.24 (m, 2H), 6.97-6.91 (m, 7H), 4.13 (t, J=5.6 Hz, 2H), 3.23 (d, J=10.8 Hz, 1H), 3.04-2.96 (m, 2H), 2.92-2.87 (m, 1H), 2.80-2.74 (m, 1H), 2.69 (d, J=10.8 Hz, 1H), 2.37-2.30 (m, 1H), 1.98-1.91 (m, 1H), 1.47 (s, 3H); ESI+MS: m/z: 316 ([M+H]$^+$).

Example-52: 3-(3-fluorophenoxy)-3-methyl-1-(2-phenoxyethyl)pyrrolidine

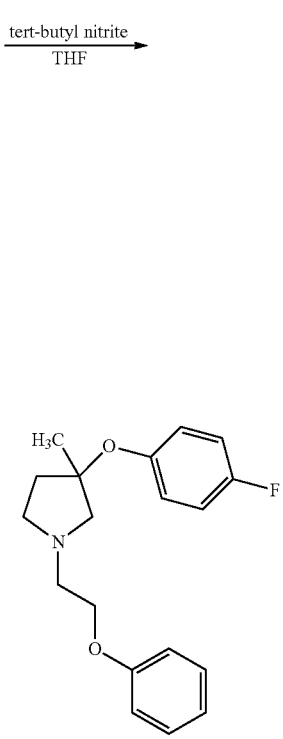

To a stirred solution of 4-fluoro-2-((3-methyl-1-(2-phenoxyethyl)pyrrolidin-3-yl)oxy)aniline (0.15 g, 0.454 mmol) in THF (1 mL) under argon atmosphere was added BF$_3$.Et$_2$O (0.064 g, 0.454 mmol, 1 equiv) and tert-butyl nitrite (0.06 g, 0.545 mmol, 1.2 equiv). The reaction was stirred at room temperature for 16 h. After completion, the volatiles removed under reduced pressure; the pH was adjusted to 7 using saturated NaHCO$_3$ and extracted with CH$_2$Cl$_2$. The organic extract was dried over sodium sulfate, filtered and concentrated. Purification by preparative HPLC afforded 0.01 g of 3-(3-fluorophenoxy)-3-methyl-1-(2-phenoxyethyl) pyrrolidine (Yield=6%). $^1$H NMR (400 MHz, DMSO-d$_6$): δ 7.28-7.19 (m, 3H), 6.94-6.90 (m, 3H), 6.78-6.67 (m, 3H), 4.14 (t, J=5.6 Hz, 2H), 3.31-3.30 (m, 1H), 3.00-2.92 (m, 3H), 2.83-2.77 (m, 2H), 2.42-2.35 (m, 1H), 2.07-2.00 (m, 1H), 1.55 (s, 3H); ESI+MS: m/z 316 ([M+H]$^+$).

181

Example-53: 3-(3-fluorophenoxy)-3-methyl-1-(2-phenoxyethyl)pyrrolidine

182

3-(2-Fluoro-4-nitrophenoxy)-3-methyl-1-(2-phenoxyethyl)pyrrolidine

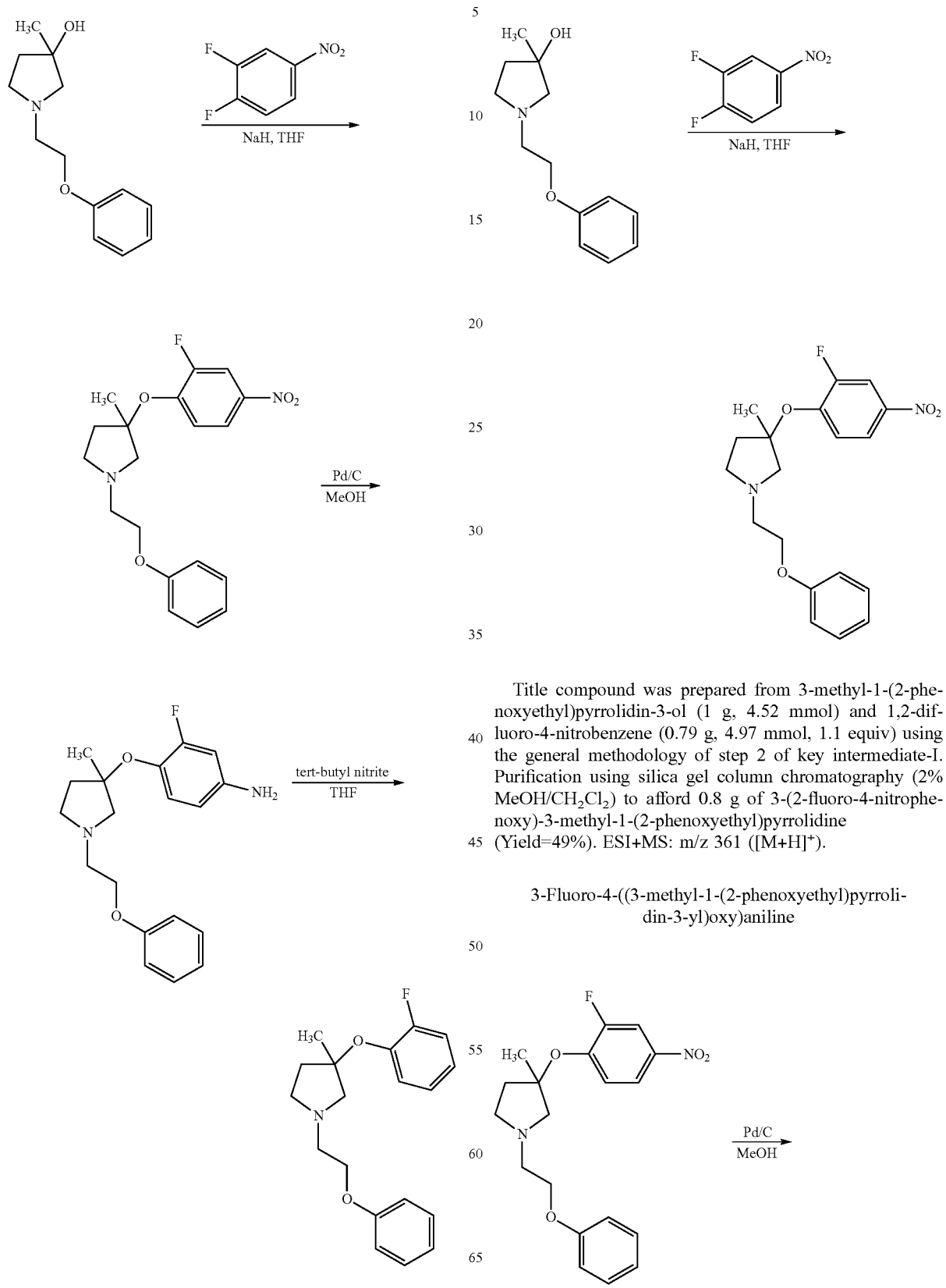

Title compound was prepared from 3-methyl-1-(2-phenoxyethyl)pyrrolidin-3-ol (1 g, 4.52 mmol) and 1,2-difluoro-4-nitrobenzene (0.79 g, 4.97 mmol, 1.1 equiv) using the general methodology of step 2 of key intermediate-I. Purification using silica gel column chromatography (2% MeOH/CH$_2$Cl$_2$) to afford 0.8 g of 3-(2-fluoro-4-nitrophenoxy)-3-methyl-1-(2-phenoxyethyl)pyrrolidine (Yield=49%). ESI+MS: m/z 361 ([M+H]$^+$).

3-Fluoro-4-((3-methyl-1-(2-phenoxyethyl)pyrrolidin-3-yl)oxy)aniline

-continued

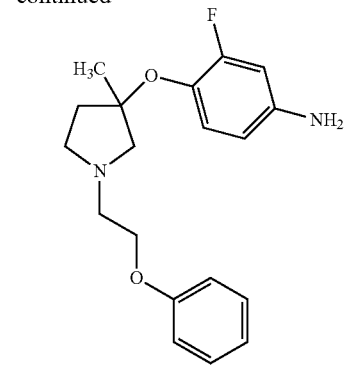

Title compound was prepared from 3-(2-fluoro-4-nitrophenoxy)-3-methyl-1-(2-phenoxyethyl)pyrrolidine (0.7 g, 1.94 mmol) using the general methodology of step 3 of key intermediate-I to afford 0.5 g of 3-fluoro-4-((3-methyl-1-(2-phenoxyethyl)pyrrolidin-3-yl)oxy)aniline (Yield=78%). ESI+MS: m/z 331 ([M+H]⁺).

3-(3-Fluorophenoxy)-3-methyl-1-(2-phenoxyethyl)pyrrolidine

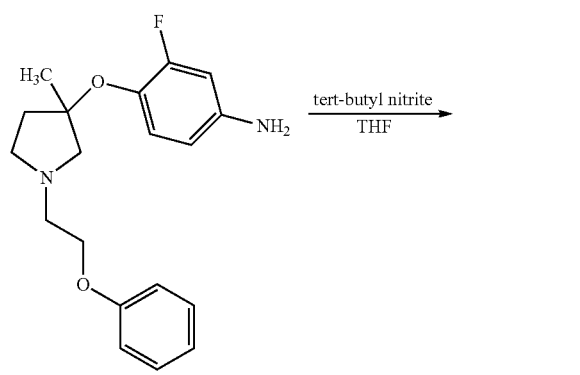

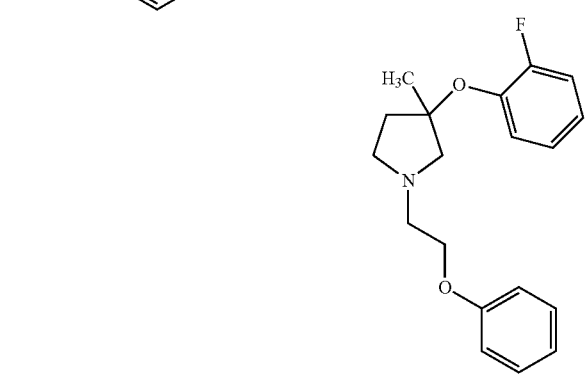

Title compound was prepared from 3-fluoro-4-((3-methyl-1-(2-phenoxyethyl)pyrrolidin-3-yl)oxy)aniline (0.25 g, 0.757 mmol) using the general methodology of Example 51. Purification using silica gel column chromatography (5% MeOH/CH$_2$Cl$_2$) and further purified by preparative HPLC to afford 0.03 g of 3-(3-fluorophenoxy)-3-methyl-1-(2-phenoxyethyl)pyrrolidine (Yield=11%). ¹HNMR (400 MHz, CDCl$_3$): δ 7.30-7.25 (m, 2H), 7.09-7.04 (m, 2H), 7.01-6.90 (m, 5H), 4.14 (t, J=4.8 Hz, 2H), 3.20 (d, J=10.4 Hz, 1H), 3.02-2.93 (m, 3H), 2.87-2.80 (m, 2H), 2.41-2.35 (m, 1H), 1.96-1.83 (m, 1H), 1.49 (s, 3H); ESI+MS: m/z: 316 ([M+H]⁺).

Example-54: 3-methyl-1-(2-phenoxyethyl)-3-(4-(trifluoromethyl)phenoxy)pyrrolidine

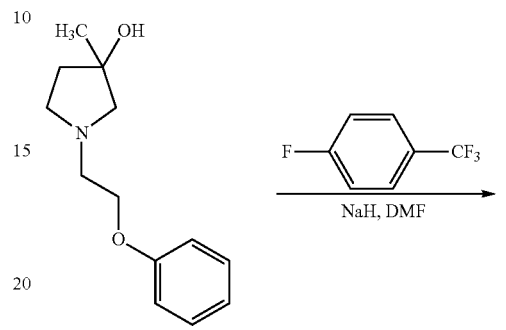

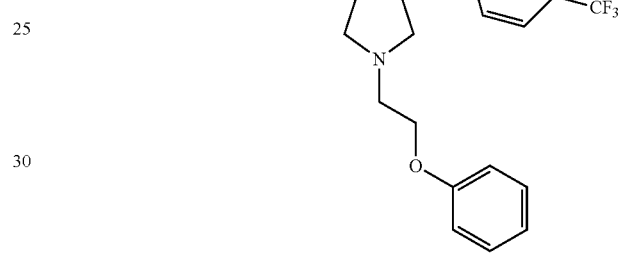

Title compound was prepared from 3-methyl-1-(2-phenoxyethyl)pyrrolidin-3-ol (0.1 g, 0.45 mmol) and 1-fluoro-4-(trifluoromethyl)benzene (0.074 g, 0.45 mmol, 1 equiv) was heated in a sealed tube for 16 h using the general methodology of step 2 of key intermediate-I. The crude was purified using preparative HPLC to afford 0.03 g of 3-methyl-1-(2-phenoxyethyl)-3-(4-(trifluoromethyl)phenoxy)pyrrolidine (Yield=17%). ¹H NMR (500 MHz, DMSO-d$_6$): δ 7.57 (d, J=9.0 Hz, 2H), 7.26 (t, J=8.5 Hz, 2H), 7.11 (d, J=8.0 Hz, 2H), 6.91-6.89 (m, 3H), 4.05 (t, J=6.0 Hz, 2H), 3.04 (d, J=10.0 Hz, 1H), 2.82-2.74 (m, 4H), 2.66-2.62 (m, 1H), 2.23-2.20 (m, 1H), 2.01-1.98 (m, 1H), 1.52 (s, 3H); ESI+MS: m/z: 366 ([M+H]⁺).

Example-55: 3-methyl-1-(2-phenoxyethyl)-3-(3-(trifluoromethyl)phenoxy)pyrrolidine

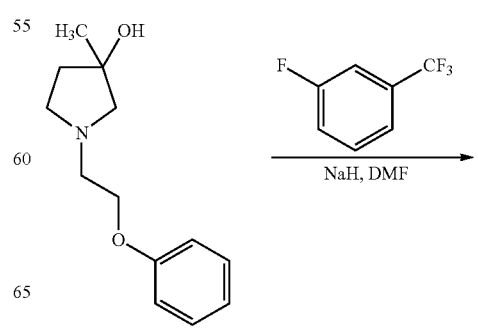

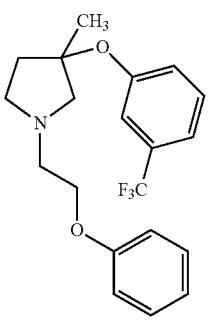

Title compound was prepared from 3-methyl-1-(2-phenoxyethyl)pyrrolidin-3-ol (0.20 g, 0.90 mmol) and 1-fluoro-3-(trifluoromethyl)benzene (0.148 g, 0.90 mmol, 1 equiv) was heated in a sealed tube for 16 h using the general methodology of step 2 of key intermediate-I. Purification using silica gel column chromatography (1% MeOH/CH$_2$Cl$_2$) to afford 0.035 g of 3-methyl-1-(2-phenoxyethyl)-3-(3-(trifluoromethyl)phenoxy)pyrrolidine (Yield=10%). $^1$H NMR (500 MHz, DMSO-d$_6$): δ 7.47-7.45 (m, 1H), 7.29-7.22 (m, 5H), 6.92-6.89 (m, 3H), 4.05 (t, J=6.0 Hz, 2H), 3.05 (d, J=10.0 Hz, 1H), 2.84-2.63 (m, 5H), 2.22-2.20 (m, 1H), 1.97-1.96 (m, 1H), 1.49 (s, 3H), ESI+MS: m/z: 366 ([M+H]$^+$). The enantiomers of 55 were separated using chiral HPLC (method R) and afforded the pure enantiomers 55a and 55b.

Example-56: 3-Methyl-1-(2-phenoxyethyl)-3-(2-(trifluoromethyl) phenoxy) pyrrolidine

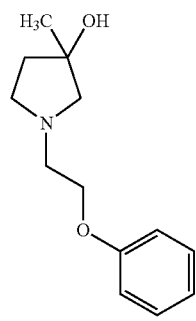 

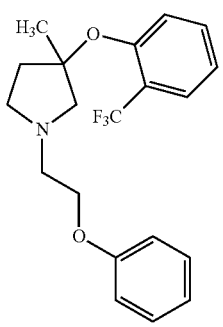

Title compound was prepared from 3-methyl-1-(2-phenoxyethyl)pyrrolidin-3-ol (0.1 g, 0.45 mmol) and 1-fluoro-2-(trifluoromethyl)benzene (0.074 g, 0.45 mmol, 1 equiv) was heated in a sealed tube for 16 h using the general methodology of step 2 of key intermediate-I. The crude was purified by preparative HPLC purification to afford 0.025 g of 3-methyl-1-(2-phenoxyethyl)-3-(2-(trifluoromethyl)phenoxy)pyrrolidine (Yield=14%). $^1$H NMR (500 MHz, DMSO-d$_6$): δ 7.58-7.51 (m, 2H), 7.29-7.24 (m, 3H), 7.05 (t, J=7.0 Hz, 1H), 6.93-6.89 (m, 3H), 4.05 (t, J=5.5 Hz, 2H), 2.99 (d, J=10.0 Hz, 1H), 2.90 (d, J=10.5 Hz, 1H), 2.83-2.75 (m, 2H), 2.73-2.69 (m, 2H), 2.28-2.22 (m, 1H), 2.03-1.99 (m, 1H), 1.49 (s, 3H); ESI+MS: m/z: 366 ([M+H]$^+$).

Example-57: 2-((3-methyl-1-(2-phenoxyethyl)pyrrolidin-3-yl)oxy)pyridine

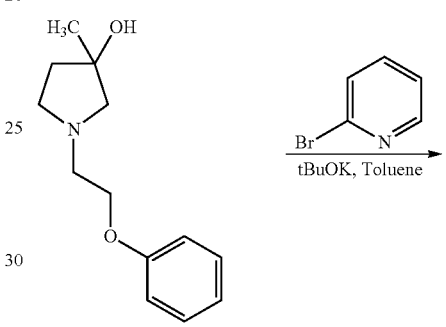

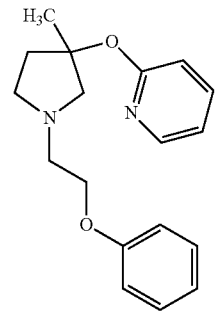

To a stirred solution of 3-methyl-1-(2-phenoxyethyl)pyrrolidin-3-ol (0.1 g, 0.45 mmol) in toluene (2 mL) were added potassium tert-butoxide (0.152 g, 1.35 mmol, 3 equiv) and 2-bromo pyridine (0.079 g, 0.45 mmol, 1 equiv) under argon atmosphere at room temperature. The reaction was heated at 120° C. in a sealed tube for 16 h. After completion, the volatiles were removed under reduced pressure; water was added to the residue and extracted with CH$_2$Cl$_2$ The organic layer was dried over sodium sulfate, filtered and concentrated under reduced pressure. Purification by preparative HPLC to afford 0.02 g of 2-((3-methyl-1-(2-phenoxyethyl)pyrrolidin-3-yl)oxy)pyridine (Yield=14%). $^1$H NMR (500 MHz, DMSO-d$_6$): δ 8.11 (d, J=3.5 Hz, 1H), 7.65 (t, J=7.0 Hz, 1H), 7.27 (t, J=7.5 Hz, 2H), 6.93-6.90 (m, 4H), 6.72 (d, J=8.0 Hz, 1H), 4.06-4.04 (m, 2H), 3.02-2.95 (m, 2H), 2.79 (br s, 2H), 2.69-2.64 (m, 2H), 2.27-2.24 (m, 1H), 2.04-2.00 (m, 1H), 1.66 (s, 3H); ESI+MS: m/z: 299 ([M+H]$^+$).

Example-58: 3-((3-methyl-1-(2-phenoxyethyl)pyrrolidin-3-yl)oxy)pyridine

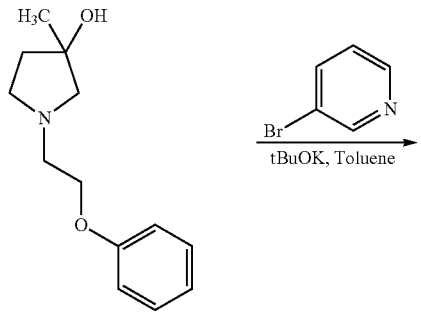

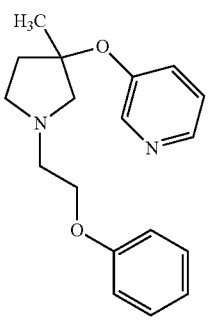

To a solution of 3-methyl-1-(2-phenoxyethyl)pyrrolidin-3-ol (0.2 g, 0.904 mmol) in DMF (2 mL) were added cesium carbonate (0.589 g, 1.808 mmol, 2 equiv) and 3-bromo pyridine (0.157 g, 0.99 mmol, 1.1 equiv) under argon atmosphere at room temperature. The reaction was heated at 120° C. for 72 h. After completion, the volatiles were removed under reduced pressure and the residue was diluted with water and extracted with diethyl ether. The organic layer was separated, dried over sodium sulfate, filtered, and dried under reduced pressure. Purification by preparative HPLC to afford 0.013 g of 3-((3-methyl-1-(2-phenoxyethyl)pyrrolidin-3-yl)oxy)pyridine (Yield=5%). $^1$H NMR (400 MHz, CDCl$_3$): δ 8.40-8.39 (m, 2H), 7.33-7.28 (m, 2H), 6.99-6.92 (m, 3H), 6.84 (d, J=5.2 Hz, 2H), 4.14 (t, J=5.6 Hz, 2H), 3.22 (d, J=10.0 Hz, 1H), 2.98-2.92 (m, 3H), 2.90-2.81 (m, 1H), 2.79-2.57 (m, 1H), 2.48-2.42 (m, 1H), 2.09-2.03 (m, 1H), 1.64 (s, 3H); ESI+MS: m/z: 299 ([M+H]$^+$).

Example-59: 4-((3-methyl-1-(2-phenoxyethyl)pyrrolidin-3-yl)oxy)pyridine

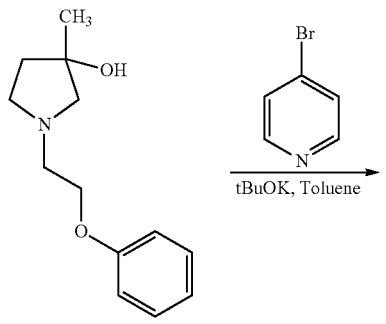

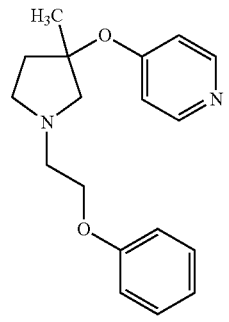

Title compound was prepared from 3-methyl-1-(2-phenoxyethyl)pyrrolidin-3-ol (0.1 g, 0.452 mmol) and 4-bromopyridine (0.079 g, 0.497 mmol, 1.1 equiv) using the general methodology of Example-57. The crude was purified by preparative HPLC to afford 0.015 g of 4-((3-methyl-1-(2-phenoxyethyl)pyrrolidin-3-yl)oxy)pyridine (Yield=10%). $^1$H NMR (500 MHz, CD$_3$OD): δ 8.28 (d, J=6.0 Hz, 2H), 7.25 (t, J=7.5 Hz, 2H), 6.97 (d, J=6.0 Hz, 2H), 6.91 (t, J=7.5 Hz, 3H), 4.12 (t, J=5.5 Hz, 2H), 3.27-3.25 (m, 1H), 2.97-2.86 (m, 4H), 2.79-2.73 (m, 1H), 2.44-2.39 (m, 1H), 2.17-2.12 (m, 1H), 1.65 (s, 3H); ESI+MS: m/z: 299 ([M+H]$^+$). The enantiomers of 59 were separated using chiral HPLC (method M) and afforded the pure enantiomers 59a and 59b.

Example-60: 2-((3-methyl-1-(2-phenoxyethyl)pyrrolidin-3-yl)oxy)pyrazine

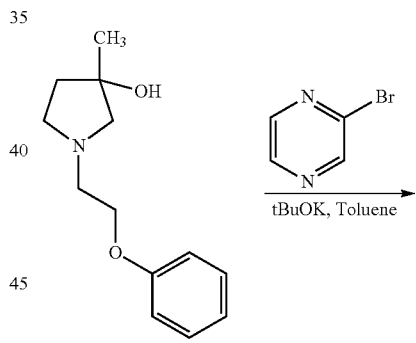

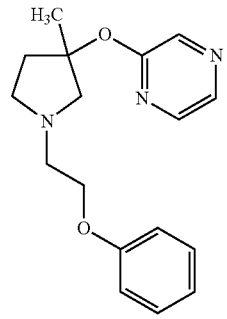

Title compound was prepared from 3-methyl-1-(2-phenoxyethyl)pyrrolidin-3-ol (0.1 g, 0.452 mmol) and 2-bromopyrazine (0.079 g, 0.497 mmol, 1.1 equiv) using the general methodology of Example-57. The crude was purified by preparative HPLC to afford 0.03 g of 2-((3-methyl-1-(2-phenoxyethyl)pyrrolidin-3-yl)oxy)pyrazine (Yield=21%). $^1$H NMR (400 MHz, DMSO-d$_6$): δ 8.20 (s, 1H), 8.16 (s, 2H), 7.27-7.25 (m, 2H), 6.93-6.91 (m, 3H), 4.07-4.04 (m, 2H), 3.07 (br s, 1H), 2.94 (br s, 1H), 2.80-2.70 (m, 4H), 2.32-2.27 (m, 1H), 2.09-2.02 (m, 1H), 1.66 (s, 3H); ESI+MS: m/z: 300 ([M+H]$^+$).

Example-61: 1-(2-(2-Fluorophenoxy)ethyl)-3-methyl-3-(3-(trifluoromethyl) phenoxy) piperidine

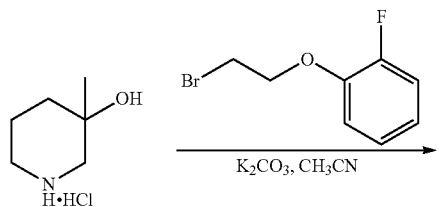

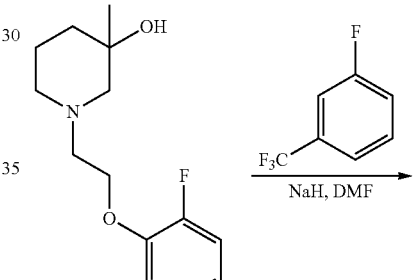

1-(2-(2-Fluorophenoxy) ethyl)-3-methylpiperidin-3-ol

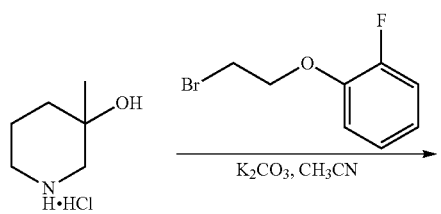

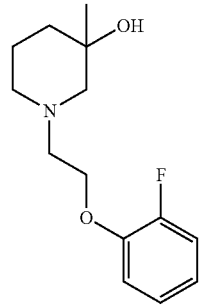

Title compound was prepared from 3-methylpiperidin-3-ol hydrochloride (0.15 g, 0.98 mmol, 1 equiv) and 1-(2-bromoethoxy)-2-fluorobenzene (0.21 g, 0.989 mmol, 1 equiv) using general methodology of Example-1. Purification using silica gel column chromatography (2% MeOH/CH$_2$Cl$_2$ as eluent) to afford 0.1 g of 1-(2-(2-(trifluoromethyl) phenoxy)ethyl)piperidin-4-one (Yield=39%).

1-(2-(2-fluorophenoxy)ethyl)-3-methyl-3-(3-(trifluoromethyl) phenoxy) piperidine

Title compound was prepared from 1-(2-(2-fluorophenoxy) ethyl)-3-methylpiperidin-3-ol (0.1 g, 0.39 mmol) and 3-fluoro benzotrifluoride (0.064 g, 0.395 mmol, 1 equiv) using the general methodology of step 2 of key intermediate-I at 100° C. for 24 h in a sealed tube. Purification using silica gel column chromatography and further purified by prep HPLC to afford 0.02 g of 1-(2-(2-fluorophenoxy) ethyl)-3-methyl-3-(3-(trifluoromethyl) phenoxy) piperidine (Yield=12%). $^1$H NMR (400 MHz, CD$_3$OD): δ 7.37-7.31 (m, 4H), 7.10-7.04 (m, 3H), 6.94-6.89 (m, 1H), 4.19-4.13 (m, 2H), 2.94 (d, J=12.0 Hz, 1H), 2.86-2.76 (m, 3H), 2.41-2.31 (m, 2H), 2.08-2.00 (m, 1H), 1.94-1.91 (m, 1H), 1.65-1.50 (m, 2H), 1.26 (s, 3H); ESI+MS: m/z: 398 ([M+H]$^+$).

Example-62: 1-(2-(2,5-Difluorophenoxy)ethyl)-3-methyl-3-(3-(trifluoromethyl) phenoxy)piperidine

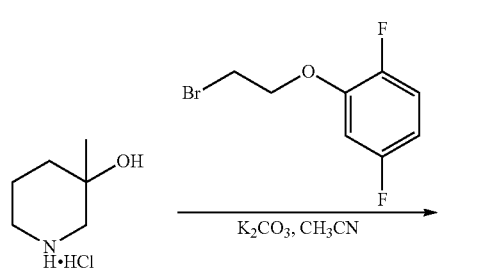

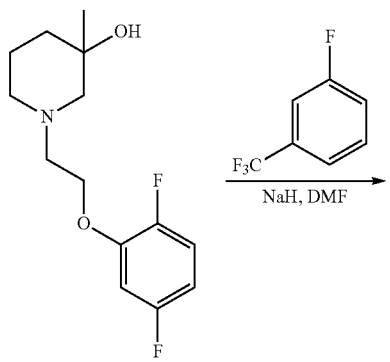

1-(2-(2,5-Difluorophenoxy)ethyl)-3-methylpiperidin-3-ol

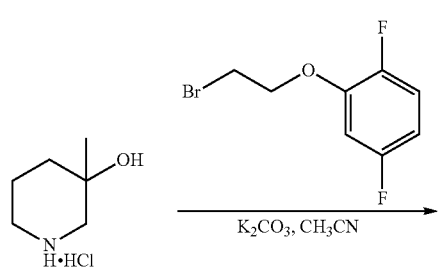

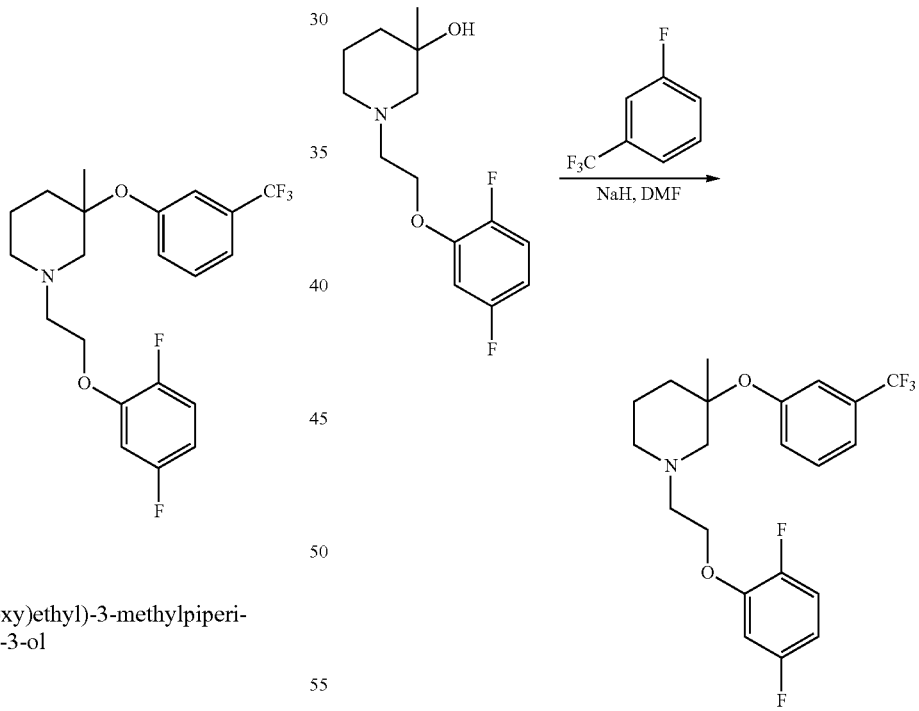

Title compound was prepared from 3-methylpiperidin-3-ol hydrochloride (0.3 g, 2.60 mmol) and 2-(2-bromoethoxy)-1,4-difluorobenzene (0.679 g, 2.87 mmol, 1.1 equiv) using the general methodology of Example-1. Purification using silica gel column chromatography (5% MeOH in $CH_2Cl_2$) to afford 0.25 g of 1-(2-(2,5-difluorophenoxy)ethyl)-3-methylpiperidin-3-ol (Yield=35.4%).

1-(2-(2,5-difluorophenoxy)ethyl)-3-methyl-3-(3-(trifluoromethyl) phenoxy)piperidine Title compound was prepared from 1-(2-(2,5-difluorophenoxy)ethyl)-3-methylpiperidin-3-ol (0.25 g, 0.92 mmol) and 1-fluoro-3-(trifluoromethyl) benzene (0.16 g, 1.02 mmol, 1.1 equiv) using the general methodology of Example-61. Purification using silica gel column chromatography (2% MeOH/$CH_2Cl_2$ as eluent) to afford 0.015 g of 1-(2-(2, 5-difluorophenoxy)ethyl)-3-methyl-3-(3-(trifluoromethyl) phenoxy)piperidine (Yield=4%). $^1$H NMR (400 MHz, $CD_3OD$): δ 7.38-7.36 (m, 2H), 7.35-7.31 (m, 2H), 7.10-7.04 (m, 1H), 6.91-6.86 (m, 1H), 6.66-6.60 (m, 1H), 4.17-4.11

(m, 2H), 2.93-2.76 (m, 4H), 2.40-2.30 (m, 2H), 2.08-2.01 (m, 1H), 1.99-1.90 (m, 1H), 1.64-1.51 (m, 2H), 1.29 (s, 3H); ESI+MS: m/z: 416 ([M+H]$^+$).

Example-63: 1-(2-(2-Chlorophenoxy)ethyl)-3-methyl-3-(3-(trifluoromethyl) phenoxy) piperidine

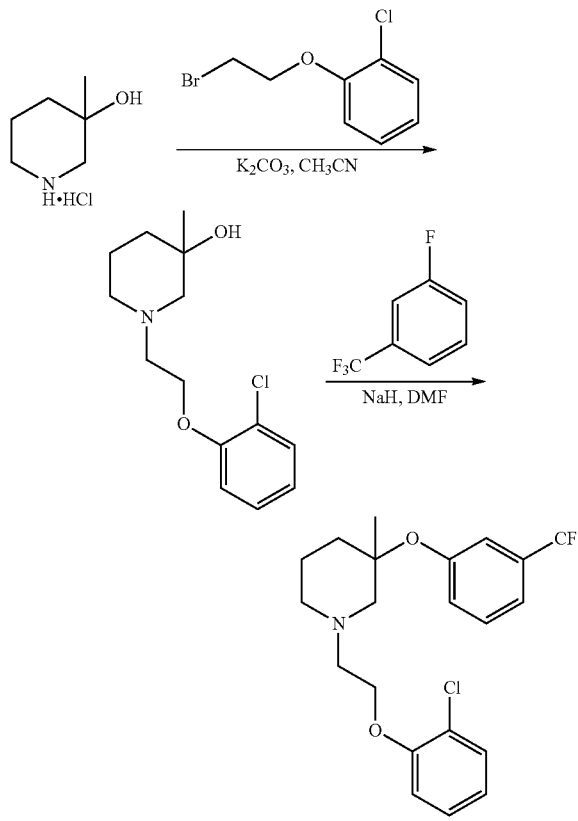

1-(2-(2-Chlorophenoxy)ethyl)-3-methylpiperidin-3-ol

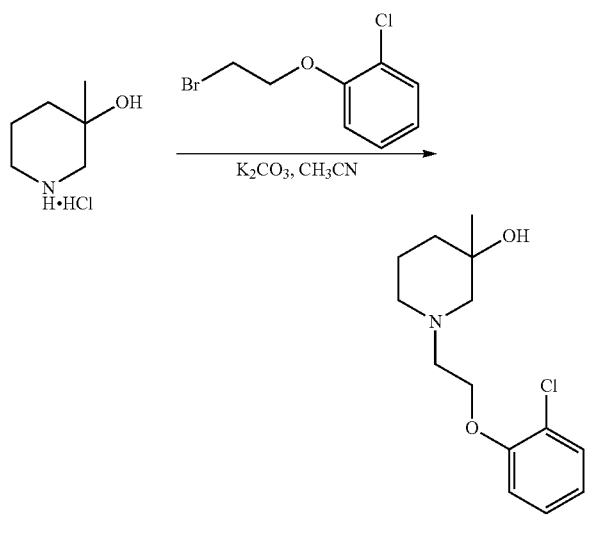

Title compound was prepared from 3-methylpiperidin-3-ol hydrochloride (0.3 g, 2.60 mmol) and 1-(2-bromoethoxy)-2-chlorobenzene (0.675 g, 2.87 mmol, 1.1 equiv) using the general methodology of Example-1. Purification using silica gel column chromatography (5% MeOH in CH$_2$Cl$_2$ as eluent) to afford 0.35 g of 1-(2-(2-chlorophenoxy)ethyl)-3-methylpiperidin-3-ol (Yield=50%).

1-(2-(2-Chlorophenoxy)ethyl)-3-methyl-3-(3-(trifluoromethyl)phenoxy)piperidine

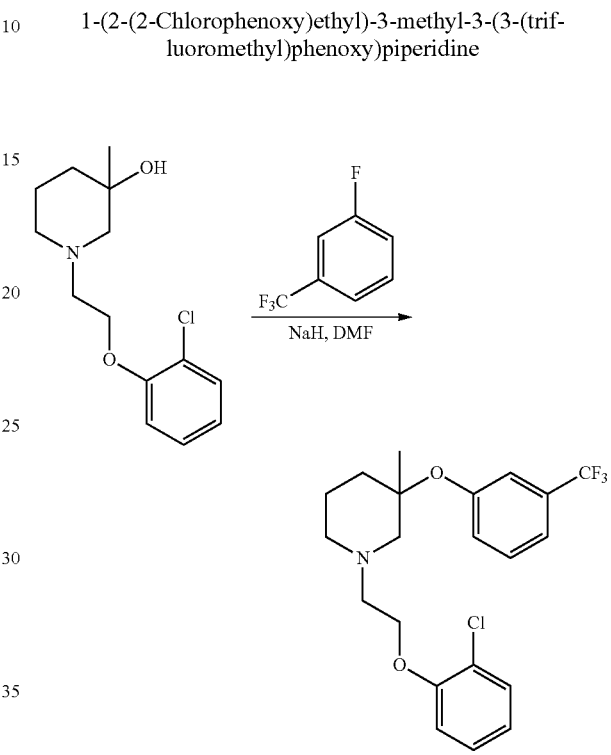

Title compound was prepared from 1-(2-(2-chlorophenoxy)ethyl)-3-methylpiperidin-3-ol (0.35 g, 1.29 mmol) and 1-fluoro-3-(trifluoromethyl)benzene (0.23 g, 1.42 mmol, 1.1 equiv) using the general methodology of Example-61. Purification using silica gel and further purified by preparative HPLC to afford 0.02 g of 1-(2-(2-chlorophenoxy)ethyl)-3-methyl-3-(3-(trifluoromethyl)phenoxy)piperidine (Yield=4%). $^1$H NMR (400 MHz, CD$_3$OD): δ 7.36-7.29 (m, 5H), 7.27-7.22 (m, 1H), 7.03 (d, J=8.4 Hz, 1H), 6.91 (t, J=7.6 Hz, 1H), 4.21-4.12 (m, 2H), 3.06-3.03 (m, 1H), 2.91-2.80 (m, 3H), 2.44-2.34 (m, 2H), 2.08-1.91 (m, 2H), 1.65-1.49 (m, 2H), 1.29 (s, 3H); ESI+MS: m/z: 414 ([M+H]$^+$).

Example-64: 1-(2-(2-fluorophenoxy)ethyl)-3-methyl-3-(3-(trifluoromethyl) phenoxy) pyrrolidine

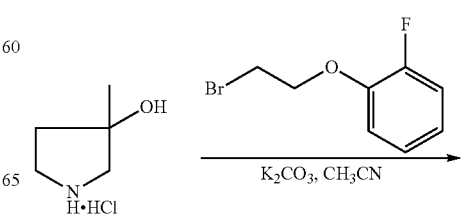

196

1-(2-(2-Fluorophenoxy)ethyl)-3-methyl-3-(3-(trifluoromethyl) phenoxy)pyrrolidine

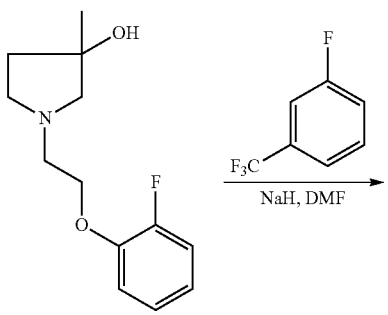

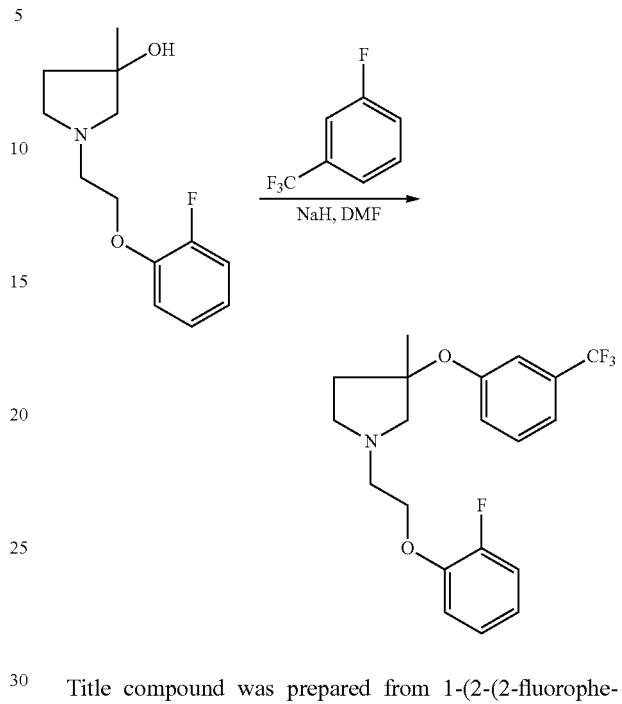

Title compound was prepared from 1-(2-(2-fluorophenoxy)ethyl)-3-methylpyrrolidin-3-ol (0.38 g, 1.58 mmol) and 3-fluoro benzotrifluoride (0.28 g, 1.74 mmol, 1.1 equiv) using the general methodology of Example-61. Purification using silica gel column chromatography and further purified by preparative HPLC to afford 0.06 g of 1-(2-(2-fluorophenoxy)ethyl)-3-methyl-3-(3-(trifluoromethyl)phenoxy)pyrrolidine (Yield=9%). $^1$H NMR (500 MHz, CD$_3$OD): δ 7.45 (t, J=8.0 Hz, 1H), 7.27-7.21 (m, 3H), 7.12-7.08 (m, 3H), 6.95-6.93 (m, 1H), 4.22 (t, J=5.5 Hz, 2H), 3.05-2.97 (m, 3H), 2.86-2.81 (m, 3H), 2.42-2.39 (m, 1H), 2.08-2.05 (m, 1H), 1.58 (s, 3H); ESI+MS: m/z: 384 ([M+H]$^+$).

Example-65: 1-(2-(2-Chlorophenoxy)ethyl)-3-methyl-3-(3-(trifluoromethyl) phenoxy) pyrrolidine 1-(2-(2-Fluorophenoxy)ethyl)-3-methylpyrrolidin-3-ol

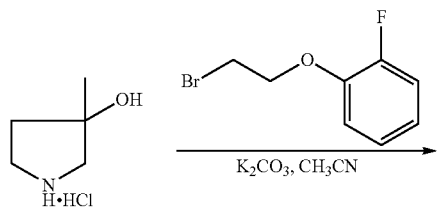

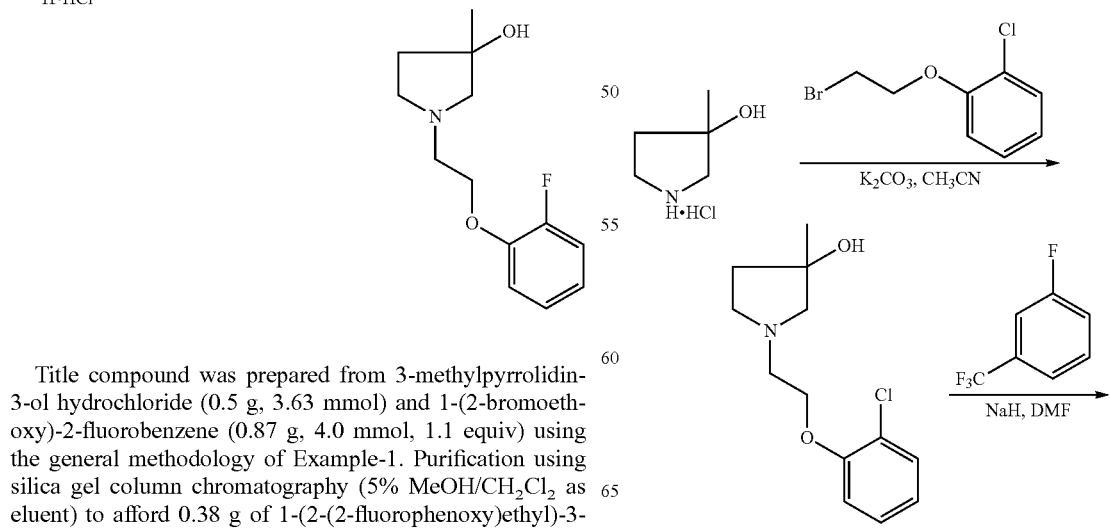

Title compound was prepared from 3-methylpyrrolidin-3-ol hydrochloride (0.5 g, 3.63 mmol) and 1-(2-bromoethoxy)-2-fluorobenzene (0.87 g, 4.0 mmol, 1.1 equiv) using the general methodology of Example-1. Purification using silica gel column chromatography (5% MeOH/CH$_2$Cl$_2$ as eluent) to afford 0.38 g of 1-(2-(2-fluorophenoxy)ethyl)-3-methylpyrrolidin-3-ol (Yield=44%).

197

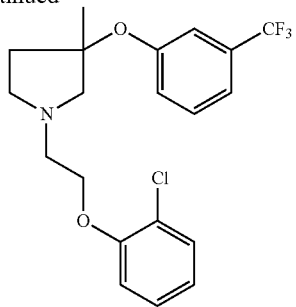

1-(2-(2-Chlorophenoxy)ethyl)-3-methylpyrrolidin-3-ol

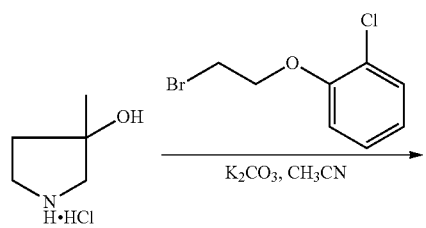

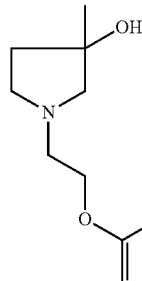

Title compound was prepared from 3-methylpyrrolidin-3-ol hydrochloride (0.5 g, 3.63 mmol) and 1-(2-bromoethoxy)-2-chlorobenzene (0.94 g, 4.0 mmol, 1.1 equiv) using the general methodology of Example-1. Purification using silica gel column chromatography (5% MeOH/CH₂Cl₂ as eluent) to afford 0.5 g of 1-(2-(2-chlorophenoxy)ethyl)-3-methylpyrrolidin-3-ol (Yield=54%).

1-(2-(2-chlorophenoxy)ethyl)-3-methyl-3-(3-(trifluoromethyl) phenoxy) pyrrolidine

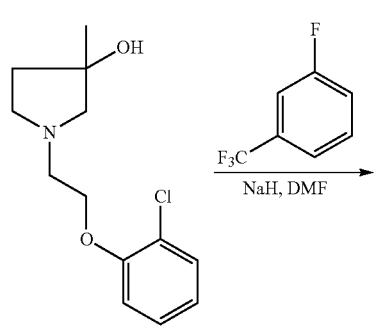

198

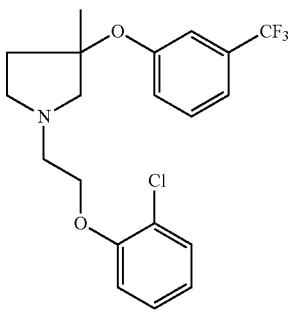

Title compound was prepared from 1-(2-(2-chlorophenoxy)ethyl)-3-methylpyrrolidin-3-ol (0.5 g, 1.95 mmol) and 3-fluoro benzotrifluoride (0.35 g, 2.15 mmol, 1.1 equiv) using the general methodology of Example-61. Purification using silica gel column chromatography (2% MeOH/CH₂Cl₂ as eluent) to afford 0.12 g of 1-(2-(2-chlorophenoxy)ethyl)-3-methyl-3-(3-(trifluoromethyl)phenoxy)pyrrolidine (Yield=14%). $^1$H NMR (400 MHz, CD$_3$OD): δ 7.42 (t, J=8.0 Hz, 1H), 7.35 (dd, J=8.0, 1.6 Hz, 1H), 7.27-7.20 (m, 4H), 7.06 (d, J=8.0 Hz, 1H), 6.92 (t, J=7.6 Hz, 1H), 4.21 (t, J=5.2 Hz, 2H), 3.38-3.35 (m, 1H), 3.09-2.96 (m, 3H), 2.90-2.80 (m, 2H), 2.42-2.35 (m, 1H), 2.08-2.01 (m, 1H), 1.57 (s, 3H); ESI+MS: m/z: 400 ([M+H]$^+$).

Example-66: 1-(2-(2,5-difluorophenoxy)ethyl)-3-methyl-3-(3-(trifluoromethyl) phenoxy)pyrrolidine

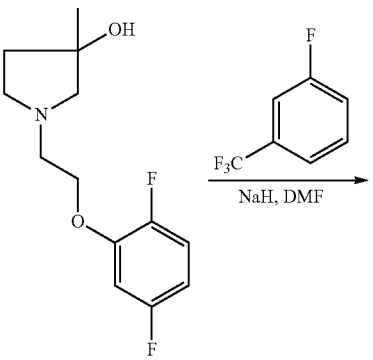

199

-continued

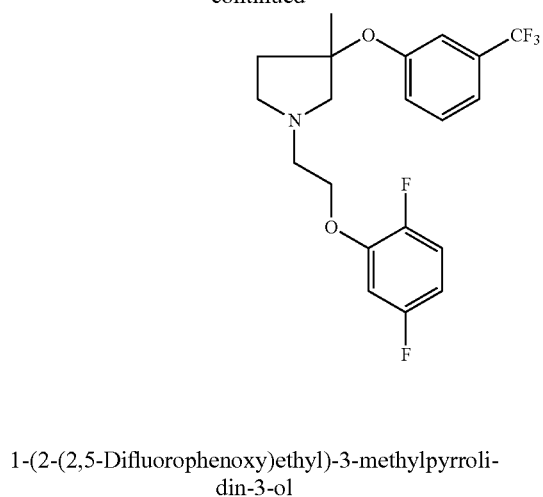

1-(2-(2,5-Difluorophenoxy)ethyl)-3-methylpyrrolidin-3-ol

200

1-(2-(2,5-difluorophenoxy)ethyl)-3-methyl-3-(3-(trifluoromethyl) phenoxy) pyrrolidine

Title compound was prepared from 1-(2-(2,5-difluorophenoxy)ethyl)-3-methylpyrrolidin-3-ol (0.2 g, 0.77 mmol) and 1-fluoro-3-(trifluoromethyl)benzene (0.14 g, 0.85 mmol, 1.1 equiv) using the general methodology of Example-61. Purification using silica gel column chromatography and further purified by preparative HPLC to afford 1-(2-(2, 5-difluorophenoxy)ethyl)-3-methyl-3-(3-(trifluoromethyl)phenoxy) pyrrolidine (Yield=0.06 g, 18%). $^1$H NMR (500 MHz, DMSO-$d_6$): δ 7.47 (t, J=8.5 Hz, 1H), 7.30-7.20 (m, 4H), 7.15-7.11 (m, 1H), 6.76-6.72 (m, 1H), 4.15 (t, J=6.0 Hz, 2H), 3.07 (d, J=10.0 Hz, 1H), 2.88-2.78 (m, 3H), 2.73-2.63 (m, 2H), 2.24-2.19 (m, 1H), 1.99-1.94 (m, 1H), 1.49 (s, 3H); ESI+MS: m/z: 402 ([M+H]$^+$).

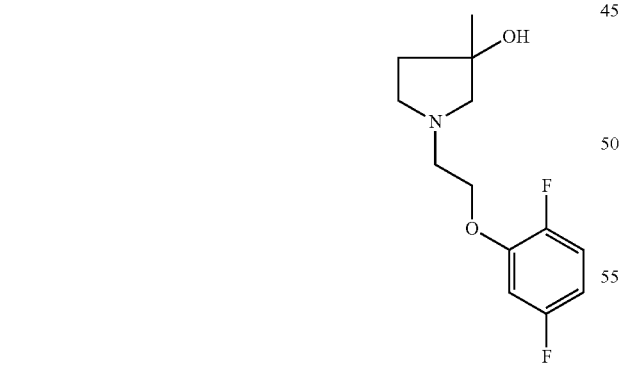

Title compound was prepared from 3-methylpyrrolidin-3-ol hydrochloride (0.5 g, 3.63 mmol) and 2-(2-bromoethoxy)-1,4-difluorobenzene (0.94 g, 4.0 mmol, 1.1 equiv) using the general methodology of Example-1. Purification using silica gel column chromatography (5% MeOH in CH$_2$Cl$_2$ as eluent) to afford 0.5 g of 1-(2-(2,5-difluorophenoxy)ethyl)-3-methylpyrrolidin-3-ol (Yield=53%).

Example-67: 4-methyl-4-phenoxy-1-(2-(3-(trifluoromethyl)phenoxy)ethyl)piperidine

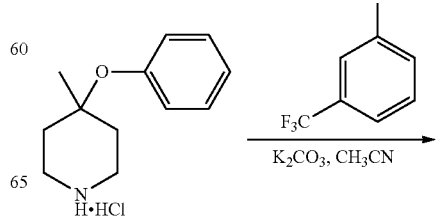

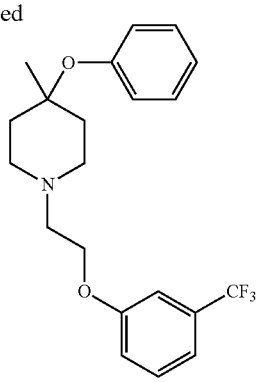

Title compound was prepared from 4-methyl-4-phenoxypiperidine hydrochloride (0.15 g, 0.65 mmol) and 1-(2-bromoethoxy)-3-(trifluoromethyl)benzene (0.17 g, 0.65 mmol) using the general methodology of Example-1. Purification using silica gel column chromatography (2% MeOH/CH$_2$Cl$_2$ as eluent) to afford 0.11 g of 4-methyl-4-phenoxy-1-(2-(3-(trifluoromethyl)phenoxy)ethyl)piperidine (Yield=43%). $^1$H NMR (400 MHz, CD$_3$OD): δ 7.47 (t, J=8.0 Hz, 1H), 7.28-7.20 (m, 5H), 7.06-6.99 (m, 3H), 4.22 (t, J=5.6 Hz, 2H), 2.92 (t, J=5.6 Hz, 2H), 2.78 (s, 4H), 2.03 (d, J=12.8 Hz, 2H), 1.79-1.72 (m, 2H), 1.28 (s, 3H); ESI+MS: m/z 380 ([M+H]$^+$).

Example-68: 1-(2-Bromoethoxy)-4-(trifluoromethyl)benzene

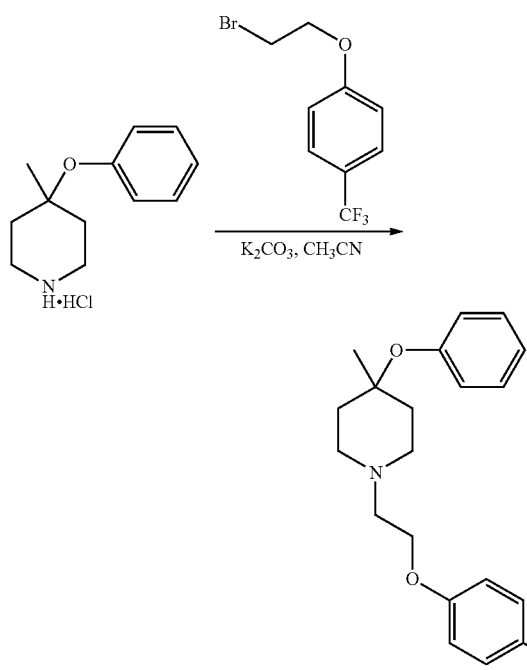

Title compound was prepared from 4-methyl-4-phenoxypiperidine hydrochloride (0.15 g, 0.659 mmol) and 1-(2-bromoethoxy)-4-(trifluoromethyl)benzene (0.177 g, 0.659 mmol, 1 equiv) using the general methodology of Example-1. Purification using silica gel column chromatography (2% MeOH/CH$_2$Cl$_2$ as eluent) to afford 0.52 g of 1-(2-bromoethoxy)-4-(trifluoromethyl)benzene (Yield=53%). $^1$H NMR (500 MHz, CD$_3$OD): δ 7.60 (d, J=8.5 Hz, 2H), 7.28 (t, J=15.5 Hz, 2H), 7.12-7.01 (m, 5H), 4.25 (t, J=5.5 Hz, 2H), 2.95-2.94 (m, 2H), 2.82-2.80 (m, 4H), 2.07-2.04 (m, 2H), 1.80-1.74 (m, 2H), 1.30 (s, 3H); ESI+MS: m/z 380 ([M+H]$^+$).

Example-69: 4-methyl-4-phenoxy-1-(2-(o-tolyloxy)ethyl)piperidine

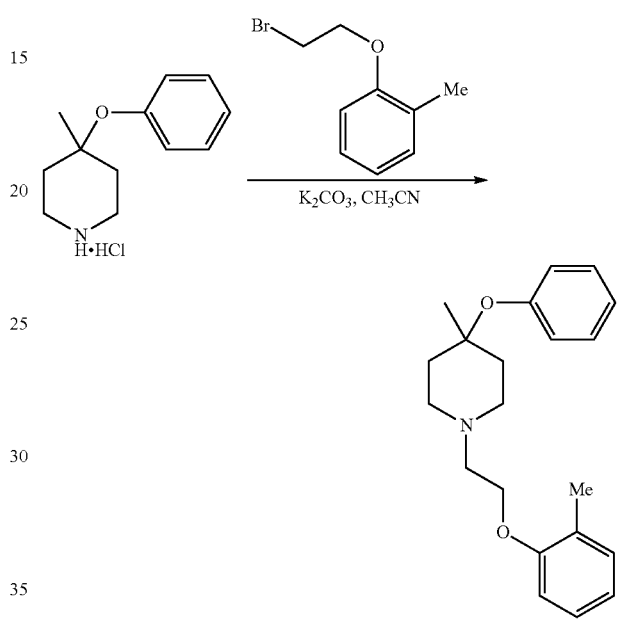

Title compound was prepared from 4-methyl-4-phenoxypiperidine hydrochloride (0.1 g, 0.439 mmol) and 1-(2-bromoethoxy)-2-methylbenzene (0.094 g, 0.439 mmol, 1 equiv) using the general methodology of Example-1. Purification using silica gel column chromatography (2% MeOH/CH$_2$Cl$_2$ as eluent) to afford 0.1 g of 4-methyl-4-phenoxy-1-(2-(o-tolyloxy)ethyl)piperidine (Yield=68%). $^1$H NMR (400 MHz, CD$_3$OD): δ 7.28-7.24 (m, 2H), 7.14-7.10 (m, 2H), 7.03-6.99 (m, 3H), 6.89 (d, J=8.0 Hz, 1H), 6.83 (t, J=7.6 Hz, 1H), 4.18 (t, J=5.6 Hz, 2H), 2.99-2.96 (m, 2H), 2.87-2.85 (m, 4H), 2.20 (s, 3H), 2.07-2.02 (m, 2H), 1.80-1.71 (m, 2H), 1.29 (s, 3H); ESI+MS: m/z 326 ([M+H]$^+$).

Example-70: 1-(2-(2-Ethylphenoxy)ethyl)-4-methyl-4-phenoxypiperidine

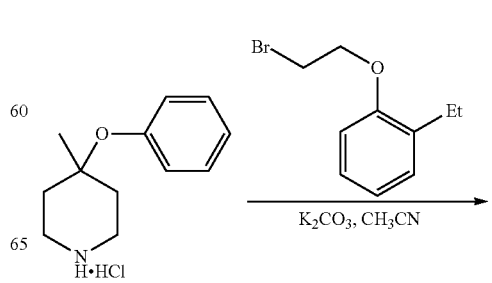

-continued

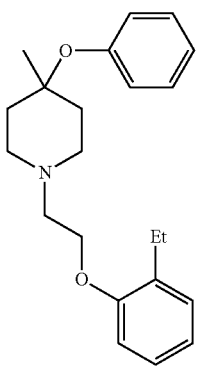

Title compound was prepared from 4-methyl-4-phenoxypiperidine hydrochloride (0.2 g, 0.87 mmol) and 1-(2-bromoethoxy)-2-ethylbenzene (0.2 g, 0.87 mmol, 1.0 equiv) using the general methodology of Example-1. Purification using silica gel column chromatography (2% MeOH/CH$_2$Cl$_2$ as eluent) to afford 0.08 g of 1-(2-(2-ethylphenoxy)ethyl)-4-methyl-4-phenoxypiperidine (Yield=26%). $^1$H NMR (400 MHz, CD$_3$OD): δ 7.26 (t, J=7.6 Hz, 2H), 7.13-7.11 (m, 2H), 7.07-6.99 (m, 3H), 6.92-6.84 (m, 2H), 4.18 (t, J=5.6 Hz, 2H), 2.96 (t, J=5.2 Hz, 2H), 2.86-2.84 (m, 4H), 2.66-2.61 (m, 2H), 2.06-2.02 (m, 2H), 1.79-1.70 (m, 2H), 1.29 (s, 3H), 1.16 (t, 3H, J=7.6 Hz); ESI+MS: m/z: 340 ([M+H]$^+$).

Example-71: 1-(2-(2-isopropylphenoxy)ethyl)-4-methyl-4-phenoxypiperidine

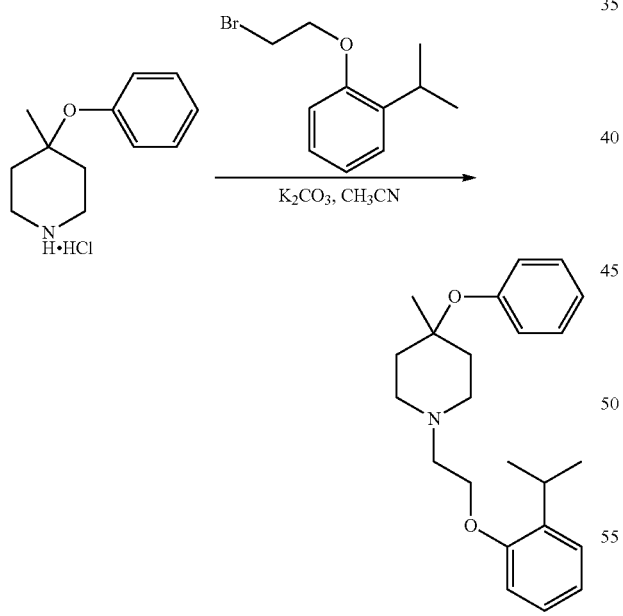

Title compound was prepared from 4-methyl-4-phenoxypiperidine hydrochloride (0.15 g, 0.65 mmol) and 1-(2-bromoethoxy)-2-isopropylbenzene (0.16 g, 0.65 mmol, 1.0 equiv) using the general methodology of Example-1. Purification using silica gel column chromatography (2% MeOH in CH$_2$Cl$_2$ as eluent) to afford 0.12 g 1-(2-(2-isopropylphenoxy)ethyl)-4-methyl-4-phenoxypiperidine (Yield=51%). $^1$H NMR (400 MHz, CD$_3$OD): δ 7.28-7.24 (m, 2H), 7.19 (d, J=7.2 Hz, 1H), 7.13 (t, J=7.2 Hz, 1H), 7.07-7.03 (m, 1H), 7.01-6.99 (m, 2H), 6.92-6.87 (m, 2H), 4.17 (t, J=5.6 Hz, 2H), 3.40-3.30 (m, 1H), 2.95 (t, J=5.6 Hz, 2H), 2.84-2.81 (m, 4H), 2.06-2.01 (m, 2H), 1.78-1.71 (m, 2H), 1.29 (s, 3H), 1.19 (d, J=6.8 Hz, 6H); ESI+MS: m/z 354 [M+H]$^+$.

Example-72: 1-(2-(2-Methoxyphenoxy)ethyl)-4-methyl-4-phenoxypiperidine

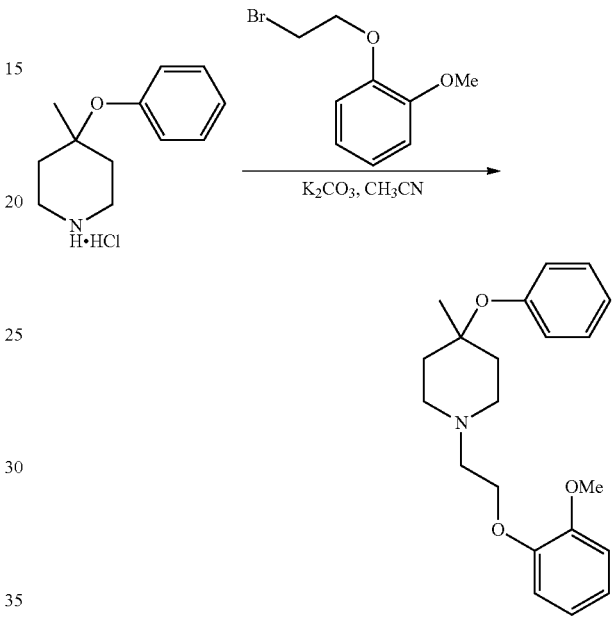

Title compound was prepared from 4-methyl-4-phenoxypiperidine hydrochloride (0.1 g, 0.439 mmol) and 1-(2-bromoethoxy)-2-methoxybenzene (0.1 g, 0.43 mmol, 1.0 equiv) using the general methodology of Example-1. Purification using silica gel column chromatography 2% MeOH in CH$_2$Cl$_2$ as eluent) to afford 0.11 g of 1-(2-(2-methoxyphenoxy)ethyl)-4-methyl-4-phenoxypiperidine (Yield=73%). $^1$H NMR (400 MHz, CD$_3$OD): δ 7.29-7.24 (m, 2H), 7.07-6.86 (m, 7H), 4.18 (t, J=5.6 Hz, 2H), 3.82 (s, 3H), 2.98-2.95 (m, 2H), 2.88-2.86 (m, 4H), 2.06-2.03 (m, 2H), 1.80-1.73 (m, 2H), 1.29 (s, 3H); ESI+MS: m/z 342 ([M+H]$^+$).

Example-73: 2-(2-(4-methyl-4-phenoxypiperidin-1-yl)ethoxy)pyridine

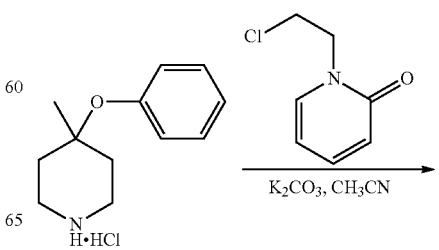

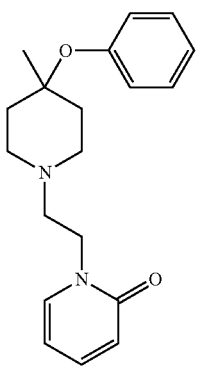

Title compound was prepared from 4-methyl-4-phenoxypiperidine hydrochloride (0.1 g, 0.43 mmol) and 1-(2-chloroethyl)pyridin-2(1H)-one (0.07 g, 0.48 mmol, 1.1 equiv) using the general methodology of Example-1. Purification using silica gel column chromatography (5% MeOH/CH₂Cl₂ as eluent) to afford 0.08 g of 1-(2-(4-methyl-4-phenoxypiperidin-1-yl)ethyl)pyridin-2(1H)-one (Yield=58%). $^1$H NMR (400 MHz, CD$_3$OD): δ 7.65-7.63 (m, 1H), 7.54-7.49 (m, 1H), 7.28-7.23 (m, 2H), 7.06-6.97 (m, 3H), 6.55-6.52 (m, 1H), 6.37 (dt, J=8.0, 1.2 Hz, 1H), 4.15 (t, J=6.8 Hz, 2H), 2.77-2.66 (m, 6H), 2.01-1.96 (m, 2H), 1.72-1.65 (m, 2H), 1.26 (s, 3H); ESI+MS: m/z 313 ([M+H]$^+$).

Example-74: 4-Methyl-1-(2-(naphthalen-2-yloxy)ethyl)-4-phenoxypiperidine

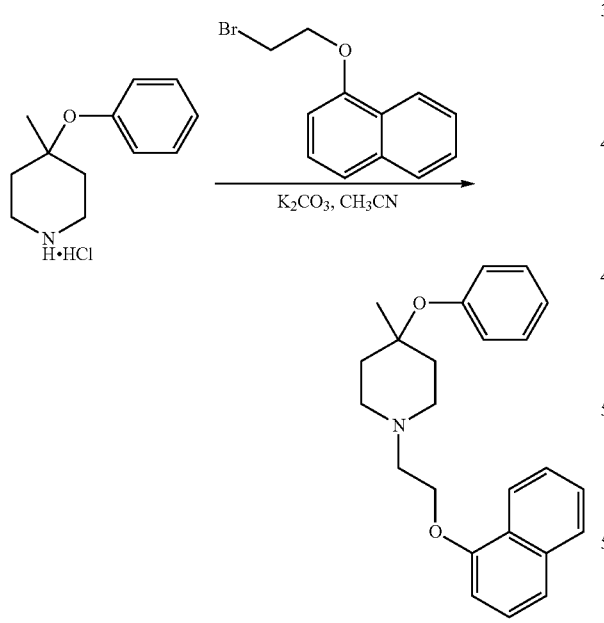

Title compound was prepared from 4-methyl-4-phenoxypiperidine hydrochloride (0.15 g, 0.65 mmol) using the general methodology of Example-1. Purification using silica gel column chromatography (2% MeOH/CH₂Cl₂ as eluent) to afford 0.12 g of 4-methyl-1-(2-(naphthalen-2-yloxy)ethyl)-4-phenoxypiperidine (Yield=48%). $^1$H NMR (400 MHz, CD$_3$OD): δ 8.25 (dd, J=8.0, 4.0 Hz, 1H), 7.80-7.78 (m, 1H), 7.49-7.35 (m, 4H), 7.28-7.23 (m, 2H), 7.06-6.99 (m, 3H), 6.94-6.92 (m, 1H), 4.37 (t, J=5.6 Hz, 2H), 3.11 (t, J=5.2 Hz, 2H), 2.96-2.87 (m, 4H), 2.09-2.04 (m, 2H), 1.81-1.71 (m, 2H), 1.29 (s, 3H); ESI+MS: m/z 362 [(M+H]$^+$).

Example-75: 1-(2-(4-Fluoro-2-(trifluoromethyl)phenoxy)ethyl)-4-methyl-4-phenoxy piperidine

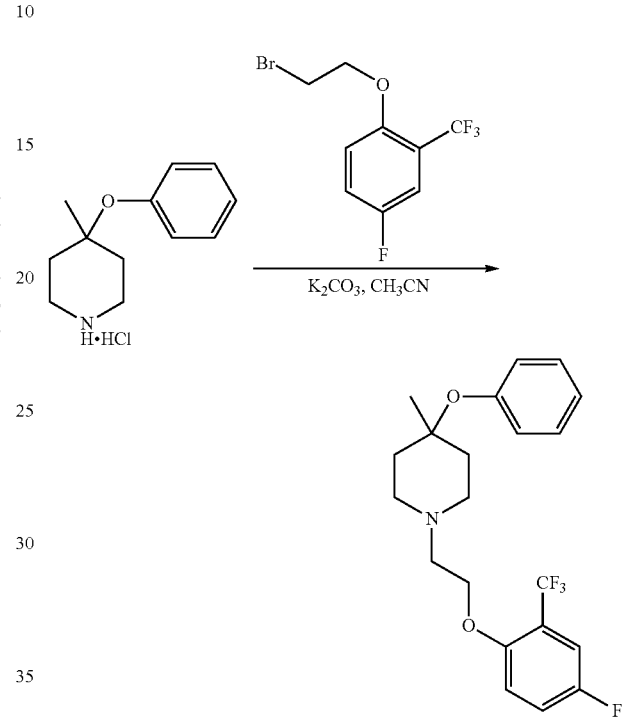

Title compound was prepared from 4-methyl-4-phenoxypiperidine hydrochloride (0.1 g, 0.43 mmol) using the general methodology of Example-1. Purification using silica gel column chromatography (2% MeOH/CH₂Cl₂ as eluent) to afford 0.08 g of 1-(2-(4-fluoro-2-(trifluoromethyl)phenoxy)ethyl)-4-methyl-4-phenoxypiperidine (Yield=45%).

$^1$H NMR (400 MHz, CD$_3$OD): δ 7.37-7.31 (m, 2H), 7.28-7.20 (m, 3H), 7.07-7.03 (m, 1H), 7.01-6.98 (m, 2H), 4.26 (t, J=5.6 Hz, 2H), 2.95 (t, J=5.2 Hz, 2H), 2.86-2.80 (m, 4H), 2.04-1.99 (m, 2H), 1.77-1.70 (m, 2H), 1.28 (s, 3H); ESI+MS: m/z 398 [(M+H)$^+$].

Example-76: 1-(2-(5-fluoro-2-(trifluoromethyl)phenoxy)ethyl)-4-methyl-4-phenoxypiperidine

-continued

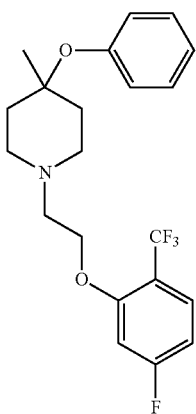

Title compound was prepared from 4-methyl-4-phenoxypiperidine hydrochloride (0.1 g, 0.43 mmol) using the general methodology of Example-1. Purification using silica gel column chromatography (2% MeOH/CH$_2$Cl$_2$ as eluent) to afford 0.07 g of 1-(2-(5-fluoro-2-(trifluoromethyl)phenoxy)ethyl)-4-methyl-4-phenoxypiperidine (Yield=37%). $^1$H NMR (400 MHz, CD$_3$OD): δ 7.62-7.58 (m, 1H), 7.27-7.23 (m, 2H), 7.06-6.97 (m, 4H), 6.81-6.76 (m, 1H), 4.25 (t, J=5.2 Hz, 2H), 2.93 (t, J=5.6 Hz, 2H), 2.84-2.74 (m, 4H), 2.03-1.98 (m, 2H), 1.75-1.68 (m, 2H), 1.26 (s, 3H); ESI+MS: m/z 398 ([M+H]$^+$).

Example-77: 1-(2-(4-methyl-4-phenoxypiperidin-1-yl)ethyl)-3-(trifluoromethyl) pyridin-2(1H)-one

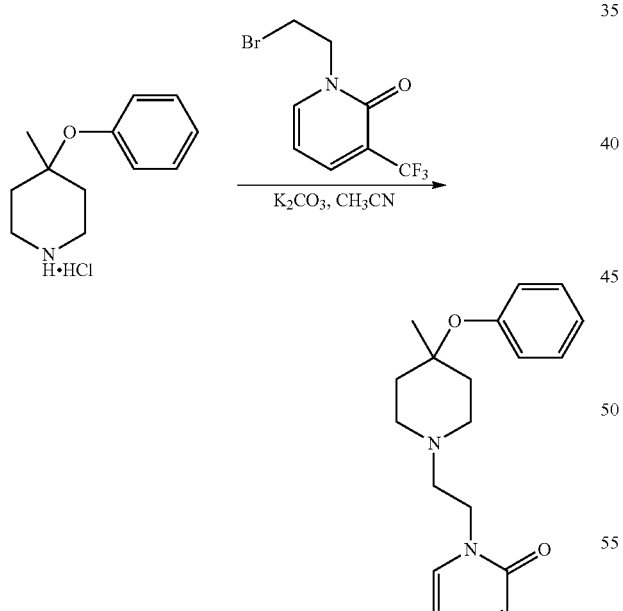

Title compound was prepared from 4-methyl-4-phenoxypiperidine hydrochloride (0.1 g, 0.43 mmol) and 1-(2-bromoethyl)-3-(trifluoromethyl)pyridin-2(1H)-one (0.17 g, 0.65 mmol, 1.5 equiv) using the general methodology of Example-1. Purification using silica gel column chromatography (2% MeOH/CH$_2$Cl$_2$ as eluent) to afford 0.04 g of 1-(2-(4-methyl-4-phenoxypiperidin-1-yl)ethyl)-3-(trifluoromethyl) pyridin-2(1H)-one (Yield=23%). $^1$H NMR (400 MHz, CD$_3$OD): δ 7.91 (t, J=6.4 Hz, 2H), 7.25 (t, J=7.6 Hz, 2H), 7.06-6.98 (m, 3H), 6.44-6.41 (m, 1H), 4.18 (t, J=6.4 Hz, 2H), 2.76-2.63 (m, 6H), 1.99-1.96 (m, 2H), 1.70-1.63 (m, 2H), 1.26 (s, 3H); ESI+MS: m/z 381 ([M+H]$^+$).

Example-78: 3-Methyl-3-phenoxy-8-(2-(2-(trifluoromethyl)phenoxy)ethyl)-8-azabicyclo[3.2.1]octane

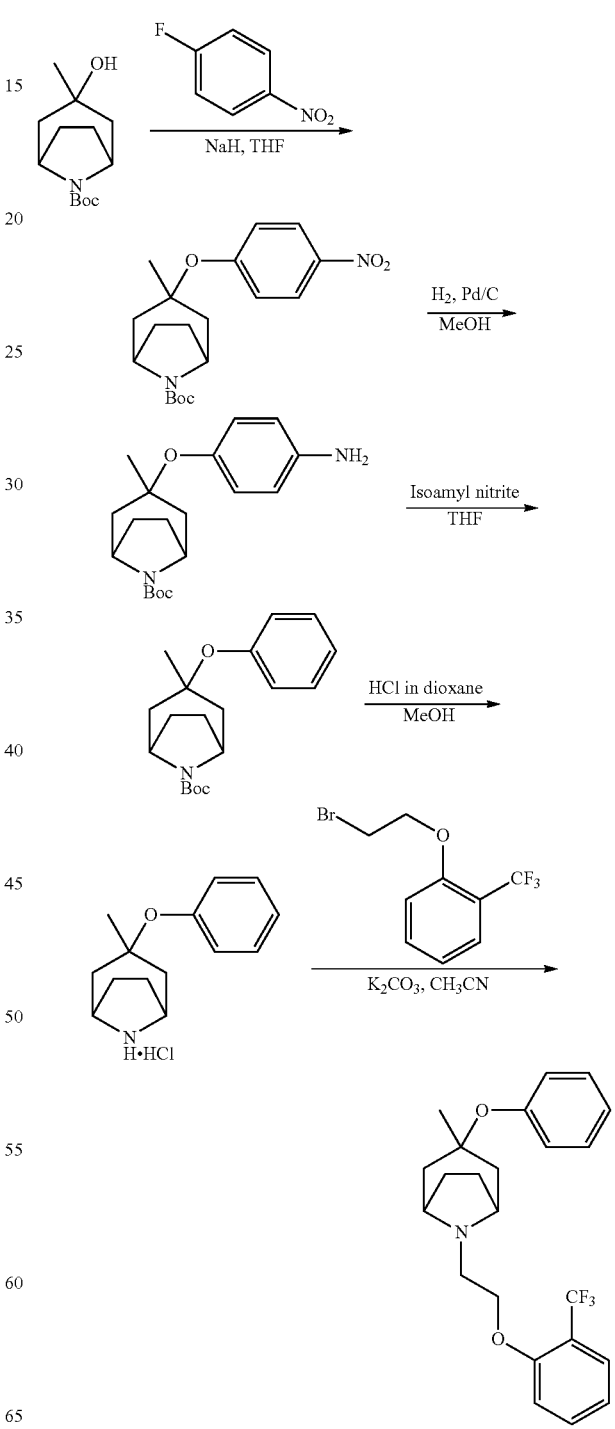

tert-butyl 3-methyl-3-(4-nitrophenoxy)-8-azabicyclo[3.2.1]octane-8-carboxylate

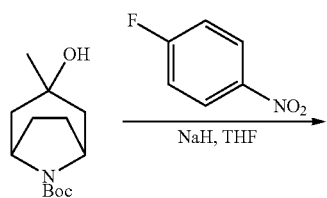

Title compound was prepared from tert-butyl (1R,5S)-3-hydroxy-3-methyl-8-azabicyclo[3.2.1]octane-8-carboxylate (0.9 g, 3.73 mmol) using the general methodology of step 2 of key intermediate-I at 80° C. 16 h. Purification using silica gel column chromatography (10% EtOAc/Hexanes as eluent) to afford 0.8 g of tert-butyl 3-methyl-3-(4-nitrophenoxy)-8-azabicyclo[3.2.1]octane-8-carboxylate (Yield=59%).

tert-butyl (1R,5S)-3-(4-aminophenoxy)-3-methyl-8-azabicyclo[3.2.1]octane-8-carboxylate

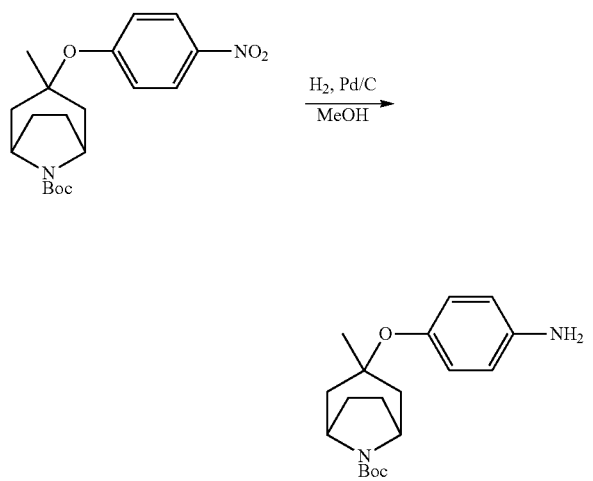

Title compound was prepared from tert-butyl 3-methyl-3-(4-nitrophenoxy)-8-azabicyclo[3.2.1]octane-8-carboxylate (0.8 g, 2.2 mmol) using general methodology of step 3 of key intermediate-I at 80° C. for 16 h. Purification using silica gel column chromatography (15% EtOAc in Hexane as eluent) to afford 0.5 g of tert-butyl (1R,5S)-3-(4-aminophenoxy)-3-methyl-8-azabicyclo[3.2.1]octane-8-carboxylate (Yield=68%).

tert-butyl (1R,5S)-3-methyl-3-phenoxy-8-azabicyclo[3.2.1]octane-8-carboxylate

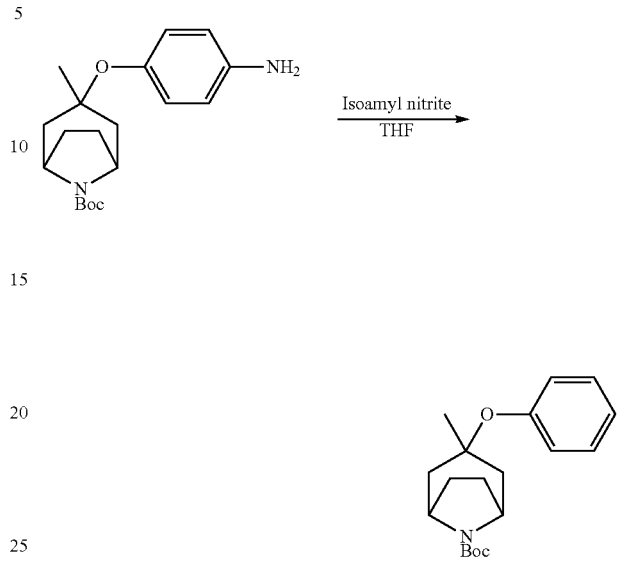

Title compound was prepared from tert-butyl (1R,5S)-3-(4-aminophenoxy)-3-methyl-8-azabicyclo[3.2.1]octane-8-carboxylate (0.5 g, 1.5 mmol) using the general methodology of step 1 of key intermediate-VI at 80° C. for 3 h. Purification using silica gel column chromatography (5% EtOAc in Hexane as eluent) to afford 0.3 g of tert-butyl (1R,5S)-3-methyl-3-phenoxy-8-azabicyclo[3.2.1]octane-8-carboxylate (Yield=62%).

(1R,5S)-3-methyl-3-phenoxy-8-azabicyclo[3.2.1]octane hydrochloride

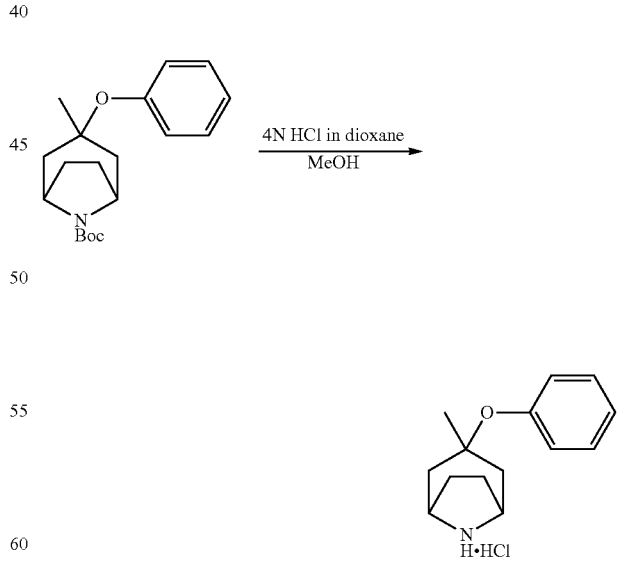

Title compound was prepared from tert-butyl (1R,5S)-3-methyl-3-phenoxy-8-azabicyclo[3.2.1]octane-8-carboxylate (0.3 g, 0.94 mmol) using general methodology of step 2 of key intermediate-VI to afford 0.2 g of 4-benzylpiperidin-4-ol hydrochloride (Yield=83%).

211

3-Methyl-3-phenoxy-8-(2-(2-(trifluoromethyl)phenoxy)ethyl)-8-azabicyclo[3.2.1]octane

212

Methyl 2-methyl-2-(4-methyl-phenoxypiperidin-1-yl)propanoate

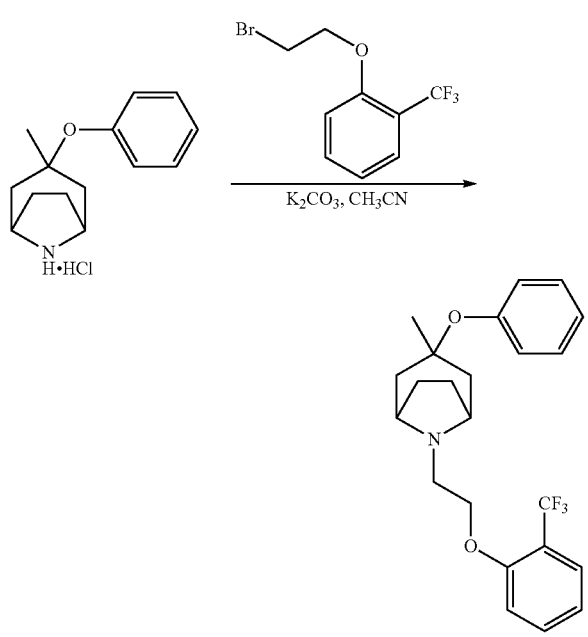

Title compound was prepared from 4-benzylpiperidin-4-ol hydrochloride (0.2 g, 0.78 mmol) using the general methodology of Example-1. Purification using silica gel column chromatography (2% MeOH in CH$_2$Cl$_2$ as eluent) to afford 0.32 g of 2-(2-(4-methyl-4-phenoxypiperidin-1-yl)ethoxy)-3-(trifluoromethyl)pyridine (Yield=39%). $^1$H NMR (400 MHz, DMSO-d$_6$): δ 7.63-7.59 (m, 2H), 7.29-7.24 (m, 3H), 7.08 (t, J=7.2 Hz, 1H), 6.96-6.94 (m, 3H), 4.19-4.17 (m, 2H), 3.28-3.26 (m, 2H), 2.73-2.70 (m, 2H), 2.13-2.09 (m, 2H), 1.97-1.95 (m, 2H), 1.80-1.77 (m, 4H), 1.23 (s, 3H); ESI+MS: m/z: 406 ([M+H]$^+$).

Example-79: 4-methyl-1-(2-methyl-1-(2-(trifluoromethyl)phenoxy)propan-2-yl)-4-phenoxypiperidine Title compound was prepared from 4-methyl-4-phenoxypiperidine hydrochloride (0.5 g, 2.19 mmol, 1 equiv) and methyl 2-bromo-2-methylpropanoate (0.43 g, 2.41 mmol, 1.1 equiv) using the general methodology of Example-1. Purification using silica gel column chromatography (2% MeOH in CH$_2$Cl$_2$ as eluent) to afford 0.4 g of 2-(2-(4-methyl-4-phenoxypiperidin-1-yl)ethoxy)-3-(trifluoromethyl)pyridine (Yield=62%).

2-methyl-2-(4-methyl-4-phenoxypiperidin-1-yl)propan-1-ol

To a stirred solution of methyl 2-methyl-2-(4-methyl-4-phenoxypiperidin-1-yl)propanoate (0.4 g, 1.37 mmol) in THF (20 mL) was added LiAlH$_4$ (0.07 mg, 2.08 mmol, 1.5 equiv) at 0° C. The reaction mixture was warmed to room temperature and stirred for 2 h. After completion, the reaction was quenched with EtOAc, Na$_2$SO$_4$ $_{(aq)}$ and extracted with EtOAc. The organic layer was dried over anhydrous Na$_2$SO$_4$ and concentrated under reduced pressure to afford 0.3 g of 2-methyl-2-(4-methyl-4-phenoxypiperidin-1-yl)propan-1-ol (Yield=78%). $^1$H NMR (400 MHz, DMSO-d$_6$): δ 7.29-7.24 (m, 2H), 7.05-7.01 (m, 1H), 6.97 (d, J=8.8 Hz, 2H), 4.14 (br s, 1H), 3.26 (s, 2H), 2.68-2.62 (m, 2H), 2.57-2.54 (m, 2H), 1.87-1.82 (m, 2H), 1.59-1.53 (m, 2H), 1.21 (s, 3H), 0.94 (s, 6H); ESI+MS: m/z: 264 ([M+H]$^+$).

213

Example-80: 4-methyl-1-(2-methyl-1-(2-(trifluoromethyl)phenoxy)propan-2-yl)-4-phenoxypiperidine

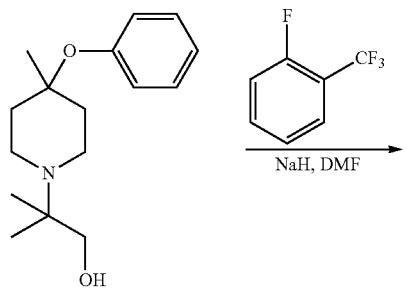

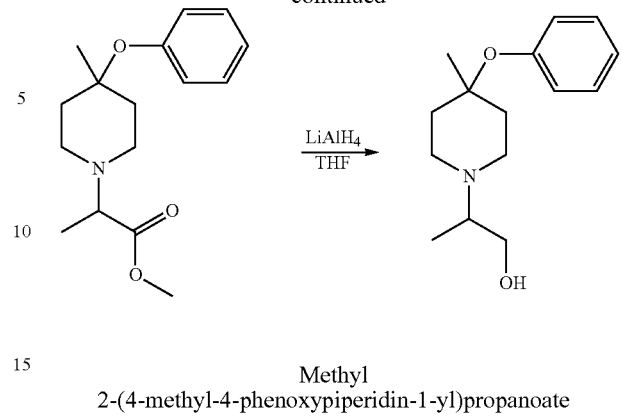

Methyl 2-(4-methyl-4-phenoxypiperidin-1-yl)propanoate

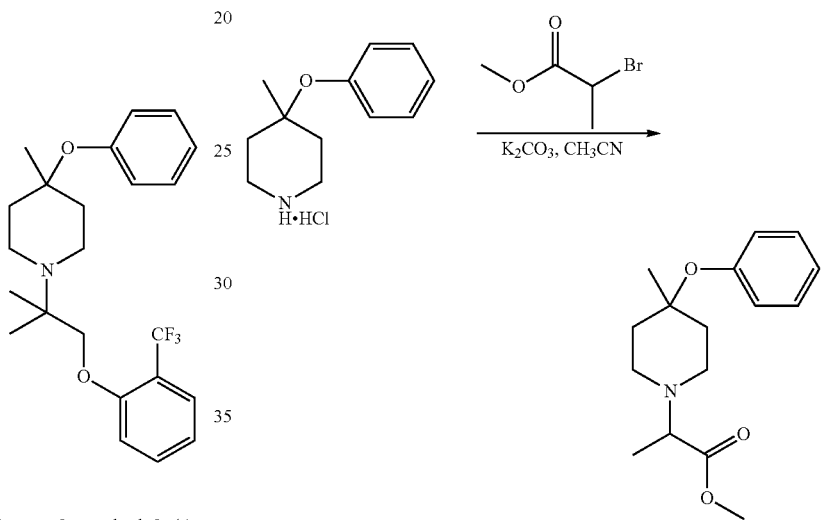

Title compound was prepared from 2-methyl-2-(4-methyl-4-phenoxypiperidin-1-yl)propan-1-ol (0.1 g, 0.38 mmol) and 1-fluoro-2-(trifluoromethyl)benzene (0.09 mg, 0.57 mmol, 1.5 equiv) using the general methodology of Example-61 and heated for 24 h. Purification using silica gel column chromatography further purified by preparative HPLC to afford 0.07 g of 4-methyl-1-(2-methyl-1-(2-(trifluoromethyl)phenoxy)propan-2-yl)-4-phenoxypiperidine (Yield=45%). $^1$H NMR (400 MHz, DMSO-d$_6$): δ 7.62-7.58 (m, 2H), 7.29-7.24 (m, 3H), 7.09-7.01 (m, 2H), 6.97-6.94 (m, 2H), 3.96 (s, 2H), 2.79-2.73 (m, 2H), 2.67-2.64 (m, 2H), 1.87-1.83 (m, 2H), 1.60-1.53 (m, 2H), 1.21 (s, 3H), 1.14 (s, 6H); ESI+MS: m/z: 408 ([M+H]$^+$).

Example-81: 2-(4-Methyl-4-phenoxypiperidin-1-yl)propan-1-ol

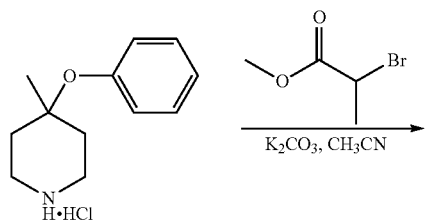

Title compound was prepared from 4-methyl-4-phenoxypiperidine hydrochloride (0.3 g, 1.31 mmol) and methyl 2-bromo-2-methylpropanoate (0.24 g, 1.44 mmol, 1.1 equiv) using the general methodology of Example-1. Purification using silica gel column chromatography (2% MeOH in CH$_2$Cl$_2$ as eluent) to afford 0.35 g of methyl 2-(4-methyl-4-phenoxypiperidin-1-yl)propanoate (Yield=96%).

2-(4-Methyl-4-phenoxypiperidin-1-yl)propan-1-ol

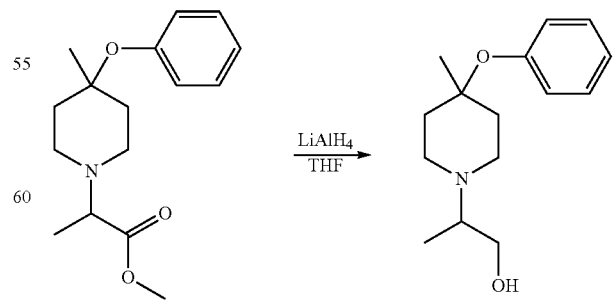

To a solution of methyl 2-(4-methyl-4-phenoxypiperidin-1-yl)propanoate (0.35 g, 1.26 mmol) in THF (10 mL) was added LiAlH₄ (0.07 mg, 1.89 mmol, 1.5 equiv) at 0° C. The reaction mixture was warmed to room temperature and stirred for 2 h. After completion, the reaction mass was quenched with EtOAc and aq. Na₂SO₄ and extracted with EtOAc. The organic layer was dried over anhydrous Na₂SO₄ and concentrated under reduced pressure to afford 0.25 g of 2-(4-methyl-4-phenoxypiperidin-1-yl)propan-1-ol (Yield=79%).

Example-82: 4-Methyl-4-phenoxy-1-(1-(2-(trifluoromethyl)phenoxy)propan-2-yl)piperidine

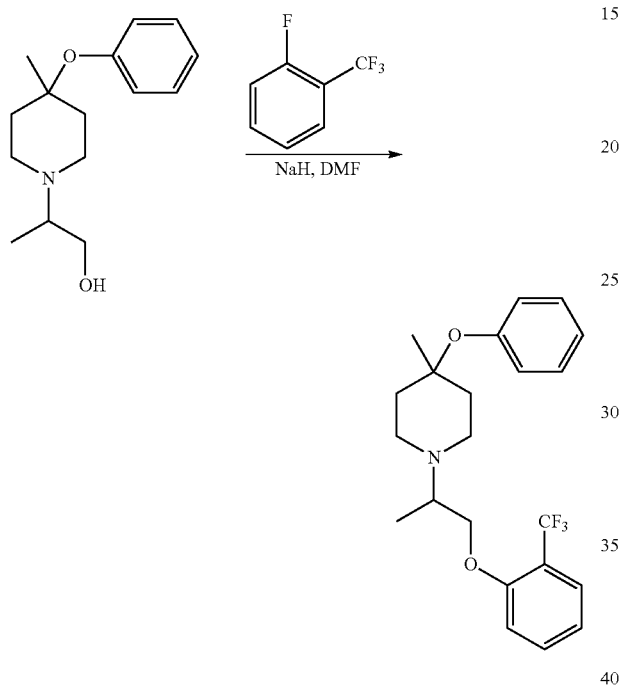

Title compound was prepared from 2-(4-methyl-4-phenoxypiperidin-1-yl)propan-1-ol (0.2 g, 0.8 mmol) and 1-fluoro-2-(trifluoromethyl) benzene (0.19 g, 1.2 mmol, 1.5 equiv) using the general methodology of Example-61. Purification using silica gel column chromatography further purified by preparative HPLC to afford 0.016 g of 4-methyl-4-phenoxy-1-(1-(2-(trifluoromethyl)phenoxy)propan-2-yl)piperidine (yield=19%). ¹H NMR (500 MHz, DMSO-d₆): δ 7.62-7.59 (m, 2H), 7.29-7.25 (m, 3H), 7.09-7.03 (m, 2H), 6.97 (d, J=8.0 Hz, 2H), 4.20-4.18 (m, 1H), 4.03-4.00 (m, 1H), 3.03-3.01 (m, 1H), 2.80-2.73 (m, 2H), 2.60-2.57 (m, 2H), 1.86-1.84 (m, 2H), 1.60-1.55 (m, 2H), 1.22 (s, 3H), 1.11 (d, J=6.5 Hz, 3H); ESI+MS: m/z 394 ([M+H]⁺).

Example-83: 2,4,6-Trimethyl-4-phenoxy-1-(2-(2-(trifluoromethyl) phenoxy)ethyl) piperidine

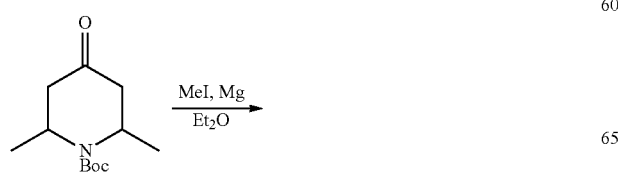

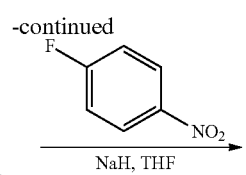

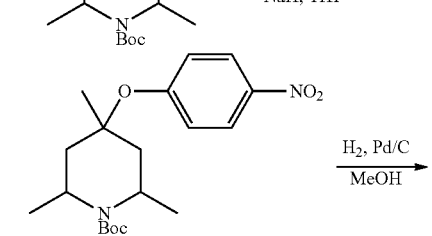

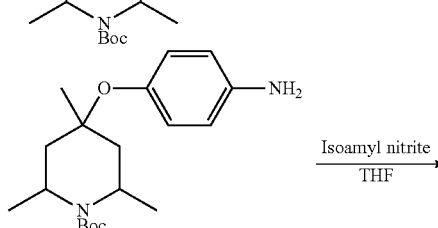

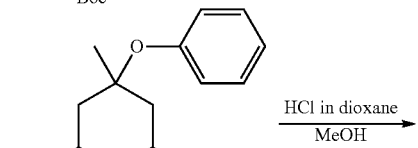

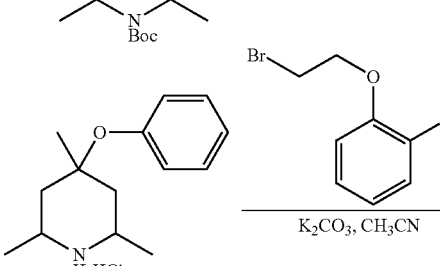

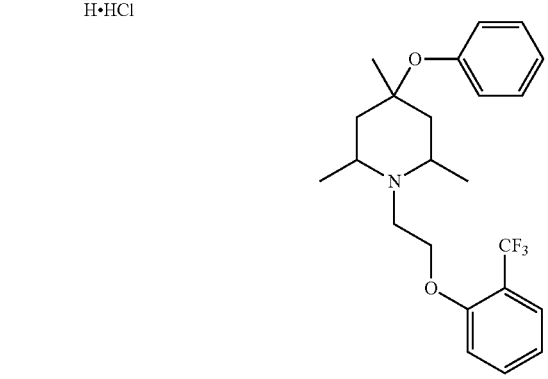

tert-butyl 4-hydroxy-2,4,6-trimethylpiperidine-1-carboxylate

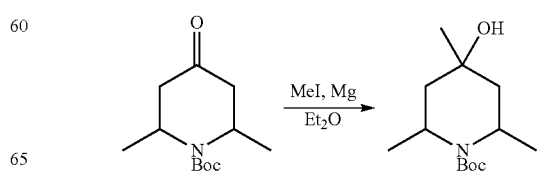

Title compound was prepared from tert-butyl 2,6-dimethyl-4-oxopiperidine-1-carboxylate (2 g, 8.8 mmol) using the general methodology of step 1 of key intermediate-I for 4 h. Purification using silica gel column chromatography (12% EtOAc/Hexanes as eluent) to afford 0.86 g of tert-butyl 4-hydroxy-2,4,6-trimethylpiperidine-1-carboxylate (Yield=40%).

tert-butyl 2,4,6-trimethyl-4-(4-nitrophenoxy)piperidine-1-carboxylate

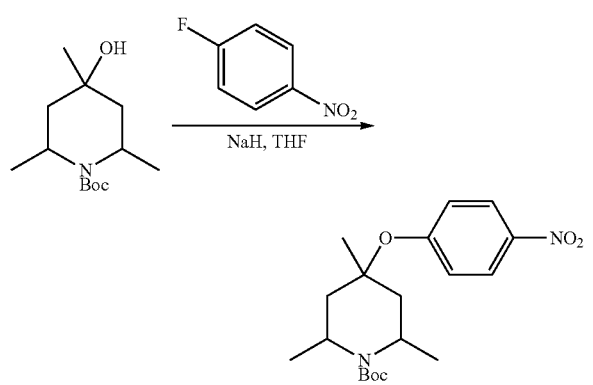

Title compound was prepared from tert-butyl 4-hydroxy-2,4,6-trimethylpiperidine-1-carboxylate (0.85 g, 3.49 mmol) and 4-fluoro nitrobenzene (0.74 g, 5.24 mmol, 1.5 equiv) using the general methodology of step 2 of key intermediate-I. Purification using silica gel column chromatography (7% EtOAc in Hexane as eluent) to afford 0.3 g of tert-butyl 2,4,6-trimethyl-4-(4-nitrophenoxy)piperidine-1-carboxylate (Yield=24%).

tert-butyl 4-(4-aminophenoxy)-2,4,6-trimethylpiperidine-1-carboxylate

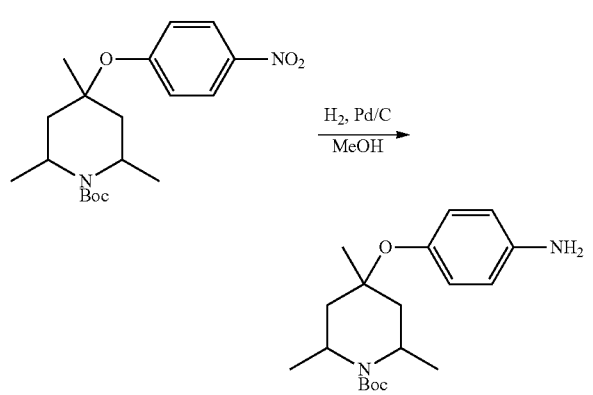

Title compound was prepared from tert-butyl 2,4,6-trimethyl-4-(4-nitrophenoxy)piperidine-1-carboxylate (0.3 g, 0.82 mmol) using the general methodology of step 3 of key intermediate-I to afford 0.23 g of tert-butyl 4-(4-aminophenoxy)-2,4,6-trimethylpiperidine-1-carboxylate (Yield: 84%).

tert-butyl 2,4,6-trimethyl-4-phenoxypiperidine-1-carboxylate

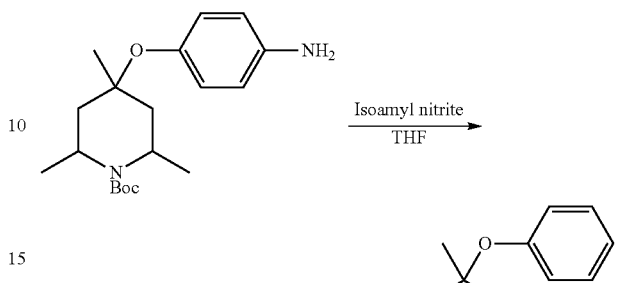

Title compound was prepared from tert-butyl 4-(4-aminophenoxy)-2,4,6-trimethylpiperidine-1-carboxylate (0.23 g, 0.68 mmol) using the general methodology of step 1 of key intermediate-VI at 80° C. for 6 h. Purification using silica gel column chromatography (7% EtOAc in Hexane as eluent) to afford 0.13 g of tert-butyl 2,4,6-trimethyl-4-phenoxypiperidine-1-carboxylate (Yield=59%).

2,4,6-Trimethyl-4-phenoxypiperidine hydrochloride

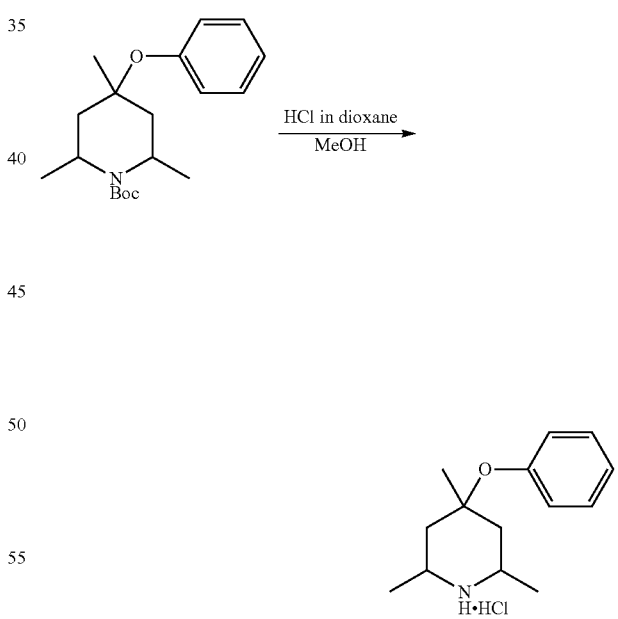

To a solution of tert-butyl 2, 4, 6-trimethyl-4-phenoxypiperidine-1-carboxylate (0.12 g, 0.36 mmol) in diethyl ether (2 mL) was added 4 M HCl in 1,4-Dioxane (1 mL) at room temperature. The reaction mixture was stirred at room temperature for 16 h. After completion, the reaction mass was concentrated under reduced pressure to obtain the 2, 4, 6-trimethyl-4-phenoxypiperidine hydrochloride (Quantitative).

2,4,6-trimethyl-4-phenoxy-1-(2-(2-(trifluoromethyl)
phenoxy) ethyl) piperidine

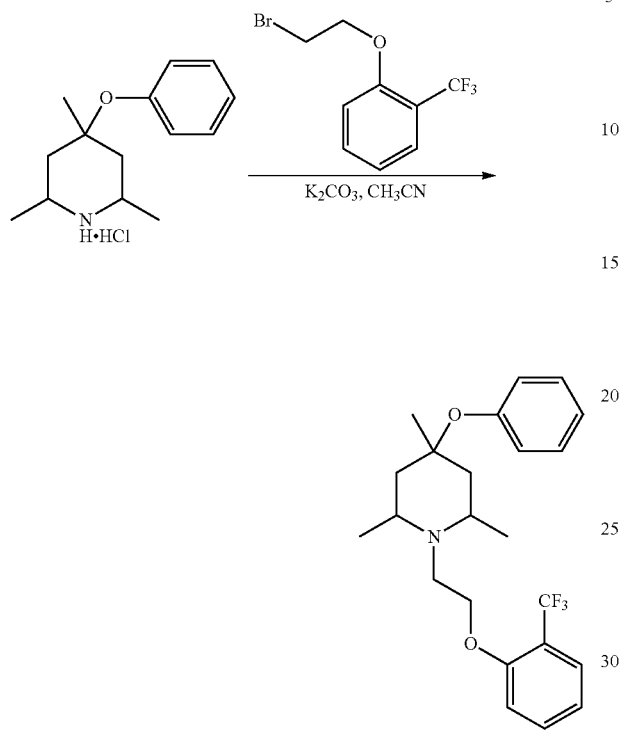

Title compound was prepared from 2,4,6-trimethyl-4-phenoxypiperidine hydrochloride (0.1 g, 0.39 mmol) and 1-(2-bromoethoxy)-2-(trifluoromethyl) benzene (0.10 g, 0.39 mmol, 1 equiv) using the general methodology of Example-1. Purification using silica gel column chromatography (2% MeOH in CH$_2$Cl$_2$ as eluent) to afford 0.019 g of 2, 4, 6-trimethyl-4-phenoxy-1-(2-(2-(trifluoromethyl)phenoxy)ethyl)piperidine (Yield=11%). $^1$H NMR (400 MHz, CD$_3$OD): δ 7.59-7.55 (m, 2H), 7.29-7.18 (m, 3H), 7.08-6.97 (m, 4H), 4.22-4.17 (m, 2H), 3.48-3.43 (m, 2H), 3.25-3.12 (m, 2H), 2.05 (d, J=14.4 Hz, 1H), 1.98-1.91 (m, 2H), 1.50-1.44 (m, 1H), 1.39-1.35 (m, 3H), 1.25 (s, 3H), 1.24-1.19 (m, 3H); ESI+MS: m/z 408 ([M+H]$^+$).

Example-84: 3-(2-Methoxyphenoxy)-3-methyl-1-(2-phenoxyethyl)pyrrolidine

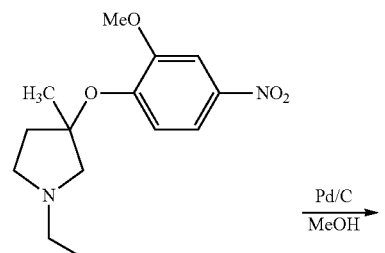

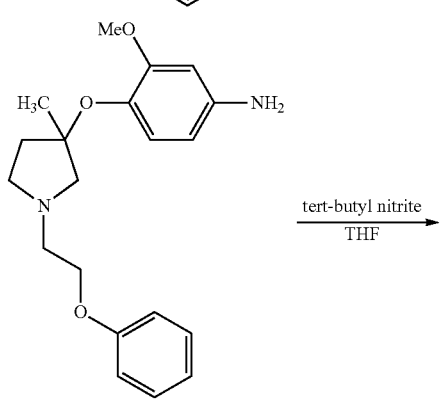

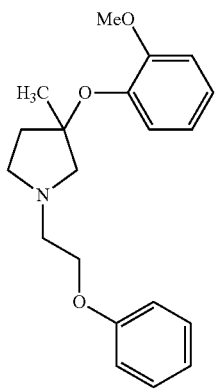

3-(2-Methoxy-4-nitrophenoxy)-3-methyl-1-(2-phenoxyethyl)pyrrolidine

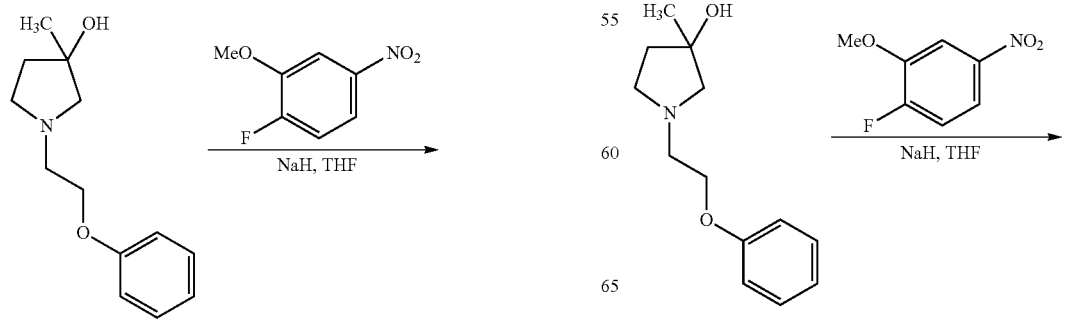

221
-continued

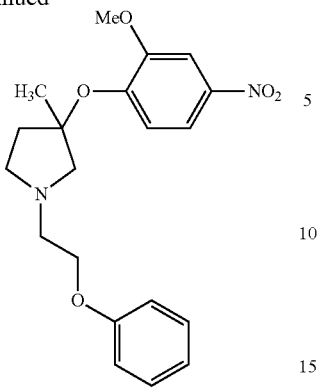

Title compound was prepared from 3-methyl-1-(2-phenoxyethyl)pyrrolidin-3-ol (0.70 g, 3.76 mmol) and 1-fluoro-2-methoxy-4-nitrobenzene (0.59 g, 3.48 mmol, 1.1 equiv) using the general methodology of step 2 of key intermediate-I. Purification using silica gel column chromatography (5% MeOH/CH$_2$Cl$_2$ as eluent) to afford 0.95 g of 3-(2-methoxy-4-nitrophenoxy)-3-methyl-1-(2-phenoxyethyl)pyrrolidine (Yield=81%). ESI+MS: m/z 373 ([M+H]$^+$).

3-Methoxy-4-((3-methyl-1-(2-phenoxyethyl)pyrrolidin-3-yl)oxy)aniline

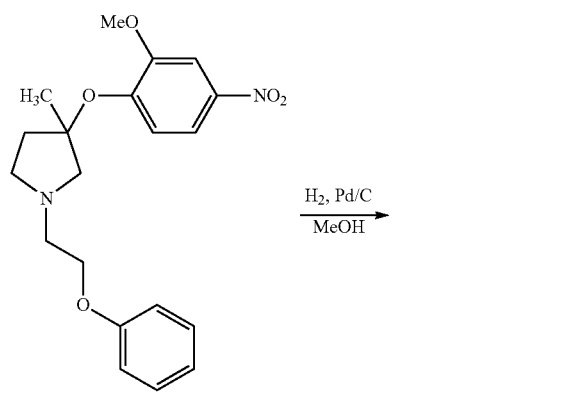

Title compound was prepared from 3-(2-methoxy-4-nitrophenoxy)-3-methyl-1-(2-phenoxyethyl)pyrrolidine (0.55 g, 1.47 mmol) using the general methodology of step 3 of key intermediate-I to afford 0.48 g of 3-methoxy-4-((3-methyl-1-(2-phenoxyethyl)pyrrolidin-3-yl)oxy)aniline (Yield=95%).

222

3-(2-Methoxyphenoxy)-3-methyl-1-(2-phenoxyethyl)pyrrolidine

Title compound was prepared from 3-methoxy-4-((3-methyl-1-(2-phenoxyethyl)pyrrolidin-3-yl)oxy)aniline (0.25 g, 0.73 mmol) using the general methodology of Example-51. The crude was purified by preparative HPLC to afford 0.015 g of 3-(2-methoxyphenoxy)-3-methyl-1-(2-phenoxyethyl)pyrrolidine (Yield=6%). $^1$H NMR (400 MHz, CD$_3$OD): δ 7.28-7.22 (m, 2H), 7.03-6.89 (m, 6H), 6.85-6.81 (m, 1H), 4.12 (t, J=5.6 Hz, 2H), 3.78 (s, 3H), 3.24 (d, J=10.8 Hz, 1H), 3.01-2.89 (m, 3H), 2.85-2.76 (m, 2H), 2.40-2.34 (m, 1H), 1.94-1.87 (m, 1H), 1.44 (s, 3H); ESI+MS: m/z 328 ([M+H]$^+$).

Example-85: 3-Methyl-1-(2-phenoxyethyl)-3-(o-tolyloxy)pyrrolidine

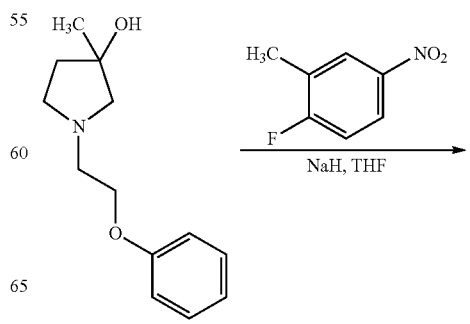

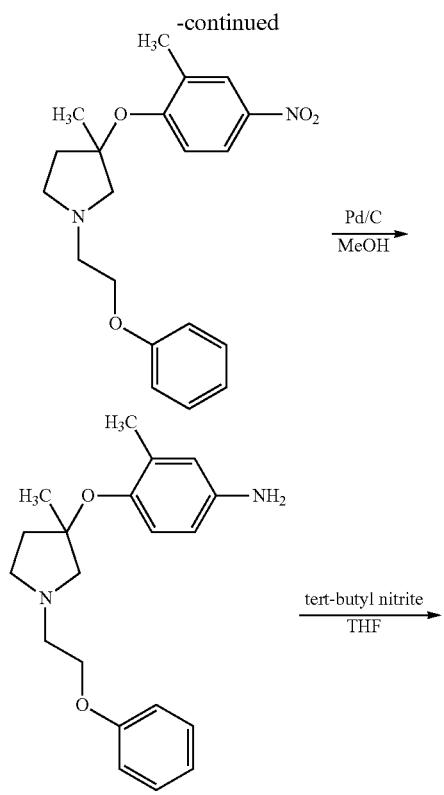

3-Methyl-3-(2-methyl-4-nitrophenoxy)-1-(2-phenoxyethyl)pyrrolidine

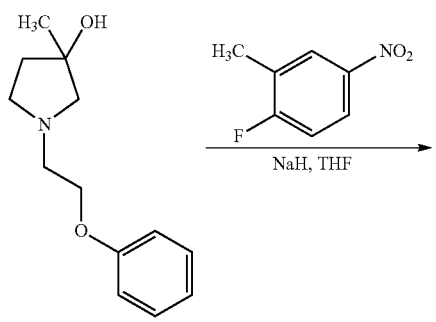

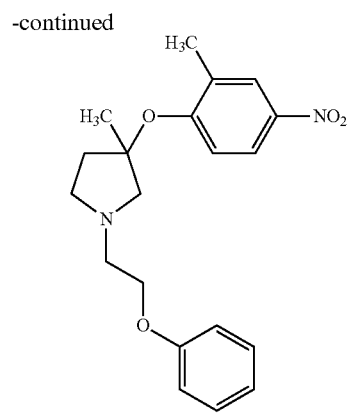

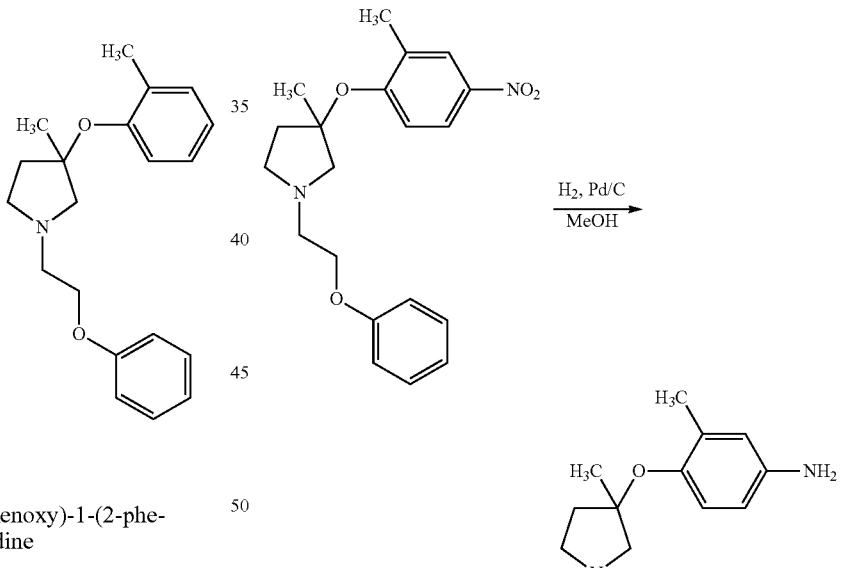

Title compound was prepared from 3-methyl-1-(2-phenoxyethyl)pyrrolidin-3-ol (0.50 g, 2.26 mmol) and 1-fluoro-2-methyl-4-nitrobenzene (0.28 g, 2.48 mmol, 1.1 equiv) using the general methodology of step 2 of key intermediate-I. Purification using silica gel column chromatography (5% MeOH/CH$_2$Cl$_2$ as eluent) to afford 0.45 g of 3-methyl-3-(2-methyl-4-nitrophenoxy)-1-(2-phenoxyethyl)pyrrolidine (Yield=48%). ESI+MS: m/z 357 ([M+H]$^+$).

3-Methyl-4-((3-methyl-1-(2-phenoxyethyl)pyrrolidin-3-yl)oxy)aniline

Title compound was prepared from 3-methyl-3-(2-methyl-4-nitrophenoxy)-1-(2-phenoxyethyl)pyrrolidine (0.40 g, 1.12 mmol) using the general methodology of step 3 of key intermediate-I to afford 0.34 g of 3-methyl-4-((3-methyl-1-(2-phenoxyethyl)pyrrolidin-3-yl)oxy)aniline (Yield=88%). ESI+MS: m/z 327 ([M+H]$^+$).

225

3-Methyl-1-(2-phenoxyethyl)-3-(o-tolyloxy)pyrrolidine

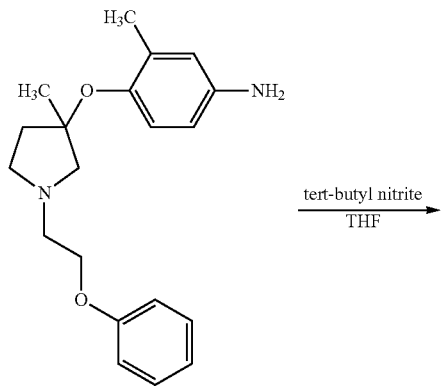

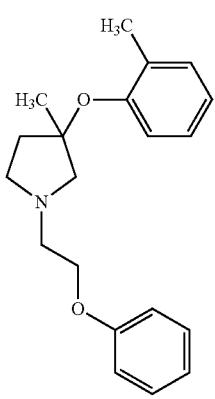

Title compound was prepared from 3-methyl-4-((3-methyl-1-(2-phenoxyethyl)pyrrolidin-3-yl)oxy)aniline (0.05 g, 0.15 mmol) using the general methodology of Example-51. The crude was purified by preparative HPLC to afford 0.009 g of 3-methyl-1-(2-phenoxyethyl)-3-(o-tolyloxy)pyrrolidine (Yield=17%). $^1$H NMR (500 MHz, CD$_3$OD): δ 7.28 (t, J=7.5 Hz, 2H), 7.14-7.06 (m, 2H), 6.95-6.92 (m, 4H), 6.85 (t, J=7.5 Hz, 1H), 4.15 (t, J=5.5 Hz, 2H), 3.28 (d, J=10.8 Hz, 1H), 3.01-2.86 (m, 5H), 2.47-2.42 (m, 1H), 2.19 (s, 3H), 2.10-2.05 (m, 1H), 1.55 (s, 3H); ESI+MS: m/z 312 ([M+H]$^+$).

Example-86: 4-(4-chlorophenoxy)-1-(2-(2-fluorophenoxy)ethyl)-4-methylpiperidine

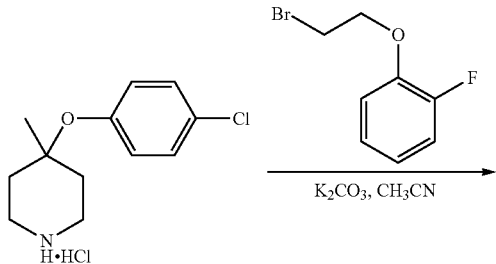

226

-continued

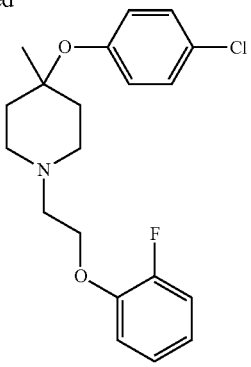

Title compound was prepared from 4-(4-chlorophenoxy)-4-methylpiperidine (0.12 g) and 1-(2-bromoethoxy)-2-fluorobenzene (0.14 g, 0.63 mmol, 1.2 equiv) using the general methodology of Example-1. The crude was purified by preparative HPLC purification to afford 0.025 g of 4-(4-chlorophenoxy)-1-(2-(2-fluorophenoxy)ethyl)-4-methylpiperidine (Yield=13%). $^1$H NMR (400 MHz, DMSO-d$_6$): δ 7.31 (d, J=8.8 Hz, 2H), 7.21-7.16 (m, 2H), 7.01 (d, J=8.8 Hz, 1H), 7.01 (d, J=8.8 Hz, 2H), 6.95-6.90 (m, 1H), 4.14 (t, J=6.0 Hz, 2H), 2.71-2.89 (m, 2H), 2.57-2.54 (m, 4H), 1.87-1.84 (m, 2H), 1.65-1.61 (m, 2H), 1.24 (s, 3H); ESI+ MS: m/z 364 ([M+H]$^+$).

Example-87: 1-(2-(2-fluorophenoxy)ethyl)-4-methyl-4-phenoxypiperidine

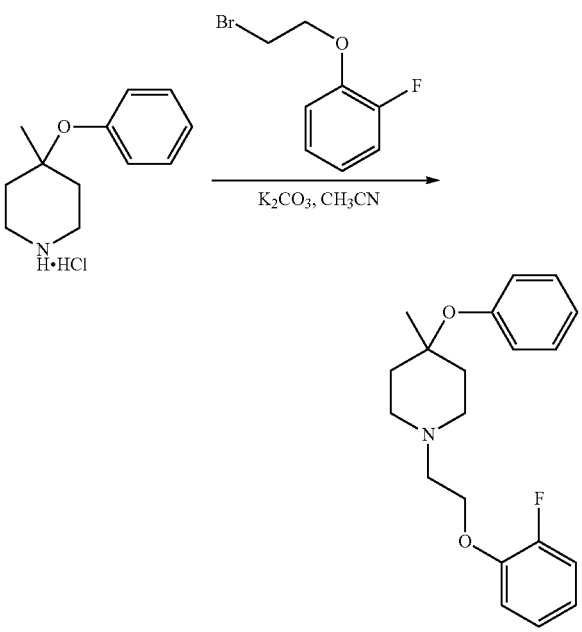

Title compound was prepared from 4-methyl-4-phenoxypiperidine (0.12 g) and 1-(2-bromoethoxy)-2-fluorobenzene (0.14 g, 0.63 mmol, 1.2 equiv) using the general methodology of Example-1. The crude was purified by preparative HPLC purification to afford 0.025 g of 1-(2-(2-fluorophenoxy)ethyl)-4-methyl-4-phenoxypiperidine (Yield=8%). $^1$H NMR (400 MHz, DMSO-d$_6$): δ 7.27 (t, J=7.6 Hz, 2H), 7.21-7.16 (m, 2H), 7.11 (t, J=7.6 Hz, 1H), 7.04 (t, J=8.0 Hz, 1H), 6.98 (d, J=8.0 Hz, 2H), 6.95-6.92 (m, 1H), 4.14 (t, J=5.6 Hz, 2H), 2.79-2.54 (m, 2H), 2.57-2.54 (m, 4H), 1.89-1.84 (m, 2H), 1.64-1.58 (m, 2H), 1.23 (s, 3H); ESI+MS: m/z 330 ([M+H]$^+$).

Example-88: 4-(4-chlorophenoxy)-1-(2-(2-chlorophenoxy)ethyl)-4-methylpiperidine

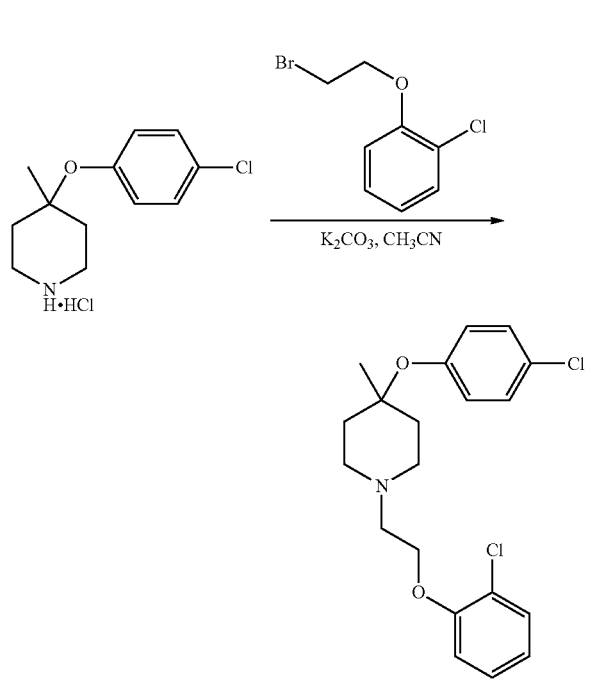

Title compound was prepared from 4-(4-chlorophenoxy)-4-methylpiperidine (0.12 g, 0.53 mmol) and 1-(2-bromoethoxy)-2-chlorobenzene (0.15 g, 0.63 mmol, 1.2 equiv) using the general methodology of Example-1. The crude was purified by preparative HPLC purification to afford 0.02 g of 4-(4-chlorophenoxy)-1-(2-(2-chlorophenoxy)ethyl)-4-methylpiperidine (Yield=9%). $^1$H NMR (400 MHz, DMSO-d$_6$): δ 7.40 (d, J=8.0 Hz, 1H), 7.32-7.27 (m, 3H), 7.16 (d, J=8.0 Hz, 1H), 7.01 (d, J=8.8 Hz, 2H), 6.94 (t, J=7.6 Hz, 1H), 4.16 (t, J=5.6 Hz, 2H), 2.78-2.75 (m, 2H), 2.62-2.58 (m, 4H), 1.90-1.84 (m, 2H), 1.64-1.62 (m, 2H), 1.23 (s, 3H); ESI+MS: m/z 381 ([M+H]$^+$).

Example-89: 1-(2-(2-Chlorophenoxy)ethyl)-4-methyl-4-phenoxypiperidine

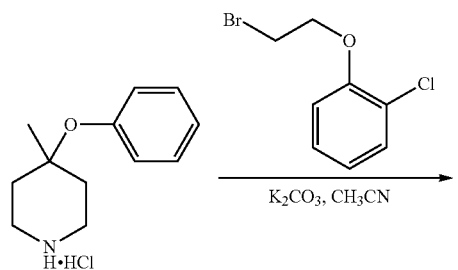

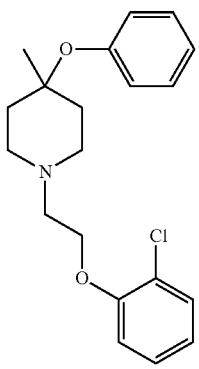

Title compound was prepared from 4-phenoxy-4-methylpiperidine (0.12 g, 0.53 mmol) and 1-(2-bromoethoxy)-2-chlorobenzene (0.15 g, 0.63 mmol, 1.2 equiv) using the general methodology of Example-1. The crude was purified by preparative HPLC purification to afford 0.01 g of 1-(2-(2-chlorophenoxy)ethyl)-4-methyl-4-phenoxypiperidine (Yield=5%). $^1$H NMR (400 MHz, DMSO-d$_6$): δ 7.41 (d, J=8.0 Hz, 1H), 7.29-7.25 (m, 3H), 7.16 (d, J=8.0 Hz, 1H), 7.04 (t, J=7.2 Hz, 1H), 6.99-6.92 (m, 3H), 4.16-4.14 (m, 2H), 2.75-2.71 (m, 2H), 2.67-2.61 (m, 4H), 1.90-1.81 (m, 2H), 1.65-1.51 (m, 2H), 1.23 (s, 3H); ESI+MS: m/z 346 ([M+H]$^+$).

Example-90: 4-(4-Chlorophenoxy)-4-methyl-1-(2-(2-(trifluoromethyl) phenoxy)ethyl) piperidine

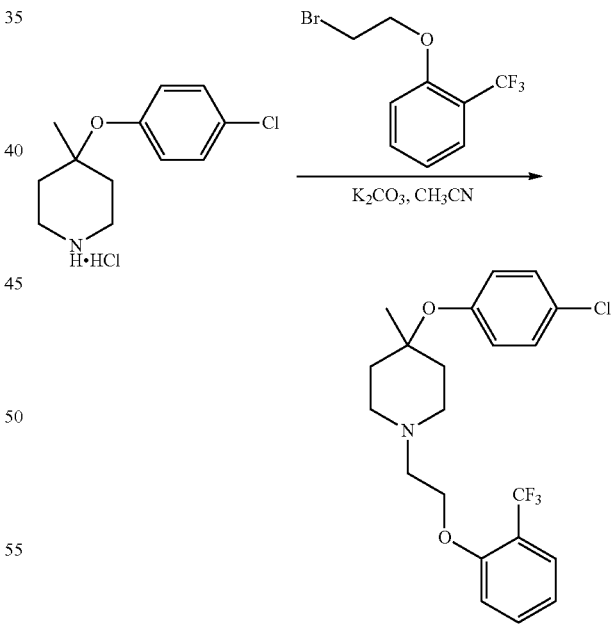

Title compound was prepared from 4-(4-chlorophenoxy)-4-methylpiperidine (0.12 g, 0.53 mmol) and 1-(2-bromoethoxy)-2-(trifluoromethyl)benzene (0.17 g, 0.63 mmol, 1.2 equiv) using the general methodology of Example-1. The crude was purified by preparative HPLC purification to afford 0.01 g of 4-(4-chlorophenoxy)-4-methyl-1-(2-(2-(trifluoromethyl)phenoxy)ethyl)piperidine (Yield=4%). $^1$H NMR (400 MHz, DMSO-d$_6$): δ 7.60 (d, J=8.0 Hz, 2H), 7.32-7.26 (m, 3H), 7.08 (d, J=8.0 Hz, 1H), 7.00 (d, J=8.8 Hz, 2H), 4.16-4.01 (m, 2H), 2.76-2.73 (m, 2H), 2.57-2.55 (m, 4H), 1.85-1.82 (m, 2H), 1.65-1.61 (m, 2H), 1.23 (s, 3H); ESI+MS: m/z 414 ([M+H]$^+$).

Example-91: 4-methyl-4-phenoxy-1-(2-(2-(trifluoromethyl)phenoxy)ethyl)piperidine

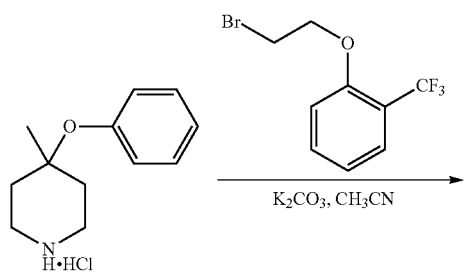

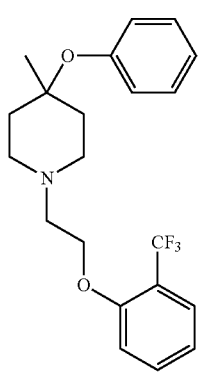

Title compound was prepared from 4-methyl-4-phenoxypiperidine (0.12 g, 0.53 mmol) and 1-(2-bromoethoxy)-2-(trifluoromethyl)benzene (0.17 g, 0.63 mmol, 1.2 equiv) using the general methodology of Example-1. The crude was purified by preparative HPLC purification to afford 0.008 g of 4-methyl-4-phenoxy-1-(2-(2-(trifluoromethyl)phenoxy)ethyl)piperidine (Yield=4%). $^1$H NMR (400 MHz, CD$_3$OD): δ 7.58 (d, J=7.6 Hz, 2H), 7.29-7.25 (m, 2H), 7.19 (d, J=8.4 Hz, 1H), 7.08-7.03 (m, 2H), 7.01-6.99 (m, 2H), 4.29 (t, J=5.6 Hz, 2H), 3.00 (t, J=5.6 Hz, 2H), 2.90-2.86 (m, 4H), 2.06-2.01 (m, 2H), 1.78-1.71 (m, 2H), 1.28 (s, 3H); ESI+MS: m/z 380 ([M+H]$^+$).

Example-92: 6-(2-(3-(4-Chlorophenoxy)-3-methylpyrrolidin-1-yl)ethoxy) benzo[d]oxazole

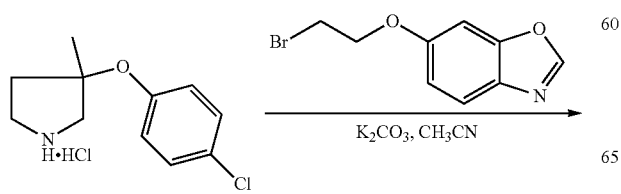

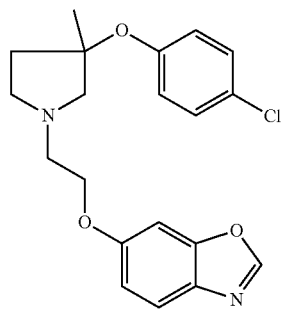

Title compound was prepared from 3-(4-chlorophenoxy)-3-methylpyrrolidine (0.07 g, 0.33 mmol) and 6-(2-bromoethoxy)benzo[d]oxazole (0.08 g, 0.33 mmol, 1 equiv) using the general methodology of Example-1. The crude was purified by preparative HPLC to afford 0.02 g of 6-(2-(3-(4-chlorophenoxy)-3-methylpyrrolidin-1-yl)ethoxy) benzo[d]oxazole (Yield=16%). $^1$H NMR (400 MHz, CD$_3$OD): δ 8.33 (s, 1H), 7.61 (d, J=8.8 Hz, 1H), 7.26 (s, 1H), 7.21-7.17 (m, 2H), 7.03 (dd, J=8.8, 2.0 Hz, 1H), 6.94-6.90 (m, 2H), 4.18 (t, J=5.6 Hz, 2H), 3.23 (d, J=5.6 Hz, 1H), 3.03-2.89 (m, 3H), 2.79-2.72 (m, 2H), 2.38-2.31 (m, 1H), 2.02-1.95 (m, 1H), 1.51 (s, 3H); ESI+MS: m/z 373 ([M+H])$^+$.

Example-93: 1-(2-Phenoxyethyl)-3-phenylpyrrolidin-3-ol

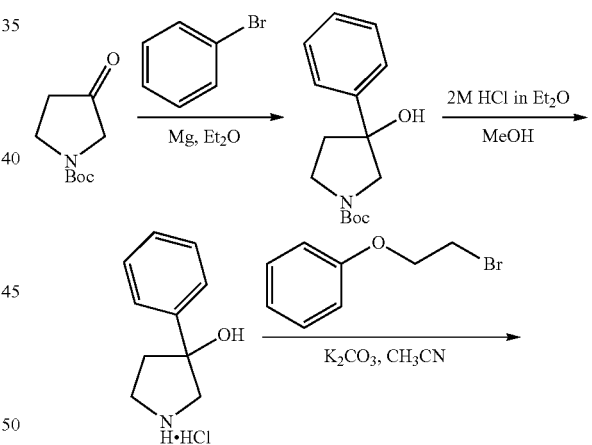

tert-butyl 3-hydroxy-3-phenylpyrrolidine-1-carboxylate

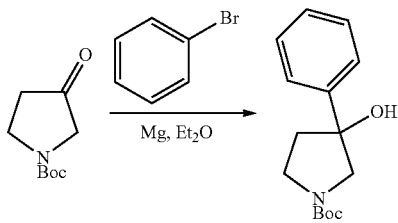

To a suspension of magnesium (0.98 g, 40.5 mmol, 3 equiv) in dry diethyl ether (20 mL) was added iodine (catalytic) and bromobenzene (6.36 g, 40.5 mmol, 3 equiv) in dry diethyl ether (10 mL) at room temperature and stirred for 30 min. This was added to a stirred solution of tert-butyl 3-oxopyrrolidine-1-carboxylate (2.5 g, 13.5 mmol) in dry THF (10 mL) at 0° C. and stirred at room temperature for 2 h. After completion, the reaction was quenched with saturated NH$_4$Cl solution at 0° C. and extracted with EtOAc. The combined organic extract was dried over sodium sulfate, filtered and concentrated under reduced pressure. Purification using silica gel column chromatography (20% EtOAc/hexanes as eluent) to afford 1.5 g of tert-butyl 3-hydroxy-3-phenylpyrrolidine-1-carboxylate (Yield=42%).

3-Phenylpyrrolidin-3-ol hydrochloride

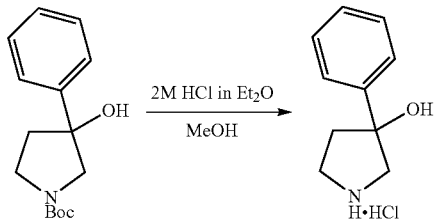

To a solution of tert-butyl 3-hydroxy-3-phenylpyrrolidine-1-carboxylate (1.5 g, 5.7 mmol) in MeOH (5 mL) was added 2 M HCl in diethyl ether (13 mL) under argon atmosphere at 0° C. The reaction was stirred at room temperature for 4 h. After completion, the solvent was removed under reduced pressure to afford 1 g of 3-phenylpyrrolidin-3-ol hydrochloride (Yield=88%).

1-(2-Phenoxyethyl)-3-phenylpyrrolidin-3-ol

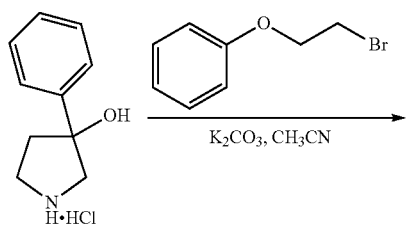

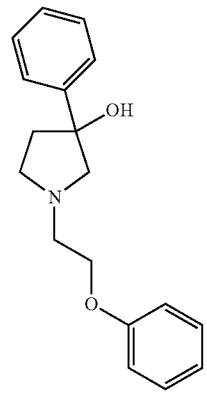

Title compound was prepared from 3-phenylpyrrolidin-3-ol hydrochloride (1 g, 5.01 mmol) and (2-bromoethoxy)benzene (1.2 g, 6.01 mmol, 1.2 equiv) using the general methodology of Example-1. Purification using silica gel column chromatography (25% EtOAc/hexanes) to afford 1.2 g of 1-(2-phenoxyethyl)-3-phenylpyrrolidin-3-ol (Yield=85%). $^1$H NMR (400 MHz, DMSO-d$_6$): δ 7.50 (d, J=8.4 Hz, 2H), 7.31-7.25 (m, 4H), 7.19 (t, J=7.6 Hz, 1H), 6.94-6.90 (m, 3H), 5.21 (br s, 1H), 4.08 (t, J=6.0 Hz, 2H), 2.99-2.82 (m, 6H), 2.14-1.98 (m, 2H); ESI+MS: m/z 284 ([M+H]$^+$).

Example-94: 3-(4-nitrophenoxy)-1-(2-phenoxyethyl)-3-phenylpyrrolidine

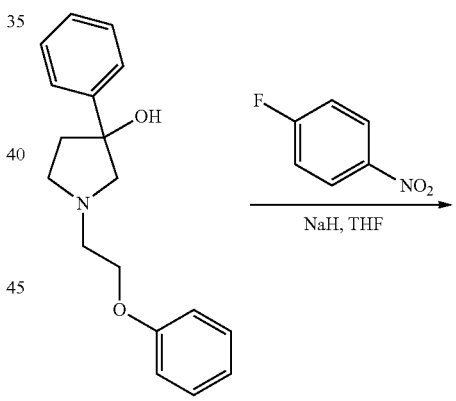

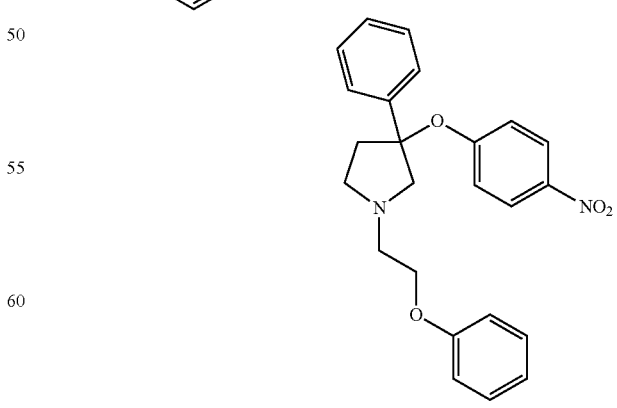

Title compound was prepared from 1-(2-phenoxyethyl)-3-phenylpyrrolidin-3-ol (1.2 g, 4.23 mmol) and 1-fluoro-4- nitrobenzene (0.71 g, 5.08 mmol, 1.2 equiv) 80° C. for 16 h using the general methodology of step 2 of key intermediate-I. Purification using silica gel column chromatography (15% EtOAc/hexanes) to afford 0.80 g of 3-(4-nitrophenoxy)-1-(2-phenoxyethyl)-3-phenylpyrrolidine (Yield=47%). $^1$H NMR (500 MHz, DMSO-$d_6$): δ 8.04 (d, J=9.5 Hz, 2H), 7.37-7.34 (m, 4H), 7.27 (t, J=8.0 Hz, 3H), 6.94-6.90 (m, 3H), 6.80 (d, J=9.5 Hz, 2H), 4.10 (d, J=5.5 Hz, 2H), 3.24-3.18 (m, 2H), 2.95-2.85 (m, 4H), 2.57-2.53 (m, 1H), 2.44-2.40 (m, 1H); ESI+MS: m/z 405 ([M+H]$^+$).

Example-95: 4-((1-(2-phenoxyethyl)-3-phenylpyrrolidin-3-yl)oxy)aniline

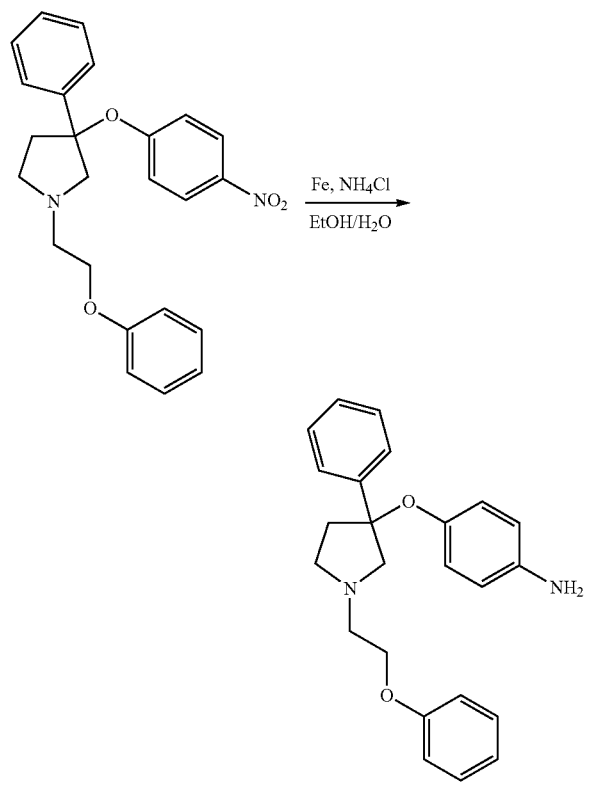

To a solution of 3-(4-nitrophenoxy)-1-(2-phenoxyethyl)-3-phenylpyrrolidine (0.60 g, 1.48 mmol, 1 equiv) in EtOH/H$_2$O (3:1, 16 mL) was added iron powder (0.41 g, 7.42 mmol, 5 equiv) and ammonium chloride (0.39 g, 7.42 mmol, 5 equiv) at room temperature. The reaction mixture was heated at 80° C. for 4 h. After completion, the reaction was filtered through celite pad; and washed with MeOH. The filtrate was concentrated under reduced pressure; residue was diluted with EtOAc and washed with water. The organic layer was dried over sodium sulfate, filtered and concentrated under reduced pressure. The obtained solid was triturated with pentane to afforded 0.4 g of 4-((1-(2-phenoxyethyl)-3-phenylpyrrolidin-3-yl)oxy)aniline (Yield=72%). $^1$H NMR (400 MHz, CD$_3$OD): δ 7.45-7.39 (m, 5H), 7.35-7.31 (m, 2H), 7.01 (t, J=7.6 Hz, 3H), 6.49 (d, J=8.8 Hz, 2H), 6.40 (d, J=6.8 Hz, 2H), 4.39-4.20 (m, 2H), 4.24 (d, J=12.0 Hz, 1H), 3.92-3.73 (m, 4H), 3.67 (d, J=12.0 Hz, 1H), 2.84-2.80 (m, 1H), 2.77-2.68 (m, 1H), 1.40-1.20 (m, 1H), 0.95-0.87 (m, 1H); ESI+MS: m/z 375 ([M+H]$^+$).

Example-96: 3-(4-chlorophenoxy)-3-methyl-1-(2-phenoxyethyl)piperidine

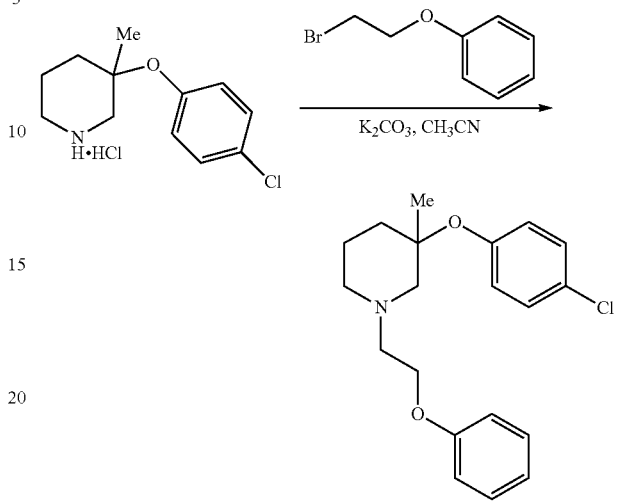

Title compound was prepared from 3-(4-chlorophenoxy)-3-methylpiperidine (0.13 g, 0.57 mmol) and (2-bromoethoxy)benzene (0.11 g, 0.57 mmol, 1 equiv) using the general methodology of Example-1. The crude was purified by preparative HPLC to afford 0.08 g of 3-(4-chlorophenoxy)-3-methyl-1-(2-phenoxyethyl)piperidine (Yield=39%). $^1$H NMR (500 MHz, DMSO-$d_6$): δ 7.27 (t, J=8.0 Hz, 2H), 7.13 (d, J=9.0 Hz, 2H), 7.06 (d, J=9.0 Hz, 2H), 6.92-6.89 (m, 3H), 3.99-3.96 (m, 2H), 2.72-2.67 (m, 1H), 2.61-2.59 (m, 3H), 2.34-2.29 (m, 1H), 2.15 (d, J=12.0 Hz, 1H), 1.83-1.70 (m, 2H), 1.51-1.47 (m, 2H), 1.16 (s, 3H); ESI+MS: 346 ([M+H]$^+$). The enantiomers of 96 were separated using chiral HPLC (method N) and afforded the pure enantiomers 96a and 96b.

Example-97: 3-(4-chlorophenoxy)-1-(2-(2-chlorophenoxy)ethyl)-3-methylpiperidine

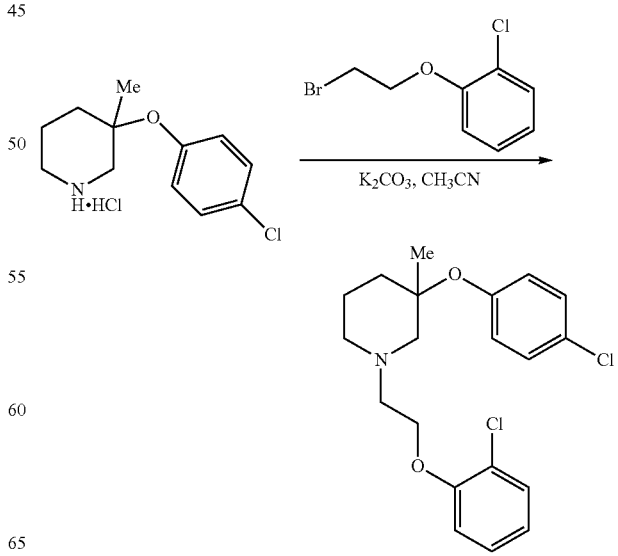

Title compound was prepared from 3-(4-chlorophenoxy)-3-methylpiperidine (0.08 g, 0.35 mmol) and 1-(2-bromoethoxy)-2-chlorobenzene (0.83 g, 0.35 mmol, 1 equiv) using the general methodology of Example-1. The crude was purified by preparative HPLC to afford 0.019 g of 3-(4-chlorophenoxy)-1-(2-(2-chlorophenoxy)ethyl)-3-methylpiperidine (Yield=14%). $^1$H NMR (400 MHz, DMSO-$d_6$): δ 7.41 (dd, J=7.6, 1.6 Hz, 1H), 7.29 (dt, J=8.4, 1.6 Hz, 1H), 7.17-7.13 (m, 3H), 7.08-7.04 (m, 2H), 6.95 (dt, J=8.8, 1.2 Hz, 1H), 4.09 (t, J=5.6 Hz, 2H), 2.74-2.66 (m, 4H), 2.38-2.32 (m, 1H), 2.25 (d, J=12.0 Hz, 1H), 1.86-1.69 (m, 2H), 1.54-1.48 (m, 2H), 1.19 (s, 3H); ESI+MS: m/z: 381 [(M+H)$^+$].

Example-98: 3-(4-Chlorophenoxy)-1-(2-(2-fluorophenoxy)ethyl)-3-methylpiperidine

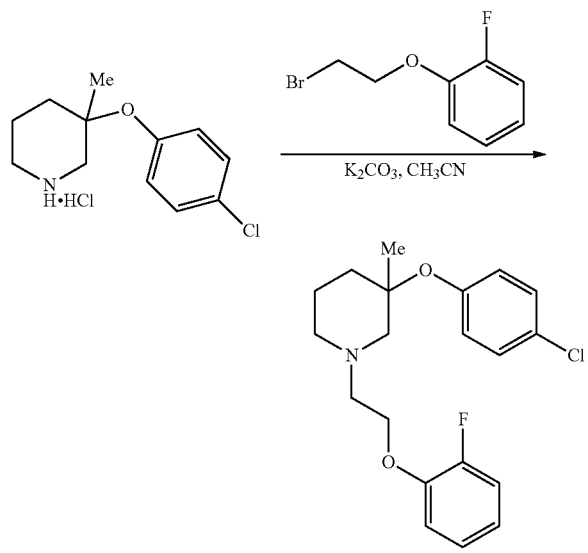

Title compound was prepared from 3-(4-chlorophenoxy)-3-methylpiperidine (0.08 g, 0.35 mmol) and 1-(2-bromoethoxy)-2-fluorobenzene (0.078 g, 0.35 mmol, 1 equiv) using the general methodology of Example-1. The crude was purified by preparative HPLC to afford 0.019 g of 3-(4-chlorophenoxy)-1-(2-(2-fluorophenoxy)ethyl)-3-methylpiperidine (Yield=14%). $^1$H NMR (400 MHz, DMSO-$d_6$): δ 7.23-7.07 (m, 7H), 6.94-6.92 (m, 1H), 4.09 (t, J=5.6 Hz, 2H), 2.74-2.60 (m, 4H), 2.32-2.28 (m, 1H), 2.20 (d, J=12.0 Hz, 1H), 1.85-1.72 (m, 2H), 1.54-148 (m, 2H), 1.17 (s, 3H); ESI+MS: m/z: 364 ([M+H]$^+$). The enantiomers of 98 were separated using chiral HPLC (method S) and afforded the pure enantiomers 98a and 98b.

Example-99: 5-(2-(3-(4-chlorophenoxy)-3-methylpiperidin-1-yl)ethoxy)benzo[d] thiazole

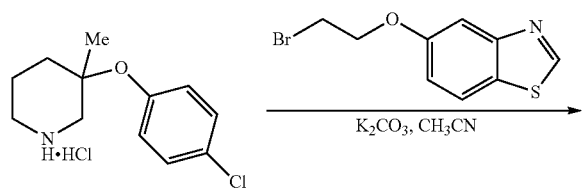

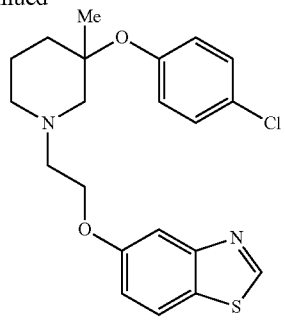

Title compound was prepared from 3-(4-chlorophenoxy)-3-methylpiperidine (0.045 g, 0.2 mmol) and 5-(2-bromoethoxy)benzo[d]thiazole (0.05 g, 0.2 mmol, 1 equiv) using the general methodology of Example-1. The crude was purified by preparative HPLC to afford 0.012 g of 5-(2-(3-(4-chlorophenoxy)-3-methylpiperidin-1-yl)ethoxy)benzo[d]thiazole (Yield=14%). $^1$H NMR (400 MHz, CD$_3$OD): δ 9.21 (s, 1H), 7.93 (d, J=9.2 Hz, 1H), 7.58 (d, J=2.4 Hz, 1H), 7.16-7.13 (m, 1H), 7.06-7.03 (m, 4H), 4.21-4.18 (m, 2H), 2.93-2.75 (m, 4H), 2.38-2.32 (m, 1H), 2.22 (d, J=12.0 Hz, 1H), 2.08-2.00 (m, 1H), 1.90-1.87 (m, 1H), 1.63-1.46 (m, 2H), 1.57 (s, 3H); ESI+MS: m/z 403 ([M+H]$^+$). The enantiomers of 99 were separated using chiral HPLC (method D) and afforded the pure enantiomers 99a and 99b.

Example-100: 3-methyl-1-(2-phenoxyethyl)-3-(3-(trifluoromethyl)phenoxy)piperidine

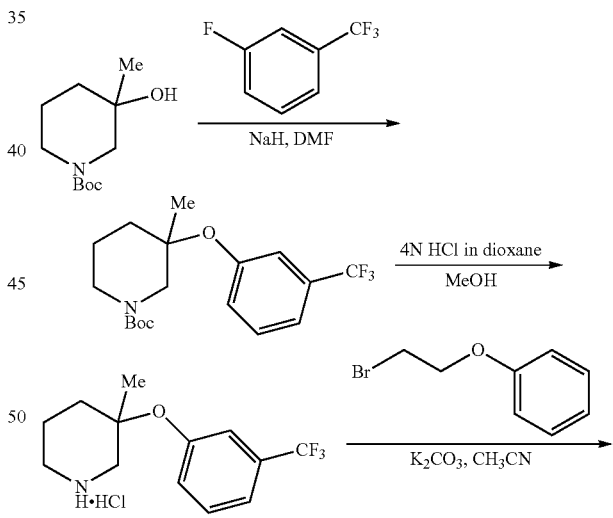

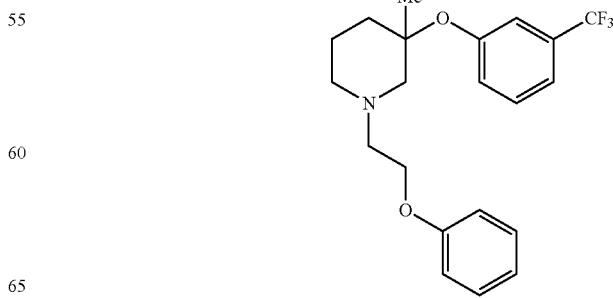

237
tert-butyl 3-methyl-3-(3-(trifluoromethyl)phenoxy) piperidine-1-carboxylate

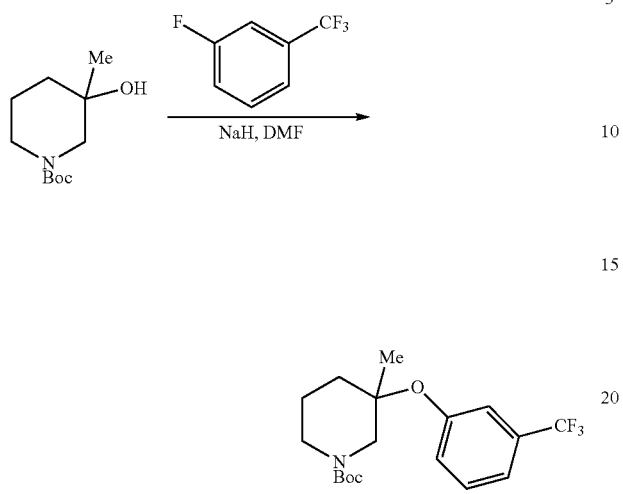

To a solution of tert-butyl 3-hydroxy-3-methylpiperidine-1-carboxylate (0.10 g, 0.46 mmol) in dry DMF (1 mL) under argon atmosphere was added sodium hydride (60% suspension, 0.027 g, 0.69 mmol, 1.5 equiv) at 0° C. The reaction was warmed to room temperature and stirred for 10 min; 3-(trifluoromethyl)-1-fluorobenzene (0.084 g, 0.511 mmol, 1.1 equiv) was added at 0° C. The reaction mixture was heated at 100° C. in sealed tube for 16 h. After completion, the reaction was diluted with water and extracted with ethyl acetate. The organic extract was dried over sodium sulfate, filtered and concentrated under reduced pressure. Purification using silica gel column chromatography (20% EtOAc/Hexanes as eluent) to afford 0.065 g of tert-butyl 3-methyl-3-(3-(trifluoromethyl)phenoxy)piperidine-1-carboxylate (Yield=39%).

3-Methyl-3-(3-(trifluoromethyl)phenoxy)piperidine

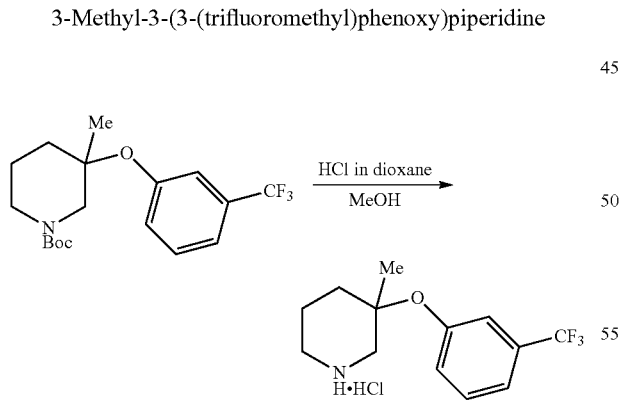

To a solution of tert-butyl 3-methyl-3-(3-(trifluoromethyl) phenoxy)piperidine-1-carboxylate (0.06 g, 0.167 mmol) in diethyl ether (2 mL) under argon atmosphere was added 4.0 M HCl in 1,4-dioxane (1 mL) at 0° C. The reaction mixture was stirred at room temperature for 16 h. After completion, the solvent was removed under reduced pressure to afford 0.047 g of 3-methyl-3-(3-(trifluoromethyl)phenoxy)piperidine (Yield=95%).

238
3-Methyl-1-(2-phenoxyethyl)-3-(3-(trifluoromethyl) phenoxy)piperidine

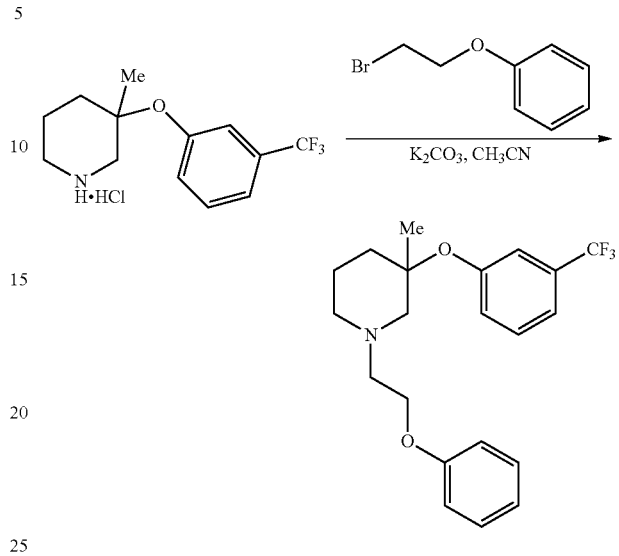

Title compound was prepared from 3-methyl-3-(3-(trifluoromethyl)phenoxy)piperidine (0.05 g, 0.17 mmol) and (2-bromoethoxy)benzene (0.037 g, 0.18 mmol, 1.1 equiv) using the general methodology of Example-1. The crude was purified by preparative HPLC to afford 0.01 g of 3-methyl-1-(2-phenoxyethyl)-3-(3-(trifluoromethyl)phenoxy)piperidine (Yield=15%). $^1$H NMR (400 MHz, DMSO-$d_6$): δ 7.41-7.39 (m, 3H), 7.34 (s, 1H), 7.29-7.24 (m, 2H), 6.94-6.88 (m, 3H), 4.01 (t, J=6.0 Hz, 2H), 2.71-2.60 (m, 4H), 2.35-2.25 (m, 2H), 1.87-1.76 (m, 2H), 1.58-1.49 (m, 2H), 1.23 (s, 3H); ESI+MS: m/z: 380 ([M+H]$^+$).

Example-101: 4-benzylidene-1-(2-(2-(trifluoromethyl)phenoxy)ethyl)piperidine

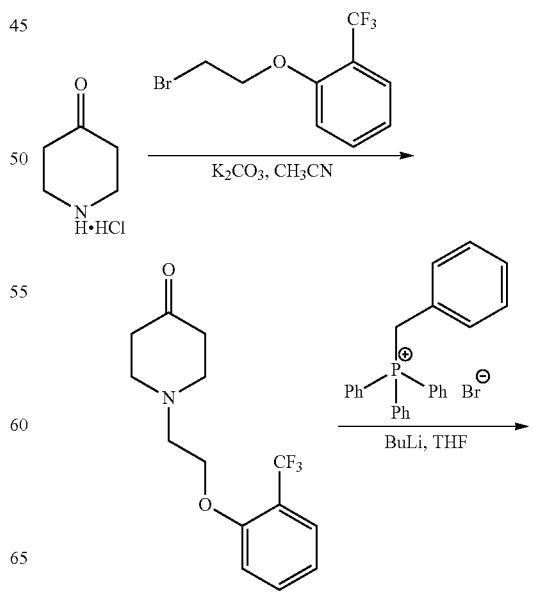

1-(2-(2-(trifluoromethyl)phenoxy)ethyl)piperidin-4-one

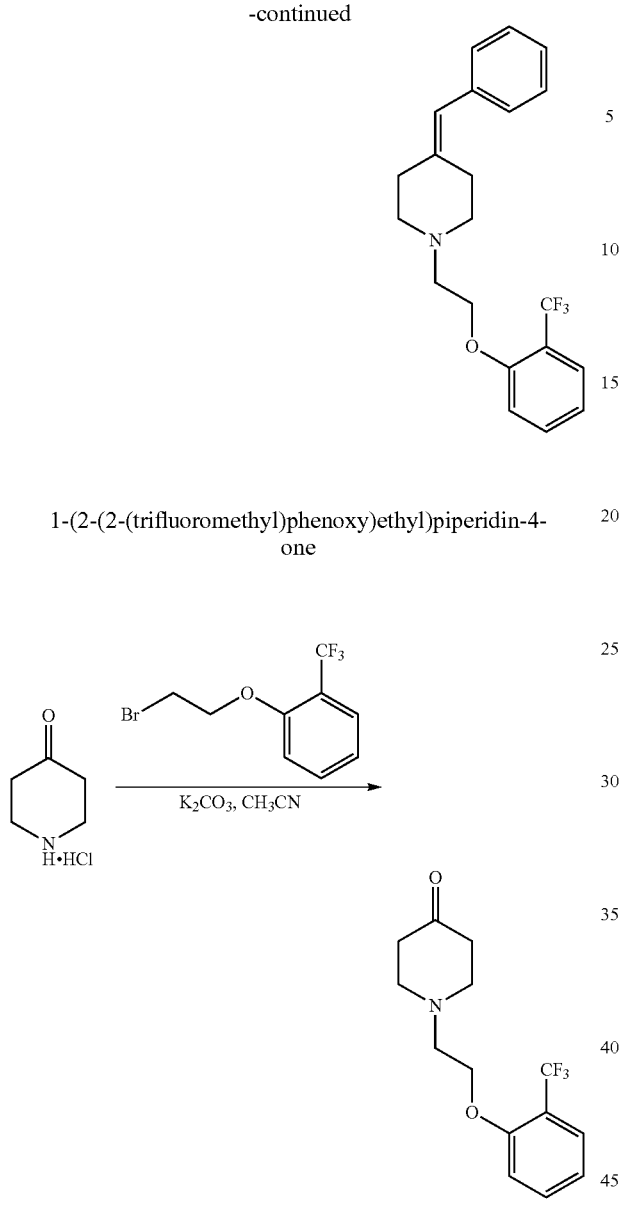

Title compound was prepared from piperidin-4-one hydrochloride (2 g, 13.02 mmol) using general methodology of Example-1. Purification using silica gel chromatography (30% EtOAc/Hexanes as eluent) to afford 2 g of 1-(2-(2-(trifluoromethyl)phenoxy)ethyl)piperidin-4-one (Yield=53%).

Benzylidenetriphenyl-15-phosphane

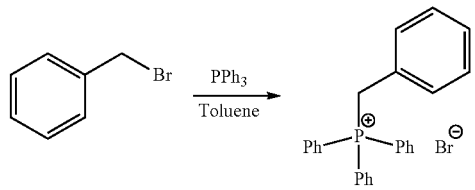 [SMILES: BrCc1ccccc1 ; c1ccc(C[P+](c2ccccc2)(c2ccccc2)c2ccccc2)cc1 ; [Br-] ; "PPh3"]

To a solution of triphenylphosphine (10 g, 38.1 mmol) in toluene (150 mL) was added benzyl bromide (7.1 g, 42 mmol, 1.1 equiv) at room temperature. The reaction mixture was stirred at 110° C. for 16 h. After completion, the obtained solid was filtered and washed with toluene to afford 10 g of benzylidenetriphenyl-15-phosphane (Yield=74%).

4-benzylidene-1-(2-(2-(trifluoromethyl)phenoxy)ethyl)piperidine

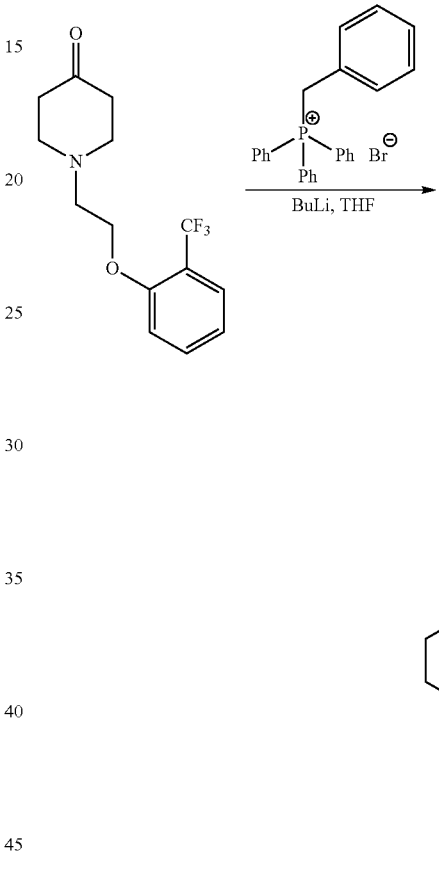

To a stirred solution of benzylidenetriphenyl-15-phosphane (9.8 g, 27.8 mmol, 4 equiv) in THF (40 mL) was added n-BuLi (1.6 M in hexane, 6.55 mL, 20.89 mmol 1.3 equiv) at 0° C. and stirred for 15 min. Then 1-(2-(2-(trifluoromethyl)phenoxy)ethyl)piperidin-4-one (2 g, 6.96 mmol, 1 equiv) was added at 0° C. and warmed to room temperature for 4 h. After completion of the reaction, quenched with saturated NH$_4$Cl and extracted with EtOAc. The organic extract was separated, dried over sodium sulfate and concentrated under reduced pressure. Purification using silica gel chromatography (25% EtOAc/Hexanes as eluent) to afford 1 g of 4-benzylidene-1-(2-(2-(trifluoromethyl)phenoxy)ethyl)piperidine (Yield=39%). $^1$H NMR (500 MHz, DMSO-d6): δ 7.63-7.59 (m, 2H), 7.33-7.27 (m, 3H), 7.21-7.18 (m, 3H), 7.08 (t, J=7.5 Hz, 1H), 6.28 (s, 1H), 4.22 (t, J=6.0 Hz, 2H), 2.74 (t, J=5.0 Hz, 2H), 2.60 (t, J=5.0 Hz, 2H), 2.52-2.50 (m, 2H), 2.41 (t, J=5.0 Hz, 2H), 2.31 (t, J=5.0 Hz, 2H); ESI+MS: m/z 362 ([M+H]$^+$).

Example-102: 1-Phenyl-6-(2-(2-(trifluoromethyl)phenoxy)ethyl)-6-azaspiro[2.5]octane

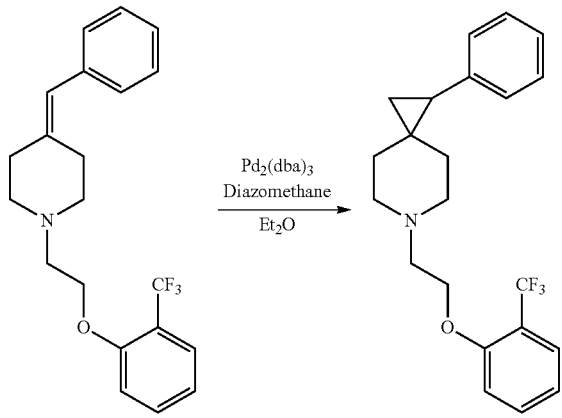 [SMILES: "Et2O" ; FC(F)(F)c1ccccc1OCCN1CCC(=Cc2ccccc2)CC1 ; FC(F)(F)c1ccccc1OCCN1CCC2(CC1)CC2c1ccccc1]

To a stirred solution of 4-benzylidene-1-(2-(2-(trifluoromethyl)phenoxy)ethyl)piperidine (0.10 mg, 0.27 mmol) in diethyl ether (5 mL) was added freshly prepared diazomethane [prepared from NMU (0.28 g, 2.77 mmol, 10 equiv), 50% aqueous KOH (10 mL)] solution in diethyl ether (10 mL) and stirred at 0° C. for 1 h. Then $Pd_2(dba)_3$ (0.025 g, 0.02 mmol, 0.1 equiv) was added and the reaction mixture was stirred at room temperature for 12 h. After completion, the reaction mass was filtered through celite bed and the filtrate was concentrated under reduced pressure. The crude was purified by preparative HPLC to afford 30 mg of 1-phenyl-6-(2-(2-(trifluoromethyl)phenoxy)ethyl)-6-azaspiro[2.5]octane (Yield=29%). $^1$H NMR (500 MHz, $CD_3OD$): δ 7.58-7.55 (m, 2H), 7.27-7.14 (m, 6H), 7.07 (t, J=7.5 Hz, 1H), 4.25 (t, J=5.5 Hz, 2H), 2.88 (t, J=5.5 Hz, 2H), 2.81-2.79 (m, 2H), 2.49-2.46 (m, 2H), 2.02-2.00 (m, 1H), 1.67-1.65 (m, 2H), 1.29-1.27 (m, 2H), 0.99 (t, J=5.5 Hz, 1H), 0.84-0.82 (m, 1H); ESI+MS: m/z 376 ([M+H]$^+$). The enantiomers of 102 were separated using chiral HPLC (method T) and afforded the pure enantiomers 102a and 102b.

Example-103: 4-(Hydroxy(phenyl)methyl)-1-(2-(2-(trifluoromethyl) phenoxy)ethyl) piperidin-4-ol

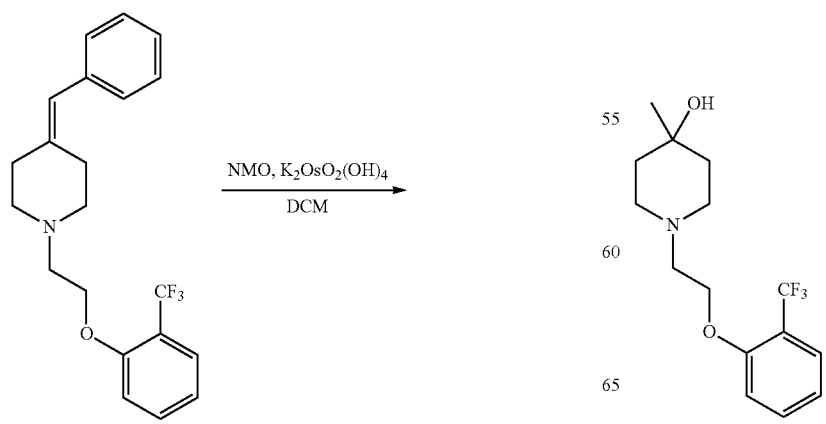

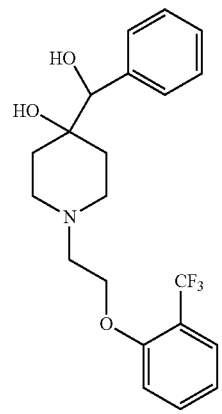

To a stirred solution of 4-benzylidene-1-(2-(2-(trifluoromethyl)phenoxy)ethyl)piperidine (0.5 g, 1.38 mmol) in $CH_2Cl_2$ (5 mL) and water (1.5 mL) were added N-Methylmorpholine N-oxide (0.19 g, 1.66 mmol, 1.2 equiv) followed by potassium osmium(VI) oxide dihydrate (0.025 g, 0.06 mmol, 0.05 equiv) at room temperature and stirred for 16 h. After completion, the reaction mass was poured into water and extracted with $CH_2Cl_2$. The organic extract layer was washed with saturated sodium thiosulphate solution, dried over sodium sulfate and concentrated under reduced pressure. Purification using silica gel chromatography (10% MeOH/$CH_2Cl_2$ as eluent) to afford 0.4 g of 4-(hydroxy(phenyl)methyl)-1-(2-(2-(trifluoromethyl)phenoxy)ethyl)piperidin-4-ol (Yield=73%). $^1$H NMR (500 MHz, $CD_3OD$): δ 7.58-7.55 (m, 2H), 7.41-7.40 (m, 2H), 7.32 (t, J=7.5 Hz, 2H), 7.27-7.24 (m, 1H), 7.17 (d, J=8.5 Hz, 1H), 7.07 (t, J=7.5 Hz, 1H), 4.42 (s, 1H), 4.26-4.24 (m, 2H), 3.71-3.69 (m, 1H), 2.92-2.90 (m, 4H), 2.64-2.56 (m, 2H), 1.82-1.72 (m, 2H), 1.43-1.40 (m, 1H); ESI+MS: m/z 396 ([M+H]$^+$).

Example-104: 4-(2-Chlorophenoxy)-4-methyl-1-(2-(2-(trifluoromethyl)phenoxy)ethyl) piperidine

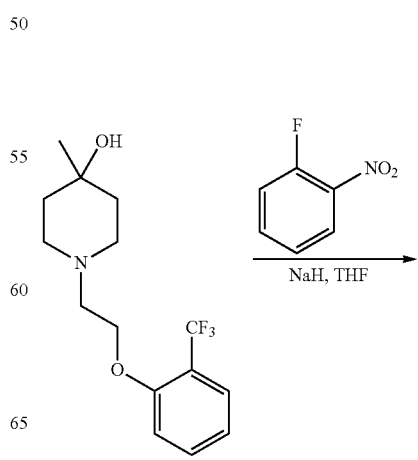

243

-continued

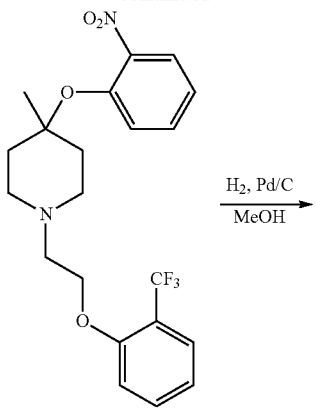

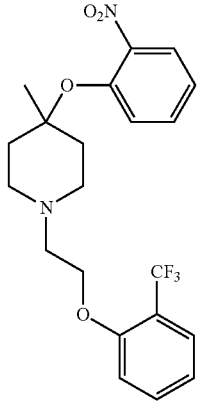

Title compound was prepared from 4-methyl-1-(2-(2-(trifluoromethyl) phenoxy) ethyl) piperidin-4-ol (0.50 g, 1.64 mmol) and 1-fluoro 2-nitro benzene (0.23 g, 1.64 mmol, 1 equiv) using the general methodology of step 2 of key Intermediate-I at 80° C. for 16 h. Purification using silica gel chromatography (2% MeOH/CH$_2$Cl$_2$ as eluent) afforded 0.5 g of 4-methyl-4-(2-nitrophenoxy)-1-(2-(2-(trifluoromethyl)phenoxy)ethyl)piperidine (Yield=71%).

2-((4-methyl-1-(2-(2-(trifluoromethyl)phenoxy) ethyl)piperidin-4-yl)oxy)aniline

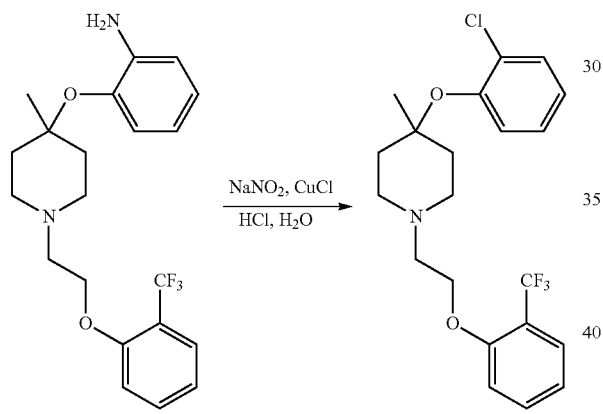

4-Methyl-4-(2-nitrophenoxy)-1-(2-(2-(trifluoromethyl)phenoxy)ethyl)piperidine

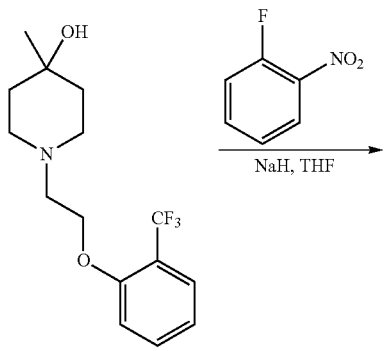

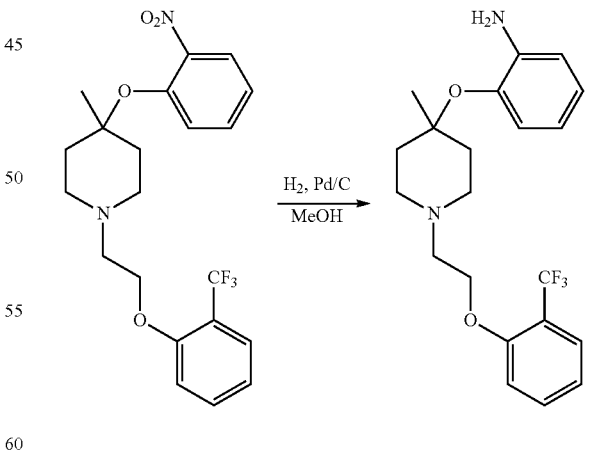

Title compound was prepared from 4-methyl-4-(2-nitrophenoxy)-1-(2-(2-(trifluoromethyl) phenoxy)ethyl)piperidine (0.5 g, 1.17 mmol) using general methodology of step 3 of Key Intermediate-I. Purification using silica gel chromatography (2% MeOH/CH$_2$Cl$_2$ as eluent) to afford 0.3 g of 2-((4-methyl-1-(2-(2-(trifluoromethyl)phenoxy)ethyl)piperidin-4-yl)oxy)aniline (Yield=64%).

4-(2-chlorophenoxy)-4-methyl-1-(2-(2-(trifluoromethyl)phenoxy)ethyl) piperidine

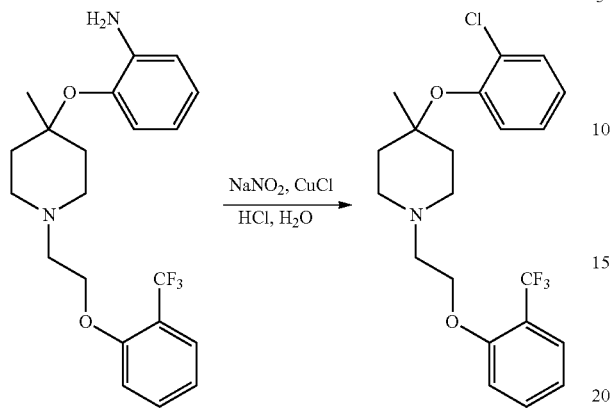

To a solution of 2-((4-methyl-1-(2-(2-(trifluoromethyl) phenoxy)ethyl)piperidin-4-yl)oxy)aniline (0.20 g, 0.50 mmol) in HCl:H$_2$O (1:1, 1.5 mL) was added NaNO$_2$ in H$_2$O (0.5 mL, 0.04 g, 0.65 mmol, 1.3 equiv) drop wise at 0° C. The reaction mixture was stirred at 0-5° C. for 1 h. Then a solution of CuCl (0.08 g, 0.81 mmol, 1.6 equiv) in HCl:H$_2$O (0.5 mL) was added at 0° C. The reaction was stirred at room temperature for 4 h. After completion, the reaction was quenched with NaOH$_{(aq)}$ and extracted with EtOAc. The organic extract was dried over sodium sulfate and concentrated under reduced pressure. The crude compound was purified by preparative HPLC to afford 0.02 g of 4-(2-chlorophenoxy)-4-methyl-1-(2-(2-(trifluoromethyl)phenoxy) ethyl)piperidine (Yield=10%). $^1$H NMR (400 MHz, DMSO-d$_6$): δ 7.62-7.58 (m, 2H), 7.44 (d, J=8.0 Hz, 1H), 7.28-7.19 (m, 3H), 7.09-7.00 (m, 2H), 4.20 (t, J=5.6 Hz, 2H), 2.74 (t, J=5.6 Hz, 2H), 2.66-2.53 (m, 4H), 2.02-1.96 (m, 2H), 1.70-1.64 (m, 2H), 1.30 (s, 3H); ESI+MS: m/z 414 ([M+H]$^+$).

Example-105: 2-((4-methyl-1-(2-(2-(trifluoromethyl)phenoxy)ethyl)piperidin-4-yl)oxy) pyridine

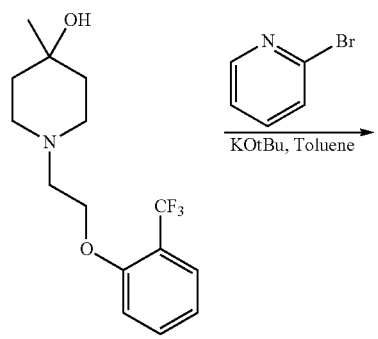

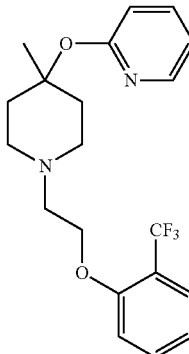

To a solution of 4-methyl-1-(2-(2-(trifluoromethyl)phenoxy)ethyl)piperidin-4-ol (0.10 g, 0.33 mmol) in toluene (1 mL) were added potassium tert-butoxide (0.11 g, 0.98 mmol, 3 equiv) and 2-bromopyridine (0.05 g, 0.36 mmol, 1.1 equiv) at room temperature. The reaction was stirred at 120° C. in sealed tube for 48 h. After completion, the reaction mass was concentrated under reduced pressure. The residue was diluted with water and extracted with EtOAc. The organic extract was separated, dried over sodium sulfate and concentrated under reduced pressure. Purification using silica gel chromatography (2% MeOH/CH$_2$Cl$_2$ as eluent) to afford 0.05 g of (4-methyl-1-(2-(2-(trifluoromethyl)phenoxy)ethyl)piperidin-4-yl)oxy)pyridine (Yield=40%). $^1$H NMR (400 MHz, DMSO-d$_6$): δ 8.10 (d, J=3.2 Hz, 1H), 7.64-7.59 (m, 3H), 7.27 (d, J=8.4 Hz, 1H), 7.10-7.06 (m, 1H), 6.92-6.90 (m, 1H), 6.72 (d, J=8.0 Hz, 1H), 4.23-4.20 (m, 2H), 2.69-2.67 (m, 2H), 2.67-2.66 (m, 2H), 2.44-2.42 (m, 2H), 2.31-2.25 (m, 2H), 1.76-1.72 (m, 2H), 1.52 (s, 3H); ESI+MS: m/z 381 ([M+H]$^+$).

Example-106: (4-Methyl-1-(2-(2-(trifluoromethyl) phenoxy)ethyl)piperidin-4-yl) (phenyl)methanone

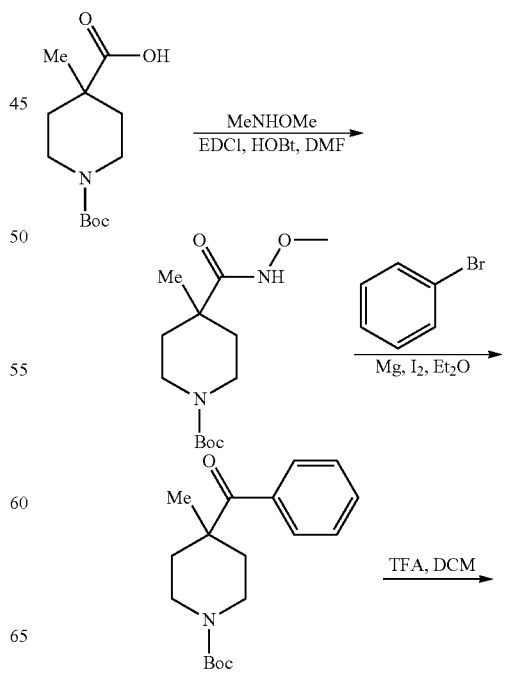

247

-continued

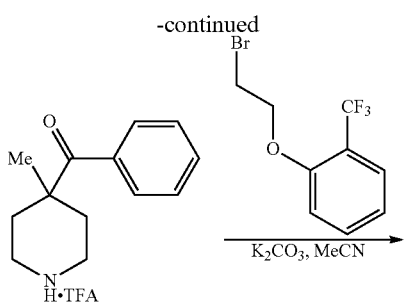

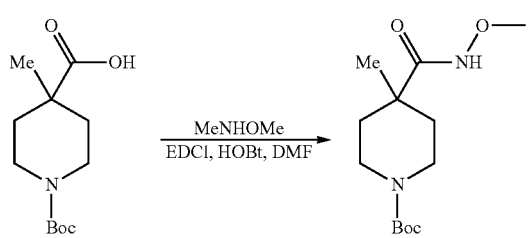 [SMILES: "MeNHOMe" ; CC(C)(C)OC(=O)N1CCC(C)(C(=O)O)CC1 ; "EDCl, HOBt, DMF" ; CONC(=O)C1(C)CCN(C(=O)OC(C)(C)C)CC1]

tert-butyl 4-(methoxy(methyl)carbamoyl)-4-methylpiperidine-1-carboxylate

To a stirred solution of 1-(tert-butoxycarbonyl)-4-methylpiperidine-4-carboxylic acid (0.20 g, 0.82 mmol) in DMF (2 mL) was added N,O-dimethyl hydroxylamine. HCl (0.05 g, 0.82 mmol, 1 equiv), EDCI (0.15 g, 0.82 mmol, 1 equiv) and HOBt (0.12 g, 0.82 mmol, 1 equiv) followed by diisopropyl ethyl amine (0.1 g, 0.82 mmol, 1 equiv) at 0° C. The reaction mixture was stirred at room temperature for 16 h. After completion, the reaction mass was quenched with water and extracted with ether. The organic extract was separated, dried over sodium sulfate and concentrated under reduced pressure. Purification using silica gel chromatography (3% MeOH/CH$_2$Cl$_2$ as eluent) to afford 0.20 g of tert-butyl 4-(methoxy(methyl)carbamoyl)-4-methylpiperidine-1-carboxylate (Yield=85%).

248 tert-butyl 4-benzoyl-4-methylpiperidine-1-carboxylate

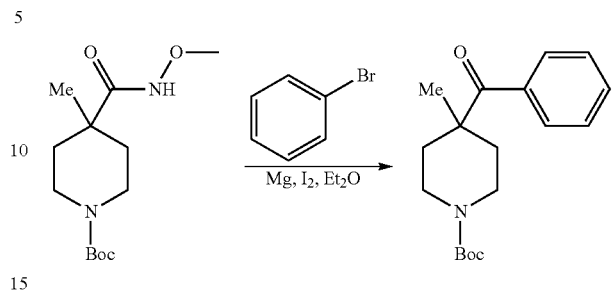

Title compound was prepared from tert-butyl 4-(methoxy(methyl)carbamoyl)-4-methylpiperidine-1-carboxylate (0.20 g, 0.69 mmol) using the general methodology of step 1 of Key Intermediate-I for 4 h. Purification using silica gel chromatography (2% MeOH/CH$_2$Cl$_2$ as eluent) to afford 0.08 g of tert-butyl 4-benzoyl-4-methylpiperidine-1-carboxylate (Yield=37%).

1-(4-benzoyl-4-methyl-1λ$^4$-piperidin-1-yl)-2,2,2-trifluoroethan-1-one

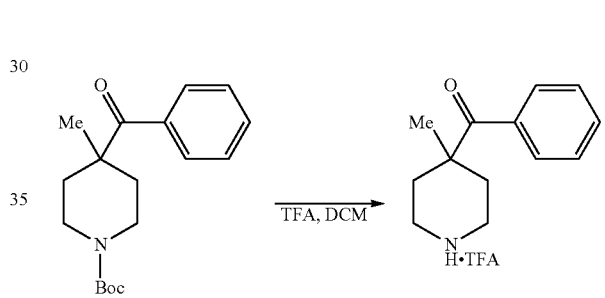

To a solution of tert-butyl 4-benzoyl-4-methylpiperidine-1-carboxylate (0.08 g, 0.26 mmol, and 1 equiv) in CH$_2$Cl$_2$ (2 mL) was added trifluoroacetic acid (1 mL) at 0-5° C. The reaction mixture was stirred at room temperature for 4 h. After completion, the volatiles were evaporated under reduced pressure. The crude was washed with ether to afford 0.04 g of 1-(4-benzoyl-4-methyl-1λ$^4$-piperidin-1-yl)-2, 2, 2-trifluoroethan-1-one (Yield=51%).

(4-Methyl-1-(2-(2-(trifluoromethyl)phenoxy)ethyl) piperidin-4-yl) (phenyl)ethanone

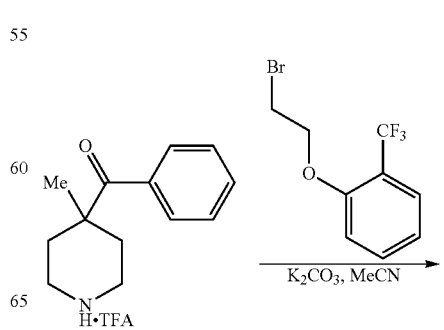

249
-continued

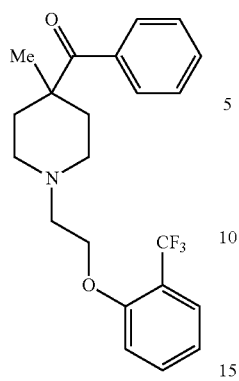

Title compound was prepared from 1-(4-benzoyl-4-methyl-1l4-piperidin-1-yl)-2, 2, 2-trifluoroethan-1-one (0.04 g, 0.13 mmol) using the general methodology of Example-1. The crude was purified using preparative HPLC to afford 0.012 g of 1-(2-(2-(trifluoromethyl)phenoxy)ethyl)piperidin-4-one (Yield=22%). $^1$H NMR (400 MHz, CD$_3$OD): δ 7.69-7.67 (m, 2H) 7.56-7.41 (m, 5H), 7.15 (d, J=8.8 Hz, 1H), 7.04 (t, J=7.6 Hz, 1H), 4.20 (t, J=5.6 Hz, 2H), 2.82-2.73 (m, 4H), 2.40-2.29 (m, 4H), 1.72-1.65 (m, 2H), 1.43 (s, 3H); ESI+MS: m/z 392 ([M+H]$^+$).

Example-107: (4-methyl-1-(2-(2-(trifluoromethyl)phenoxy)ethyl)piperidin-4-yl)(phenyl)methanol

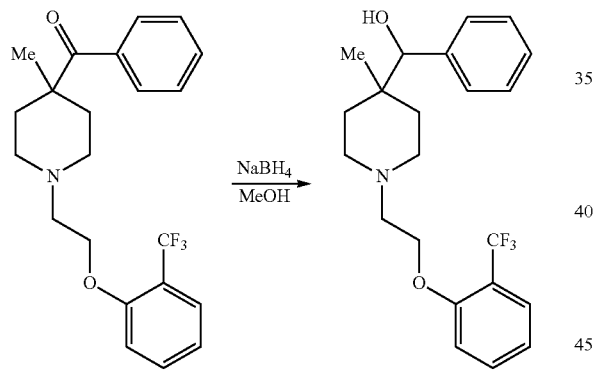

To a stirred solution of (4-Methyl-1-(2-(2-(trifluoromethyl)phenoxy)ethyl)piperidin-4-yl) (phenyl)ethanone (200 mg, 0.51 mmol) in MeOH (10 mL) was added NaBH$_4$ (39 mg, 1.02 mmol) at 0° C. The reaction mixture was stirred at RT for 2 hours. After completion of the reaction, volatiles were concentrated under reduced pressure, water was added and the mixture was extracted with EtOAc. The organic layer was separated, dried over Na$_2$SO$_4$ and concentrated. The crude compound was purified by column chromatography eluting with 2% MeOH in DCM to afford 0.18 g of (4-methyl-1-(2-(2-(trifluoromethyl)phenoxy)ethyl)piperidin-4-yl)(phenyl)methanol (Yield=90%). $^1$H NMR (400 MHz, DMSO-d6): δ 7.62-7.58 (m, 2H), 7.30-7.18 (m, 6H), 7.07 (t, J=7.6 Hz, 1H), 5.13 (d, J=4.0 Hz, 1H), 4.24 (d, J=4.0 Hz, 1H), 4.17 (t, J=6.0 Hz, 2H), 2.72-2.67 (m, 4H), 2.26-2.15 (m, 2H), 1.62-1.55 (m, 2H), 1.39-1.33 (m, 1H), 0.91 (d, J=12.8 Hz, 1H), 0.76 (s, 3H); ESI+MS: m/z 394 ([M+H]$^+$). The enantiomers of 107 were separated using chiral HPLC (method B) and afforded the pure enantiomers 107a and 107b.

250

Example-108: 3-(4-Chlorophenoxy)-3-methyl-1-(2-methyl-1-phenoxypropan-2-yl)piperidine

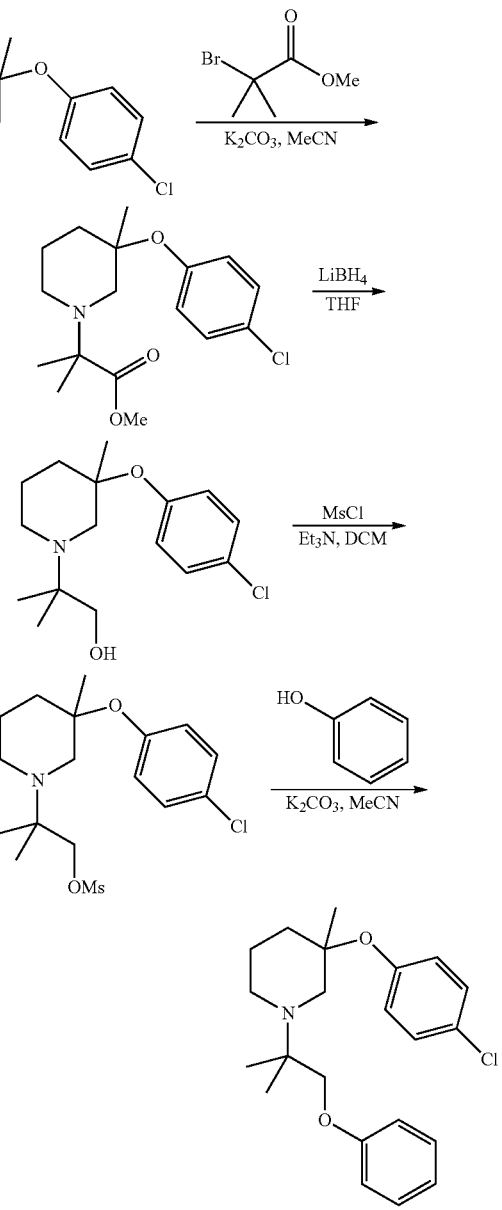

Methyl 2-(3-(4-chlorophenoxy)-3-methylpiperidin-1-yl)-2-methylpropanoate

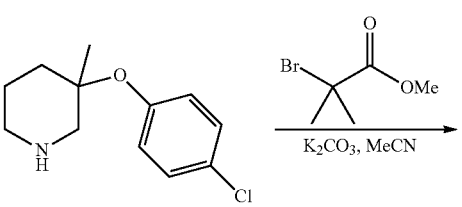

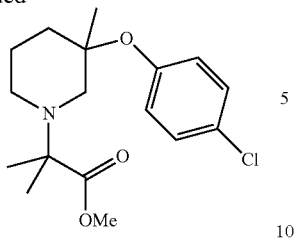

Title compound was prepared from 3-(4-chlorophenoxy)-3-methylpiperidine (0.40 g, 1.77 mmol) using the general methodology of Example-1. Purification using silica gel chromatography (30% EtOAc/Hexanes as eluent) afforded 0.28 g of Methyl 2-(3-(4-chlorophenoxy)-3-methylpiperidin-1-yl)-2-methylpropanoate (Yield=48%).

2-(3-(4-Chlorophenoxy)-3-methylpiperidin-1-yl)-2-methylpropan-1-ol

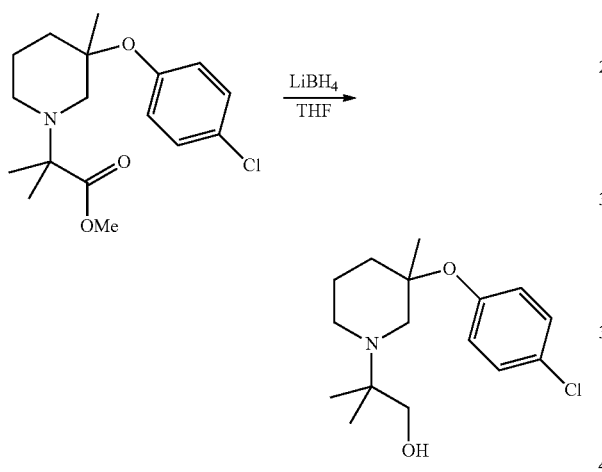

To a solution of Methyl 2-(3-(4-chlorophenoxy)-3-methylpiperidin-1-yl)-2-methylpropanoate (0.12 g, 0.36 mmol) in ethanol (1 mL) and THF (2 mL) was added LiBH$_4$ (0.024 g, 1.1 mmol, 3 equiv) at 0° C. The reaction mixture was stirred at room temperature for 16 h. After completion, the reaction was quenched with cold water and extracted with EtOAc. The organic layer was separated, dried over sodium sulfate and concentrated under pressure. Purification using silica gel chromatography (2% MeOH/CH$_2$Cl$_2$ as eluent) to afford 0.06 g of 2-(3-(4-chlorophenoxy)-3-methylpiperidin-1-yl)-2-methylpropan-1-ol (Yield=54%).

2-(3-(4-Chlorophenoxy)-3-methylpiperidin-1-yl)-2-methylpropyl methanesulfonate

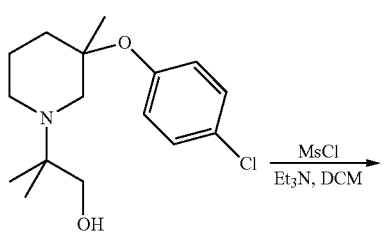

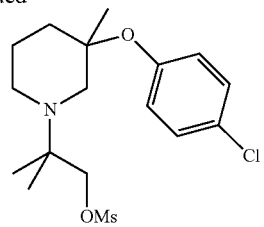

To a stirred solution of 2-(3-(4-chlorophenoxy)-3-methylpiperidin-1-yl)-2-methylpropan-1-ol (0.10 g, 0.33 mmol) in CH$_2$Cl$_2$ (4 mL) were added triethyl amine (0.05 g, 0.50 mmol, 1.5 equiv) and mesyl chloride (0.04 g, 0.40 mmol, 1.2 equiv) at 0° C. The reaction mixture was stirred at room temperature for 16 h. After completion, diluted with water and extracted with CH$_2$Cl$_2$. The organic extract was separated, dried over sodium sulfate and concentrated under reduced pressure to afford 0.095 g of 2-(3-(4-chlorophenoxy)-3-methylpiperidin-1-yl)-2-methylpropyl methanesulfonate (Yield=75%).

3-(4-chlorophenoxy)-3-methyl-1-(2-methyl-1-phenoxypropan-2-yl)piperidine

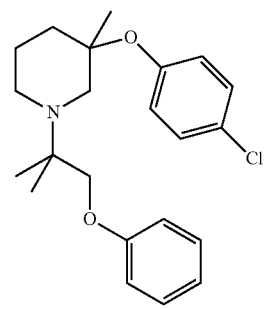

Title compound was prepared from 2-(3-(4-chlorophenoxy)-3-methylpiperidin-1-yl)-2-methylpropyl methanesulfonate (0.09 g, 0.24 mmol) and phenol (0.04 g, 0.48 mmol, 2 equiv) using the general methodology of Example-1. The crude was purified using preparative HPLC to afford 0.015 g of 3-(4-chlorophenoxy)-3-methyl-1-(2-methyl-1-phenoxypropan-2-yl)piperidine (Yield=16%). $^1$H NMR (400 MHz, CD$_3$OD): δ 7.26-7.18 (m, 4H), 7.06-6.94 (m, 5H), 2.69-2.65 (m, 3H), 2.56-2.52 (m, 3H), 1.83-1.75 (m, 1H), 1.73-1.57 (m, 3H), 1.31 (s, 3H), 1.24 (s, 6H); ESI+MS: m/z 374 ([M+H]$^+$).

Example-109: 2-(2-(4-methyl-4-phenoxypiperidin-1-yl)ethoxy)benzonitrile

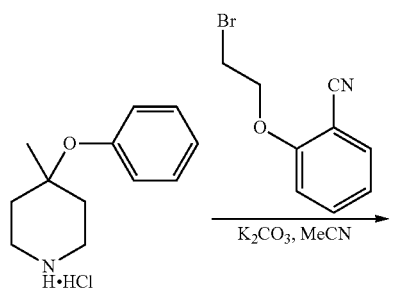

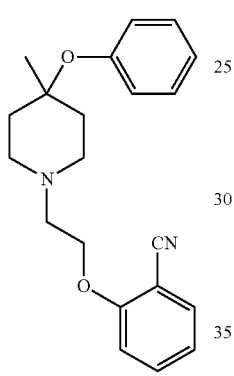

Title compound was prepared from 4-methyl-4-phenoxypiperidine hydrochloride (0.10 g, 0.44 mmol) and 2-(2-bromoethoxy)benzonitrile (0.12 g, 0.52 mmol, 1.2 equiv) using the general methodology of Example-1. Purification using silica gel chromatography (2% MeOH/CH$_2$Cl$_2$ as eluent) to afford 0.12 g of 2-(2-(4-methyl-4-phenoxypiperidin-1-yl)ethoxy)benzonitrile (Yield=80%). $^1$H NMR (500 MHz, CD$_3$OD): δ 7.65 (t, J=8.5 Hz, 2H), 7.29-7.20 (m, 3H), 7.11-7.01 (m, 4H), 4.33 (t, J=5.5 Hz, 2H), 2.98 (t, J=5.5 Hz, 2H), 2.87-2.85 (m, 4H), 2.05-2.03 (m, 2H), 1.79-1.73 (m, 2H), 1.29 (s, 3H); ESI+MS: m/z 337 ([M+H]$^+$).

Example-110: 4-methyl-4-phenoxy-1-(2-(2-(trifluoromethoxy) phenoxy) ethyl) piperidine

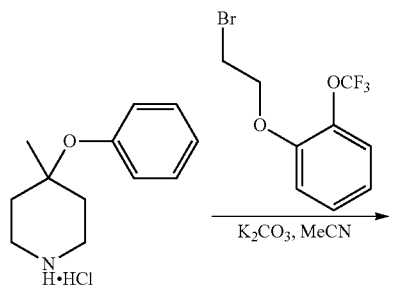

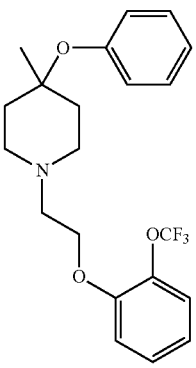

Title compound was prepared from 4-methyl-4-phenoxypiperidine (0.10 g, 0.52 mmol) and 1-(2-bromoethoxy)-2-(trifluoromethoxy)benzene (0.14 g, 0.52 mmol, 1 equiv) using the general methodology of Example-1. The crude was purified using silica gel chromatography (2% MeOH/CH$_2$Cl$_2$ as eluent) to afford 0.12 g of the 4-methyl-4-phenoxy-1-(2-(2-(trifluoromethoxy) phenoxy)ethyl)piperidine (Yield=56%). $^1$H NMR (500 MHz, CD$_3$OD): δ 7.34-7.18 (m, 5H), 7.08-7.00 (m, 4H), 4.26 (t, J=5.5 Hz, 2H), 2.95 (t, J=5.5 Hz, 2H), 2.84-2.83 (m, 4H), 2.05-2.02 (m, 2H), 1.78-1.73 (m, 2H), 1.03 (s, 3H); ESI+MS: m/z 396 ([M+H]$^+$).

Example-111: N,N-dimethyl-2-(2-(4-methyl-4-phenoxypiperidin-1-yl)ethoxy)aniline

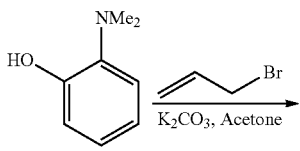

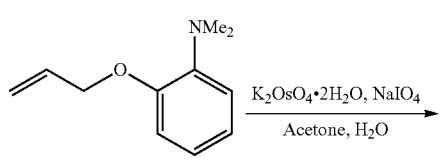

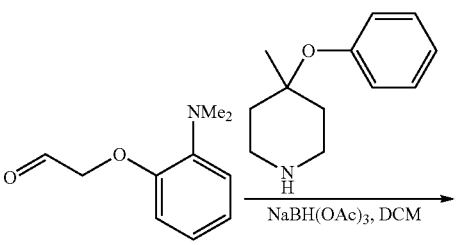

2-(Allyloxy)-N,N-dimethylaniline

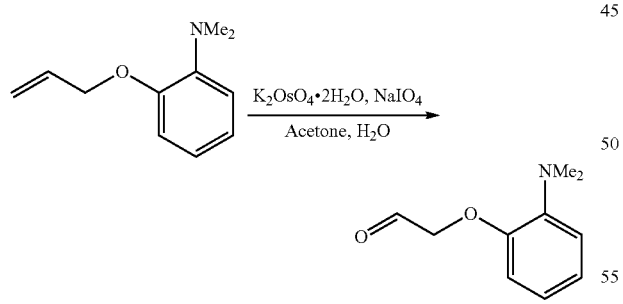

To a solution of 2-(dimethylamino)phenol (0.5 g, 3.64 mmol) in acetone (10 mL) was added potassium carbonate (1.5 g, 10.9 mmol, 3 equiv) at room temperature. Then allyl bromide (0.66 g, 5.4 mmol, 1.5 equiv) was added and maintained the reaction at 80° C. for 16 h. After completion, the reaction mass was filtered and the filtrate was concentrated under reduced pressure. Then water was added to the residue and extracted with EtOAc. The organic extract was separated, dried over anhydrous $Na_2SO_4$ and concentrated under reduced pressure. Purification using silica gel chromatography (15% EtOAc/Hexanes as eluent) to afford 0.9 g of 2-(allyloxy)-N,N-dimethylaniline (Quantitative)

2-(2-(Dimethylamino)phenoxy)acetaldehyde

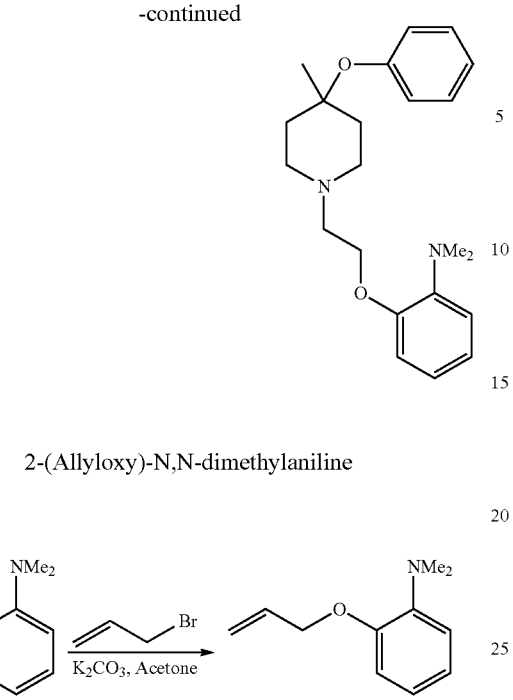

To a stirred solution of 2-(allyloxy)-N,N-dimethylaniline (0.20 g, 1.12 mmol) in mixture of acetone:$H_2O$ (3:2.5 mL) was added potassium osmium(VI) oxide dihydrate (0.015 g, 0.03 mmol, 0.03 equiv) at 0° C. and stirred for 10 min. Then sodium periodate (0.96 g, 4.5 mmol, 4 equiv) was added portion wise to the reaction mixture and stirred at room temperature for 3 h. After completion, the reaction was filtered; the filtrate was concentrated under reduced pressure. The residue was diluted with water and extracted with EtOAc. The organic extract was separated, dried over sodium sulfate and concentrated under reduced pressure. Purification using silica gel chromatography (2% MeOH/$CH_2Cl_2$ as eluent) to afford 0.08 g of 2-(2-(dimethylamino) phenoxy)acetaldehyde (Yield=39%).

N,N-dimethyl-2-(2-(4-methyl-4-phenoxypiperidin-1-yl)ethoxy)aniline

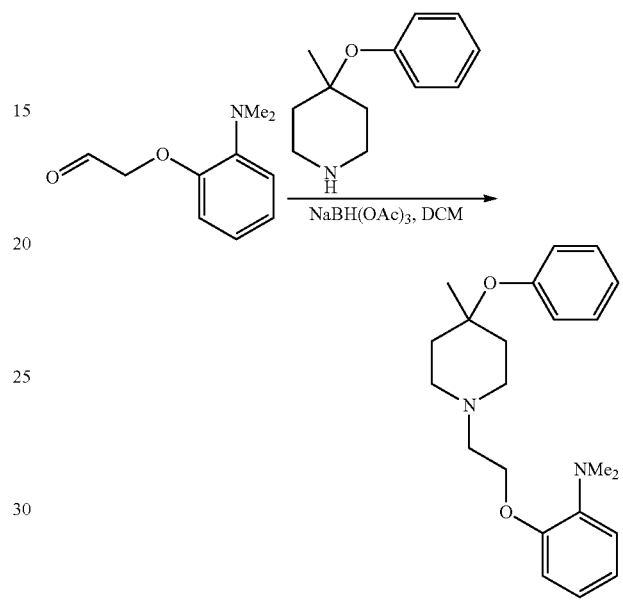

To a stirred solution of 4-methyl-4-phenoxypiperidine (0.10 g, 0.52 mmol) in $CH_2Cl_2$ (3 mL) were added sodium triacetoxyborohydride (0.33 g, 1.56 mmol, 3 equiv), 2-(2-(dimethylamino)phenoxy)acetaldehyde (0.09 g, 0.52 mmol, 1 equiv) and acetic acid (1 mL) at 0° C. The reaction mixture was stirred at room temperature for 16 h. After completion, the reaction mass was diluted with water and extracted with $CH_2Cl_2$. The organic extract was separated, dried over sodium sulfate and concentrated under reduced pressure. Purification using silica gel chromatography (2% MeOH/$CH_2Cl_2$ as eluent) to afford 0.08 g of N, N-dimethyl-2-(2-(4-methyl-4-phenoxypiperidin-1-yl)ethoxy)aniline (Yield=4%). $^1$H NMR (400 MHz, $CD_3OD$): δ 7.28-7.24 (m, 2H), 7.06-6.90 (m, 7H), 4.19 (t, J=6.0 Hz, 2H), 2.95 (t, J=6.0 Hz, 2H), 2.80-2.78 (m, 4H), 2.74 (s, 6H), 2.05-2.00 (m, 2H), 1.77-1.70 (m, 2H), 1.28 (s, 3H); ESI+MS: m/z 355 ([M+H]$^+$).

Example-112: N,4-Dimethyl-N-phenyl-1-(2-(2-(trifluoromethylphenoxy)ethyl) piperidin-4-amine

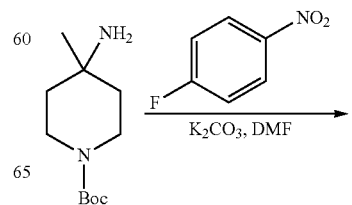

258 tert-butyl 4-methyl-4-((4-nitrophenyl)amino)piperidine-1-carboxylate

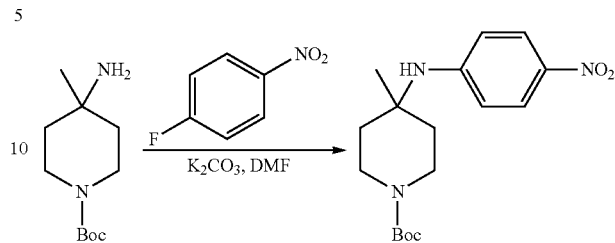

To a stirred solution of tert-butyl 4-amino-4-methylpiperidine-1-carboxylate (0.50 g, 2.33 mmol) in DMF (10 mL) was added $K_2CO_3$ (967 mg, 7.0 mmol) at RT. After 10 minutes, 1-fluoro-4-nitrobenzene (395 mg, 2.8 mmol) was added at RT and the mixture was stirred at 110° C. for 48 h. The reaction was quenched with water and extracted with EtOAc. The organic layer was separated, dried over $Na_2SO_4$, filtered and concentrated. The crude compound was purified by column chromatography eluting with 20% EtOAc in hexane to afford 0.20 g of tert-butyl 4-methyl-4-((4-nitrophenyl)amino)piperidine-1-carboxylate (Yield=25%).

tert-butyl 4-methyl-4-(methyl(4-nitrophenyl)amino)piperidine-1-carboxylate

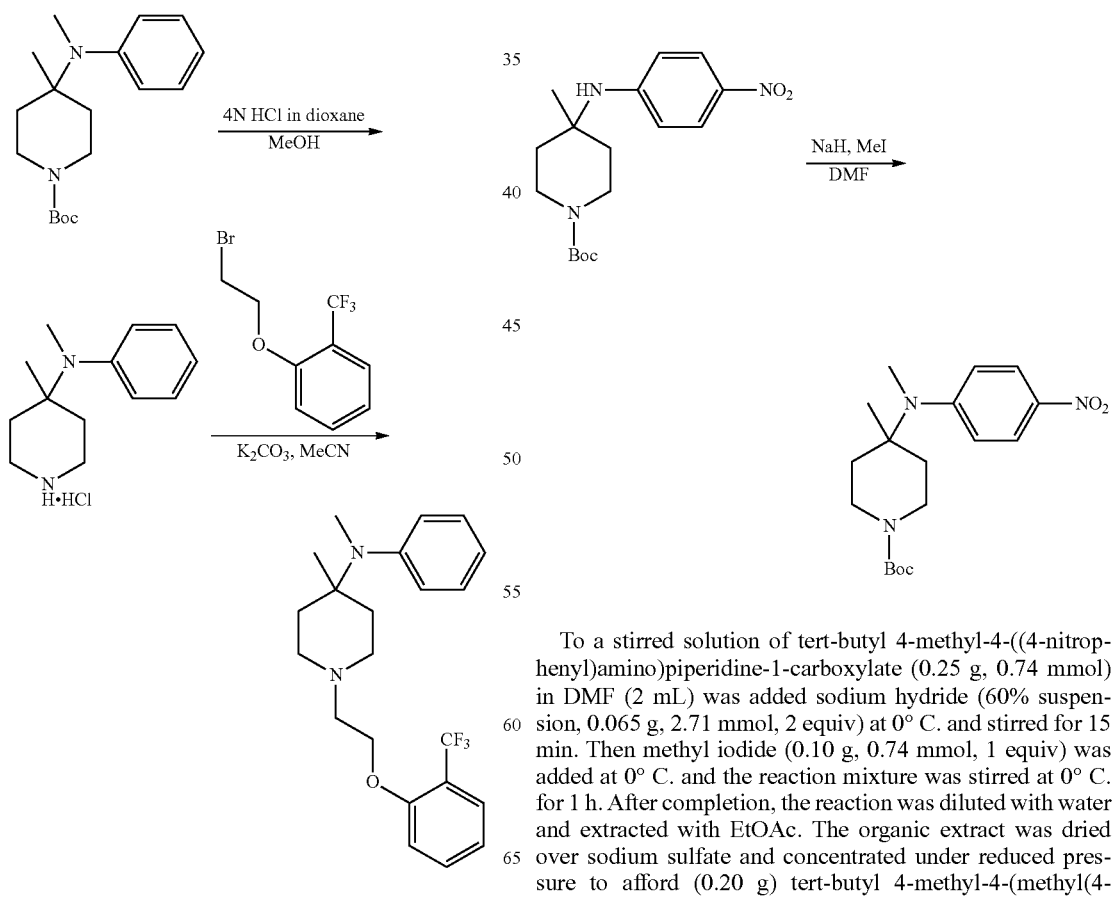

To a stirred solution of tert-butyl 4-methyl-4-((4-nitrophenyl)amino)piperidine-1-carboxylate (0.25 g, 0.74 mmol) in DMF (2 mL) was added sodium hydride (60% suspension, 0.065 g, 2.71 mmol, 2 equiv) at 0° C. and stirred for 15 min. Then methyl iodide (0.10 g, 0.74 mmol, 1 equiv) was added at 0° C. and the reaction mixture was stirred at 0° C. for 1 h. After completion, the reaction was diluted with water and extracted with EtOAc. The organic extract was dried over sodium sulfate and concentrated under reduced pressure to afford (0.20 g) tert-butyl 4-methyl-4-(methyl(4-nitrophenyl)amino)piperidine-1-carboxylate (Yield=77%).

257

-continued

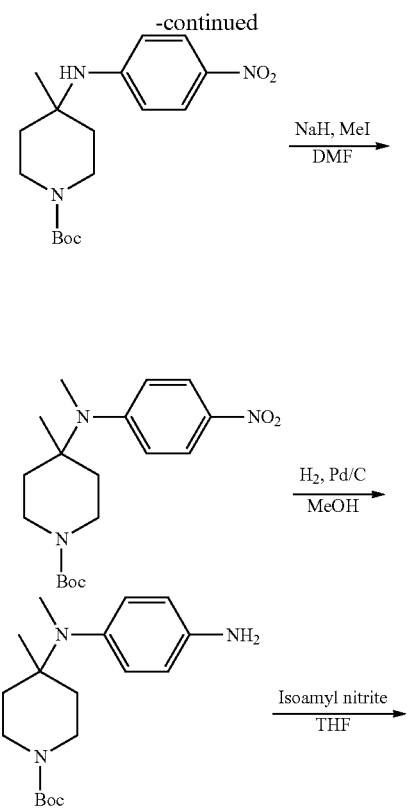

259 tert-butyl 4-((4-aminophenyl)(methyl)amino)-4-methylpiperidine-1-carboxylate

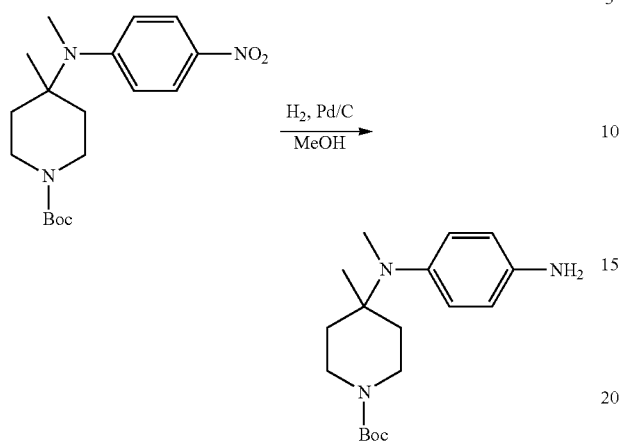

Title compound was prepared from tert-butyl 4-methyl-4-(methyl(4-nitrophenyl)amino) piperidine-1-carboxylate (0.25 g, 0.71 mmol) using general methodology of step 3 of Key-Intermediate-I to afford 0.20 g of tert-butyl 4-((4-aminophenyl)(methyl) amino)-4-methylpiperidine-1-carboxylate (Yield=88%).

tert-butyl 4-methyl-4-(methyl(phenyl)amino)piperidine-1-carboxylate

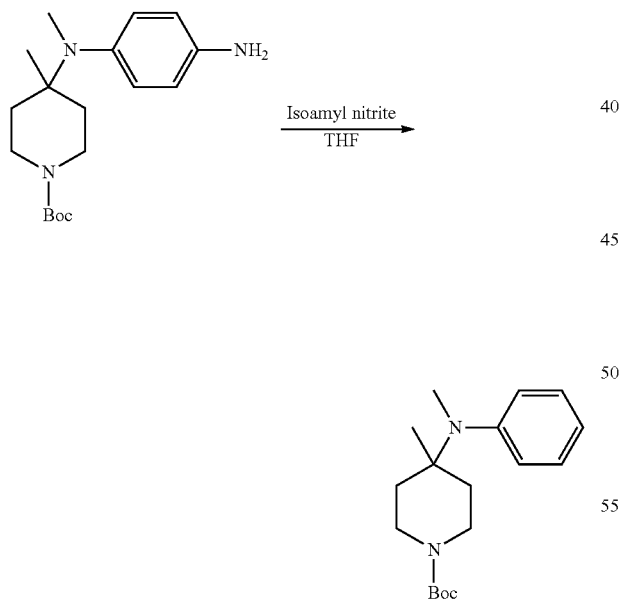

Title compound was prepared from tert-butyl 4-((4-aminophenyl)(methyl)amino)-4-methylpiperidine-1-carboxylate (0.20 g, 0.62 mmol) using the general methodology of step 1 of key Intermediate-VI at 80° C. for 1 h. Purification using silica gel chromatography (20% EtOAc/Hexanes as eluent) to afford 0.09 g of tert-butyl 4-methyl-4-(methyl (phenyl)amino)piperidine-1-carboxylate (Yield=47%).

260

N,4-Dimethyl-N-phenylpiperidin-4-amine hydrochloride

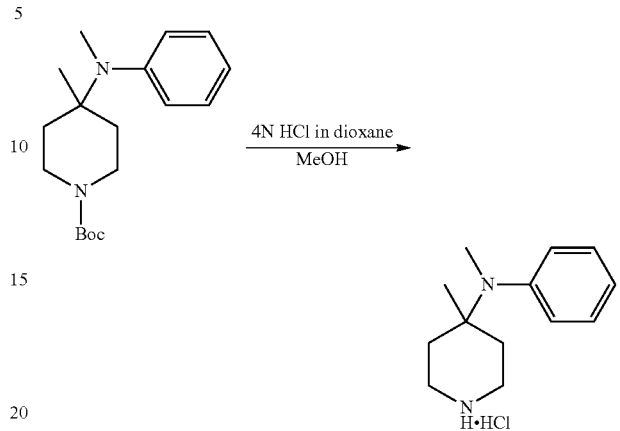

Title compound was prepared from tert-butyl 4-methyl-4-(methyl(phenyl)amino)piperidine-1-carboxylate (0.09 g, 0.29 mmol) using general methodology of step 2 of key Intermediate-VI. The crude was triturated with diethyl ether to afford 0.06 g of N,4-dimethyl-N-phenylpiperidin-4-amine hydrochloride (Yield=84%).

N,4-Dimethyl-N-phenyl-1-(2-(2-(trifluoromethyl)phenoxy)ethyl) piperidine-4-amine

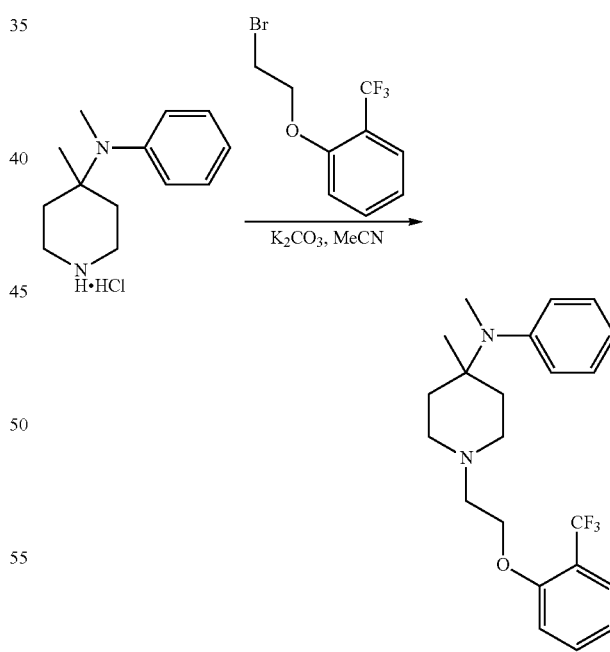

Title compound was prepared from N,4-dimethyl-N-phenylpiperidin-4-amine hydrochloride (0.06 g, 0.25 mmol) using general methodology of Example-1. Purification using silica gel chromatography (10% MeOH/CH$_2$Cl$_2$ as eluent) to afford 0.04 g of the N,4-dimethyl-N-phenyl-1-(2-(2-(trifluoromethyl)phenoxy)ethyl)piperidin-4-amine (Yield=41%).
$^1$H NMR (400 MHz, CD$_3$OD): δ 7.62-7.58 (m, 2H), 7.30-

7.26 (m, 2H), 7.23-7.20 (m, 3H), 7.15-7.11 (m, 2H), 4.38 (t, J=5.2 Hz, 2H), 3.31-3.30 (m, 4H), 2.97-2.95 (m, 2H), 2.73 (s, 3H), 2.05-2.02 (m, 2H), 1.68-1.61 (m, 2H), 1.17 (s, 3H); ESI+MS: m/z 393 ([M+H]$^+$).

Example-113: 1-phenyl-7-(2-(2-(trifluoromethyl)phenoxy)ethyl)-1,7-diazaspiro[3.5] nonane

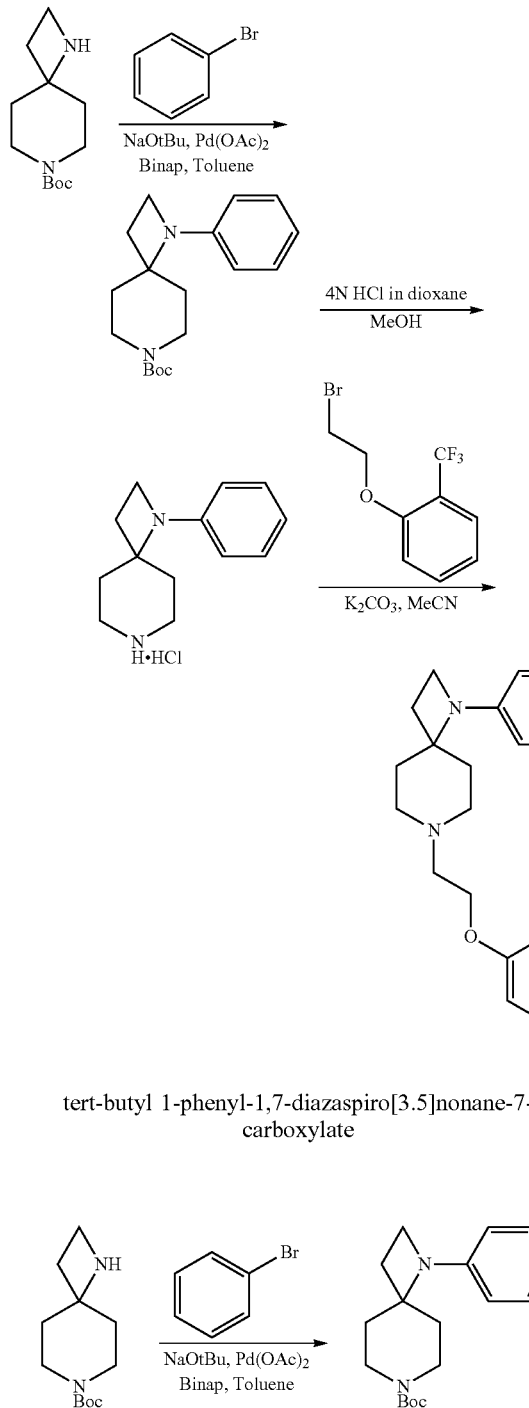

tert-butyl 1-phenyl-1,7-diazaspiro[3.5]nonane-7-carboxylate

To a solution of tert-butyl-1,7-diazaspiro[3.5]nonane-7-carboxylate hydrochloride (0.30 g, 1.14 mmol) in toluene (2 mL) were added sodium tertiary butoxide (0.33 g, 3.40 mmol, 3 equiv), Pd(OAc)$_2$ (0.025 g, 0.11 mmol, 0.1 equiv) followed by (+/−) BINAP (0.035 g, 0.05 mmol, 0.05 equiv) at room temperature and degassed for 15 min with argon. The reaction mixture was maintained at 110° C. for 16 h in sealed tube. After completion, the reaction was diluted with water and extracted with EtOAc. The organic extract was separated, dried over sodium sulfate and concentrated under reduced pressure. Purification using silica gel chromatography (10% EtOAc in Hexane as eluent) to afford 0.15 g of tert-butyl 1-phenyl-1, 7-diazaspiro[3.5]nonane-7-carboxylate (Yield=43%).

1-Phenyl-1,7-diazaspiro[3.5]nonane hydrochloride

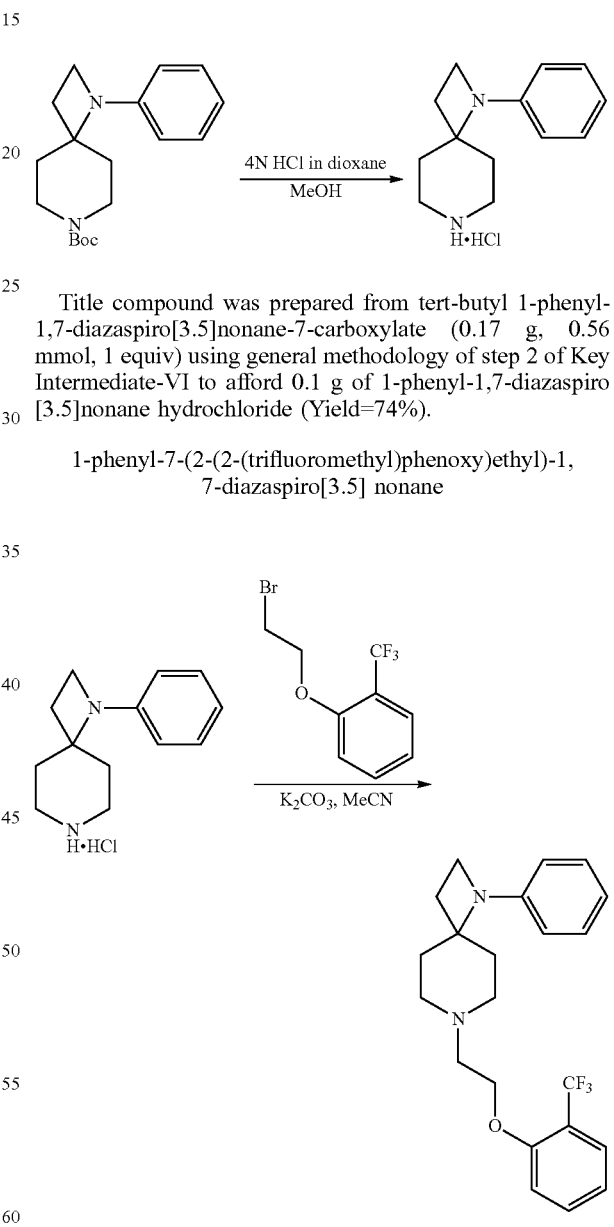

Title compound was prepared from tert-butyl 1-phenyl-1,7-diazaspiro[3.5]nonane-7-carboxylate (0.17 g, 0.56 mmol, 1 equiv) using general methodology of step 2 of Key Intermediate-VI to afford 0.1 g of 1-phenyl-1,7-diazaspiro[3.5]nonane hydrochloride (Yield=74%).

1-phenyl-7-(2-(2-(trifluoromethyl)phenoxy)ethyl)-1,7-diazaspiro[3.5] nonane

Title compound was prepared from 1-phenyl-1,7-diazaspiro[3.5]nonane hydrochloride (0.10 g, 0.42 mmol) using the general methodology of Example-1. The crude was purified using preparative HPLC to afford 0.012 g of the 1-phenyl-7-(2-(2-(trifluoromethyl)phenoxy)ethyl)-1,7-diazaspiro[3.5]nonane (Yield=7%). $^1$H NMR (400 MHz, CD$_3$OD): δ 7.58-7.54 (m, 2H), 7.19-7.11 (m, 3H), 7.05 (t, J=7.6 Hz, 1H), 6.67 (t, J=7.6 Hz, 1H), 6.57-6.66 (m, 2H), 4.25 (t, J=5.6 Hz, 2H), 3.69-3.65 (m, 2H), 3.06-3.03 (m, 2H), 2.87 (t, J=5.6 Hz, 2H), 2.36-2.25 (m, 4H), 2.14 (t, J=7.2 Hz, 2H), 1.74-1.71 (m, 2H); ESI+MS: m/z 391 ([M+H]$^+$).

Example-114: 4-benzyl-1-(2-(2-(trifluoromethyl)phenoxy)ethyl)piperidin-4-ol

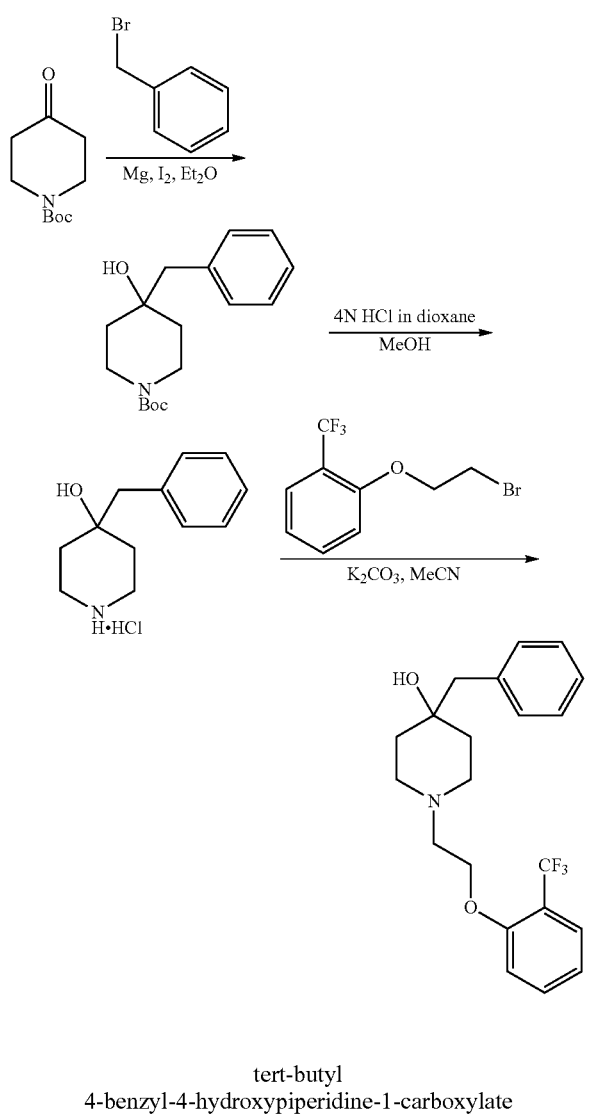

tert-butyl 4-benzyl-4-hydroxypiperidine-1-carboxylate

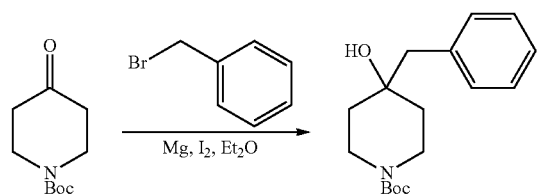

Title compound was prepared from tert-butyl 4-oxopiperidine-1-carboxylate (3 g, 15.06 mmol) and (bromomethyl)benzene (5.15 g, 30.1 mmol, 2 equiv) using general methodology of step 1 of key Intermediate-I for 4 h. Purification using silica gel chromatography (20% EtOAc/Hexanes as eluent) to afford 2 g of tert-butyl 4-benzyl-4-hydroxypiperidine-1-carboxylate (Yield=45%).

4-benzylpiperidin-4-ol hydrochloride

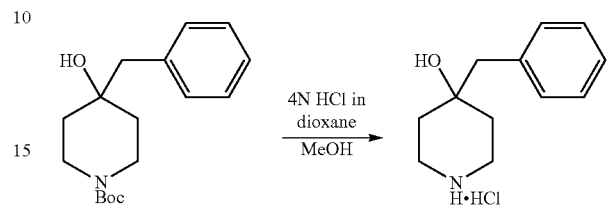

Title compound was prepared from tert-butyl 4-benzyl-4-hydroxypiperidine-1-carboxylate (1 g, 3.43 mmol) using general methodology of step 2 of key intermediate-VI to afford 0.75 g of 4-benzylpiperidin-4-ol hydrochloride (Yield=96%).

4-benzyl-1-(2-(2-(trifluoromethyl)phenoxy)ethyl)piperidin-4-ol

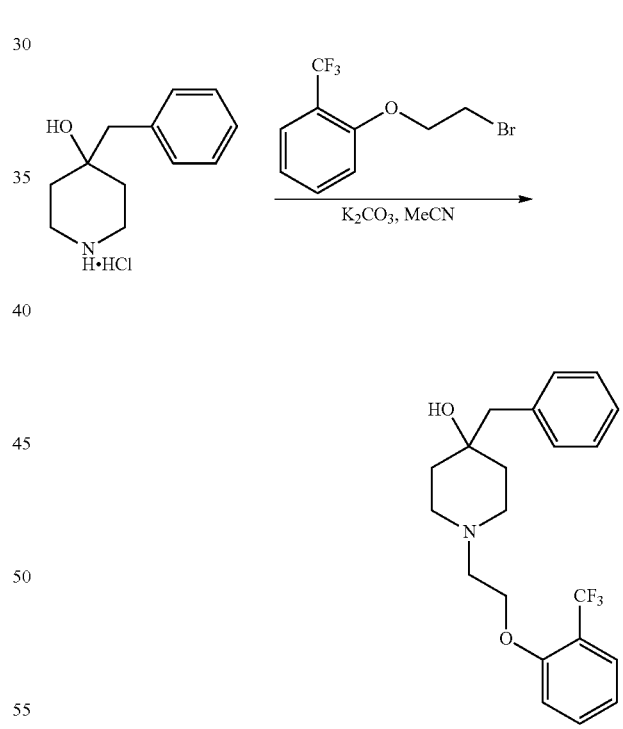

Title compound was prepared from 4-benzylpiperidin-4-ol hydrochloride (0.75 g, 3.29 mmol) using the general methodology of Example-1. Purification using silica gel chromatography (5% MeOH/CH$_2$Cl$_2$ as eluent) to afford 0.8 g of the 4-benzyl-1-(2-(2-(trifluoromethyl)phenoxy)ethyl)piperidin-4-ol (Yield=64%). $^1$H NMR (400 MHz, CD$_3$OD): δ 7.57-7.53 (m, 2H), 7.28-7.15 (m, 6H), 7.05 (t, J=7.6 Hz, 1H), 4.23 (t, J=5.6 Hz, 2H), 2.89 (t, J=5.6 Hz, 2H), 2.84-2.81 (m, 2H), 2.76 (s, 2H), 2.65-2.59 (m, 2H), 1.76-1.68 (m, 2H), 1.56-1.53 (m, 2H); ESI+MS: m/z 380 ([M+H]$^+$).

Example-115: 4-benzyl-4-fluoro-1-(2-(2-(trifluoromethyl)phenoxy)ethyl)piperidine

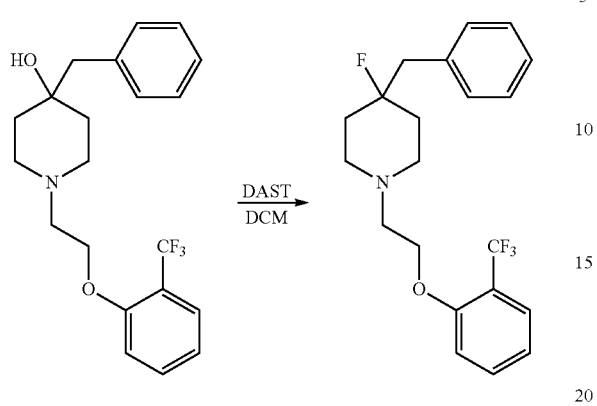

To a stirred solution of 4-benzyl-1-(2-(2-(trifluoromethyl)phenoxy)ethyl)piperidin-4-ol (0.2 g, 0.52 mmol) in CH$_2$Cl$_2$ (5 mL) was added DAST (0.10 g, 0.63 mmol, 1.2 equiv) at −78° C. The reaction mixture was stirred at 0° C. for 1 h. After completion, the reaction mass was quenched with saturated NaHCO$_3$ solution and extracted with CH$_2$Cl$_2$. The organic extract was dried over sodium sulfate and concentrated under reduced pressure. Purification using silica gel chromatography (4% MeOH/CH$_2$Cl$_2$ as eluent) to afford 0.05 g of 4-benzyl-4-fluoro-1-(2-(2-(trifluoromethyl)phenoxy)ethyl) (Yield=25%). $^1$H NMR (400 MHz, CD$_3$OD): δ 7.57-7.53 (m, 2H), 7.29-7.15 (m, 6H), 7.04 (t, J=7.6 Hz, 1H), 4.23 (t, J=5.6 Hz, 2H), 2.94 (s, 1H), 2.88-2.85 (m, 5H), 2.51-2.45 (m, 2H), 1.83-1.69 (m, 4H); ESI+MS: m/z 382 ([M+H]$^+$).

Example-116: 3-(4-Methyl-4-phenoxypiperidin-1-yl)-1-(2-(trifluoromethyl)phenyl) propan-1-one

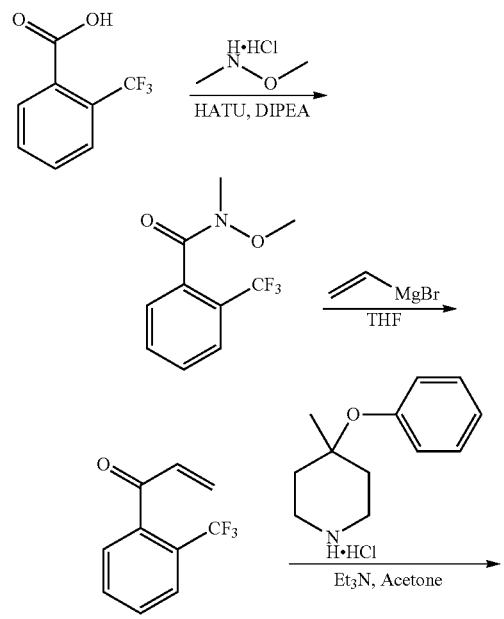

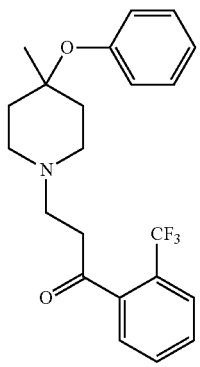

N-Methoxy-N-methyl-2-(trifluoromethyl)benzamide

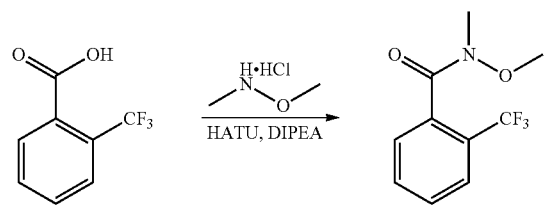

To a stirred solution of 2-(trifluoromethyl)benzoic acid (3 g, 15.78 mmol) and N,O-dimethylhydroxylamine hydrochloride (1.84 g, 18.94 mmol, 1.2 equiv) in DMF (20 mL) was added HATU (9.0 g, 23.7 mmol) and DIPEA (5.47 mL, 31.6 mmol). The reaction mixture was stirred at RT for 16 h. After completion of the reaction (monitored by TLC), the mixture was diluted with water and extracted with ethyl acetate. The organic layer was dried over anhydrous Na$_2$SO$_4$ and concentrated. Purification using silica gel column chromatography (50% EtOAc/Hexanes as eluent) afforded 3 g of N-methoxy-N-methyl-2-(trifluoromethyl) benzamide (Yield=82%).

1-(2-(trifluoromethyl)phenyl)prop-2-en-1-one

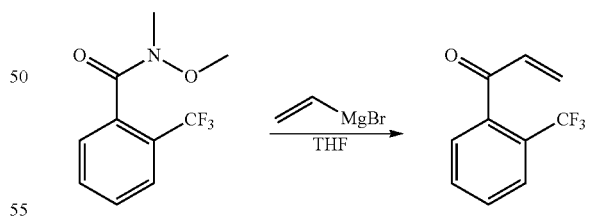

To a solution N-methoxy-N-methyl-2-(trifluoromethyl) benzamide (1 g, 4.29 mmol) in THF (10 mL) was added vinyl magnesium bromide (5.2 mL, 5.15 mmol, 1.2 equiv) under argon atmosphere at 0° C.; the reaction mixture was stirred at room temperature for 12 h, quenched with saturated ammonium chloride and extracted with ethyl acetate. The organic extract was dried over sodium sulfate and concentrated under reduced pressure. Purification using silica gel column chromatography (20% EtOAc/Hexanes as eluent) to afford 0.2 g of 1-(2-(trifluoromethyl)phenyl)prop-2-en-1-one (Yield=23%).

3-(4-methyl-4-phenoxypiperidin-1-yl)-1-(2-(trifluoromethyl)phenyl) propan-1-one

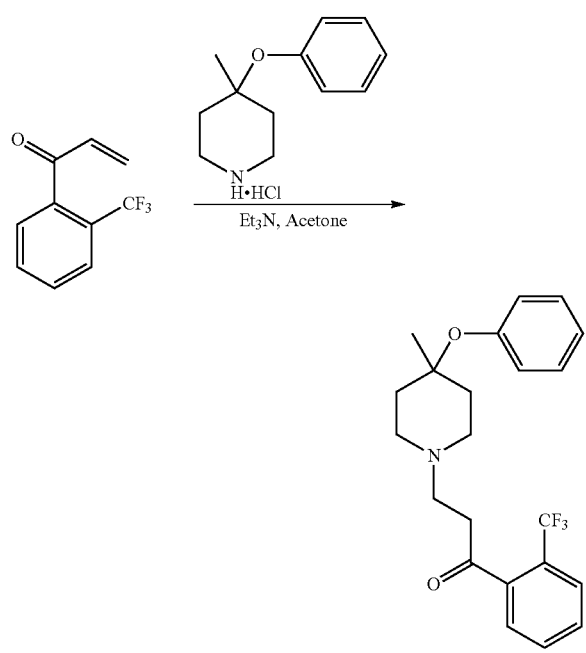

To a solution of 4-methyl-4-phenoxypiperidine hydrochloride (0.1 g, 0.43 mmol) and 1-(2-(trifluoromethyl)phenyl)prop-2-en-1-one (0.088 g, 0.43 mmol, 1 equiv) in acetone (0.5 mL) under argon atmosphere was added triethylamine (0.18 mL, 1.30 mmol, 3 equiv) at room temperature. The reaction mixture was heated at 80° C. in sealed tube for 16 h. After completion, the reaction was diluted with water and extracted with ethyl acetate. The organic extract was dried over sodium sulfate, filtered and concentrated under reduced pressure. Purification using silica gel column chromatography to afford 0.05 g of 3-(4-methyl-4-phenoxypiperidin-1-yl)-1-(2-(trifluoromethyl)phenyl)propan-1-one (Yield=29%). $^1$H NMR (400 MHz, DMSO-d$_6$): δ 7.83-7.68 (m, 4H), 7.27 (t, J=7.6 Hz, 2H), 7.06-6.96 (m, 3H), 3.09-3.07 (m, 2H), 2.67-2.66 (m, 2H), 2.46-2.44 (m, 4H), 1.84-1.82 (m, 2H), 1.59-1.53 (m, 2H), 1.22 (s, 3H); ESI+MS: m/z 392 ([M+H]$^+$).

Example-117: 4-(4-(4-chlorophenoxy)-4-methylpiperidin-1-yl)-2-(2-(trifluoromethyl)phenyl)butan-2-ol

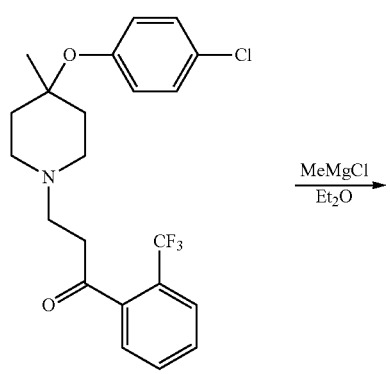

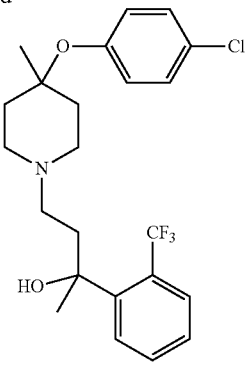

Title compound was prepared from 3-(4-(4-chlorophenoxy)-4-methylpiperidin-1-yl)-1-(2-(trifluoromethyl)phenyl)propan-1-one (0.05 g, 0.12 mmol) using the general methodology of step 1 key intermediate-I. Purification by column chromatography (2% MeOH/CH$_2$Cl$_2$ as eluent) to afford 0.02 g of 4-(4-(4-chlorophenoxy)-4-methylpiperidin-1-yl)-2-(2-(trifluoromethyl)phenyl)butan-2-ol (Yield=39%). $^1$H NMR (400 MHz, DMSO-d$_6$): δ 7.75-7.73 (m, 1H), 7.65-7.63 (m, 1H), 7.60-7.56 (m, 1H), 7.40 (t, J=7.6 Hz, 1H), 7.31-7.27 (m, 2H), 7.00-6.96 (m, 2H), 6.48 (s, 1H), 2.58-2.55 (m, 1H), 2.43-2.36 (m, 2H), 2.34-2.30 (m, 3H), 2.28-2.11 (m, 1H), 1.97-1.90 (m, 1H), 1.80-1.78 (m, 2H), 1.57-1.51 (m, 2H), 1.48 (s, 3H), 1.20 (s, 3H); ESI+MS: m/z 442 ([M+H]$^+$).

Example-118: 4-Methyl-4-phenoxy-1-(3-(2-(trifluoromethyl)phenyl)propyl)piperidine

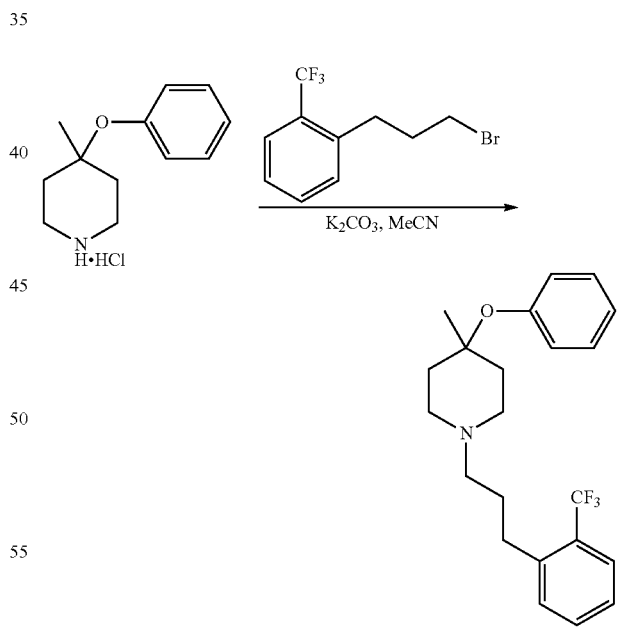

Title compound was prepare from 4-methyl-4-phenoxypiperidine hydrochloride (0.1 g, 0.43 mmol) and 1-(3-bromopropyl)-2-(trifluoromethyl)benzene (0.11 g, 0.43 mmol, 1 equiv) using the general methodology of Example-1. Purification by column chromatography (2% MeOH/CH$_2$Cl$_2$ as eluent) to afford 0.11 g of 4-methyl-4-phenoxy-1-(3-(2-(trifluoromethyl)phenyl)propyl)piperidine (Yield=65%). $^1$H NMR (400 MHz, CD$_3$OD): δ 7.63 (d, J=8.0 Hz, 1H), 7.54 (t, J=7.6 Hz, 1H), 7.46 (d, J=7.6 Hz, 1H), 7.35 (t, J=7.6 Hz, 1H), 7.29-7.23 (m, 2H), 7.07-7.03 (m, 1H), 6.98 (d, J=8.0 Hz, 2H), 2.84-2.81 (m, 6H), 2.70-2.67 (m, 2H), 2.07-2.04 (m, 2H), 1.96-1.88 (m, 2H), 1.78-1.71 (m, 2H), 1.27 (s, 3H); ESI+MS: m/z 378 ([M+H]$^+$).

Example-119: 4-methyl-4-phenoxy-1-(3-(2-(trifluoromethyl)phenyl)propyl)piperidine

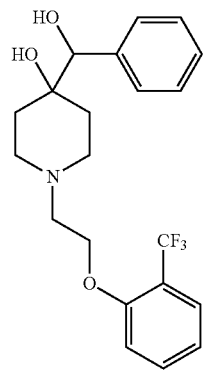

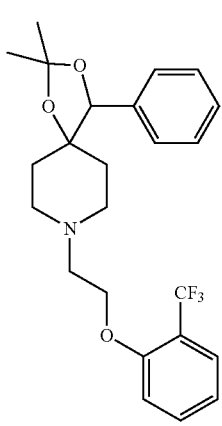

To a stirred solution of 4-(hydroxy(phenyl)methyl)-1-(2-(2-(trifluoromethyl) phenoxy) ethyl)piperidin-4-ol (0.04 g, 0.1 mmol) in acetone (5 mL) under argon atmosphere were added 2,2-dimethoxy propane (0.105 g 1.01 mmol, 10 equiv) and 10-camphorsulfonic acid (0.011 g, 0.051 mmol, 0.5 equiv) at room temperature and the reaction was stirred for 5 h. After completion, the reaction was quenched with saturated NaHCO$_3$ and extracted with CH$_2$Cl$_2$. The organic layer was dried over sodium sulfate, filtered and concentrated under reduced pressure. Purification using silica gel column chromatography (2% MeOH/CH$_2$Cl$_2$ as eluent) afforded 0.015 g of 4-methyl-4-phenoxy-1-(3-(2-(trifluoromethyl) phenyl) propyl)piperidine (Yield=34%). $^1$H NMR (400 MHz, CD$_3$OD): δ 7.55-7.51 (m, 2H), 7.39-7.30 (m, 5H), 7.12 (d, J=8.4 Hz, 1H), 7.03 (t, J=7.6 Hz, 1H), 4.87 (s, 1H), 4.17 (t, J=5.6 Hz, 2H), 2.83-2.80 (m, 1H), 2.75-2.72 (m, 2H), 2.63-2.56 (m, 1H), 2.53-2.52 (m, 1H), 2.49-2.46 (m, 1H) 1.94-1.93 (m, 1H), 1.79-1.77 (m, 1H), 1.56 (s, 3H), 1.47 (s, 3H), 1.47-1.46 (m, 1H), 0.90-0.79 (m, 1H); ESI+MS: m/z 436 ([M+H]$^+$).

Example-120: 4-(4-chlorophenoxy)-4-methyl-1-(4-phenoxybutyl)piperidine

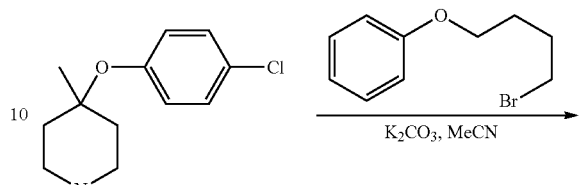

Title compound was prepared from 4-(4-chlorophenoxy)-4-methylpiperidine (0.1 g, 0.44 mmol) and (4-bromobutoxy)benzene (0.122 g, 0.53 mmol, 1.2 equiv) using the general methodology of Example-1. The crude was purified by preparative HPLC purification to afford 0.018 g of 4-(4-chlorophenoxy)-4-methyl-1-(4-phenoxybutyl)piperidine (Yield=11%). $^1$H NMR (400 MHz, CD$_3$OD): δ 7.26-7.22 (m, 4H), 6.99-6.97 (m, 2H), 6.91-6.87 (m, 3H), 4.00 (t, J=6.0 Hz, 2H), 2.65-2.57 (m, 4H), 2.52-2.48 (m, 2H), 2.02-1.97 (m, 2H), 1.81-1.68 (m, 6H), 1.27 (s, 3H); ESI+MS: m/z 374 ([M+H]$^+$).

Example-121: 4-Methyl-4-phenoxy-1-(4-phenoxybutyl)piperidine

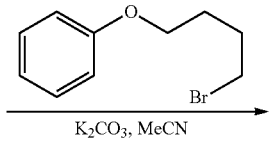

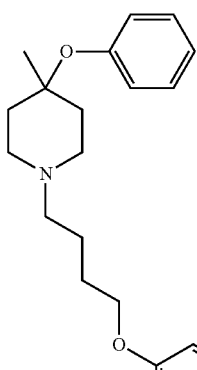

Title compound was prepared from 4-(4-chlorophenoxy)-4-methylpiperidine (0.09 g, 0.4 mmol) and (4-bromobutoxy)benzene (0.11 g, 0.47 mmol, 1.2 equiv) using the general methodology of Example-1. The crude was purified by preparative HPLC purification to afford 0.008 g of 4-methyl-4-phenoxy-1-(4-phenoxybutyl)piperidine (Yield=6%). $^1$H NMR (400 MHz, CD$_3$OD): δ 7.28-7.22 (m, 4H), 7.06-6.98 (m, 3H), 6.90-6.87 (m, 3H), 4.00 (t, J=6.0 Hz, 2H), 2.64-2.63 (m, 4H), 2.51-2.47 (m, 2H), 2.03-1.98 (m, 2H), 1.81-1.67 (m, 6H), 1.27 (s, 3H); ESI+MS: m/z 340 ([M+H]$^+$).

Example-122: 4-(4-Chlorophenoxy)-1-(2-(5-fluoro-2-(trifluoromethyl)phenoxy)ethyl)-4-methylpiperidine

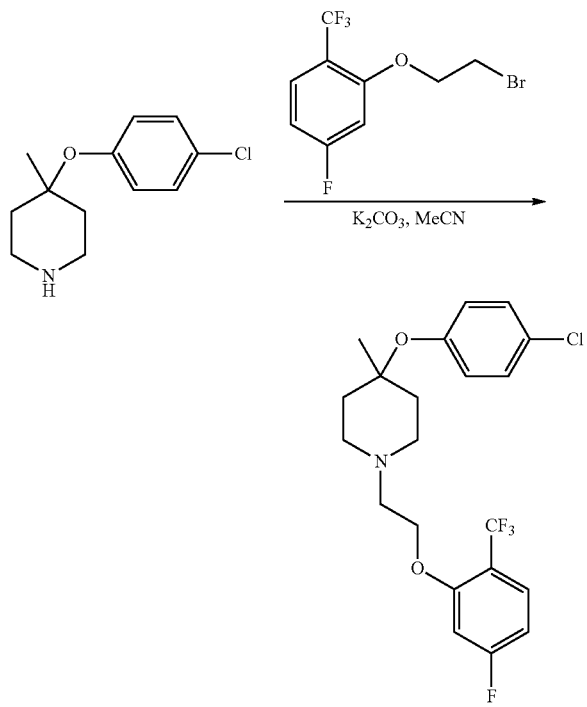

Title compound was prepared from 4-(4-chlorophenoxy)-4-methylpiperidine (0.12 g, 0.53 mmol) and 2-(2-bromoethoxy)-4-fluoro-1-(trifluoromethyl)benzene using the general methodology of Example-1. Purification by column chromatography (2% MeOH/CH$_2$Cl$_2$ as eluent) to afford 0.01 g of 4-(4-chlorophenoxy)-1-(2-(5-fluoro-2-(trifluoromethyl)phenoxy)ethyl)-4-methylpiperidine (Yield=4%). $^1$H NMR (400 MHz, CD$_3$OD): δ 7.63-7.60 (m, 1H), 7.27-7.23 (m, 2H), 7.04-6.96 (m, 3H), 6.83-6.78 (m, 1H), 4.26 (t, J=5.6 Hz, 2H), 2.93 (t, J=5.2 Hz, 2H), 2.79-2.76 (m, 4H), 2.03-1.97 (m, 2H), 1.76-1.69 (m, 2H), 1.28 (s, 3H); ESI+MS: m/z 432 ([M+H]$^+$).

Example-123: 4-methoxy-4-methyl-1-(2-(2-(trifluoromethyl)phenoxy)ethyl) piperidine

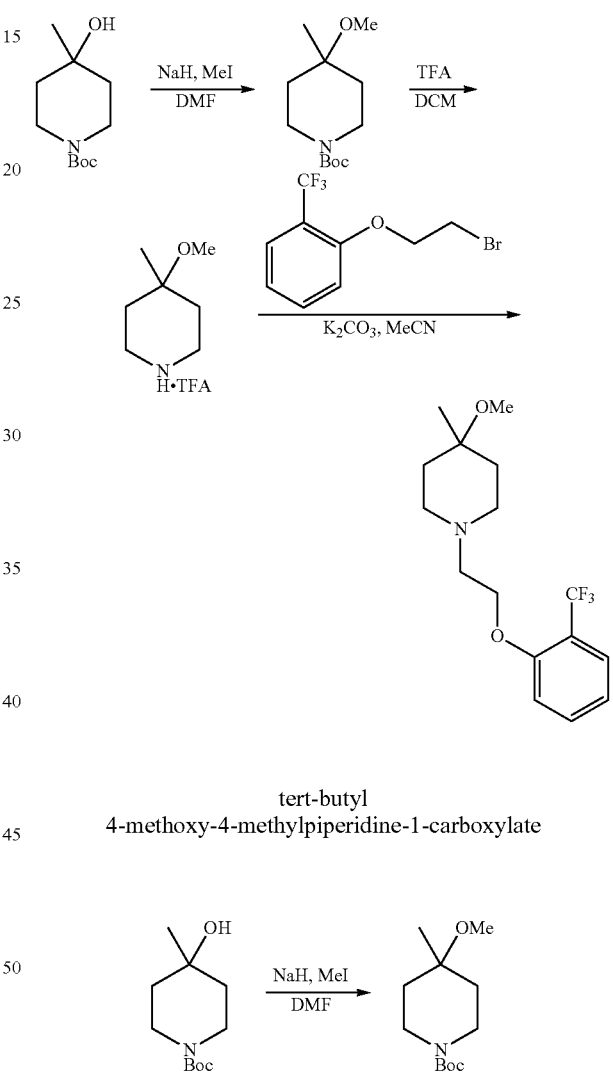

tert-butyl 4-methoxy-4-methylpiperidine-1-carboxylate

To a solution of tert-butyl 4-hydroxy-4-methylpiperidine-1-carboxylate (0.15 g, 0.69 mmol) in DMF (0.5 mL) under argon atmosphere were added sodium hydride (60%, suspension, 0.11 g, 4.67 mmol, 4 equiv) and iodomethane (0.198 mL, 1.3 mmol, 2 equiv) at 0° C. The reaction mixture was stirred at room temperature for 12 h. After completion, the reaction was quenched with ice cold water and extracted with EtOAc. The combined organic extract was dried sodium sulfate and concentrated under reduced pressure. Purification using silica gel column chromatography (10% EtOAc/Hexanes as eluent) to afford 0.1 g of tert-butyl 4-methoxy-4-methylpiperidine-1-carboxylate (Yield=63%).

2,2,2-trifluoro-1-(4-methoxy-4-methyl-1λ⁴-piperidin-1-yl)ethan-1-one

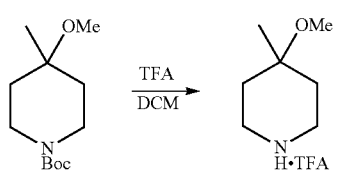

To a solution of tert-butyl 4-methoxy-4-methylpiperidine-1-carboxylate (0.1 g, 0.43 mmol) in CH$_2$Cl$_2$ was added trifluoroacetic acid (0.16 mL, 2.18 mmol, 5 equiv) at 0-5° C. The reaction was stirred at room temperature for 4 h. After completion, the volatiles were removed under reduced pressure to afford 0.1 g of 2,2,2-trifluoro-1-(4-methoxy-4-methyl-1λ⁴-piperidin-1-yl)ethan-1-one (Quantitative).

4-methoxy-4-methyl-1-(2-(2-(trifluoromethyl)phenoxy)ethyl) piperidine

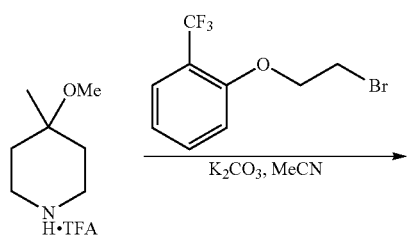

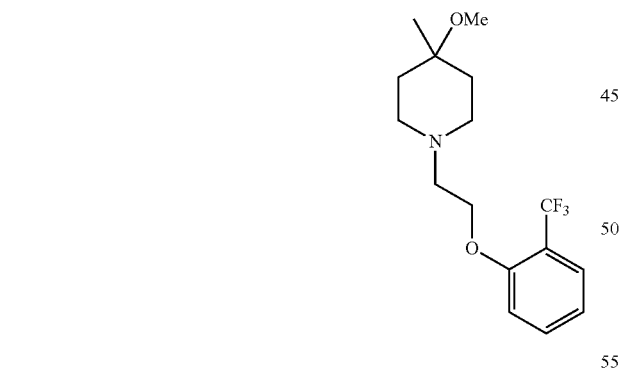

Title compound was prepared from 4-methoxy-4-methylpiperidine (0.1 g, 0.4 mmol) using the general methodology of Example-1. Purification using column chromatography (2% MeOH/CH$_2$Cl$_2$ as eluent) to afford 0.1 g of 4-(4-chlorophenoxy)-1-(2-(5-fluoro-2-(trifluoromethyl)phenoxy)ethyl)-4-methylpiperidine (Yield=69%). ¹H NMR (400 MHz, CD$_3$OD): δ 7.59-7.55 (m, 2H), 7.19 (d, J=8.8 Hz, 1H), 7.08 (t, J=8.0 Hz, 1H), 4.30 (t, J=5.6 Hz, 2H), 3.19 (s, 3H), 3.06-3.03 (m, 2H), 2.90-2.87 (m, 2H), 2.76-2.70 (m, 2H), 1.85 (d, J=13.2 Hz, 2H), 1.67-1.60 (m, 2H), 1.18 (s, 3H); ESI+MS: m/z 318 ([M+H]⁺).

Example-124: 4-Methyl-1-(2-(2-(trifluoromethyl)phenoxy)ethyl)piperidin-4-ol

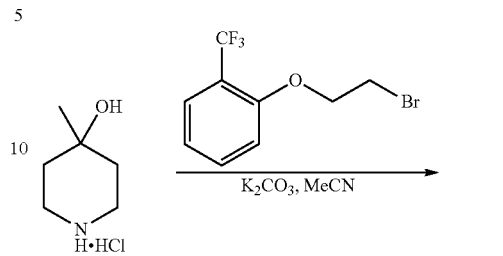

Title compound was prepared from 4-methylpiperidin-4-ol hydrochloride (3 g, 19.7 mmol) using the general methodology of Example-1. Purification using column chromatography (2% MeOH/CH$_2$Cl$_2$ as eluent) to afford 4 g of 4-methyl-1-(2-(2-(trifluoromethyl)phenoxy)ethyl)piperidin-4-ol (Yield=67%). ¹H NMR (400 MHz, CD$_3$OD): δ 7.58-7.55 (m, 2H), 7.18 (d, J=8.8 Hz, 1H), 7.06 (t, J=7.6 Hz, 1H), 4.28 (t, J=5.2 Hz, 2H), 2.99-2.97 (m, 2H), 2.83-2.72 (m, 4H), 1.72-1.63 (m, 4H), 1.22 (s, 3H); ESI+MS: m/z 304 ([M+H]⁺).

Example-125: 4-(4-Chlorophenoxy)-4-methyl-1-(2-(4-(trifluoromethyl)phenoxy) ethyl) piperidine

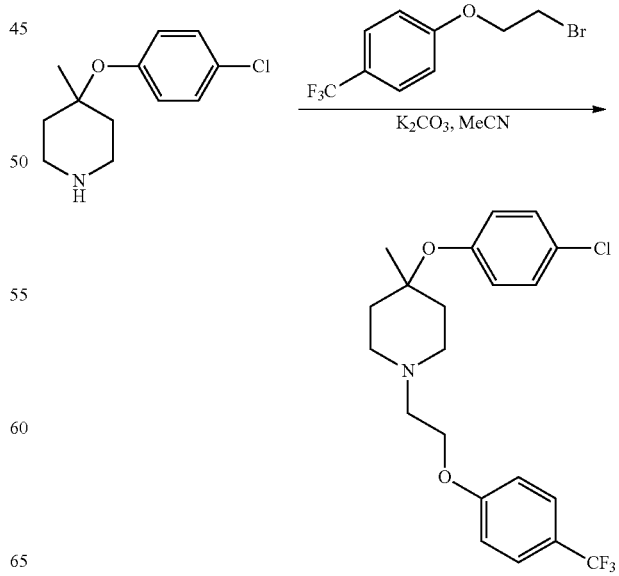

Title compound was prepared from 4-(4-chlorophenoxy)-4-methylpiperidine (0.15 g, 0.66 mmol) using the general methodology of Example-1. The crude was purified by preparative HPLC to afford 0.05 g of 4-(4-chlorophenoxy)-4-methyl-1-(2-(4-(trifluoromethyl)phenoxy) ethyl) piperidine (Yield=18%). $^1$H NMR (400 MHz, CD$_3$OD): δ 7.58 (d, J=8.8 Hz, 2H), 7.27-7.23 (m, 2H), 7.09 (d, J=8.4 Hz, 2H), 7.00-6.96 (m, 2H), 4.22 (t, J=11.2 Hz, 2H), 2.90 (t, J=5.6 Hz, 2H), 2.75-2.70 (m, 4H), 2.03-2.00 (m, 2H), 1.78-1.71 (m, 2H), 1.29 (s, 3H); ESI+MS: m/z 414 [M+H]$^+$).

Example-126: 4-(Benzyloxy)-4-methyl-1-(2-(2-(trifluoromethyl) phenoxy) ethyl) piperidine

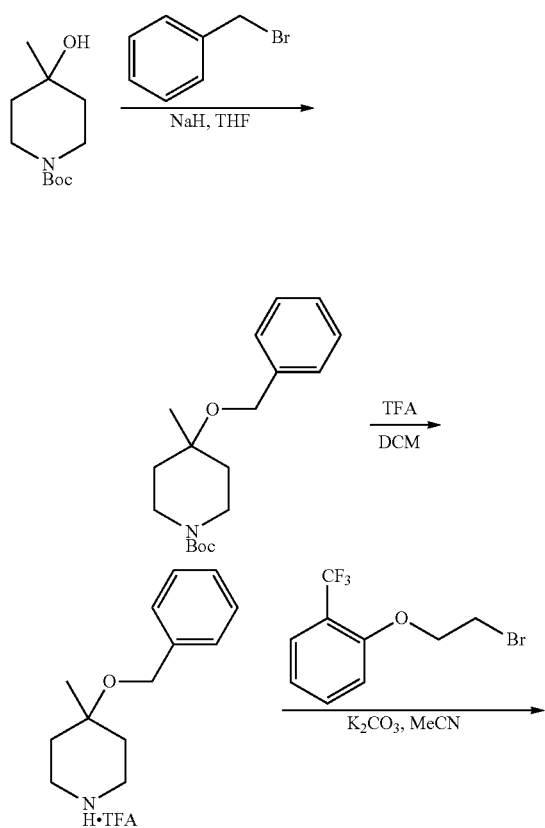

tert-butyl 4-(benzyloxy)-4-methylpiperidine-1-carboxylate

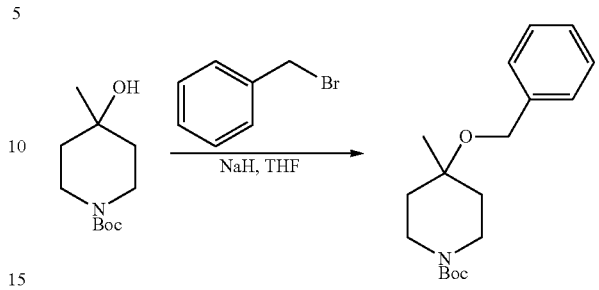

To a solution of tert-butyl 4-hydroxy-4-methylpiperidine-1-carboxylate (0.3 g, 1.39 mmol) in THF (5 mL) were added sodium hydride (60% suspension, 0.22 g 9.29 mmol, 4 equiv) under argon atmosphere and benzyl bromide (0.477 g, 2.79 mmol, 2 equiv) at 0° C. The reaction mixture was stirred at room temperature for 12 h. After completion, the reaction was quenched with cold water and extracted with EtOAc. The organic extract was dried over sodium sulfate, filtered and concentrated under reduced pressure. Purification using silica gel column chromatography (10% EtOAc/Hexanes as eluent) to afford 0.12 g of tert-butyl 4-(benzyloxy)-4-methylpiperidine-1-carboxylate (Yield=28%).

1-(4-(benzyloxy)-4-methyl-1λ$^4$-piperidin-1-yl)-2,2,2-trifluoroethan-1-one

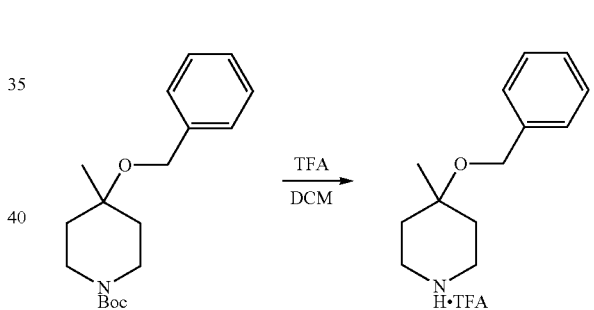

Title compound was prepared from tert-butyl 4-(benzyloxy)-4-methylpiperidine-1-carboxylate (0.12 g, 0.39 mmol) using the general methodology of Example 123 to afford 0.1 g of 1-(4-(benzyloxy)-4-methyl-1λ$^4$-piperidin-1-yl)-2,2,2-trifluoroethan-1-one (Quantitative).
ESI+MS: m/z 206 ([M+H]$^+$).

4-(benzyloxy)-4-methyl-1-(2-(2-(trifluoromethyl) phenoxy) ethyl) piperidine

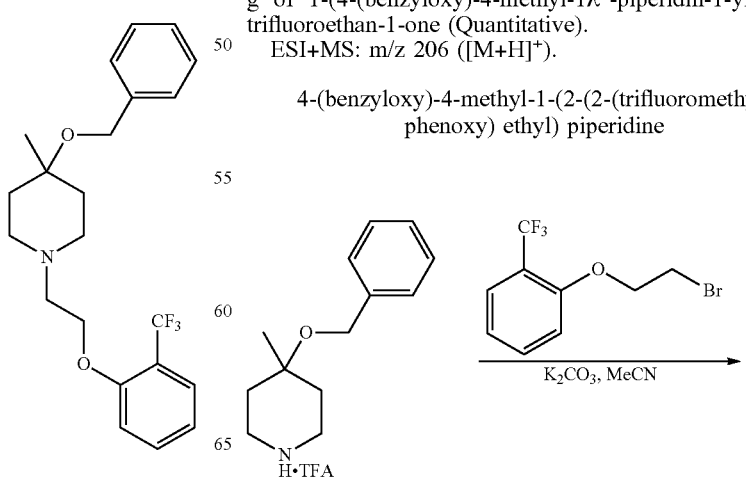

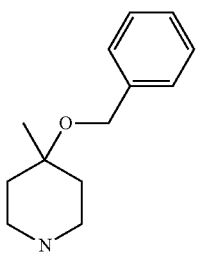

Title compound was prepared from 4-(benzyloxy)-4-methylpiperidine as TFA salt (0.1 g, 0.33 mmol) using the general methodology of Example-1. The crude was purified using silica gel column chromatography (2% MeOH/CH$_2$Cl$_2$ as eluent) to afford 0.07 g of 4-(benzyloxy)-4-methyl-1-(2-(2-(trifluoromethyl) phenoxy) ethyl) piperidine (Yield=54%). $^1$H NMR (400 MHz, CD$_3$OD): δ 7.59-7.56 (m, 2H), 7.35-7.33 (m, 2H), 7.29 (t, J=6.8 Hz, 2H), 7.24-7.18 (m, 2H), 7.08 (t, J=7.6 Hz, 1H), 4.44 (s, 2H), 4.30 (t, J=5.2 Hz, 2H), 3.07-3.04 (m, 2H), 2.92-2.79 (m, 4H), 1.99-1.96 (m, 2H), 1.72 (dt, J=11.6, 4.4 Hz, 2H), 1.30 (s, 3H); ESI+MS: m/z 394 ([M+H]$^+$).

Example-127: 6-(2-(4-(4-chlorophenoxy)-4-methylpiperidin-1-yl)ethoxy)benzo[d] oxazole

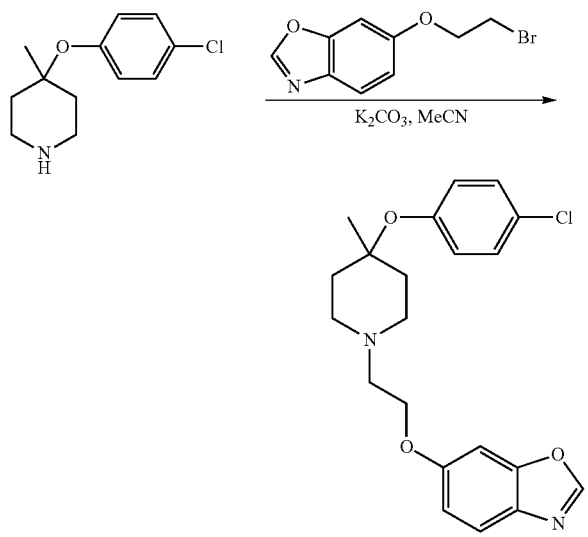

Title compound was prepared from 4-(4-chlorophenoxy)-4-methylpiperidine (0.08 g, 0.354 mmol) using the general methodology of Example-1. Purification using silica gel column chromatography (4% MeOH/CH$_2$Cl$_2$ as eluent) and preparative HPLC to afford 0.006 g of 6-(2-(4-(4-chlorophenoxy)-4-methylpiperidin-1-yl)ethoxy) benzo[d]oxazole (Yield=4%).

$^1$H NMR (400 MHz, CD$_3$OD): δ 8.35 (s, 1H), 7.62 (d, J=8.8 Hz, 1H), 7.30 (d, J=2.4 Hz, 1H), 7.25 (dd, J=6.8, 2.4 Hz, 2H), 7.07 (dd, J=6.8, 2.4 Hz, 1H), 6.99 (dd, J=6.8, 2.0 Hz, 2H), 4.26 (t, J=5.6 Hz, 2H), 3.05-3.03 (m, 2H), 2.91-2.89 (m, 4H), 2.06 (d, J=13.2 Hz, 2H), 1.83-1.76 (m, 2H), 1.29 (s, 3H); ESI+MS: m/z 387 ([M+H]$^+$).

Example-128: 3-(2-(4-(4-chlorophenoxy)-4-methylpiperidin-1-yl)ethoxy)-4-(trifluoromethyl)pyridine

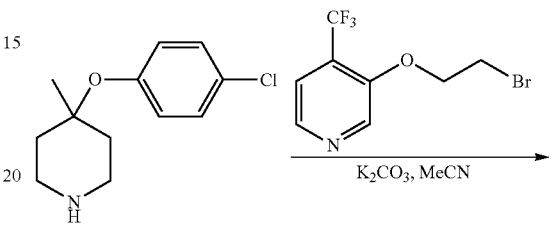

Title compound was prepared from 4-(4-chlorophenoxy)-4-methylpiperidine (0.09 g, 0.399 mmol) using the general methodology of Example-1. Purification using silica gel column chromatography (4% MeOH/CH$_2$Cl$_2$ as eluent) and preparative HPLC to afford 0.015 g of 3-(2-(4-(4-chlorophenoxy)-4-methylpiperidin-1-yl)ethoxy)-4-(trifluoromethyl) pyridine (Yield=9%). $^1$H NMR (400 MHz, CD$_3$OD): δ 8.60 (s, 1H), 8.36 (d, J=5.2 Hz, 1H), 7.61 (d, J=4.8 Hz, 1H), 7.25 (d, J=8.8 Hz, 2H), 6.98 (d, J=8.8 Hz, 2H), 4.42 (t, J=5.6 Hz, 2H), 2.94 (t, J=5.6 Hz, 2H), 2.77-2.74 (m, 4H), 2.01-1.97 (m, 2H), 1.75-1.68 (m, 2H), 1.28 (s, 3H); ESI+MS: m/z 415 ([M+H]$^+$).

Example-129: 2-(4-(4-chlorophenoxy)-4-methylpiperidin-1-yl)-N-(2-(trifluoromethyl) phenyl)acetamide

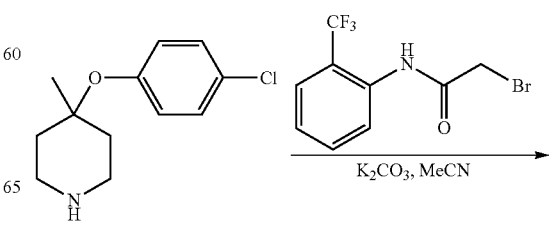

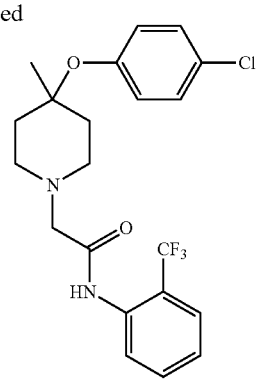

Title compound was prepared from 4-(4-chlorophenoxy)-4-methylpiperidine (0.2 g, 0.886 mmol) using the general methodology of Example-1. Purification using silica gel column chromatography (15% EtOAc/Hexanes as eluent) afforded 0.04 g of 2-(4-(4-chlorophenoxy)-4-methylpiperidin-1-yl)-N-(2-(trifluoromethyl)phenyl)acetamide (Yield=11%). ¹H NMR (400 MHz, CD₃OD): δ 8.23 (d, J=8.4 Hz, 1H), 7.69 (d, J=8.0 Hz, 1H), 7.62 (t, J=7.6 Hz, 1H), 7.31 (t, J=7.6 Hz, 1H), 7.26-7.23 (m, 2H), 7.01-6.98 (m, 2H), 3.21 (s, 2H), 2.84-2.78 (m, 2H), 2.72-2.67 (m, 2H), 2.04 (d, J=14.0 Hz, 2H), 1.82-1.74 (m, 2H), 1.30 (s, 3H); ESI+MS: m/z 427 ([M+H]⁺).

Example-130: 4-Methyl-1-(2-phenoxyethyl)piperidin-4-ol

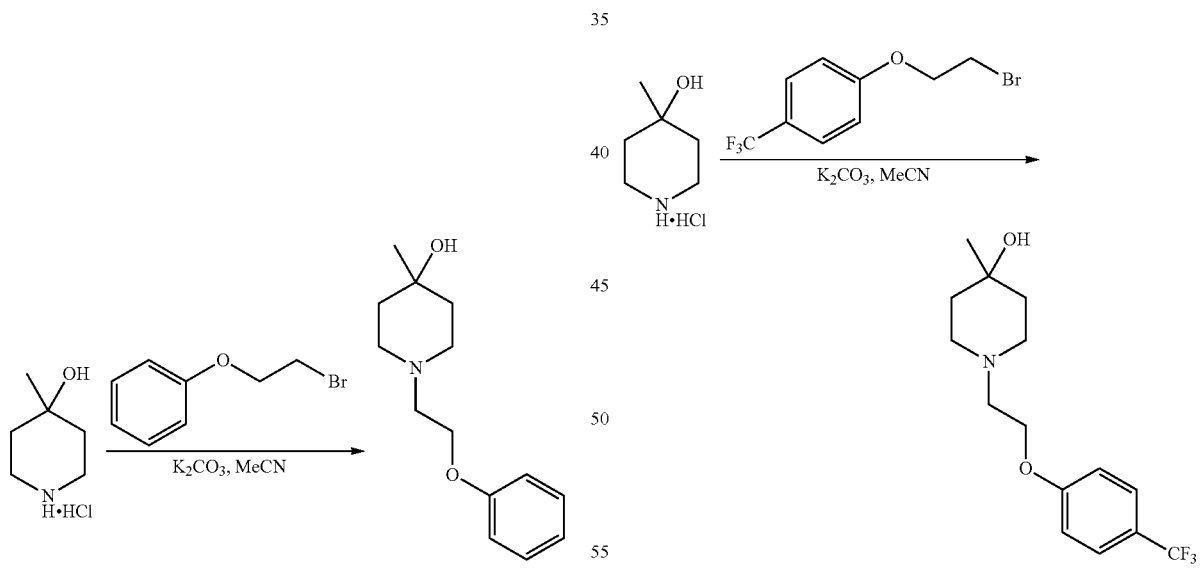

Title compound was prepared from 4-methylpiperidin-4-ol hydrochloride (0.1 g, 0.65 mmol) using the general methodology of Example-1. Purification using silica gel column chromatography (3% MeOH/CH₂Cl₂ as eluent) to afford 0.1 g of 1-(2-(2-fluorophenoxy)ethyl)-4-methyl-N-phenylpiperidine-4-carboxamide (Yield=64%). ¹H NMR (400 MHz, CD₃OD): δ 7.29-7.25 (m, 2H), 6.95-6.91 (m, 3H), 4.17 (t, J=5.2 Hz, 2H), 2.96 (t, J=5.6 Hz, 2H), 2.84-2.81 (m, 2H), 2.76-2.70 (m, 2H), 1.75-1.63 (m, 4H), 1.23 (s, 3H); ESI+MS: m/z 236 ([M+H]⁺).

Example-131: 1-(2-(2-fluorophenoxy)ethyl)-4-methylpiperidin-4-ol

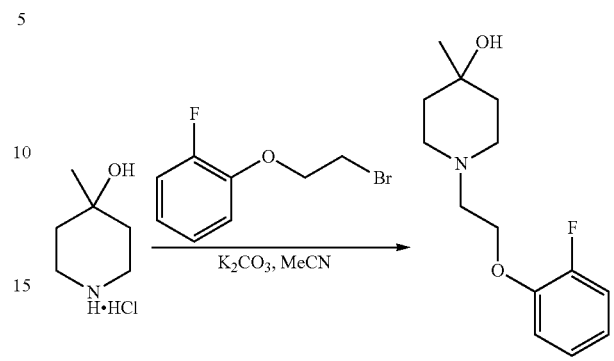

Title compound was prepared from 4-methylpiperidin-4-ol hydrochloride (0.1 g, 0.659 mmol) and Int-2 (Broad-sai-D2R-027) using the general methodology of Example-1. Purification using silica gel column chromatography (3% MeOH/CH₂Cl₂ as eluent) and preparative HPLC to afford 0.1 g of 1-(2-(2-fluorophenoxy)ethyl)-4-methylpiperidin-4-ol (Yield=60%). ¹H NMR (400 MHz, CD₃OD): δ 7.14-7.08 (m, 3H), 6.97-6.94 (m, 1H), 4.24 (t, J=5.5 Hz, 2H), 2.97-2.95 (m, 2H), 2.81-2.73 (m, 4H), 1.74-1.65 (m, 4H), 1.24 (s, 3H); ESI+MS: m/z 254 ([M+H]⁺).

Example-132: 4-methyl-1-(2-(4-(trifluoromethyl)phenoxy)ethyl)piperidin-4-ol

Title compound was prepared from 4-methylpiperidin-4-ol hydrochloride (0.1 g, 0.659 mmol) using the general methodology of Example-1. Purification using silica gel column chromatography (50% EtOAc/Hexanes as eluent) to afford 0.06 g of 4-methyl-1-(2-(4-(trifluoromethyl)phenoxy)ethyl)piperidin-4-ol (Yield=28%). ¹H NMR (400 MHz, CD₃OD): δ 7.59 (d, J=8.8 Hz, 2H), 7.10 (d, J=9.6 Hz, 2H), 4.24 (t, J=5.6 Hz, 2H), 2.97-2.94 (m, 2H), 2.81-2.68 (m, 4H), 1.74-1.64 (m, 4H), 1.24 (s, 3H); ESI+MS: m/z 304 ([M+H]⁺).

Example-133: 3-methyl-8-(2-(2-(trifluoromethyl)phenoxy)ethyl)-8-azabicyclo[3.2.1] octan-3-ol

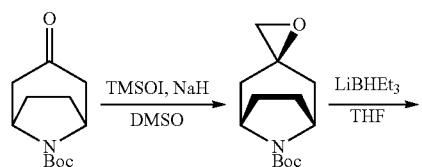

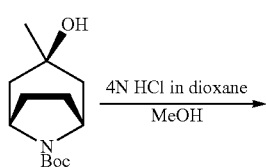

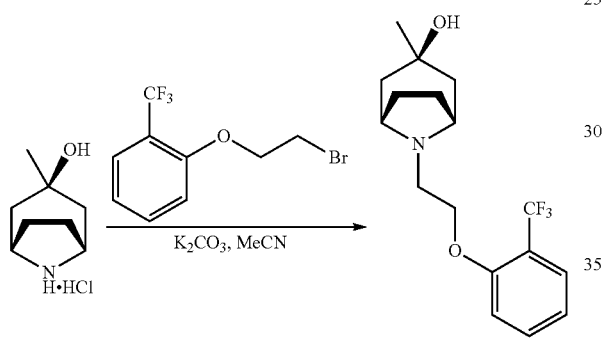

tert-butyl (1R,5S)-8-azaspiro[bicyclo[3.2.1]octane-3,2'-oxirane]-8-carboxylate

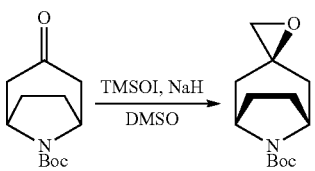

To a solution of 60% sodium hydride (0.4 g, 16.65 mmol, 1.5 equiv) in DMSO (5 mL) under argon atmosphere was added trimethyl sulfoxonium iodide (3.66 g, 16.65 mmol, 1.5 equiv) portion wise at room temperature. The reaction was stirred at room temperature for 1 h. To this was added a solution of (1R,5S)-tert-butyl 3-oxo-8-azabicyclo[3.2.1] octane-8-carboxylate (2.5 g 11.10 mmol) in DMSO (5 mL) and stirred at room temperature for 24 h. After completion, reaction was diluted with water and extracted with diethyl ether. The organic extracts were dried over sodium sulfate, filtered and concentrated under reduced pressure to afford 2 g of tert-butyl (1R,5S)-8-azaspiro[bicyclo[3.2.1]octane-3,2'-oxirane]-8-carboxylate (Yield=75%)

tert-butyl (1R,5S)-3-hydroxy-3-methyl-8-azabicyclo[3.2.1]octane-8-carboxylate

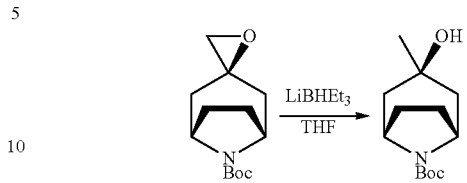

To a solution of tert-butyl (1R,5S)-8-azaspiro[bicyclo[3.2.1]octane-3,2'-oxirane]-8-carboxylate (2 g, 8.36 mmol) in THF (30 mL) under argon atmosphere was added 1.0 M triethyl borohydride solution in THF (10.87 mL, 10.86 mmol, 1.3 equiv) at 0° C. The reaction was stirred at room temperature for 2 h. After completion, the reaction was diluted with water and extracted with EtOAc. The organic extract was dried over sodium sulphate and concentrated under reduced pressure. Purification using silica gel column chromatography (15% EtOAc/Hexanes as eluent) to afford 1.6 g of tert-butyl (1R,5S)-3-hydroxy-3-methyl-8-azabicyclo[3.2.1]octane-8-carboxylate (Yield=79%).

(1R,5S)-3-methyl-8-azabicyclo[3.2.1]octan-3-ol hydrochloride

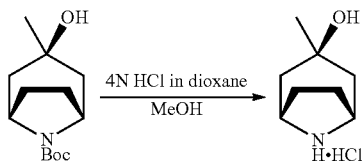

Title compound was prepared from tert-butyl (1R,5S)-3-hydroxy-3-methyl-8-azabicyclo[3.2.1]octane-8-carboxylate (1.6 g, 6.63 mmol) using the general methodology of step 2 of key Intermediate-VI and the reaction was stirred for 6 h. The crude was washed with diethyl ether to afford 1 g of (1R,5S)-3-methyl-8-azabicyclo[3.2.1]octan-3-ol hydrochloride (Quantitative).

3-methyl-8-(2-(2-(trifluoromethyl)phenoxy)ethyl)-8-azabicyclo[3.2.1] octan-3-ol

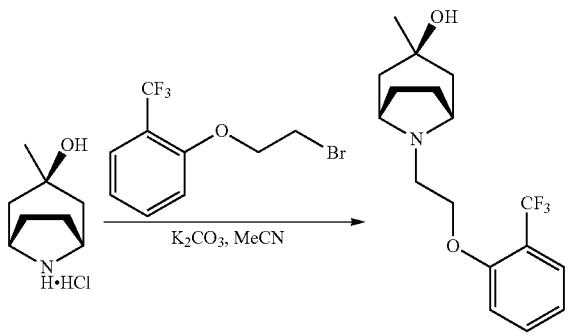

Title compound was prepared from (1R, 5S)-3-methyl-8-azabicyclo[3.2.1]octan-3-ol hydrochloride (1 g, 5.63 mmol)

using the general methodology of Example-1. Purification using silica gel column chromatography (2% MeOH/CH$_2$Cl$_2$ as eluent) to afford 1 g 3-methyl-8-(2-(2-(trifluoromethyl)phenoxy)ethyl)-8-azabicyclo[3.2.1]octan-3-ol (Yield=54%). $^1$H NMR (400 MHz, DMSO-d$_6$): δ 7.63-7.59 (m, 2H), 7.27 (d, J=8.4 Hz, 1H), 7.08 (t, J=7.6 Hz, 1H), 4.19 (br s, 2H), 3.92 (br s, 1H), 3.24-3.22 (m, 2H), 2.73-2.71 (m, 1H), 2.07 (br s, 2H), 1.75-1.52 (m, 6H), 1.00 (s, 3H); ESI+MS: m/z 330 [M+H]$^+$].

Example-134: 3-Methyl-1-(2-(2-(trifluoromethyl)phenoxy)ethyl)piperidin-3-ol

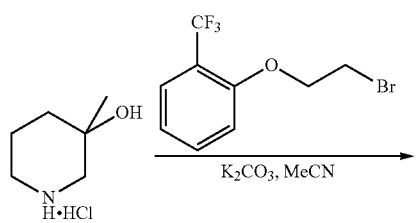

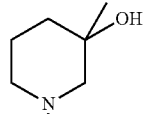

Title compound was prepared from 3-methylpiperidin-3-ol hydrochloride (0.1 g, 0.659 mmol) using the general methodology of Example-1. Purification using silica gel column chromatography (50% EtOAc/Hexanes as eluent) to afford 0.06 g of 3-methyl-1-(2-(2-(trifluoromethyl)phenoxy)ethyl)piperidin-3-ol (Yield=29%). $^1$H NMR (400 MHz, DMSO-d$_6$): δ 7.65 (d, J=8.0 Hz, 2H), 7.27 (d, J=8.0 Hz, 1H), 7.07 (t, J=7.6 Hz, 1H), 4.21-4.18 (m, 2H), 4.05 (br s, 1H), 2.75-2.70 (m, 2H), 2.49-2.43 (m, 2H), 2.36-2.26 (m, 2H), 1.62-1.58 (m, 1H), 1.43-1.30 (m, 3H), 1.06 (s, 3H); ESI+MS: m/z 304 [M+H]$^+$.

Example-135: 1-(4-Chlorophenyl)-8-(2-(2-(trifluoromethyl)phenoxy)ethyl)-1,8-diazaspiro[4.5]decane

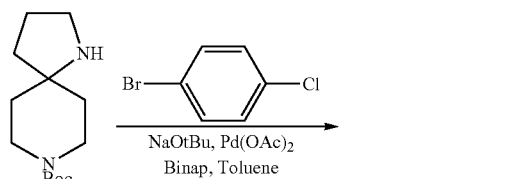

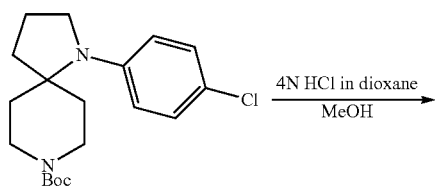

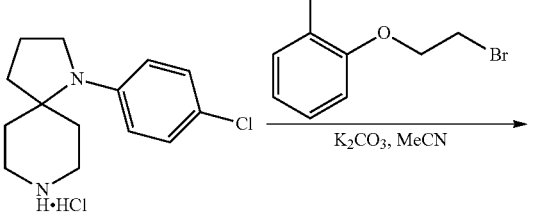

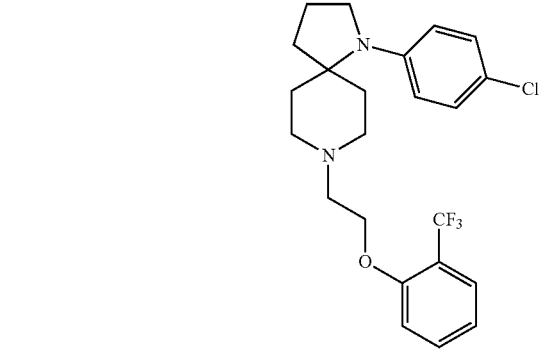

tert-butyl 1-(4-chlorophenyl)-1,8-diazaspiro[4.5]decane-8-carboxylate

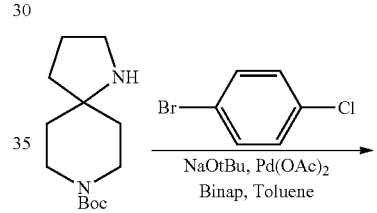

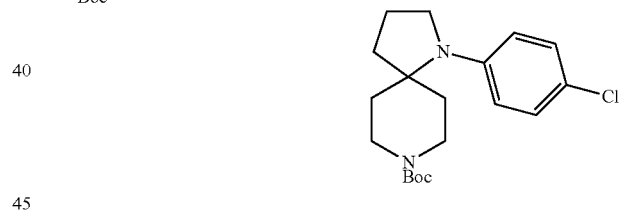

Title compound was prepared from tert-butyl 1,8-diazaspiro[4.5]decane-8-carboxylate (0.1 g, 0.416 mmol) and 1-bromo-4-chlorobenzene (0.08 g, 0.416 mmol, 1.0 equiv) using the general methodology of Example 113. Purification using silica gel column chromatography (30% EtOAc/Hexanes as eluent) to afford 0.1 g of tert-butyl 1-(4-chlorophenyl)-1,8-diazaspiro[4.5]decane-8-carboxylate (Yield=69%). ESI+MS: m/z 351 ([M+H]$^+$).

1-(4-Chlorophenyl)-1,8-diazaspiro[4.5]decane hydrochloride

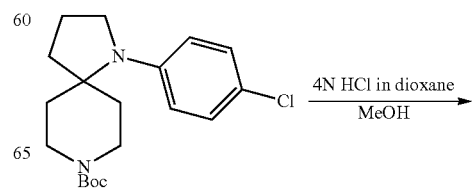

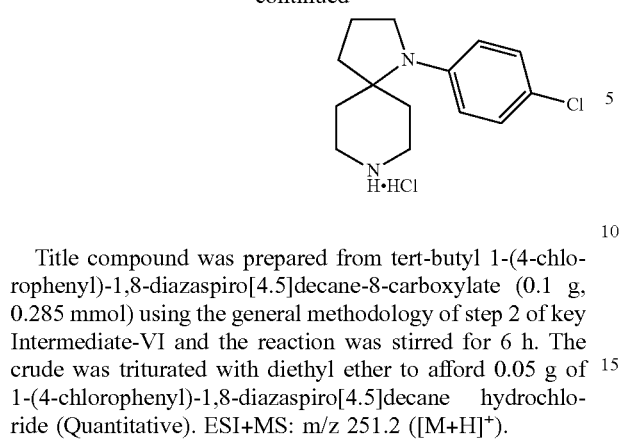

Title compound was prepared from tert-butyl 1-(4-chlorophenyl)-1,8-diazaspiro[4.5]decane-8-carboxylate (0.1 g, 0.285 mmol) using the general methodology of step 2 of key Intermediate-VI and the reaction was stirred for 6 h. The crude was triturated with diethyl ether to afford 0.05 g of 1-(4-chlorophenyl)-1,8-diazaspiro[4.5]decane hydrochloride (Quantitative). ESI+MS: m/z 251.2 ([M+H]$^+$).

1-(4-Chlorophenyl)-8-(2-(2-(trifluoromethyl)phenoxy)ethyl)-1,8-diazaspiro[4.5]decane

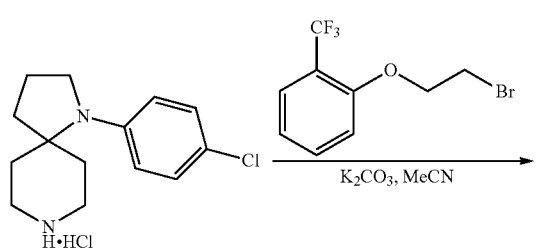

Title compound was prepared from 1-(4-chlorophenyl)-1,8-diazaspiro[4.5]decane hydrochloride (0.05 g, 0.174 mmol) using the general methodology of Example-1. Purification using silica gel column chromatography (3% MeOH/CH$_2$Cl$_2$ as eluent) further purified by preparative HPLC to afford 0.03 g of 1-(4-chlorophenyl)-8-(2-(2-(trifluoromethyl)phenoxy)ethyl)-1,8-diazaspiro[4.5]decane (Yield=39%). $^1$H NMR (400 MHz, CD$_3$OD): δ 7.57-7.53 (m, 2H), 7.18 (d, J=8.4 Hz, 1H), 7.10-7.03 (m, 3H), 6.86 (d, J=9.2 Hz, 2H), 4.25 (t, J=5.6 Hz, 2H), 3.31-3.27 (m, 2H), 3.09-3.04 (m, 2H), 2.88 (t, J=5.6 Hz, 2H), 2.60 (dt, J=13.2, 4.4 Hz, 2H), 2.37 (dt, J=12.4 Hz, J=4.4 Hz, 2H), 2.02-1.98 (m, 2H), 1.93-1.86 (m, 2H), 1.29 (d, J=14.0 Hz, 2H); Ion Trap: m/z: 439 ([M+H]$^+$).

Example-136: 1-(4-Chlorophenyl)-7-(2-(2-(trifluoromethyl)phenoxy)ethyl)-1,7-diazaspiro[3.5]nonane

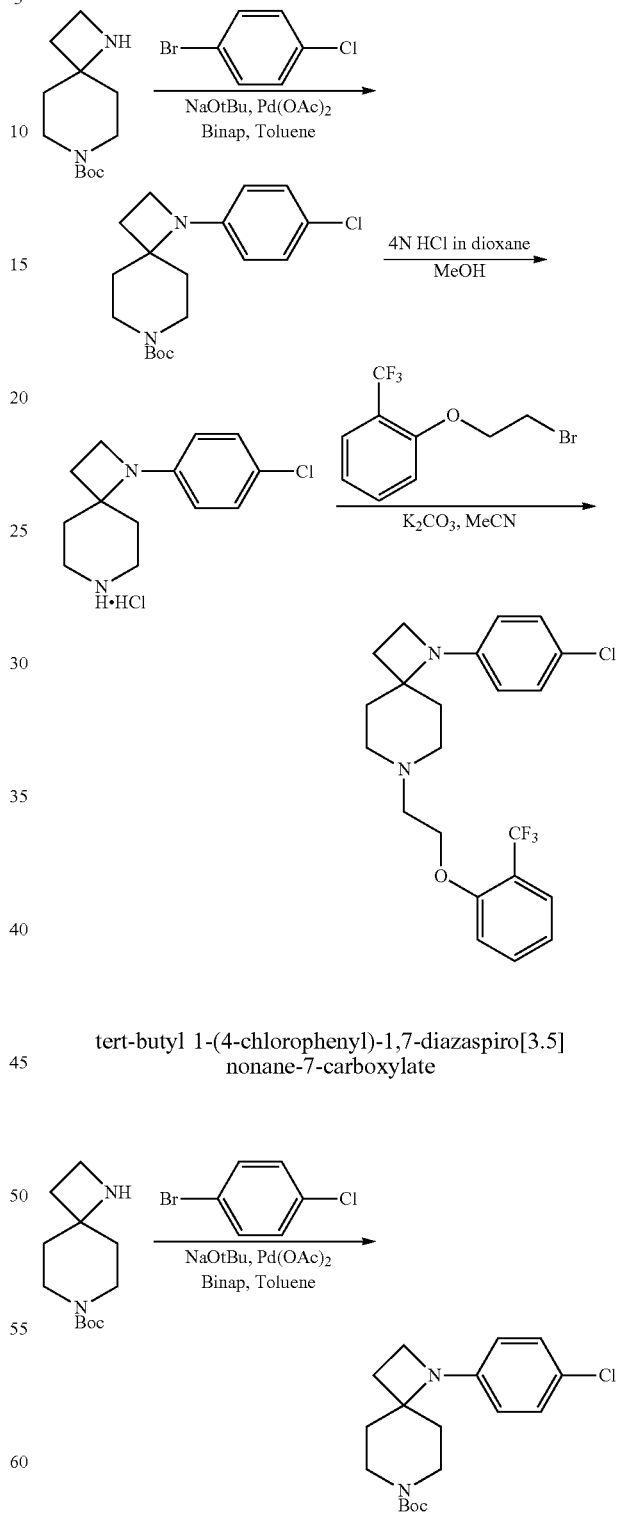

tert-butyl 1-(4-chlorophenyl)-1,7-diazaspiro[3.5]nonane-7-carboxylate

Title compound was prepared from tert-butyl 1,7-diazaspiro[3.5]nonane-7-carboxylate hydrochloride (0.5 g, 1.90 mmol) and 1-bromo-4-chlorobenzene (0.364 g, 1.903 mmol, 1.0 eq) using the general methodology of Example 113.

Purification using silica gel column chromatography (30% EtOAc/Hexanes as eluent) to afford 0.4 g of 1-(4-chlorophenyl)-8-(2-(2-(trifluoromethyl)phenoxy)ethyl)-1,8-diazaspiro[4.5]decane (Yield=62%).

1-(4-Chlorophenyl)-1,7-diazaspiro[3.5]nonane hydrochloride

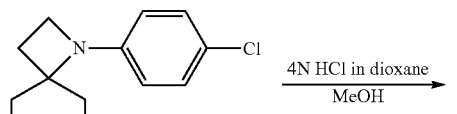

Title compound was prepared from tert-butyl 1-(4-chlorophenyl)-1,8-diazaspiro[4.5]decane-8-carboxylate (0.45 g, 1.336 mmol) using the general methodology of step 2 of key Intermediate-VI to afford 0.3 g of 1-(4-chlorophenyl)-1,7-diazaspiro[3.5]nonane hydrochloride (Quantitative).

1-(4-Chlorophenyl)-7-(2-(2-(trifluoromethyl)phenoxy)ethyl)-1,7-diazaspiro[3.5]nonane

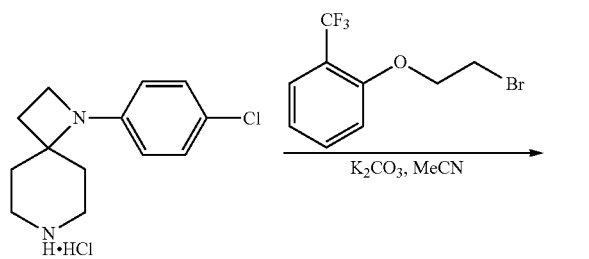

Title compound was prepared from 1-(4-chlorophenyl)-1,7-diazaspiro[3.5]nonane hydrochloride (0.15 g, 0.549 mmol) using the general methodology of Example-1. Purification using silica gel column chromatography (3% MeOH/CH$_2$Cl$_2$ as eluent) followed by preparative HPLC purification to afford 0.02 g of 1-(4-chlorophenyl)-8-(2-(2-(trifluoromethyl)phenoxy)ethyl)-1,8-diazaspiro[4.5]decane (Yield=9%). $^1$H NMR (400 MHz, CD$_3$OD): δ 7.59-7.55 (m, 2H), 7.19 (d, J=8.8 Hz, 1H), 7.11-7.05 (m, 3H), 6.50 (d, J=8.8 Hz, 2H), 4.26 (t, J=5.6 Hz, 2H), 3.67 (t, J=7.2 Hz, 2H), 3.08-3.06 (m, 2H), 2.89 (t, J=5.6 Hz, 2H), 2.30 (d, J=9.2 Hz, 4H), 2.16 (t, J=7.2 Hz, 2H), 1.73 (d, J=9.2 Hz, 2H); ESI+MS: m/z: 425 ([M+H]$^+$).

Example-137: 1-(4-chlorophenyl)-7-(2-(2-fluorophenoxy)ethyl)-1,7-diazaspiro[3.5] nonane

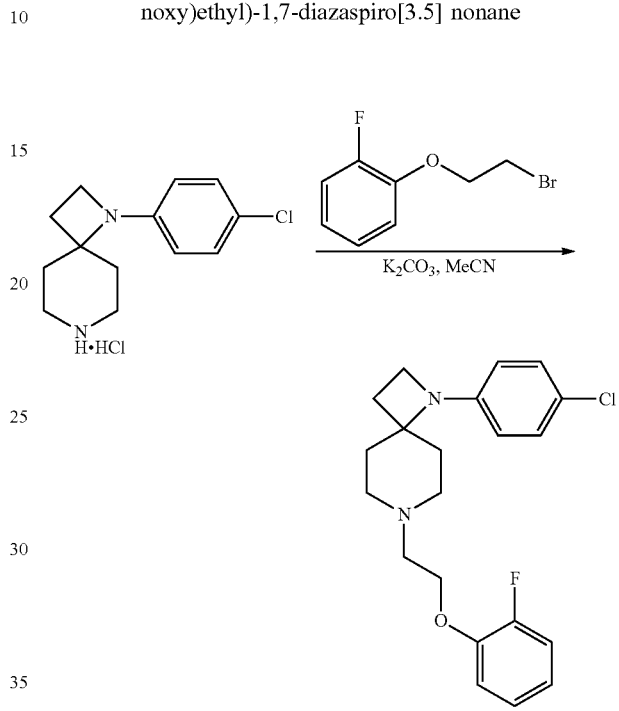

Title compound was prepared from 1-(4-chlorophenyl)-1,7-diazaspiro[3.5]nonane hydrochloride (0.15 g, 0.54 mmol) using the general methodology of Example-1. Purification using silica gel column chromatography (3% MeOH/CH$_2$Cl$_2$ as eluent) followed by preparative HPLC purification to afford 0.02 g of 1-(4-chlorophenyl)-7-(2-(2-fluorophenoxy)ethyl)-1,7-diazaspiro[3.5] nonane (Yield=10%). $^1$H NMR (400 MHz, CD$_3$OD): δ 7.11-7.06 (m, 5H), 6.95-6.90 (m, 1H), 6.51 (d, J=8.8 Hz, 2H), 4.20 (t, J=5.6 Hz, 2H), 3.67 (t, J=7.6 Hz, 2H), 3.07 (d, J=9.6 Hz, 2H), 2.85 (t, J=5.6 Hz, 2H), 2.36-2.23 (m, 4H), 2.16 (t, J=7.2 Hz, 2H), 1.74 (d, J=10.4 Hz, 2H); ESI+MS: m/z: 375 ([M+H]$^+$).

Example-138: 4-methyl-1-(3-(2-(trifluoromethyl) phenoxy)propyl)piperidin-4-ol

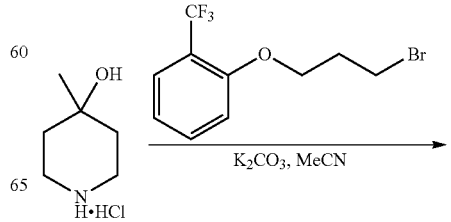

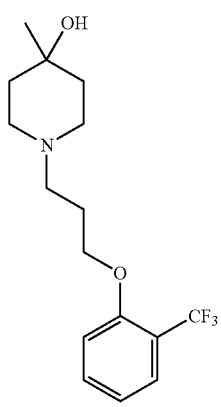

Title compound was prepared from 4-methylpiperidin-4-ol hydrochloride (0.1 g 0.659 mmol) using the general methodology of Example-1. Purification using silica gel column chromatography (3% MeOH/CH$_2$Cl$_2$ as eluent) to afford 0.07 g of 4-methyl-1-(3-(2-(trifluoromethyl)phenoxy)propyl)piperidin-4-ol (Yield=33%). $^1$H NMR (400 MHz, CD$_3$OD): δ 7.55-7.51 (m, 2H), 7.14 (d, J=8.4 Hz, 1H), 7.02 (t, J=7.6 Hz, 1H), 4.12 (t, J=6.0 Hz, 2H), 2.65-2.61 (m, 4H), 2.54-2.48 (m, 2H), 2.06-1.99 (m, 2H), 1.65-1.62 (m, 4H), 1.20 (s, 3H); ESI+MS: m/z: 318 ([M+H]$^+$).

Example-139: 3-Methyl-1-(2-(2-(trifluoromethyl)phenoxy)ethyl)pyrrolidin-3-ol

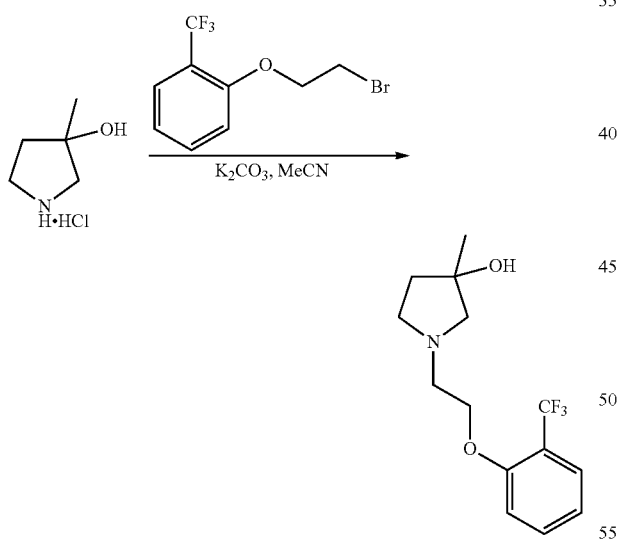

Title compound was prepared from 3-methylpyrrolidin-3-ol hydrochloride (0.3 g, 2.18 mmol) using the general methodology of Example-1. Purification using silica gel column chromatography (2% MeOH/CH$_2$Cl$_2$ as eluent) to afford 0.12 g of 3-methyl-1-(2-(2-(trifluoromethyl)phenoxy)ethyl)pyrrolidin-3-ol (Yield=19%). $^1$H NMR (500 MHz, DMSO-d$_6$): δ 7.60 (t, J=8.0 Hz, 2H), 7.26 (d, J=8.5 Hz, 1H), 7.08 (t, J=8.0 Hz, 1H), 4.50 (br s, 1H) 4.17 (t, J=6.0 Hz, 2H), 2.82-2.80 (m, 2H), 2.71-2.55 (m, 4H), 1.73-1.65 (m, 2H), 1.22 (s, 3H); ESI+MS: m/z: 290 [M+H].

Example-140: 1-((2,3-dihydrobenzo[b][1,4]dioxin-2-yl)methyl)-4-methylpiperidin-4-ol

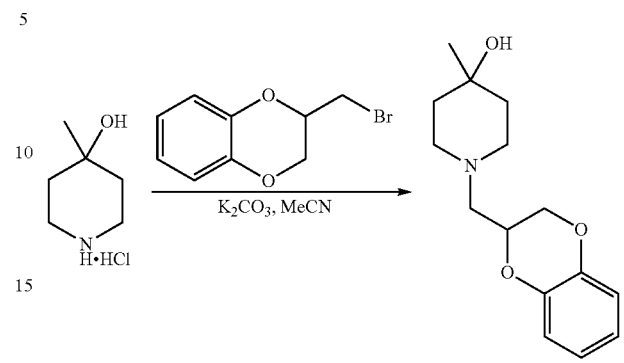

Title compound was prepared from 4-methylpiperidin-4-ol hydrochloride (0.20 g, 1.32 mmol) using the general methodology of Example-1. Purification using preparative HPLC afforded 0.05 g of 1-((2,3-dihydrobenzo[b][1,4]dioxin-2-yl)methyl)-4-methylpiperidin-4-ol (Yield=15%). $^1$H NMR (400 MHz, DMSO-d$_6$): δ 6.82 (m, 4H), 4.29 (m, 2H), 4.07 (s, 1H), 3.92 (m, 1H), 2.53 (m, 3H), 2.42 (m, 3H), 1.45 (m, 4H), 1.09 (s, 3H); ESI+MS: m/z: 264 ([M+H]$^+$). The enantiomers of 140 were separated using chiral HPLC (method D) and afforded the pure enantiomers 140a and 140b.

Example-141: 4-methyl-1-(2-(2-(methylsulfonyl)phenoxy)ethyl)-4-phenoxypiperidine

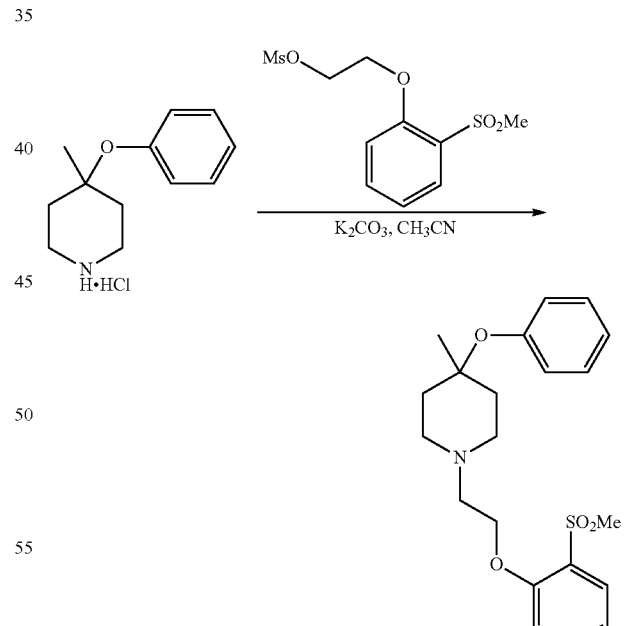

Title compound was prepared from 4-methyl-4-phenoxypiperidine hydrochloride (0.1 g, 0.44 mmol) using the general methodology of Example-1. Purification using silica gel column chromatography (3% MeOH/CH$_2$Cl$_2$ as eluent) to afford 0.025 g of 4-methyl-1-(2-(2-(methylsulfonyl)phenoxy)ethyl)-4-phenoxypiperidine (Yield=15%). $^1$H NMR (400 MHz, DMSO-d6): δ 7.80-7.78 (m, 1H), 7.68-7.64 (m, 1H), 7.31-7.25 (m, 3H), 7.14 (t, J=8.0 Hz, 1H), 7.06-6.97 (m, 3H), 4.27 (t, J=4 Hz, 2H), 3.37 (s, 3H), 2.58-2.49 (m, 6H), 1.87-1.84 (m, 2H), 1.61-1.55 (m, 2H), 1.23 (s, 3H); ESI+MS: m/z 390 ([M+H]⁺).

Example-142: 4-(4-chlorophenoxy)-1-((2,3-dihydrobenzo[b][1,4]dioxin-2-yl)methyl)-4-methylpiperidine

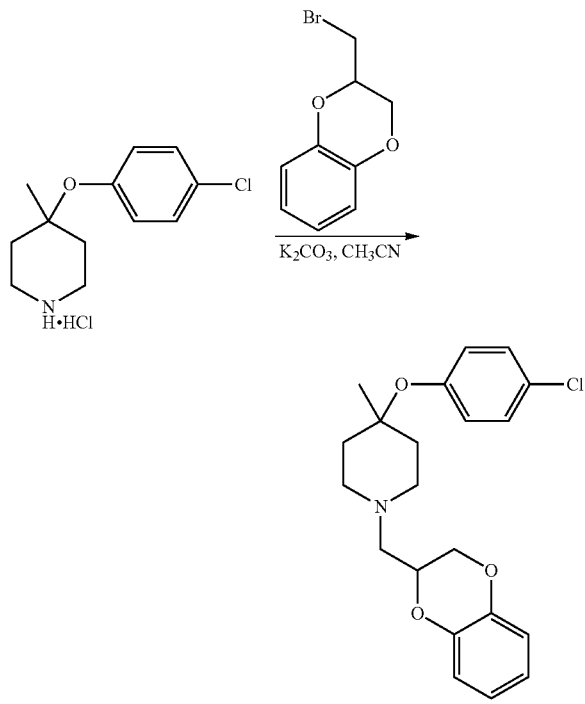

Title compound was prepared from 4-(4-chlorophenoxy)-4-methylpiperidine hydrochloride (0.05 g, 0.19 mmol) using the general methodology of Example-1. Purification using preparative HPLC afforded 0.015 g of 4-(4-chlorophenoxy)-1-((2,3-dihydrobenzo[b][1,4]dioxin-2-yl)methyl)-4-methylpiperidine (Yield=21%). ¹H NMR (400 MHz, CD₃OD): δ 7.32 (m, 2H), 7.02 (m, 2H), 6.83 (m, 4H), 4.31 (m, 2H), 3.95 (m, 1H), 2.57 (m, 6H), 1.87 (m, 2H), 1.64 (m, 2H), 1.24 (s, 3H); ESI+MS: m/z 374 ([M+H]⁺). The enantiomers of 142 were separated using chiral HPLC (method D) and afforded the pure enantiomers 142a and 142b.

Example-143: 4-(4-chlorophenoxy)-1-(2-(cyclohexyloxy)ethyl)-4-methylpiperidine

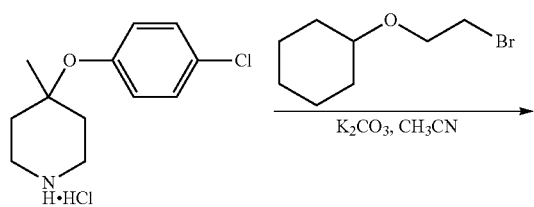

-continued

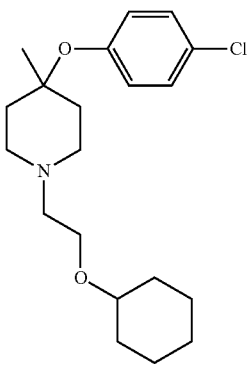

Title compound was prepared from 4-(4-chlorophenoxy)-4-methylpiperidine hydrochloride (0.1 g, 0.38 mmol) using the general methodology of Example-1. Purification using silica gel column chromatography (2% MeOH/CH₂Cl₂ as eluent) afforded 0.05 g of 4-(4-chlorophenoxy)-1-(2-(cyclohexyloxy)ethyl)-4-methylpiperidine (Yield=37%). ¹H NMR (500 MHz, CD₃OD): δ 7.27-7.26 (d, J=8.5 Hz, 2H), 7.00 (d, J=4.5 Hz, 2H), 3.67 (t, J=5.5 Hz, 2H), 3.32-3.20 (m, 1H), 2.78-2.74 (m, 6H), 2.03-2.01 (m, 2H), 1.93-1.91 (m, 2H), 1.78-1.72 (m, 4H), 1.85-1.75 (m, 1H), 1.33-1.27 (m, 8H); ESI+MS: m/z 352 ([M+H]⁺).

Example-144: 5-chloro-1'-(2-phenoxyethyl)-3H-spiro[benzofuran-2,3'-pyrrolidine]

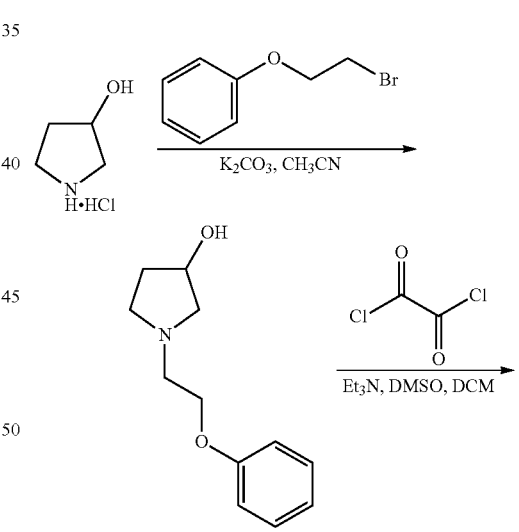

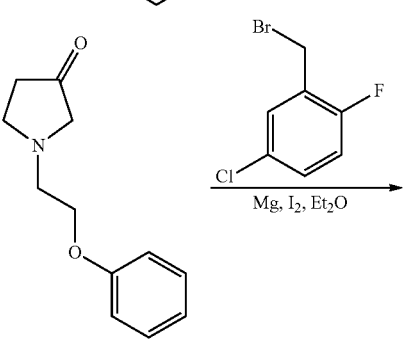

293

-continued

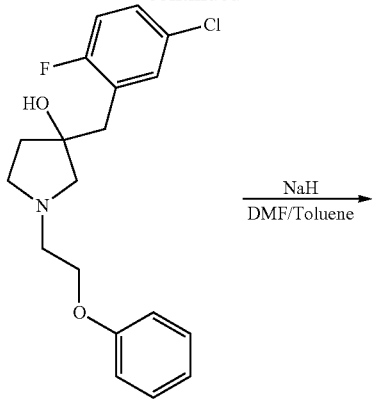

→ NaH, DMF/Toluene →

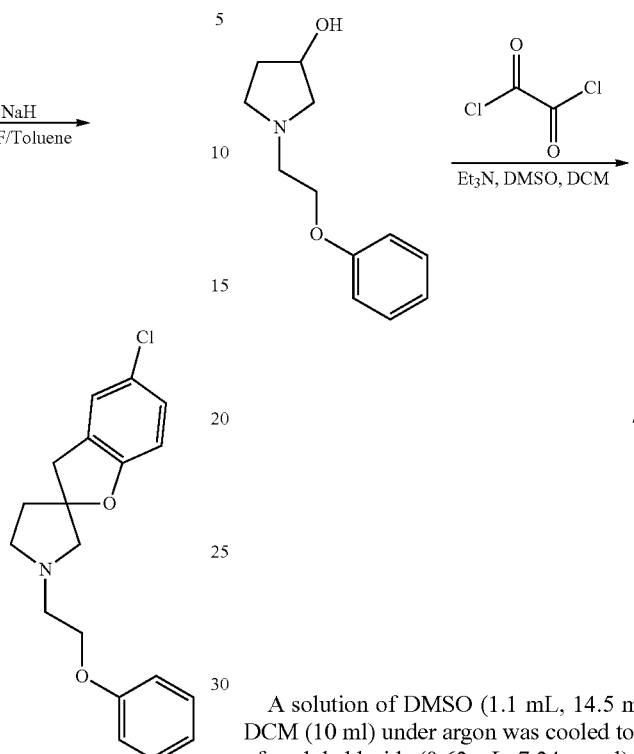

1-(2-phenoxyethyl)pyrrolidin-3-ol

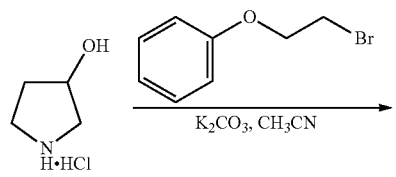

→ K₂CO₃, CH₃CN →

Title compound was prepared from pyrrolidin-3-ol hydrochloride (2.0 g, 16.2 mmol) using the general methodology of Example-1. Purification using silica gel column chromatography (2% MeOH/CH₂Cl₂ as eluent) afforded 2.41 g of 1-(2-phenoxyethyl)pyrrolidin-3-ol (Yield=72%).

294

1-(2-phenoxyethyl)pyrrolidin-3-one

→ Et₃N, DMSO, DCM →

A solution of DMSO (1.1 mL, 14.5 mmol) in anhydrous DCM (10 ml) under argon was cooled to −78° C. A solution of oxalyl chloride (0.62 mL, 7.24 mmol) in DCM (5 ml) was added dropwise and the mixture was stirred at −78° C. for 1 h. A solution of 1-(2-phenoxyethyl)pyrrolidin-3-ol (1.0 g, 4.82 mmol) in DCM (7 ml) was then added dropwise over 30 minutes and the mixture was stirred for 3 h at −78° C. Then, triethylamine (2.7 mL, 19.3 mmol) was added and the reaction mixture was stirred at RT for 1 hour. Water (20 mL) was added and the organic layer separated. The aqueous phase was extracted twice with DCM (10 mL). The combined organic extracts were dried over sodium sulfate, filtered and concentrated. Purification using silica gel chromatography using a gradient of MeOH in DCM afforded 620 mg of 1-(2-phenoxyethyl)pyrrolidin-3-one (Yield=63%). ESI+MS: m/z 206 ([M+H]⁺).

3-(5-chloro-2-fluorobenzyl)-1-(2-phenoxyethyl)pyrrolidin-3-ol

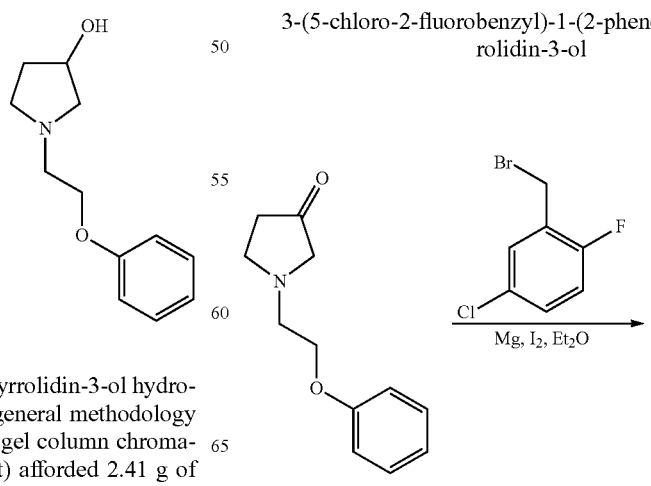

→ Mg, I₂, Et₂O →

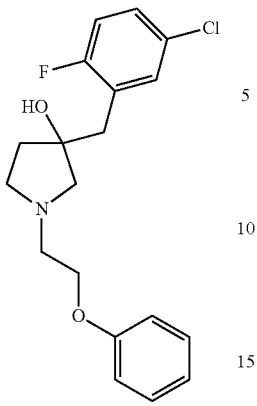

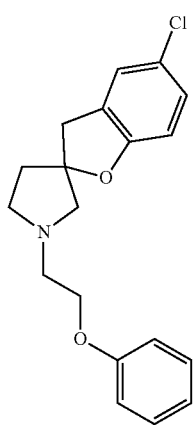

Magnesium turnings (53 mg, 2.19 mmol) and a crystal of iodine in diethyl ether (1 ml) were placed under Argon atmosphere and the mixture was warmed to 35° C. When color disappeared, 2-(bromomethyl)-4-chloro-1-fluorobenzene (408 mg, 1.83 mmol) in diethyl ether (0.5 ml) was added dropwise. The reaction mixture was kept at 35° C. overnight. A solution of 1-(2-phenoxyethyl)pyrrolidin-3-one (250 mg, 1.22 mmol) in 1.5 ml of diethyl ether was added dropwise over 15 minutes. At the end of the addition, the reaction mixture was stirred for 2 h at RT. The reaction mixture was then extracted with ethyl acetate and aq.NH$_4$Cl. The organic layer was dried over Na$_2$SO$_4$, filtered and concentrated. Purification using silica gel chromatography using a gradient of ethyl acetate in hexanes afforded 210 mg of 3-(5-chloro-2-fluorobenzyl)-1-(2-phenoxyethyl)pyrrolidin-3-ol (Yield=50%). ESI+MS: m/z 350 ([M+H]$^+$).

3-(5-chloro-2-fluorobenzyl)-1-(2-phenoxyethyl)pyrrolidin-3-ol (75 mg, 0.21 mmol) was dissolved in DMF/Toluene 1/1 (10 mL) under argon. NaH (14 mg, 0.34 mmol) was added in 1 portion and the mixture was stirred at 90° C. After 15 h, reaction was complete and extracted with ethyl acetate and aq.NH4Cl. The organic layer was dried on Na2SO4, filtered and concentrated under reduced pressure. Purification using a gradient of DCM/MeOH afforded 29 mg of 5-chloro-1'-(2-phenoxyethyl)-3H-spiro[benzofuran-2,3'-pyrrolidine] (Yield=41%). $^1$H NMR (300 MHz, CDCl$_3$): δ 7.27 (t, J=7.5 Hz, 2H), 7.15-7.00 (m, 2H), 7.00-6.85 (m, 3H), 6.68 (d, J=8.4 Hz, 1H), 4.12 (t, J=5.5 Hz, 2H), 3.30-3.10 (m, 3H), 3.05 (m, 1H), 2.96 (t, J=5.3 Hz, 2H), 2.85-2.70 (m, 2H), 2.40-2.30 (m, 1H), 2.10-2.00 (m, 1H); ESI+MS: m/z 330 ([M+H]$^+$).

5-chloro-1'-(2-phenoxyethyl)-3H-spiro[benzofuran-2,3'-pyrrolidine]

Example-145: (3aS,9aR)-7-chloro-2-(2-phenoxyethyl)-1,2,3,3a,9,9a-hexahydrochromeno[2,3-c]pyrrole

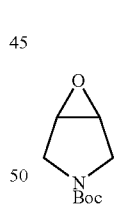 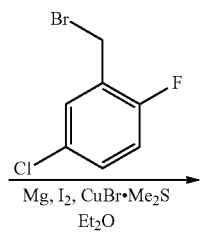

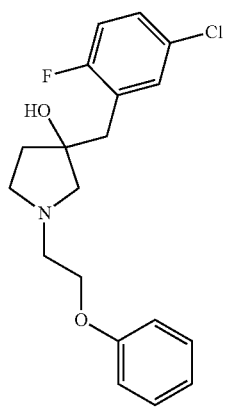

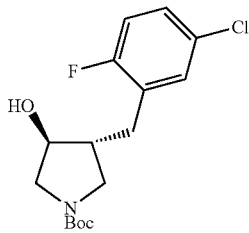

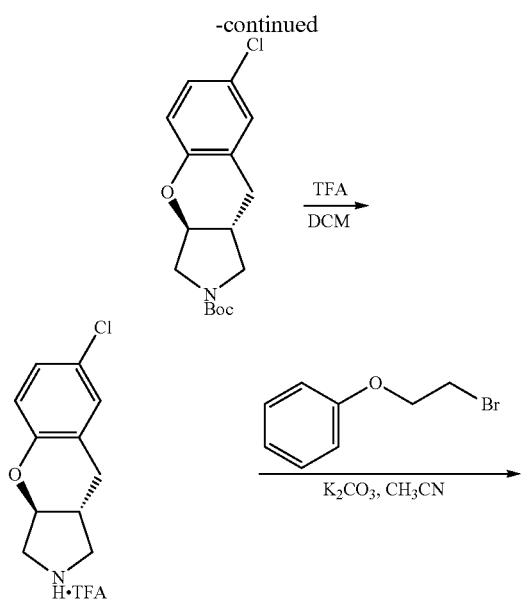

(3R,4S)-tert-butyl 3-(5-chloro-2-fluorobenzyl)-4-hydroxypyrrolidine-1-carboxylate

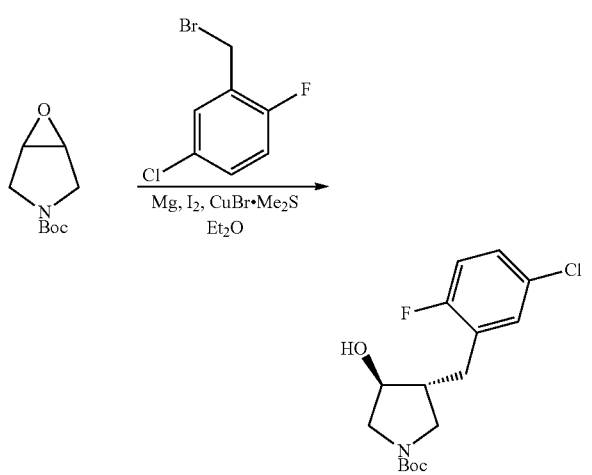

To magnesium turnings (41 mg, 1.7 mmol) in diethyl ether (1 ml) under Argon atmosphere was added a crystal of iodine and the mixture was warmed to 35° C. When color disappeared, 2-(bromomethyl)-4-chloro-1-fluorobenzene (317 mg, 1.42 mmol) in diethyl ether (0.7 ml) was added dropwise over 15 minutes. The reaction mixture was kept at 35° C. overnight. Copper (I) bromide dimethylsulfide complex (19.4 mg, 0.094 mmol) was added and the solution turned dark brown rapidly. The solution was stirred at 35° C. for 1 h. Then, a solution of tert-butyl 6-oxa-3-azabicyclo[3.1.0]hexane-3-carboxylate (175 mg, 0.95 mmol) in diethyl ether (1 ml) was added dropwise and stirring was continued at 35° C. After 1 hour, the reaction mixture was extracted with ethyl acetate/aq.NH$_4$Cl. The organic layer was dried over Na$_2$SO$_4$, filtered and concentrated. Purification using silica gel column chromatography and a gradient of ethyl acetate in hexanes as eluent afforded 77 mg of (3R,4S)-tert-butyl 3-(5-chloro-2-fluorobenzyl)-4-hydroxypyrrolidine-1-carboxylate (Yield=25%).

(3aS,9aR)-tert-butyl 7-chloro-3,3a,9,9a-tetrahydrochromeno[2,3-c]pyrrole-2(1H)-carboxylate

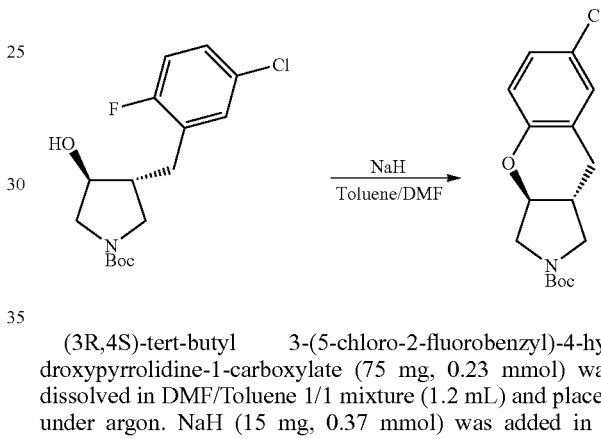

(3R,4S)-tert-butyl 3-(5-chloro-2-fluorobenzyl)-4-hydroxypyrrolidine-1-carboxylate (75 mg, 0.23 mmol) was dissolved in DMF/Toluene 1/1 mixture (1.2 mL) and placed under argon. NaH (15 mg, 0.37 mmol) was added in 1 portion and the mixture was stirred at 90° C. overnight. The reaction mixture was extracted with ethyl acetate and aq.NH$_4$Cl, the organic layer was dried over Na$_2$SO$_4$, filtered and concentrated. Purification using silica gel column chromatography and a gradient of ethyl acetate in hexanes as eluent afforded 24 mg of (3aS,9aR)-tert-butyl 7-chloro-3,3a,9,9a-tetrahydrochromeno[2,3-c]pyrrole-2(1H)-carboxylate (Yield=34%).

(3aS,9aR)-7-chloro-1,2,3,3a,9,9a-hexahydrochromeno[2,3-c]pyrrole trifluoroacetic acid salt (3aS,9aR)-tert-butyl 7-chloro-3,3a,9,9a-tetrahydrochromeno[2,3-c]pyrrole-2(1H)-carboxylate (24 mg, 0.08 mmol)

was dissolved in DCM (0.8 mL) under argon and TFA (88 mg, 0.78 mmol) was added dropwise at RT. After 3 h, solvents were evaporated and then coevaporate with toluene twice. The crude was used in the next step without further purification (Yield=quantitative). ESI+MS: m/z 210 ([M+H]⁺).

(3aS,9aR)-7-chloro-2-(2-phenoxyethyl)-1,2,3,3a,9,9a-hexahydrochromeno[2,3-c]pyrrole

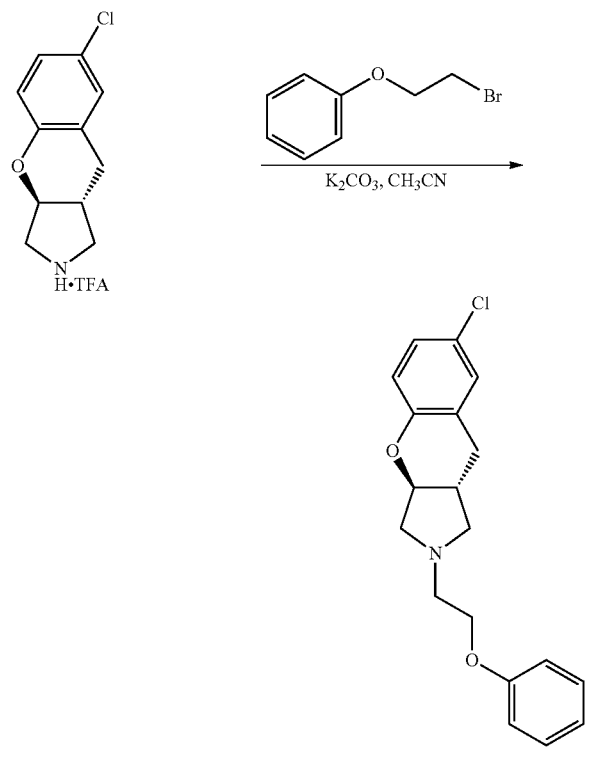

Title compound was prepared from (3aS,9aR)-7-chloro-1,2,3,3a,9,9a-hexahydrochromeno[2,3-c]pyrrole trifluoroacetic acid salt (25 mg, 0.08 mmol) using the general methodology of Example-1. Purification using silica gel column chromatography (5% MeOH/CH₂Cl₂ as eluent) afforded 16 mg of (3aS,9aR)-7-chloro-2-(2-phenoxyethyl)-1,2,3,3a,9,9a-hexahydrochromeno[2,3-c]pyrrole (Yield=63%). ¹H NMR (300 MHz, CDCl₃): δ 7.33-7.24 (m, 2H), 7.10-7.03 (m, 2H), 7.00-6.88 (m, 3H), 6.82-6.75 (m, 1H), 4.15-3.95 (m, 3H), 3.32-3.22 (m, 2H), 3.18-2.95 (m, 3H), 2.86 (dd, J=15.8 Hz, J=5.2 Hz, 1H), 2.77-2.63 (m, 2H), 2.40-2.20 (m, 1H); ESI+MS: m/z 330 ([M+H]⁺).

Example-146: 4-(4-chlorophenoxy)-4-methyl-1-(2-(2-(trifluoromethoxy)phenoxy)ethyl) piperidine

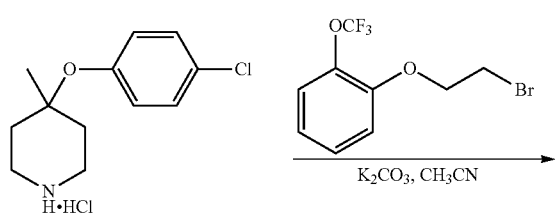

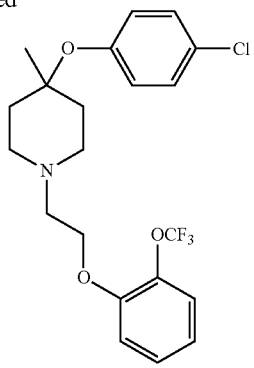

Title compound was prepared from 4-(4-chlorophenoxy)-4-methylpiperidine hydrochloride (0.07 g, 0.27 mmol) using the general methodology of Example-1. Purification using silica gel column chromatography (5% MeOH/CH₂Cl₂ as eluent) afforded 0.05 g of 4-(4-chlorophenoxy)-4-methyl-1-(2-(2-(trifluoromethoxy)phenoxy)ethyl)piperidine (Yield=44%). ¹H NMR (400 MHz, DMSO-d6): δ 7.35-7.24 (m, 5H), 7.02-6.98 (m, 3H), 4.16 (t, J=5.6 Hz, 2H), 2.74 (t, J=5.6 Hz, 2H), 2.60-2.57 (m, 4H), 1.86-1.83 (m, 2H), 1.64-1.57 (m, 2H), 1.23 (s, 3H); ESI+MS: m/z 430 ([M+H]⁺).

Example-147: 5-(2-(4-(4-chlorophenoxy)-4-methylpiperidin-1-yl)ethoxy)-2-(trifluoromethyl)pyridine

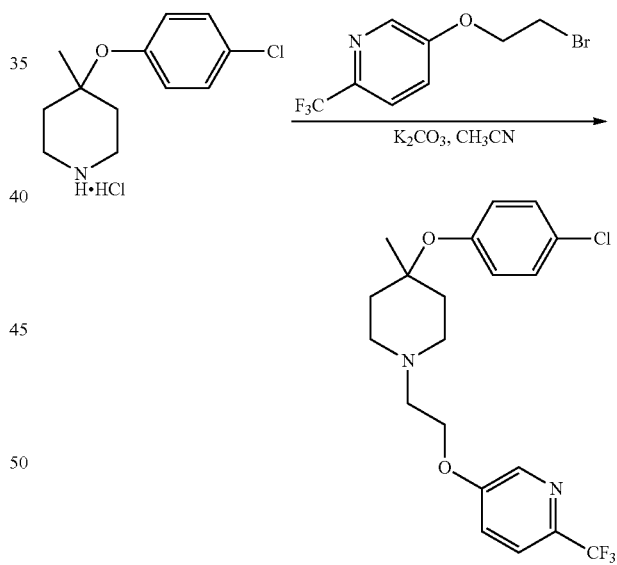

Title compound was prepared from 4-(4-chlorophenoxy)-4-methylpiperidine hydrochloride (0.05 g, 0.19 mmol) using the general methodology of Example-1. Purification using silica gel column chromatography (3% MeOH/CH₂Cl₂ as eluent) afforded 0.05 g of 5-(2-(4-(4-chlorophenoxy)-4-methylpiperidin-1-yl)ethoxy)-2-(trifluoromethyl)pyridine (Yield=63%). ¹H NMR (400 MHz, DMSO-d6): δ 8.44 (d, J=2.4 Hz, 1H), 7.82 (d, J=8.4 Hz, 1H), 7.62 (dd, J=8.8 Hz, J=2.8 Hz, 1H), 7.33-7.29 (m, 2H), 7.02-6.99 (m, 2H), 4.25 (t, J=5.6 Hz, 2H), 2.76 (t, J=5.6 Hz, 2H), 2.58-2.55 (m, 4H), 1.88-1.83 (m, 2H), 1.65-1.58 (m, 2H), 1.24 (s, 3H); ESI+MS: m/z 415 ([M+H]⁺).

Example-148: 2-(2-(4-(4-chlorophenoxy)-4-methylpiperidin-1-yl)ethoxy)-5-(trifluoromethyl) pyridine

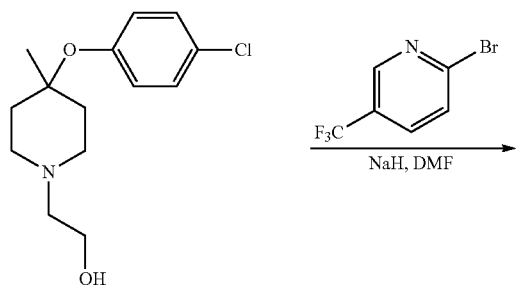

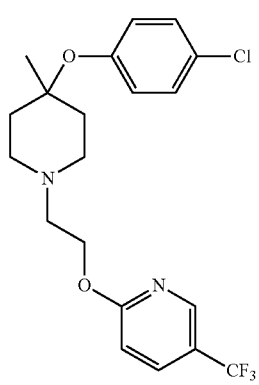

Title compound was prepared from 2-(4-(4-chlorophenoxy)-4-methylpiperidin-1-yl)ethanol (0.45 g, 1.67 mmol) and 2-bromo-5-(trifluoromethyl)pyridine (0.75 g, 3.34 mmol) using the general methodology of step 2 of key intermediate-I. Purification using preparative HPLC afforded 0.02 g of 2-(2-(4-(4-chlorophenoxy)-4-methylpiperidin-1-yl)ethoxy)-5-(trifluoromethyl)pyridine (Yield=3%). $^1$H NMR (400 MHz, CD$_3$OD): δ 8.46-8.45 (m, 1H), 7.94-7.91 (m, 1H), 7.25-7.22 (m, 2H), 6.99-6.93 (m, 3H), 4.56 (t, J=5.6 Hz, 2H), 2.87 (t, J=5.6 Hz, 2H), 2.75-2.67 (m, 4H), 2.02-1.97 (m, 2H), 1.76-1.69 (m, 2H), 1.27 (s, 3H); ESI+MS: m/z 415 ([M+H]$^+$).

Example-149: 4-(4-chlorophenoxy)-1-(2-(4-fluorophenoxy)ethyl)-4-methylpiperidine

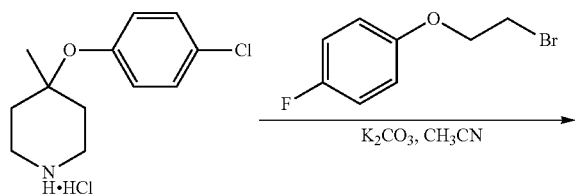

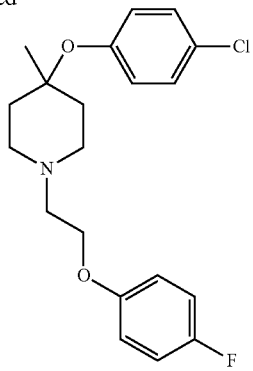

Title compound was prepared from 4-(4-chlorophenoxy)-4-methylpiperidine hydrochloride (0.10 g, 0.38 mmol) using the general methodology of Example-1. Purification using silica gel column chromatography (3% MeOH/CH$_2$Cl$_2$ as eluent) afforded 0.08 g of 4-(4-chlorophenoxy)-1-(2-(4-fluorophenoxy)ethyl)-4-methylpiperidine (Yield=58%). $^1$H NMR (400 MHz, CD$_3$OD): δ 7.26-7.22 (m, 2H), 7.01-6.96 (m, 4H), 6.94-6.90 (m, 2H), 4.11 (t, J=5.6 Hz, 2H), 2.85 (t, J=5.6 Hz, 2H), 2.76-2.67 (m, 4H), 2.03-1.98 (m, 2H), 1.77-1.70 (m, 2H), 1.28 (s, 3H); ESI+MS: m/z 364 ([M+H]$^+$).

Example-150: 4-(4-chlorophenoxy)-4-methyl-1-(2-(p-tolyloxy)ethyl)piperidine

Title compound was prepared from 4-(4-chlorophenoxy)-4-methylpiperidine hydrochloride (0.05 g, 0.19 mmol) using the general methodology of Example-1. Purification using silica gel column chromatography (2% MeOH/CH$_2$Cl$_2$ as eluent) afforded 0.05 g of 4-(4-chlorophenoxy)-4-methyl-1-(2-(p-tolyloxy)ethyl)piperidine (Yield=73%). $^1$H NMR (400 MHz, DMSO-d6): δ 7.32-7.29 (m, 2H), 7.07-6.99 (m, 4H), 6.81 (d, J=8.4 Hz, 2H), 4.02 (t, J=6.0 Hz, 2H), 2.69 (t, J=5.6 Hz, 2H), 2.56-2.54 (m, 4H), 2.22 (s, 3H), 1.87-1.84 (m, 2H), 1.65-1.59 (m, 2H), 1.23 (s, 3H); ESI+MS: m/z 360 ([M+H]$^+$).

Example-151: 4-(4-chlorophenoxy)-1-(2-(4-chlorophenoxy)ethyl)-4-methylpiperidine

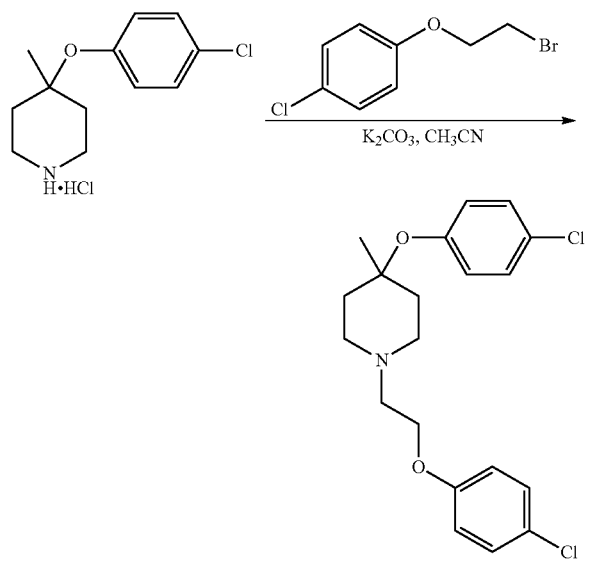

Title compound was prepared from 4-(4-chlorophenoxy)-4-methylpiperidine hydrochloride (0.05 g, 0.19 mmol) using the general methodology of Example-1. Purification using silica gel column chromatography (2% MeOH/CH$_2$Cl$_2$ as eluent) afforded 0.05 g of 4-(4-chlorophenoxy)-1-(2-(4-chlorophenoxy)ethyl)-4-methylpiperidine (Yield=69%). $^1$H NMR (400 MHz, CD$_3$OD): δ 7.27-7.23 (m, 4H), 7.00-6.96 (m, 2H), 6.93-6.90 (m, 2H), 4.13 (t, J=5.6 Hz, 2H), 2.86 (t, J=5.6 Hz, 2H), 2.76-2.68 (m, 4H), 2.04-1.97 (m, 2H), 1.78-1.71 (m, 2H), 1.28 (s, 3H); ESI+MS: m/z 381 ([M+H]$^+$).

Example-152: 4-(4-chlorophenoxy)-4-methyl-1-(2-(4-(methylsulfonyl)phenoxy)ethyl)piperidine

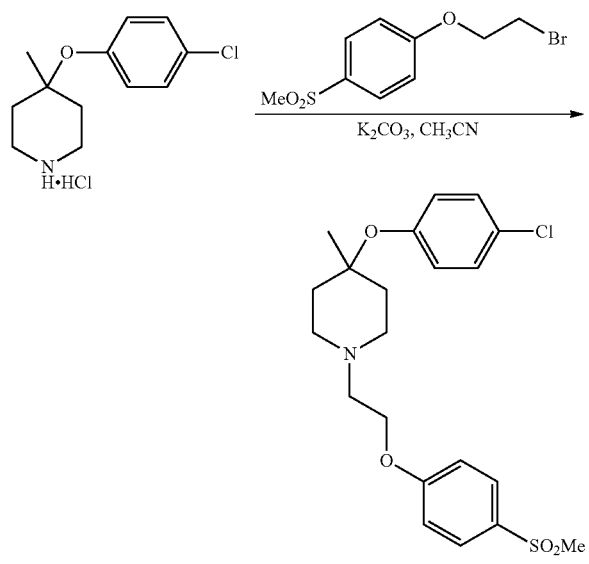

Title compound was prepared from 4-(4-chlorophenoxy)-4-methylpiperidine hydrochloride (0.05 g, 0.19 mmol) using the general methodology of Example-1. Purification using silica gel column chromatography (3% MeOH/CH$_2$Cl$_2$ as eluent) afforded 0.05 g of 4-(4-chlorophenoxy)-4-methyl-1-(2-(4-(methylsulfonyl)phenoxy)ethyl)piperidine (Yield=62%). $^1$H NMR (400 MHz, DMSO-d6): δ 7.82 (d, J=9.2 Hz, 2H), 7.31 (d, J=8.8 Hz, 2H), 7.16 (d, J=8.8 Hz, 2H), 7.01 (d, J=9.2 Hz, 2H), 4.19 (t, J=5.6 Hz, 2H), 3.14 (s, 3H), 2.74 (t, J=5.6 Hz, 2H), 2.58-2.55 (m, 4H), 1.87-1.84 (m, 2H), 1.66-1.59 (m, 2H), 1.24 (s, 3H); ESI+MS: m/z 424 ([M+H]$^+$).

Example-153: 1-(4-(2-(4-(4-chlorophenoxy)-4-methylpiperidin-1-yl)ethoxy)phenyl)ethanone

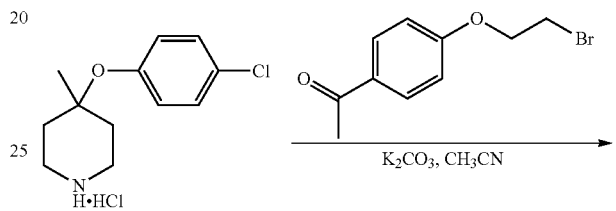

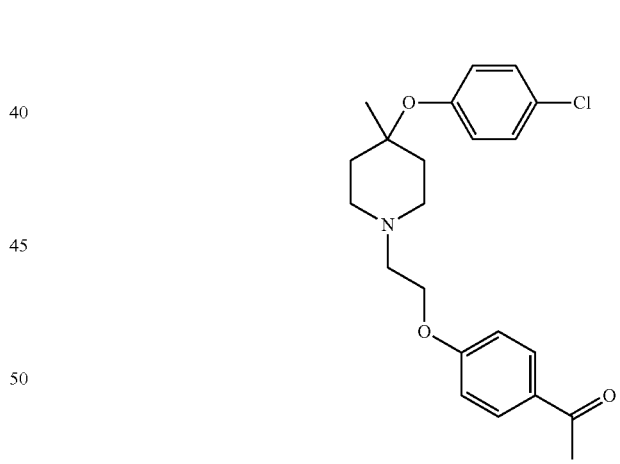

Title compound was prepared from 4-(4-chlorophenoxy)-4-methylpiperidine hydrochloride (0.20 g, 0.76 mmol) using the general methodology of Example-1. Purification using silica gel column chromatography (3% MeOH/CH$_2$Cl$_2$ as eluent) afforded 0.20 g of 1-(4-(2-(4-(4-chlorophenoxy)-4-methylpiperidin-1-yl)ethoxy)phenyl)ethanone (Yield=68%). $^1$H NMR (400 MHz, DMSO-d6): δ 7.92-7.89 (m, 2H), 7.33-7.29 (m, 2H), 7.05-6.99 (m, 4H), 4.17 (t, J=6.0 Hz, 2H), 2.74 (t, J=5.6 Hz, 2H), 2.57-2.52 (m, 4H), 2.51-2.50 (m, 3H), 1.87-1.84 (m, 2H), 1.66-1.59 (m, 2H), 1.23 (s, 3H); ESI+MS: m/z 388 ([M+H]$^+$).

Example-154: 1-(4-(2-(4-(4-chlorophenoxy)-4-methylpiperidin-1-yl)ethoxy)phenyl)ethanol

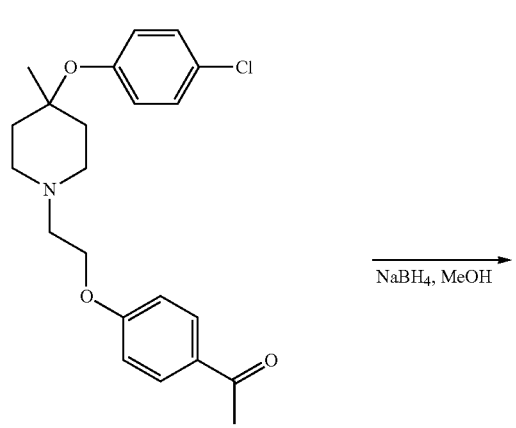

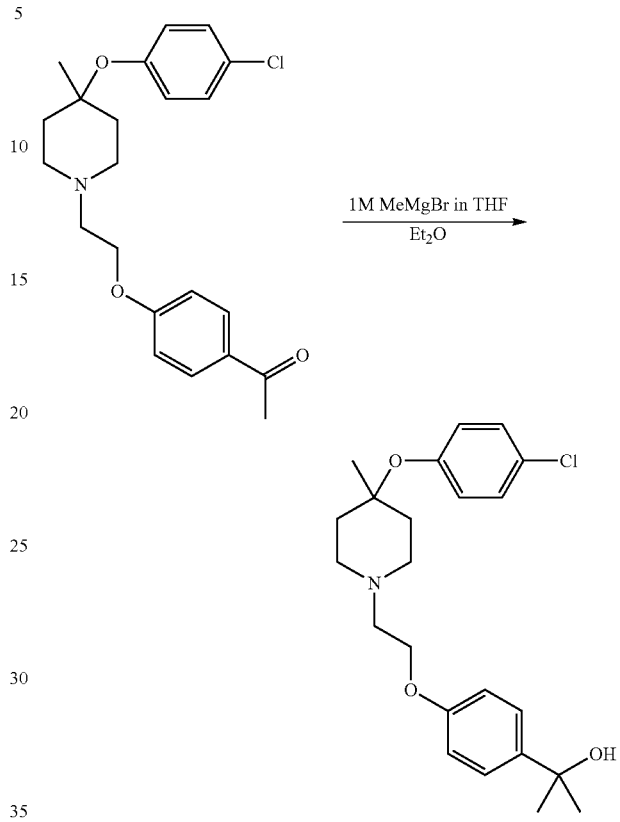

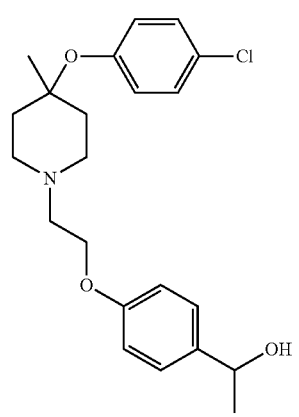

Title compound was prepared from 1-(4-(2-(4-(4-chlorophenoxy)-4-methylpiperidin-1-yl)ethoxy)phenyl)ethanone (0.10 g, 0.26 mmol) using the general methodology of Example 107. Purification using silica gel column chromatography (3% MeOH/CH$_2$Cl$_2$ as eluent) afforded 0.50 g of 1-(4-(2-(4-(4-chlorophenoxy)-4-methylpiperidin-1-yl)ethoxy)phenyl)ethanol (Yield=50%). $^1$H NMR (400 MHz, DMSO-d6): δ 7.33-7.29 (m, 2H), 7.24-7.21 (m, 2H), 7.03-6.99 (m, 2H), 6.88-6.85 (m, 2H), 4.99 (t, J=4.0 Hz, 1H), 4.67-4.62 (m, 1H), 4.06-4.02 (m, 2H), 2.72-2.70 (m, 2H), 2.56-2.50 (m, 4H), 1.87-1.84 (m, 2H), 1.64-1.62 (m, 2H), 1.28 (d, J=6.4 Hz, 3H), 1.24 (s, 3H); ESI+MS: m/z 390 ([M+H]$^+$).

Example-155: 2-(4-(2-(4-(4-chlorophenoxy)-4-methylpiperidin-1-yl)ethoxy)phenyl)propan-2-ol Title compound was prepared from 1-(4-(2-(4-(4-chlorophenoxy)-4-methylpiperidin-1-yl)ethoxy)phenyl)ethanone (0.10 g, 0.26 mmol) using the general methodology of step 1 of key intermediate-I. Purification using silica gel column chromatography (5% MeOH/CH$_2$Cl$_2$ as eluent) afforded 0.50 g of 2-(4-(2-(4-(4-chlorophenoxy)-4-methylpiperidin-1-yl)ethoxy)phenyl)propan-2-ol (Yield=29%). $^1$H NMR (400 MHz, DMSO-d6): δ 7.35-7.29 (m, 4H), 7.00 (d, J=8.8 Hz, 2H), 6.84 (d, J=8.8 Hz, 2H), 4.86 (s, 1H), 4.04 (t, J=6.0 Hz, 2H), 2.70 (t, J=6.0 Hz, 2H), 2.55-2.50 (m, 4H), 1.88-1.83 (m, 2H), 1.65-1.59 (m, 2H), 1.37 (s, 6H), 1.23 (s, 3H); ESI+MS: m/z 404 ([M+H]$^+$).

Example-156: 4-(4-chlorophenoxy)-1-(2-(3-fluoro-2-(trifluoromethyl)phenoxy)ethyl)-4-methylpiperidine

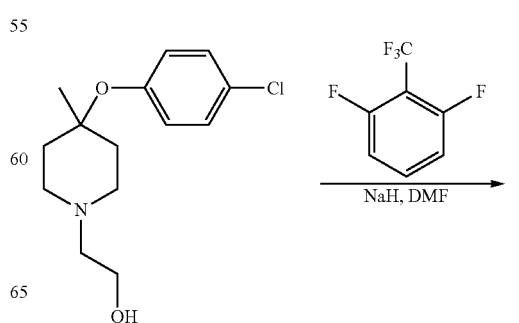

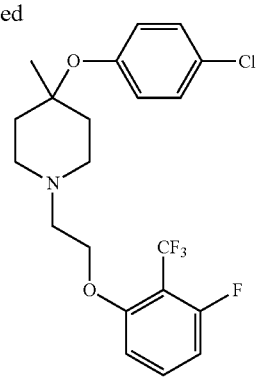

Title compound was prepared from 2-(4-(4-chlorophenoxy)-4-methylpiperidin-1-yl)ethanol (0.10 g, 0.37 mmol) and 1,3-difluoro-2-(trifluoromethyl)benzene (68 mg, 0.37 mmol) using the general methodology of step 2 of key intermediate-I. Purification using preparative HPLC afforded 0.035 g of 4-(4-chlorophenoxy)-1-(2-(3-fluoro-2-(trifluoromethyl)phenoxy)ethyl)-4-methylpiperidine (Yield=22%). $^1$H NMR (400 MHz, DMSO-d6): δ 7.66-7.60 (m, 1H), 7.32-7.28 (m, 2H), 7.13 (d, J=8.4 Hz, 1H), 7.02-6.94 (m, 3H), 4.22 (t, J=5.6 Hz, 2H), 2.74 (t, J=5.6 Hz, 2H), 2.59-2.49 (m, 4H), 1.85-1.82 (m, 2H), 1.63-1.56 (m, 2H), 1.23 (s, 3H); ESI+MS: m/z 432 ([M+H]$^+$).

Example-157: 4-(4-chlorophenoxy)-1-(2-(4-fluoro-2-(trifluoromethyl)phenoxy)ethyl)-4-methylpiperidine

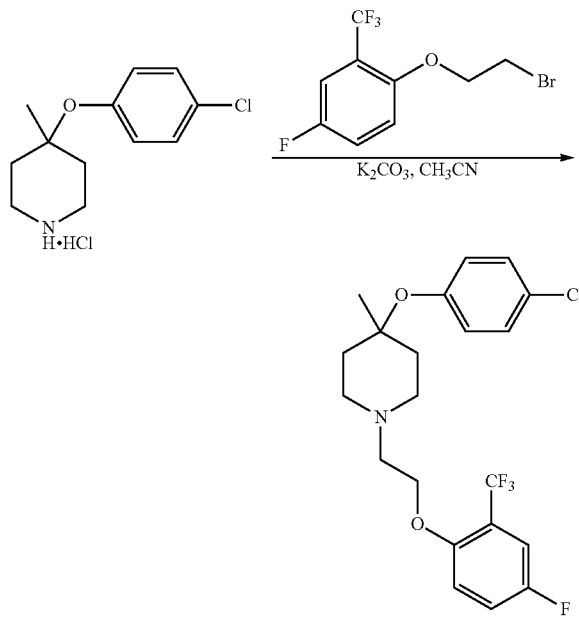

Title compound was prepared from 4-(4-chlorophenoxy)-4-methylpiperidine hydrochloride (0.20 g, 0.76 mmol) using the general methodology of Example-1. Purification using silica gel column chromatography (2% MeOH/CH$_2$Cl$_2$ as eluent) afforded 0.16 g of 4-(4-chlorophenoxy)-1-(2-(4-fluoro-2-(trifluoromethyl)phenoxy)ethyl)-4-methylpiperidine (Yield=49%). $^1$H NMR (400 MHz, CD$_3$OD): δ 7.36-7.30 (m, 2H), 7.27-7.19 (m, 3H), 7.00-6.96 (m, 2H), 4.25 (t, J=5.6 Hz, 2H), 2.92 (t, J=5.6 Hz, 2H), 2.80-2.76 (m, 4H), 2.03-1.97 (m, 2H), 1.76-1.69 (m, 2H), 1.28 (s, 3H); ESI+MS: m/z 432 ([M+H]$^+$).

Example-158: 4-(4-chlorophenoxy)-1-(2-(4-fluoro-2-(methylsulfonyl)phenoxy)ethyl)-4-methylpiperidine

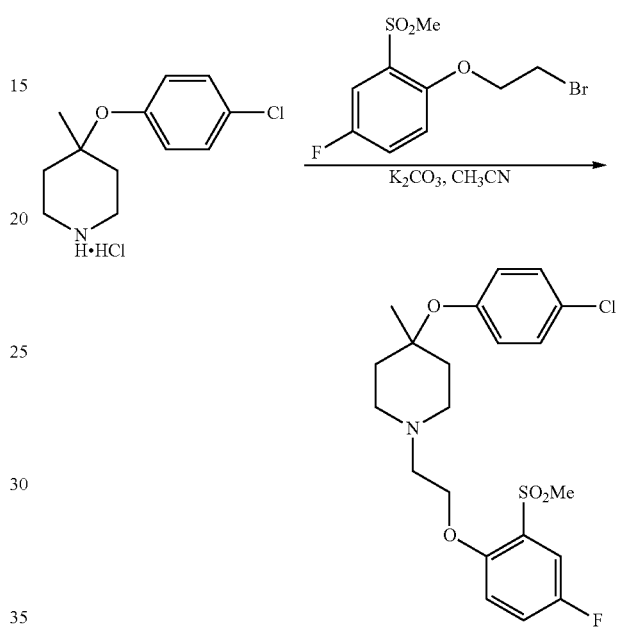

Title compound was prepared from 4-(4-chlorophenoxy)-4-methylpiperidine hydrochloride (0.10 g, 0.38 mmol) using the general methodology of Example-1. Purification using silica gel column chromatography (3% MeOH/CH$_2$Cl$_2$ as eluent) afforded 0.07 g of 4-(4-chlorophenoxy)-1-(2-(4-fluoro-2-(methylsulfonyl)phenoxy)ethyl)-4-methylpiperidine (Yield=42%). $^1$H NMR (400 MHz, DMSO-d6): δ 7.59-7.52 (m, 2H), 7.37-7.29 (m, 3H), 7.03-6.99 (m, 2H), 4.25 (t, J=4.8 Hz, 2H), 3.38 (s, 3H), 2.75 (t, J=5.6 Hz, 2H), 2.57-2.55 (m, 4H), 1.86-1.81 (m, 2H), 1.61-1.55 (m, 2H), 1.23 (s, 3H); ESI+MS: m/z 442 ([M+H]$^+$).

Example-159: 4-(4-chlorophenoxy)-1-(2-(5-fluoro-2-methoxyphenoxy)ethyl)-4-methylpiperidine

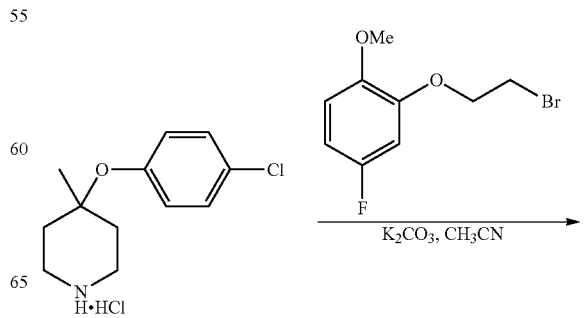

-continued

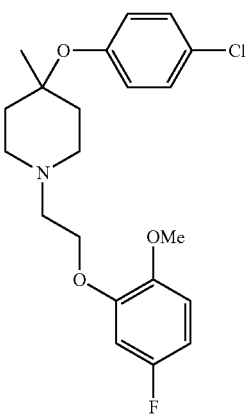

Title compound was prepared from 4-(4-chlorophenoxy)-4-methylpiperidine hydrochloride (0.10 g, 0.38 mmol) using the general methodology of Example-1. Purification using silica gel column chromatography (5% MeOH/CH₂Cl₂ as eluent) afforded 0.07 g of 4-(4-chlorophenoxy)-1-(2-(5-fluoro-2-methoxyphenoxy)ethyl)-4-methylpiperidine (Yield=40%). ¹H NMR (400 MHz, DMSO-d6): δ 7.33-7.29 (m, 2H), 7.03-6.99 (m, 2H), 6.91-6.89 (m, 2H), 6.67 (dt, J=11.6 Hz, J=3.2 Hz, 1H), 4.06 (t, J=5.6 Hz, 2H), 3.72 (s, 3H), 2.73-2.70 (m, 2H), 2.57-2.55 (m, 4H), 1.86-1.83 (m, 2H), 1.65-1.58 (m, 2H), 1.23 (s, 3H); ESI+MS: m/z 394 ([M+H]⁺).

Example-160: 4-(4-chlorophenoxy)-1-(2-(4-fluoro-2-methoxyphenoxy)ethyl)-4-methyl piperidine

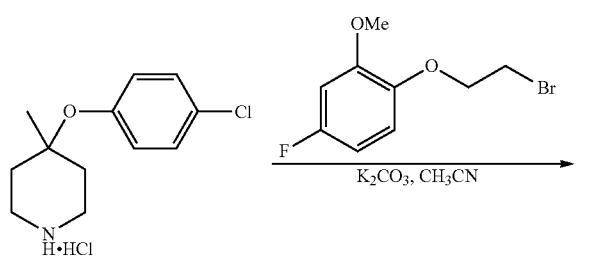

Title compound was prepared from 4-(4-chlorophenoxy)-4-methylpiperidine hydrochloride (0.12 g, 0.46 mmol) using the general methodology of Example-1. Purification using silica gel column chromatography (5% MeOH/CH₂Cl₂ as eluent) afforded 0.07 g of 4-(4-chlorophenoxy)-1-(2-(4-fluoro-2-methoxyphenoxy)ethyl)-4-methylpiperidine (Yield=39%). ¹H NMR (400 MHz, DMSO-d6): δ 7.27-7.23 (m, 2H), 7.02-6.92 (m, 3H), 6.77 (dd, J=10.4 Hz, J=3.2 Hz, 1H), 6.61-6.56 (m, 1H), 4.12 (t, J=5.6 Hz, 2H), 3.83 (s, 3H), 2.87-2.84 (m, 2H), 2.79-2.70 (m, 4H), 2.00-1.97 (m, 2H), 1.77-1.70 (m, 2H), 1.28 (s, 3H); ESI+MS: m/z 394 ([M+H]⁺).

Example-161: 5-(2-(4-(4-chlorophenoxy)-4-methylpiperidin-1-yl)ethoxy)thiazole

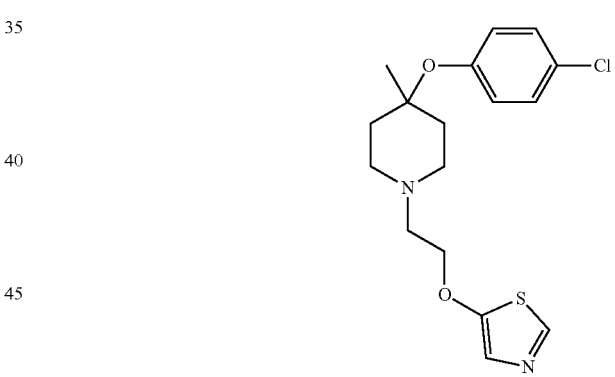

Na-metal (34 mg, 1.48 mmol) was added to 2-(4-(4-chlorophenoxy)-4-methylpiperidin-1-yl)ethanol (0.20 g, 0.74 mmol) and the mixture was heated at 120° C. for 5 h. Then 5-bromo thiazole (195 mg, 1.19 mmol) was added and the reaction mixture was heated at 80° C. for 48 h. The reaction mixture was cooled to RT, quenched with water and extracted with EtOAc. The organic layer was separated, dried over Na₂SO₄ and concentrated under reduced pressure. The crude compound was purified by column chromatography eluting with 2% MeOH in DCM and further purified by preparative HPLC to obtain 5 mg of 5-(2-(4-(4-chlorophenoxy)-4-methylpiperidin-1-yl)ethoxy)thiazole (Yield 2%). ¹HNMR (400 MHz, CD3OD): δ 8.35 (s, 1H), 7.25-7.22 (m, 3H), 6.97 (d, J=8.8 Hz, 2H), 4.26 (t, J=5.2 Hz, 2H), 2.87 (t, J=5.2 Hz, 2H), 2.72-2.70 (m, 4H), 2.0-1.98 (m, 2H), 1.77-1.69 (m, 2H), 1.27 (s, 3H); ESI+MS: m/z 353 ([M+H]⁺).

311

Example-162: 2-(2-(4-(4-chlorophenoxy)-4-methylpiperidin-1-yl)ethoxy)-3-(trifluoromethyl)pyridine

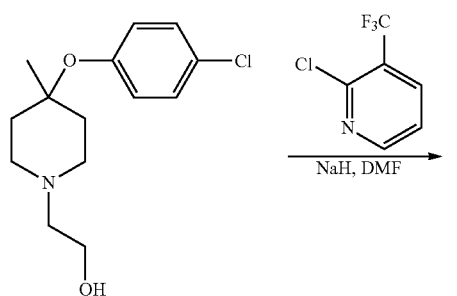

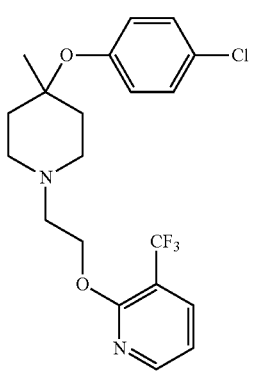

Title compound was prepared from 2-(4-(4-chlorophenoxy)-4-methylpiperidin-1-yl)ethanol (0.10 g, 0.37 mmol) and 2-chloro-3-(trifluoromethyl)pyridine (135 mg, 0.74 mmol) using the general methodology of step 2 of key intermediate-I. Purification using preparative HPLC afforded 0.05 g of 2-(2-(4-(4-chlorophenoxy)-4-methylpiperidin-1-yl)ethoxy)-3-(trifluoromethyl)pyridine (Yield=33%). ¹H NMR (400 MHz, CD3OD): δ 8.35 (dd, J=4.8 Hz, J=1.2 Hz, 1H), 7.98 (dd, J=7.6 Hz, J=0.8 Hz, 1H), 7.26-7.22 (m, 2H), 7.10-7.07 (m, 1H), 6.99-6.95 (m, 2H), 4.62 (t, J=5.6 Hz, 2H), 2.90 (t, J=6.0 Hz, 2H), 2.77-2.74 (m, 4H), 2.01-1.97 (m, 2H), 1.75-1.68 (m, 2H), 1.27 (s, 3H); ESI+MS: m/z 415 ([M+H]⁺).

Example-163: 3-(2-(4-(4-chlorophenoxy)-4-methylpiperidin-1-yl)ethoxy)-2-(trifluoromethyl)pyridine

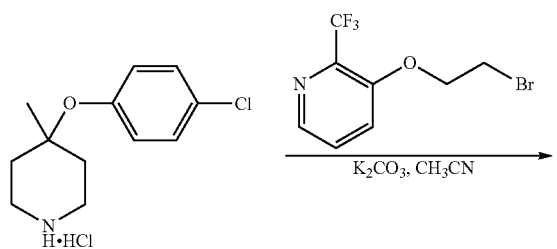

312

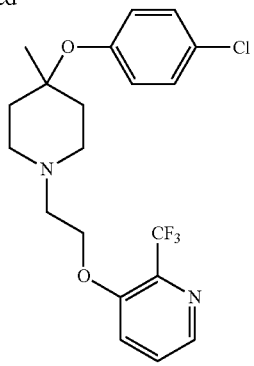

Title compound was prepared from 4-(4-chlorophenoxy)-4-methylpiperidine hydrochloride (0.07 g, 0.46 mmol) using the general methodology of Example-1. Purification using silica gel column chromatography (5% MeOH/CH₂Cl₂ as eluent) afforded 0.07 g of 3-(2-(4-(4-chlorophenoxy)-4-methylpiperidin-1-yl)ethoxy)-2-(trifluoromethyl)pyridine (Yield=63%). ¹H NMR (400 MHz, DMSO-d6): δ 8.24 (d, J=4.4 Hz, 1H), 7.82 (d, J=8.4 Hz, 1H), 7.69-7.66 (m, 1H), 7.32-7.29 (m, 2H), 7.02-6.97 (m, 2H), 4.28 (t, J=5.6 Hz, 2H), 2.75 (t, J=5.6 Hz, 2H), 2.59-2.56 (m, 4H), 1.85-1.81 (m, 2H), 1.62-1.55 (m, 2H), 1.22 (s, 3H); ESI+MS: m/z 415 ([M+H]⁺).

Example-164: 2-((4-methyl-1-(2-(4-(trifluoromethyl)phenoxy)ethyl)piperidin-4-yl)oxy)pyridine

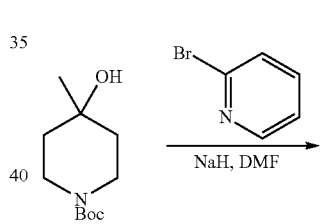

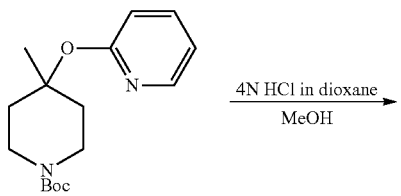

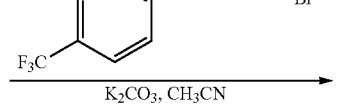

313

-continued

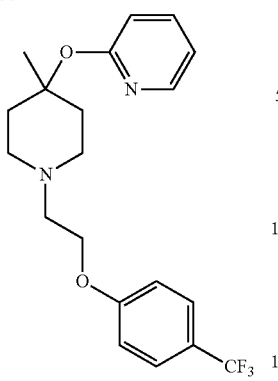

tert-butyl 4-methyl-4-(pyridin-2-yloxy)piperidine-1-carboxylate

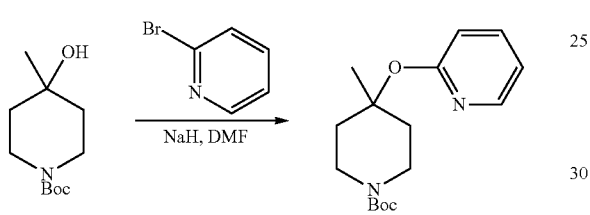

Title compound was prepared from tert-butyl 4-hydroxy-4-methylpiperidine-1-carboxylate (0.50 g, 2.32 mmol) and 2-bromopyridine (0.73 g, 4.64 mmol) using the general methodology of Example 61. Purification using silica gel column chromatography (2% EA/Hexanes) afforded 0.20 g of tert-butyl 4-methyl-4-(pyridin-2-yloxy)piperidine-1-carboxylate (Yield=30%).

2-((4-methylpiperidin-4-yl)oxy)pyridine hydrochloride

Title compound was prepared from tert-butyl 4-methyl-4-(pyridin-2-yloxy)piperidine-1-carboxylate (0.2 g, 0.68 mmol) using general methodology of step 2 of key intermediate-VI to afford 0.12 g of 2-((4-methylpiperidin-4-yl)oxy)pyridine hydrochloride (Yield=77%).

314

2-((4-methyl-1-(2-(4-(trifluoromethyl)phenoxy)ethyl)piperidin-4-yl)oxy)pyridine

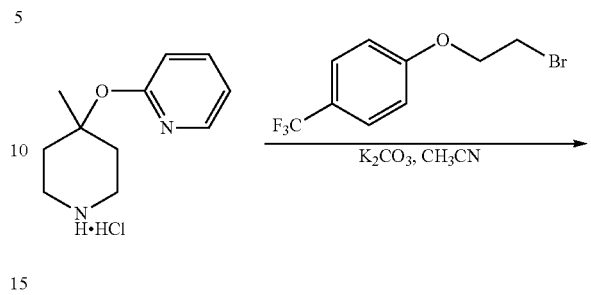

Title compound was prepared from 2-((4-methylpiperidin-4-yl)oxy)pyridine hydrochloride (0.12 g, 0.53 mmol) using the general methodology of Example-1. Purification using preparative HPLC afforded 0.05 g of 2-((4-methyl-1-(2-(4-(trifluoromethyl)phenoxy)ethyl)piperidin-4-yl)oxy)pyridine (Yield=25%). $^1$H NMR (400 MHz, DMSO-d6): δ 8.10-8.08 (m, 1H), 7.66-7.61 (m, 3H), 7.11 (d, J=8.8 Hz, 2H), 6.92-6.89 (m, 1H), 6.72 (d, J=8.0 Hz, 1H), 4.14 (t, J=6.0 Hz, 2H), 2.70-2.66 (m, 2H), 2.64-2.59 (m, 2H), 2.40-2.34 (m, 2H), 2.34-2.27 (m, 2H), 1.74-1.68 (m, 2H), 1.57 (s, 3H); ESI+MS: m/z 381 ([M+H]$^+$).

Example-165: 1-(2-(5-chloro-2-(trifluoromethyl)phenoxy)ethyl)-4-(4-chlorophenoxy)-4-methylpiperidine

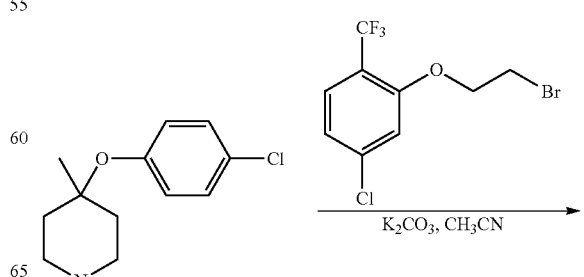

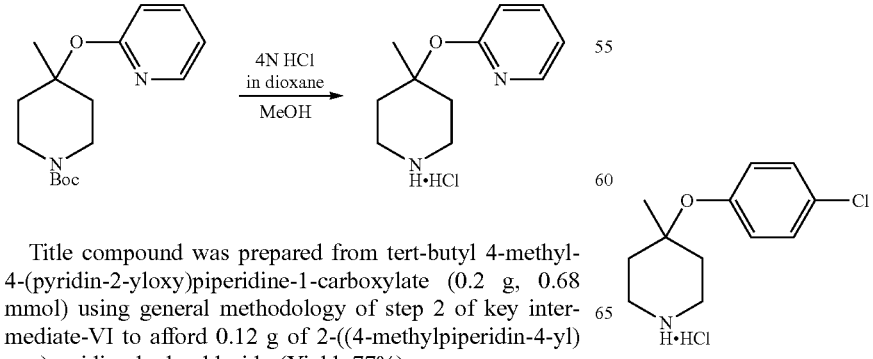

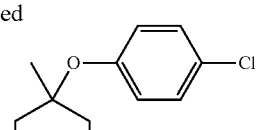

Title compound was prepared from 4-(4-chlorophenoxy)-4-methylpiperidine hydrochloride (0.05 g, 0.19 mmol) using the general methodology of Example-1. Purification using silica gel column chromatography (3% MeOH/CH$_2$Cl$_2$ as eluent) afforded 0.05 g of 1-(2-(5-chloro-2-(trifluoromethyl)phenoxy)ethyl)-4-(4-chlorophenoxy)-4-methylpiperidine (Yield=59%). $^1$H NMR (400 MHz, DMSO-d6): δ 7.61 (d, J=8.0 Hz, 1H), 7.43 (m, 1H), 7.32-7.28 (m, 2H), 7.15 (dd, J=1.2 Hz, J=8.4 Hz, 1H), 7.02-6.98 (m, 2H), 4.25 (t, J=5.6 Hz, 2H), 2.73 (t, J=5.6 Hz, 2H), 2.59-2.55 (m, 4H), 1.86-1.80 (m, 2H), 1.62-1.56 (m, 2H), 1.22 (s, 3H); ESI+MS: m/z 449 ([M+H]$^+$).

Example-166: 7-(2-(4-(4-chlorophenoxy)-4-methylpiperidin-1-yl)ethoxy)-3,4-dihydroquinolin-2(1H)-one

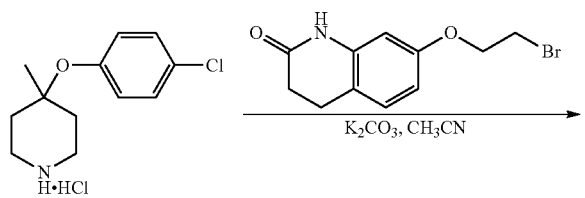

Title compound was prepared from 4-(4-chlorophenoxy)-4-methylpiperidine hydrochloride (0.07 g, 0.27 mmol) using the general methodology of Example-1. Purification using silica gel column chromatography (3% MeOH/CH$_2$Cl$_2$ as eluent) afforded 0.05 g of 7-(2-(4-(4-chlorophenoxy)-4-methylpiperidin-1-yl)ethoxy)-3,4-dihydroquinolin-2(1H)-one (Yield=45%). $^1$H NMR (400 MHz, CD$_3$OD): δ 7.28-7.22 (m, 2H), 7.07 (d, J=8.4 Hz, 1H), 7.02-6.96 (m, 2H), 6.58 (dd, J=8.0 Hz, J=2.4 Hz, 1H), 6.48 (d, J=2.4 Hz, 1H), 4.12 (t, J=5.2 Hz, 2H), 2.89-2.84 (m, 4H), 2.80-2.67 (m, 4H), 2.54 (dd, J=8.4 Hz, J=6.8 Hz, 2H), 2.04-1.98 (m, 2H), 1.78-1.70 (m, 2H), 1.29 (s, 3H); ESI+MS: m/z 415 ([M+H]$^+$).

Example-167: 4-(2-(4-(4-chlorophenoxy)-4-methylpiperidin-1-yl)ethoxy)-3-(trifluoromethyl)pyridine

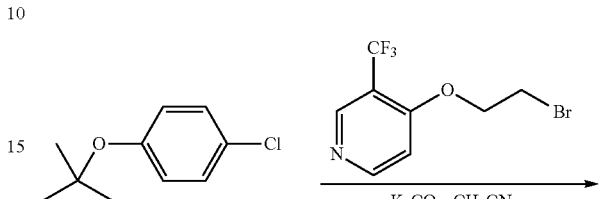

Title compound was prepared from 4-(4-chlorophenoxy)-4-methylpiperidine hydrochloride (0.05 g, 0.19 mmol) using the general methodology of Example-1. Purification using silica gel column chromatography (3% MeOH/CH$_2$Cl$_2$ as eluent) followed by preparative HPLC afforded 0.015 g of 4-(2-(4-(4-chlorophenoxy)-4-methylpiperidin-1-yl)ethoxy)-3-(trifluoromethyl)pyridine (Yield=19%). $^1$H NMR (400 MHz, DMSO-d6): δ 8.70-8.64 (m, 2H), 7.36 (d, J=6.0 Hz, 1H), 7.35-7.27 (m, 2H), 7.02-6.97 (m, 2H), 4.33 (t, J=5.6 Hz, 2H), 2.77 (t, J=5.6 Hz, 2H), 2.65-2.55 (m, 4H), 1.87-1.80 (m, 2H), 1.65-1.55 (m, 2H), 1.23 (s, 3H); ESI+MS: m/z 415 ([M+H]$^+$).

Example-168: N-(2-(4-(4-chlorophenoxy)-4-methylpiperidin-1-yl)ethyl)-2-(trifluoromethyl) aniline

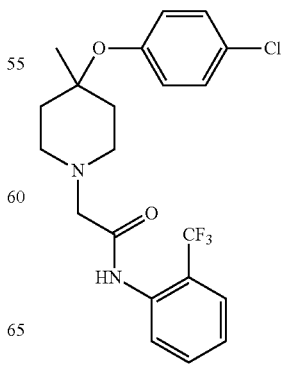

317
-continued

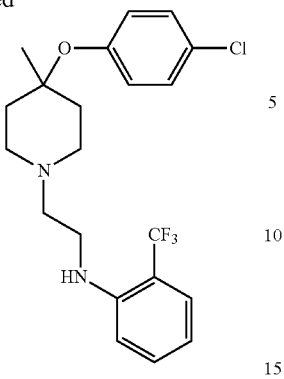

318
-continued

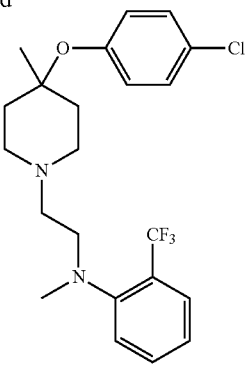

To a solution of 2-(4-(4-chlorophenoxy)-4-methylpiperidin-1-yl)-N-(2-(trifluoromethyl)phenyl) acetamide (0.05 g, 0.12 mmol) in dry THF (5 mL) were added NaBH$_4$ (0.044 g, 1.17 mmol) and I$_2$ (0.21 g, 0.82 mmol) at 0° C. The mixture was stirred at 80° C. for 16 h. Solvents were evaporated and the crude reaction mass was diluted with water and extracted with ethyl acetate. The organic layer was dried with Na$_2$SO$_4$, filtered and concentrated. Purification using silica gel column chromatography (5% MeOH/ CH$_2$Cl$_2$ as eluent) afforded 0.012 g of N-(2-(4-(4-chlorophenoxy)-4-methylpiperidin-1-yl)ethyl)-2-(trifluoromethyl) aniline (Yield=25%). $^1$H NMR (400 MHz, CD$_3$OD): δ 7.43-7.35 (m, 2H), 7.27-7.22 (m, 2H), 7.02-6.96 (m, 2H), 6.82 (d, J=8.4 Hz, 1H), 6.7 (t, J=7.6 Hz, 1H), 3.35-3.25 (m, 2H), 2.70 (t, J=6.0 Hz, 2H), 2.67-2.60 (m, 4H), 2.06-1.96 (m, 2H), 1.75-1.68 (m, 2H), 1.28 (s, 3H); ESI+MS: m/z 413 ([M+H]$^+$).

Example-169: N-(2-(4-(4-chlorophenoxy)-4-methylpiperidin-1-yl)ethyl)-N-methyl-2-(trifluoromethyl) aniline To a stirred solution of N-(2-(4-(4-chlorophenoxy)-4-methylpiperidin-1-yl)ethyl)-2-(trifluoromethyl)aniline (100 mg, 0.24 mmol) in MeOH (10 mL) were added HCHO (11 mg, 0.36 mmol) and NaCNBH$_3$ (45 mg, 0.72 mmol) at 0° C. The reaction mixture was stirred at RT for 48 h. After 48 h, HCHO (11 mg, 0.36 mmol) and NaCNBH$_3$ (45 mg, 0.72 mmol) were added at 0° C. and the reaction mixture was stirred at RT for 4 days. After completion of the reaction (monitored by LCMS), volatiles were removed under reduced pressure. The residue was basified with sat. aq. NaHCO$_3$ and extracted with DCM. The organic layer was dried over anhydrous Na$_2$SO$_4$ and concentrated under reduced pressure. Purification using silica gel column chromatography (50% EA/Hexanes as eluent) followed by preparative HPLC afforded 0.016 g of N-(2-(4-(4-chlorophenoxy)-4-methylpiperidin-1-yl)ethyl)-N-methyl-2-(trifluoromethyl)aniline (Yield=15%). $^1$H NMR (400 MHz, CD$_3$OD): δ 7.65-7.50 (m, 3H), 7.31-7.22 (m, 3H), 7.00-6.93 (m, 2H), 3.17-3.10 (m, 2H), 2.70 (s, 3H), 2.65-2.50 (m, 6H), 2.00-1.92 (m, 2H), 1.73-1.63 (m, 2H), 1.26 (s, 3H); ESI+MS: m/z 427 ([M+H]$^+$).

Example-170: N-(2-(4-(4-chlorophenoxy)-4-methylpiperidin-1-yl)ethyl)-N-(2-(trifluoromethyl)phenyl)acetamide

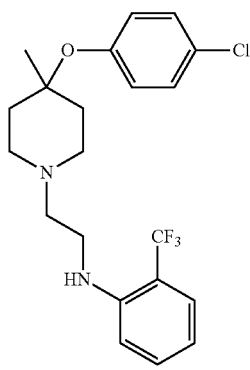

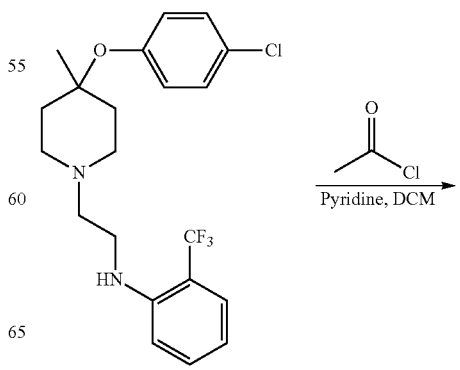

-continued

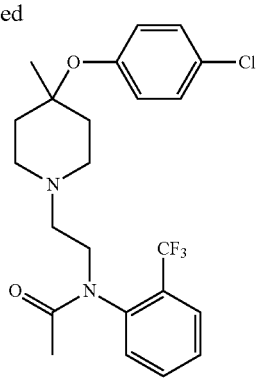

To a stirred solution of N-(2-(4-(4-chlorophenoxy)-4-methylpiperidin-1-yl)ethyl)-2-(trifluoromethyl)aniline (50 mg, 0.12 mmol) in DCM (5 mL) were added pyridine (2 mL, 24.7 mmol) and acetyl chloride (0.026 mL, 0.36 mmol) at 0° C. The reaction mixture was stirred at RT for 12 h. After completion of the reaction (monitored by LCMS), the mixture was diluted in water and extracted with DCM. The organic layer was dried over anhydrous $Na_2SO_4$ and concentrated under reduced pressure. Purification using preparative HPLC afforded 0.020 g of N-(2-(4-(4-chlorophenoxy)-4-methylpiperidin-1-yl)ethyl)-N-(2-(trifluoromethyl)phenyl) acetamide (Yield=36%). $^1$H NMR (400 MHz, $CD_3OD$): δ 7.94-7.80 (m, 2H), 7.75-7.62 (m, 2H), 7.34 (d, J=9.0 Hz, 2H), 7.07 (d, J=8.0 Hz, 2H), 4.47-4.37 (m, 2H), 3.48-3.20 (m, 6H), 2.14-2.02 (m, 2H), 1.95-1.80 (m, 2H), 1.70 (s, 3H), 1.35-1.25 (m, 3H); ESI+MS: m/z 455 ([M+H]$^+$).

Example-171: 2-(2-(4-(4-chlorophenoxy)-4-methylpiperidin-1-yl)ethoxy)-8-(trifluoromethyl)quinoline

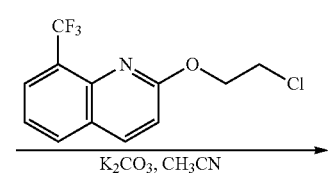

Title compound was prepared from 4-(4-chlorophenoxy)-4-methylpiperidine hydrochloride (0.05 g, 0.19 mmol) using the general methodology of Example-1. Purification using silica gel column chromatography (5% MeOH/$CH_2Cl_2$ as eluent) afforded 0.01 g of 2-(2-(4-(4-chlorophenoxy)-4-methylpiperidin-1-yl)ethoxy)-8-(trifluoromethyl)quinoline (Yield=11%). $^1$H NMR (400 MHz, $CD_3OD$): δ 8.22 (d, J=9.2 Hz, 1H), 8.05-7.99 (m, 2H), 7.49 (t, J=8.0 Hz, 1H), 7.25-7.21 (m, 2H), 7.07 (d, J=8.8 Hz, 1H), 6.99-6.95 (m, 2H), 4.72 (t, J=6.0 Hz, 2H), 2.97 (t, J=6.0 Hz, 2H), 2.78-2.73 (m, 4H), 2.04-1.98 (m, 2H), 1.77-1.71 (m, 2H), 1.28 (s, 3H); ESI+MS: m/z 465 ([M+H]$^+$).

Example-172: 1-(2-(4-(4-chlorophenoxy)-4-methylpiperidin-1-yl)ethyl)-8-(trifluoromethyl)quinolin-2(1H)-one

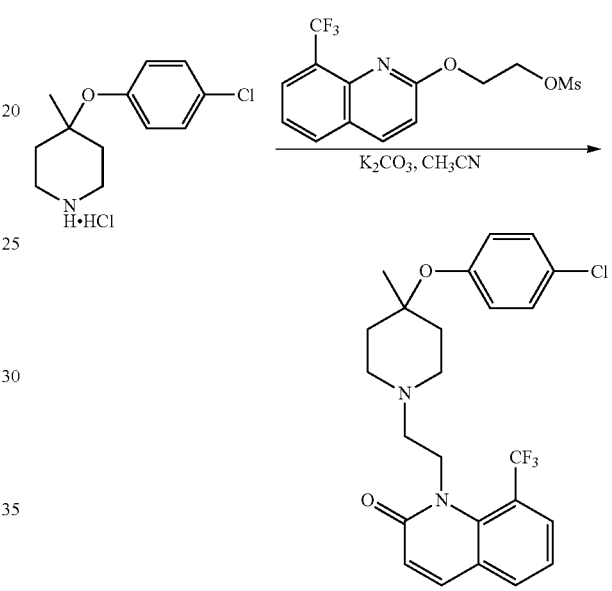

Title compound was prepared from 4-(4-chlorophenoxy)-4-methylpiperidine hydrochloride (0.05 g, 0.19 mmol) using the general methodology of Example-1. Purification using preparative HPLC afforded 0.004 g of 1-(2-(4-(4-chlorophenoxy)-4-methylpiperidin-1-yl)ethyl)-8-(trifluoromethyl)quinolin-2(1H)-one (Yield=6%). $^1$H NMR (400 MHz, $CD_3OD$): δ 7.98 (dd, J=8.0 Hz, J=1.6 Hz, 1H), 7.89-7.86 (m, 2H), 7.41 (t, J=8.0 Hz, 1H), 7.23-7.19 (m, 2H), 6.89-6.85 (m, 2H), 6.68 (d, J=9.2 Hz, 1H), 4.54 (t, J=6.0 Hz, 2H), 2.53 (t, J=6.0 Hz, 2H), 2.44-2.38 (m, 2H), 2.30-2.25 (m, 2H), 1.67-1.62 (m, 2H), 1.31-1.25 (m, 2H), 1.28 (s, 3H); ESI+MS: m/z 465 ([M+H]$^+$).

Example-173: 4-(2-(4-methyl-4-phenoxypiperidin-1-yl)ethoxy)pyridine

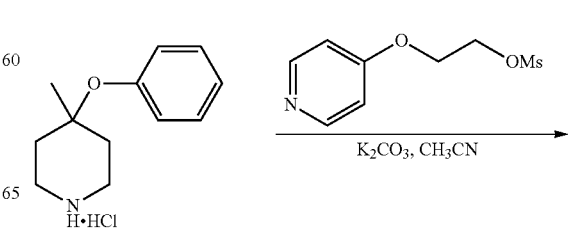

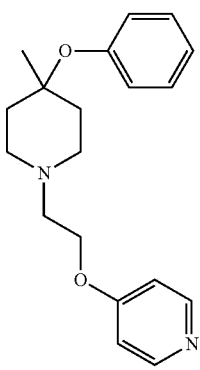

Title compound was prepared from 4-methyl-4-phenoxypiperidine hydrochloride (0.10 g, 0.44 mmol) using the general methodology of Example-1. Purification using silica gel column chromatography (3% MeOH/CH$_2$Cl$_2$ as eluent) afforded 0.015 g of 4-(2-(4-methyl-4-phenoxypiperidin-1-yl)ethoxy)pyridine (Yield=11%). $^1$H NMR (400 MHz, DMSO-d6): δ 8.78 (d, J=6.4 Hz, 2H), 7.53 (d, J=6.4 Hz, 2H), 7.32 (t, J=8.0 Hz, 2H), 7.13-7.06 (m, 3H), 4.73-4.70 (m, 2H), 3.72-3.42 (m, 6H), 2.12-2.09 (m, 2H), 1.97-1.91 (m, 2H), 1.26 (s, 3H); ESI+MS: m/z 313 ([M+H]$^+$).

Example-174: 2-(2-(4-methyl-4-phenoxypiperidin-1-yl)ethoxy)pyridine

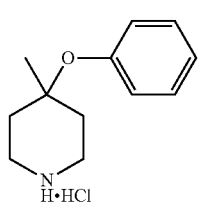

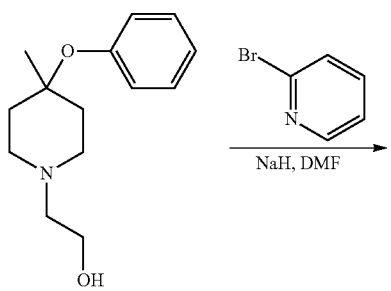

Title compound was prepare from 2-(4-methyl-4-phenoxypiperidin-1-yl)ethanol (0.15 g, 0.64 mmol) and 2-bromopyridine (151 mg, 0.96 mmol) using the general methodology of Example 61. Purification using silica gel column chromatography (5% MeOH/CH$_2$Cl$_2$ as eluent) afforded 0.15 g of 2-(2-(4-methyl-4-phenoxypiperidin-1-yl)ethoxy)pyridine (Yield=75%). $^1$H NMR (500 MHz, CD$_3$OD): δ 8.12 (d, J=5.0 Hz, 1H), 7.68 (t, J=9.5 Hz, 1H), 7.27 (t, J=6.5 Hz, 2H), 7.07-6.94 (m, 4H), 6.82 (d, J=8.0 Hz, 1H), 4.47 (t, J=7.0 Hz, 2H), 2.91 (t, J=5.5 Hz, 2H), 2.79 (bs, 4H), 2.03 (t, J=13.5 Hz, 2H), 1.78-1.73 (m, 2H), 1.29 (s, 3H); ESI+MS: m/z 313 ([M+H]$^+$).

Example-175: 4-(2-(4-methyl-4-phenoxypiperidin-1-yl)ethoxy)-1H-indole

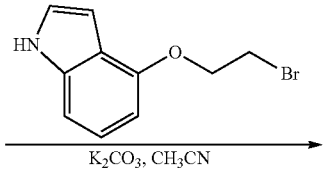

Title compound was prepared from 4-methyl-4-phenoxypiperidine hydrochloride (0.075 g, 0.33 mmol) using the general methodology of Example-1. Purification using silica gel column chromatography (3% MeOH/CH$_2$Cl$_2$ as eluent) afforded 0.06 g of 4-(2-(4-methyl-4-phenoxypiperidin-1-yl)ethoxy)-1H-indole (Yield=51%). $^1$H NMR (400 MHz, DMSO-d6): δ 11.06 (s, 1H), 7.28 (t, J=15.5 Hz, 2H), 7.21 (s, 1H), 7.07-6.96 (m, 5H), 6.50 (d, J=6.0 Hz, 1H), 6.40 (s, 1H), 4.20 (s, 2H), 2.89-2.64 (m, 6H), 1.89 (bs, 2H), 1.66 (bs, 2H), 1.25 (s, 3H); ESI+MS: m/z 351 ([M+H]$^+$).

Example-176: 4-isopropyl-1-(2-(2-(trifluoromethyl)phenoxy)ethyl)piperidin-4-ol

323
-continued

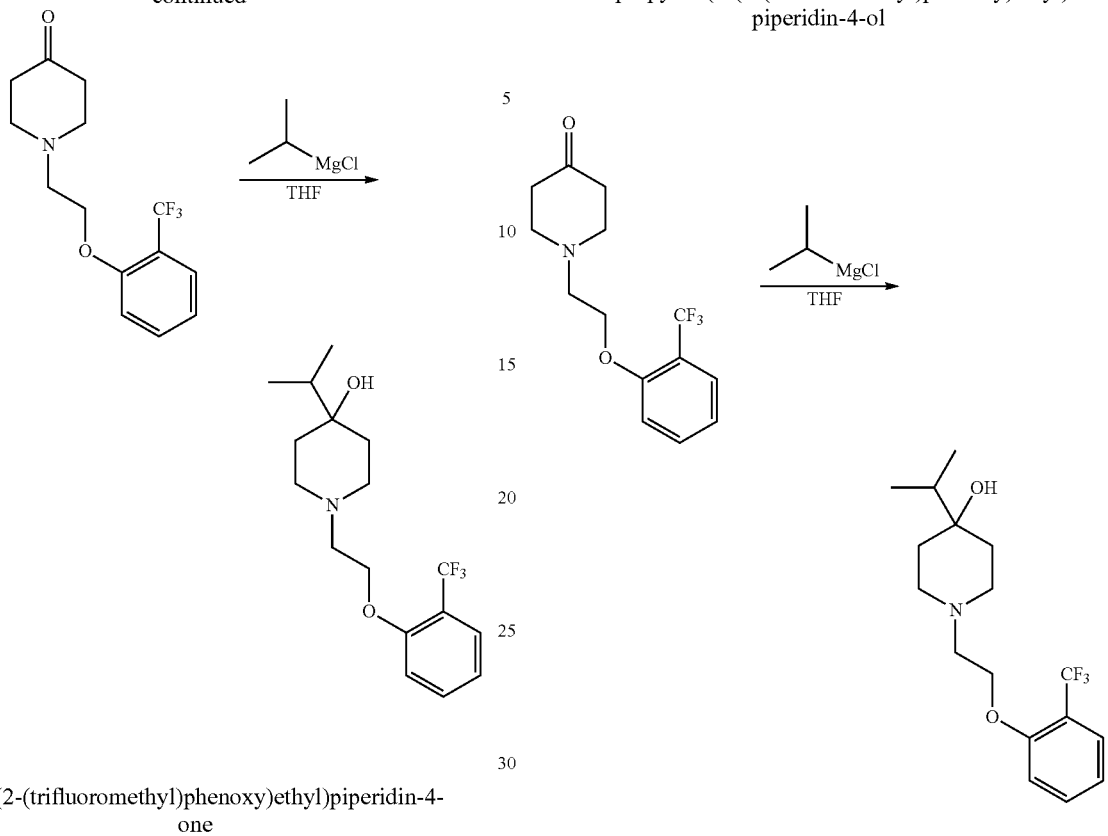

1-(2-(2-(trifluoromethyl)phenoxy)ethyl)piperidin-4-one

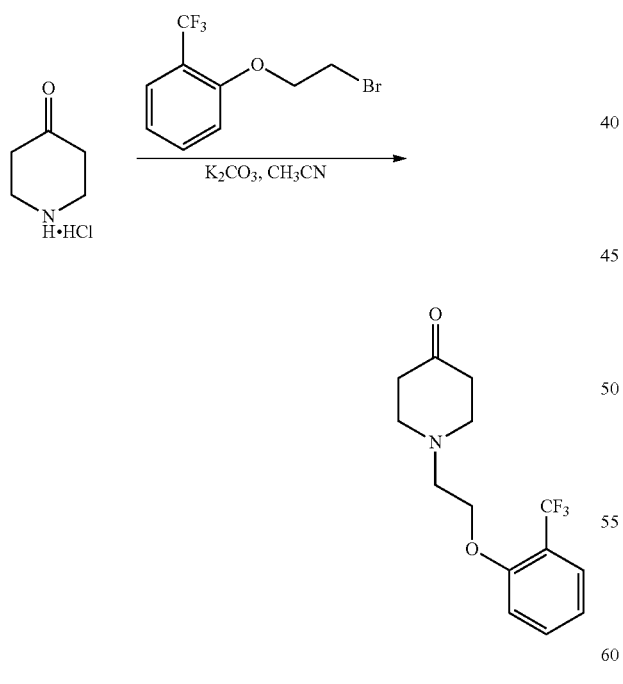

Title compound was prepared from piperidin-4-one hydrochloride (2.0 g, 13.0 mmol) using the general methodology of Example-1. Purification using silica gel column chromatography (30% EA/Hexanes as eluent) afforded 2.5 g of 1-(2-(2-(trifluoromethyl)phenoxy)ethyl)piperidin-4-one (Yield=67%).

324
4-isopropyl-1-(2-(2-(trifluoromethyl)phenoxy)ethyl) piperidin-4-ol

To a stirred solution of 1-(2-(2-(trifluoromethyl)phenoxy) ethyl)piperidin-4-one (200 mg, 0.70 mmol) in dry THF (5 mL) under argon atmosphere was added isopropyl magnesium chloride (2M in THF, 1 mL, 2.0 mmol) at 0° C. The reaction mixture was warmed to RT and stirred for 2 h. After completion of the reaction (monitored by TLC), the mixture was quenched with $NH_4Cl$ solution at 0° C. and extracted with EtOAc. The combined organic layers was dried over anhydrous $Na_2SO_4$ and concentrated under reduced pressure. The crude compound was purified by column preparative HPLC and afforded 10 mg of 4-isopropyl-1-(2-(2-(trifluoromethyl)phenoxy)ethyl)piperidin-4-ol as colorless syrup (Yield=5%). $^1$H NMR (400 MHz, $CD_3OD$): δ 7.58-7.54 (m, 2H), 7.18 (d, J=8.8 Hz, 1H), 7.08-7.04 (m, 1H), 4.28 (t, J=5.6 Hz, 2H), 2.98-2.91 (m, 4H), 2.69-2.63 (m, 2H), 1.74-1.66 (m, 2H), 1.63-1.54 (m, 3H), 0.92 (d, J=6.8 Hz, 6H); ESI+MS: m/z 332 ([M+H]$^+$).

Example-177: 4-methyl-1'-(2-(trifluoromethyl)phenyl)-[1,3'-bipiperidin]-4-ol

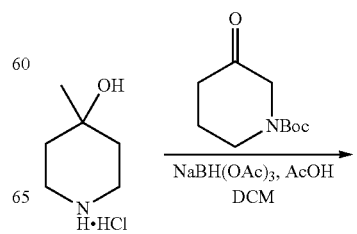

325

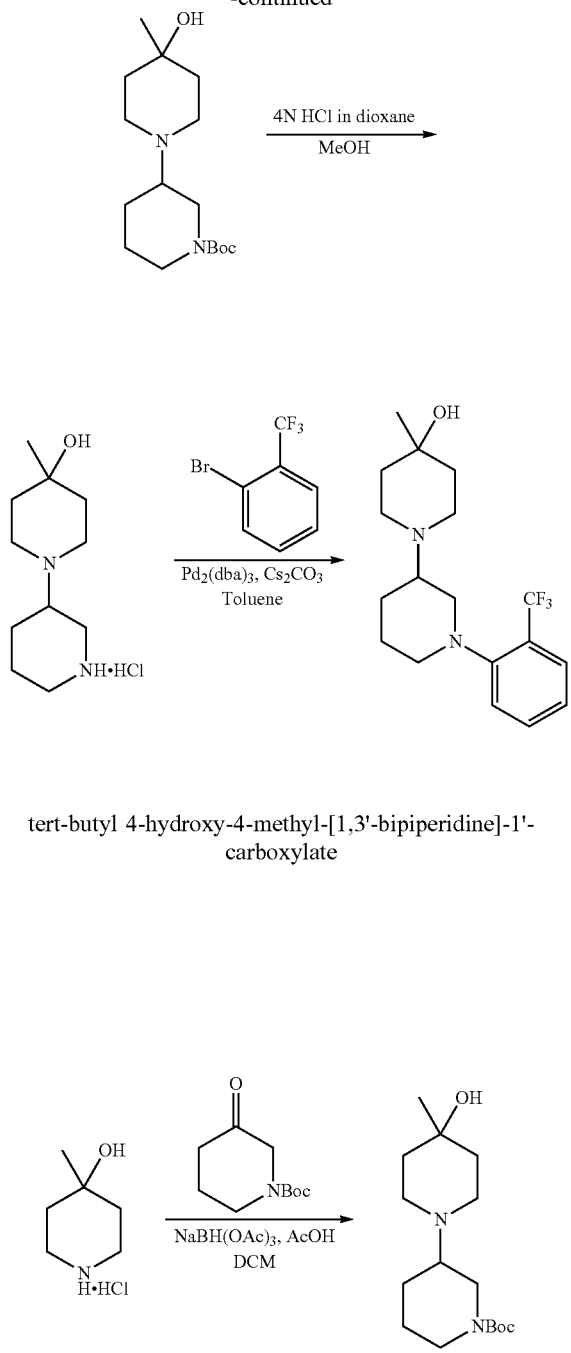

tert-butyl 4-hydroxy-4-methyl-[1,3'-bipiperidine]-1'-carboxylate

To a stirred solution of 4-methylpiperidin-4-ol hydrochloride (100 mg, 0.66 mmol) and tert-butyl 3-oxopiperidine-1-carboxylate (131 mg, 0.66 mmol) in DCM (2 mL) were added NaBH(OAc)₃ (210 mg, 0.99 mmol) followed by acetic acid (0.038 mL, 0.66 mmol) at 0° C. The reaction mixture was stirred at RT for 16 h. After completion (monitored by TLC), the reaction was diluted with sat. aq. NaHCO₃ and extracted with DCM. The organic layer was dried over anhydrous Na₂SO₄ and concentrated under reduced pressure. The crude material was purified by silica gel column chromatography (gradient of MeOH in DCM) and afforded 0.05 g of tert-butyl 4-hydroxy-4-methyl-[1,3'-bipiperidine]-1'-carboxylate (Yield=25%).

326

4-methyl-[1,3'-bipiperidin]-4-ol hydrochloride

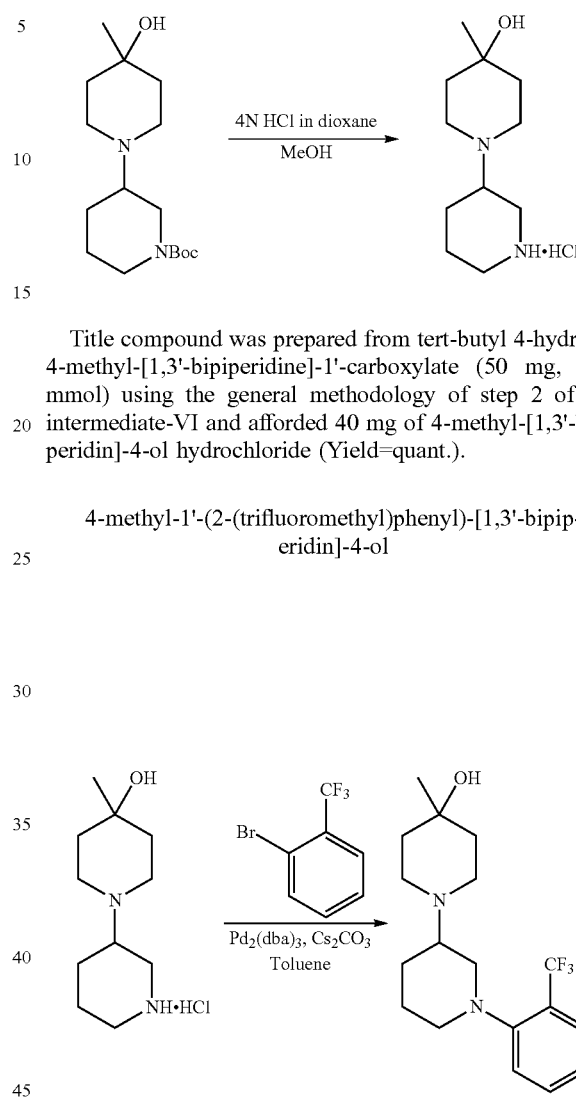

Title compound was prepared from tert-butyl 4-hydroxy-4-methyl-[1,3'-bipiperidine]-1'-carboxylate (50 mg, 0.17 mmol) using the general methodology of step 2 of key intermediate-VI and afforded 40 mg of 4-methyl-[1,3'-bipiperidin]-4-ol hydrochloride (Yield=quant.).

4-methyl-1'-(2-(trifluoromethyl)phenyl)-[1,3'-bipiperidin]-4-ol

To a stirred solution of 4-methyl-[1,3'-bipiperidin]-4-ol hydrochloride (40 mg, 0.17 mmol) and 1-bromo-2-(trifluoromethyl) benzene (38 mg, 0.17 mmol) in toluene (2 mL) was added Cs₂CO₃ (167 mg, 0.51 mmol) and (+/−)-BINAP (11 mg, 0.017 mmol) at room temperature. The reaction mixture was degased with argon for 10 min then Pd₂(dba)₃ (16 mg, 0.017 mmol) was added and the reaction mixture was heated at 100° C. in a sealed tube for 16 h. After completion of the reaction (monitored by TLC), the mixture was diluted with water and extracted with DCM. The organic layer was dried over anhydrous Na₂SO₄ and concentrated under reduced pressure. The crude residue was purified by preparative HPLC to afford 20 mg of 4-methyl-1'-(2-(trifluoromethyl)phenyl)-[1,3'-bipiperidin]-4-ol as a thick syrup (Yield=35%). ¹H NMR (400 MHz, DMSO-d6): δ 7.62 (t, J=7.6 Hz, 2H), 7.51 (d, J=8.0 Hz, 1H), 7.29 (t, J=7.6 Hz, 1H), 4.00 (brs, 1H), 3.18-3.05 (m, 1H), 2.85 (d, J=10.0 Hz, 1H), 2.65-2.40 (m, 7H), 1.87 (d, J=10.6 Hz, 1H), 1.76 (d, J=12.4 Hz, 1H), 1.58-1.51 (m, 1H), 1.41-1.31 (m, 5H), 1.05 (s, 3H); ESI+MS: m/z 343 ([M+H]⁺).

Example-178: 1-(4-chlorophenyl)-8-((2,3-dihydrobenzo[b][1,4]dioxin-2-yl)methyl)-1,8-diazaspiro[4.5]decane

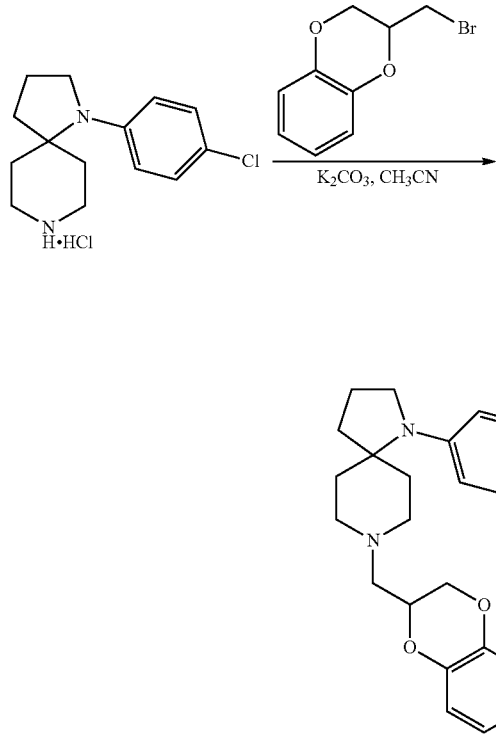

Title compound was prepared from 1-(4-chlorophenyl)-1,8-diazaspiro[4.5]decane hydrochloride (0.04 g, 0.14 mmol) using the general methodology of Example-1. Purification using silica gel column chromatography (5% MeOH/CH$_2$Cl$_2$ as eluent) afforded 0.025 g of 1-(4-chlorophenyl)-8-((2,3-dihydrobenzo[b][1,4]dioxin-2-yl)methyl)-1,8-diazaspiro[4.5]decane (Yield=45%). $^1$H NMR (400 MHz, DMSO-d6): δ 7.19-7.15 (m, 2H), 6.87-6.81 (m, 4H), 6.81-6.74 (m, 2H), 4.37-4.31 (m, 2H), 4.01-3.96 (m, 1H), 3.24 (t, J=6.4 Hz, 2H), 2.99-2.96 (m, 1H), 2.89-2.86 (m, 1H), 2.59 (d, J=5.6 Hz, 2H), 2.45-2.44 (m, 1H), 2.26-2.12 (m, 2H), 1.96-1.94 (m, 2H), 1.88-1.81 (m, 2H), 1.25-1.20 (m, 3H); ESI+MS: m/z 399 ([M+H]$^+$). The enantiomers of 178 were separated using chiral HPLC (method U) and afforded the pure enantiomers 178a and 178b.

Example-179: 1'-(2-(2-(trifluoromethyl)phenoxy)ethyl)-3H-spiro[benzofuran-2,4'-piperidine]

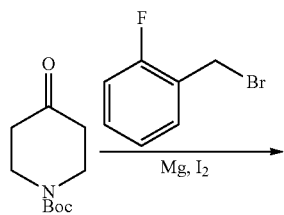

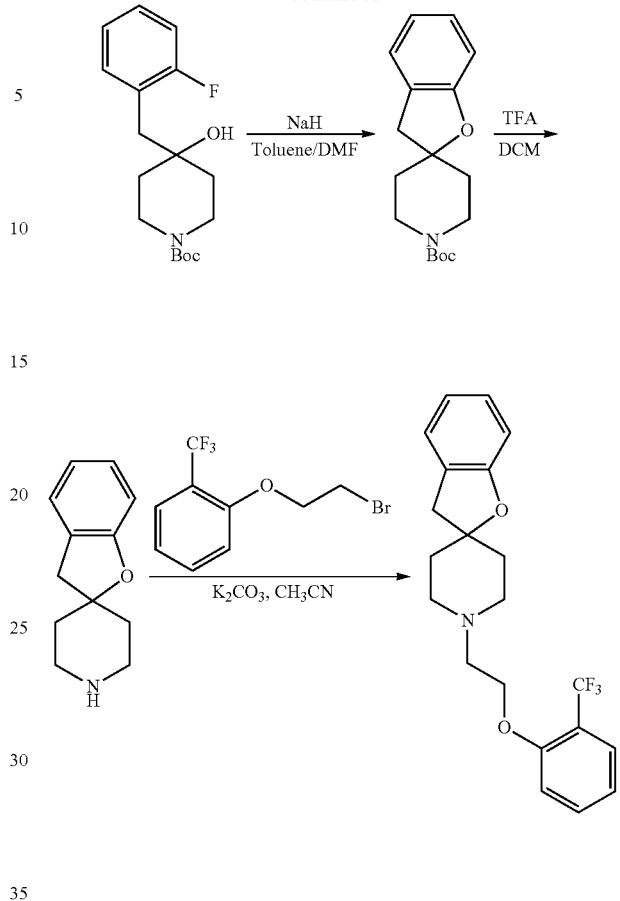

tert-butyl 4-(2-fluorobenzyl)-4-hydroxypiperidine-1-carboxylate

Magnesium turnings (220 mg, 9.0 mmol) and a crystal of iodine were dissolved in diethyl ether (5 ml). The resulting mixture was warmed to 35° C. When color disappeared, 2-(bromomethyl)-4-chloro-1-fluorobenzene (0.91 mL, 7.53 mmol) in diethyl ether (3 mL) was added dropwise over 30 minutes. The reaction mixture was kept at 35° C. overnight. A solution of tert-butyl 4-oxopiperidine-1-carboxylate (1.0 g, 5.0 mmol) in 5 ml of diethyl ether was then added dropwise over 15 minutes. Stirring was continued for 1 h at RT. The reaction mixture was then extracted with ethyl acetate/aq.NH$_4$Cl. The combined organic layer was dried over Na$_2$SO$_4$, filtered and concentrated. Purification using silica gel column chromatography (gradient EA/Hexanes as eluent) afforded 900 mg of tert-butyl 4-(2-fluorobenzyl)-4-hydroxypiperidine-1-carboxylate (Yield=58%).

329
tert-butyl 3H-spiro[benzofuran-2,4'-piperidine]-1'-carboxylate

330
1'-(2-(2-(trifluoromethyl)phenoxy)ethyl)-3H-spiro[benzofuran-2,4'-piperidine]

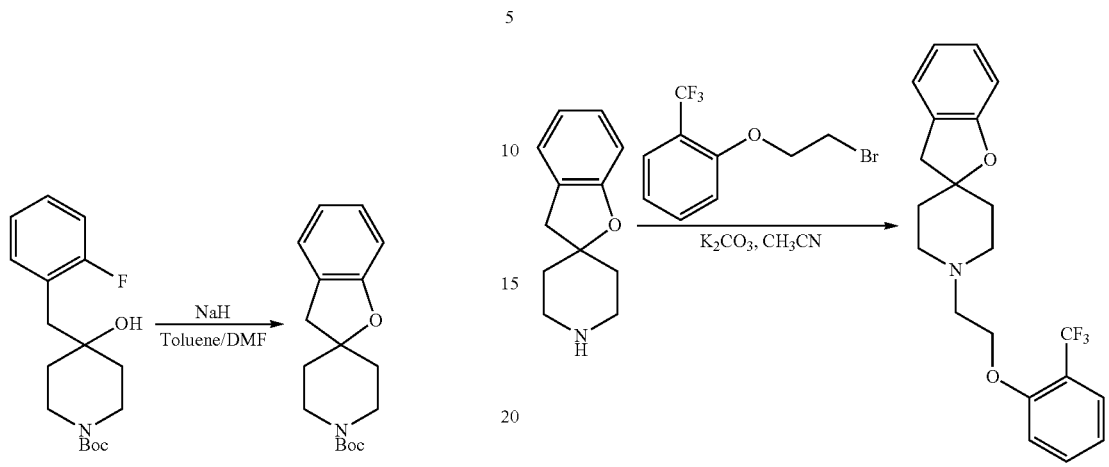

tert-Butyl 4-(2-fluorobenzyl)-4-hydroxypiperidine-1-carboxylate (900 mg, 2.9 mmol) was dissolved in a DMF/Toluene solution (1/1, 14 mL) under argon. NaH (198 mg, 4.95 mmol) was added in 1 portion and the mixture was stirred at 90° C. After 20 h, the mixture was extracted with ethyl acetate/aq.NH$_4$Cl. The combined organic layer was dried over Na$_2$SO$_4$, filtered and concentrated. Purification using silica gel column chromatography (gradient MeOH/DCM as eluent) afforded 580 mg of tert-butyl 3H-spiro[benzofuran-2,4'-piperidine]-1'-carboxylate (Yield=69%).

3H-spiro[benzofuran-2,4'-piperidine]

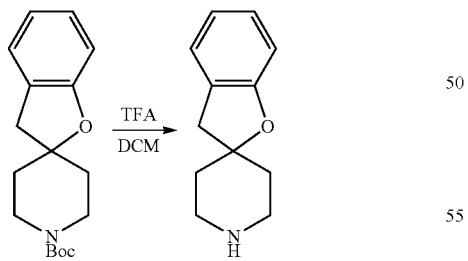

tert-butyl 3H-spiro[benzofuran-2,4'-piperidine]-1'-carboxylate (580 mg, 2.0 mmol) was dissolved in DCM (2 mL) and TFA (1.5 mL, 20.0 mmol) was added dropwise. After 3 h at room temperature, solvents were evaporated, the mixture was dissolved in DCM and washed with aq.NaHCO$_3$. The organic layer was dried over Na$_2$SO$_4$, filtered and concentrated to afford 350 mg of 3H-spiro[benzofuran-2,4'-piperidine] (Yield=92%).

Title compound was prepared from 3H-spiro[benzofuran-2,4'-piperidine] (0.05 g, 0.26 mmol) using the general methodology of Example-1. Purification using silica gel column chromatography (3% MeOH/CH$_2$Cl$_2$ as eluent) afforded 0.06 g of 1'-(2-(2-(trifluoromethyl) phenoxy)ethyl)-3H-spiro[benzofuran-2,4'-piperidine] (Yield=60%). $^1$H NMR (300 MHz, CDCl$_3$): δ 7.56 (d, J=7.5 Hz, 1H), 7.47 (t, J=8.0 Hz, 1H), 7.16-7.05 (m, 2H), 7.03-6.95 (m, 2H), 6.85-6.72 (m, 2H), 4.21 (t, J=5.7 Hz, 2H), 2.99 (s, 2H), 2.92 (t, J=5.6 Hz, 2H), 2.85-2.60 (m, 4H), 2.05-1.90 (m, 2H), 1.88-1.75 (m, 2H); ESI+MS: m/z 378 ([M+H]$^+$).

One of skill in the art would understand the present invention to encompass subgenera that may be derived from the foregoing genera, subgenera and list of exemplary compounds, as herein disclosed or herein listed. Further, from the foregoing and the disclosure herein, the skilled person can readily select suitable moieties for any of the variable substituents identified in the formulae herein described.

Example-180: 3-(4-chlorophenoxy)-1-(2-(3-fluorophenoxy)ethyl)-3-methylpyrrolidine

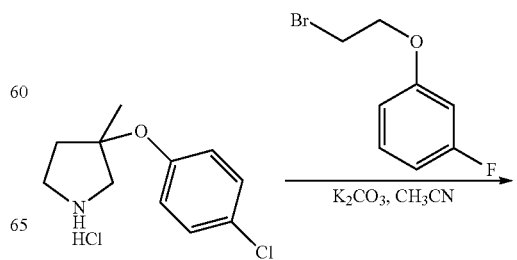

331
-continued

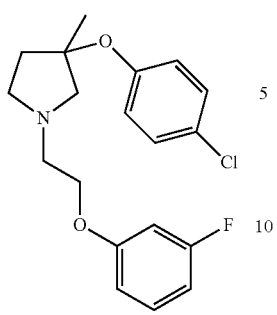

Title compound was prepared from 3-(4-chlorophenoxy)-3-methylpyrrolidine hydrochloride (0.10 g) and 1-(2-bromo-ethoxy)-2-fluorobenzene (0.14 g, 0.63 mmol, 1.2 equiv) using the general methodology of Example-1. The crude was purified by preparative HPLC purification to afford 0.09 g of 3-(4-chlorophenoxy)-1-(2-(3-fluorophenoxy)ethyl)-3-methylpyrrolidine (Yield=54%). $^1$H NMR (400 MHz, DMSO-$d_6$): δ 7.33-7.24 (m, 3H), 6.99-6.95 (m, 2H), 6.87-6.72 (m, 3H), 4.08 (t, J=11.6 Hz, 2H), 3.00 (d, J=10.0 Hz, 1H), 2.86-2.76 (m, 3H), 2.72-2.60 (m, 2H), 2.22-2.15 (m, 1H), 1.96-1.89 (m, 1H), 1.45 (s, 3H); ESI+MS: m/z 350 ([M+H]$^+$).

Example-181: 1'-(2-phenoxyethyl)-3H-spiro[benzofuran-2,3'-pyrrolidine]

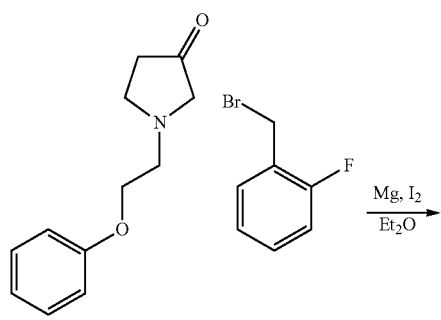

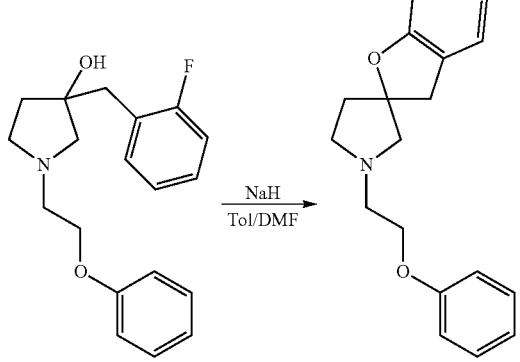

332
3-(2-fluorobenzyl)-1-(2-phenoxyethyl)pyrrolidin-3-ol (Compound 300)

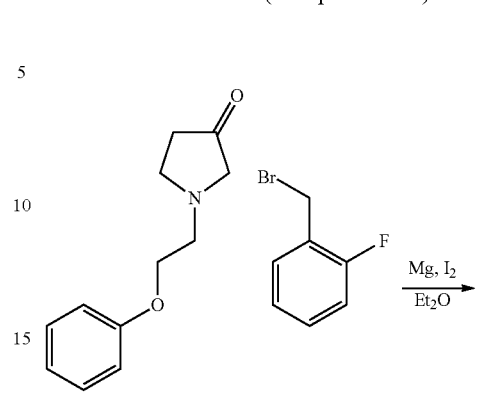

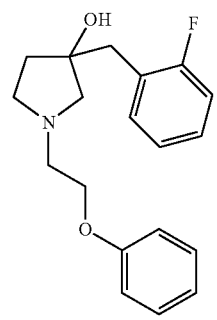

Title compound was prepared from 1-(2-phenoxyethyl)pyrrolidin-3-one (0.25 g, 1.22 mmol) and 1-(bromomethyl)-2-fluorobenzene (0.35 g, 1.83 mmol) using the methodology of step 1 of Example-179. The crude was purified by silica gel chromatography to afford 0.13 g of 3-(2-fluorobenzyl)-1-(2-phenoxyethyl)pyrrolidin-3-ol (Yield=33%). ESI+MS: m/z 316.3 ([M+H]$^+$).

1'-(2-phenoxyethyl)-3H-spiro[benzofuran-2,3'-pyrrolidine]

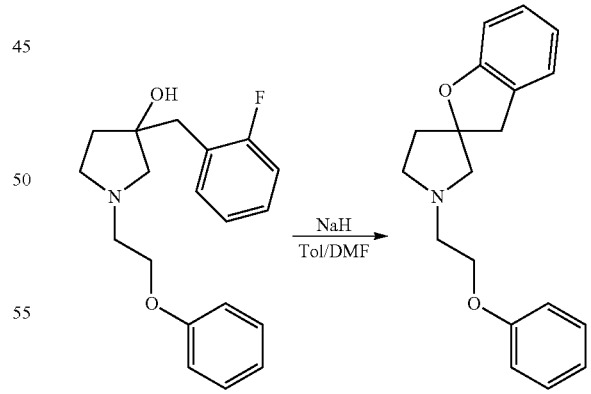

Title compound was prepared from 3-(2-fluorobenzyl)-1-(2-phenoxyethyl)pyrrolidin-3-ol (0.12 g, 0.38 mmol) using the methodology of step 2 of Example-179. The crude was purified by silica gel chromatography to afford 0.054 g of 1'-(2-phenoxyethyl)-3H-spiro[benzofuran-2,3'-pyrrolidine] (Yield=48%). $^1$H NMR (400 MHz, CDCl$_3$): δ 7.33-7.26 (m, 2H), 7.16-7.07 (m, 2H), 6.97-6.75 (m, 5H), 4.12 (t, J=5.9 Hz, 2H), 3.30-3.10 (m, 3H), 3.10-3.00 (m, 1H), 2.96 (t, J=5.9 Hz, 2H), 2.80-2.72 (m, 2H), 2.43-2.32 (m, 1H), 2.10-1.98 (m, 1H); ESI+MS: m/z 296.3 ([M+H]$^+$).

Example-182: 3-(2-(4-(4-chlorophenoxy)-4-methylpiperidin-1-yl)ethoxy)pyridine

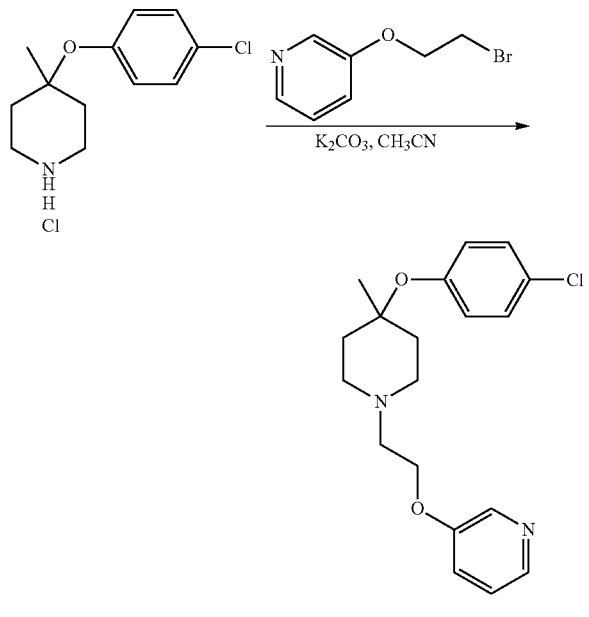

Title compound was prepared from 4-(4-chlorophenoxy)-4-methylpiperidine hydrochloride (0.1 g, 0.38 mmol) using the general methodology of Example-1. Purification using silica gel column chromatography (5% MeOH/CH$_2$Cl$_2$ as eluent) afforded 0.025 g of 3-(2-(4-(4-chlorophenoxy)-4-methylpiperidin-1-yl)ethoxy)pyridine (Yield=19%). $^1$H NMR (400 MHz, DMSO-d6): δ 8.29 (d, J=2.4 Hz, 1H), 8.16 (d, J=4.2 Hz, 1H), 7.42-7.37 (m, 1H), 7.31 (d, J=8.8 Hz, 3H), 7.01 (d, J=8.7 Hz, 2H), 4.17-4.13 (m, 2H), 2.77-2.70 (m, 2H), 2.60-2.53 (m, 4H), 1.89-1.82 (m, 2H), 1.66-1.59 (m, 2H), 1.24 (s, 3H); ESI+MS: m/z 347 ([M+H]$^+$).

Example-183: 4-(2-(4-(4-chlorophenoxy)-4-methylpiperidin-1-yl)ethoxy)pyridine

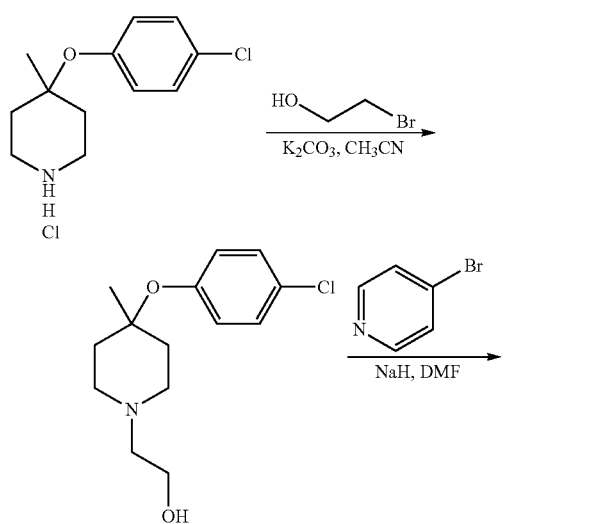

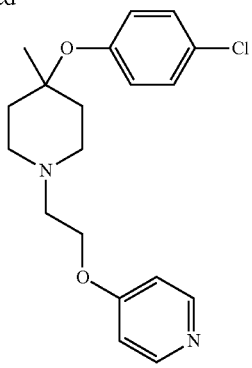

2-(4-(4-chlorophenoxy)-4-methylpiperidin-1-yl)ethan-1-ol

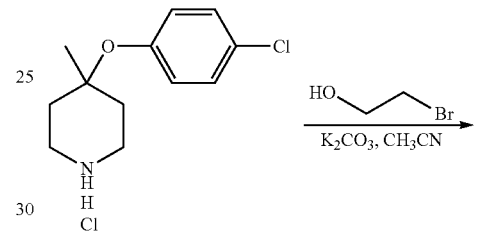

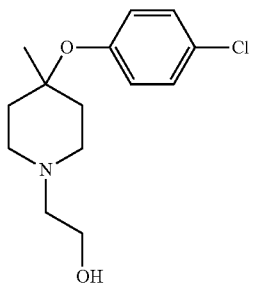

Title compound was prepared from 4-(4-chlorophenoxy)-4-methylpiperidine hydrochloride (0.5 g, 1.91 mmol) using the general methodology of Example-1. Purification using silica gel column chromatography (10% MeOH/CH$_2$Cl$_2$ as eluent) afforded 0.35 g of 2-(4-(4-chlorophenoxy)-4-methylpiperidin-1-yl)ethan-1-ol (Yield=68%). ESI+MS: m/z 270.0 ([M+H]$^+$).

4-(2-(4-(4-chlorophenoxy)-4-methylpiperidin-1-yl)ethoxy)pyridine

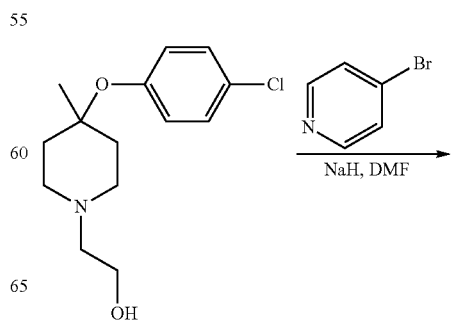

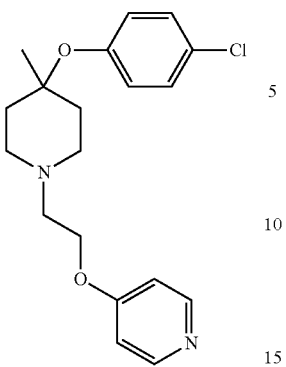

Title compound was prepared from 2-(4-methyl-4-phenoxypiperidin-1-yl)ethanol (0.05 g, 0.19 mmol) and 4-bromopyridine (43 mg, 0.22 mmol) using the general methodology of Example 61. Purification using silica gel column chromatography (5% MeOH/CH$_2$Cl$_2$ as eluent) afforded 0.025 g of 4-(2-(4-(4-chlorophenoxy)-4-methylpiperidin-1-yl)ethoxy)pyridine (Yield=39%). $^1$H NMR (500 MHz, CD$_3$OD): δ 8.38-8.34 (m, 2H), 7.31 (d, J=8.8 Hz, 2H), 7.01 (d, J=8.9 Hz, 2H), 6.98-6.95 (m, 2H), 4.16 (t, J=5.8 Hz, 2H), 2.73 (t, J=5.7 Hz, 2H), 2.60-2.54 (m, 4H), 1.89-1.82 (m, 2H), 1.67-1.58 (m, 2H), 1.24 (s, 3H); ESI+MS: m/z 346.9 ([M+H]$^+$).

Example-184: 5-(2-(4-(4-chlorophenoxy)-4-methylpiperidin-1-yl)ethoxy)-2-(trifluoromethyl)phenol

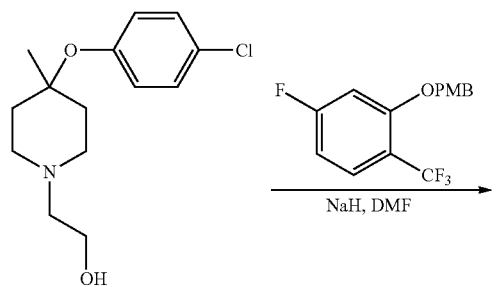

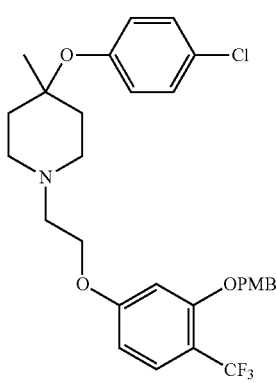

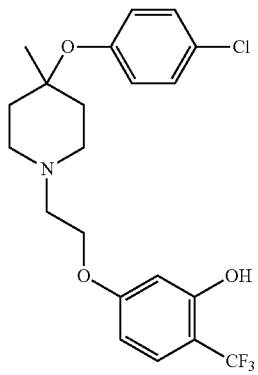

4-(4-chlorophenoxy)-1-(2-(3-((4-methoxybenzyl)oxy)-4-(trifluoromethyl)phenoxy)ethyl)-4-methylpiperidine

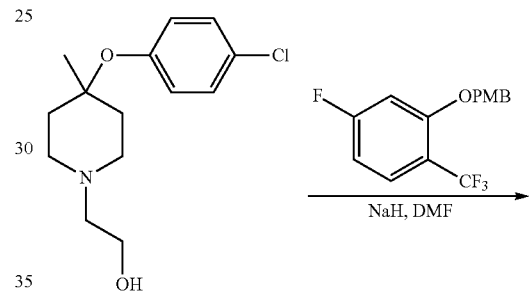

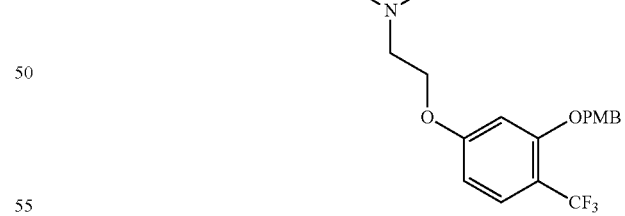

Title compound was prepared from 2-(4-methyl-4-phenoxypiperidin-1-yl)ethanol (0.30 g, 1.11 mmol) and 4-fluoro-2-((4-methoxybenzyl)oxy)-1-(trifluoromethyl)benzene (334 mg, 1.11 mmol) using the general methodology of Example 61. Purification using silica gel column chromatography (5% MeOH/CH$_2$Cl$_2$ as eluent) afforded 0.4 g of 4-(4-chlorophenoxy)-1-(2-(3-((4-methoxybenzyl)oxy)-4-(trifluoromethyl)phenoxy)ethyl)-4-methylpiperidine (Yield=65%). ESI+MS: m/z 550.4 ([M+H]$^+$).

5-(2-(4-(4-chlorophenoxy)-4-methylpiperidin-1-yl)ethoxy)-2-(trifluoromethyl)phenol

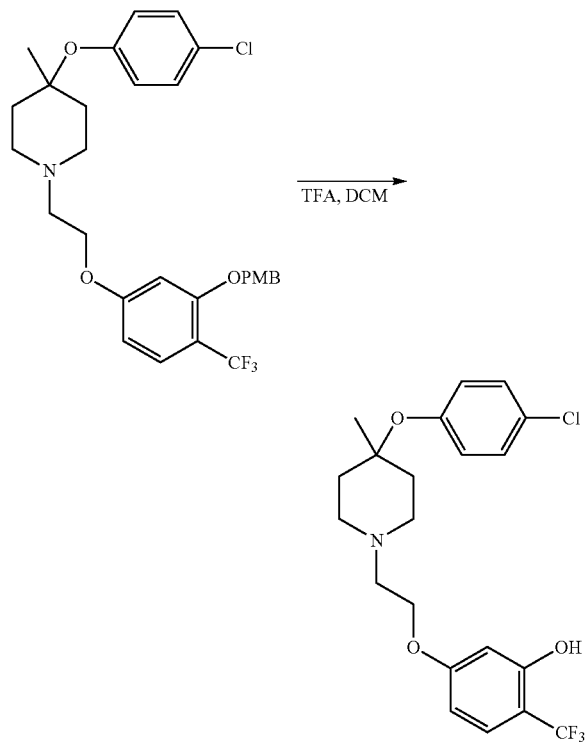

4-(4-chlorophenoxy)-1-(2-(3-((4-methoxybenzyl)oxy)-4-(trifluoromethyl)phenoxy)ethyl)-4-methylpiperidine (0.25 g, 0.46 mmol) was dissolved in DCM (5 mL) and the mixture was cooled to 0° C. trifluoroacetic acid (0.175 mL, 2.27 mmol) was added dropwise and the mixture was stirred at room temperature overnight. The reaction mixture was then diluted in saturated aqueous NaHCO₃ and extracted with DCM. The organic layers were dried over Na2SO4, filtered and concentrated. Purification using silica gel column chromatography (2% MeOH/CH₂Cl₂ as eluent) afforded 0.04 g of 5-(2-(4-(4-chlorophenoxy)-4-methylpiperidin-1-yl)ethoxy)-2-(trifluoromethyl)phenol (Yield=21%). ¹H NMR (500 MHz, CD₃OD): δ 10.46 (bs, 1H), 7.38 (d, J=8.4 Hz, 1H), 7.33-7.29 (m, 2H), 7.02-6.98 (m, 2H), 6.52-6.47 (m, 2H), 4.06 (t, J=6.0 Hz, 2H), 2.70 (t, J=5.6 Hz, 2H), 2.56-2.53 (m, 4H), 1.88-1.83 (m, 2H), 1.65-1.58 (m, 2H), 1.23 (s, 3H); ESI+MS: m/z 430.4 ([M+H]⁺).

Example-185: 4-(2-(4-(4-chlorophenoxy)-4-methylpiperidin-1-yl)ethoxy)benzonitrile

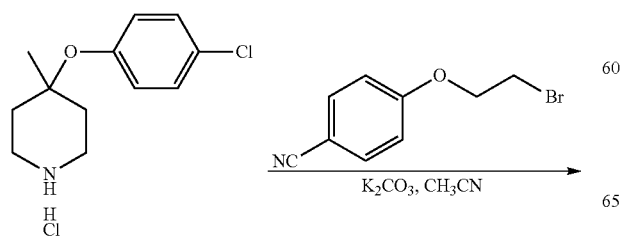

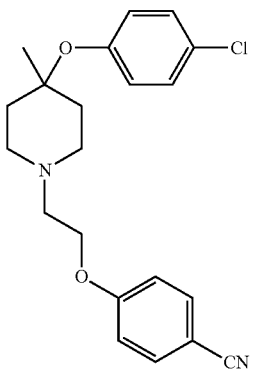

Title compound was prepared from 4-(4-chlorophenoxy)-4-methylpiperidine hydrochloride (0.07 g, 0.27 mmol) using the general methodology of Example-1. Purification using silica gel column chromatography (5% MeOH/CH₂Cl₂ as eluent) afforded 0.06 g of 4-(2-(4-(4-chlorophenoxy)-4-methylpiperidin-1-yl)ethoxy)benzonitrile (Yield=61%). ¹H NMR (500 MHz, DMSO-d6): δ 7.75 (d, J=8.5 Hz, 2H), 7.31 (d, J=9.0 Hz, 2H), 7.11 (d, J=9.0 Hz, 2H), 7.00 (d, J=8.5 Hz, 2H), 4.17 (t, J=5.5 Hz, 2H), 2.73 (t, J=5.5 Hz, 2H), 2.60-2.55 (m, 4H), 1.86-1.83 (m, 2H), 1.64-1.58 (m, 2H), 1.23 (s, 3H); ESI+MS: m/z 371.0 ([M+H]⁺).

Example-186: 1-(2-((1H-pyrazol-4-yl)oxy)ethyl)-4-(4-chlorophenoxy)-4-methylpiperidine

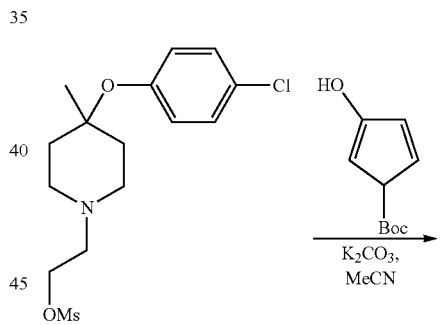

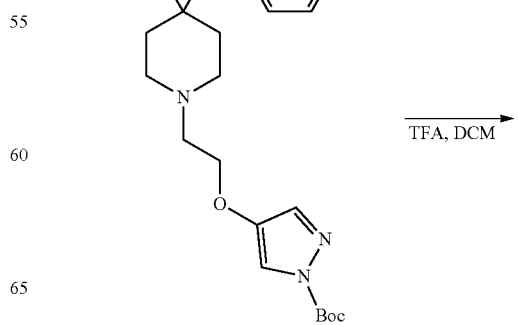

339

-continued tert-butyl 4-(2-(4-(4-chlorophenoxy)-4-methylpiperidin-1-yl)ethoxy)-1H-pyrazole-1-carboxylate

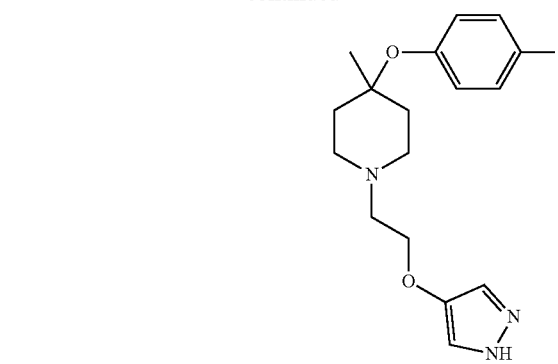

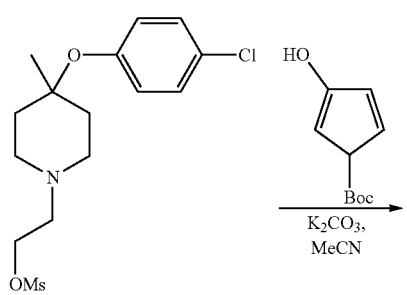

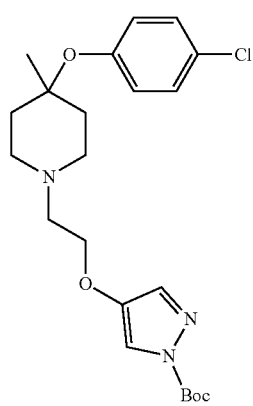

Title compound was prepared from 2-(4-(4-chlorophenoxy)-4-methylpiperidin-1-yl)ethyl methanesulfonate (0.1 g, 0.29 mmol) using the general methodology of Example-1. Purification using silica gel column chromatography (2% MeOH/CH$_2$Cl$_2$ as eluent) afforded 0.05 g of tert-butyl 4-(2-(4-(4-chlorophenoxy)-4-methylpiperidin-1-yl)ethoxy)-1H-pyrazole-1-carboxylate (Yield=40%). ESI+MS: m/z 436.1 ([M+H]$^+$).

340

1-(2-((1H-pyrazol-4-yl)oxy)ethyl)-4-(4-chlorophenoxy)-4-methylpiperidine

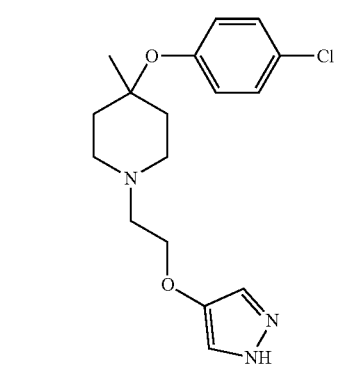

To a stirred solution of tert-butyl 4-(2-(4-(4-chlorophenoxy)-4-methylpiperidin-1-yl)ethoxy)-1H-pyrazole-1-carboxylate (0.05 g, 0.12 mmol) in DCM (5 mL), was added TFA (0.044 mL, 0.57 mmol) at 0° C. The reaction mixture was stirred at RT for 2 h. The solvent was removed under reduced pressure. Purification using silica gel column chromatography (10% MeOH/CH$_2$Cl$_2$ as eluent) afforded 0.015 g of 1-(2-((1H-pyrazol-4-yl)oxy)ethyl)-4-(4-chlorophenoxy)-4-methylpiperidine (Yield=39%). $^1$H NMR (400 MHz, DMSO-d6): δ 12.31 (br s, 1H), 7.43 (br s, 1H), 7.31 (d, J=8.8 Hz, 2H), 7.23 (br s, 1H), 7.01 (d, J=8.8 Hz, 2H), 3.92 (t, J=5.8 Hz, 2H), 2.64 (t, J=5.9 Hz, 2H), 2.53-2.50 (m, 4H), 1.88-1.82 (m, 2H), 1.66-1.57 (m, 2H), 1.23 (s, 3H); ESI+MS: m/z 336.0 ([M+H]$^+$).

Example-187: 1-(2-(2-(4-(4-chlorophenoxy)-4-methylpiperidin-1-yl)ethoxy)-5-fluorophenyl)ethan-1-one

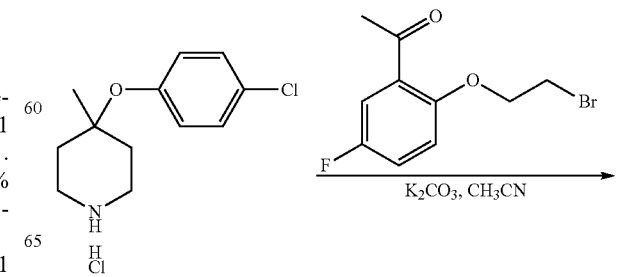

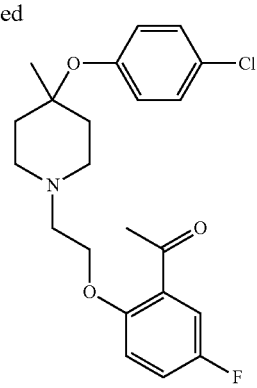

Title compound was prepared from 4-(4-chlorophenoxy)-4-methylpiperidine hydrochloride (0.1 g, 0.38 mmol) using the general methodology of Example-1. Purification using silica gel column chromatography afforded 0.06 g of 1-(2-(2-(4-(4-chlorophenoxy)-4-methylpiperidin-1-yl)ethoxy)-5-fluorophenyl)ethan-1-one (Yield=39%). $^1$H NMR (400 MHz, DMSO-d6): δ 7.42-7.35 (m, 1H), 7.34-7.29 (m, 3H), 7.23 (dd, J=9.1 Hz, J=4.3 Hz, 1H), 7.01 (d, J=8.8 Hz, 2H), 4.19 (t, J=5.6 Hz, 2H), 2.76 (t, J=5.1 Hz, 2H), 2.59 (s, 3H), 2.57-2.53 (m, 4H), 1.89-1.82 (m, 2H), 1.64-1.56 (m, 2H), 1.24 (s, 3H); ESI+MS: m/z 406.0 ([M+H]$^+$).

Example-188: 4-(4-chlorophenoxy)-1-(2-(2-methoxyphenoxy)ethyl)-4-methylpiperidine

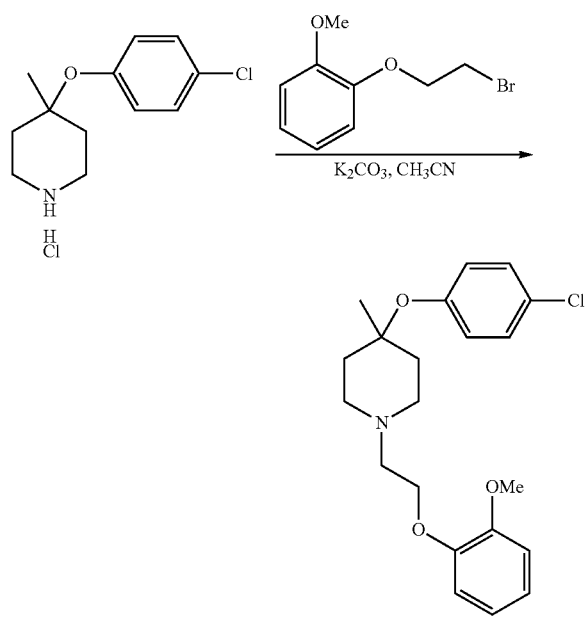

Title compound was prepared from 4-(4-chlorophenoxy)-4-methylpiperidine hydrochloride (0.1 g, 0.38 mmol) using the general methodology of Example-1. Purification using silica gel column chromatography afforded 0.11 g of 4-(4-chlorophenoxy)-1-(2-(2-methoxyphenoxy)ethyl)-4-methylpiperidine (Yield=77%). $^1$H NMR (500 MHz, CD$_3$OD): δ 7.27 (d, J=8.5 Hz, 2H), 7.03-6.88 (m, 6H), 4.19 (t, J=5.5 Hz, 2H), 3.83 (s, 3H), 3.03-2.83 (m, 6H), 2.05 (t, J=13.5 Hz, 2H), 1.83-1.76 (m, 2H), 1.30 (s, 3H); ESI+MS: m/z 376.1 ([M+H]$^+$).

Example-189: 4-(4-chlorophenoxy)-1-(2-(4,5-difluoro-2-methoxyphenoxy)ethyl)-4-methylpiperidine

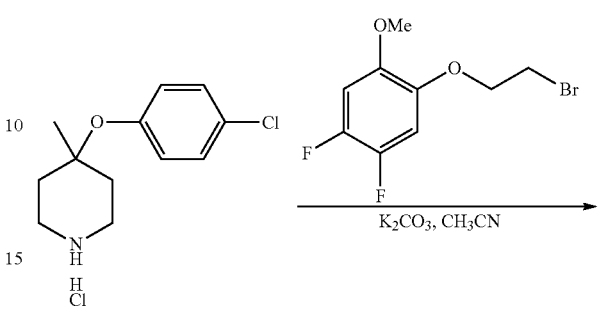

Title compound was prepared from 4-(4-chlorophenoxy)-4-methylpiperidine hydrochloride (0.07 g, 0.27 mmol) using the general methodology of Example-1. Purification using silica gel column chromatography afforded 0.03 g of 4-(4-chlorophenoxy)-1-(2-(4,5-difluoro-2-methoxyphenoxy)ethyl)-4-methylpiperidine (Yield=27%). $^1$H NMR (500 MHz, CD$_3$OD): δ 7.25 (d, J=8.0 Hz, 2H), 7.01-6.92 (m, 4H), 4.14 (t, J=5.5 Hz, 2H), 3.80 (s, 3H), 2.93 (t, J=5.5 Hz, 2H), 2.85-2.80 (m, 4H), 2.06-1.99 (m, 2H), 1.80-1.72 (m, 2H), 1.29 (s, 3H); ESI+MS: m/z 412.1 ([M+H]$^+$).

Example-190: 4-(4-chlorophenoxy)-1-(2-(5-fluoro-2-isopropoxyphenoxy)ethyl)-4-methylpiperidine

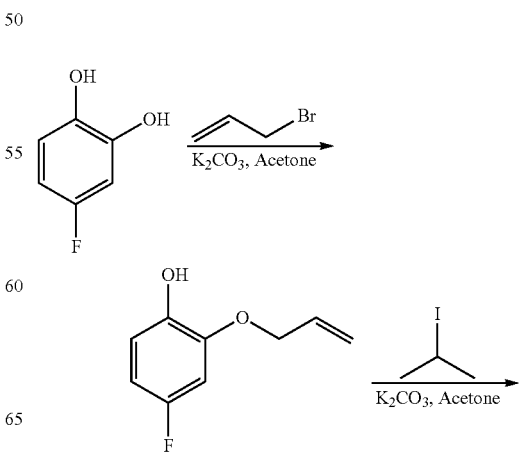

-continued

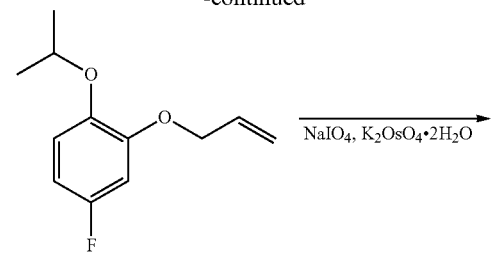

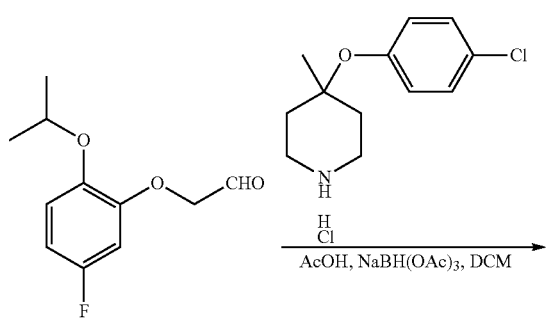

2-(allyloxy)-4-fluorophenol

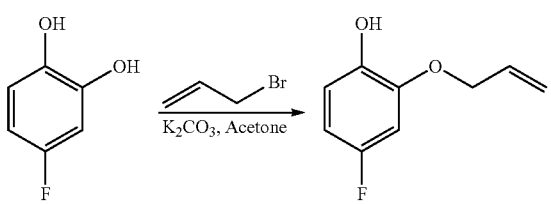

Title compound was prepared from 4-fluorobenzene-1,2-diol (2.0 g, 15.61 mmol) using the general methodology of Int-3. Purification using silica gel column chromatography afforded 1.2 g of 2-(allyloxy)-4-fluorophenol (Yield=46%). ESI+MS: m/z 167.0 ([M−H]⁻).

2-(allyloxy)-4-fluoro-1-isopropoxybenzene

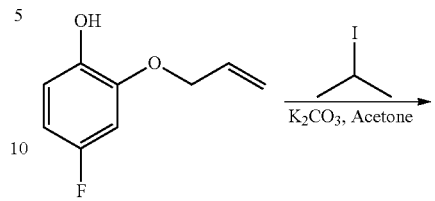

Title compound was prepared from 2-(allyloxy)-4-fluorophenol (2.0 g, 15.61 mmol) using the general methodology of Int-3. Purification using silica gel column chromatography afforded 0.4 g of 2-(allyloxy)-4-fluoro-1-isopropoxybenzene (Yield=64%).

2-(5-fluoro-2-isopropoxyphenoxy)acetaldehyde

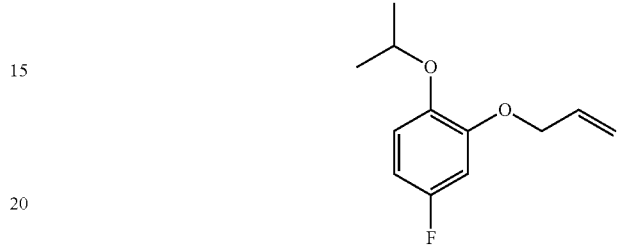

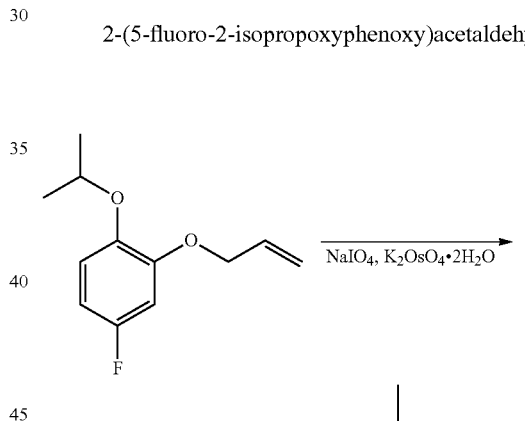

To a stirred solution of 2-(allyloxy)-4-fluoro-1-isopropoxybenzene (0.4 g, 1.9 mmol) in acetone:water (3:2) was added potassium osmium (VI) oxide dihydrate (0.025 g, 0.067 mmol) and NaIO₄ (1.63 g, 7.61 mmol) at 0° C. The reaction mixture was stirred at room temperature for 4 h. The reaction mass was filtered and concentrated under reduced pressure. Then water was added and extracted with EtOAc. The organic layer was separated, dried over anhydrous Na₂SO₄ and concentrated under reduced pressure and afforded 0.3 g of 2-(5-fluoro-2-isopropoxyphenoxy)acetaldehyde (Yield=74%). ESI+MS: m/z 213.3 ([M+H]⁺).

4-(4-chlorophenoxy)-1-(2-(5-fluoro-2-isopropoxyphenoxy)ethyl)-4-methylpiperidine

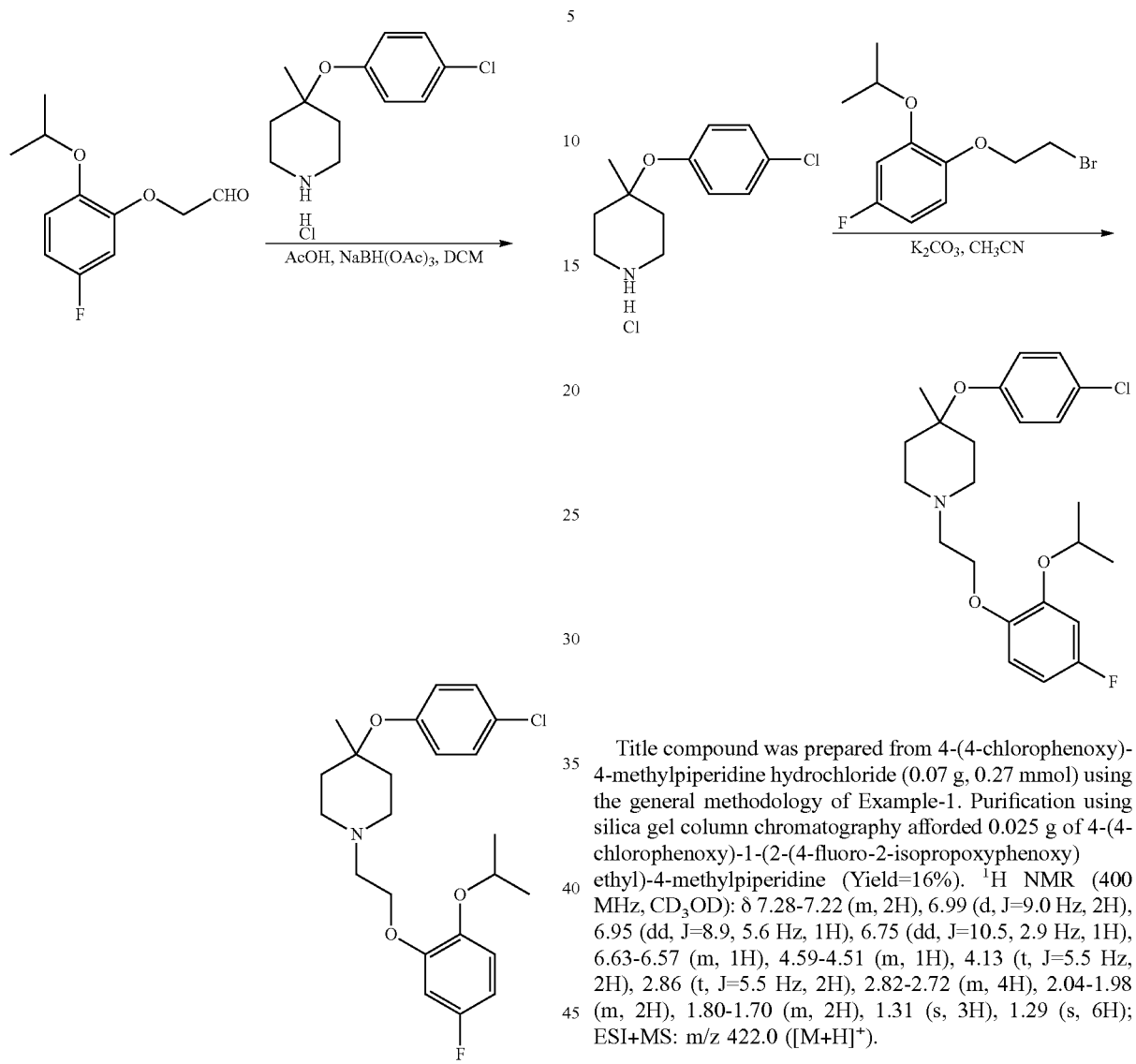

To a stirred solution of 4-(4-chlorophenoxy)-4-methylpiperidine hydrochloride (0.37 g, 1.41 mmol) and 2-(5-fluoro-2-isopropoxyphenoxy)acetaldehyde (0.3 g, 1.41 mmol) in DCM (10 mL) were added NaBH(OAc)3 (0.897 g, 4.23 mmol) and AcOH (0.08 mL, 1.41 mmol) at 0° C. The reaction mixture was stirred at room temperature for 16 h. After completion, the reaction was diluted with DCM. The organic layer was washed with water, brine, dried over anhydrous Na₂SO₄ and concentrated under reduced pressure. Purification using silica gel column chromatography followed by preparative HPLC afforded 0.05 g of 4-(4-chlorophenoxy)-1-(2-(5-fluoro-2-isopropoxyphenoxy)ethyl)-4-methylpiperidine (Yield=9%). $^1$H NMR (400 MHz, CD₃OD): δ 7.28-7.22 (m, 2H), 7.02-6.96 (m, 2H), 6.91 (dd, J=8.9, 5.7 Hz, 1H), 6.80 (dd, J=10.3, 3.0 Hz, 1H), 6.63-6.57 (m, 1H), 4.46-4.38 (m, 1H), 4.16 (t, J=5.5 Hz, 2H), 2.90 (t, J=5.5 Hz, 2H), 2.83-2.73 (m, 4H), 2.05-1.97 (m, 2H), 1.78-1.69 (m, 2H), 1.29 (s, 3H), 1.26 (d, J=6.0 Hz, 6H); ESI+MS: m/z 422.4 ([M+H]⁺).

Example-191: 4-(4-chlorophenoxy)-1-(2-(4-fluoro-2-isopropoxyphenoxy)ethyl)-4-methylpiperidine Title compound was prepared from 4-(4-chlorophenoxy)-4-methylpiperidine hydrochloride (0.07 g, 0.27 mmol) using the general methodology of Example-1. Purification using silica gel column chromatography afforded 0.025 g of 4-(4-chlorophenoxy)-1-(2-(4-fluoro-2-isopropoxyphenoxy)ethyl)-4-methylpiperidine (Yield=16%). $^1$H NMR (400 MHz, CD₃OD): δ 7.28-7.22 (m, 2H), 6.99 (d, J=9.0 Hz, 2H), 6.95 (dd, J=8.9, 5.6 Hz, 1H), 6.75 (dd, J=10.5, 2.9 Hz, 1H), 6.63-6.57 (m, 1H), 4.59-4.51 (m, 1H), 4.13 (t, J=5.5 Hz, 2H), 2.86 (t, J=5.5 Hz, 2H), 2.82-2.72 (m, 4H), 2.04-1.98 (m, 2H), 1.80-1.70 (m, 2H), 1.31 (s, 3H), 1.29 (s, 6H); ESI+MS: m/z 422.0 ([M+H]⁺).

Example-192: 4-(4-chlorophenoxy)-4-isopropyl-1-(2-(2-(trifluoromethyl)phenoxy)ethyl)piperidine

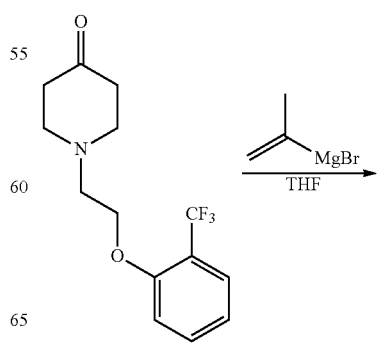

-continued

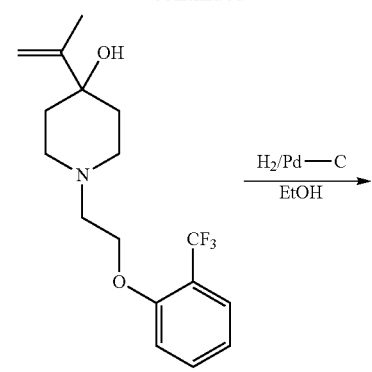

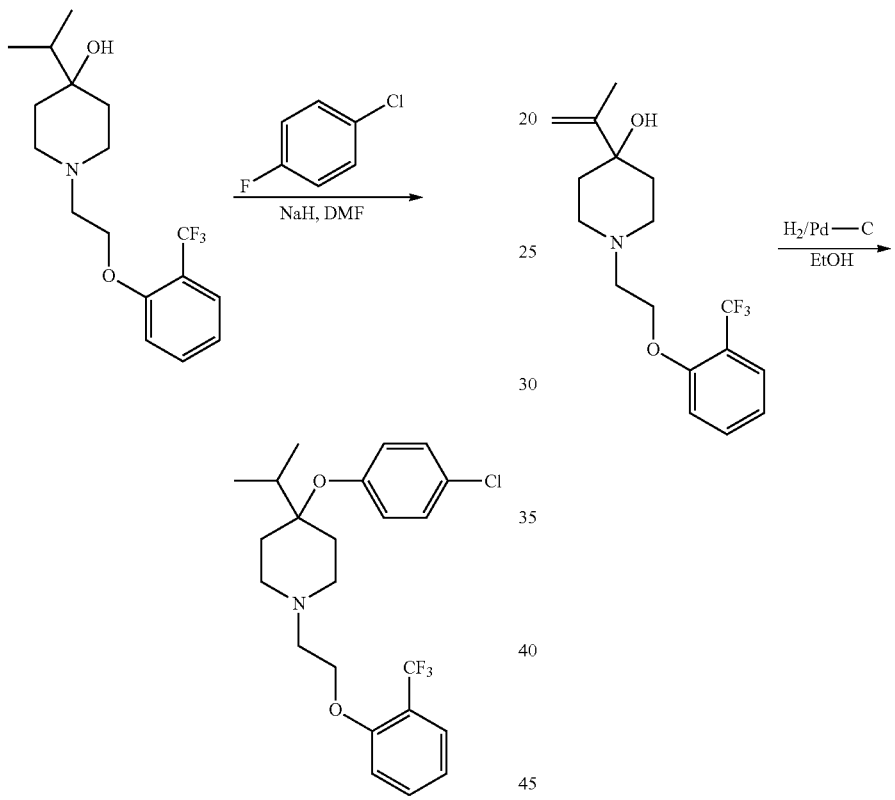

4-(prop-1-en-2-yl)-1-(2-(2-(trifluoromethyl)phenoxy)ethyl)
piperidin-4-ol:

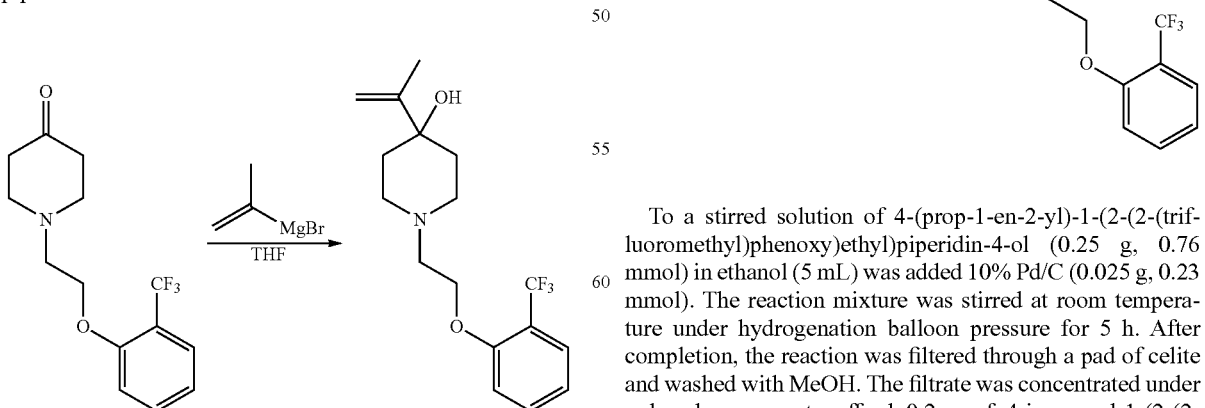

To a stirred solution of 1-(2-(2-(trifluoromethyl)phenoxy)ethyl)piperidin-4-one (0.5 g, 1.74 mmol) in THF (5 mL) was added dropwise isopropenyl magnesium bromide (0.5M in THF, 5.2 mL, 2.61 mmol) at 0° C. The reaction mixture was stirred at 0° C. for 2 h. The reaction was quenched with aq.NH₄Cl and extracted with EtOAc. The organic layer was separated, dried over Na₂SO₄, filtered and concentrated. Purification by silica gel chromatography, eluting with 5% MeOH, afforded 0.25 g of 4-(prop-1-en-2-yl)-1-(2-(2-(trifluoromethyl)phenoxy)ethyl)piperidin-4-ol (Yield=44%). ESI+MS: m/z 329.9 ([M+H]⁺).

4-isopropyl-1-(2-(2-(trifluoromethyl)phenoxy)ethyl)
piperidin-4-ol

To a stirred solution of 4-(prop-1-en-2-yl)-1-(2-(2-(trifluoromethyl)phenoxy)ethyl)piperidin-4-ol (0.25 g, 0.76 mmol) in ethanol (5 mL) was added 10% Pd/C (0.025 g, 0.23 mmol). The reaction mixture was stirred at room temperature under hydrogenation balloon pressure for 5 h. After completion, the reaction was filtered through a pad of celite and washed with MeOH. The filtrate was concentrated under reduced pressure to afford 0.2 g of 4-isopropyl-1-(2-(2-(trifluoromethyl)phenoxy)ethyl)piperidin-4-ol (Yield=80%). ESI+MS: m/z 332.3 ([M+H]⁺).

4-(4-chlorophenoxy)-4-isopropyl-1-(2-(2-(trifluoromethyl)phenoxy)ethyl)piperidine

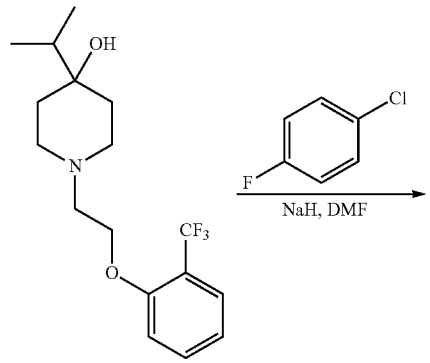

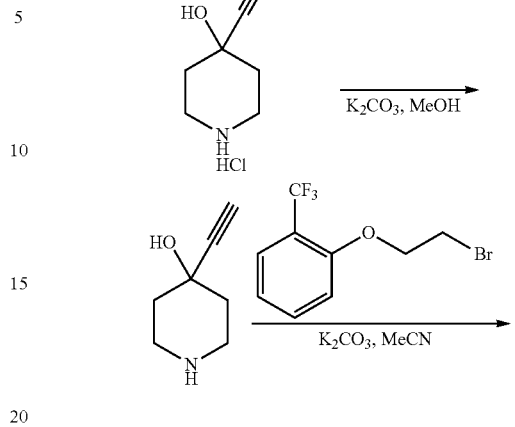

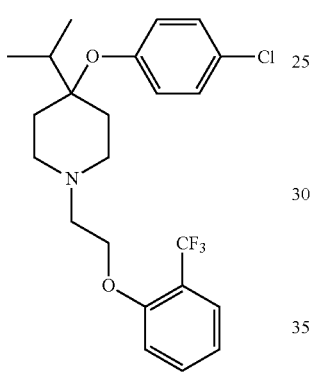

Title compound was prepared from 4-isopropyl-1-(2-(2-(trifluoromethyl)phenoxy)ethyl)piperidin-4-ol (0.2 g, 0.60 mmol) using the general methodology of Example-61. Purification using silica gel column chromatography afforded 9 mg of 4-(4-chlorophenoxy)-4-isopropyl-1-(2-(2-(trifluoromethyl)phenoxy)ethyl)piperidine (Yield=4%). $^1$H NMR (400 MHz, CD$_3$OD): δ 7.59-7.53 (m, 2H), 7.23-7.19 (m, 2H), 7.17 (d, J=8.4 Hz, 1H), 7.05 (t, J=7.6 Hz, 1H), 7.00-6.96 (m, 2H), 4.24 (t, J=5.6 Hz, 2H), 2.91-2.81 (m, 4H), 2.67-2.55 (m, 2H), 2.35-2.27 (m, 1H), 1.94-1.82 (m, 4H), 0.99 (d, J=6.8 Hz, 6H); ESI+MS: m/z 441.9 ([M+H]$^+$).

Example-193: 4-(4-chlorophenoxy)-4-ethynyl-1-(2-(2-(trifluoromethyl)phenoxy)ethyl)piperidine

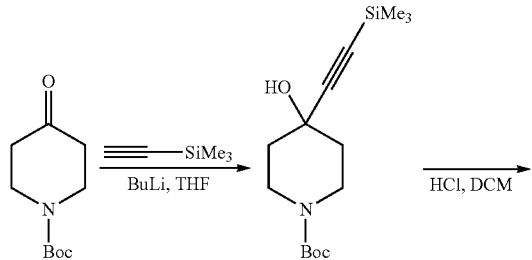

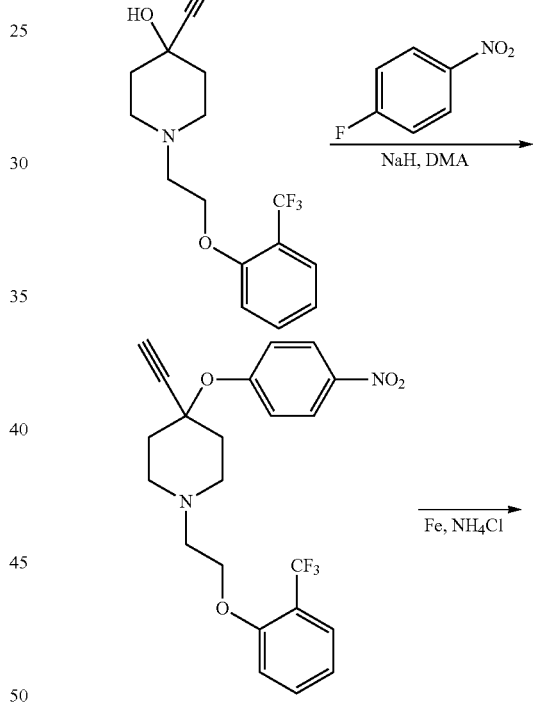

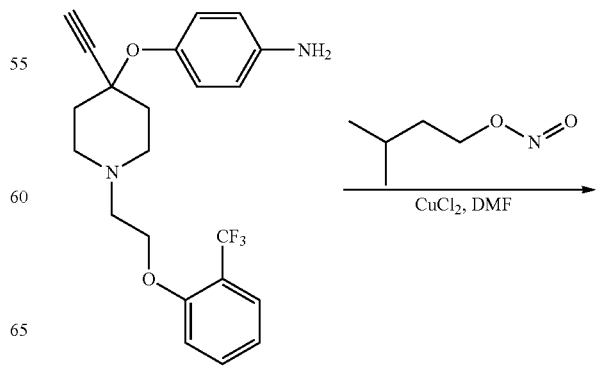

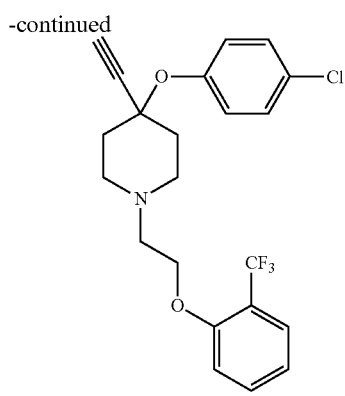

tert-butyl 4-hydroxy-4-((trimethylsilyl)ethynyl)piperidine-1-carboxylate

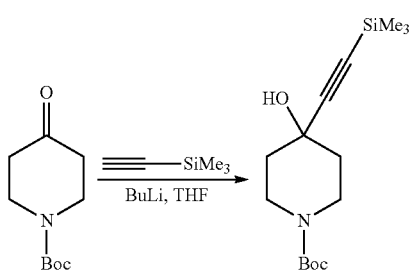

To a stirred solution of ethynyltrimethylsilane (5.92 g, 60.2 mmol) in THF (50 mL) was added n-BuLi (1.6 M in hexane, 3.8 mL, 60.2 mmol) dropwise at −40° C. The reaction mixture was stirred at −40° C. for 1 h. To the mixture was added a solution of tert-butyl 4-oxopiperidine-1-carboxylate (10.0 g, 50.2 mmol) in THF (50 mL) dropwise at −60° C. After stirring at −60° C. for 30 min, the reaction mixture was allowed to warm to room temperature and was stirred for 16 h. The reaction was quenched with sat.NH$_4$Cl and extracted with ethyl acetate. The organic layer was dried over anhydrous Na$_2$SO$_4$, filtered and concentrated. Purification by silica gel chromatography (eluent 10% ethyl acetate in hexanes) afforded 6.0 g of tert-butyl 4-hydroxy-4-((trimethylsilyl)ethynyl)piperidine-1-carboxylate (Yield=41%).

4-((trimethylsilyl)ethynyl)piperidin-4-ol

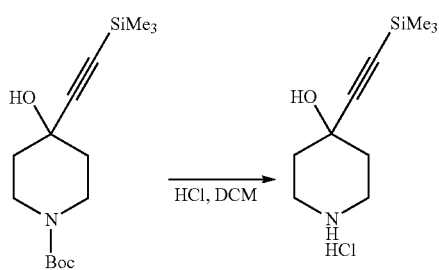 [SMILES: CC(C)(C)OC(=O)N1CCC(O)(C#C[Si](C)(C)C)CC1 ; C[Si](C)(C)C#CC1(O)CCNCC1 ; Cl]

Title compound was prepared from tert-butyl 4-hydroxy-4-((trimethylsilyl)ethynyl)piperidine-1-carboxylate (5.0 g, 16.8 mmol) using the general methodology of step 2 of key intermediate-VI and afforded 3.5 g of 4-((trimethylsilyl)ethynyl)piperidin-4-ol (Yield=89%).

4-ethynylpiperidin-4-ol

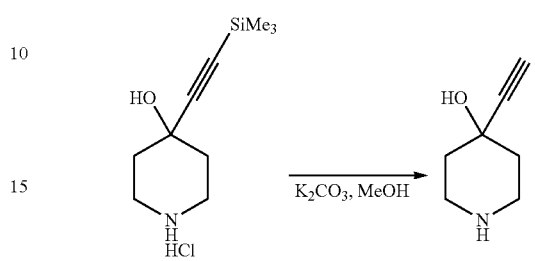

To a stirred solution of 4-((trimethylsilyl)ethynyl)piperidin-4-ol hydrochloride (3.3 g, 14.1 mmol) in MeOH (5 mL) was added K$_2$CO$_3$ (5.85 g, 42.3 mmol). The reaction mixture was maintained at room temperature for 16 h. Solvent was evaporated and the mixture was diluted with water and extracted with DCM. The organic layer was dried over anhydrous Na$_2$SO$_4$, filtered and concentrated to afford 1.3 g of 4-ethynylpiperidin-4-ol (Yield=74%).

4-ethynyl-1-(2-(2-(trifluoromethyl)phenoxy)ethyl)piperidin-4-ol (Compound 302)

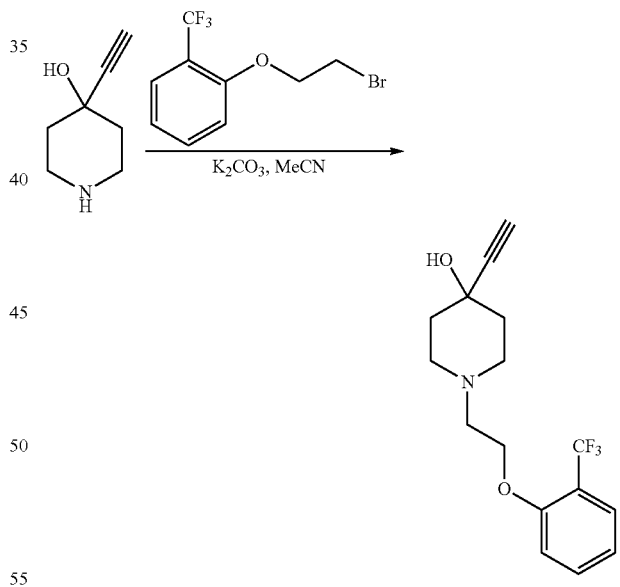

To a stirred solution of 4-ethynylpiperidin-4-ol (1.2 g, 9.6 mmol) in acetonitrile (30 mL) was added K$_2$CO$_3$ (3.97 g, 28.8 mmol) and 1-(2-bromoethoxy)-2-(trifluoromethyl)benzene (2.6 g, 9.6 mmol) at room temperature. The reaction mixture was heated at 80° C. for 16 h. The reaction mixture was diluted with water and extracted with DCM. The organic layer was dried over anhydrous Na$_2$SO$_4$, filtered and concentrated. Purification by silica gel chromatography (eluent 2% MeOH in DCM) afforded 2.5 g of 4-ethynyl-1-(2-(2-(trifluoromethyl)phenoxy)ethyl)piperidin-4-ol (Yield=83%). ESI+MS: m/z 314.0 ([M+H]$^+$).

353

4-ethynyl-4-(4-nitrophenoxy)-1-(2-(2-(trifluoromethyl)phenoxy)ethyl)piperidine

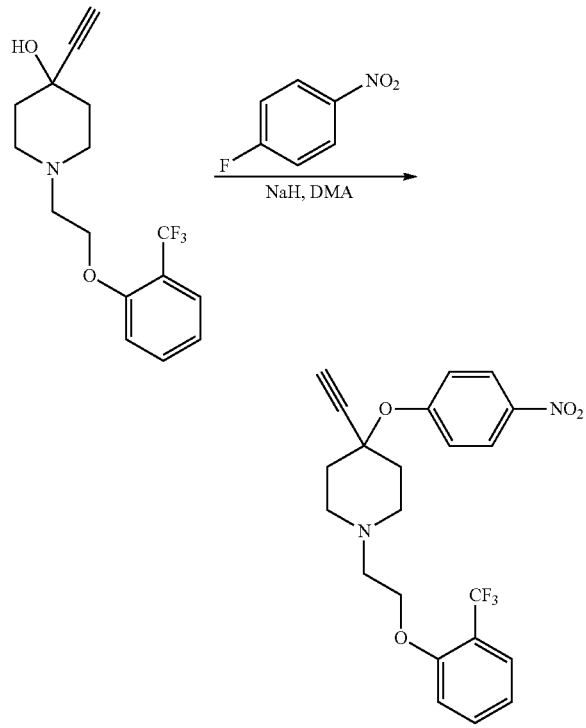

To a stirred solution of 4-ethynyl-1-(2-(2-(trifluoromethyl)phenoxy)ethyl)piperidin-4-ol (1.5 g, 4.79 mmol) in DMA (10 mL) was added NaH (0.17 g, 7.2 mmol) at 0° C. The reaction mixture was stirred at 50° C. for 1 h. Then 1-fluoro-4-nitrobenzene (1.0 g, 7.2 mmol) was added and the reaction mixture was heated at 80° C. for 16 h. The reaction was diluted with water and extracted with ethyl acetate. The organic layer was dried over anhydrous $Na_2SO_4$, filtered and concentrated. Purification by silica gel chromatography (eluent 2% MeOH in DCM) afforded 1.3 g of 4-ethynyl-4-(4-nitrophenoxy)-1-(2-(2-(trifluoromethyl)phenoxy)ethyl)piperidine (Yield=63%). ESI+MS: m/z 435.1 ([M+H]+).

4-((4-ethynyl-1-(2-(2-(trifluoromethyl)phenoxy)ethyl)piperidin-4-yl)oxy)aniline

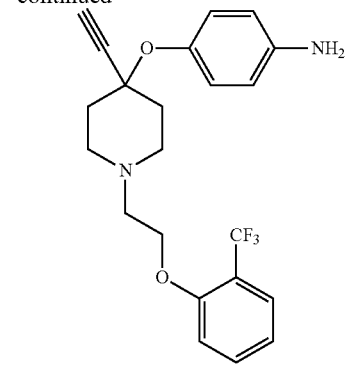

To a stirred solution of 4-ethynyl-4-(4-nitrophenoxy)-1-(2-(2-(trifluoromethyl)phenoxy)ethyl)piperidine (1.2 g, 2.76 mmol) in EtOH:$H_2O$ (1:1, 10 mL) was added Iron (0.23 g, 4.14 mmol) followed by $NH_4Cl$ (0.22 g, 4.14 mmol). The reaction mixture was heated at 80° C. for 5 h. The reaction mixture was filtered through a pad of celite, and the filtrate was concentrated under reduced pressure and diluted with sat.$NaHCO_3$ solution. The aqueous layer was extracted with ethyl acetate, dried over anhydrous $Na_2SO_4$, filtered and concentrated. Purification by silica gel chromatography (eluent with 50% ethyl acetate in hexanes) afford 1.0 g of 4-((4-ethynyl-1-(2-(2-(trifluoromethyl)phenoxy)ethyl)piperidin-4-yl)oxy)aniline (Yield=90%). ESI+MS: m/z 405.1 ([M+H]+).

4-(4-chlorophenoxy)-4-ethynyl-1-(2-(2-(trifluoromethyl)phenoxy)ethyl)piperidine To a stirred solution of 4-((4-ethynyl-1-(2-(2-(trifluoromethyl)phenoxy)ethyl)piperidin-4-yl)oxy)aniline (0.1 g, 0.25 mmol) in DMF (4 mL) was added isoamyl nitrite (0.05 mL, 0.37 mmol) dropwise. The reaction mixture was stirred at room temperature for 15 min. Then CuCl$_2$ (0.05 g, 0.37 mmol) was added and the mixture was stirred for 4 h. The reaction was quenched with a solution of sat.NaHCO$_3$ and extracted with ethyl acetate. The organic layer was separated, dried over anhydrous Na$_2$SO$_4$ and concentrated. Purification by Preparative HPLC afforded 8 mg of 4-(4-chlorophenoxy)-4-ethynyl-1-(2-(2-(trifluoromethyl)phenoxy)ethyl)piperidine (Yield=8%). $^1$H NMR (400 MHz, CD$_3$OD): δ 7.58-7.51 (m, 2H), 7.26-7.15 (m, 5H), 7.04 (t, J=7.6 Hz, 1H), 4.24 (t, J=5.4 Hz, 2H), 3.19 (s, 1H), 2.92-2.84 (m, 4H), 2.72-2.65 (m, 2H), 2.07 (t, J=5.5 Hz, 4H); ESI+MS: m/z 424.0 ([M+H]$^+$).

Example-194: 4-ethynyl-4-phenoxy-1-(2-(2-(trifluoromethyl)phenoxy)ethyl)piperidine

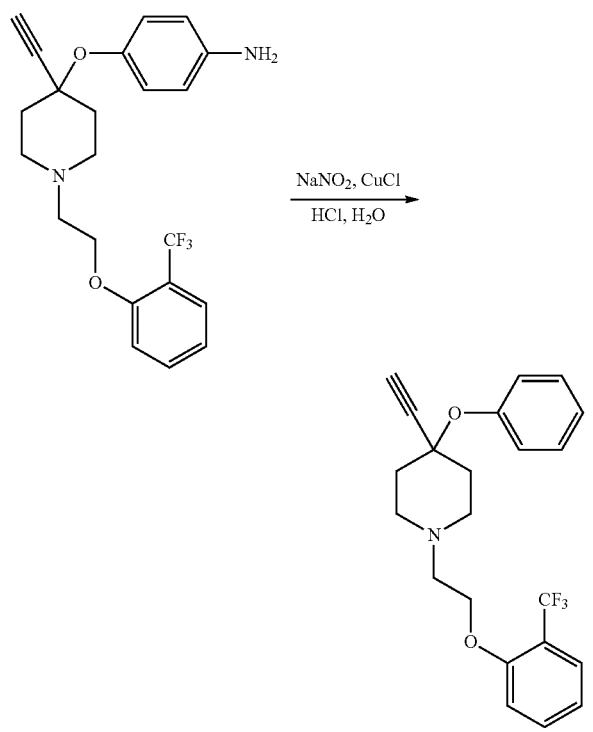

To a stirred solution of 4-((4-ethynyl-1-(2-(2-(trifluoromethyl)phenoxy)ethyl)piperidin-4-yl)oxy)aniline (0.1 g, 0.25 mmol) in 37% HCl:H$_2$O (1:1, 1 mL) was added sodium nitrite (0.022 g, 0.32 mmol) at 0° C. The reaction mixture was stirred at 0° C. for 1 h. The reaction mixture was added to a solution of CuCl (0.04 g, 0.40 mmol) in 37% HCl:H$_2$O (1:1, 1 mL) at 0° C. The reaction mixture was stirred at room temperature for 16 h. The reaction was basified with a solution of 50% NaOH and extracted with ethyl acetate. The organic layer was separated, dried over anhydrous Na$_2$SO$_4$ and concentrated. Purification by Preparative HPLC afforded 15 mg of 4-ethynyl-4-phenoxy-1-(2-(2-(trifluoromethyl)phenoxy)ethyl)piperidine (Yield=16%). $^1$H NMR (400 MHz, CD$_3$OD): δ 7.59-7.52 (m, 2H), 7.29-7.15 (m, 5H), 7.08-6.98 (m, 2H), 4.25 (t, J=5.5 Hz, 2H), 3.15 (s, 1H), 2.93-2.84 (m, 4H), 2.73-2.65 (m, 2H), 2.09 (br t, J=5.4 Hz, 4H); ESI+MS: m/z 390.4 ([M+H]$^+$).

Example-195: 1-(2-(4-(4-chlorophenoxy)-4-methylpiperidin-1-yl)ethyl)-3-(trifluoromethyl)pyridin-2(1H)-one

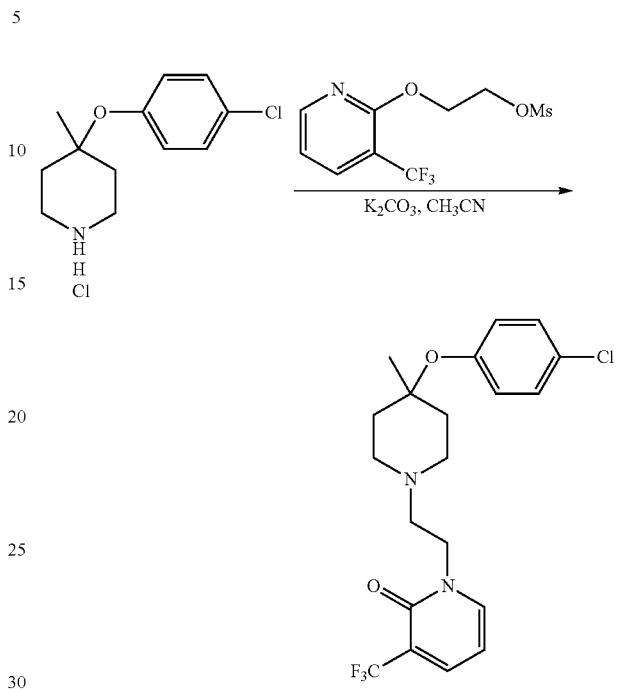

Title compound was prepared from 4-(4-chlorophenoxy)-4-methylpiperidine hydrochloride (0.05 g, 0.19 mmol) using the general methodology of Example-1. Purification using silica gel column chromatography afforded 0.018 g of 1-(2-(4-(4-chlorophenoxy)-4-methylpiperidin-1-yl)ethyl)-3-(trifluoromethyl)pyridin-2(1H)-one (Yield=23%). $^1$H NMR (400 MHz, CD$_3$OD): δ 7.97 (d, J=6.8 Hz, 1H), 7.90 (d, J=6.6 Hz, 1H), 7.30 (d, J=9.6 Hz, 2H), 7.00 (d, J=8.8 Hz, 2H), 6.35 (t, J=6.8 Hz, 1H), 4.06 (t, J=6.0 Hz, 2H), 2.65-2.57 (m, 2H), 2.57-2.53 (m, 4H), 1.86-1.78 (m, 2H), 1.63-1.52 (m, 2H), 1.23 (s, 3H); ESI+MS: m/z 415.3 ([M+H]$^+$).

Example-196: (1R,3s,5S)-3-methyl-8-(2-(2-(trifluoromethyl)phenoxy)ethyl)-8-azabicyclo[3.2.1]octan-3-ol

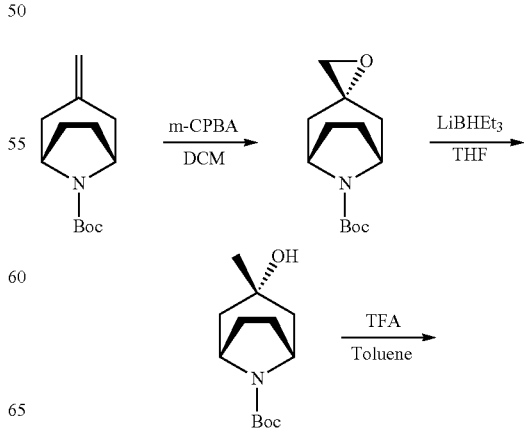

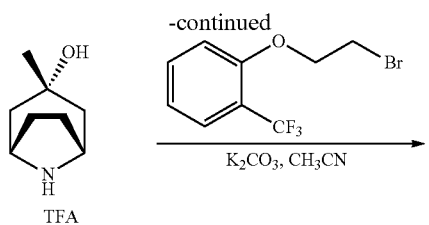

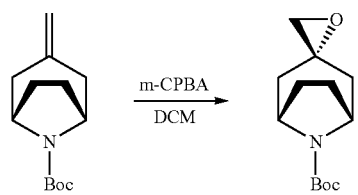

butyl (1R,3s,5S)-8-azaspiro[bicyclo[3.2.1]octane-3, 2'-oxirane]-8-carboxylate

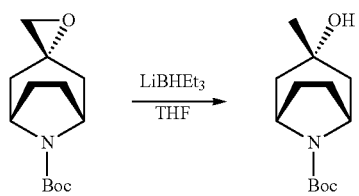

To a solution of (1R,5S)-tert-butyl 3-methylene-8-azabicyclo[3.2.1]octane-8-carboxylate (8.9 g, 39.9 mmol) in DCM (133 mL) was added m-CPBA portionwise (14.3 g, 63.8 mmol) and the solution was stirred at room temperature for 15 h. The reaction mixture was diluted in sat. aq. NaHCO₃ and extracted with DCM. The 2 stereoisomers were separated by flash chromatography (Hexane/EtOAc 95:5) and afforded 2.6 g of tert-butyl (1R,3s,5S)-8-azaspiro [bicyclo[3.2.1]octane-3,2'-oxirane]-8-carboxylate (Yield=27%). ¹H NMR (400 MHz, CDCl₃): δ 4.45-4.25 (m, 2H), 2.76 (s, 2H), 2.35-2.10 (m, 2H), 2.10-1.90 (m, 2H), 1.80-1.60 (m, 2H), 1.50 (s, 9H), 1.30-1.20 (m, 2H).

tert-butyl (1R,3s,5S)-3-hydroxy-3-methyl-8-azabicyclo[3.2.1]octane-8-carboxylate To a stirred solution of tert-butyl (1R,3s,5S)-8-azaspiro [bicyclo[3.2.1]octane-3,2'-oxirane]-8-carboxylate (2.6 g, 10.9 mmol) in THF (50 mL) was added LiBHEt₃ (1.0 M in THF, 12 mL, 12 mmol) at 0° C. The reaction mass was stirred at 0° C. for 2 h. The reaction mixture was diluted with sat. NH₄Cl solution and extracted with ethyl acetate. The organic layer was separated, dried over anhydrous Na₂SO₄, filtered and concentrated. Purification by flash chromatography (Hexane/EtOAc 70:30) afforded 1.6 g of tert-butyl (1R,3s,5S)-3-hydroxy-3-methyl-8-azabicyclo[3.2.1]octane-8-carboxylate (Yield=61%). ¹H NMR (400 MHz, DMSO-d6): δ 4.41 (s, 1H), 4.05-3.95 (m, 2H), 1.90-1.75 (m, 4H), 1.70-1.60 (m, 4H), 1.40 (s, 9H), 1.34 (s, 3H). ESI+MS: m/z 242.0 ([M+H]⁺).

(1R,3s,5S)-3-hydroxy-3-methyl-8-azabicyclo[3.2.1] octan-8-ium 2,2,2-trifluoroacetate

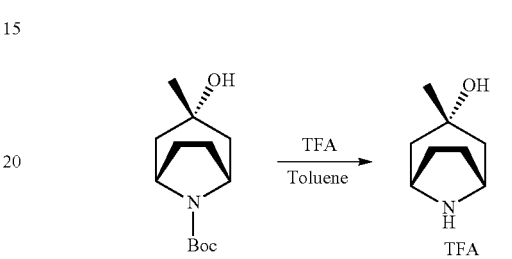

tert-butyl (1R,3s,5S)-3-hydroxy-3-methyl-8-azabicyclo [3.2.1]octane-8-carboxylate (200 mg, 0.83 mmol) was dissolved in Toluene (3 ml) and TFA (0.5 ml) was added dropwise. The reaction mixture was stirred for 1 hour and the solvents were evaporated and coevaporated again with fresh toluene to afford 210 mg of (1R,3s,5S)-3-hydroxy-3-methyl-8-azabicyclo[3.2.1]octan-8-ium 2,2,2-trifluoroacetate (Yield=quant.).

(1R,3s,5S)-3-methyl-8-(2-(2-(trifluoromethyl)phenoxy)ethyl)-8-azabicyclo[3.2.1]octan-3-ol

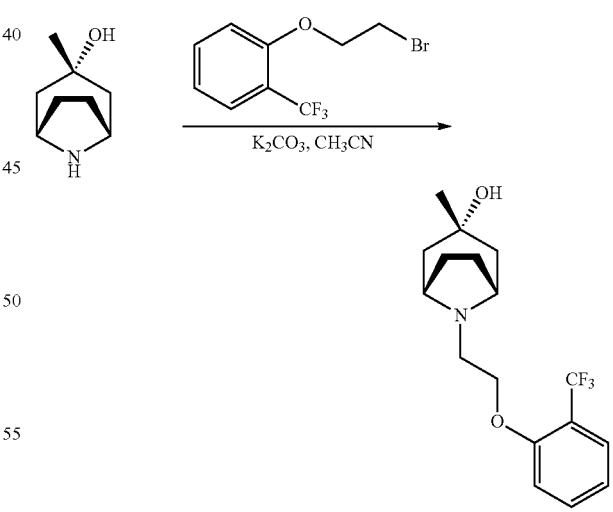

Title compound was prepared from (1R,3s,5S)-3-hydroxy-3-methyl-8-azabicyclo[3.2.1]octan-8-ium 2,2,2-trifluoroacetate (0.25 g, 0.98 mmol) using the general methodology of Example-1. Purification using silica gel column chromatography afforded 0.11 g of (1R,3s,5S)-3-methyl-8-(2-(2-(trifluoromethyl)phenoxy)ethyl)-8-azabicyclo[3.2.1] octan-3-ol (Yield=34%). ¹H NMR (400 MHz, CD₃OD): δ 7.97 (d, J=6.8 Hz, 1H), 7.90 (d, J=6.6 Hz, 1H), 7.30 (d, J=9.6

Hz, 2H), 7.00 (d, J=8.8 Hz, 2H), 6.35 (t, J=6.8 Hz, 1H), 4.06 (t, J=6.0 Hz, 2H), 2.65-2.57 (m, 2H), 2.57-2.53 (m, 4H), 1.86-1.78 (m, 2H), 1.63-1.52 (m, 2H), 1.23 (s, 3H); ESI+ MS: m/z 415.3 ([M+H]$^+$).

Example-197: (1R,3s,5S)-3-methyl-8-(2-(2-(trifluoromethyl)phenoxy)ethyl)-8-azabicyclo[3.2.1]octan-3-ol

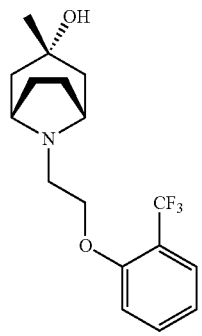 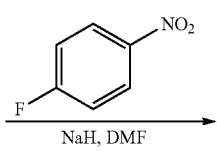

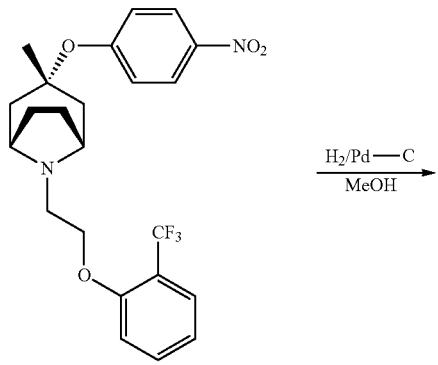

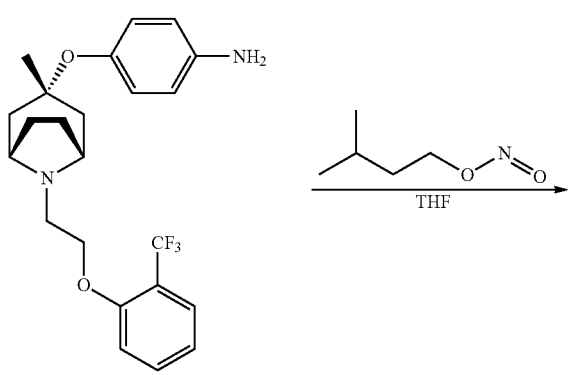

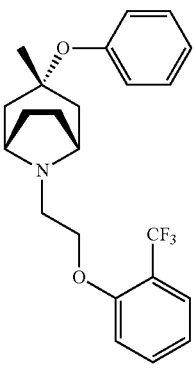

(1R,3s,5S)-3-methyl-3-(4-nitrophenoxy)-8-(2-(2-(trifluoromethyl)phenoxy)ethyl)-8-azabicyclo[3.2.1]octane

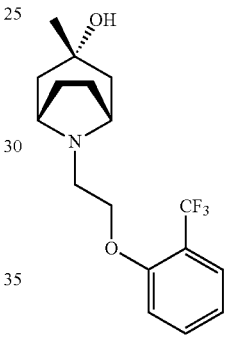

To a suspension of (1R,3s,5S)-3-methyl-8-(2-(2-(trifluoromethyl)phenoxy)ethyl)-8-azabicyclo[3.2.1]octan-3-ol (0.1 g, 0.3 mmol) in dry DMF (1 mL), was added NaH (24 mg, 0.61 mmol). The mixture was stirred at 80° C. for 1 h and then cooled to −70° C. A solution of 1-fluoro-4-nitrobenzene (55 uL, 0.52 mmol) in dry DMF (0.5 ml) was added dropwise. The reaction was left to warm up to room temperature and left stirring overnight. The mixture was poured in water and extracted with EtOAc, the organic phase washed with water, dried (Na$_2$SO$_4$), filtered and concentrated. Purification by silica gel chromatography (DCM/MeOH 99:1) afforded 76 mg of (1R,3s,5S)-3-methyl-3-(4-nitrophenoxy)-8-(2-(2-(trifluoromethyl)phenoxy)ethyl)-8-azabicyclo[3.2.1]octane (Yield=56%).

361

4-(((1R,3s,5S)-3-methyl-8-(2-(2-(trifluoromethyl)phenoxy)ethyl)-8-azabicyclo[3.2.1]octan-3-yl)oxy)aniline

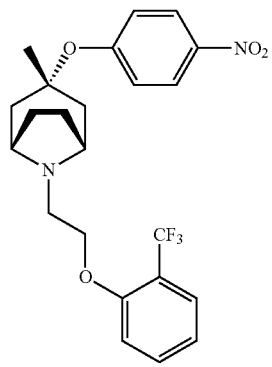

H₂/Pd—C / MeOH →

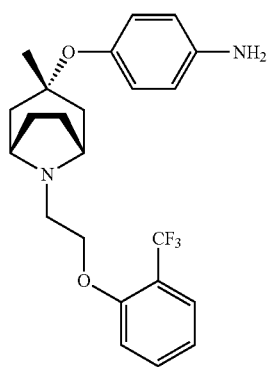

To a stirred solution of (1R,3s,5S)-3-methyl-3-(4-nitrophenoxy)-8-(2-(2-(trifluoromethyl)phenoxy)ethyl)-8-azabicyclo[3.2.1]octane (0.07 g, 0.16 mmol) in MeOH (0.8 mL) was added 10% Pd/C (10 mg) at room temperature and the reaction was stirred for 16 h under H₂ balloon atmosphere. After completion, the reaction mass was filtered through a pad of celite and the filtrate was concentrated. Purification by silica gel chromatography afforded 0.035 g of 4-(((1R,3s,5S)-3-methyl-8-(2-(2-(trifluoromethyl)phenoxy)ethyl)-8-azabicyclo[3.2.1]octan-3-yl)oxy)aniline (Yield=54%).

(1R,3s,5S)-3-methyl-8-(2-(2-(trifluoromethyl)phenoxy)ethyl)-8-azabicyclo[3.2.1]octan-3-ol

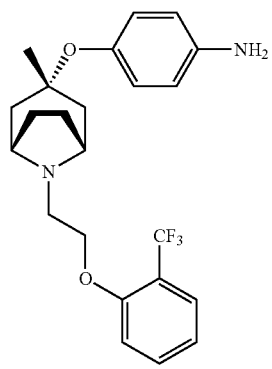

362

-continued

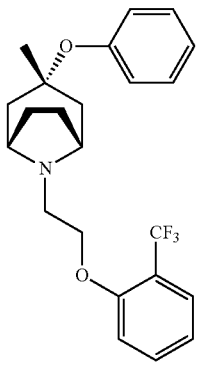

Title compound was prepared from 4-(((1R,3s,5S)-3-methyl-8-(2-(2-(trifluoromethyl)phenoxy)ethyl)-8-azabicyclo[3.2.1]octan-3-yl)oxy)aniline (0.035 g, 0.08 mmol) using the general methodology of Key intermediate VI and afforded 0.016 g of (1R,3s,5S)-3-methyl-8-(2-(2-(trifluoromethyl)phenoxy)ethyl)-8-azabicyclo[3.2.1]octan-3-ol (Yield=46%). ¹H NMR (400 MHz, CDCl₃): δ 7.58-7.55 (m, 1H), 7.53-7.45 (m, 1H), 7.25-7.18 (m, 2H), 7.06-6.97 (m, 5H), 4.27 (t, J=5.6 Hz, 2H), 3.56 (br s, 2H), 3.07-3.01 (m, 2H), 2.62-2.52 (m, 2H), 2.10-2.00 (m, 2H), 1.80-1.70 (m, 4H), 1.26 (s, 3H); ESI+MS: m/z 407.5 ([M+H]⁺).

Example-198: N,4-dimethyl-1-(2-(2-(trifluoromethyl)phenoxy)ethyl)piperidine-4-carboxamide

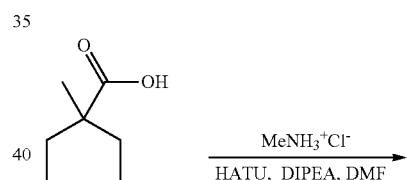

MeNH₃⁺Cl⁻ / HATU, DIPEA, DMF →

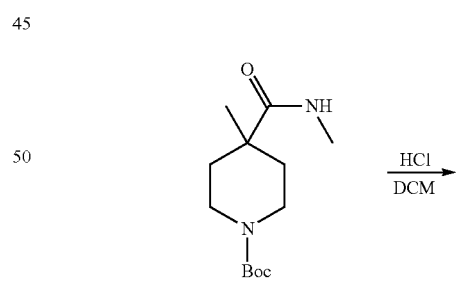

HCl / DCM →

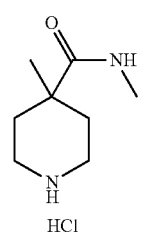 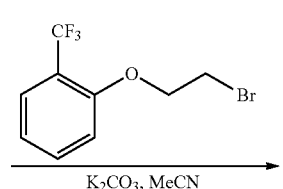

K₂CO₃, MeCN →

363

-continued

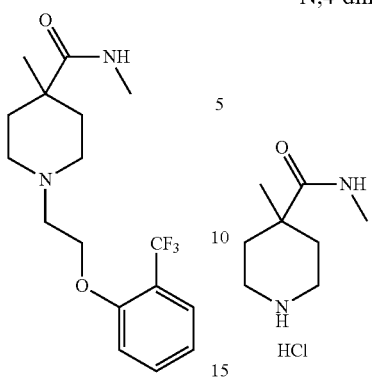

tert-butyl 4-methyl-4-(methylcarbamoyl)piperidine-1-carboxylate

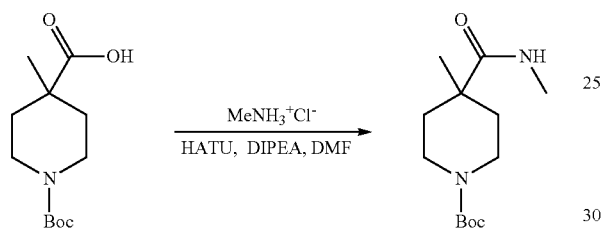

To a stirred solution of 1-(tert-butoxycarbonyl)-4-methylpiperidine-4-carboxylic acid (1.0 g, 4.11 mmol) in DMF (10 mL) was added methyl amine hydrochloride (0.36 g, 5.34 mmol), HATU (2.34 g, 6.2 mmol) followed by DIPEA (2.66 g, 20.55 mmol) at 0° C. The reaction mixture was stirred at room temperature for 16 h. After completion, the mixture was quenched with water and extracted with diethyl ether. The organic layer was separated, dried over Na₂SO₄, filtered and concentrated. Purification by silica gel chromatography eluting with 3% MeOH in DCM afforded 0.8 g of tert-butyl 4-methyl-4-(methylcarbamoyl)piperidine-1-carboxylate (Yield=76%).

N,4-dimethylpiperidine-4-carboxamide hydrochloride

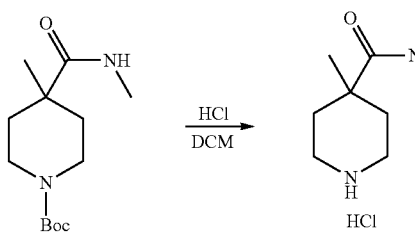

To a stirred solution of tert-butyl 4-methyl-4-(methylcarbamoyl)piperidine-1-carboxylate (0.6 g, 2.34 mmol) in DCM (5 mL) was added 4.0M HCl in 1,4-Dioxane (0.7 mL, 28.0 mmol) at 0° C. The reaction mixture was stirred at room temperature for 4 h. After completion, volatiles were concentrated under reduced pressure to afford 0.45 g of N,4-dimethylpiperidine-4-carboxamide hydrochloride (Yield=quant.).

364

N,4-dimethyl-1-(2-(2-(trifluoromethyl)phenoxy)ethyl)piperidine-4-carboxamide

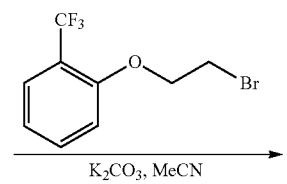

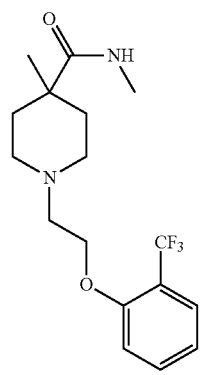

Title compound was prepared from N,4-dimethylpiperidine-4-carboxamide hydrochloride (0.45 g, 2.34 mmol) using the general methodology of Example-1. Purification using silica gel column chromatography afforded 0.2 g of N,4-dimethyl-1-(2-(2-(trifluoromethyl)phenoxy)ethyl)piperidine-4-carboxamide (Yield=25%). ¹H NMR (400 MHz, CD₃OD): δ 7.58 (m, 2H), 7.19 (d, J=8.8 Hz, 1H), 7.09 (t, J=7.6 Hz, 1H), 4.32 (t, J=5.2 Hz, 2H), 3.11-2.98 (m, 4H), 2.74 (s, 3H), 2.73-2.65 (m, 2H), 2.21-2.14 (m, 2H), 1.65-1.57 (m, 2H), 1.19 (s, 3H); ESI+MS: m/z 345.4 ([M+H]⁺).

Example-199: N,4-dimethyl-1-(2-phenoxyethyl)piperidine-4-carboxamide

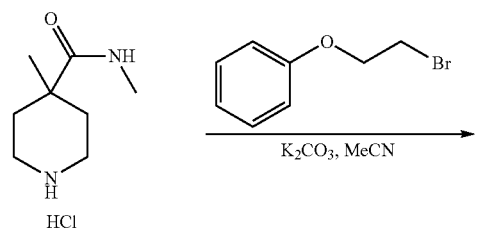

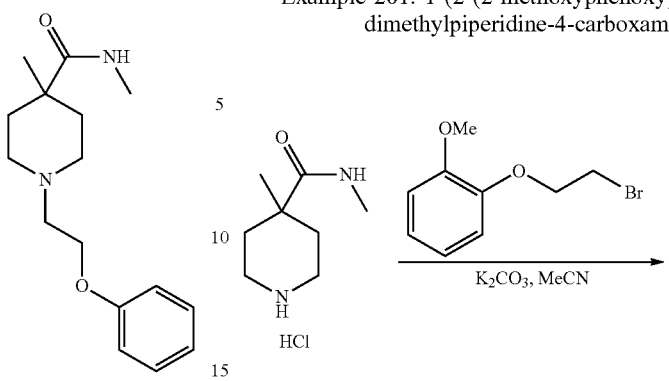

Title compound was prepared from N,4-dimethylpiperidine-4-carboxamide hydrochloride (0.1 g, 0.52 mmol) using the general methodology of Example-1. Purification using silica gel column chromatography afforded 0.05 g of N,4-dimethyl-1-(2-phenoxyethyl)piperidine-4-carboxamide (Yield=35%). $^1$H NMR (400 MHz, CD$_3$OD): δ 7.29-7.23 (m, 2H), 6.95-6.89 (m, 3H), 4.13 (t, J=5.6 Hz, 2H), 2.86-2.78 (m, 4H), 2.73 (s, 3H), 2.48-2.38 (m, 2H), 2.15-2.07 (m, 2H), 1.62-1.52 (m, 2H), 1.16 (s, 3H); ESI+MS: m/z 277.3 ([M+H]$^+$).

Example-200: 1-(2-(2-fluorophenoxy)ethyl)-N,4-dimethylpiperidine-4-carboxamide

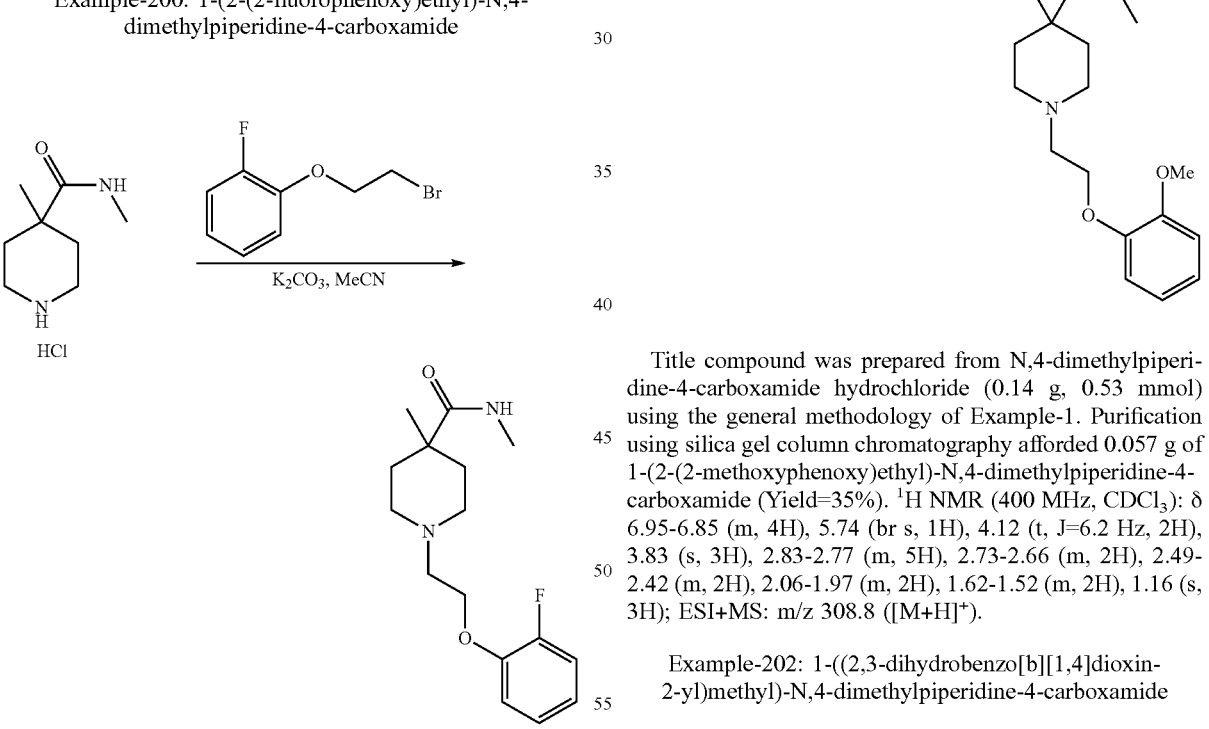

Title compound was prepared from N,4-dimethylpiperidine-4-carboxamide hydrochloride (0.14 g, 0.53 mmol) using the general methodology of Example-1. Purification using silica gel column chromatography afforded 0.054 g of 1-(2-(2-fluorophenoxy)ethyl)-N,4-dimethylpiperidine-4-carboxamide (Yield=34%). $^1$H NMR (400 MHz, CDCl$_3$): δ 7.11-6.85 (m, 4H), 5.72 (br s, 1H), 4.17 (t, J=5.9 Hz, 2H), 2.85-2.78 (m, 5H), 2.76-2.70 (m, 2H), 2.52-2.45 (m, 2H), 2.10-1.99 (m, 2H), 1.65-1.55 (m, 2H), 1.19 (s, 3H); ESI+MS: m/z 294.8 ([M+H]$^+$).

Example-201: 1-(2-(2-methoxyphenoxy)ethyl)-N,4-dimethylpiperidine-4-carboxamide

Title compound was prepared from N,4-dimethylpiperidine-4-carboxamide hydrochloride (0.14 g, 0.53 mmol) using the general methodology of Example-1. Purification using silica gel column chromatography afforded 0.057 g of 1-(2-(2-methoxyphenoxy)ethyl)-N,4-dimethylpiperidine-4-carboxamide (Yield=35%). $^1$H NMR (400 MHz, CDCl$_3$): δ 6.95-6.85 (m, 4H), 5.74 (br s, 1H), 4.12 (t, J=6.2 Hz, 2H), 3.83 (s, 3H), 2.83-2.77 (m, 5H), 2.73-2.66 (m, 2H), 2.49-2.42 (m, 2H), 2.06-1.97 (m, 2H), 1.62-1.52 (m, 2H), 1.16 (s, 3H); ESI+MS: m/z 308.8 ([M+H]$^+$).

Example-202: 1-((2,3-dihydrobenzo[b][1,4]dioxin-2-yl)methyl)-N,4-dimethylpiperidine-4-carboxamide

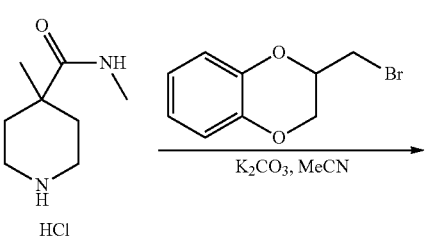

367

-continued

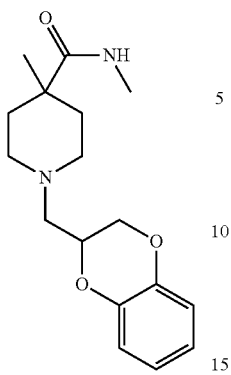

Title compound was prepared from N,4-dimethylpiperidine-4-carboxamide hydrochloride (0.3 g, 1.56 mmol) using the general methodology of Example-1. Purification using silica gel column chromatography afforded 0.06 g of 1-((2,3-dihydrobenzo[b][1,4]dioxin-2-yl)methyl)-N,4-dimethylpiperidine-4-carboxamide (Yield=13%). ¹H NMR (400 MHz, DMSO-d6): δ 7.50-7.44 (m, 1H), 6.87-6.77 (m, 4H), 4.33-4.24 (m, 2H), 3.96-3.88 (m, 1H), 2.57 (d, J=4.4 Hz, 1H), 2.55-2.45 (m, 6H), 2.30-2.10 (m, 2H), 1.99-1.92 (m, 2H), 1.40-1.31 (m, 2H), 1.04 (s, 3H); ESI+MS: m/z 305.3 ([M+H]⁺). The enantiomers of 202 were separated using chiral HPLC (method K) and afforded the pure enantiomers 202a and 202b.

Example-203: —N-cyclopropyl-1-((2,3-dihydrobenzo[b][1,4]dioxin-2-yl)methyl)-4-methylpiperidine-4-carboxamide

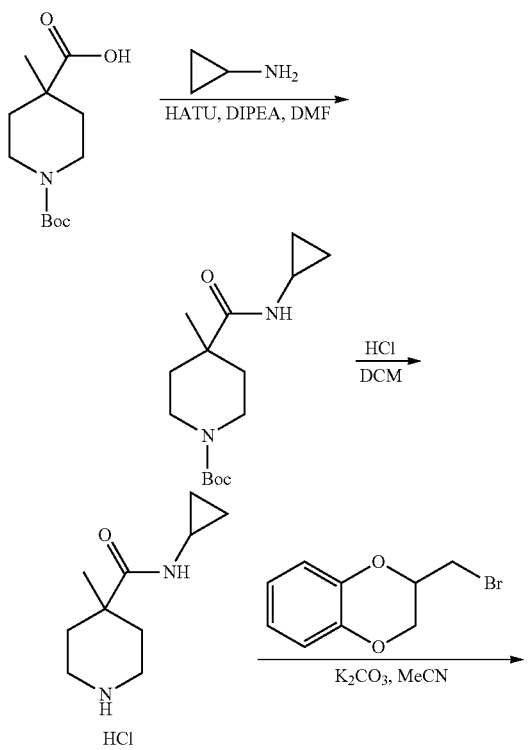

368

-continued

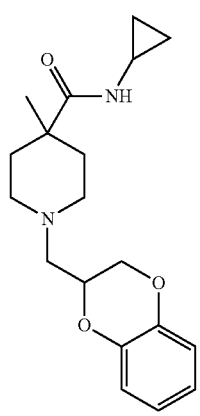

tert-butyl 4-(cyclopropylcarbamoyl)-4-methylpiperidine-1-carboxylate

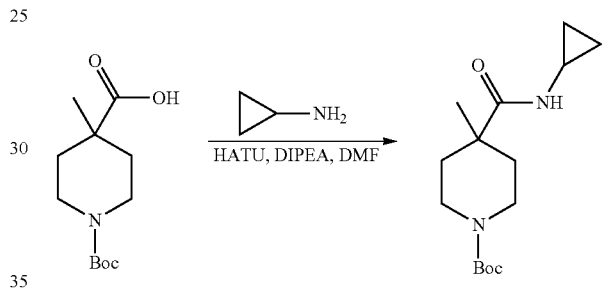

Title compound was prepared from 1-(tert-butoxycarbonyl)-4-methylpiperidine-4-carboxylic acid (0.5 g, 2.06 mmol) following the conditions reported for example 198. Purification by silica gel chromatography eluting with 7% MeOH in DCM afforded 0.5 g of tert-butyl 4-(cyclopropylcarbamoyl)-4-methylpiperidine-1-carboxylate (Yield=86%).

N-cyclopropyl-4-methylpiperidine-4-carboxamide hydrochloride

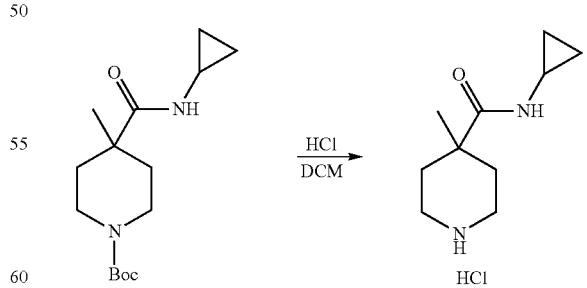

Title compound was prepared from tert-butyl 4-(cyclopropylcarbamoyl)-4-methylpiperidine-1-carboxylate (0.5 g, 1.77 mmol) following the conditions reported for example 198 and afforded 0.3 g of N-cyclopropyl-4-methylpiperidine-4-carboxamide hydrochloride (Yield=77%).

369

N-cyclopropyl-1-((2,3-dihydrobenzo[b][1,4]dioxin-2-yl)methyl)-4-methylpiperidine-4-carboxamide

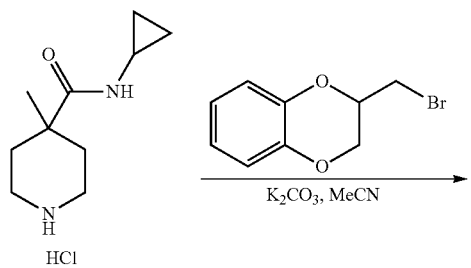

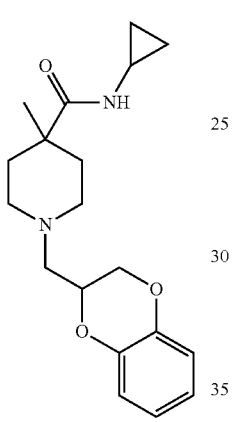

Title compound was prepared from N-cyclopropyl-4-methylpiperidine-4-carboxamide hydrochloride (0.3 g, 1.37 mmol) using the general methodology of Example-1. Purification using silica gel column chromatography afforded 0.1 g of N-cyclopropyl-1-((2,3-dihydrobenzo[b][1,4]dioxin-2-yl)methyl)-4-methylpiperidine-4-carboxamide (Yield=22%). $^1$H NMR (500 MHz, DMSO-d6): δ 7.45 (d, J=3.5 Hz, 1H), 6.86-6.78 (m, 4H), 4.33-4.24 (m, 2H), 3.95-3.89 (m, 2H), 2.65-2.58 (m, 2H), 2.50-2.44 (m, 3H), 2.24-2.09 (m, 2H), 1.99-1.92 (m, 2H), 1.36-1.28 (m, 2H), 1.02 (s, 3H), 0.61-0.55 (m, 2H), 0.43-0.38 (m, 2H); ESI+ MS: m/z 331.1 ([M+H]$^+$). The enantiomers of 203 were separated using chiral HPLC (method U) and afforded the pure enantiomers 203a and 203b.

Example-204: 1-((2,3-dihydrobenzo[b][1,4]dioxin-2-yl)methyl)-4-methyl-N-phenylpiperidine-4-carboxamide

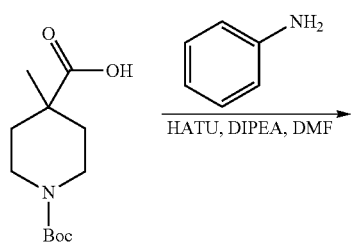

370

-continued

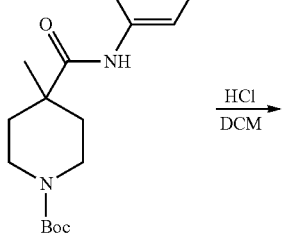

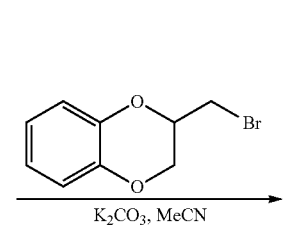

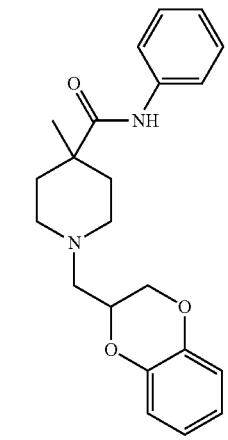

Title compound was prepared from 1-(tert-butoxycarbonyl)-4-methylpiperidine-4-carboxylic acid and aniline following the conditions reported for example 198. Purification by silica gel chromatography afforded 0.26 g of 1-((2,3-dihydrobenzo[b][1,4]dioxin-2-yl)methyl)-4-methyl-N-phenylpiperidine-4-carboxamide (Yield=45%). $^1$H NMR (500 MHz, DMSO-d6): δ 9.21 (s, 1H), 7.62 (d, J=7.6 Hz, 2H), 7.27 (t, J=8.0 Hz, 2H), 7.02 (t, J=7.5 Hz, 1H), 6.86-6.76 (m, 4H), 4.34-4.23 (m, 2H), 3.93 (dd, J=11.3 Hz, J=6.9, Hz, 1H), 2.70-2.54 (m, 2H), 2.50-2.48 (m, 2H), 2.36-2.18 (m, 2H), 2.14 (d, J=13.0 Hz, 2H), 1.51-1.44 (m, 2H), 1.20 (s, 3H); ESI+MS: m/z 367.1 ([M+H]$^+$). The enantiomers of 204 were separated using chiral HPLC (method D) and afforded the pure enantiomers 204a and 204b.

Example-205: (S)-1-((2,3-dihydrobenzo[b][1,4]dioxin-2-yl)methyl)-N,N,4-trimethylpiperidine-4-carboxamide

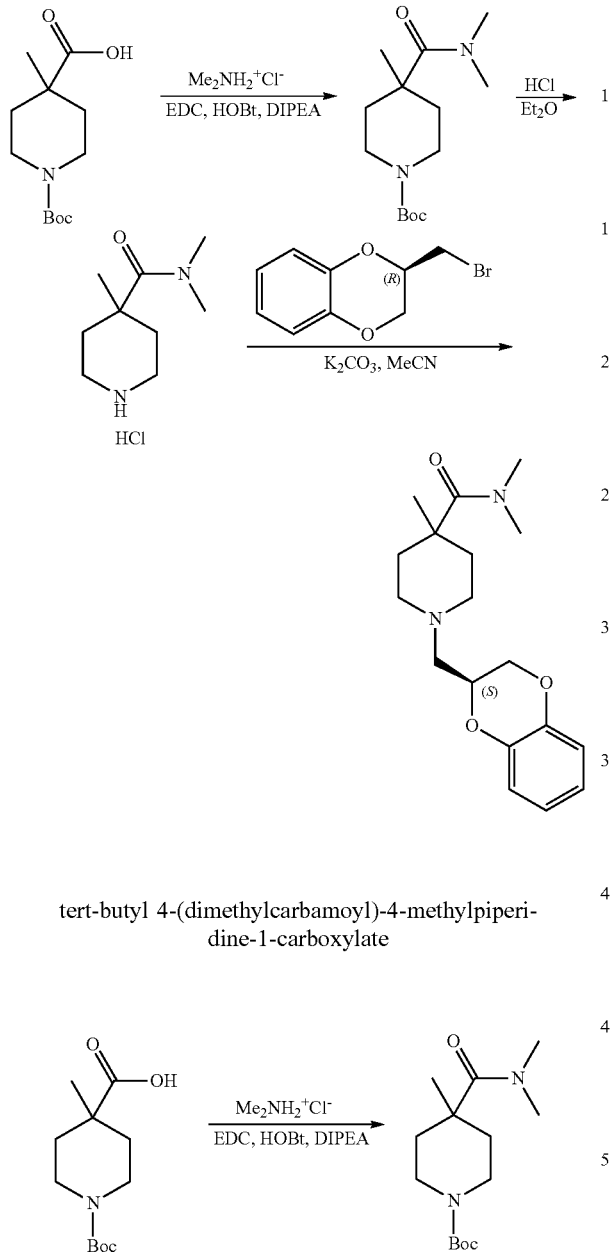

tert-butyl 4-(dimethylcarbamoyl)-4-methylpiperidine-1-carboxylate

To a cooled solution of N-Boc-4-methylpiperidine-4-carboxylic acid (0.50 g, 2.05 mmol) at 0° C. in dry CH$_2$Cl$_2$ (7 mL) was added diisopropylethylamine (0.54 mL, 3.08 mmol), hydroxybenzotriazole (0.31 g, 2.26 mmol) and dimethylamine hydrochloride (0.24 g, 2.88 mmol). EDC.HCl (0.43 g, 2.26 mmol) was then added at 0° C. and the mixture was left to warm up to room temperature and left stirring overnight. The resulting suspension was filtered through celite and washed with DCM. The filtrate was washed with 1 N aq. sol. HCl, sat. aq. K$_2$CO$_3$, H$_2$O and brine. The organic layer was dried over Na$_2$SO$_4$ and the solvent removed under reduced pressure. The product was obtained as white powder (0.52 g, 94% yield). $^1$H-NMR (300 MHz, CDCl$_3$): δ 3.59 (br s, 2H), 3.19 (br s, 2H), 3.02 (s, 6H), 2.20-2.10 (m, 2H), 1.43 (s, 9H), 1.27 (s, 3H).

N,N,4-trimethylpiperidine-4-carboxamide hydrochloride

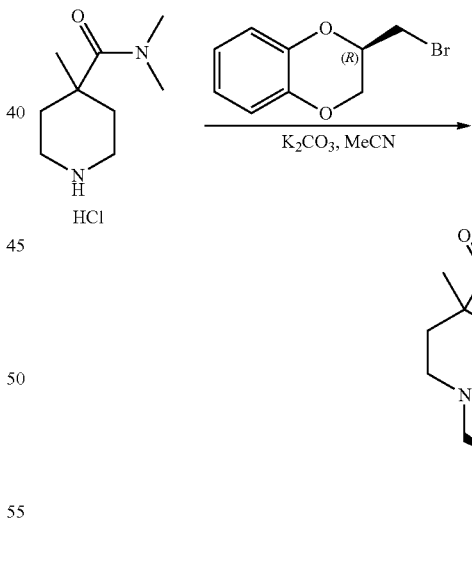

To a solution of tert-butyl 4-(dimethylcarbamoyl)-4-methylpiperidine-1-carboxylate (0.52 g, 1.92 mmol) in Et$_2$O (2 mL) was added dropwise HCl (2 mL, 8.00 mmol, 4 N dioxane solution) under N$_2$. The reaction mixture was stirred for 2 hours and the solvent was removed under reduced pressure to obtain product as white solid (0.38 g, 97% yield). $^1$H-NMR (300 MHz, DMSO-d6): δ 9.20-8.75 (br m, 2H), 3.56 (s, 6H), 3.20-3.02 (m, 2H), 2.82 (br s, 2H), 2.20-2.00 (m, 2H), 1.71-1.55 (m, 1H), 1.20 (s, 3H). ESI–MS calcd for C9H18N2O m/z 170.14, found 171.61 [M+H]+.

(S)-1-((2,3-dihydrobenzo[b][1,4]dioxin-2-yl)methyl)-N,N,4-trimethylpiperidine-4-carboxamide Title compound was prepared from N,N,4-trimethylpiperidine-4-carboxamide hydrochloride (0.08 g, 0.40 mmol) using the general methodology of example 1. Purification by silica gel chromatography afforded 0.032 g of (S)-1-((2,3-dihydrobenzo[b][1,4]dioxin-2-yl)methyl)-N,N,4-trimethylpiperidine-4-carboxamide (Yield=25%). [α]$_D^{25}$=–17.1° (CHCl$_3$; c=0.11). $^1$H NMR (300 MHz, CDCl$_3$): δ 6.93-6.77 (m, 4H), 4.38-4.26 (m, 2H), 3.96 (ddd, J=11.7, 7.7, 2.3 Hz, 1H), 3.04 (s, 6H), 2.82-2.38 (m, 6H), 2.33 (s, 2H), 2.28-2.18 (m, 2H), 1.65-1.53 (m, 2H), 1.27 (s, 3H); ESI+MS: m/z 319.6 ([M+H]$^+$).

Example-206: (S)-(1-((2,3-dihydrobenzo[b][1,4] dioxin-2-yl)methyl)-4-methylpiperidin-4-yl)(pyrrolidin-1-yl)methanone

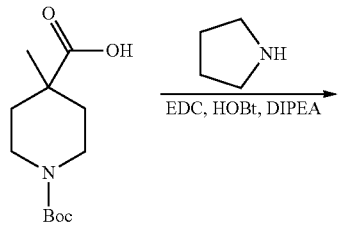

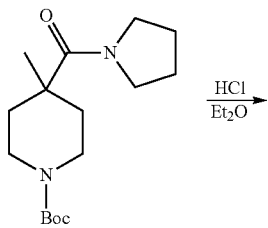

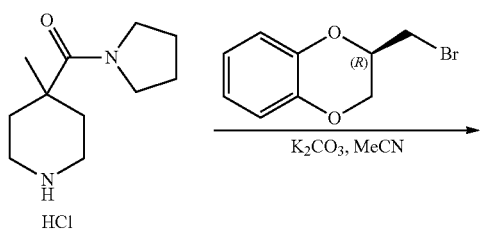

Title compound was prepared using the same strategy employed for example 205 by replacing dimethylamine hydrochloride with pyrrolidine. [α]$_D^{25}$=−11.4° (CHCl$_3$; c=0.26). $^1$H NMR (300 MHz, CDCl$_3$): δ 6.92-6.78 (m, 4H), 4.33-4.23 (m, 2H), 4.02-3.92 (m, 1H), 3.54 (t, J=6.8 Hz, 4H), 2.77-2.20 (m, 9H), 1.86 (br s, 4H), 1.60-1.48 (m, 2H), 1.21 (s, 3H); ESI+MS: m/z 319.6 ([M+H]$^+$).

Example-207: (S)-1-(1-((2,3-dihydrobenzo[b][1,4] dioxin-2-yl)methyl)-4-methylpiperidin-4-yl)-N-methylmethanamine

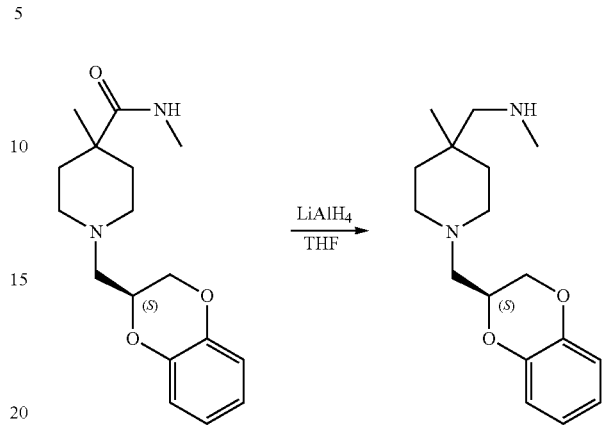

To a cooled solution of (S)-1-((2,3-dihydrobenzo[b][1,4] dioxin-2-yl)methyl)-N,4-dimethylpiperidine-4-carboxamide (100 mg, 0.33 mmol) in an. THF (0.65 mL) at 0° C. was added lithium aluminum hydride (12 mg, 0.33 mmol), under Ar. The mixture was stirred at room temperature overnight and then was quenched with 2 M aq. sol. of HCl. The solution was diluted with CH$_2$Cl$_2$ and Na$_2$CO$_3$ was added until the pH of the solution was basic. The organic layer was separated and the aqueous layer was extracted with CHCl$_3$. Organic layers were collected, dried over Na$_2$SO$_4$ and concentrated. Purification by flash chromatography (CH$_2$Cl$_2$/CH$_3$OH 80:20) afforded product as colorless oil (34 mg, 36% yield). [α]$_D^{25}$=−11.8° (CHCl$_3$; c=0.12). $^1$H-NMR (400 MHz, Chloroform-d): δ 6.90-6.78 (m, 4H), 4.33-4.27 (m, 2H), 3.97 (dd, J=11.6, 7.7 Hz, 1H), 2.70-2.63 (m, 2H), 2.63-2.53 (m, 2H), 2.51-2.46 (m, 6H), 2.45-2.35 (m, 1H), 1.63-1.53 (m, 2H), 1.50-1.40 (m, 2H), 1.01 (s, 3H). ESI+MS: m/z 291.3 ([M+H]$^+$).

Example-208: (S)—N-(1-((2,3-dihydrobenzo[b][1,4] dioxin-2-yl)methyl)-4-methylpiperidin-4-yl)acetamide

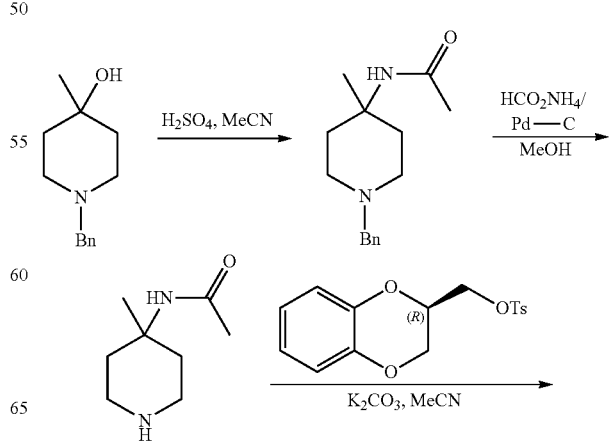

-continued

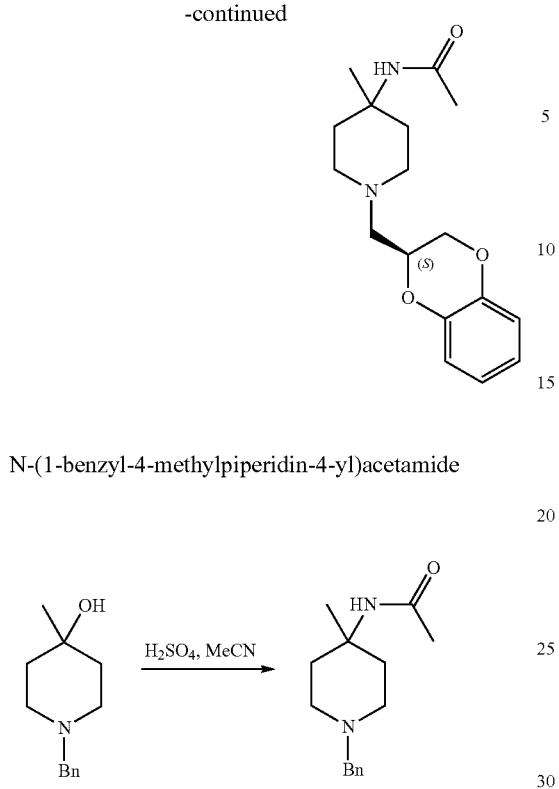

N-(1-benzyl-4-methylpiperidin-4-yl)acetamide

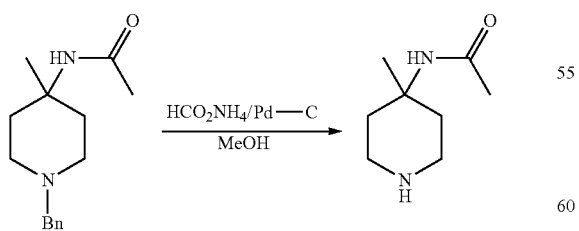

To a cooled solution of 1-benzyl-4-methylpiperidin-4-ol (0.30 g, 1.46 mmol) in CH$_3$CN (2.2 mL, 40.9 mmol) at 0° C. was added dropwise concentrated H$_2$SO$_4$ (1.48 mL, 27.8 mmol) so that the temperature did not exceed 30° C. After the addition, the mixture was stirred at room temperature for 16 hours. For termination of the reaction the resulting oil was poured onto ice and adjusted to pH 10 with a 3 M aq. KOH solution. The aqueous phase was extracted with CH$_2$Cl$_2$, dried over Na$_2$SO$_4$, filtered and the solvent was removed under reduced pressure. The resulting white solid was levigated with n-hexane to obtain product (0.34 g, 94% yield). $^1$H-NMR (300 MHz, DMSO-d$_6$): δ 7.35-7.20 (m, 5H), 3.41 (s, 2H), 2.43-2.32 (m, 2H), 2.26-2.11 (m, 2H), 2.06-1.95 (m, 2H), 1.78 (s, 3H), 1.42 (ddd, J=13.8, 10.1, 3.8 Hz, 2H), 1.23 (s, 3H). ESI–MS calcd for C$_{15}$H$_{22}$N$_2$O m/z 246.17, found 246.41 [M]$^+$.

N-(4-methylpiperidin-4-yl)acetamide

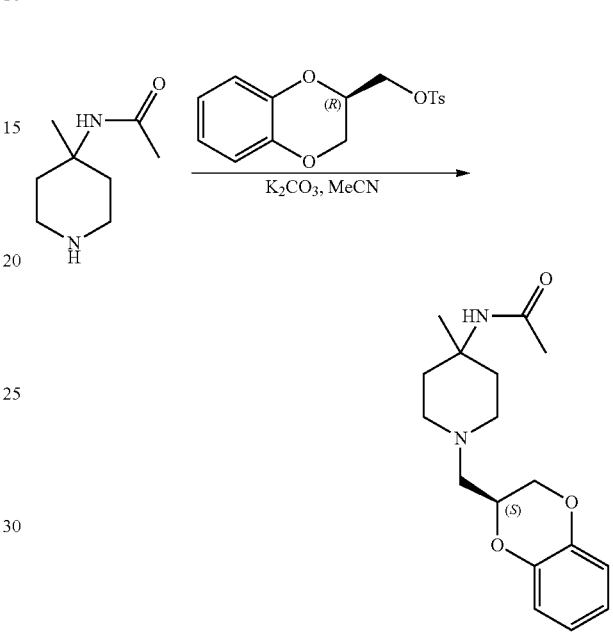

To a degassed solution of N-(1-benzyl-4-methylpiperidin-4-yl)acetamide (0.70 g, 2.84 mmol) in CH$_3$OH (17 mL) was added NH$_4$HCO$_2$ (0.82 g, 13.00 mmol, dried under vacuum) and Pd/C (10%, 140 mg). The mixture was flushed with Ar and left stirring for 2 hour at 65° C. The mixture was filtered and solvent was removed under reduced pressure to afford the product as a colorless thick oil (0.42 g, 95% yield). $^1$H-NMR (300 MHz, DMSO-d$_6$): δ 7.29 (br s, 1H), 2.68 (bs, 4H), 2.03-1.92 (m, 2H), 1.79 (s, 3H), 1.40-1.26 (m, 2H), 1.23 (s, 3H). ESI–MS calcd for C$_8$H$_{16}$N$_2$O m/z 156.13, found 157.20 [M+H]$^+$.

(S)—N-(1-((2,3-dihydrobenzo[b][1,4]dioxin-2-yl)methyl)-4-methylpiperidin-4-yl)acetamide To a stirred solution of N-(4-methylpiperidin-4-yl)acetamide (98 mg, 0.62 mmol) and (R)-(2,3-dihydrobenzo[b][1,4]dioxin-2-yl)methyl 4-methylbenzenesulfonate (100 mg, 0.31 mmol) in CH$_3$CN (1.6 mL) was added K$_2$CO$_3$ (65 mg, 0.47 mmol) at room temperature. The reaction mixture was stirred at 80° C. for 18 hours and then diluted with H$_2$O and extracted with EtOAc. The organic layer was dried over Na$_2$SO$_4$, filtered and concentrated. The crude residue was purified by flash chromatography (CH$_2$Cl$_2$/CH$_3$OH 95:5) to afford pure product as white solid (72 mg, 76% yield). [α]$_D^{25}$=−15.4° (CHCl$_3$; c=0.17). $^1$H-NMR (300 MHz, CDCl$_3$): δ 6.92-6.78 (m, 4H), 5.09 (br s, 1H), 4.35-4.25 (m, 2H), 3.98 (dd, J=11.6, 7.6 Hz, 1H), 2.77-2.53 (m, 4H), 2.46-2.26 (m, 2H), 2.11-1.98 (m, 2H), 1.96 (s, 3H), 1.75-1.62 (m, 2H), 1.40 (s, 3H). ESI–MS calcd for C$_{17}$H$_{24}$N$_2$O$_3$ m/z 304.18, found 305.34 [M+H]$^+$.

Example-209: (S)—N-(1-((2,3-dihydrobenzo[b][1,4]dioxin-2-yl)methyl)-4-methylpiperidin-4-yl)cyclopropanecarboxamide

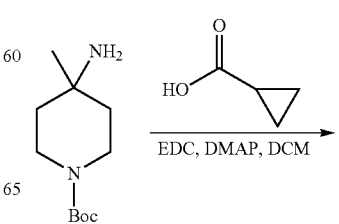

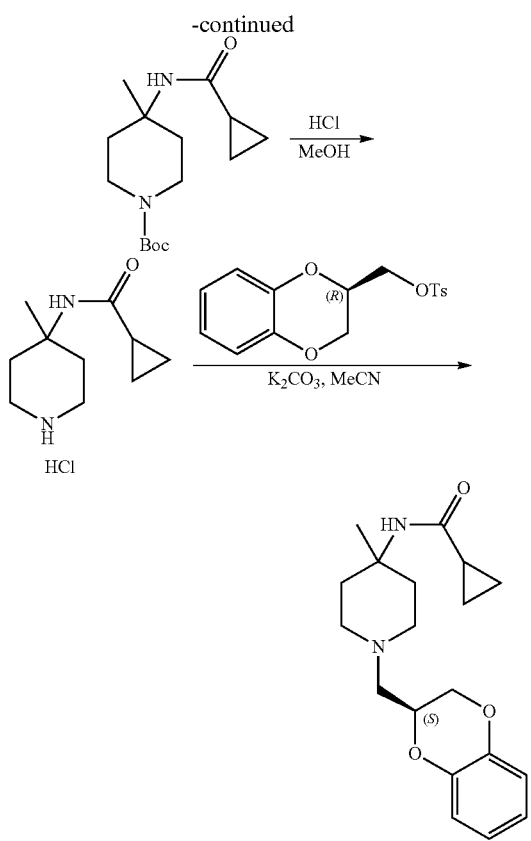

tert-butyl 4-(cyclopropanecarboxamido)-4-methylpiperidine-1-carboxylate

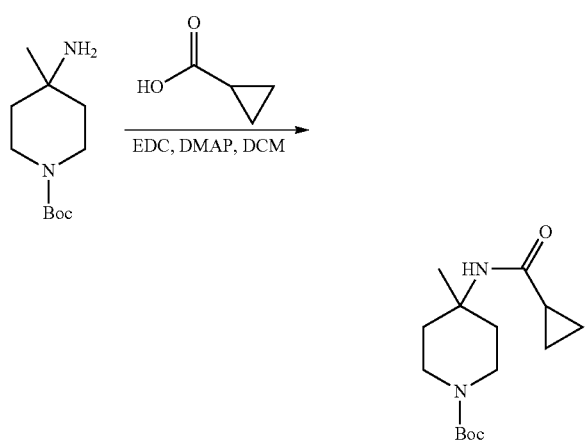

To a cooled solution of cyclopropanecarboxylic acid (67.6 µl, 0.85 mmol) at 0° C. in dry DCM (4 ml) was added 1-(3-Dimethylaminopropyl)-3-ethylcarbodiimidehydrochloride (171 mg, 0.89 mmol) and N,N-dimethylpyridin-4-amine (109 mg, 0.89 mmol) and the mixture was stirred for 30 minutes. tert-butyl 4-amino-4-methylpiperidine-1-carboxylate (200 mg, 0.933 mmol) was added at 0° C. and the reaction mixture was left to warm up to room temperature and left stirring overnight. The resulting suspension was filtered through a pad of celite and eluted with DCM. The residue was successively washed with 0.1M aq. K₂CO₃, 0.1M aq. HCl and water. The organic phase was dried (Na₂SO₄), filtered and concentrated to afford 171 mg of tert-butyl 4-(cyclopropanecarboxamido)-4-methylpiperidine-1-carboxylate as a white foam (Yield=71%). ESI+MS: m/z: 283.1 ([M+H]⁺).

N-(4-methylpiperidin-4-yl)cyclopropanecarboxamide hydrochloride

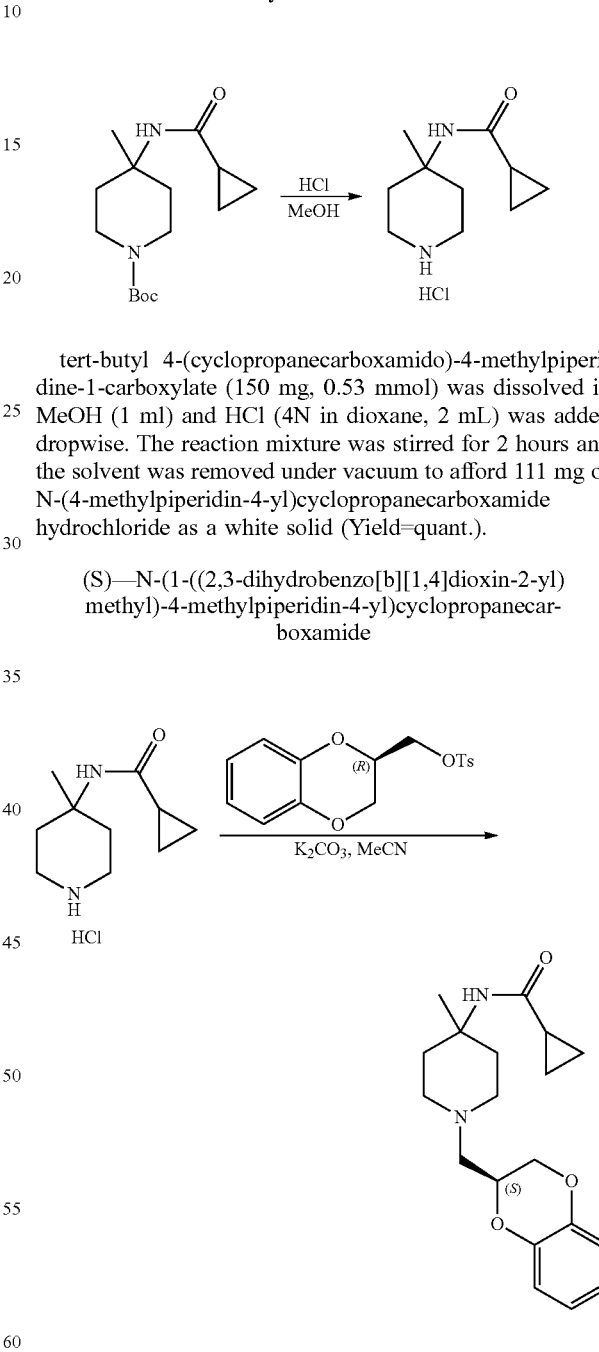

tert-butyl 4-(cyclopropanecarboxamido)-4-methylpiperidine-1-carboxylate (150 mg, 0.53 mmol) was dissolved in MeOH (1 ml) and HCl (4N in dioxane, 2 mL) was added dropwise. The reaction mixture was stirred for 2 hours and the solvent was removed under vacuum to afford 111 mg of N-(4-methylpiperidin-4-yl)cyclopropanecarboxamide hydrochloride as a white solid (Yield=quant.).

(S)—N-(1-((2,3-dihydrobenzo[b][1,4]dioxin-2-yl)methyl)-4-methylpiperidin-4-yl)cyclopropanecarboxamide Title compound was prepared from N-(4-methylpiperidin-4-yl)cyclopropanecarboxamide hydrochloride (0.10 g, 0.46 mmol) using the general methodology of Example-1. Purification using silica gel column chromatography (DCM/MeOH 95/5) afforded 0.07 g of (S)—N-(1-((2,3-dihydrobenzo[b][1,4]dioxin-2-yl)methyl)-4-methylpiperidin-4-yl)cyclopropanecarboxamide (Yield=46%). $[\alpha]_D^{25}=-10.8°$ (CHCl₃; c=0.17). ¹H NMR (300 MHz, CDCl₃): δ 6.91-6.79 (m, 4H), 5.26 (br s, 1H), 4.36-4.25 (m, 2H), 3.98 (dd, J=11.7, 7.6 Hz, 1H), 2.78-2.53 (m, 4H), 2.48-2.30 (m, 2H), 2.15-2.05 (m, 2H), 1.75-1.60 (m, 2H), 1.39 (s, 3H), 1.35-1.23 (m, 1H), 0.95-0.88 (m, 2H), 0.73-0.63 (m, 2H); ESI+MS: m/z: 331.4 ([M+H]⁺).

Example-210: (S)—N-(1-((7-fluoro-2,3-dihydrobenzo[b][1,4]dioxin-2-yl)methyl)-4-methylpiperidin-4-yl)acetamide

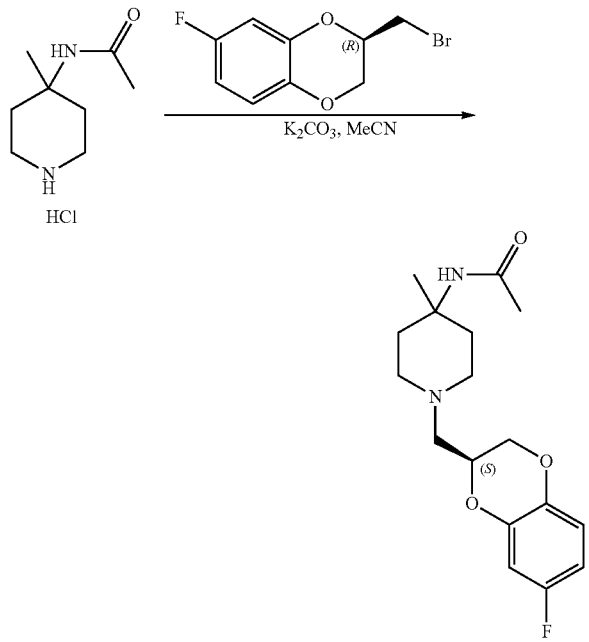

Title compound was prepared from N-(4-methylpiperidin-4-yl)acetamide hydrochloride (0.038 g, 0.24 mmol) using the general methodology of Example-1. Purification using silica gel column chromatography (DCM/MeOH 94/6) afforded 0.023 g of (S)—N-(1-((7-fluoro-2,3-dihydrobenzo[b][1,4]dioxin-2-yl)methyl)-4-methylpiperidin-4-yl)acetamide (Yield=59%). [α]_D^{25}=−15.8° (CHCl₃; c=0.29). ¹H NMR (400 MHz, CDCl₃): δ 6.78 (dd, J=8.9, 5.4 Hz, 1H), 6.60 (dd, J=9.4, 2.9 Hz, 1H), 6.54 (ddd, J=8.9, 8.1, 3.0 Hz, 1H), 5.07 (br s, 1H), 4.32-4.23 (m, 2H), 3.94 (dd, J=11.2, 7.0 Hz, 1H), 2.74-2.53 (m, 4H), 2.45-2.28 (m, 2H), 2.11-2.01 (m, 2H), 1.96 (s, 3H), 1.67 (ddd, J=14.0, 9.8, 5.3 Hz, 2H), 1.40 (s, 3H); ESI+MS: m/z: 323.3 ([M+H]⁺).

Example-211: (S)—N-(1-((7-bromo-2,3-dihydrobenzo[b][1,4]dioxin-2-yl)methyl)-4-methylpiperidin-4-yl)acetamide

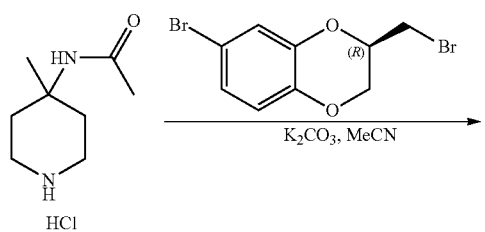

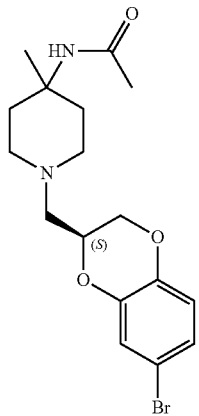

Title compound was prepared from N-(4-methylpiperidin-4-yl)acetamide hydrochloride (0.036 g, 0.23 mmol) using the general methodology of Example-1. Purification using silica gel column chromatography (DCM/MeOH 95/5) afforded 0.036 g of (S)—N-(1-((7-bromo-2,3-dihydrobenzo[b][1,4]dioxin-2-yl)methyl)-4-methylpiperidin-4-yl)acetamide (Yield=83%). [α]_D^{25}=−15.0° (CHCl₃; c=0.33). ¹H NMR (300 MHz, CDCl₃): δ 7.02 (d, J=2.3 Hz, 1H), 6.93 (dd, J=8.6, 2.3 Hz, 1H), 6.73 (d, J=8.6 Hz, 1H), 5.07 (br s, 1H), 4.27 (dd, J=11.7, 2.3 Hz, 2H), 3.96 (dd, J=11.8, 7.5 Hz, 1H), 2.73-2.52 (m, 4H), 2.45-2.27 (m, 2H), 2.10-2.00 (m, 2H), 1.96 (s, 3H), 1.72-1.60 (m, 2H), 1.40 (s, 3H); ESI+MS: m/z: 383.3 ([M+H]⁺).

Example-212: (S)—N-(1-((2,3-dihydrobenzo[b][1,4]dioxin-2-yl)methyl)-4-methylpiperidin-4-yl)-2,2,2-trifluoroacetamide

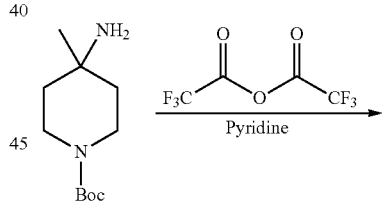

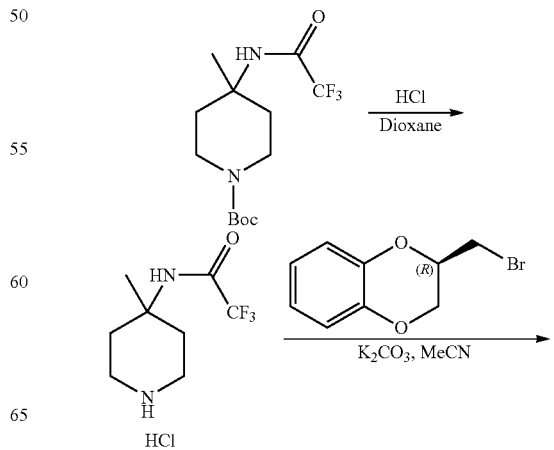

tert-butyl 4-methyl-4-(2,2,2-trifluoroacetamido)piperidine-1-carboxylate

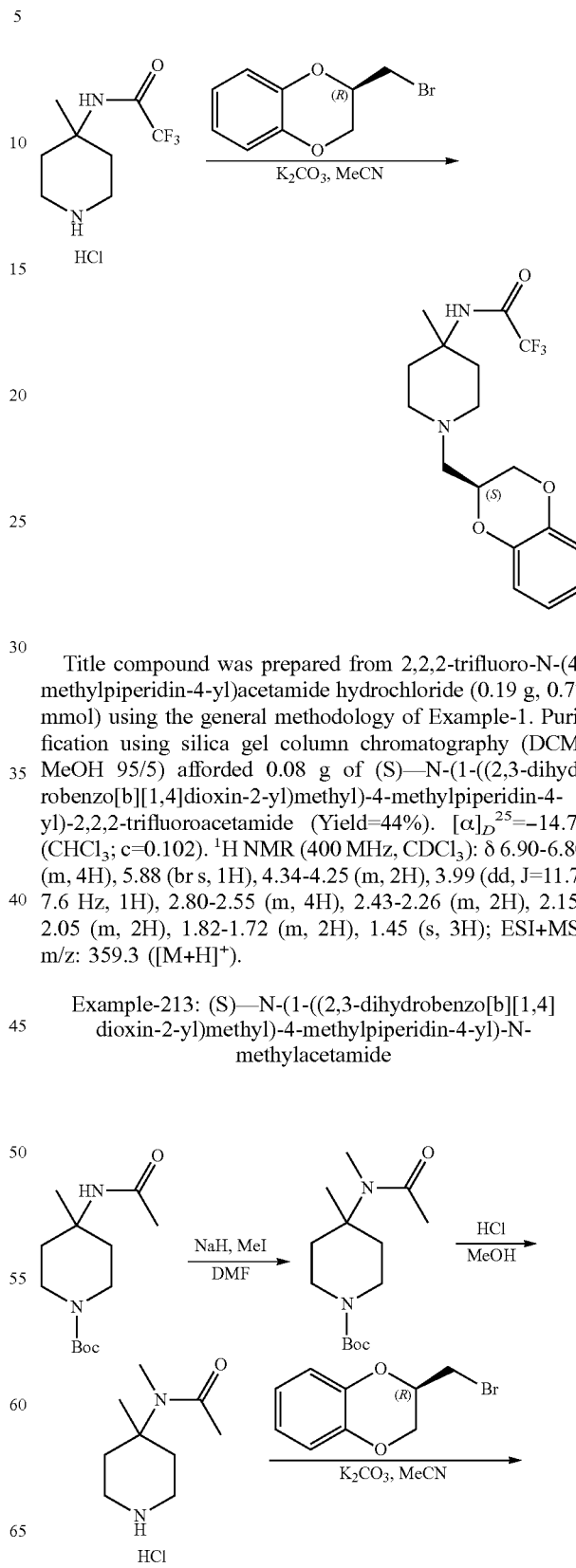

To a solution of tert-butyl 4-amino-4-methylpiperidine-1-carboxylate (190 mg, 0.89 mmol) in Pyridine (0.6 ml) at 0° C. was slowly added 2,2,2-trifluoroacetic anhydride (0.129 ml, 0.93 mmol) and the reaction mixture was stirred at 0° C. for 2 hours. The reaction mixture was diluted with DCM, washed with brine, dried over Na2SO4, filtered and concentrated. Purification by silica gel chromatography afforded 247 mg of tert-butyl 4-methyl-4-(2,2,2-trifluoroacetamido)piperidine-1-carboxylate (Yield=90%). ESI–MS: m/z: 309.3 ([M–H]⁻).

2,2,2-trifluoro-N-(4-methylpiperidin-4-yl)acetamide hydrochloride

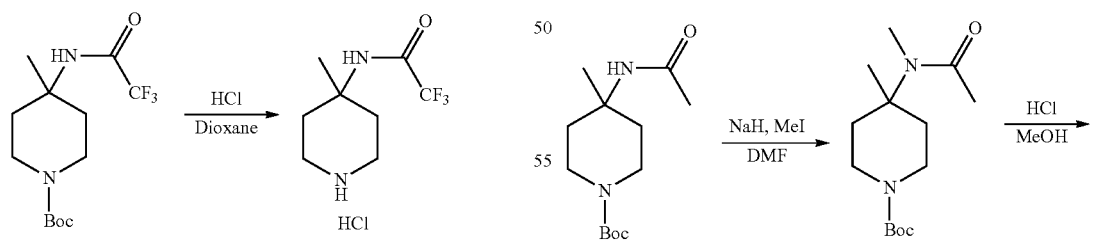

A solution of HCl 4N in dioxane (0.8 ml, 3.18 mmol) was added to tert-butyl 4-methyl-4-(2,2,2-trifluoroacetamido)piperidine-1-carboxylate (247 mg, 0.80 mmol) and the mixture was left stirring for 1 h at 25° C. The solvents were removed under reduced pressure and afforded 0.2 g of 2,2,2-trifluoro-N-(4-methylpiperidin-4-yl)acetamide hydrochloride as a white solid (Yield=quant.). ESI–MS: m/z: 245.1 ([M–H]⁻).

(S)—N-(1-((2,3-dihydrobenzo[b][1,4]dioxin-2-yl)methyl)-4-methylpiperidin-4-yl)-2,2,2-trifluoroacetamide

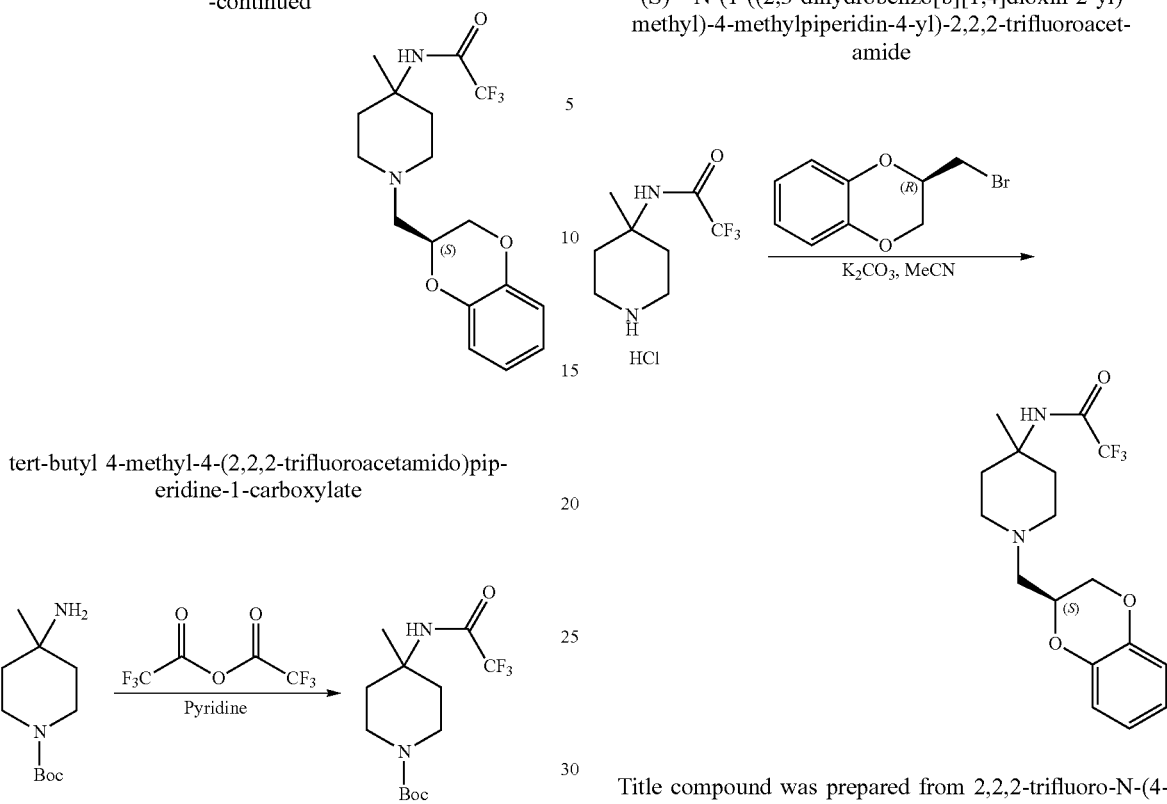

Title compound was prepared from 2,2,2-trifluoro-N-(4-methylpiperidin-4-yl)acetamide hydrochloride (0.19 g, 0.77 mmol) using the general methodology of Example-1. Purification using silica gel column chromatography (DCM/MeOH 95/5) afforded 0.08 g of (S)—N-(1-((2,3-dihydrobenzo[b][1,4]dioxin-2-yl)methyl)-4-methylpiperidin-4-yl)-2,2,2-trifluoroacetamide (Yield=44%). $[\alpha]_D^{25}$=−14.7° (CHCl3; c=0.102). ¹H NMR (400 MHz, CDCl3): δ 6.90-6.80 (m, 4H), 5.88 (br s, 1H), 4.34-4.25 (m, 2H), 3.99 (dd, J=11.7, 7.6 Hz, 1H), 2.80-2.55 (m, 4H), 2.43-2.26 (m, 2H), 2.15-2.05 (m, 2H), 1.82-1.72 (m, 2H), 1.45 (s, 3H); ESI+MS: m/z: 359.3 ([M+H]⁺).

Example-213: (S)—N-(1-((2,3-dihydrobenzo[b][1,4]dioxin-2-yl)methyl)-4-methylpiperidin-4-yl)-N-methylacetamide -continued

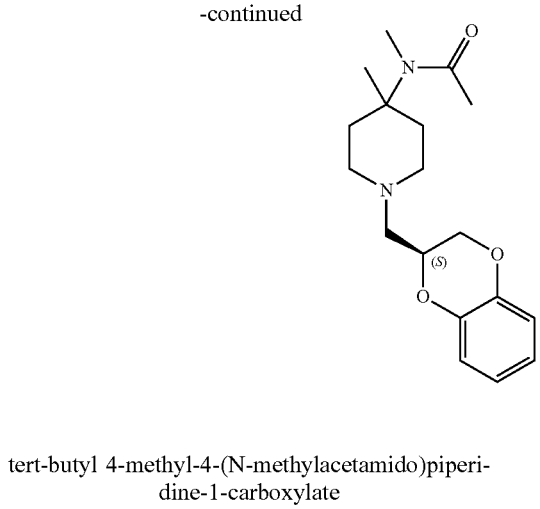

tert-butyl 4-methyl-4-(N-methylacetamido)piperidine-1-carboxylate

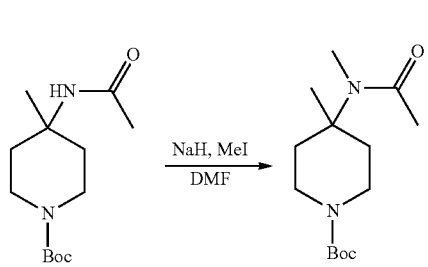

A solution of tert-butyl 4-acetamido-4-methylpiperidine-1-carboxylate (0.25 g, 0.98 mmol) in an. DMF (3.25 ml) was added sodium hydride (0.047 g, 1.17 mmol) at 0° C. and was left stirring for 1 hour at 40° C. Iodomethane (0.091 ml, 1.46 mmol) was added dropwise and the reaction was stirred at room temperature for 2 hours. Then 10% aq. NaHCO$_3$ (25 mL) was added and the mixture was extracted with Et2O and the collected organic phases were washed with 0.1 M aq. HCl, water and brine. The organic phase was dried (MgSO4), filtered and concentrated. Purification by silica gel chromatography (Hexane/EtOAc 7:3) afforded 164 mg of tert-butyl 4-methyl-4-(N-methylacetamido)piperidine-1-carboxylate as a white solid (Yield=62%). ESI+MS: m/z: 271.4 ([M+H]$^+$).

N-methyl-N-(4-methylpiperidin-4-yl)acetamide hydrochloride

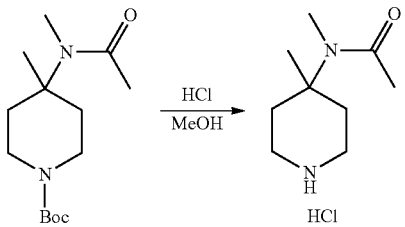 [SMILES: "MeOH" ; CC(=O)N(C)C1(C)CCN(C(=O)OC(C)(C)C)CC1 ; Cl ; CC(=O)N(C)C1(C)CCNCC1 ; Cl]

A solution of HCl in dioxane (0.6 mL, 2.22 mmol) was added to tert-butyl 4-methyl-4-(N-methylacetamido)piperidine-1-carboxylate (150 mg, 0.56 mmol) in MeOH (1.1 mL) and the mixture was left stirring for 1 h at 25° C. The solvents were removed under reduced pressure and afforded 0.12 g of N-methyl-N-(4-methylpiperidin-4-yl)acetamide hydrochloride as a white solid (Yield=quant.).

(S)—N-(1-((2,3-dihydrobenzo[b][1,4]dioxin-2-yl)methyl)-4-methylpiperidin-4-yl)-N-methylacetamide

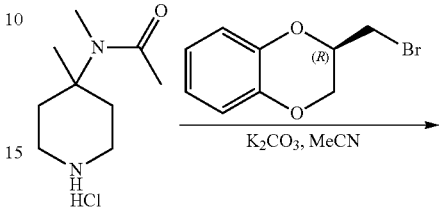

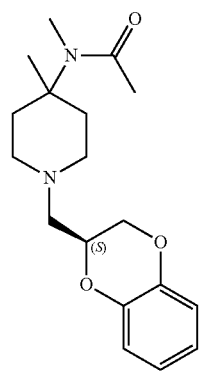

Title compound was prepared from N-methyl-N-(4-methylpiperidin-4-yl)acetamide hydrochloride (0.09 g, 0.44 mmol) using the general methodology of Example-1. Purification using silica gel column chromatography (DCM/MeOH 95/5) afforded 0.036 g of (S)—N-(1-((2,3-dihydrobenzo[b][1,4]dioxin-2-yl)methyl)-4-methylpiperidin-4-yl)-N-methylacetamide (Yield=83%). $[\alpha]_D^{25}=-8.7°$ (CHCl$_3$; c=0.16). $^1$H NMR (400 MHz, CDCl$_3$): δ 6.88-6.80 (m, 4H), 4.32-4.21 (m, 2H), 4.02 (ddd, J=17.2, 11.1, 6.2 Hz, 1H), 3.78-3.67 (m, 1H), 3.63-3.40 (m, 2H), 3.39-3.20 (m, 1H), 2.73-2.55 (m, 2H), 2.27 (s, 3H), 2.09 (s, 3H), 1.80-1.68 (m, 2H), 1.45-1.30 (m, 2H), 0.93 (s, 3H); ESI+MS: m/z: 319.3 ([M+H]$^+$).

Example-214: (4-(4-chlorobenzyl)-1-(2-(2-(trifluoromethyl)phenoxy)ethyl)piperidin-4-yl)methanol

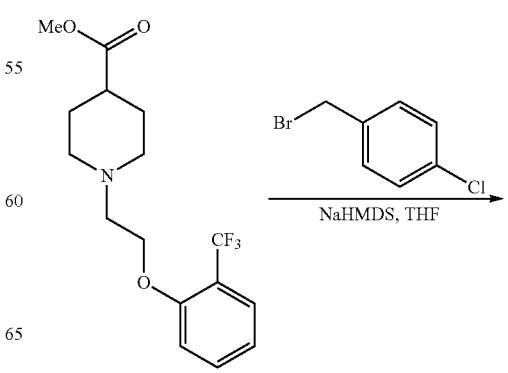

-continued

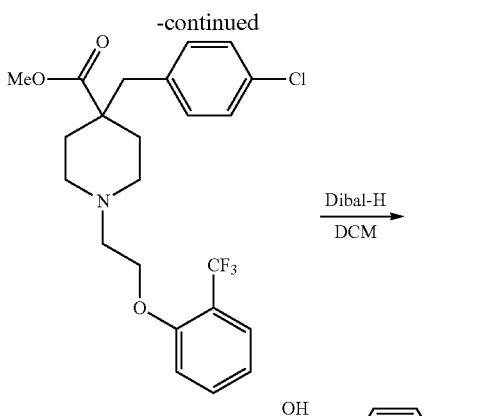

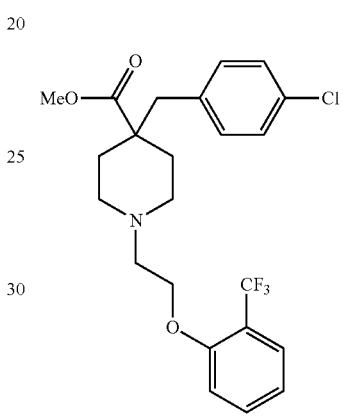

methyl 4-(4-chlorobenzyl)-1-(2-(2-(trifluoromethyl)phenoxy)ethyl)piperidine-4-carboxylate

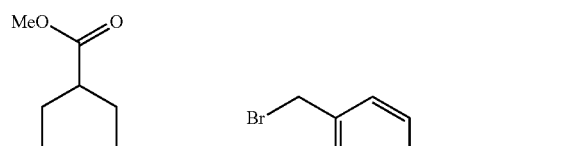

To a stirred solution of methyl 1-(2-(2-(trifluoromethyl)phenoxy)ethyl)piperidine-4-carboxylate (0.2 g, 0.6 mmol) in THF (2 mL) was added NaHMDS (1M solution in THF, 0.73 mL) at −78° C. The reaction mixture was stirred at −78° C. for 30 min. A solution of p-chlorobenzyl bromide 0.15 g, 0.72 mmol) in THF (1 mL) was added at −78° C. The reaction mixture was allowed to warm to room temperature and was stirred for 16 h. Water was added to the reaction mixture and extracted with EtOAc. The organic layer was separated, dried over Na₂SO₄, filtered and concentrated. Purification by column chromatography eluting with 1% MeOH in DCM afforded 36 mg of methyl 4-(4-chlorobenzyl)-1-(2-(2-(trifluoromethyl)phenoxy)ethyl)piperidine-4-carboxylate as thick syrup (Yield=13%). ESI+MS: m/z: 456.1 ([M+H]⁺).

(4-(4-chlorobenzyl)-1-(2-(2-(trifluoromethyl)phenoxy)ethyl)piperidin-4-yl)methanol

To a stirred solution of methyl 4-(4-chlorobenzyl)-1-(2-(2-(trifluoromethyl)phenoxy)ethyl)piperidine-4-carboxylate (0.1 g, 0.22 mmol) in DCM (2 mL) was added DIBAL (1.0 M solution in toluene) at 0° C. The reaction mixture was stirred at room temperature for 16 h. The reaction was quenched with cold water and extracted with DCM. The organic layer was separated, dried over Na₂SO₄, filtered and concentrated. Purification by column chromatography eluting with 8% MeOH in DCM afforded 40 mg of (4-(4-chlorobenzyl)-1-(2-(2-(trifluoromethyl)phenoxy)ethyl)piperidin-4-yl)methanol as colorless syrup (Yield=43%). ¹H NMR (400 MHz, CD₃OD): δ7.58-7.54 (m, 2H), 7.27-7.24 (m, 2H), 7.20-7.17 (m, 3H), 7.07 (t, J=7.6 Hz, 1H). 4.28 (t, J=5.6 Hz, 2H), 2.99 (t, J=5.2 Hz, 2H), 2.88-2.82 (m, 2H), 2.77-2.68 (m, 4H), 1.60-1.50 (m, 4H); ESI+MS: m/z: 428.1 ([M+H]⁺).

Example-215: 4-(4-chlorobenzyl)-4-methyl-1-(2-(2-(trifluoromethyl)phenoxy)ethyl)piperidine

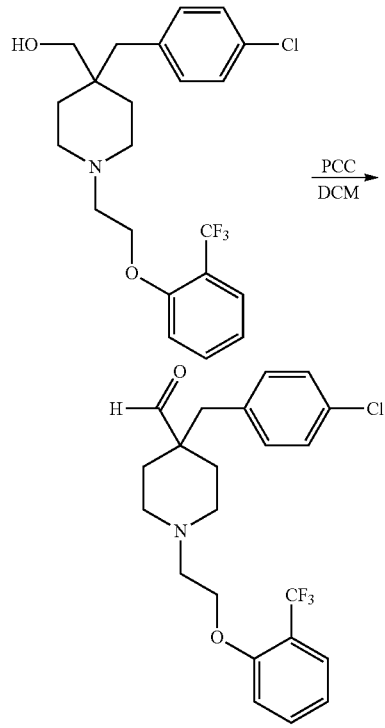

4-(4-chlorobenzyl)-1-(2-(2-(trifluoromethyl)phenoxy)ethyl)piperidine-4-carbaldehyde

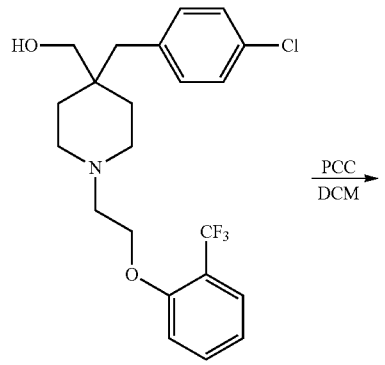

-continued

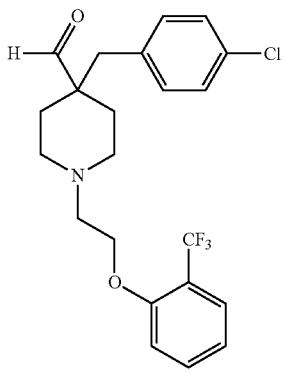

To a stirred solution of (4-(4-chlorobenzyl)-1-(2-(2-(trifluoromethyl)phenoxy)ethyl)piperidin-4-yl)methanol (0.3 g, 0.7 mmol) in DCM (10 mL) was added PCC (0.3 g, 1.4 mmol) at 0° C. The reaction mixture was stirred at room temperature for 5 h. After completion, the reaction was diluted with DCM, filtered through celite bed and washed with DCM. The filtrate was concentrated under reduced pressure. Purification by flash chromatography eluting with 3% MeOH in DCM afforded 0.2 g of 4-(4-chlorobenzyl)-1-(2-(2-(trifluoromethyl)phenoxy)ethyl)piperidine-4-carbaldehyde as thick syrup (Yield=67%). ESI+MS: m/z: 426.0 ([M+H]$^+$).

4-(4-chlorobenzyl)-4-methyl-1-(2-(2-(trifluoromethyl)phenoxy)ethyl)piperidine

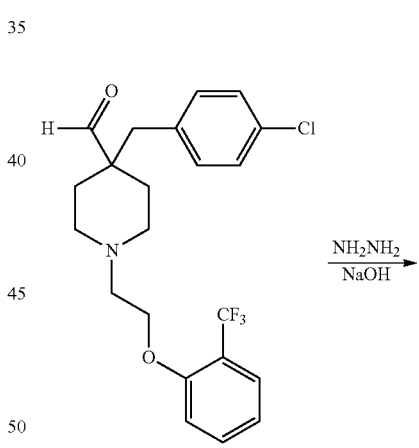

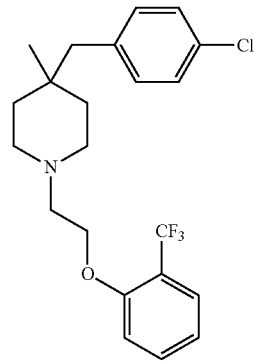

389

To a stirred solution of 4-(4-chlorobenzyl)-1-(2-(2-(trifluoromethyl)phenoxy)ethyl)piperidine-4-carbaldehyde (0.2 g, 0.47 mmol) in ethylene glycol (1 mL) was added hydrazine hydrate (0.07 g, 1.4 mmol) followed by NaOH (0.056 mg, 1.4 mmol) at room temperature. The reaction mixture was heated at 180° C. for 16 h. After completion, the reaction was diluted with cold water and extracted with EtOAc. The organic layer was separated, dried over $Na_2SO_4$, filtered and concentrated. Purification by silica gel chromatography eluting with 2% MeOH in DCM followed by Preparative HPLC afforded 45 mg of 4-(4-chlorobenzyl)-4-methyl-1-(2-(2-(trifluoromethyl)phenoxy)ethyl)piperidine as colorless syrup (Yield=23%). $^1$H NMR (400 MHz, $CD_3OD$): δ 7.59-7.53 (m, 2H), 7.27-7.23 (m, 2H), 7.19-7.11 (m, 3H), 7.05 (t, J=7.6 Hz, 1H), 4.25 (t, J=5.6 Hz, 2H), 2.89 (t, J=5.6 Hz, 2H), 2.83-2.77 (m, 2H), 2.58 (s, 2H), 2.54 (t, J=9.6 Hz, 2H), 1.64-1.56 (m, 2H), 1.40-1.34 (m, 2H), 0.90 (s, 3H); ESI+MS: m/z: 412.0 ([M+H]$^+$).

Example-216: 1-(4-chlorophenyl)-6-(2-(2-(trifluoromethyl)phenoxy)ethyl)-6-azaspiro[2.5]octane

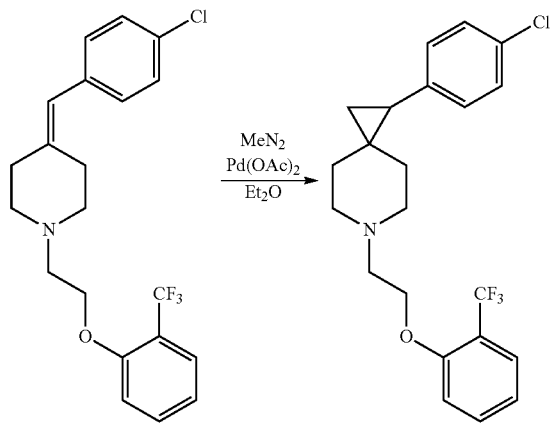 [SMILES: "Et2O" ; "MeN2Pd(OAc)2" ; FC(F)(F)c1ccccc1OCCN1CCC(=Cc2ccc(Cl)cc2)CC1 ; FC(F)(F)c1ccccc1OCCN1CCC2(CC1)CC2c1ccc(Cl)cc1]

To a solution of 4-(4-chlorobenzylidene)-1-(2-(2-(trifluoromethyl)phenoxy)ethyl)piperidine (0.1 g, 0.25 mmol) in diethyl ether (15 mL) was added diazomethane (10 mL) at 0° C. and the reaction mixture was stirred for 2 h at 0° C. Pd(OAc)$_2$ (57 mg, 0.25 mmol) was then added and the reaction was stirred for 2 h. After completion, the reaction mass was diluted with diethyl ether and filtered through a celite bed and the filtrate was concentrated under reduced pressure. Purification by Preparative HPLC afforded 7 mg of 1-(4-chlorophenyl)-6-(2-(2-(trifluoromethyl)phenoxy)ethyl)-6-azaspiro[2.5]octane as a thick syrup (Yield=7%). $^1$H NMR (400 MHz, $CD_3OD$): δ 7.58-7.53 (m, 2H), 7.24-7.21 (m, 2H), 7.18-7.14 (m, 3H), 7.05 (t, J=7.6 Hz, 1H), 4.23 (t, J=5.6 Hz, 2H), 2.90-2.83 (m, 2H) 2.82-2.70 (m, 2H), 2.52-2.38 (m, 2H), 1.99-1.95 (m, 1H), 1.70-1.58 (m, 2H), 1.30-1.20 (m, 2H), 0.97-0.94 (m, 1H), 0.87-0.82 (m, 1H); ESI+MS: m/z: 410.4 ([M+H]$^+$). The enantiomers of 216 were separated using chiral HPLC (method N) and afforded the pure enantiomers 216a and 216b.

390

Example-217: N-cyclohexyl-N,4-dimethyl-1-(2-(2-(trifluoromethyl)phenoxy)ethyl)piperidin-4-amine

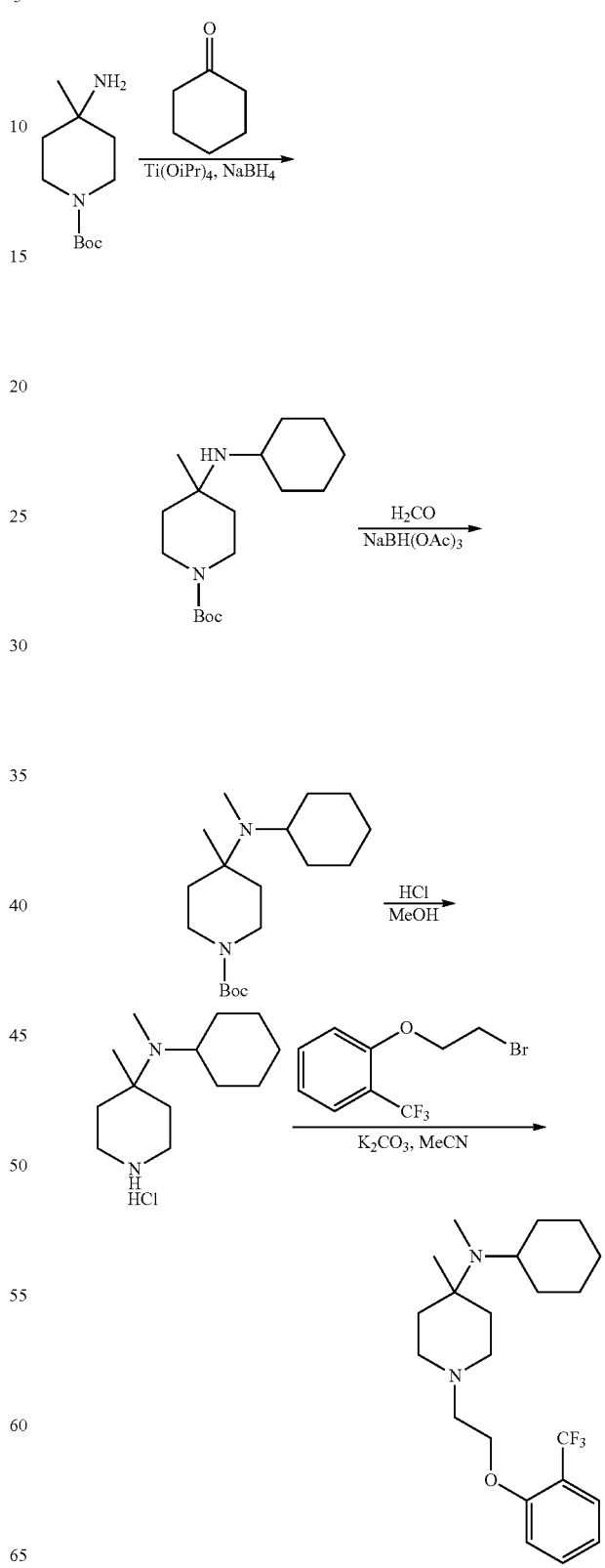

391 tert-butyl 4-(cyclohexylamino)-4-methylpiperidine-1-carboxylate

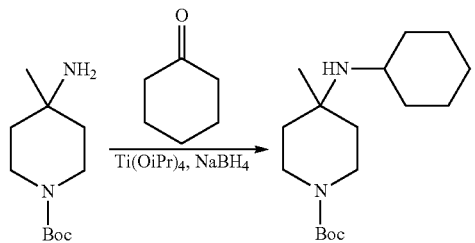

To a stirred solution of tert-butyl 4-amino-4-methylpiperidine-1-carboxylate (0.3 g, 1.4 mmol) and cyclohexanone (0.14 g, 1.4 mmol) in ethanol (5 mL) was added Ti(iOPr)$_4$ (1.2 g, 4.2 mmol) at room temperature. The reaction mixture was stirred at 80° C. for 16 h. Then NaBH$_4$ was added at room temperature and the reaction mixture was heated at 80° C. for 24 h. The reaction was quenched with water and diluted with EtOAc. The organic layer was dried over anhydrous Na$_2$SO$_4$, filtered and concentrated under reduced pressure to obtain crude material. The crude residue was purified by silica gel column chromatography with 1% MeOH in DCM to afford 0.08 g of tert-butyl 4-(cyclohexylamino)-4-methylpiperidine-1-carboxylate as colorless syrup (Yield=20%). ESI+MS: m/z: 297.4 ([M+H]$^+$).

tert-butyl 4-(cyclohexyl(methyl)amino)-4-methylpiperidine-1-carboxylate

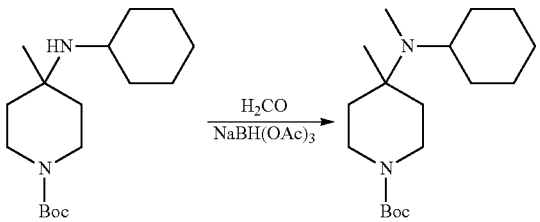

To a stirred solution of tert-butyl 4-(cyclohexylamino)-4-methylpiperidine-1-carboxylate (0.15 g, 0.51 mmol) in DCM (5 mL) was added 37% aq. formaldehyde (0.13 mL, 1.52 mmol) at 0° C. Then NaBH(OAc)$_3$ (0.21 g, 1.01 mmol) was added at 0° C. and the reaction was allowed to warm to room temperature and stirred for 16 h. The reaction was quenched with 2N NaOH and extracted with DCM. The organic layer was dried over anhydrous Na$_2$SO$_4$, filtered and concentrated. Purification by flash chromatography eluting with 20% EtOAc in Hexane afforded 0.1 g of tert-butyl 4-(cyclohexyl(methyl)amino)-4-methylpiperidine-1-carboxylate as thick syrup (Yield=64%). ESI+MS: m/z: 311.4 ([M+H]$^+$).

392

N-cyclohexyl-N,4-dimethylpiperidin-4-amine hydrochloride

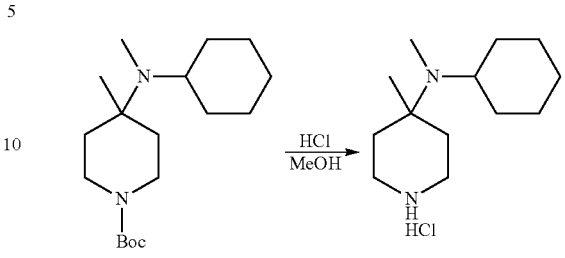

To a stirred solution of tert-butyl 4-(cyclohexyl(methyl)amino)-4-methylpiperidine-1-carboxylate (0.1 g, 0.32 mmol) in MeOH (1 mL) was added 4M HCl in 1,4-Dioxane (0.4 mL, 1.6 mmol) at 0° C. The reaction mixture was stirred at room temperature for 4 h. After completion of the reaction, volatiles were concentrated under reduced pressure to afford 60 mg of N-cyclohexyl-N,4-dimethylpiperidin-4-amine hydrochloride (Yield=75%).

N-cyclohexyl-N,4-dimethyl-1-(2-(2-(trifluoromethyl)phenoxy)ethyl)piperidin-4-amine

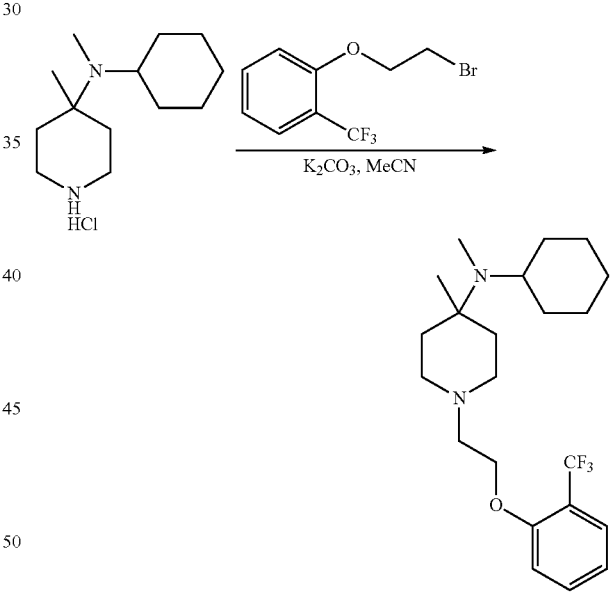

Title compound was prepared from N-cyclohexyl-N,4-dimethylpiperidin-4-amine hydrochloride (0.06 g, 0.24 mmol) using the general methodology of Example-1. Purification using silica gel column chromatography afforded 0.03 g of N-cyclohexyl-N,4-dimethyl-1-(2-(2-(trifluoromethyl)phenoxy)ethyl)piperidin-4-amine (Yield=31%). $^1$H NMR (400 MHz, CD$_3$OD): δ 7.59-7.53 (m, 2H), 7.17 (d, J=8.8 Hz, 1H), 7.05 (t, J=7.6 Hz, 1H), 4.24 (t, J=5.5 Hz, 2H), 2.86 (t, J=5.5 Hz, 2H), 2.80-2.70 (m, 3H), 2.57-2.49 (m, 2H), 2.22 (s, 3H), 1.93-1.84 (m, 2H), 1.79-1.74 (m, 2H), 1.71-1.50 (m, 5H), 1.48-1.36 (m, 2H), 1.34-1.25 (m, 2H), 1.15-1.06 (m, 1H), 1.04 (s, 3H); ESI+MS: m/z: 399.0 ([M+H]$^+$).

Example-219: 4-methyl-N-phenyl-1-(2-(2-(trifluoromethyl)phenoxy)ethyl)piperidine-4-carboxamide

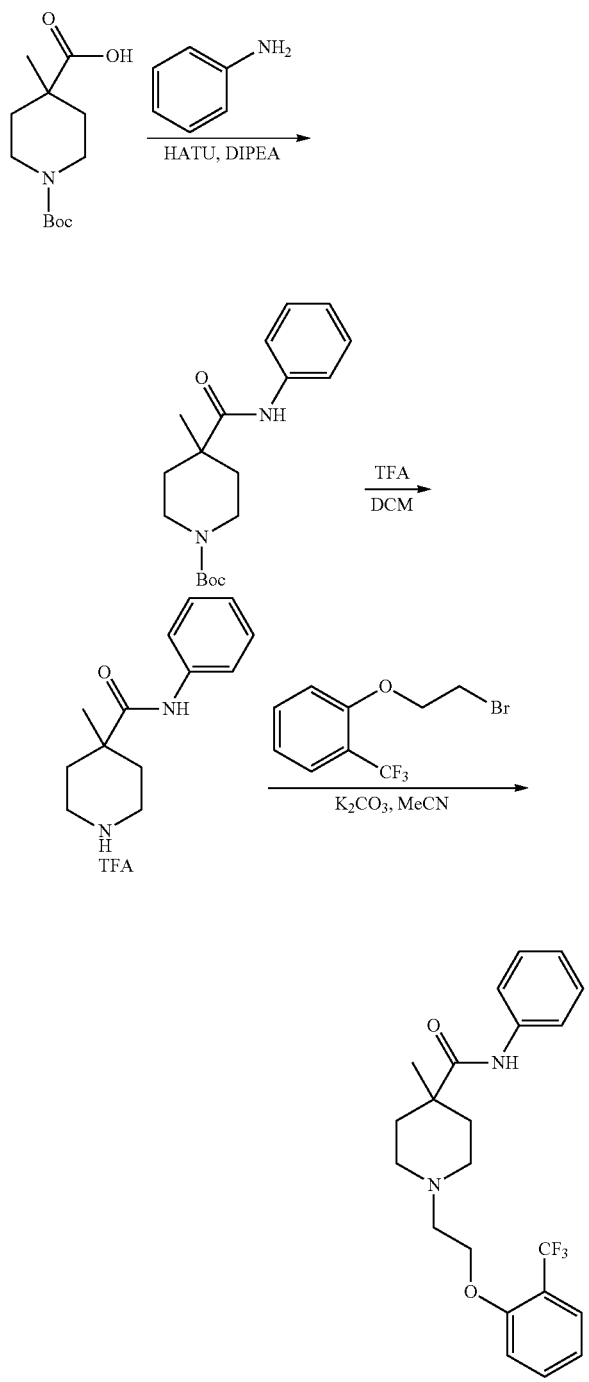

Title compound was prepared using the same strategy employed for example 205 by replacing dimethylamine hydrochloride with aniline. $^1$H NMR (400 MHz, CD$_3$OD): δ 7.57-7.49 (m, 4H), 7.31 (t, J=8.4 Hz, 2H), 7.16 (d, J=8.4 Hz, 1H), 7.10 (t, J=7.2 Hz, 1H), 7.04 (t, J=7.6 Hz, 1H), 4.25 (t, J=5.6 Hz, 2H), 3.33-3.30 (m, 1H), 2.90-2.80 (m, 4H), 2.52 (t, J=9.6 Hz, 2H), 2.27-2.22 (m, 2H), 1.67-1.60 (m, 2H), 1.30 (s, 3H); ESI+MS: m/z 407.5 ([M+H]$^+$).

Example-220: 1-(2-(2-fluorophenoxy)ethyl)-4-methyl-N-phenylpiperidine-4-carboxamide

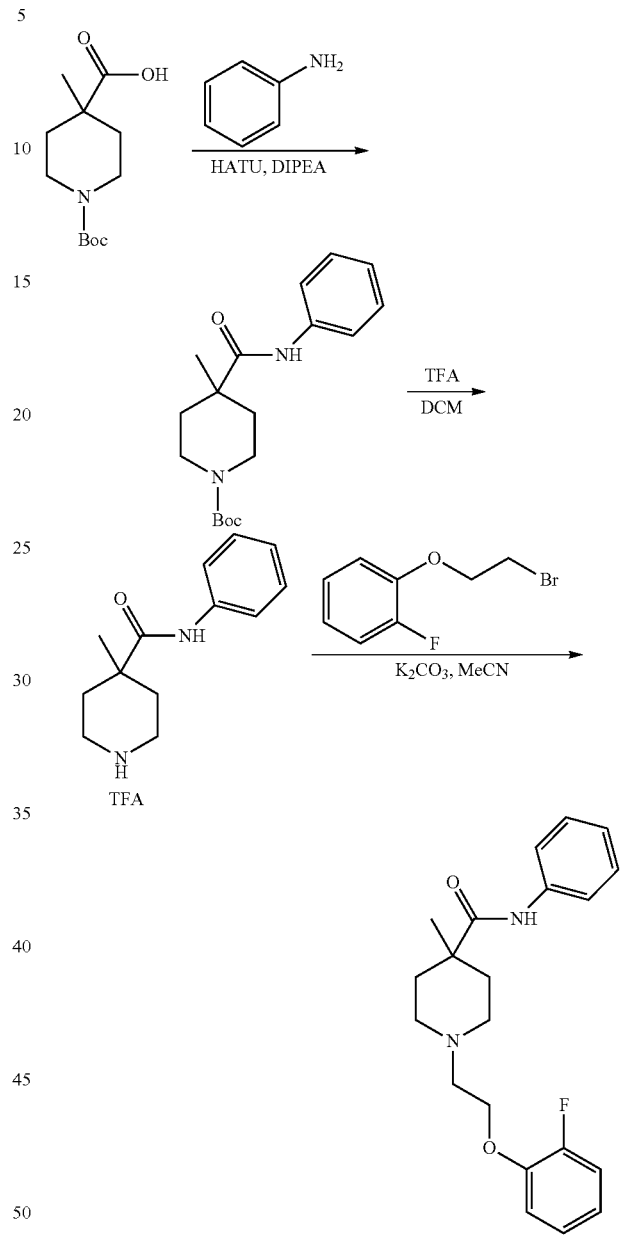

Title compound was prepared using the same strategy employed for example 219 by replacing 1-(2-bromoethoxy)-2-(trifluoromethyl)benzene with 1-(2-bromoethoxy)-2-fluorobenzene. $^1$H NMR (400 MHz, DMSO-d$_6$): δ 9.27 (br s, 1H), 7.63 (d, J=8.0 Hz, 2H), 7.29 (t, J=8.0, 2H), 7.23-7.18 (m, 2H), 7.12 (t, J=8.0 Hz, 1H), 7.04 (t, J=8.0 Hz, 1H), 6.98-6.91 (m, 1H), 4.18 (br s, 2H), 2.90-2.66 (m, 4H), 2.32-2.10 (m, 4H), 1.60-1.45 (m, 2H), 1.23 (s, 3H); ESI+MS: m/z 357.0 ([M+H]$^+$).

Example-221: Chiral Separation Using HPLC

Mixtures of stereoisomers (e.g., enantiomers or diastereomers) described herein were separated with one of Method A to Method R of chiral HPLC. The earlier-eluted stereoisomer was designated with "a", and the later-eluted stereoisomer was designated with "b". For example, enantiomers of 203 were separated using chiral HPLC, Method U, and afforded the pure enantiomers 203a and 203b, wherein 203a was the earlier-eluted stereoisomer, and 203b was the later-eluted stereoisomer.

Method A:
 Column: Chiralpak ADH (250×4.6 mm, 5 μm)
 Eluent A: n-Hexanes
 Eluent B: Ethanol
 Elution using A:B 75:25 at 1 ml/min
Method B:
 Column: Chiralpak ADH (250×4.6 mm, 5 μm)
 Eluent A: 0.1% DEA in n-Hexanes
 Eluent B: Ethanol
 Elution using A:B 80:20 at 1 ml/min
Method C:
 Column: Chiralpak IA (250×4.6 mm, 5 μm)
 Eluent A: 0.1% DEA in n-Hexanes
 Eluent B: DCM/Methanol 80:20
 Elution using A:B 98:2 at 1 ml/min
Method D:
 Column: Chiralpak ADH (250×4.6 mm, 5 μm)
 Eluent A: 0.1% DEA in n-Hexanes
 Eluent B: Ethanol/Methanol 50:50
 Elution using A:B 75:25 at 1 ml/min
Method E:
 Column: Chiralpak IC (250×4.6 mm, 5 μm)
 Eluent A: 0.1% DEA in n-Hexanes
 Eluent B: DCM/Methanol 50:50
 Elution using A:B 90:10 at 1 ml/min
Method F:
 Column: Chiralpak IC (250×4.6 mm, 5 μm)
 Eluent A: 0.1% DEA in n-Hexanes
 Eluent B: Ethanol
 Elution using A:B 95:5 at 1 ml/min
Method G:
 Column: Chiralpak IA (250×4.6 mm, 5 μm)
 Eluent A: 0.1% DEA in n-Hexanes
 Eluent B: DCM/Methanol 50:50
 Elution using A:B 90:10 at 1 ml/min
Method H:
 Column: Chiralpak IB (250×4.6 mm, 5 μm)
 Eluent A: 0.1% DEA in n-Hexanes
 Eluent B: DCM/Methanol 50:50
 Elution using A:B 90:10 at 1 ml/min
Method I:
 Column: Chiralpak IA (250×4.6 mm, 5 μm)
 Eluent A: n-Hexanes
 Eluent B: DCM/Methanol 50:50
 Elution using A:B 80:20 at 1 ml/min
Method J:
 Column: Chiralpak IA (250×4.6 mm, 5 μm)
 Eluent A: n-Hexanes
 Eluent B: Ethanol
 Elution using A:B 70:30 at 1 ml/min
Method K:
 Column: Chiralpak ADH (250×4.6 mm, 5 μm)
 Eluent A: 0.1% DEA in n-Hexanes
 Eluent B: Ethanol
 Elution using A:B 85:15 at 1 ml/min
Method L:
 Column: Chiralpak IA (250×4.6 mm, 5 μm)
 Eluent A: 0.1% DEA in n-Hexanes
 Eluent B: Isopropanol
 Elution using A:B 90:10 at 1 ml/min
Method M:
 Column: Chiralpak IA (250×4.6 mm, 5 μm)
 Eluent A: 0.1% DEA in n-Hexanes
 Eluent B: Ethanol
 Elution using A:B 85:15 at 1 ml/min
Method N:
 Column: Chiralcel ODH (250×4.6 mm, 5 μm)
 Eluent A: 0.1% TFA in n-Hexanes
 Eluent B: Ethanol/Methanol 50:50
 Elution using A:B 90:10 at 1 ml/min
Method P:
 Column: Chiralpak ADH (250×4.6 mm, 5 μm)
 Eluent A: 0.1% DEA in n-Hexanes
 Eluent B: Isopropanol
 Elution using A:B 90:10 at 1 ml/min
Method R:
 Column: Chiralpak IB (250×4.6 mm, 5 μm)
 Eluent A: 0.1% DEA in n-Hexanes
 Eluent B: Isopropanol
 Elution using A:B 95:5 at 1 ml/min
Method S:
 Column: Chiralpak ADH (250×4.6 mm, 5 μm)
 Eluent A: 0.1% TFA in n-Hexanes
 Eluent B: Ethanol/Methanol 50:50
 Elution using A:B 95:5 at 1 ml/min
Method T:
 Column: Chiralpak IC (250×4.6 mm, 5 μm)
 Eluent A: 0.1% DEA in n-Hexanes
 Eluent B: DCM/Methanol 80:20
 Elution using A:B 99:1 at 1 ml/min
Method U:
 Column: Chiralpak ODH (250×4.6 mm, 5 μm)
 Eluent A: 0.1% DEA in n-Heptane
 Eluent B: Ethanol
 Elution using A:B 80:20 at 1 ml/min Example-222: Biological Activity Suitable cell lines for use in the below assays, e.g., Gi/cAMP and β-arrestin assays include CHO—K1 cell expressing human D2R/0-arrestin (purchased from DiscoveR$_X$). The cell lines were grown or maintained in growth media comprising Ham's F-12 (Cellgro 10-080-CV), 10% HI FBS (Gibco 16140), 1×Penn/Strep/Glutamine (Gibco #10378), 600 ug/ml Geneticin (Gibco #10131) and 300 ug/ml Hygromycin (Invitrogen 10687-010).

Cells were prepared for assays by growing cultures for up to 2 weeks (from about 6-20 passages). A vial of frozen cells was thawed in a water bath held at 37° C. The cells were then transferred into a 50 ml tube with 10 ml growth media. The vial was rinsed with growth media and the contents transferred to the 50 ml tube. The 50 ml tube was centrifuged at 1200 rpm for 5 minutes at room temperature. The supernatant was decanted and the pellet of cells were re-suspended in growth media and grown at 37° C., 95% humidity, 5% $CO_2$. When the cells reached about 90% confluence (approximately 3 days between passages), the cells were passaged and used for either the agonist or antagonist assays as described below.

β-Arrestin Agonist Assay

The cells were prepared for β-arrestin assays as described above. The assays were performed using a PathHunter® β-Arrestin Detecting Kit (DiscoveR$_X$). The cells were grown on 225 mm dishes, then washed once with 1×PBS (Cellgro), followed by digestion with 2.5 ml 1× Detachment reagent (DRX 92-0009) for approximately 2 minutes. Plating 2 reagent ((DRX 93-0563R2B, 10 ml) was added to the plate, and the cells were transferred into a 50 ml centrifuge tube and centrifuged at room temperature using BD Dynac III at 1200 rpm for 5 minutes. The supernatant was decanted and the pellet was re-suspended in Plating 2 reagent at an optimized density of $2.5 \times 10^5$ cells/ml. The cells were then plated onto white 384 well plates, to a final cell density of 5000 cells/20 μl/well. The plates were then transferred to a humidified incubator maintained at 37° C., 5% $CO_2$, and incubated for 24 hours prior to testing. The compounds were then pin-transferred (100 nL) to the cells, and was incubated for 90 minutes at 37° C. The detection reagent (9.6 μL, Buffer:Emerald II:Galactor-Star in a 19:5:1 ratio, i.e., 14.06 mL:3.7 mL:0.74 mL=18.5 mL) was then added to the agonist plates. The plates were then incubated for 60 minutes at room temperature in the dark, before reading the assay results using the protocol Luminescence (Aperture luminescence 384-well) on an EnVision® detection instrument (Perkin Elmer).

β-Arrestin Antagonist Assay

The cells were prepared for β-arrestin assays as described above. The assays were performed using a PathHunter® β-Arrestin Detecting Kit (DiscoveR$_X$). The cells were grown on 225 mm dishes, then washed once with 1×PBS (Cellgro), followed by digestion with 2.5 ml 1× Detachment reagent (DRX 92-0009) for approximately 2 minutes. Plating 2 reagent ((DRX 93-0563R2B, 10 ml) was added to the plate, and the cells were transferred into a 50 ml centrifuge tube and centrifuged at room temperature using BD Dynac III at 1200 rpm for 5 minutes. The supernatant was decanted and the pellet was re-suspended in Plating 2 reagent at an optimized density of $2.5 \times 10^5$ cells/ml. The cells were then plated onto white 384 well plates, to an optimized final cell density of 5000 cells/20 μl/well. The plates were then transferred to a humidified incubator maintained at 37° C., 5% $CO_2$, and incubated for 24 hours prior to testing. The compounds were then pin-transferred (100 nL) to the cells, and incubated for 10 minutes at 37° C., before addition of Quinpirole (5 uL of a 650 nM solution, 78.5 μl of quinpirole (100 μM in DMSO) into 12 mL Plating 2 reagent) to each well, to final concentration of 130 nM. The plates were then incubated for 90 minutes at 37° C. before addition of the detection reagents (12 μL, Buffer:Emerald II:Galactor-Star=19:5:1 ratio 14.06 mL:3.7 mL:0.74 mL=18.5 mL) to the plates. The plates were then incubated for 60 minutes at room temperature in the dark before reading the assay results using the protocol Luminescence (Aperture luminescence 384-well) on an EnVision® detection instrument (Perkin Elmer).

Gi/cAMP Agonist Assay

The cells were prepared for Gi/cAMP assays as described above. The assays were performed using a PE Lance Ultra cAMP kit (TRF0263). The cells were grown on 225 mm dishes, then washed once with 1×PBS (Cellgro) before digestion with 2.5 ml 1× Detachment reagent (DRX 92-0009) for about 2 minutes. PBS (20 ml) was then added to the plate, and the cells were transferred to a 50 ml centrifuge tube, and centrifuged at room temperature using BD Dynac III, at 1200 rpm for 5 minutes. The supernatant was decanted and the pellet was re-suspended in stimulation buffer at an optimal density of $6.67 \times 10e5$ cells/ml, before plating onto white 384 well plates (15 μl/well) to a final concentration of 10,000 cells/15 μl/well. Compounds were pin-transferred (100 nL) to the cells, and incubated for 10 min. at 37° C. Forskolin (5 μl of a 10 μM solution, 12 μL Forskolin (10 mM in DMSO) into 12 mL Stimulation buffer) was then added to each well to final concentration to 2.5 μM Forskolin, and the plates were then incubated at room temperature for 30 minutes. Eu-cAMP tracer solution (10 μl, PerkinElmer, 360 μl of Tracer in 17.64 ml kit buffer) and ULight-anti-cAMP solution (10 μl, 120 μL antibody in 17.88 ml kit buffer) was then added to each well. The plates were then incubated at room temperature for about 1 hr in the dark before reading the assay results using protocol Lance (Excitation 320 nm, Emission filter 665 nm, second emission filter 615 nm, Top mirror Lance Delfia) on an EnVision® detection instrument (Perkin Elmer).

Gi/cAMP Antagonist Assay

The cells were prepared for Gi/cAMP assays as described above. The assays were performed using a PE Lance Ultra cAMP kit (TRF0263). The cells were grown on 225 mm dishes, then washed once with 1×PBS (Cellgro) before digestion with 2.5 ml 1× Detachment reagent (DRX 92-0009) for about 2 minutes. PBS (20 ml) was then added to the plate, and the cells were transferred to a 50 ml centrifuge tube, and centrifuged at room temperature using BD Dynac III, at 1200 rpm for 5 minutes. The supernatant was decanted and the pellet was re-suspended in stimulation buffer at an optimized density of $6.67 \times 10e5$ cells/ml, before plating onto white 384 well plates (15 μl/well) to a final concentration of about 10,000 cells/15 μl/well. Chemical plate was pin-transferred (100 nL) to the cells, and incubated for 10 min. at 37° C. A 5 μl mixture containing Forskolin (10 μM, 12 μL Forskolin (10 mM in DMSO) into 12 mL stimulation buffer) and Quinpirole (10.8 nM, 131 μL Quinpirole (1 μM in DMSO) into 12 mL Forskolin buffer) were added to each well to a final concentration of 2.5 μM Forskolin and 2.7 nM Quinpirole. The plates were then incubated at room temperature for about 30 minutes before addition of Eu-cAMP tracer solution (10 μl, PerkinElmer) and then ULight-anti-cAMP solution (10 μl) to each well. Following incubation at room temperature for 1 hr in the dark, the assay results were read using protocol Lance (Excitation 320 nm, Emission filter 665 nm, second emission filter 615 nm, Top mirror Lance Delfia) on an EnVision® detection instrument (Perkin Elmer).

Pharmacokinetic Studies on Mice Brains

Twelve male C57BL/6 mice were weighed and administered intraperitoneally with a dose of test compound (Examples 90, 157, 125) solution formulation. The dosing volume administered for the intraperitoneal route was at 10 mL/kg. Blood samples (approximately 60 μL) were collected from retro-orbital plexus of each mouse under light isoflurane anesthesia at 0.08, 0.5, 1, 2, 4, and 8 hr. Following the collection of blood, plasma was also harvested by centrifugation and stored at −70° C. until analysis. After collection of plasma, the animals were euthanized and brain samples were isolated at 0.08, 0.5, 1, 2, 4, and 8 hr. Tissue samples (brain) were homogenized using ice-cold phosphate buffer saline (pH 7.4) and homogenates were stored below −70° C. until analysis. Total homogenate volume was three times the tissue weight. Concentrations of test compound in mouse plasma and brain samples were determined by LC-MS/MS method.

Identical extraction procedures were used for the plasma/brain homogenate study samples and the spiked plasma calibration standards: A 25 μL sample of either study sample (plasma/brain) or spiked calibration standard was added to individual pre-labeled micro-centrifuge tubes. A volume of 100 μL of IS (antipyrine, 500 ng/mL) prepared in acetonitrile was then added to the micro-centrifuge tubes, except in a sample used as a negative control where only acetonitrile was added and vortexed for 5 minutes. Samples were centrifuged for 20 minutes at the speed of 4000 rpm at 4° C. Following centrifugation, 100 μL of the supernatant was sampled from each centrifuge tube and transferred into insert vials. These vials remained within the auto-sampler for the LC/MS/MS analysis. Standards used for calibration were prepared by spiking 10 μL of the test compound in 190 μL of control (used as a negative control) mouse plasma/brain homogenate.

The plasma and brain concentration-time data of test compounds was provided for data analysis. The plasma and brain concentration-time data was then used for the pharmacokinetic analysis. Non-Compartmental-Analysis module in Phoenix® WinNonlin® (Version 6.3) was used to assess the pharmacokinetic parameters. Peak plasma concentrations ($C_{max}$) and time for the peak plasma concentrations ($T_{max}$) were the observed values. The areas under the concentration time curve ($AUC_{last}$ and $AUC_{inf}$) were calculated by linear trapezoidal rule. The terminal elimination rate constant, ke was determined by regression analysis of the linear terminal portion of the log plasma concentration-time curve.

Figure 2:
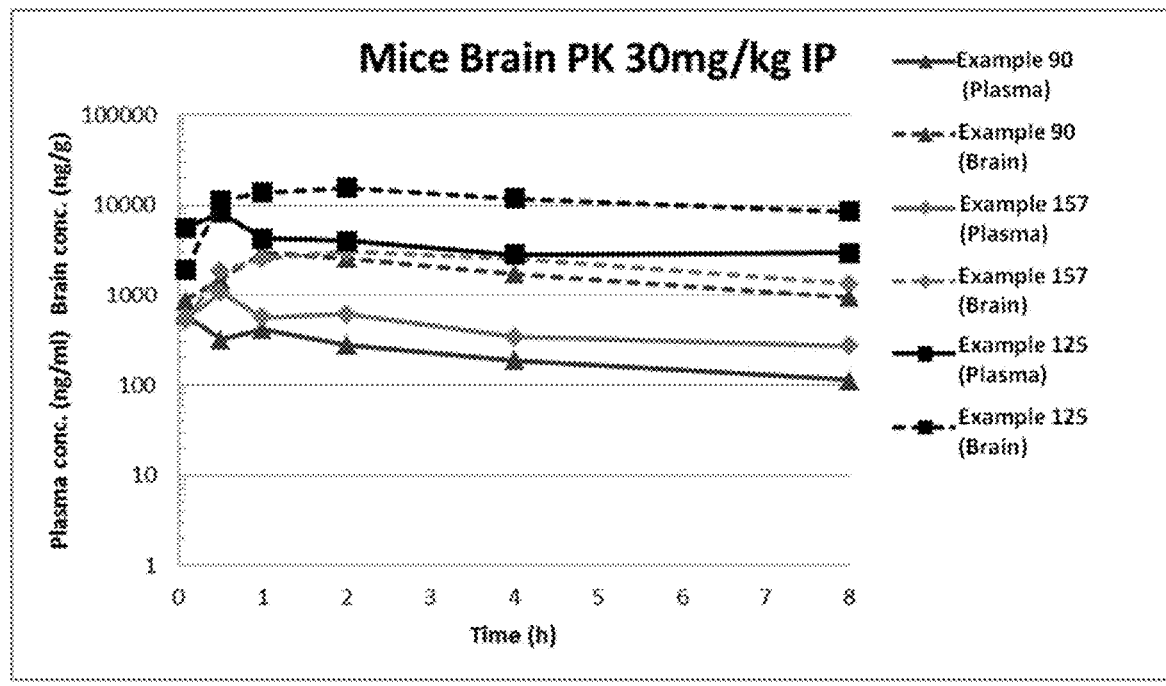
FIG. 2 shows pharmacokinetic and brain distribution of compounds 90, 125, and 157 following a single intraperitoneal dose administration of 30 mg/kg in male C57BL/6 mice.

Illustrative results are presented in FIG. 2, the pharmacokinetic parameters are as follow:

|  | Plasma | | | Brain | | | | | |
| --- | --- | --- | --- | --- | --- | --- | --- | --- | --- |
|  | AUC μmol/ L · Hr | $T_{1/2}$ hr | Cmax μmol/L | AUC μmol/ L · Hr | $T_{1/2}$ hr | Cmax μmol/L | B/P Cmax | B/P AUC | Brain Protein Binding |
| Compound 90 | 4.4 | 4.7 | 1.44 | 34.2 | 4.2 | 7.23 | 5.0 | 7.8 | >99.9% |
| Compound 157 | 14.0 | 6.2 | 2.47 | 70.4 | 6.0 | 7.03 | 2.9 | 5.0 | >99.9% |
| Compound 125 | 69.6 | 13.4 | 19.8 | 222.3 | 7.0 | 37.9 | 1.9 | 3.2 | 99.8% |

Positron Emission Tomography Studies on Rodents

All animal procedures were performed in accordance with the National Institutes of Health Guide for the Care and Use of Laboratory Animals and were approved by the Massachusetts General Hospital Institutional Animal Care and Use Facility. Male Sprague-Dawley rats (8-14 weeks old, Charles River Labs) were used for the study with animals pair-housed on a diurnal 12:12 light/dark cycle with free access to food and water. The rats were stabilized under anesthesia (2% isoflurane in 1.5 L/min oxygen) before an intravenous (i.v.) catheter was placed in the lateral tail vein (BD Angiocath #381112, 24 G) and non-radiolabeled test compounds were administered 5-180 minutes prior to radiotracer administration. All test compounds (vehicle, compound of Example 90, Clozapine) were solubilized in a solution of (10% DMSO, 10% Tween-80, 80% saline) and injected at a volume ≤2 mL/kg. Baseline control scans were obtained from pretreatment time-matched control animals administered an equivalent volume of vehicle alone. Respiration of each animal was monitored for the duration of the procedure.

Carbon 11-labeled raclopride ([$^{11}$C]RAC) was synthesized from the O-desmethyl RAC precursor and [11C] methyl iodide and subsequently purified by high-performance liquid chromatography as previously described (Farde L, et al. (1985) PNAS, USA 82(11):3863-3867). For each scan, 1.0±0.15 mCi [$^{11}$C]RAC radiotracer was administered via i.v. catheter in a volume ≤1.5 mL in a vehicle containing (10% ethanol, 90% saline). Positron emission tomography (PET) and skeletal computed tomography (CT) data were collected using a GammaMedica Triumph trimodal PET/SPECT/CT scanner (Quebec, Canada) or PET data alone using a Concorde Microsystems R4 microPET scanner (Knoxville, TN, USA). Each [$^{11}$C]RAC scan included subtraction of random coincidences collected in a delayed time window. Scatter-corrected sinograms were reconstructed using a 3-dimensional iterative maximum likelihood expectation maximization (3D-MLEM) algorithm with 16 iterations yielding an image resolution of ~1.5 mm FWHM (Full Width at Half Maximum). Pixel size in reconstructed images was 0.26 mm transaxially, 0.6 mm slice thickness. Regions of Interest (ROIs) were drawn on reconstructed images estimating peak [$^{11}$C]RAC uptake in striata (averaged between left and right hemispheres) and cerebellum as reference region for non-displaceable (ND) tracer uptake. ROI dimensions, placement and striatal D2/D3 binding potential ($BP_{ND}$) were evaluated by graphical analysis using Logan distribution volume ratio (DVR) linearization as previously described ($BP_{ND}$=DVR-1; Alexoff D, et al. (2002) J Nuc Med 44(5): 815-822; Logan J, et al. (1996) J Cerebral Blood Flow and Metabolism 16(5):843-840).

Figure 3:
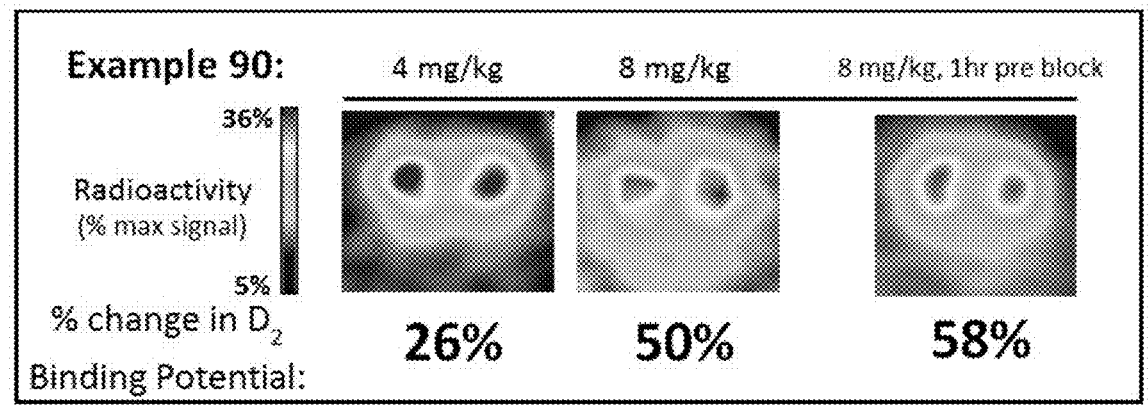
FIG. 3 shows positron emission tomography at different doses of Compound 90 in comparison with clozapine. Compound 90 competes with the radiotracer [$^{11}$C]Raclopride. Scans 1 hour after administration demonstrate continued high occupancy in the striatum. This matches the time of amphetamine challenge in the behavior. Occupancies are on par with Clozapine.
Figure 3:
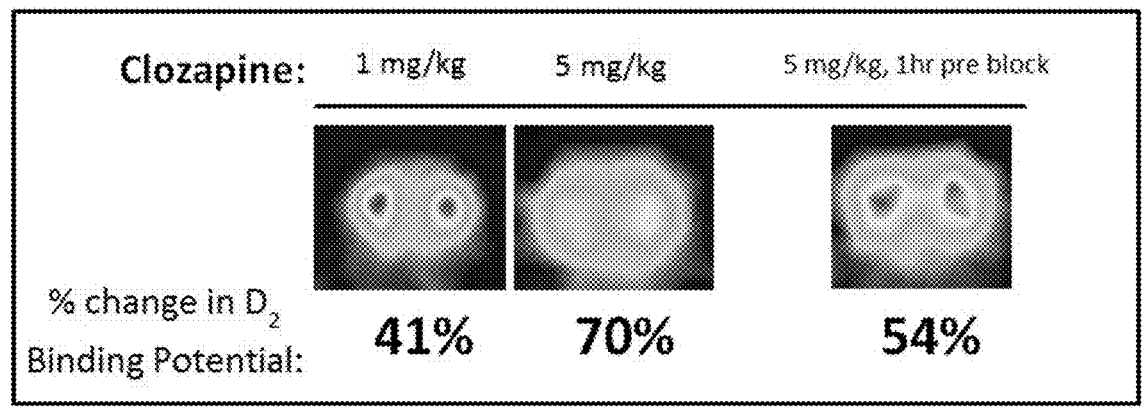
Figure 4A:
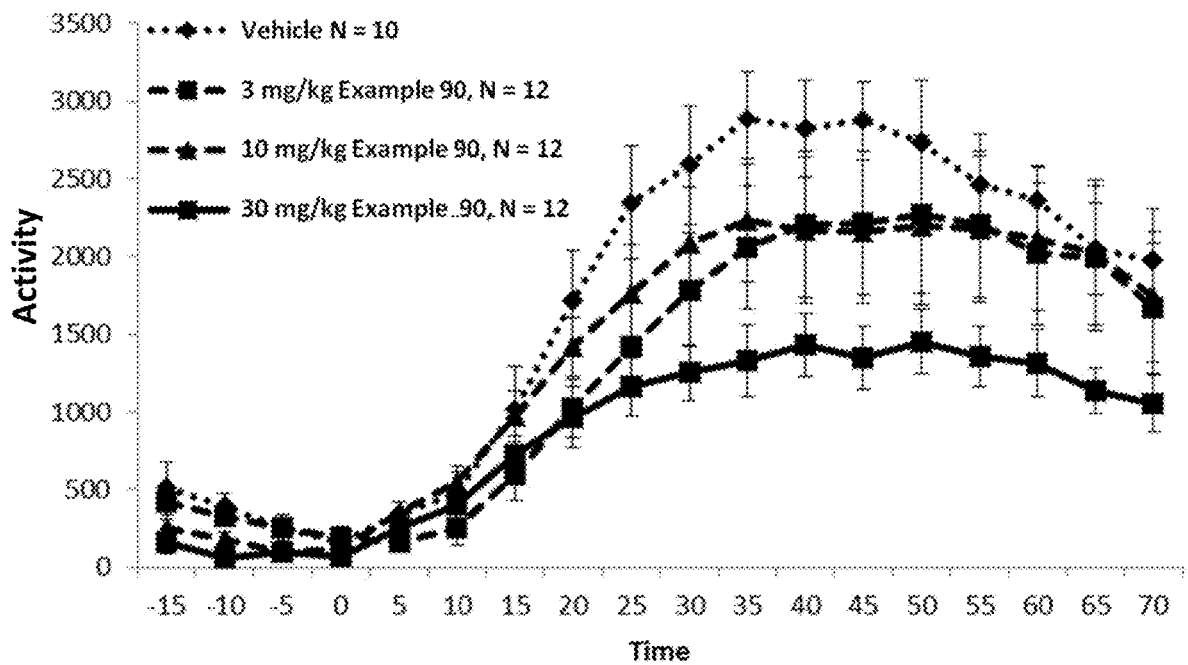
FIG. 4A shows the effect of Compound 90 in comparison with vehicle to attenuate amphetamine induced hyperactivity (AIH) over time. Compound 90 dose-dependently attenuates AIH in mice and shows efficacy at 30 mg/kg.
Figure 4B:
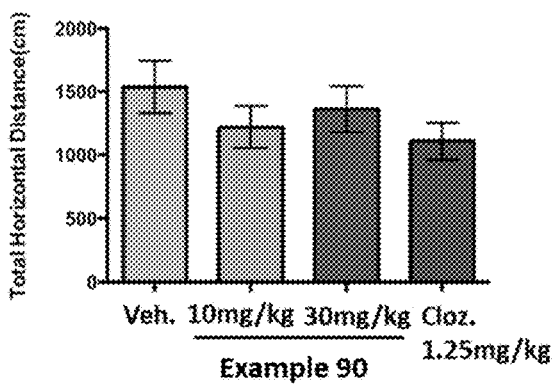
FIG. 4B shows a bar graph representation of AIH data. "Veh." denotes vehicle. "Cloz." denotes clozapine.
Figure 4B:
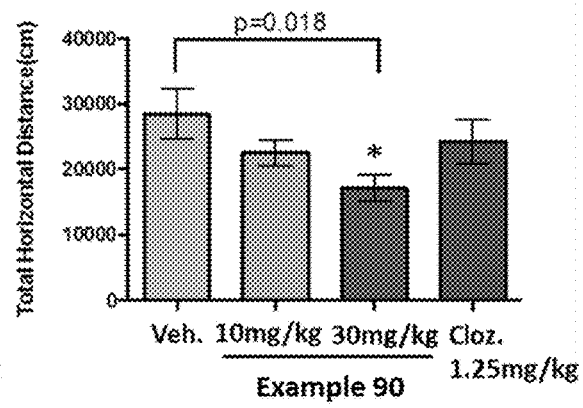
Figure 4C:
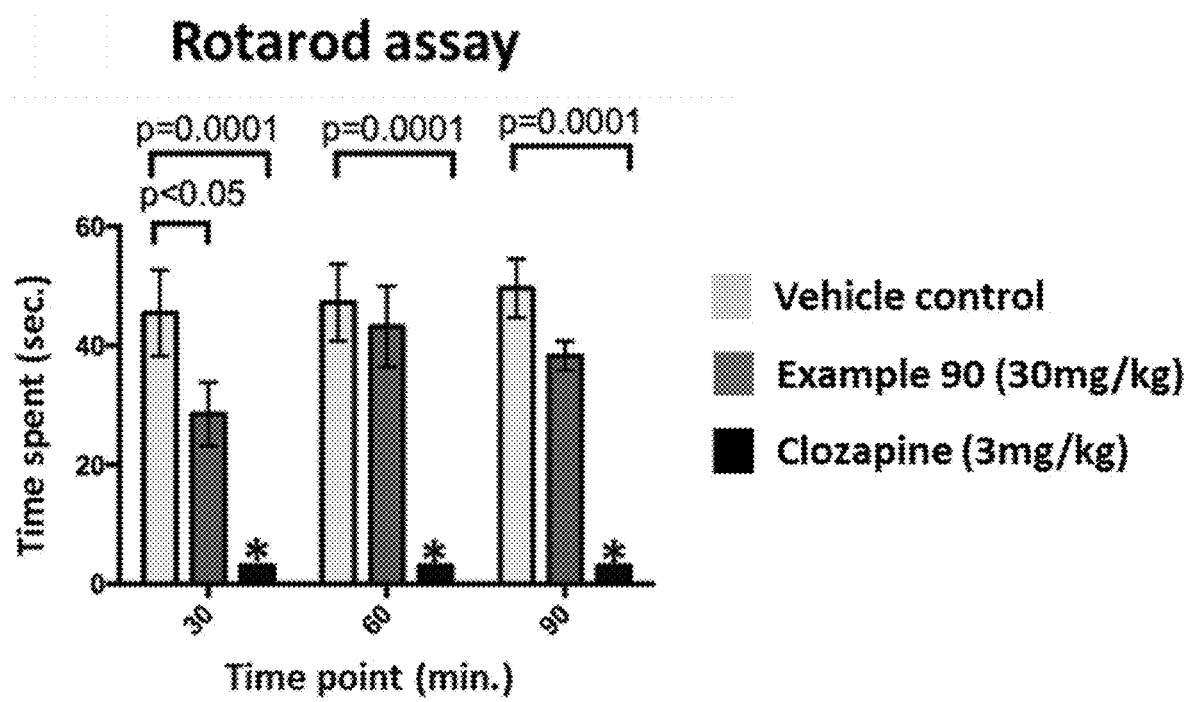
FIG. 4C shows rotarod performance after treatment with Example 90 or Clozapine. Example 90 does not induce motoric side effects at 30 mg/kg IP in mice.

Illustrative results are presented in FIG. 3.

Amphetamine Induced Hyperactivity Studies

Amphetamine-induced hyperactivity (AIH) was examined in eight identical open-field chambers (16.5"×16"×12"; AccuScan Instruments, Columbus, OH). Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days as follows:

Day 1: Mice were acclimated to the injection procedure by injecting 30 minutes prior to being placed in the chambers (to match the timing of day 3 compound administration). Mice were then placed into the open-field for 20 minutes and then removed for a saline injection (to match the timing of amphetamine administration on day 3). Mice were placed back into the open-field for an additional 30 minutes, at which point the mice were returned to their home cage.

Day 2 was run identically to Day 1, with the exception that the second day lasted for one hour (20 minutes→injection→40 minutes).

Day 3 was the amphetamine challenge day. Mice were pre-treated with D2 antagonist compounds (compound of Example 90) 30 minutes prior to being placed in the open field. After 20 minutes, mice were removed and challenged with amphetamine, following protocols known to one skilled in the art, for example Jones C. A, et. al. *Br J Pharmacol.* 2011, 164(4):1162-1194; Pan J Q, et. al. *Neuropsychopharmacology.* 2011, 36(7):1397-1411.

Illustrative results are presented in FIG. 4.

Rotarod Performance

In the test, mice are placed on a horizontally oriented, rotating cylinder (rod) suspended above a cage floor, which is low enough not to injure the animal, but high enough to induce avoidance of fall. The mice naturally try to stay on the rotating cylinder, or rotarod, and avoid falling to the ground. Mice are administered clozaril at 3 mg/kg (test group); or a compound of Formula (I) (either 10 mg/kg or 30 mg/kg or vehicle). The mice have an average weight of 20 grams (as do the mice in all examples herein). The length of time that a given animal stays on this rotating rod is a measure of the animal's balance, coordination, physical condition, and motor-planning. The speed of the rotarod is mechanically driven, and is held constant.

Heatmap

Figure 5:
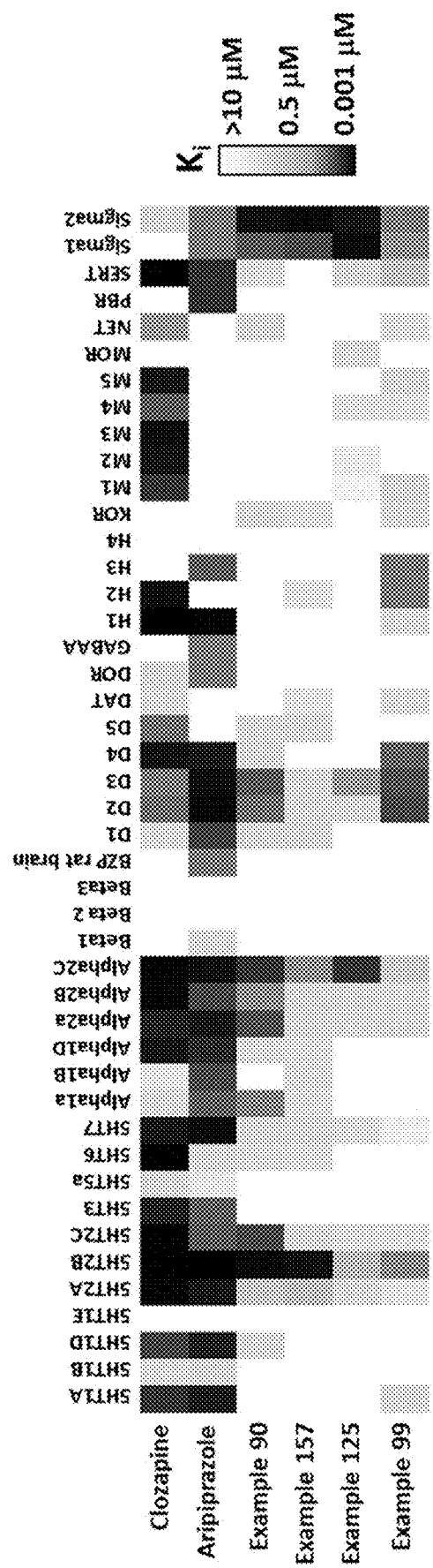
FIG. 5 shows a heat map representation of binding across various GPCR receptors for compounds of the invention (compounds 90, 157, 125, and 99) and control compounds (clozapine and aripiprazole). Clozapine and other antipsychotics bind to many receptors in the brain. The inventive compounds showed a cleaner binding profile.
Figure 6A:
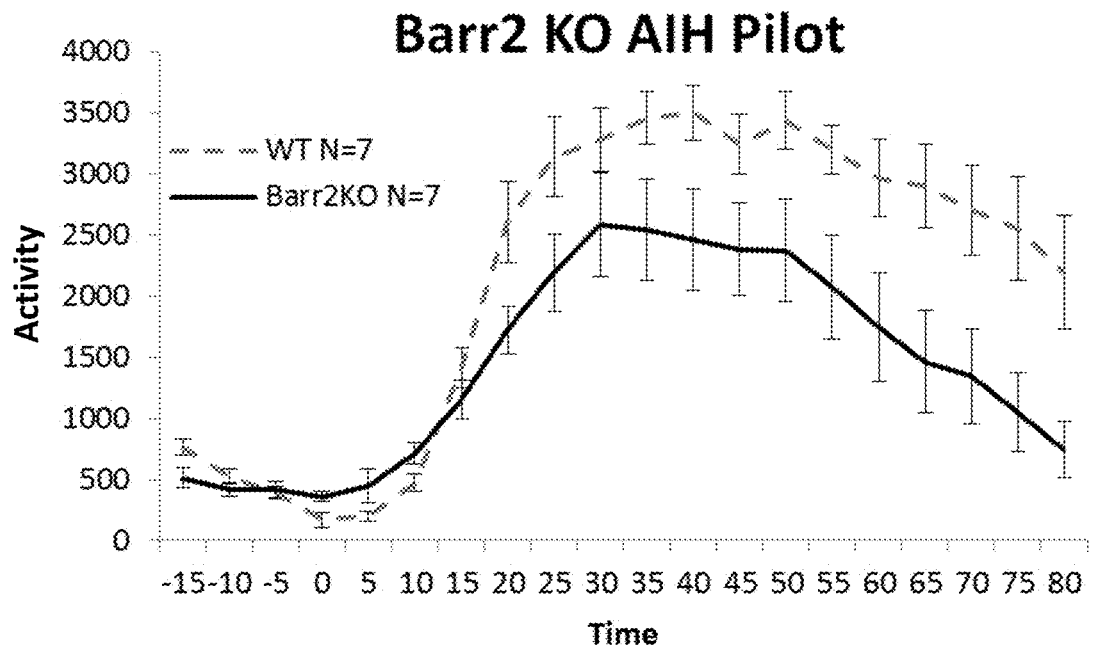
FIGS. 6A to 6C show βArr2 KO mice and confirming the phenotype. One is able to replicate the decreased sensitivity to amphetamine (FIG. 6A & FIG. 6B) and apomorphine (FIG. 6C) in the βArr2 KO mice.
Figure 6B:
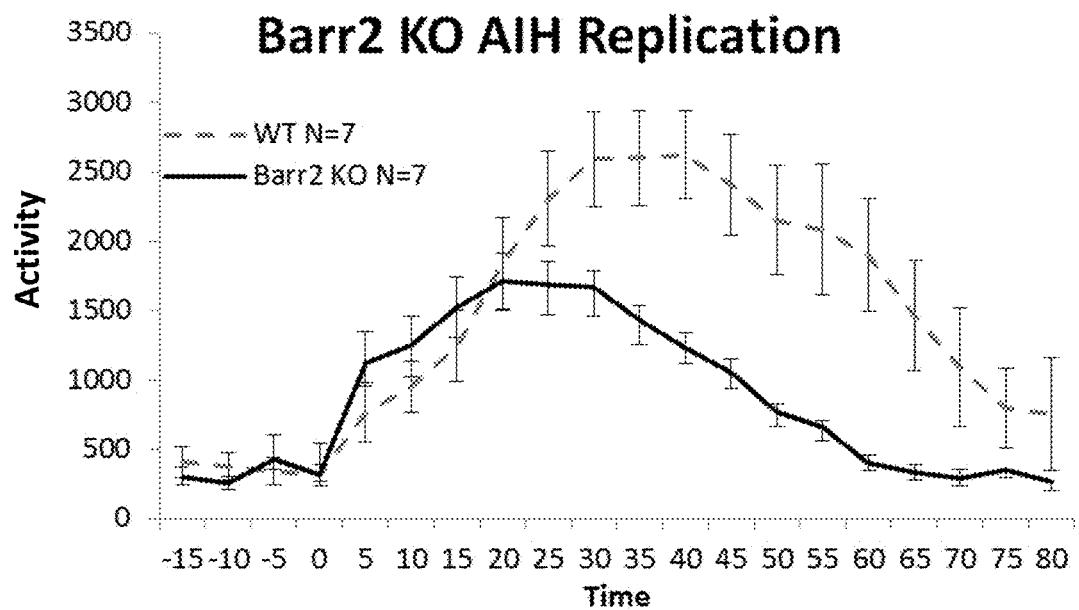
Figure 6C:
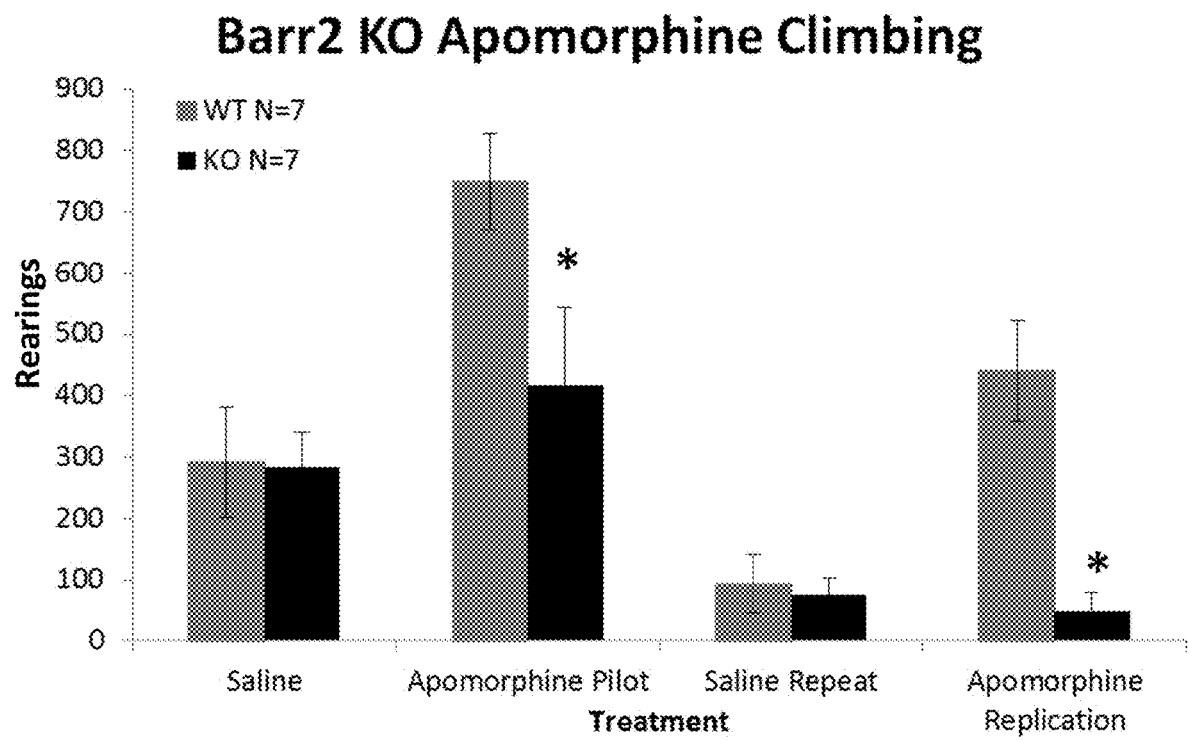
Figure 7A:
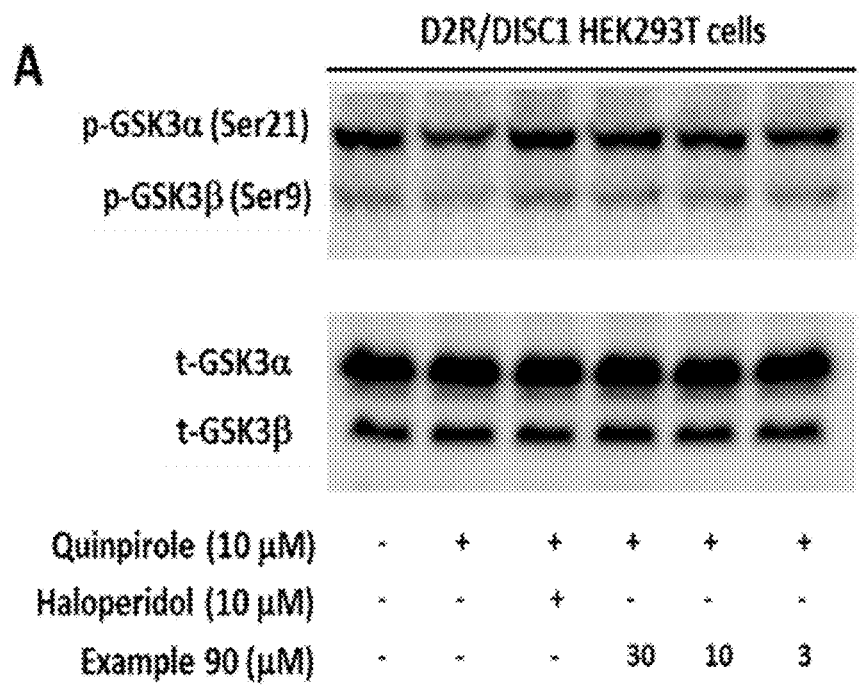
FIGS. 7A to 7C show Example 90 inhibiting D2R-mediated GSK3 signaling. Example 90 blocks β-arrestin signaling downstream of D2R and leads to modulation of GSK3 signaling.
Figure 7B:
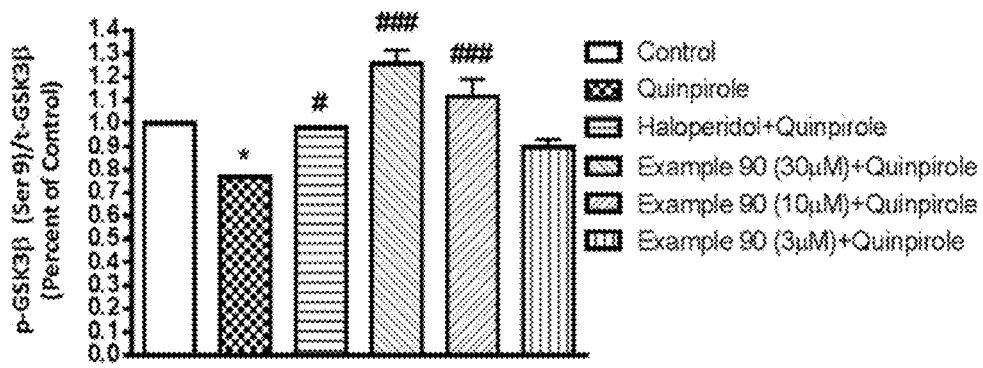
Figure 7C:
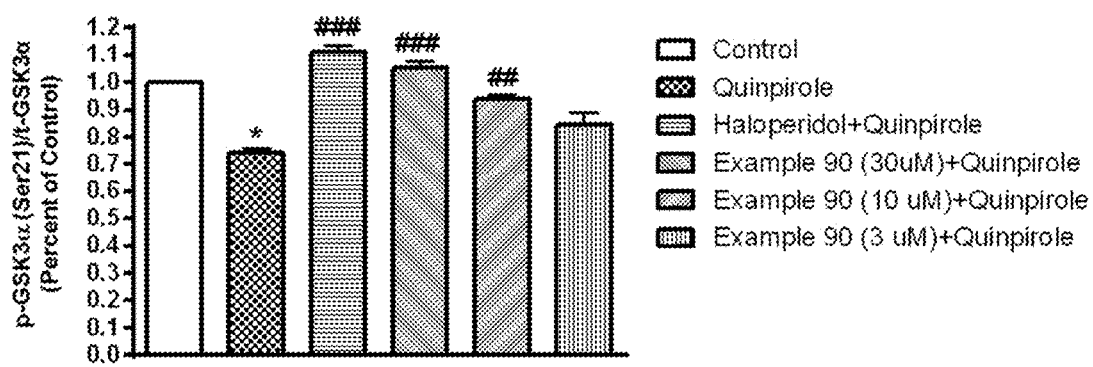

The heatmap of FIG. 5 represents binding across various relevant CNS biological targets including GPCRs, transporters, etc. for clozapine, aripiprazole and amisulpride, alongside exemplary compounds of the invention—Examples 90, 157, 125, and 99.

Results of Gi/cAMP and β-Arrestin Antagonist and Agonist Assays Using CHO—K1 Cell Line Expressing Human D2R/β-Arrestin Herein exemplified compounds were analyzed by way of the foregoing Gi/cAMP and β-arrestin antagonist and agonist assays using CHO—K1 cell line expressing human D2R/β-arrestin and thus both the Gi/cAMP and β-arrestin pathways were monitored in both agonist and antagonist (Quinpirole was used as agonist) modes. FIG. 1 shows representative curves obtained for selected D2 ligands: Clozapine, Aripiprazole, and compounds of the invention 90, 157, 158, and 125. Compounds 90, 157 and 158 are representative β-arrestin biased D2R antagonists. Compound 125 is a representative cAMP-biased agonist. Table 1 tabulates the results as to the various exemplified compounds, in dopamine β-arrestin and cAMP assays in agonist and antagonist modes. In table 1, Emax is higher than 20%.

Table 1. Biological data from testing compounds in the foregoing Gi/cAMP and β-arrestin antagonist and agonist assays using CHO—K1 cell line expressing human D2R/β-arrestin. Both the Gi/cAMP and β-arrestin pathways were monitored in both agonist and antagonist (quinpirole used as agonist) modes. The D2 binding Ki values were determined using a radioligand binding assay. $EC_{50}$ or $IC_{50}$ values were categorized as follows. Emax values for a given pathway ranged from 10-100%.

TABLE 1

(A = <0.1 µM, B = 0.1-1.0 µM, C = 1.0-10.0 µM, D = 10.0-30.0 µM, E = >30 µM)

| Compound # | D2 binding $K_i$ | β-arrestin Antagonist | cAMP Antagonist | β-arrestin Agonist | cAMP Agonist |
|---|---|---|---|---|---|
| Aripiprazole | A | A | A | A | A |
| Clozapine | B | B | B | E | E |
| Cariprazine | | A | E | A | A |
| UNC9994 | | B or C | E | B or C | A |
| UNC9975 | | B or A | B | E | B or A |
| D,L-Stepholidine | | A | A | E | E |
| Quinpirole | | E | E | B or A | A |
| Dopamine | | E | E | B or C | A |
| Apomorphine | | E | E | A | A |
| MLS1547 | | C | E | E | A |
| 1 | C | C | E | E | A |
| 1a | | B | E | E | A |
| 1b | | C | A | E | B |
| 2 | | B | B | E | E |
| 3 | | C | B | E | E |
| 4 | | C | B | E | E |
| 5 | | B | A | E | E |
| 6 | | C | B | E | E |
| 7 | D | E | E | E | E |
| 7a | | E | E | E | E |
| 7b | | E | E | E | C |
| 8 | | C | B | E | E |
| 9 | | B | E | E | A |

TABLE 1-continued (A = <0.1 µM, B = 0.1-1.0 µM, C = 1.0-10.0 µM, D = 10.0-30.0 µM, E = >30 µM)

| Compound # | D2 binding $K_i$ | β-arrestin Antagonist | cAMP Antagonist | β-arrestin Agonist | cAMP Agonist |
|---|---|---|---|---|---|
| 10 | | C | E | E | A |
| 11 | | C | B | E | A |
| 12 | | E | E | A | A |
| 12a | | B | E | A | A |
| 12b | | E | E | A | A |
| 13 | | C | B | E | E |
| 14 | | C | B | E | A |
| 15 | | C | C | E | A |
| 16 | | C | E | E | B |
| 17 | | D | C | E | E |
| 18 | | C | E | E | B |
| 18a | | C | E | E | A |
| 18b | C | C | E | E | B |
| 19 | | E | E | C | A |
| 20 | | D | E | E | A |
| 21 | | C | C | E | E |
| 22 | | C | B | E | A |
| 23 | | B | E | E | A |
| 24 | | E | E | A | A |
| 25 | | C | C | E | E |
| 26 | | C | B | E | E |
| 27 | B | C | B | E | E |
| 28 | | B | A | E | E |
| 29 | | C | C | E | E |
| 30 | | E | E | C | B |
| 31 | | C | B | E | E |
| 32 | | C | E | E | B |
| 33 | | C | B | E | E |
| 34 | | E | E | C | B |
| 35 | | C | E | E | A |
| 36 | | C | B | E | B |
| 37 | | C | B | E | E |
| 38 | | E | E | B | A |
| 39 | | B | E | E | A |
| 40 | | C | E | E | B |
| 41 | | D | E | E | B |
| 42 | | C | E | E | A |
| 43 | | C | E | E | E |
| 44 | | E | E | B | A |
| 45 | | C | E | E | A |
| 47 | | C | E | E | B |
| 48 | | D | E | E | A |
| 49 | | D | E | E | B |
| 50 | | D | E | E | A |
| 51 | | B | E | E | A |
| 52 | | C | E | E | A |
| 53 | | C | E | E | A |
| 54 | C | C | D | E | B |
| 55 | C | C | E | E | A |
| 55a | | C | B | E | E |
| 55b | | D | E | E | A |
| 56 | | C | C | E | A |
| 57 | | C | E | E | B |
| 58 | | E | E | C | A |
| 59 | C | E | E | D | A |
| 59a | | D | E | E | B |
| 59b | D | E | E | C | A |
| 60 | | E | E | B | A |
| 61 | | C | B | E | E |
| 62 | | C | C | E | E |
| 63 | | C | C | E | E |
| 64 | | D | E | E | B |
| 65 | | C | B | E | E |
| 66 | | C | D | E | A |
| 67 | | B | E | E | A |
| 68 | B | E | E | E | A |
| 69 | | B | E | A | A |
| 70 | | B | D | E | A |
| 71 | | B | B | E | E |
| 72 | | B | A | E | A |
| 73 | | E | E | E | E |
| 74 | | B | E | B | A |
| 75 | | B | B | E | E |

TABLE 1-continued (A = <0.1 μM, B = 0.1-1.0 μM, C = 1.0-10.0 μM, D = 10.0-30.0 μM, E = >30 μM)

| Compound # | D2 binding $K_i$ | β-arrestin Antagonist | cAMP Antagonist | β-arrestin Agonist | cAMP Agonist |
|---|---|---|---|---|---|
| 76 |  | B | E | E | A |
| 77 |  | E | E | E | D |
| 78 | B | B | C | E | D |
| 80 |  | C | C | E | D |
| 81 |  | D | E | E | C |
| 83 |  | C | B | E | E |
| 84 |  | C | E | E | C |
| 85 |  | C | E | E | A |
| 86 | A | E | E | A | A |
| 87 |  | E | E | A | A |
| 88 |  | A | E | A | A |
| 89 |  | A | E | A | A |
| 90 | B | B | E | C | A |
| 91 | B | A | E | E | A |
| 92 |  | C | B | E | A |
| 93 |  | C | B | E | B |
| 94 |  | C | C | E | B |
| 96 | B | B | A | E | E |
| 96a |  | C | B | E | E |
| 96b |  | C | B | E | E |
| 97 |  | B | A | E | E |
| 98 |  | B | A | E | E |
| 98a | A | A | A | E | E |
| 98b |  | C | B | E | E |
| 99 | B | B | A | E | E |
| 99a |  | C | B | E | E |
| 99b |  | D | C | E | E |
| 100 |  | C | B | E | E |
| 101 |  | C | C | E | E |
| 102 |  | C | C | E | B |
| 102a | B | B | B | E | A |
| 102b |  | B | B | E | E |
| 103 |  | B | B | E | E |
| 104 |  | B | C | E | D |
| 105 |  | B | A | E | A |
| 106 | A | B | A | E | E |
| 107 |  | B | B | D | A |
| 107a |  | A | A | E | A |
| 107b |  | B | D | B | A |
| 108 |  | D | C | E | E |
| 109 |  | A | E | A | A |
| 110 | A | B | E | E | A |
| 111 |  | C | B | E | E |
| 112 | B | B | E | E | B |
| 113 |  | B | B | E | E |
| 114 |  | A | A | E | E |
| 115 |  | C | C | E | E |
| 116 |  | D | C | E | E |
| 117 |  | D | C | E | E |
| 118 |  | B | B | E | A |
| 119 |  | C | C | E | E |
| 120 |  | D | E | E | C |
| 121 |  | C | E | B | A |
| 122 | B | B | E | E | A |
| 123 | A | B | B | E | E |
| 124 |  | B | A | E | E |
| 125 | C | E | E | D | B |
| 126 |  | A | A | E | E |
| 127 |  | C | E | B | A |
| 128 |  | C | B | E | C |
| 129 |  | E | E | E | E |
| 130 |  | D | E | C | B |
| 131 |  | C | E | B | A |
| 132 |  | D | C | E | E |
| 133 |  | B | B | E | E |
| 134 |  | D | C | E | E |
| 135 | A | A | A | E | E |
| 136 |  | B | A | E | E |
| 137 | A | A | A | E | E |
| 138 |  | B | B | E | E |
| 139 |  | C | C | E | E |
| 140 | D | B | E | C | A |
| 140a |  | D | E | E | B |
| 140b |  | B | E | B | A |
| 141 |  | B | B | E | C |
| 142 |  | E | E | B | A |
| 142a |  | E | E | A | A |
| 142b |  | E | E | C | B |
| 143 |  | D | E | E | D |
| 144 | B | C | B | E | E |
| 145 |  | D | B | E | E |
| 146 |  | B | E | B | B |
| 147 |  | E | E | A | A |
| 148 |  | E | E | E | D |
| 149 |  | C | E | B | A |
| 150 |  | E | E | B | A |
| 151 |  | E | E | B | A |
| 152 |  | D | D | E | D |
| 153 |  | C | C | E | E |
| 154 |  | D | B | E | E |
| 155 |  | C | C | E | E |
| 156 |  | E | E | B | A |
| 157 | B | B | B | E | B |
| 158 |  | C | B | E | B |
| 159 |  | B | C | E | A |
| 160 |  | C | B | E | E |
| 161 |  | D | E | B | A |
| 162 |  | B | A | E | C |
| 163 |  | E | E | C | A |
| 164 | D | D | E | E | B |
| 165 |  | C | E | D | C |
| 166 |  | C | C | E | C |
| 167 |  | C | C | E | C |
| 168 |  | C | C | E | E |
| 169 |  | C | B | E | E |
| 170 |  | E | E | E | E |
| 171 |  | E | E | E | B |
| 172 |  | E | E | E | C |
| 173 |  | E | E | C | B |
| 174 |  | E | E | B | A |
| 175 |  | A | E | B | A |
| 176 |  | B | A | E | E |
| 177 |  | C | C | E | E |
| 178 |  | A | A | E | E |
| 178a |  | B | A | E | E |
| 178b |  | B | A | E | D |
| 179 |  | C | B | E | E |
| 180 |  | C | E | E | A |
| 181 |  | C | A | E | E |
| 182 |  | E | E | B | A |
| 183 |  | C | E | C | B |
| 184 |  | D | E | E | C |
| 185 |  | D | E | E | C |
| 186 |  | C | B | C | B |
| 187 |  | C | C | E | B |
| 188 |  | B | C | E | B |
| 189 |  | C | C | E | C |
| 190 |  | C | B | E | B |
| 191 |  | C | B | E | E |
| 192 |  | C | B | E | C |
| 193 |  | C | E | C | A |
| 194 |  | C | E | B | A |
| 195 |  | E | E | E | E |
| 196 |  | D | C | E | E |
| 197 |  | B | A | E | E |
| 198 | A | A | A | E | E |
| 199 |  | C | E | E | B |
| 200 |  | C | B | E | B |
| 201 |  | C | B | E | E |
| 202 |  | B | B | E | A |
| 202a |  | D | C | E | B |
| 202b | C | B | B | E | B |
| 203 |  | B | C | E | A |
| 203a |  | B | C | E | A |
| 203b |  | D | D | E | E |
| 204 |  | C | B | E | B |

TABLE 1-continued (A = <0.1 μM, B = 0.1-1.0 μM, C = 1.0-10.0 μM,
D = 10.0-30.0 μM, E = >30 μM)

| Compound # | D2 binding $K_i$ | β-arrestin Antagonist | cAMP Antagonist | β-arrestin Agonist | cAMP Agonist |
|---|---|---|---|---|---|
| 204a |  | C | C | E | E |
| 204b | B | C | B | E | A |
| 205 | B | B | E | B | A |
| 206 | B | A | E | A | A |
| 207 |  | C | E | C | C |
| 208 | B | A | E | B | A |
| 209 | B | A | E | E | A |
| 210 | B | B | E | B | A |
| 211 | A | A | A | E | E |
| 212 |  | B | E | C | A |
| 213 |  | E | E | E | C |
| 214 |  | C | C | E | C |
| 215 |  | C | D | C | C |
| 216 |  | D | E | E | E |
| 216a |  | C | C | E | E |
| 216b |  | D | E | E | D |
| 217 |  | C | C | E | B |
| 219 |  | B | B | E | E |
| 220 |  | B | B | E | B |
| 300 |  | D | E | E | B |
| 301 |  | C | B | E | E |
| 302 |  | A | A | E | E |
| 303 |  | D | E | E | B |

Aripiprazole is of the formula:

Clozapine is of the formula:

Cariprazine is of the formula:

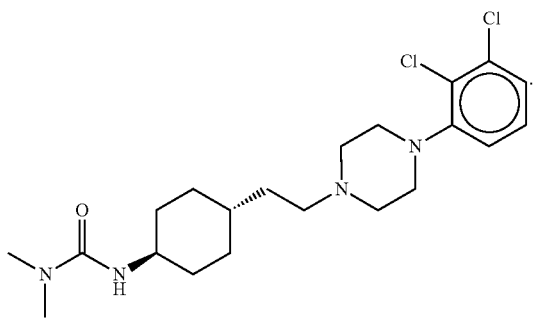

UNC9994 is of the formula:

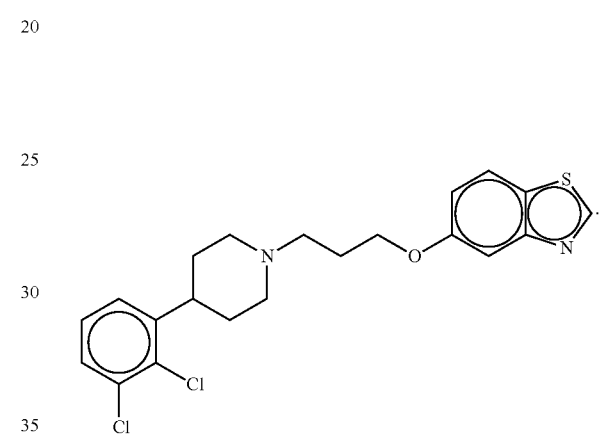

UNC9975 is of the formula:

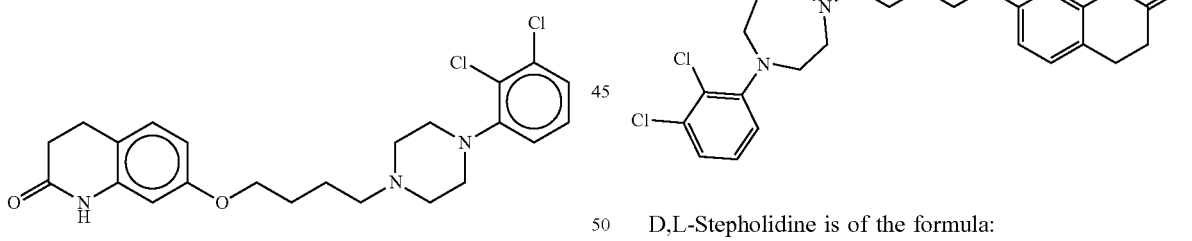

D,L-Stepholidine is of the formula:

Quinpirole is of the formula:

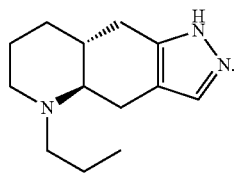 [SMILES: CCCN1CCC[C@@H]2Cc3[nH]ncc3C[C@H]21]

Dopamine is of the formula:

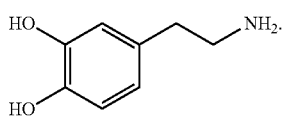

Apomorphine is of the formula:

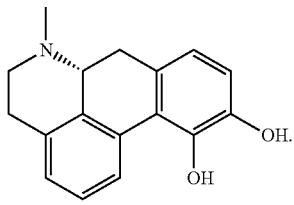 [SMILES: CN1CCc2cccc3c2[C@H]1Cc1ccc(O)c(O)c1-3]

MLS1547 is of the formula:

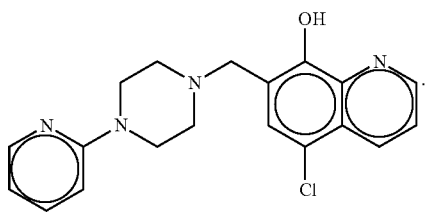

Compound 300 is of the formula:

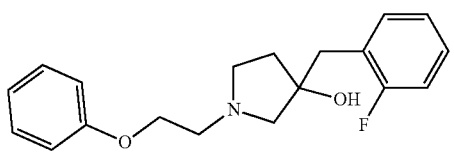 [SMILES: OC1(Cc2ccccc2F)CCN(CCOc2ccccc2)C1]

Compound 301 is of the formula:

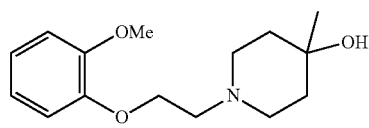 [SMILES: COc1ccccc1OCCN1CCC(C)(O)CC1]

Compound 302 is of the formula:

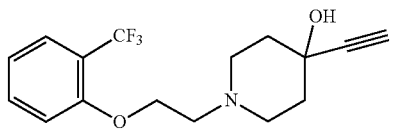 [SMILES: C#CC1(O)CCN(CCOc2ccccc2C(F)(F)F)CC1]

Compound 303 is of the formula:

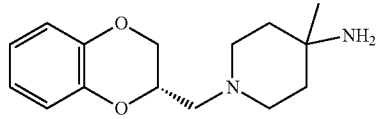 [SMILES: CC1(N)CCN(C[C@H]2COc3ccccc3O2)CC1]

EQUIVALENTS

The foregoing examples are presented for the purpose of illustrating the invention and should not be construed as imposing any limitation on the scope of the invention. It will be readily apparent that numerous modifications and alterations may be made to the specific embodiments of the invention described above and illustrated in the examples without departing from the principles underlying the invention. All such modifications and alterations not departing from the spirit or scope of the present invention are intended to be embraced by this application.

What is claimed is:

1. A method of modulating D2 receptor activity, comprising administering to a subject in need thereof an effective amount of a compound of Formula I:

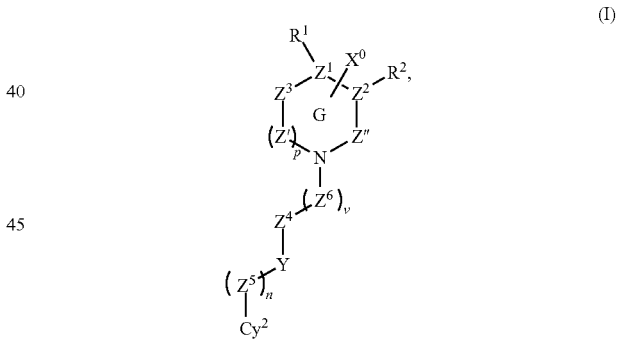

or a stereoisomer, racemate, or tautomer thereof, or a pharmaceutically acceptable salt thereof,
wherein:
$X^1$ is X-Cy$^1$, C(O)NR$^4$R$^{4'}$, NR$^4$C(O)R$^{4'}$, or CR$^3$R$^{3'}$—NR$^4$R$^{4'}$, and is bonded to $Z^1$ or $Z^2$;
X is C(O), CR$^3$R$^{3'}$, NR$^4$, O, S, S(O), or S(O)$_2$, and is bonded to $Z^1$ or $Z^2$;
$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;
each $R^4$ is independently H, $C_1$-$C_6$ alkyl, or $C_1$-$C_6$ haloalkyl;
$R^{4'}$ is $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$Z^1$ is $CR^7$;

$R^7$ is H, halogen, $C_1$-$C_6$ alkyl, or $C_1$-$C_6$ haloalkyl, or when $X^o$ or $X$ is bonded to $Z^1$, absent;

$R^1$ is H, halogen, OH, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Z^2$ is $CR^8$;

$R^8$ is H, halogen, $C_1$-$C_6$ alkyl, or $C_1$-$C_6$ haloalkyl, or when $X^o$ or $X$ is bonded to $Z^2$, absent;

$R^2$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy; or two $R^{18}$ together with the carbon atom to which they are bonded form a $C(O)$;

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, $C(O)$—$(C_1$-$C_3$ alkyl), $S(O)_q$—$(C_1$-$C_3)$ alkyl, $NH_2$, $N(C_1$-$C_6$ alkyl)$_2$, CN, $C_6$-$C_{10}$ aryl, or $NO_2$;

$Z^3$ is $C(R^9)_2$;

each $R^9$ is independently H, halogen, $C_1$-$C_6$ alkyl, or $C_1$-$C_6$ haloalkyl;

p is 1;

$Z'$ is $C(R^{12})_2$;

each $R^{12}$ is independently H, $C_1$-$C_3$ alkyl, $C_1$-$C_3$ haloalkyl, or halogen;

$Z''$ is $C(R^{13})_2$;

each $R^{13}$ is independently H, $C_1$-$C_3$ alkyl, $C_1$-$C_3$ haloalkyl, or halogen;

$Z^6$ is $C(R^{14})_2$;

v is 1;

each $R^{14}$ is independently H or $C_1$-$C_3$ alkyl;

$Z^4$ is $C(R^{10})_2$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, $C(O)$—$C_1$-$C_3$ alkyl, $S(O)_q$—$C_1$-$C_3$ alkyl, $NH_2$, $N(C_1$-$C_6$ alkyl)$_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form $C(O)$;

Y is $NR^6$, O, S, or $S(O)_2$;

$R^6$ is H, $C_1$-$C_6$ alkyl, or $C_1$-$C_6$ haloalkyl;

n is 0;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

provided that:

when $X^o$ or $X$ forms a bond with $Z^1$, then $R^1$ is not H;

when $X^o$ or $X$ forms a bond with $Z^2$, then $R^2$ is not H;

when $X$ is bonded to $Z^1$ and is $NR^4$, O, S, S(O), or $S(O)_2$, then $R^1$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl;

when $X$ is bonded to $Z^2$ and is $NR^4$, O, S, S(O), or $S(O)_2$, then $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl;

when $X$ is NH and is bonded to $Z^1$, and $R^1$ is $C(O) NH_2$, then $Cy^1$ is not unsubstituted phenyl, when $X$ is $CH_2$ and is bonded to $Z^1$, and $R^1$ is OH or halogen, then $Cy^1$ is not optionally substituted phenyl, benzoimidazolyl, benzoimidazolonyl, or dihydroquinoxaline-2,3-dione; and when $X$ is $C(O)$ and is bonded to $Z^1$, Y is O, and $R^1$ is OH or methoxy, then $Cy^1$ is not optionally substituted phenyl.

2. A method of treating a psychotic disorder comprising administering to a subject in need thereof a therapeutically effective amount of a compound of Formula I:

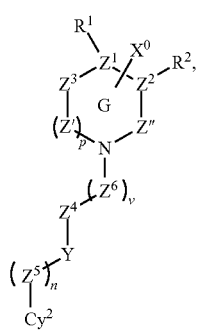

(I)

or a stereoisomer, racemate, or tautomer thereof, or a pharmaceutically acceptable salt thereof, in combination with a pharmaceutically acceptable excipient or carrier, wherein:

$X^0$ is X-$Cy^1$, C(O)$NR^4R^{4'}$, $NR^4$C(O)$R^{4'}$, or $CR^3R^{3'}$—$NR^4R^{4'}$, and is bonded to $Z^1$ or $Z^2$;

X is C(O), $CR^3R^{3'}$, $NR^4$, O, S, S(O), or S(O)$_2$, and is bonded to $Z^1$ or $Z^2$;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

each $R^4$ is independently H, $C_1$-$C_6$ alkyl, or $C_1$-$C_6$ haloalkyl;

$R^{4'}$ is $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$Z^1$ is $CR^7$;

$R^7$ is H, halogen, $C_1$-$C_6$ alkyl, or $C_1$-$C_6$ haloalkyl, or when $X^0$ or X is bonded to $Z^1$, absent;

$R^1$ is H, halogen, OH, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Z^2$ is $CR^8$;

$R^8$ is H, halogen, $C_1$-$C_6$ alkyl, or $C_1$-$C_6$ haloalkyl, or when $X^0$ or X is bonded to $Z^2$, absent;

$R^2$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy; or two $R^{18}$ together with the carbon atom to which they are bonded form a C(O);

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, $NH_2$, $N(C_1$-$C_6$ alkyl)$_2$, CN, $C_6$-$C_{10}$ aryl, or $NO_2$;

$Z^3$ is $C(R^9)_2$;

each $R^9$ is independently H, halogen, $C_1$-$C_6$ alkyl, or $C_1$-$C_6$ haloalkyl;

p is 1;

$Z'$ is $C(R^{12})_2$;

each $R^{12}$ is independently H, $C_1$-$C_3$ alkyl, $C_1$-$C_3$ haloalkyl, or halogen;

$Z''$ is $C(R^{13})_2$;

each $R^{13}$ is independently H, $C_1$-$C_3$ alkyl, $C_1$-$C_3$ haloalkyl, or halogen;

$Z^6$ is $C(R^{14})_2$;

v is 1;

each $R^{14}$ is independently H or $C_1$-$C_3$ alkyl;

$Z^4$ is $C(R^{10})_2$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, $NH_2$, $N(C_1$-$C_6$ alkyl)$_2$, CN, $C_6$-$C_{10}$ aryl, or $NO_2$; or two $R^{17}$ together with the carbon atoms to which they are bonded form a $C_6$-$C_{10}$ aryl or heteroaryl optionally substituted with one or more $R^{19}$, or each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is $NR^6$, O, S, or S(O)$_2$;

$R^6$ is H, $C_1$-$C_6$ alkyl, or $C_1$-$C_6$ haloalkyl;

n is 0;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

provided that:
when $X^0$ or X forms a bond with $Z^1$, then $R^1$ is not H;
when $X^0$ or X forms a bond with $Z^2$, then $R^2$ is not H;
when X is bonded to $Z^1$ and is $NR^4$, O, S, S(O), or $S(O)_2$, then $R^1$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl;
when X is bonded to $Z^2$ and is $NR^4$, O, S, S(O), or $S(O)_2$, then $R^2$ is not OH, $C_1$-$C_6$ alkoxy, $NR^{20}R^{21}$, $C_1$-$C_6$ haloalkoxy, $S(O)_q$—$C_1$-$C_6$ alkyl, $S(O)_2NR^{20}R^{21}$, or $NR^{20}S(O)_2$—$C_1$-$C_6$ alkyl;
when X is NH and is bonded to $Z^1$, and $R^1$ is C(O) $NH_2$, then $Cy^1$ is not unsubstituted phenyl,
when X is $CH_2$ and is bonded to $Z^1$, and $R^1$ is OH or halogen, then $Cy^1$ is not optionally substituted phenyl, benzoimidazolyl, benzoimidazolonyl, or dihydroquinoxaline-2,3-dione; and when X is C(O) and is bonded to $Z^1$, Y is O, and $R^1$ is OH or methoxy, then $Cy^1$ is not optionally substituted phenyl.

3. The method of claim 2, wherein the compound is of Formula (II):

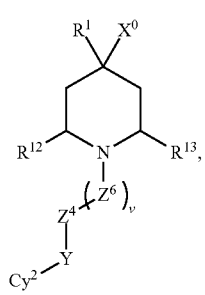

(II)

or a stereoisomer, racemate, or tautomer thereof, or a pharmaceutically acceptable salt thereof, wherein:
$R^1$ is halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy.

4. The method of claim 2, wherein the compound is of Formula (III):

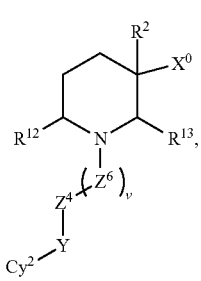

(III)

or a stereoisomer, racemate, or tautomer thereof, or a pharmaceutically acceptable salt thereof, wherein:
$X^0$ is X-$Cy^1$; and
$R^2$ is halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy.

5. The method of claim 2, wherein the compound is of formula (XI):

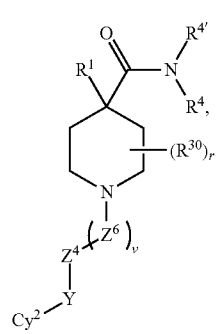

(XI)

or a stereoisomer, racemate, or tautomer thereof, or a pharmaceutically acceptable salt thereof, wherein:
$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, $C(O)NR^{20}R^{21}$, $S(O)_q$—$C_1$-$C_6$ alkyl, $S(O)_2NR^{20}R^{21}$, $NR^{20}S(O)_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;
$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;
each $R^{30}$ is independently halogen, $C_{1-3}$ alkyl, or $C_{1-3}$ haloalkyl; and
r is 0, 1, 2, 3, or 4.

6. The method of claim 2, wherein the compound is of formula (XII):

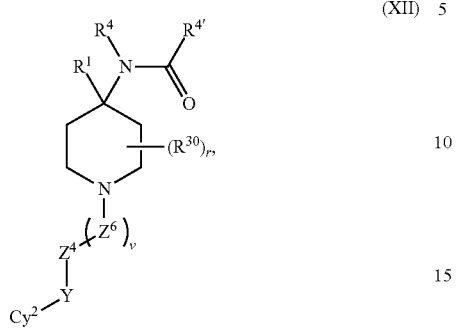

(XII)

or a stereoisomer, racemate, or tautomer thereof, or a pharmaceutically acceptable salt thereof, wherein:

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2$$NR^{20}R^{21}$, $NR^{20}$S(O)$_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

each $R^{30}$ is independently halogen, $C_{1-3}$ alkyl, or $C_{1-3}$ haloalkyl; and r is 0, 1, 2, 3, or 4.

7. The method of claim 2, wherein the compound is of formula (XIII):

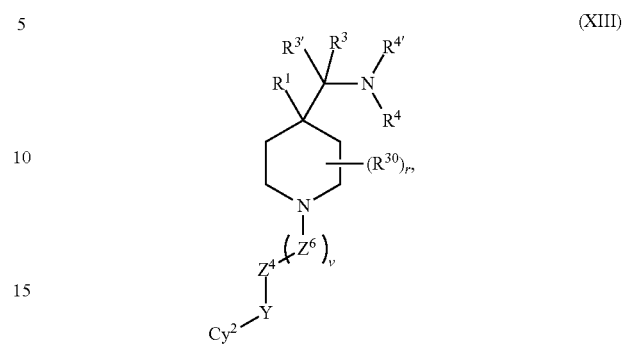

(XIII)

or a stereoisomer, racemate, or tautomer thereof, or a pharmaceutically acceptable salt thereof, wherein:

$R^1$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2$$NR^{20}R^{21}$, $NR^{20}$S(O)$_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

each $R^{30}$ is independently halogen, $C_{1-3}$ alkyl, or $C_{1-3}$ haloalkyl; and r is 0, 1, 2, 3, or 4.

8. The method of claim 2, wherein the compound is of the formula:

| Formula Number | Formula |
|---|---|
| 38 | |
| 67 | |
| 68 | |

-continued
| Formula Number | Formula |
|---|---|
| 69 | 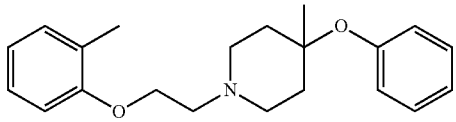 [SMILES: Cc1ccccc1OCCN1CCC(C)(Oc2ccccc2)CC1] |
| 70 | 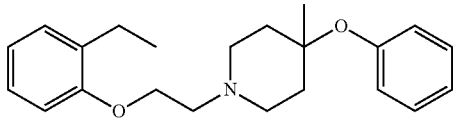 [SMILES: CCc1ccccc1OCCN1CCC(C)(Oc2ccccc2)CC1] |
| 71 | 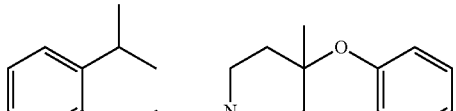 |
| 72 | 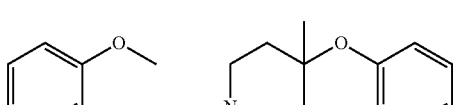 |
| 74 | 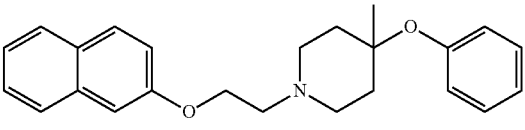 [SMILES: CC1(Oc2ccccc2)CCN(CCOc2ccc3ccccc3c2)CC1] |
| 75 | 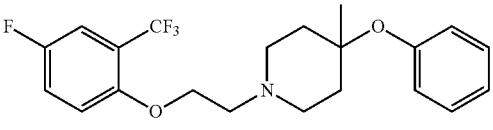 [SMILES: CC1(Oc2ccccc2)CCN(CCOc2ccc(F)cc2C(F)(F)F)CC1] |
| 76 | 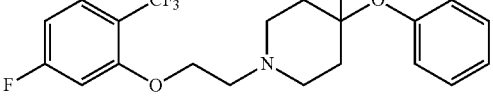 |
| 80 | 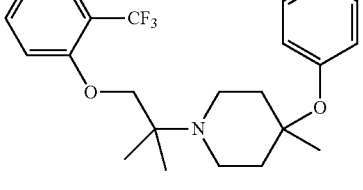 |
| 82 | 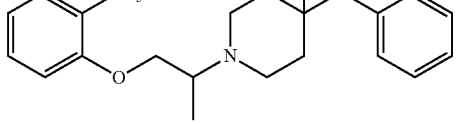 |
| 83 | 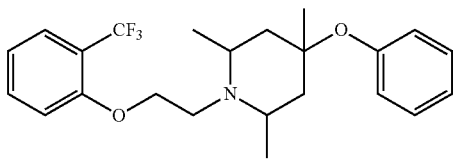 [SMILES: CC1CC(C)(Oc2ccccc2)CC(C)N1CCOc1ccccc1C(F)(F)F] |

-continued

| Formula Number | Formula |
|---|---|
| 86 | 2-(2-fluorophenoxy)ethyl-[4-methyl-4-(4-chlorophenoxy)piperidine] |
| 87 | 2-(2-fluorophenoxy)ethyl-[4-methyl-4-phenoxypiperidine] |
| 88 | 2-(2-chlorophenoxy)ethyl-[4-methyl-4-(4-chlorophenoxy)piperidine] |
| 89 | 2-(2-chlorophenoxy)ethyl-[4-methyl-4-phenoxypiperidine] |
| 90 | 2-(2-trifluoromethylphenoxy)ethyl-[4-methyl-4-(4-chlorophenoxy)piperidine] |
| 91 | 2-(2-trifluoromethylphenoxy)ethyl-[4-methyl-4-phenoxypiperidine] |
| 103 | 2-(2-trifluoromethylphenoxy)ethyl-[4-hydroxy-4-(hydroxy(phenyl)methyl)piperidine] |
| 104 | 2-(2-trifluoromethylphenoxy)ethyl-[4-methyl-4-(2-chlorophenoxy)piperidine] |
| 105 | 2-(2-trifluoromethylphenoxy)ethyl-[4-methyl-4-(pyridin-2-yloxy)piperidine] |
| 106 | 2-(2-trifluoromethylphenoxy)ethyl-[4-methyl-4-benzoylpiperidine] |
| 107 | 2-(2-trifluoromethylphenoxy)ethyl-[4-methyl-4-(hydroxy(phenyl)methyl)piperidine] |

-continued
| Formula Number | Formula |
|---|---|
| 109 | 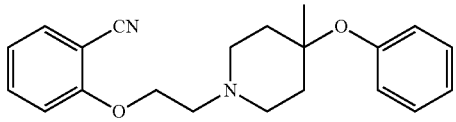 [SMILES: CC1(Oc2ccccc2)CCN(CCOc2ccccc2C#N)CC1] |
| 110 | 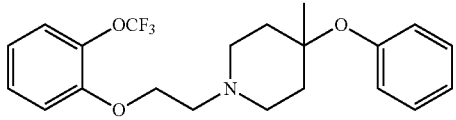 [SMILES: CC1(Oc2ccccc2)CCN(CCOc2ccccc2OC(F)(F)F)CC1] |
| 111 | 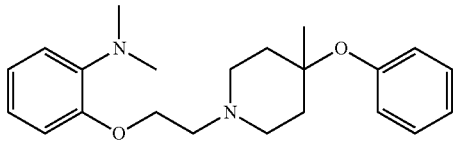 [SMILES: CN(C)c1ccccc1OCCN1CCC(C)(Oc2ccccc2)CC1] |
| 112 | 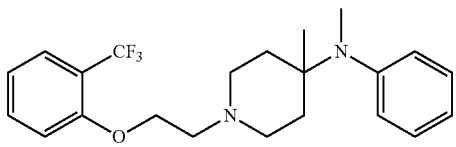 [SMILES: CN(c1ccccc1)C1(C)CCN(CCOc2ccccc2C(F)(F)F)CC1] |
| 122 | 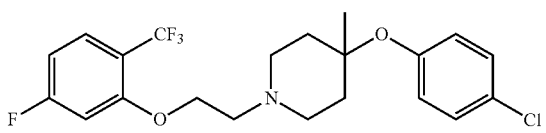 [SMILES: CC1(Oc2ccc(Cl)cc2)CCN(CCOc2cc(F)ccc2C(F)(F)F)CC1] |
| 125 | 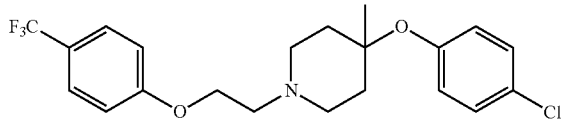 [SMILES: CC1(Oc2ccc(Cl)cc2)CCN(CCOc2ccc(C(F)(F)F)cc2)CC1] |
| 126 | 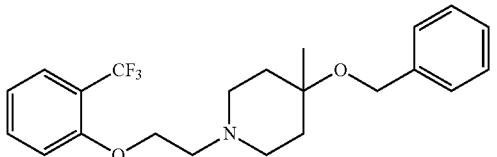 |
| 127 | 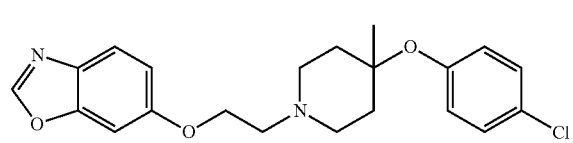 [SMILES: CC1(Oc2ccc(Cl)cc2)CCN(CCOc2ccc3ncoc3c2)CC1] |
| 128 | 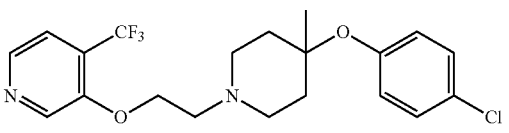 [SMILES: CC1(Oc2ccc(Cl)cc2)CCN(CCOc2cnccc2C(F)(F)F)CC1] |
| 129 | 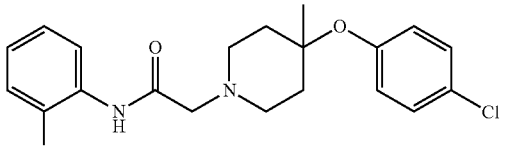 |

-continued

| Formula Number | Formula |
|---|---|
| 141 | 2-(SO2Me)phenyl-O-CH2CH2-N(4-methyl-4-phenoxypiperidine) |
| 143 | cyclohexyl-O-CH2CH2-N(4-methyl-4-(4-chlorophenoxy)piperidine) |
| 146 | 2-(OCF3)phenyl-O-CH2CH2-N(4-methyl-4-(4-chlorophenoxy)piperidine) |
| 147 | 6-(CF3)pyridin-3-yl-O-CH2CH2-N(4-methyl-4-(4-chlorophenoxy)piperidine) |
| 148 | 5-(CF3)pyridin-2-yl-O-CH2CH2-N(4-methyl-4-(4-chlorophenoxy)piperidine) |
| 149 | 4-F-phenyl-O-CH2CH2-N(4-methyl-4-(4-chlorophenoxy)piperidine) |
| 150 | 4-Me-phenyl-O-CH2CH2-N(4-methyl-4-(4-chlorophenoxy)piperidine) |
| 151 | 4-Cl-phenyl-O-CH2CH2-N(4-methyl-4-(4-chlorophenoxy)piperidine) |
| 152 | 4-(MeO2S)phenyl-O-CH2CH2-N(4-methyl-4-(4-chlorophenoxy)piperidine) |
| 153 | 4-acetylphenyl-O-CH2CH2-N(4-methyl-4-(4-chlorophenoxy)piperidine) |
| 154 | 4-(1-hydroxyethyl)phenyl-O-CH2CH2-N(4-methyl-4-(4-chlorophenoxy)piperidine) |

-continued

| Formula Number | Formula |
|---|---|
| 155 | |
| 156 | |
| 157 | |
| 158 | |
| 159 | |
| 160 | |
| 161 | |
| 162 | |
| 163 | |
| 164 | |
| 165 | |

-continued
| Formula Number | Formula |
|---|---|
| 166 | 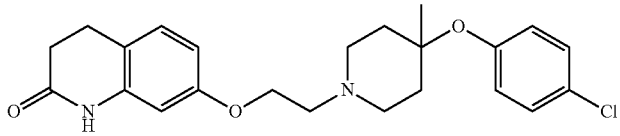 [SMILES: CC1(Oc2ccc(Cl)cc2)CCN(CCOc2ccc3c(c2)NC(=O)CC3)CC1] |
| 167 | 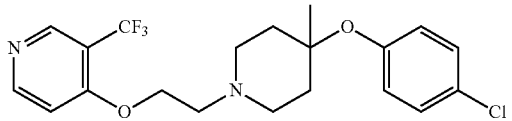 [SMILES: CC1(Oc2ccc(Cl)cc2)CCN(CCOc2ccncc2C(F)(F)F)CC1] |
| 168 | 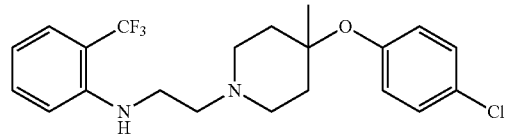 [SMILES: CC1(Oc2ccc(Cl)cc2)CCN(CCNc2ccccc2C(F)(F)F)CC1] |
| 169 | 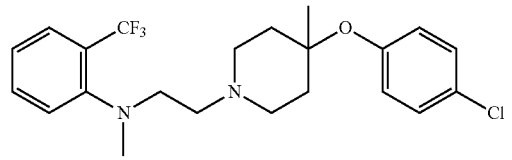 [SMILES: CN(CCN1CCC(C)(Oc2ccc(Cl)cc2)CC1)c1ccccc1C(F)(F)F] |
| 170 | 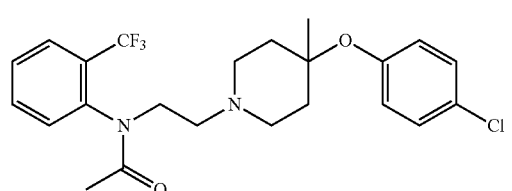 |
| 171 | 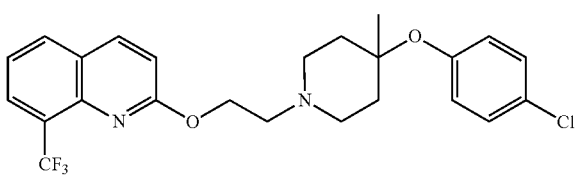 [SMILES: CC1(Oc2ccc(Cl)cc2)CCN(CCOc2ccc3cccc(C(F)(F)F)c3n2)CC1] |
| 173 | 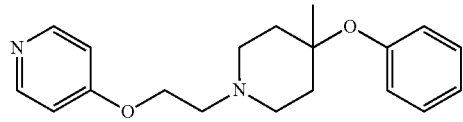 [SMILES: CC1(Oc2ccccc2)CCN(CCOc2ccncc2)CC1] |
| 174 | 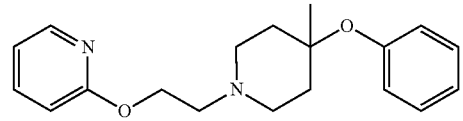 [SMILES: CC1(Oc2ccccc2)CCN(CCOc2ccccn2)CC1] |
| 175 | 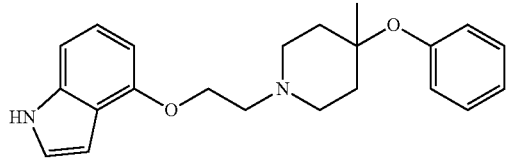 [SMILES: CC1(Oc2ccccc2)CCN(CCOc2cccc3[nH]ccc23)CC1] |
| 182 | 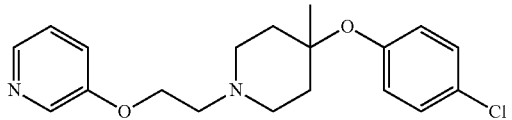 [SMILES: CC1(Oc2ccc(Cl)cc2)CCN(CCOc2cccnc2)CC1] |

-continued

| Formula Number | Formula |
|---|---|
| 183 | |
| 184 | |
| 185 | |
| 186 | |
| 187 | |
| 188 | |
| 189 | |
| 190 | |
| 191 | |

-continued
| Formula Number | Formula |
|---|---|
| 192 | 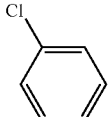 |
| 215 | 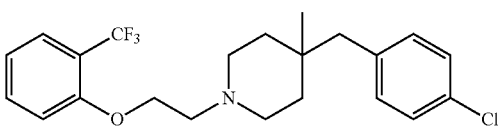 [SMILES: CC1(Cc2ccc(Cl)cc2)CCN(CCOc2ccccc2C(F)(F)F)CC1] |
| 217 | 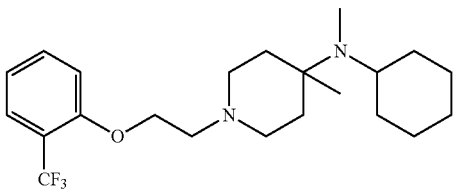 [SMILES: CN(C1CCCCC1)C1(C)CCN(CCOc2ccccc2C(F)(F)F)CC1] |
| 61 | 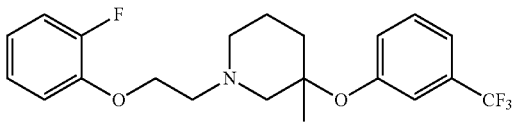 |
| 62 | 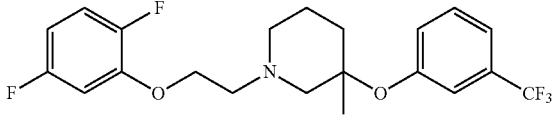 [SMILES: CC1(Oc2cccc(C(F)(F)F)c2)CCCN(CCOc2cc(F)ccc2F)C1] |
| 63 | 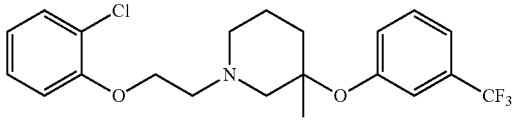 [SMILES: CC1(Oc2cccc(C(F)(F)F)c2)CCCN(CCOc2ccccc2Cl)C1] |
| 96 | 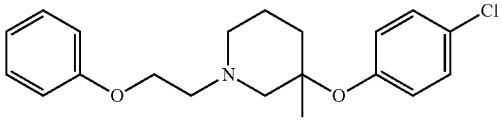 [SMILES: CC1(Oc2ccc(Cl)cc2)CCCN(CCOc2ccccc2)C1] |
| 97 | 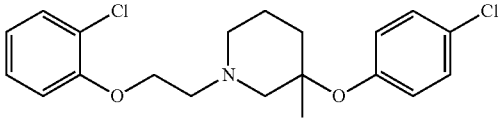 [SMILES: CC1(Oc2ccc(Cl)cc2)CCCN(CCOc2ccccc2Cl)C1] |
| 98 | 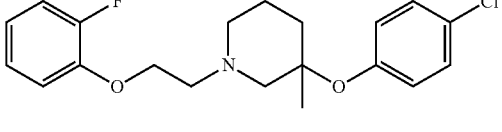 |
| 99 | 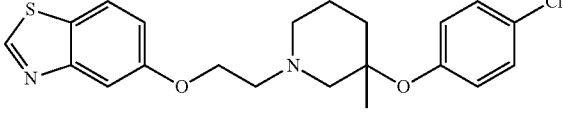 |

-continued
| Formula Number | Formula |
|---|---|
| 100 | 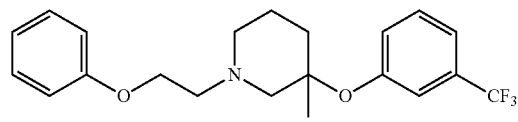 [SMILES: CC1(Oc2cccc(C(F)(F)F)c2)CCCN(CCOc2ccccc2)C1] |
| 108 | 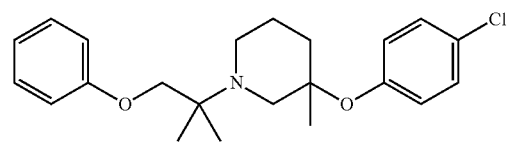 [SMILES: CC1(Oc2ccc(Cl)cc2)CCCN(C(C)(C)COc2ccccc2)C1] |
| 198 | 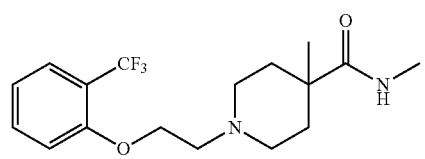 |
| 199 | 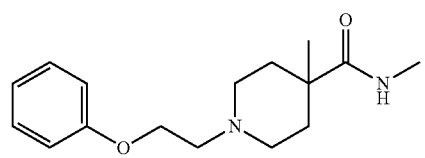 [SMILES: CNC(=O)C1(C)CCN(CCOc2ccccc2)CC1] |
| 200 | 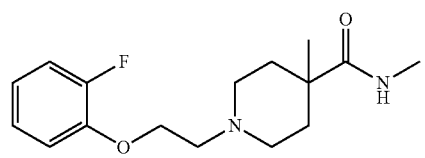 [SMILES: CNC(=O)C1(C)CCN(CCOc2ccccc2F)CC1] |
| 201 | 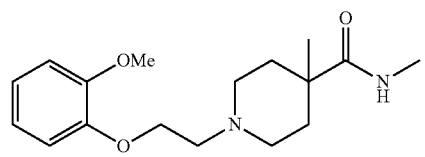 [SMILES: CNC(=O)C1(C)CCN(CCOc2ccccc2OC)CC1] |
| 219 | 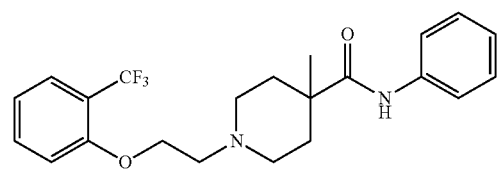 |
| 220 | 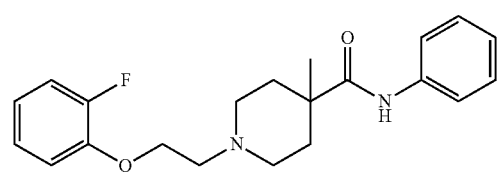 [SMILES: CC1(C(=O)Nc2ccccc2)CCN(CCOc2ccccc2F)CC1] | or a stereoisomer, racemate, or tautomer thereof, or a pharmaceutically acceptable salt thereof.

9. The method of claim 2, wherein $X^0$ is X-Cy$^1$, and X is O.

10. The method of claim 2, wherein $X^0$ is C(O)NR$^4$R$^{4'}$ or NR$^4$C(O)R$^{4'}$.

11. The method of claim 2, wherein Cy$^1$ is phenyl optionally substituted with one or more R$^{16}$.

12. The method of claim 2, wherein R$^1$ is —CH$_3$.

13. The method of claim 2, wherein Y is O.

14. The method of claim 2, wherein Cy$^2$ is phenyl optionally substituted with one or more R$^{17}$.

15. The method of claim 2, wherein the compound is of the formula:

| Formula Number | Formula |
|---|---|
| 76 | |
| 90 | |
| 91 | |
| 110 | |
| 122 | |
| 146 | |
| 157 | | or a stereoisomer, racemate, or tautomer thereof, or a pharmaceutically acceptable salt thereof.

16. The method of claim 3, wherein the compound is of the formula:

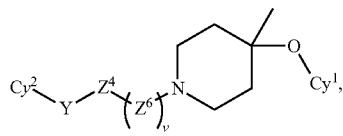

or a stereoisomer, racemate, or tautomer thereof, or a pharmaceutically acceptable salt thereof.

17. The method of claim 3, wherein the compound is of the formula:

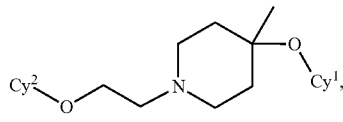

or a stereoisomer, racemate, or tautomer thereof, or a pharmaceutically acceptable salt thereof.

18. The method of claim 3, wherein the compound is of the formula:

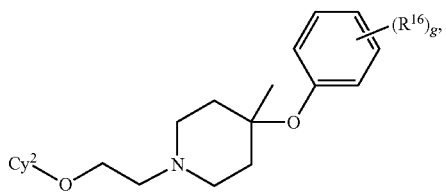

or a stereoisomer, racemate, or tautomer thereof, or a pharmaceutically acceptable salt thereof, wherein g is 0, 1, 2, 3, 4, or 5.

19. The method of claim 3, wherein the compound is of the formula:

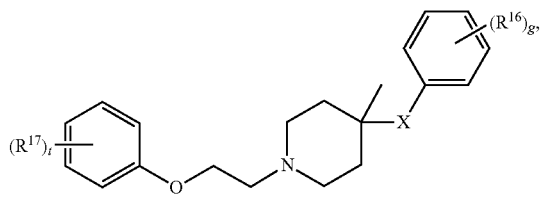

or a stereoisomer, racemate, or tautomer thereof, or a pharmaceutically acceptable salt thereof, wherein g is 0, 1, 2, 3, 4, or 5; and t is 0, 1, 2, 3, 4, or 5.

20. The method of claim 3, wherein the compound is of the formula:

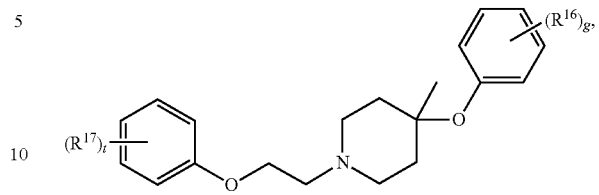

or a stereoisomer, racemate, or tautomer thereof, or a pharmaceutically acceptable salt thereof, wherein g is 0, 1, 2, 3, 4, or 5; and t is 0, 1, 2, 3, 4, or 5.

21. The method of claim 3, wherein the compound is of the formula:

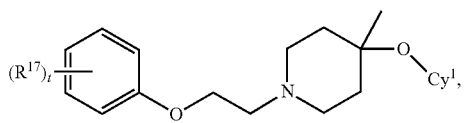

or a stereoisomer, racemate, or tautomer thereof, or a pharmaceutically acceptable salt thereof, wherein t is 0, 1, 2, 3, 4, or 5.

22. The method of claim 10, or a stereoisomer, racemate, or tautomer thereof, or a pharmaceutically acceptable salt thereof, wherein $R^{4'}$ is $C_1$-$C_6$ alkyl, $C_1$-$C_6$ haloalkyl, or $C_3$-$C_8$ cycloalkyl, wherein the cycloalkyl is optionally substituted with one or more $R^{17}$.

23. The method of claim 2, wherein the psychotic disorder is schizophrenia.

24. The method of claim 2, wherein the psychotic disorder is brief psychotic disorder.

25. The method of claim 2, wherein the psychotic disorder is delusional disorder.

26. The method of claim 2, wherein the psychotic disorder is schizoaffective disorder.

27. The method of claim 2, wherein the psychotic disorder is schizophreniform.

28. The method of claim 2, wherein the psychotic disorder is shared psychotic disorder.

29. The method of claim 8, wherein the psychotic disorder is schizophrenia.

30. A method of preventing a psychotic disorder comprising administering to a subject in need thereof a prophylactically effective amount of a compound of Formula I:

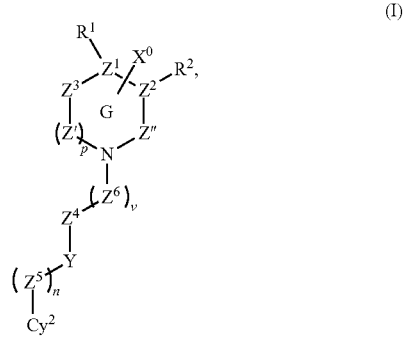

(I)

or a stereoisomer, racemate, or tautomer thereof, or a pharmaceutically acceptable salt thereof, in combination with a pharmaceutically acceptable excipient or carrier, wherein:

$X^0$ is X-$Cy^1$, C(O)$NR^4R^{4'}$, $NR^4$C(O)$R^{4'}$, or $CR^3R^{3'}$—$NR^4R^{4'}$, and is bonded to $Z^1$ or $Z^2$;

X is C(O), $CR^3R^{3'}$, $NR^4$, O, S, S(O), or S(O)$_2$, and is bonded to $Z^1$ or $Z^2$;

$R^3$ and $R^{3'}$ are each independently H, $C_1$-$C_6$ alkyl, OH, $C_1$-$C_6$ alkoxy, $C_1$-$C_6$ haloalkyl, $C_1$-$C_6$ haloalkoxy, or halogen;

each $R^4$ is independently H, $C_1$-$C_6$ alkyl, or $C_1$-$C_6$ haloalkyl;

$R^{4'}$ is $C_1$-$C_6$ alkyl, $C_1$-$C_6$ haloalkyl, $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

or $R^4$ and $R^{4'}$ on the same nitrogen atom together with the nitrogen atom form a monocyclic, 4- to 7-membered heterocyclyl ring optionally substituted with one or more $R^{18}$;

$Z^1$ is $CR^7$;

$R^7$ is H, halogen, $C_1$-$C_6$ alkyl, or $C_1$-$C_6$ haloalkyl, or when $X^0$ or X is bonded to $Z^1$, absent;

$R^1$ is H, halogen, OH, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2NR^{20}R^{21}$, $NR^{20}$S(O)$_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

$Z^2$ is $CR^8$;

$R^8$ is H, halogen, $C_1$-$C_6$ alkyl, or $C_1$-$C_6$ haloalkyl, or when $X^0$ or X is bonded to $Z^2$, absent;

$R^2$ is H, halogen, OH, $C_1$-$C_6$ alkyl, $C_1$-$C_6$ haloalkyl, $C_1$-$C_6$ alkoxy, $C_1$-$C_6$ haloalkoxy, $NR^{20}R^{21}$, C(O)$NR^{20}R^{21}$, S(O)$_q$—$C_1$-$C_6$ alkyl, S(O)$_2NR^{20}R^{21}$, $NR^{20}$S(O)$_2$—$C_1$-$C_6$ alkyl, $C_6$-$C_{10}$ aryl, benzyl, heteroaryl comprising one 5- or 6-membered ring and one to four heteroatoms independently selected from N, O, and S, $C_3$-$C_6$ cycloalkyl, or heterocyclyl comprising one 4- to 6-membered ring and one to four heteroatoms independently selected from N, O, and S, wherein the aryl, benzyl, heteroaryl, cycloalkyl, and heterocyclyl are independently optionally substituted with one or more substituents independently selected from halogen, $C_1$-$C_6$ alkyl, OH, $C_1$-$C_6$ alkoxy, $C_1$-$C_6$ haloalkyl, and $C_1$-$C_6$ haloalkoxy;

each $R^{18}$ is independently halogen, $C_1$-$C_6$ alkyl, $C_1$-$C_6$ alkoxy, $C_1$-$C_6$ haloalkyl, or $C_1$-$C_6$ haloalkoxy; or two $R^{18}$ together with the carbon atom to which they are bonded form a C(O);

q is 0, 1, or 2;

$R^{20}$ and $R^{21}$ are each independently H, $C_1$-$C_6$ alkyl, $C_1$-$C_6$ haloalkyl, or $C_6$-$C_{10}$ aryl, wherein the aryl is optionally substituted with one or more substituents independently selected from $C_1$-$C_6$ alkyl, $C_1$-$C_6$ alkoxy, $C_1$-$C_6$ haloalkyl, $C_1$-$C_6$ haloalkoxy, and halogen;

$Cy^1$ is $C_6$-$C_{10}$ aryl, benzyl, or heteroaryl comprising one or two 5- or 6-membered rings and one to four heteroatoms independently selected from N, O, and S, wherein each ring is aromatic or partially unsaturated, wherein the aryl, benzyl, and heteroaryl are independently optionally substituted with one or more $R^{16}$;

each $R^{16}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—($C_1$-$C_3$ alkyl), S(O)$_q$—($C_1$-$C_3$) alkyl, $NH_2$, N($C_1$-$C_6$ alkyl)$_2$, CN, $C_6$-$C_{10}$ aryl, or $NO_2$;

$Z^3$ is $C(R^9)_2$;

each $R^9$ is independently H, halogen, $C_1$-$C_6$ alkyl, or $C_1$-$C_6$ haloalkyl;

p is 1;

$Z'$ is $C(R^{12})_2$;

each $R^{12}$ is independently H, $C_1$-$C_3$ alkyl, $C_1$-$C_3$ haloalkyl, or halogen;

$Z''$ is $C(R^{13})_2$;

each $R^{13}$ is independently H, $C_1$-$C_3$ alkyl, $C_1$-$C_3$ haloalkyl, or halogen;

$Z^6$ is $C(R^{14})_2$;

v is 1;

each $R^{14}$ is independently H or $C_1$-$C_3$ alkyl;

$Z^4$ is $C(R^{10})_2$;

each $R^{17}$ is independently halogen, $C_1$-$C_6$ alkyl, OH, $C_1$-$C_6$ alkoxy, $C_1$-$C_6$ haloalkyl, $C_1$-$C_6$ haloalkoxy, C(O)—$C_1$-$C_3$ alkyl, S(O)$_q$—$C_1$-$C_3$ alkyl, $NH_2$, N($C_1$-$C_6$ alkyl)$_2$, CN, $C_6$-$C_{10}$ aryl, or $NO_2$; or two $R^{17}$ together with the carbon atoms to which they are bonded form a $C_0$-$C_{i0}$ aryl or heteroaryl optionally substituted with one or more $R^{19}$, or each $R^{19}$ is independently $C_1$-$C_6$ alkyl, $C_1$-$C_6$ alkoxy, $C_1$-$C_6$ haloalkyl, $C_1$-$C_6$ haloalkoxy, or halogen;

each $R^{10}$ is independently H, $C_1$-$C_6$ alkyl, $C_1$-$C_6$ haloalkyl, or halogen; or two $R^{10}$ together with the carbon atom to which they are bonded, form C(O);

Y is $NR^6$, O, S, or S(O)$_2$;

$R^6$ is H, $C_1$-$C_6$ alkyl, or $C_1$-$C_6$ haloalkyl;

n is 0;

$Cy^2$ is $C_3$-$C_8$ cycloalkyl, heterocyclyl comprising one 4- to 7-membered ring and one to four heteroatoms independently selected from N, O, and S, $C_6$-$C_{10}$ aryl, or heteroaryl comprising one or two 5- or 6-membered rings and one to four heteroatoms independently selected from N, O, and S, wherein the cycloalkyl, heterocyclyl, aryl, and heteroaryl are independently optionally substituted with one or more $R^{17}$;

provided that:

when $X^0$ or X forms a bond with $Z^1$, then $R^1$ is not H;

when $X^0$ or X forms a bond with $Z^2$, then $R^2$ is not H;

when X is bonded to $Z^1$ and is $NR^4$, O, S, S(O), or S(O)$_2$, then $R^1$ is not OH, $C_1$-$C_6$ alkoxy, $NR^{20}R^{21}$, $C_1$-$C_6$ haloalkoxy, S(O)$_q$—$C_1$-$C_6$ alkyl, S(O)$_2NR^{20}R^{21}$, or $NR^{20}$S(O)$_2$—$C_1$-$C_6$ alkyl;

when X is bonded to $Z^2$ and is $NR^4$, O, S, S(O), or S(O)$_2$, then $R^2$ is not OH, $C_1$-$C_6$ alkoxy, $NR^{20}R^{21}$, $C_1$-$C_6$ haloalkoxy, S(O)$_q$—$C_1$-$C_6$ alkyl, S(O)$_2NR^{20}R^{21}$, or $NR^{20}$S(O)$_2$—$C_1$-$C_6$ alkyl;

when X is NH and is bonded to $Z^1$, and $R^1$ is C(O) $NH_2$, then $Cy^1$ is not unsubstituted phenyl, when X is $CH_2$ and is bonded to $Z^1$, and $R^1$ is OH or halogen, then $Cy^1$ is not optionally substituted phenyl, benzoimidazolyl, benzoimidazolonyl, or dihydroquinoxaline-2,3-dione; and when X is C(O) and is bonded to $Z^1$, Y is O, and $R^1$ is OH or methoxy, then $Cy^1$ is not optionally substituted phenyl.

31. The method of claim 1, wherein the compound is of the formula:
| Formula Number | Formula |
|---|---|
| 38 | 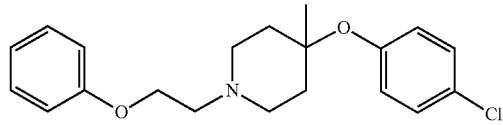 [SMILES: CC1(Oc2ccc(Cl)cc2)CCN(CCOc2ccccc2)CC1] |
| 67 | 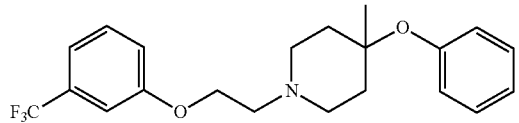 [SMILES: CC1(Oc2ccccc2)CCN(CCOc2cccc(C(F)(F)F)c2)CC1] |
| 68 | 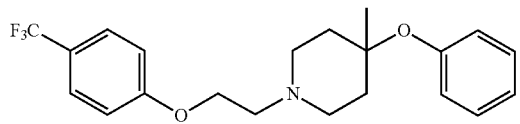 [SMILES: CC1(Oc2ccccc2)CCN(CCOc2ccc(C(F)(F)F)cc2)CC1] |
| 69 | 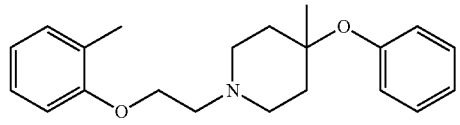 [SMILES: Cc1ccccc1OCCN1CCC(C)(Oc2ccccc2)CC1] |
| 70 | 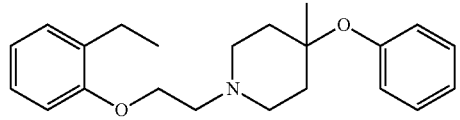 [SMILES: CCc1ccccc1OCCN1CCC(C)(Oc2ccccc2)CC1] |
| 71 | 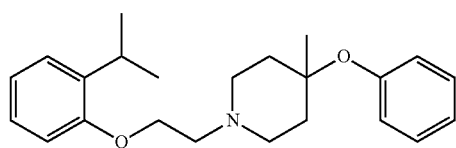 [SMILES: CC(C)c1ccccc1OCCN1CCC(C)(Oc2ccccc2)CC1] |
| 72 | 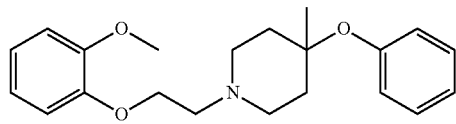 [SMILES: COc1ccccc1OCCN1CCC(C)(Oc2ccccc2)CC1] |
| 74 | 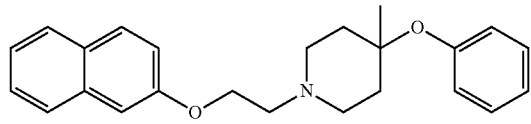 [SMILES: CC1(Oc2ccccc2)CCN(CCOc2ccc3ccccc3c2)CC1] |
| 75 | 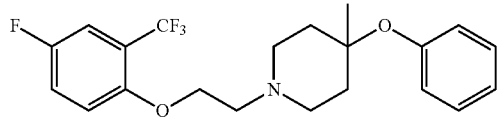 [SMILES: CC1(Oc2ccccc2)CCN(CCOc2ccc(F)cc2C(F)(F)F)CC1] |
| 76 | 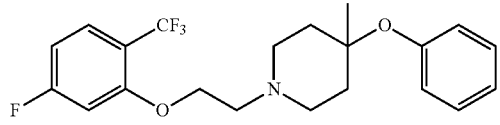 [SMILES: CC1(Oc2ccccc2)CCN(CCOc2cc(F)ccc2C(F)(F)F)CC1] |

-continued
| Formula Number | Formula |
|---|---|
| 80 | 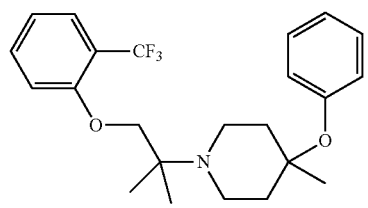 [SMILES: CC1(Oc2ccccc2)CCN(C(C)(C)COc2ccccc2C(F)(F)F)CC1] |
| 82 | 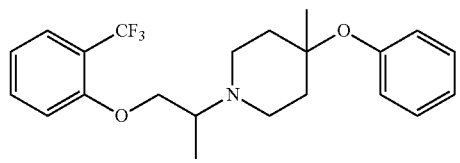 [SMILES: CC(COc1ccccc1C(F)(F)F)N1CCC(C)(Oc2ccccc2)CC1] |
| 83 | 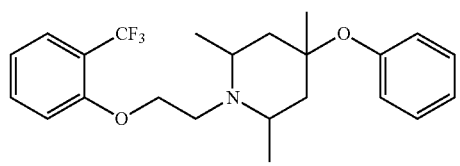 [SMILES: CC1CC(C)(Oc2ccccc2)CC(C)N1CCOc1ccccc1C(F)(F)F] |
| 86 | 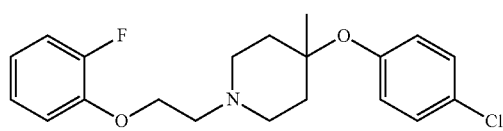 |
| 87 | 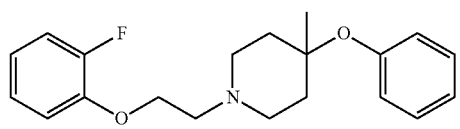 [SMILES: CC1(Oc2ccccc2)CCN(CCOc2ccccc2F)CC1] |
| 88 | 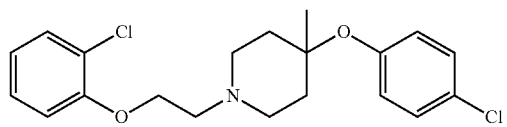 |
| 89 | 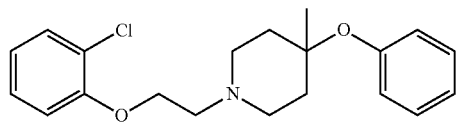 [SMILES: CC1(Oc2ccccc2)CCN(CCOc2ccccc2Cl)CC1] |
| 90 | 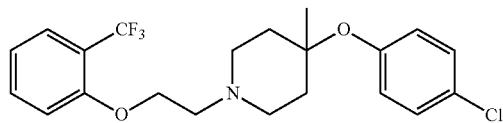 |
| 91 | 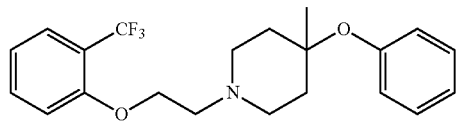 [SMILES: CC1(Oc2ccccc2)CCN(CCOc2ccccc2C(F)(F)F)CC1] |
| 103 | 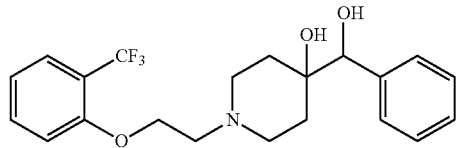 [SMILES: OC(c1ccccc1)C1(O)CCN(CCOc2ccccc2C(F)(F)F)CC1] |

-continued
| Formula Number | Formula |
|---|---|
| 104 | 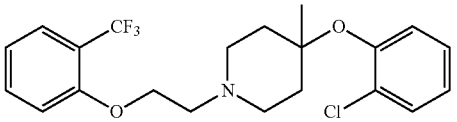 [SMILES: CC1(Oc2ccccc2Cl)CCN(CCOc2ccccc2C(F)(F)F)CC1] |
| 105 | 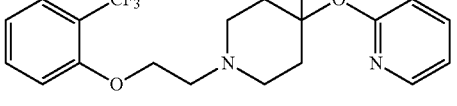 |
| 106 | 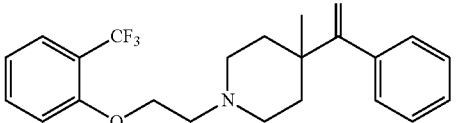 |
| 107 | 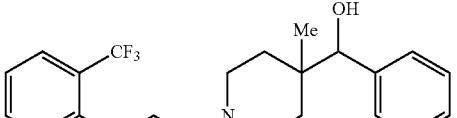 |
| 109 | 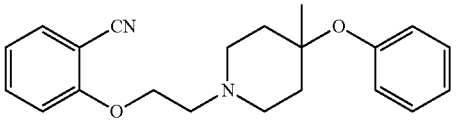 [SMILES: CC1(Oc2ccccc2)CCN(CCOc2ccccc2C#N)CC1] |
| 110 | 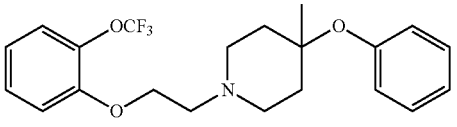 [SMILES: CC1(Oc2ccccc2)CCN(CCOc2ccccc2OC(F)(F)F)CC1] |
| 111 | 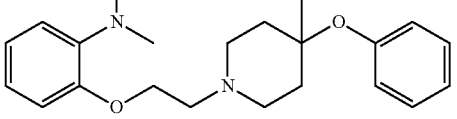 |
| 112 | 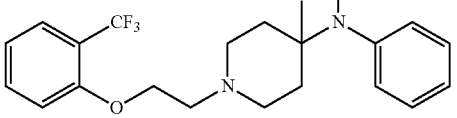 |
| 122 | 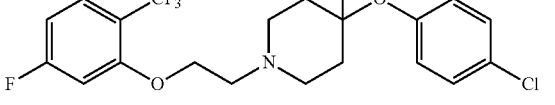 |
| 125 | 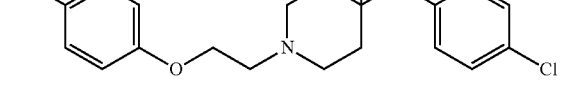 |

-continued
| Formula Number | Formula |
|---|---|
| 126 | 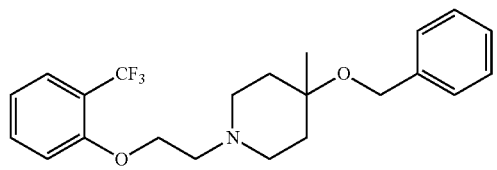 [SMILES: CC1(OCc2ccccc2)CCN(CCOc2ccccc2C(F)(F)F)CC1] |
| 127 | 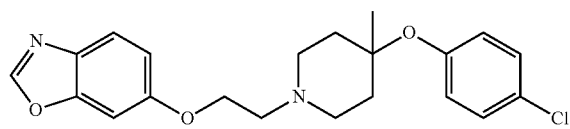 [SMILES: CC1(Oc2ccc(Cl)cc2)CCN(CCOc2ccc3ncoc3c2)CC1] |
| 128 | 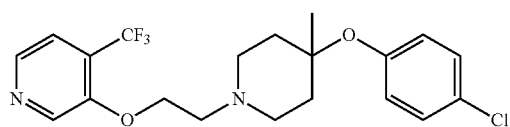 [SMILES: CC1(Oc2ccc(Cl)cc2)CCN(CCOc2cnccc2C(F)(F)F)CC1] |
| 129 | 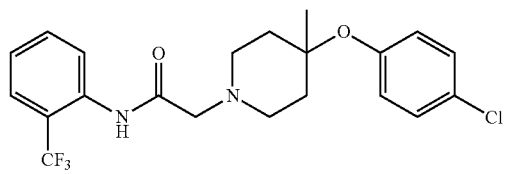 [SMILES: CC1(Oc2ccc(Cl)cc2)CCN(CC(=O)Nc2ccccc2C(F)(F)F)CC1] |
| 141 | 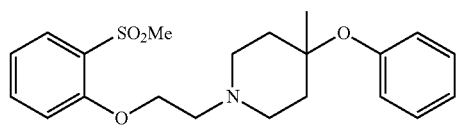 [SMILES: CC1(Oc2ccccc2)CCN(CCOc2ccccc2S(C)(=O)=O)CC1] |
| 143 | 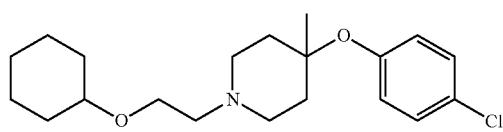 [SMILES: CC1(Oc2ccc(Cl)cc2)CCN(CCOC2CCCCC2)CC1] |
| 146 | 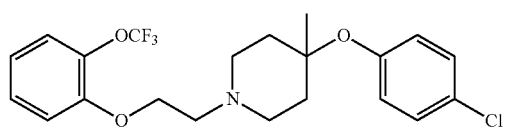 |
| 147 | 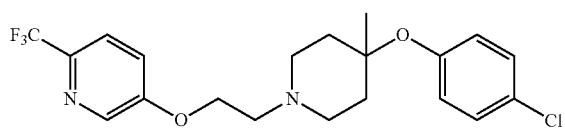 [SMILES: CC1(Oc2ccc(Cl)cc2)CCN(CCOc2ccc(C(F)(F)F)nc2)CC1] |
| 148 | 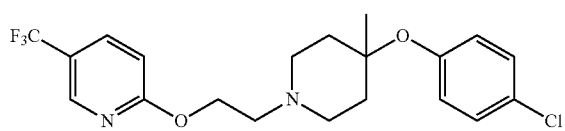 [SMILES: CC1(Oc2ccc(Cl)cc2)CCN(CCOc2ccc(C(F)(F)F)cn2)CC1] |
| 149 | 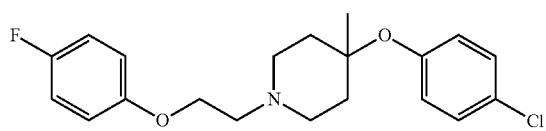 [SMILES: CC1(Oc2ccc(Cl)cc2)CCN(CCOc2ccc(F)cc2)CC1] |
| 150 | 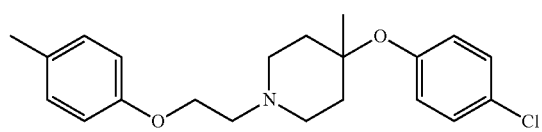 [SMILES: Cc1ccc(OCCN2CCC(C)(Oc3ccc(Cl)cc3)CC2)cc1] |

-continued
| Formula Number | Formula |
|---|---|
| 151 | 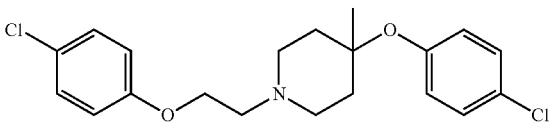 [SMILES: CC1(Oc2ccc(Cl)cc2)CCN(CCOc2ccc(Cl)cc2)CC1] |
| 152 | 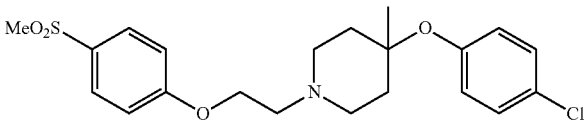 [SMILES: CC1(Oc2ccc(Cl)cc2)CCN(CCOc2ccc(S(C)(=O)=O)cc2)CC1] |
| 153 | 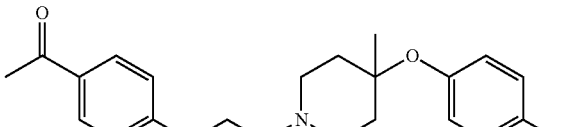 |
| 154 | 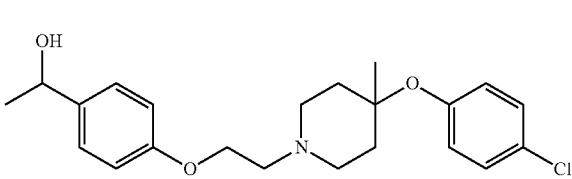 [SMILES: CC(O)c1ccc(OCCN2CCC(C)(Oc3ccc(Cl)cc3)CC2)cc1] |
| 155 | 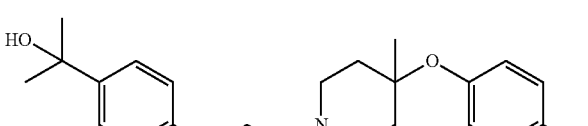 |
| 156 | 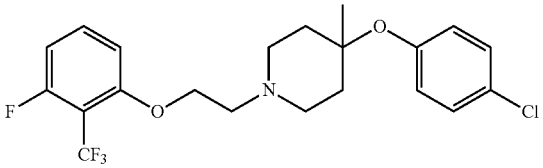 [SMILES: CC1(Oc2ccc(Cl)cc2)CCN(CCOc2cccc(F)c2C(F)(F)F)CC1] |
| 157 | 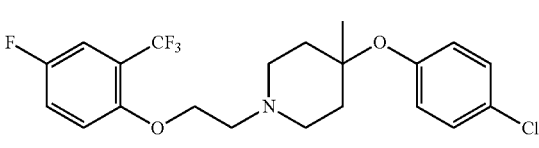 [SMILES: CC1(Oc2ccc(Cl)cc2)CCN(CCOc2ccc(F)cc2C(F)(F)F)CC1] |
| 158 | 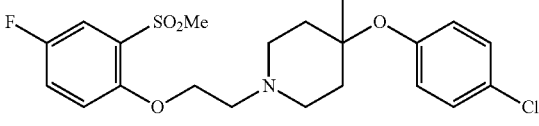 [SMILES: CC1(Oc2ccc(Cl)cc2)CCN(CCOc2ccc(F)cc2S(C)(=O)=O)CC1] |
| 159 | 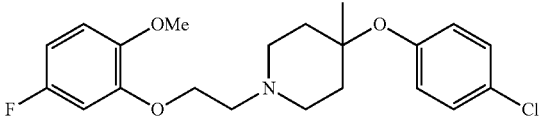 [SMILES: COc1ccc(F)cc1OCCN1CCC(C)(Oc2ccc(Cl)cc2)CC1] |
| 160 | 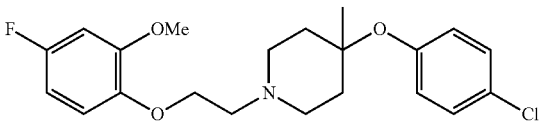 [SMILES: COc1cc(F)ccc1OCCN1CCC(C)(Oc2ccc(Cl)cc2)CC1] |

-continued
| Formula Number | Formula |
|---|---|
| 161 | 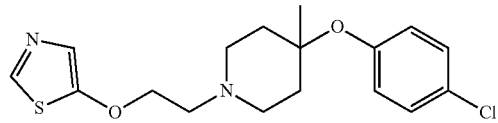 [SMILES: CC1(Oc2ccc(Cl)cc2)CCN(CCOc2cncs2)CC1] |
| 162 | 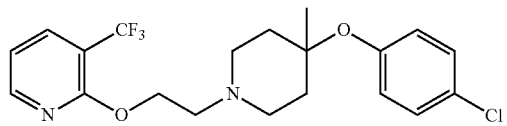 |
| 163 | 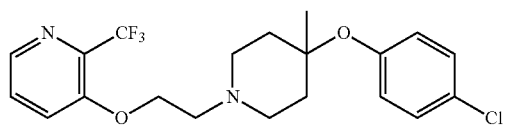 [SMILES: CC1(Oc2ccc(Cl)cc2)CCN(CCOc2cccnc2C(F)(F)F)CC1] |
| 164 | 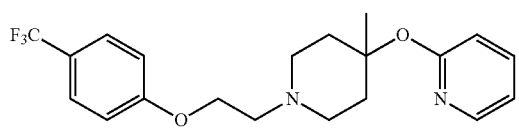 [SMILES: CC1(Oc2ccccn2)CCN(CCOc2ccc(C(F)(F)F)cc2)CC1] |
| 165 | 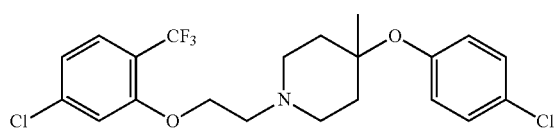 [SMILES: CC1(Oc2ccc(Cl)cc2)CCN(CCOc2cc(Cl)ccc2C(F)(F)F)CC1] |
| 166 | 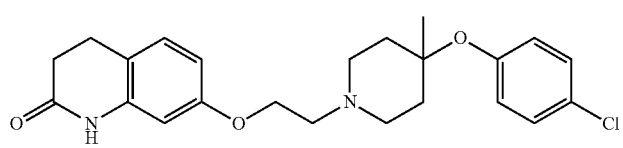 [SMILES: CC1(Oc2ccc(Cl)cc2)CCN(CCOc2ccc3c(c2)NC(=O)CC3)CC1] |
| 167 | 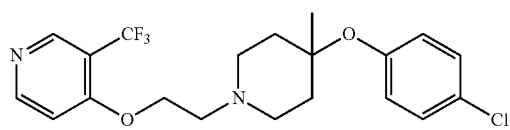 [SMILES: CC1(Oc2ccc(Cl)cc2)CCN(CCOc2ccncc2C(F)(F)F)CC1] |
| 168 | 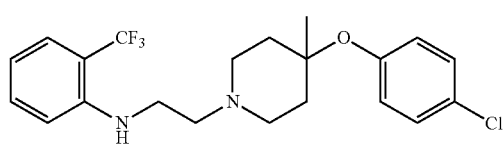 [SMILES: CC1(Oc2ccc(Cl)cc2)CCN(CCNc2ccccc2C(F)(F)F)CC1] |
| 169 | 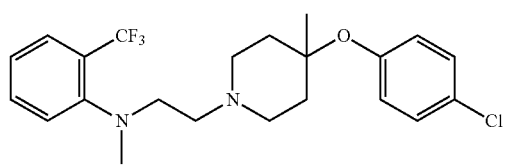 [SMILES: CN(CCN1CCC(C)(Oc2ccc(Cl)cc2)CC1)c1ccccc1C(F)(F)F] |
| 170 | 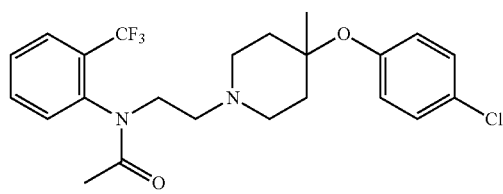 [SMILES: CC(=O)N(CCN1CCC(C)(Oc2ccc(Cl)cc2)CC1)c1ccccc1C(F)(F)F] |

| Formula Number | Formula |
|---|---|
| 171 | 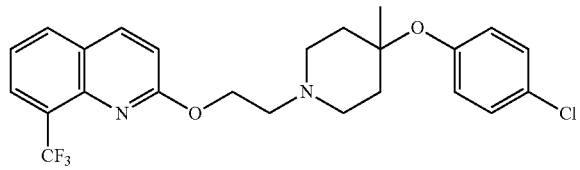 [SMILES: CC1(Oc2ccc(Cl)cc2)CCN(CCOc2ccc3cccc(C(F)(F)F)c3n2)CC1] |
| 173 | 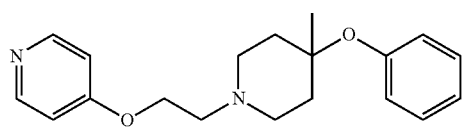 [SMILES: CC1(Oc2ccccc2)CCN(CCOc2ccncc2)CC1] |
| 174 | 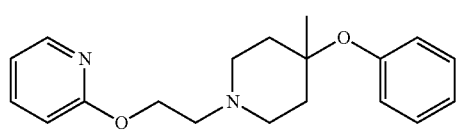 [SMILES: CC1(Oc2ccccc2)CCN(CCOc2ccccn2)CC1] |
| 175 | 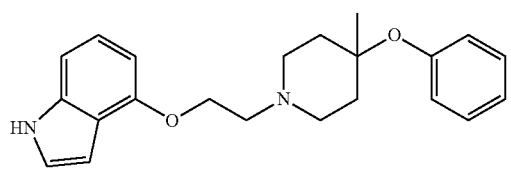 [SMILES: CC1(Oc2ccccc2)CCN(CCOc2cccc3[nH]ccc23)CC1] |
| 182 | 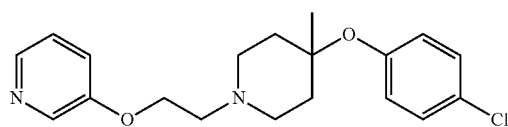 [SMILES: CC1(Oc2ccc(Cl)cc2)CCN(CCOc2cccnc2)CC1] |
| 183 | 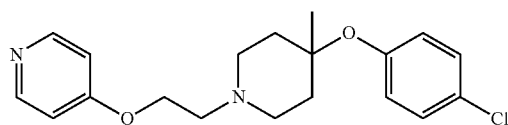 [SMILES: CC1(Oc2ccc(Cl)cc2)CCN(CCOc2ccncc2)CC1] |
| 184 | 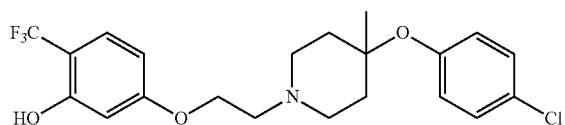 [SMILES: CC1(Oc2ccc(Cl)cc2)CCN(CCOc2ccc(C(F)(F)F)c(O)c2)CC1] |
| 185 | 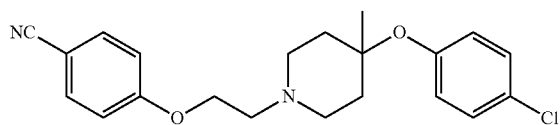 [SMILES: CC1(Oc2ccc(Cl)cc2)CCN(CCOc2ccc(C#N)cc2)CC1] |
| 186 | 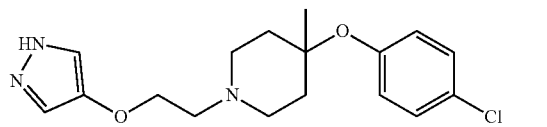 [SMILES: CC1(Oc2ccc(Cl)cc2)CCN(CCOc2cn[nH]c2)CC1] |
| 187 | 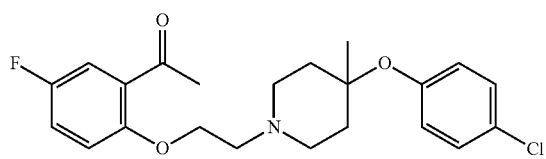 [SMILES: CC(=O)c1cc(F)ccc1OCCN1CCC(C)(Oc2ccc(Cl)cc2)CC1] |

-continued
| Formula Number | Formula |
|---|---|
| 188 | 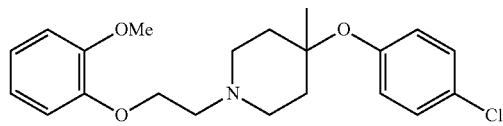 |
| 189 | 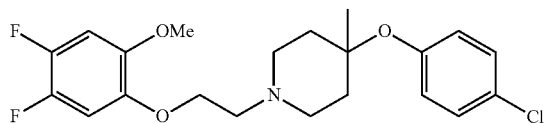 [SMILES: COc1cc(F)c(F)cc1OCCN1CCC(C)(Oc2ccc(Cl)cc2)CC1] |
| 190 | 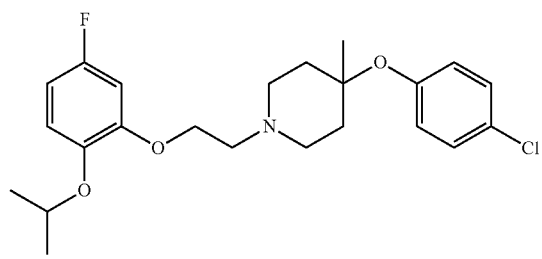 [SMILES: CC(C)Oc1ccc(F)cc1OCCN1CCC(C)(Oc2ccc(Cl)cc2)CC1] |
| 191 | 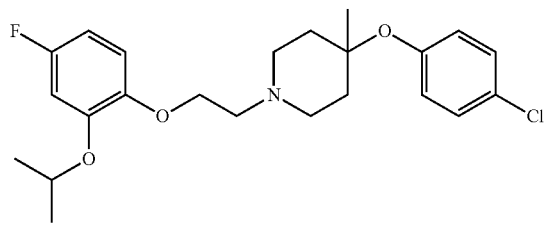 [SMILES: CC(C)Oc1cc(F)ccc1OCCN1CCC(C)(Oc2ccc(Cl)cc2)CC1] |
| 192 | 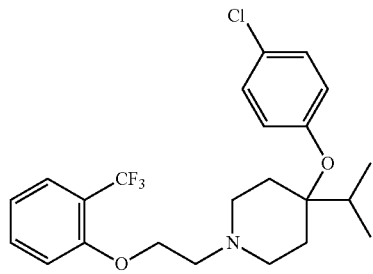 [SMILES: CC(C)C1(Oc2ccc(Cl)cc2)CCN(CCOc2ccccc2C(F)(F)F)CC1] |
| 215 | 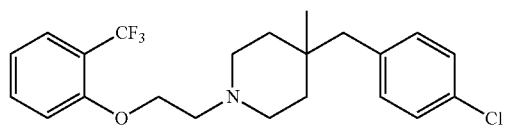 |
| 217 | 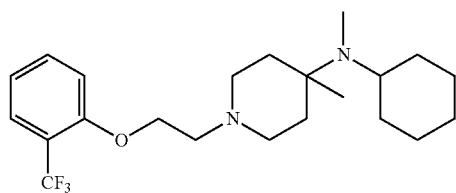 [SMILES: CN(C1CCCCC1)C1(C)CCN(CCOc2ccccc2C(F)(F)F)CC1] |
| 61 | 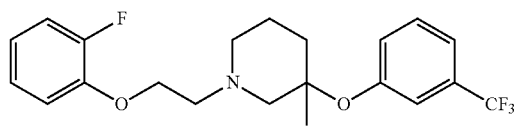 [SMILES: CC1(Oc2cccc(C(F)(F)F)c2)CCCN(CCOc2ccccc2F)C1] |

-continued
| Formula Number | Formula |
|---|---|
| 62 | 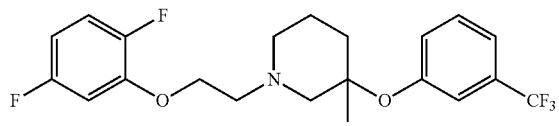 [SMILES: CC1(Oc2cccc(C(F)(F)F)c2)CCCN(CCOc2cc(F)ccc2F)C1] |
| 63 | 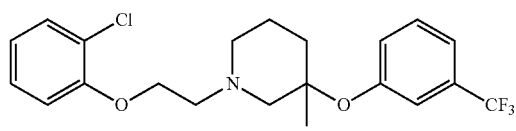 |
| 96 | 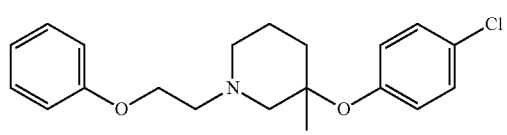 [SMILES: CC1(Oc2ccc(Cl)cc2)CCCN(CCOc2ccccc2)C1] |
| 97 | 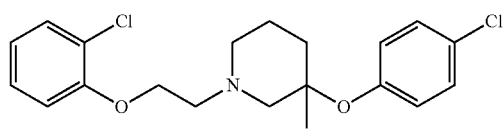 |
| 98 | 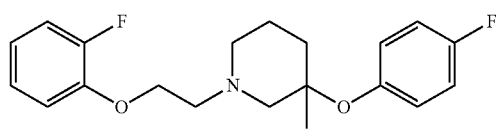 [SMILES: CC1(Oc2ccc(F)cc2)CCCN(CCOc2ccccc2F)C1] |
| 99 | 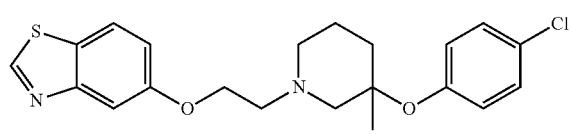 [SMILES: CC1(Oc2ccc(Cl)cc2)CCCN(CCOc2ccc3scnc3c2)C1] |
| 100 | 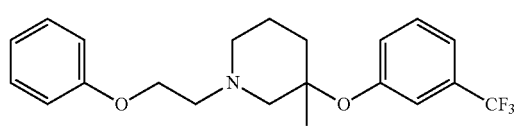 [SMILES: CC1(Oc2cccc(C(F)(F)F)c2)CCCN(CCOc2ccccc2)C1] |
| 108 | 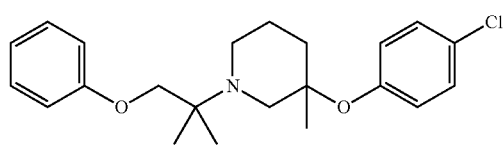 [SMILES: CC1(Oc2ccc(Cl)cc2)CCCN(C(C)(C)COc2ccccc2)C1] |
| 198 | 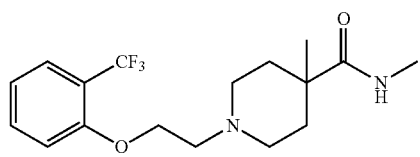 [SMILES: CNC(=O)C1(C)CCN(CCOc2ccccc2C(F)(F)F)CC1] |
| 199 | 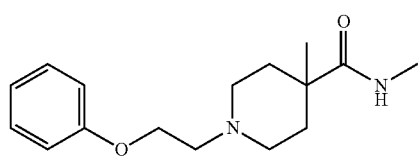 [SMILES: CNC(=O)C1(C)CCN(CCOc2ccccc2)CC1] |

-continued

| Formula Number | Formula |
|---|---|
| 200 | 2-fluorophenoxyethyl-piperidine-4-methyl-N-methylcarboxamide |
| 201 | 2-methoxyphenoxyethyl-piperidine-4-methyl-N-methylcarboxamide |
| 219 | 2-(trifluoromethyl)phenoxyethyl-piperidine-4-methyl-N-phenylcarboxamide |
| 220 | 2-fluorophenoxyethyl-piperidine-4-methyl-N-phenylcarboxamide | or a stereoisomer, racemate, or tautomer thereof, or a pharmaceutically acceptable salt thereof.

32. The method of claim 30, wherein the compound is of the formula:

| Formula Number | Formula |
|---|---|
| 38 | 1-(2-phenoxyethyl)-4-methyl-4-(4-chlorophenoxy)piperidine |
| 67 | 1-(2-(3-trifluoromethylphenoxy)ethyl)-4-methyl-4-phenoxypiperidine |
| 68 | 1-(2-(4-trifluoromethylphenoxy)ethyl)-4-methyl-4-phenoxypiperidine |
| 69 | 1-(2-(2-methylphenoxy)ethyl)-4-methyl-4-phenoxypiperidine |

-continued
| Formula Number | Formula |
|---|---|
| 70 | 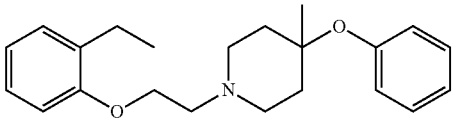 |
| 71 | 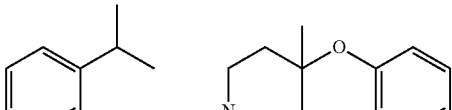 |
| 72 | 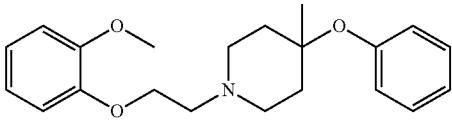 |
| 74 | 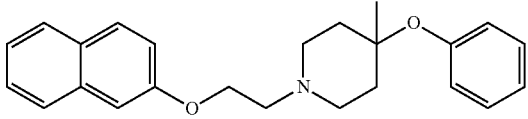 [SMILES: CC1(Oc2ccccc2)CCN(CCOc2ccc3ccccc3c2)CC1] |
| 75 | 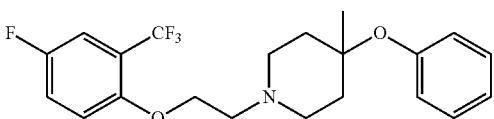 |
| 76 | 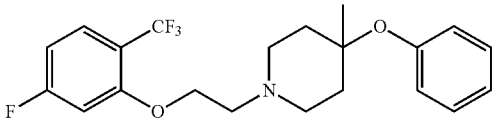 [SMILES: CC1(Oc2ccccc2)CCN(CCOc2cc(F)ccc2C(F)(F)F)CC1] |
| 80 | 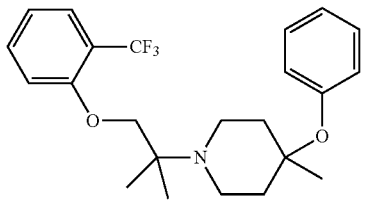 [SMILES: CC1(Oc2ccccc2)CCN(C(C)(C)COc2ccccc2C(F)(F)F)CC1] |
| 82 | 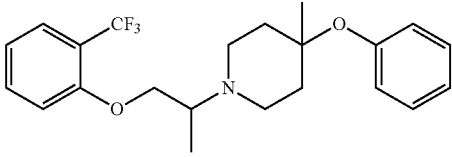 [SMILES: CC(COc1ccccc1C(F)(F)F)N1CCC(C)(Oc2ccccc2)CC1] |
| 83 | 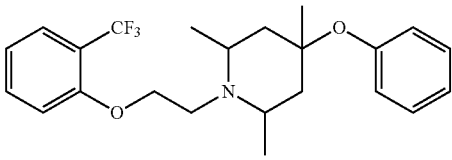 [SMILES: CC1CC(C)(Oc2ccccc2)CC(C)N1CCOc1ccccc1C(F)(F)F] |
| 86 | 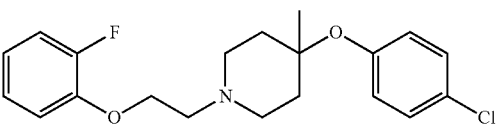 |

-continued

| Formula Number | Formula |
|---|---|
| 87 | 2-fluorophenoxyethyl-(4-methyl-4-phenoxypiperidine) |
| 88 | 2-chlorophenoxyethyl-(4-methyl-4-(4-chlorophenoxy)piperidine) |
| 89 | 2-chlorophenoxyethyl-(4-methyl-4-phenoxypiperidine) |
| 90 | 2-(trifluoromethyl)phenoxyethyl-(4-methyl-4-(4-chlorophenoxy)piperidine) |
| 91 | 2-(trifluoromethyl)phenoxyethyl-(4-methyl-4-phenoxypiperidine) |
| 103 | 2-(trifluoromethyl)phenoxyethyl-(4-hydroxy-4-(hydroxy(phenyl)methyl)piperidine) |
| 104 | 2-(trifluoromethyl)phenoxyethyl-(4-methyl-4-(2-chlorophenoxy)piperidine) |
| 105 | 2-(trifluoromethyl)phenoxyethyl-(4-methyl-4-(pyridin-2-yloxy)piperidine) |
| 106 | 2-(trifluoromethyl)phenoxyethyl-(4-methyl-4-benzoylpiperidine) |
| 107 | 2-(trifluoromethyl)phenoxyethyl-(4-methyl-4-(hydroxy(phenyl)methyl)piperidine) |
| 109 | 2-cyanophenoxyethyl-(4-methyl-4-phenoxypiperidine) |

-continued

| Formula Number | Formula |
|---|---|
| 110 | 2-(OCF₃)phenoxy-ethyl-N-(4-methyl-4-phenoxy-piperidine) |
| 111 | 2-(N,N-dimethylamino)phenoxy-ethyl-N-(4-methyl-4-phenoxy-piperidine) |
| 112 | 2-(CF₃)phenoxy-ethyl-N-(4-methyl-4-(N-methyl-N-phenylamino)-piperidine) |
| 122 | 2-(CF₃)-5-fluoro-phenoxy-ethyl-N-(4-methyl-4-(4-chlorophenoxy)-piperidine) |
| 125 | 4-(CF₃)phenoxy-ethyl-N-(4-methyl-4-(4-chlorophenoxy)-piperidine) |
| 126 | 2-(CF₃)phenoxy-ethyl-N-(4-methyl-4-benzyloxy-piperidine) |
| 127 | benzoxazol-6-yloxy-ethyl-N-(4-methyl-4-(4-chlorophenoxy)-piperidine) |
| 128 | 4-(CF₃)pyridin-3-yloxy-ethyl-N-(4-methyl-4-(4-chlorophenoxy)-piperidine) |
| 129 | N-(2-(CF₃)phenyl)-2-(4-methyl-4-(4-chlorophenoxy)-piperidin-1-yl)acetamide |
| 141 | 2-(SO₂Me)phenoxy-ethyl-N-(4-methyl-4-phenoxy-piperidine) |

-continued
| Formula Number | Formula |
|---|---|
| 143 | 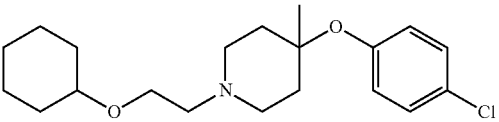 [SMILES: CC1(Oc2ccc(Cl)cc2)CCN(CCOC2CCCCC2)CC1] |
| 146 | 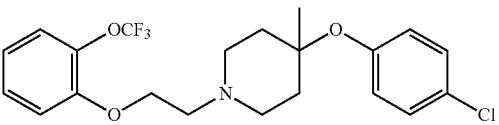 [SMILES: CC1(Oc2ccc(Cl)cc2)CCN(CCOc2ccccc2OC(F)(F)F)CC1] |
| 147 | 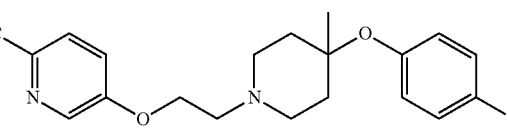 |
| 148 | 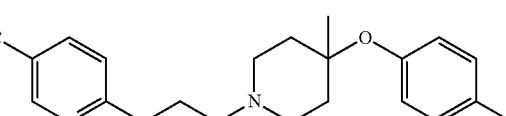 |
| 149 | 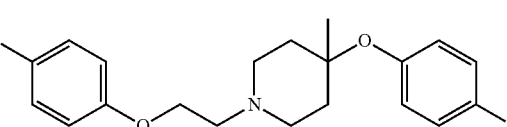 |
| 150 | 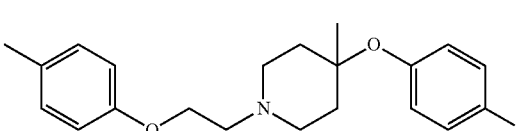 |
| 151 | 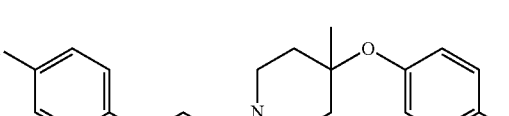 |
| 152 | 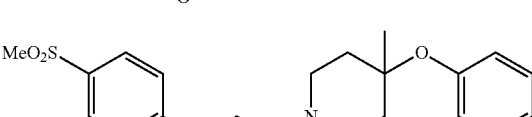 |
| 153 | 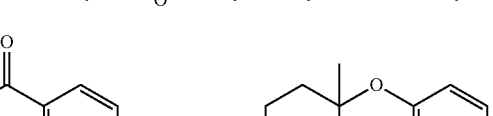 |
| 154 | 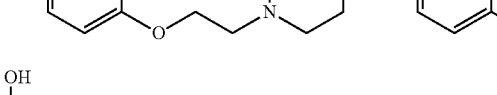 |
| 155 | 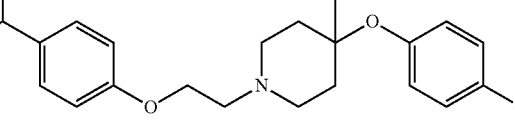 |

-continued

| Formula Number | Formula |
|---|---|
| 156 | |
| 157 | |
| 158 | |
| 159 | |
| 160 | |
| 161 | |
| 162 | |
| 163 | |
| 164 | |
| 165 | |
| 166 | |

-continued

| Formula Number | Formula |
|---|---|
| 167 | |
| 168 | |
| 169 | |
| 170 | |
| 171 | |
| 173 | |
| 174 | |
| 175 | |
| 182 | |
| 183 | |

| Formula Number | Formula |
|---|---|
| 184 | 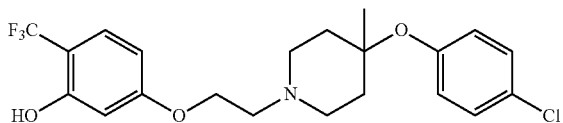 [SMILES: CC1(Oc2ccc(Cl)cc2)CCN(CCOc2ccc(C(F)(F)F)c(O)c2)CC1] |
| 185 | 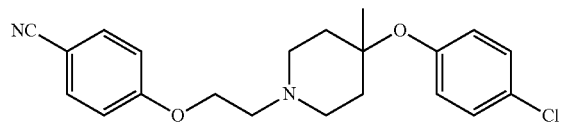 [SMILES: CC1(Oc2ccc(Cl)cc2)CCN(CCOc2ccc(C#N)cc2)CC1] |
| 186 | 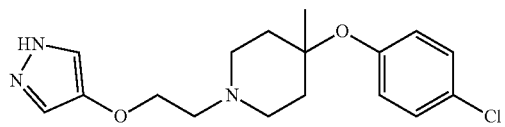 [SMILES: CC1(Oc2ccc(Cl)cc2)CCN(CCOc2cn[nH]c2)CC1] |
| 187 | 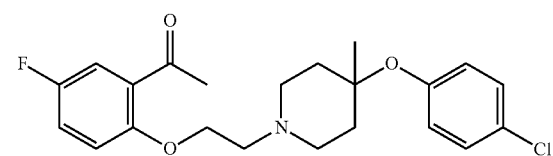 [SMILES: CC(=O)c1cc(F)ccc1OCCN1CCC(C)(Oc2ccc(Cl)cc2)CC1] |
| 188 | 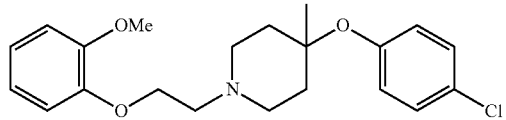 |
| 189 | 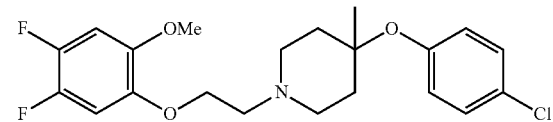 [SMILES: COc1cc(F)c(F)cc1OCCN1CCC(C)(Oc2ccc(Cl)cc2)CC1] |
| 190 | 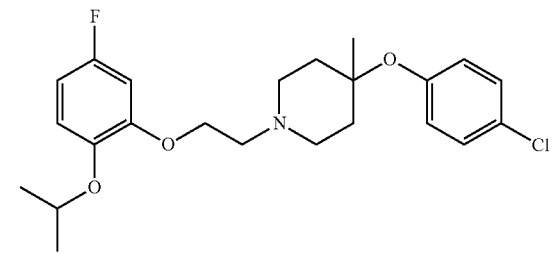 [SMILES: CC(C)Oc1ccc(F)cc1OCCN1CCC(C)(Oc2ccc(Cl)cc2)CC1] |
| 191 | 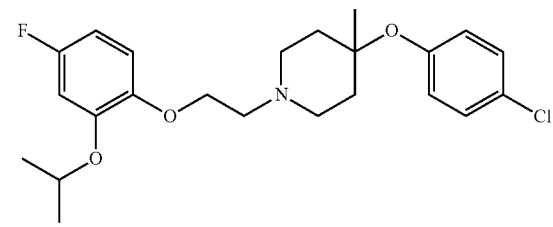 [SMILES: CC(C)Oc1cc(F)ccc1OCCN1CCC(C)(Oc2ccc(Cl)cc2)CC1] |

-continued
| Formula Number | Formula |
|---|---|
| 192 | 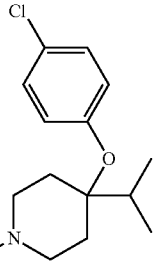 |
| 215 | 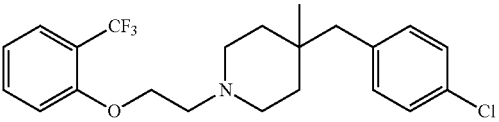 |
| 217 | 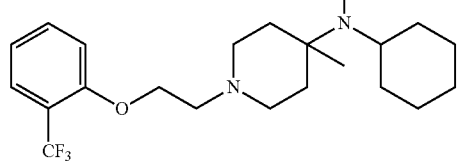 |
| 61 | 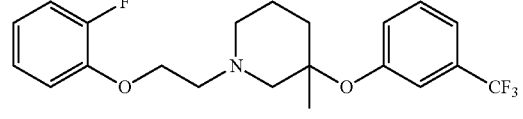 |
| 62 | 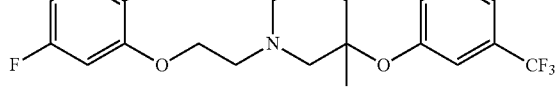 |
| 63 | 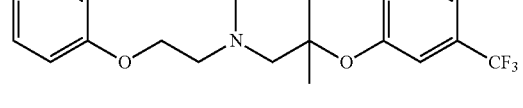 |
| 96 | 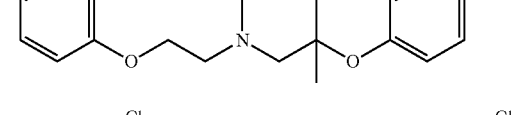 |
| 97 | 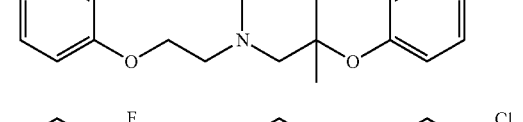 |
| 98 | 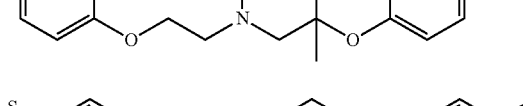 |
| 99 | 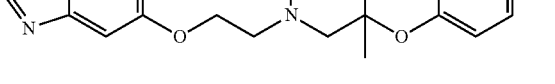 |

| Formula Number | Formula |
|---|---|
| 100 | |
| 108 | |
| 198 | |
| 199 | |
| 200 | |
| 201 | |
| 219 | |
| 220 | | or a stereoisomer, racemate, or tautomer thereof, or a pharmaceutically acceptable salt thereof.

33. The method of claim 8, wherein the psychotic disorder is brief psychotic disorder.

34. The method of claim 8, wherein the psychotic disorder is delusional disorder.

35. The method of claim 8, wherein the psychotic disorder is schizoaffective disorder.

36. The method of claim 8, wherein the psychotic disorder is schizophreniform.

37. The method of claim 8, wherein the psychotic disorder is shared psychotic disorder.

* * * * *